US012622905B2

(12) United States Patent
Cook et al.

(10) Patent No.: US 12,622,905 B2
(45) Date of Patent: May 12, 2026

(54) ARYL PLADIENOLIDES FOR THE TREATMENT OF NEOPLASTIC DISORDERS

(71) Applicant: Eisai R&D Management Co., Ltd., Tokyo (JP)

(72) Inventors: Andrew Cook, Stow, MA (US); Dominic Reynolds, Stoneham, MA (US); Cheng Zhong, Belmont, MA (US); Ryan Brawn, Sudbury, MA (US); Shelby Ellery, Boston, MA (US); Thiwanka Samarakoon, Westwood, MA (US); Xiang Liu, Winchester, MA (US); Sudeep Prajapati, Somerville, MA (US); Megan Sheehan, Allston, MA (US); Jason T. Lowe, East Bridgewater, MA (US); James Palacino, Wellesley, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

(21) Appl. No.: 18/180,063

(22) Filed: Mar. 7, 2023

(65) Prior Publication Data

US 2023/0301990 A1 Sep. 28, 2023

Related U.S. Application Data

(62) Division of application No. 17/046,528, filed as application No. PCT/US2019/026992 on Apr. 11, 2019, now Pat. No. 11,679,107.

(Continued)

(51) Int. Cl.

| | |
|---|---|
| ***C07D 313/16*** | (2006.01) |
| ***A61K 9/00*** | (2006.01) |
| ***A61K 31/496*** | (2006.01) |
| ***A61K 31/497*** | (2006.01) |
| ***A61K 31/506*** | (2006.01) |
| ***A61K 31/5377*** | (2006.01) |
| ***A61K 31/5386*** | (2006.01) |
| ***A61K 31/541*** | (2006.01) |
| ***A61K 31/551*** | (2006.01) |

(Continued)

(52) U.S. Cl.

CPC .......... *A61K 31/496* (2013.01); *A61K 9/0053* (2013.01); *A61K 31/497* (2013.01); *A61K 31/506* (2013.01); *A61K 31/5377* (2013.01); *A61K 31/5386* (2013.01); *A61K 31/541* (2013.01); *A61K 31/551* (2013.01); *A61K 38/191* (2013.01); *A61K 38/2013* (2013.01); *A61K 38/2066* (2013.01); *A61K 38/208* (2013.01); *A61K 38/2086* (2013.01); *A61K 38/217* (2013.01); *A61K 39/3955* (2013.01); *A61P 35/00* (2018.01); *C07D 313/00* (2013.01); *C07D 405/06* (2013.01); *C07D 405/10* (2013.01); *C07D 405/12* (2013.01); *C07D 405/14* (2013.01); *C07D 407/12* (2013.01); *C07D 409/12* (2013.01); *C07D 413/10* (2013.01); *C07D 413/12* (2013.01); *C07D 413/14* (2013.01); *C07D 417/10* (2013.01); *C07D 453/02* (2013.01); *C07D 471/10* (2013.01); *C07D 487/04* (2013.01); *C07D 491/107* (2013.01); *C07D 498/08* (2013.01); *C07B 2200/05* (2013.01)

(58) Field of Classification Search

CPC .................................................... C07D 313/16

USPC .......................................................... 549/346

See application file for complete search history.

(56) References Cited

U.S. PATENT DOCUMENTS

| | | | |
|---|---|---|---|
| 5,707,989 | A | 1/1998 | Himmelsbach et al. |
| 2005/0245514 | A1 | 11/2005 | Kotake et al. |

(Continued)

FOREIGN PATENT DOCUMENTS

| | | | |
|---|---|---|---|
| EP | 1380579 | A1 | 1/2004 |
| EP | 1 508 570 | A1 | 2/2005 |

(Continued)

OTHER PUBLICATIONS

International Search Report and Written Opinion for PCT/US2019/026992 dated Jul. 26, 2019 (15 pages).

(Continued)

*Primary Examiner* — Douglas M Willis

(74) *Attorney, Agent, or Firm* — Finnegan, Henderson, Farabow, Garrett & Dunner, LLP

(57) ABSTRACT

The present disclosure provides novel pladienolide compounds according to Formula I:

I

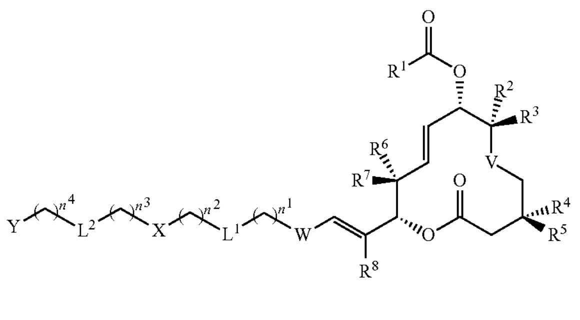

pharmaceutical compositions containing such compounds, and methods for using the compounds as therapeutic agents. These compounds may be useful in the treatment of cancer, particularly cancers in which agents that target the spliceosome and mutations therein are known to be useful. Also (Continued)

provided herein are methods of treating cancers by administering at least one compound disclosed herein and at least one additional therapy.

23 Claims, No Drawings

Specification includes a Sequence Listing.

Related U.S. Application Data

(60) Provisional application No. 62/656,865, filed on Apr. 12, 2018, provisional application No. 62/679,658, filed on Jun. 1, 2018, provisional application No. 62/814,824, filed on Mar. 6, 2019, provisional application No. 62/814,828, filed on Mar. 6, 2019.

(51) Int. Cl.

| | |
|---|---|
| ***A61K 38/19*** | (2006.01) |
| ***A61K 38/20*** | (2006.01) |
| ***A61K 38/21*** | (2006.01) |
| ***A61K 39/395*** | (2006.01) |
| ***A61P 35/00*** | (2006.01) |
| ***C07D 313/00*** | (2006.01) |
| ***C07D 405/06*** | (2006.01) |
| ***C07D 405/10*** | (2006.01) |
| ***C07D 405/12*** | (2006.01) |
| ***C07D 405/14*** | (2006.01) |
| ***C07D 407/12*** | (2006.01) |
| ***C07D 409/12*** | (2006.01) |
| ***C07D 413/10*** | (2006.01) |
| ***C07D 413/12*** | (2006.01) |
| ***C07D 413/14*** | (2006.01) |
| ***C07D 417/10*** | (2006.01) |
| ***C07D 453/02*** | (2006.01) |
| ***C07D 471/10*** | (2006.01) |
| ***C07D 487/04*** | (2006.01) |
| ***C07D 491/107*** | (2006.01) |
| ***C07D 498/08*** | (2006.01) |

(56) References Cited

U.S. PATENT DOCUMENTS

| | | | |
|---|---|---|---|
| 2006/0079572 | A1 | 4/2006 | Mizui et al. |
| 2006/0235002 | A1 | 10/2006 | Nagai et al. |
| 2008/0214564 | A1 | 9/2008 | Ishihara et al. |
| 2008/0275059 | A1 | 11/2008 | Kotake et al. |
| 2009/0215134 | A1 | 8/2009 | Machida et al. |
| 2014/0275010 | A1 | 9/2014 | Zheng et al. |

FOREIGN PATENT DOCUMENTS

| | | | |
|---|---|---|---|
| EP | 1 712 642 | A1 | 10/2006 |
| EP | 2136209 | A1 | 12/2009 |
| EP | 2 168 961 | A1 | 3/2010 |
| NC | 2016/0005345 | | 5/2017 |
| RU | 97105695 | A | 4/1999 |
| RU | 2394906 | C2 | 7/2010 |
| WO | WO 02/060890 | A1 | 8/2002 |
| WO | WO 2007/110704 | A2 | 10/2007 |
| WO | WO 2008/111464 | A1 | 9/2008 |
| WO | WO 2008/111466 | A1 | 9/2008 |
| WO | WO 2013/148324 | A1 | 10/2013 |
| WO | WO 2015/175594 | A1 | 11/2015 |
| WO | WO 2017/087667 | A1 | 5/2017 |

OTHER PUBLICATIONS

Muller, S. et al., “Synthesis of a Pladienolide B Analogue with the Fully Functionalized Core Structure,” *Organic Letters*, 2011, vol. 13, No. 15, pp. 3940-3943.

Leon et al., (2017) “A Challenging Pie to Splice: Drugging the Spliceosome” Angew Chem Int Ed Engl. 56(40):12052-12063.

SEQUENCE LISTING

```
Sequence total quantity: 64
SEQ ID NO: 1            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 1
SPTLPPRSL                                                              9

SEQ ID NO: 2            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 2
HPSIKRGLSS L                                                           11

SEQ ID NO: 3            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 3
LLLPHHVL                                                               8

SEQ ID NO: 4            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 4
RTAPGVRPPF                                                             10

SEQ ID NO: 5            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 5
RPQKSIQAL                                                              9

SEQ ID NO: 6            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 6
APAPPPLPA                                                              9
```

-continued

```
SEQ ID NO: 7            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 7
RPRPSFPVSL                                                                   10

SEQ ID NO: 8            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 8
RPKHGDGFSL                                                                   10

SEQ ID NO: 9            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 9
GPAPGKTGL                                                                    9

SEQ ID NO: 10           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 10
EAARKGNSL                                                                    9

SEQ ID NO: 11           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 11
RIKEKIEEL                                                                    9

SEQ ID NO: 12           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 12
EIKKRFRQF                                                                    9

SEQ ID NO: 13           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 13
HESAAMAET                                                                    9

SEQ ID NO: 14           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 14
```

-continued

```
ALKLKQVGV                                                    9

SEQ ID NO: 15         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 15
DLKKRHITF                                                    9

SEQ ID NO: 16         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 16
DVKRNDIAM                                                    9

SEQ ID NO: 17         moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 17
IPSDHILTPA                                                   10

SEQ ID NO: 18         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 18
TVFSTSSLK                                                    9

SEQ ID NO: 19         moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 19
ITSCLLNF                                                     8

SEQ ID NO: 20         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 20
RASPVRGQL                                                    9

SEQ ID NO: 21         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 21
VVRKPVIAL                                                    9

SEQ ID NO: 22         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
```

```
SEQUENCE: 22
LLSEKKKIS                                                         9

SEQ ID NO: 23           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 23
APASKPRPRL                                                        10

SEQ ID NO: 24           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 24
RYGQLSEKF                                                         9

SEQ ID NO: 25           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 25
VYISNVSKL                                                         9

SEQ ID NO: 26           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 26
LPTKETPSF                                                         9

SEQ ID NO: 27           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 27
GEAPPPPPA                                                         9

SEQ ID NO: 28           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 28
LEEISKQEI                                                         9

SEQ ID NO: 29           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 29
IYNHITVKI                                                         9

SEQ ID NO: 30           moltype = AA  length = 160
FEATURE                 Location/Qualifiers
REGION                  1..160
                        note = Description of Artificial Sequence: Synthetic
                         polypeptide
source                  1..160
```

```
                       mol_type = protein
                       organism = synthetic construct
SEQUENCE: 30
VDLEPTVIGE LTSVTQVRSQ GAGTGGLSWG GSAGHSPTLP PRSLSLLLLP HHVLQMKFAL  60
ALTASSSTLS NSSQARKMLP ITMPEGTTPL ARRSLTSCWT EFASWLTSAP VFRASWFSTA  120
LVGELVLGSP RCSWNVSQLI MARSPSWSSP FTRRPRFPQL                       160

SEQ ID NO: 31          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 31
APPRSHPSIK RGLSSL                                                 16

SEQ ID NO: 32          moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 32
MVRRARWPGG RGEARKAPRT APGVRPPF                                    28

SEQ ID NO: 33          moltype = AA  length = 199
FEATURE                Location/Qualifiers
REGION                 1..199
                       note = Description of Artificial Sequence: Synthetic
                        polypeptide
source                 1..199
                       mol_type = protein
                       organism = synthetic construct
SEQUENCE: 33
WVNCLFVSGR AAAGGGGGGA VPPYLELAGP PFLLLTLIRI GLGRRSGRAG GRAGTQCGGE  60
RGPGFAAFRP LRPFRRLRVC AVCVRGSALG RSVGLPRGGA AGAPFSSSPA PHPRRVLCRC  120
LLFLFFSCHD RRGDSQPYQV PAEAGVEGLE GAGGGREGLL LERRPQKSIQ ALRCNTSETS  180
TADPLKIPGL VPLALSSKV                                              199

SEQ ID NO: 34          moltype = AA  length = 101
FEATURE                Location/Qualifiers
REGION                 1..101
                       note = Description of Artificial Sequence: Synthetic
                        polypeptide
source                 1..101
                       mol_type = protein
                       organism = synthetic construct
SEQUENCE: 34
MPLPVQVFNL QVTSRGRPGP PRPRAPRHWG RAEVEQGRGA CARSRSGTLR AGPPRAARVG  60
GCRAEGASPP WLRAAIGGRR AAPAPPPLPA AHGRGSRPPR R                     101

SEQ ID NO: 35          moltype = AA  length = 162
FEATURE                Location/Qualifiers
REGION                 1..162
                       note = Description of Artificial Sequence: Synthetic
                        polypeptide
source                 1..162
                       mol_type = protein
                       organism = synthetic construct
SEQUENCE: 35
QPAQPRTGAP ARRPRPRPSF PVSLRSAAPP TGTAGGTGRF VLRPGESGAG GGGDAWDTGL  60
QARRGTAAGT SGAPNRSQLS SLTFPAQLRR IGVSGRKPGA GGRLGPGSRT CAPRCLPRAR  120
RGPGAHPRGG RCPPAETALF REAEEGTQKY SLPSDPAGQA AF                    162

SEQ ID NO: 36          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 36
FRLHTGPVSP VGGRRQMGRP KHGDGFSLQV CSFIMEQNG                        39

SEQ ID NO: 37          moltype = AA  length = 71
FEATURE                Location/Qualifiers
```

```
REGION                  1..71
                        note = Description of Artificial Sequence: Synthetic
                         polypeptide
source                  1..71
                        mol_type = protein
                        organism = synthetic construct
SEQUENCE: 37
GVVEITGEPP CSCRGEEEAS RAGRAGGVRL KRGSRGPGEL NVGPAPGKTG LLIPLLRNWE  60
CGSLLRALSA L                                                       71

SEQ ID NO: 38           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 38
KMGFPEAARK GNSL                                                    14

SEQ ID NO: 39           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 39
LEARIKEKIE ELQQALI                                                 17

SEQ ID NO: 40           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 40
EIKKRFRQFK QAVYKQ                                                  16

SEQ ID NO: 41           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 41
AHESAAMAET LQHVPS                                                  16

SEQ ID NO: 42           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 42
NRPSVQAALK LKQVGV                                                  16

SEQ ID NO: 43           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 43
KTDDLKKRHI TFTLGCGIC                                               19

SEQ ID NO: 44           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 44
MKLDEDVKRN DIAMAI                                                  16
```

```
SEQ ID NO: 45          moltype = AA  length = 26
FEATURE                Location/Qualifiers
REGION                 1..26
                       note = Description of Artificial Sequence: Synthetic peptide
source                 1..26
                       mol_type = protein
                       organism = synthetic construct
SEQUENCE: 45
NSISQIPSDH ILTPALFITF MTILDL                                          26

SEQ ID NO: 46          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 46
TVFSTSSLKL NQPQKYLKMK SWPC                                            24

SEQ ID NO: 47          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 47
AEEDRRKKVI TSCLLNFNLS KAQS                                            24

SEQ ID NO: 48          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 48
RSFSTSAQVG QTRGGLQAEA PRPGPRASPV RGQL                                 34

SEQ ID NO: 49          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 49
RGYVVRKPVI ALSVKI                                                     16

SEQ ID NO: 50          moltype = AA  length = 86
FEATURE                Location/Qualifiers
REGION                 1..86
                       note = Description of Artificial Sequence: Synthetic
                        polypeptide
source                 1..86
                       mol_type = protein
                       organism = synthetic construct
SEQUENCE: 50
VDMDFGTGGQ GAGPVGRGKD WSCTLAVHLL SEKKKISFSQ IDRAWGGSQG TVLDKWGPGV  60
VSELHPSAKE VSVGRNSVES LMTWAS                                          86

SEQ ID NO: 51          moltype = AA  length = 66
FEATURE                Location/Qualifiers
REGION                 1..66
                       note = Description of Artificial Sequence: Synthetic
                        polypeptide
source                 1..66
                       mol_type = protein
                       organism = synthetic construct
SEQUENCE: 51
EKGSHEEEVR VPALSWGRPR APAPASKPRP RLDLNCLWLR PQPIFLWKLR PRPVPAATPL  60
TGPLPL                                                                66

SEQ ID NO: 52          moltype = AA  length = 17
FEATURE                Location/Qualifiers
REGION                 1..17
```

```
                        note = Description of Artificial Sequence: Synthetic peptide
source                  1..17
                        mol_type = protein
                        organism = synthetic construct
SEQUENCE: 52
RYGQLSEKFN RRKVMDS                                                 17

SEQ ID NO: 53           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 53
MVYISNVSKL CFSKM                                                   15

SEQ ID NO: 54           moltype = AA  length = 48
FEATURE                 Location/Qualifiers
REGION                  1..48
                        note = Description of Artificial Sequence: Synthetic
                         polypeptide
source                  1..48
                        mol_type = protein
                        organism = synthetic construct
SEQUENCE: 54
NTLPTKETPS FLLNPHTSWV PRPHREAPRL RVGVAAPLQR PLPALHSH               48

SEQ ID NO: 55           moltype = AA  length = 58
FEATURE                 Location/Qualifiers
REGION                  1..58
                        note = Description of Artificial Sequence: Synthetic
                         polypeptide
source                  1..58
                        mol_type = protein
                        organism = synthetic construct
SEQUENCE: 55
FGDIYLGEAP PPPPAARRPG PCGCQDQARS RKEVVAPAGS PRKSRHRRIV ARTQRPLG    58

SEQ ID NO: 56           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 56
GSASDLLEEI SKQEISF                                                 17

SEQ ID NO: 57           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 57
QLIYNHITVK INLQGD                                                  16

SEQ ID NO: 58           moltype = AA  length = 4
FEATURE                 Location/Qualifiers
REGION                  1..4
                        note = Description of Unknown: DEAH box helicase 9 (DHX9)
                         peptide
source                  1..4
                        mol_type = protein
                        organism = unidentified
SEQUENCE: 58
DEAH                                                               4

SEQ ID NO: 59           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 59
actctcttcc gcatcgctgt                                              20
```

-continued

```
SEQ ID NO: 60          moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 60
ccgacgggtt tccgatccaa                                              20

SEQ ID NO: 61          moltype = DNA  length = 18
FEATURE                Location/Qualifiers
misc_feature           1..18
                       note = Description of Artificial Sequence: Synthetic probe
source                 1..18
                       mol_type = other DNA
                       organism = synthetic construct
SEQUENCE: 61
ctgttgggct cgcggttg                                                18

SEQ ID NO: 62          moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 62
tggcatcaga ttgcaaagac                                              20

SEQ ID NO: 63          moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 63
acgccgggtg atgtatctat                                              20

SEQ ID NO: 64          moltype = DNA  length = 20
FEATURE                Location/Qualifiers
misc_feature           1..20
                       note = Description of Artificial Sequence: Synthetic probe
source                 1..20
                       mol_type = other DNA
                       organism = synthetic construct
SEQUENCE: 64
cgaaacgcac ccgtcagacg                                              20
```

ARYL PLADIENOLIDES FOR THE TREATMENT OF NEOPLASTIC DISORDERS

The present application is a division of application Ser. No. 17/046,528, filed Oct. 9, 2020, which is a national stage filing under 35 U.S.C. § 371 of International Application No. PCT/US2019/026992, filed on Apr. 11, 2019, which claims the benefit of priority to U.S. Provisional Application No. 62/656,865 filed Apr. 12, 2018; U.S. Provisional Application No. 62/679,658 filed Jun. 1, 2018; U.S. Provisional Application No. 62/814,824 filed Mar. 6, 2019; and U.S. Provisional Application No. 62/814,828 filed Mar. 6, 2019, all of which are incorporated herein by reference.

STATEMENT REGARDING SEQUENCE LISTING

The sequence listing associated with this application is provided in xml format and is hereby incorporated by reference in its entirety into the specification. The name of the xml file containing the sequence listing is 080610036.xml; the file is 83,919 bytes; was created on Mar. 1, 2023 and is being submitted via Patent Center with the filing of this application.

Disclosed herein are novel organic compounds and pharmaceutical compositions containing such compounds. These compounds may be useful in the treatment of cancer, particularly cancers in which agents that target the spliceosome and mutations therein are known to be useful. These compounds may also be useful in treating cancer when administered in combination with at least one additional therapy.

In eukaryote organisms, newly synthesized messenger RNAs typically have multiple introns, which are excised to provide the mature mRNA. The spliceosome is a multisubunit complex that accomplishes this task. The spliceosome consists of five small nuclear RNAs (snRNAs; U1-6) in combination with a variety of proteins. Mutations in spliceosome genes have been found in various types of cancers.

For example, mutations in the splicing factor 3B subunit 1 (SF3B1) of the spliceosome exist in a number of cancers and comprise a target for anticancer agents. Such cancers include, but are not limited to, myelodysplastic syndrome (MDS), leukemia such as chronic lymphocytic leukemia (CLL), chronic myelomonocytic leukemia (CMML), and acute myeloid leukemia (AML), and solid tumors such as breast cancer and uveal melanoma.

Compounds isolated from the bacteria *Streptomyces platensis* (Sakai, Takashi; Sameshima, Tomohiro; Matsufuji, Motoko; Kawamura, Naoto; Dobashi, Kazuyuki; Mizui, Yoshiharu. Pladienolides, New Substances from Culture of *Streptomyces platensis* Mer-11107. I. Taxonomy, Fermentation, Isolation and Screening. The Journal of Antibiotics. 2004, Vol. 57, No. 3.), termed pladienolides and discovered while screening for inhibitors of the vascular endothelial growth factor (VEGF) promoter, inhibit expression of a reporter gene controlled by human VEGF promoter, which inhibition is known to be a useful mechanism of action for anticancer agents.

These compounds also inhibit proliferation of U251 human glioma cells in vitro. The most potent of these compounds, Pladienolide B, inhibits VEGF-promoted gene expression with an $IC_{50}$ of 1.8 nM, and inhibits glioma cell proliferation with an $IC_{50}$ of 3.5 nM. The structure of pladienolide B is known, (Sakai, Takashi; Sameshima, Tomohiro; Matsufuji, Motoko; Kawamura, Naoto; Dobashi, Kazuyuki; Mizui, Yoshiharu. Pladienolides, New Substances from Culture of *Streptomyces platensis* Mer-11107. II. Physico-chemical Properties and Structure Elucidation. *The Journal of Antibiotics*. Vol. 57, No. 3. (2004)) and pladienolide B is known to target the SF3b spliceosome to inhibit splicing and alter the pattern of gene expression (Kotake et al., "Splicing factor SF3b as a target of the antitumor natural product pladienolide", Nature Chemical Biology 2007, 3, 570-575).

Certain pladienolide B compounds, as well as other pladienolide compounds, are likewise known, as disclosed the following patent applications: WO 2002/060890; WO 2004/011459; WO 2004/011661; WO 2004/050890; WO 2005/052152; WO 2006/009276; WO 2008/126918; and WO 2015/175594. For example, a pladienolide compound, (8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide, also known as E7107, is a semisynthetic derivative of the natural product pladienolide D, and the results of its Phase I study have been reported. As another example, the pladienolide pyridine compound (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate (also named "(2S,3S,4E,6S,7R,10R)-7,10-dihydroxy-3,7-dimethyl-12-oxo-2-((2E,4E,6R)-6-(pyridin-2-yl)hepta-2,4-dien-2-yl)oxacyclododec-4-en-6-yl 4-methylpiperazine-1-carboxylate"), also known as H3B-8800, has received orphan drug designation for the treatment of certain hematological cancers.

However, additional agents useful in the treatment of cancer, particularly cancers in which agents that target the spliceosome and mutations therein are known to be useful, are needed.

Immune checkpoint blockade (ICB) has recently proven to be a paradigm shift for the treatment of several different cancer types. However, not all patients demonstrate robust/durable responses to ICB. See, e.g., Zappasodi, R. et al. Emerging Concepts for Immune Checkpoint Blockade-Based Combination Therapies. *Cancer Cell* 33, 581-598, doi:10.1016/j.ccell.2018.03.005 (2018); and Wolchok, J. D. et al. Overall Survival with Combined Nivolumab and Ipilimumab in Advanced Melanoma. *N Engl J Med* 377, 1345-1356, doi:10.1056/NEJMoa1709684 (2017). Therefore, there also exists a need to discover complementary therapeutic agents to administer in combination with ICB or any other therapy to improve and/or maximize patient response.

Disclosed herein are compounds of Formula I:

I

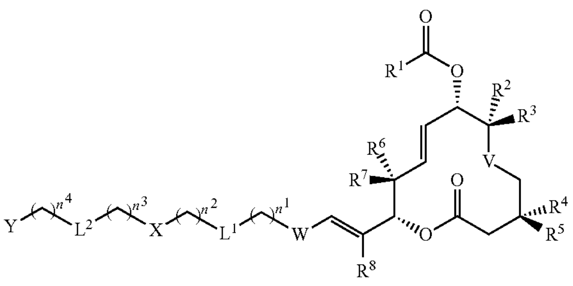

and pharmaceutically acceptable salts thereof, wherein:

$R^1$ is chosen from:

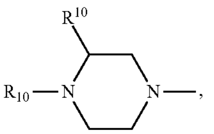, 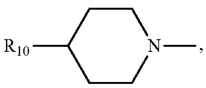, 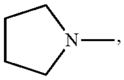,

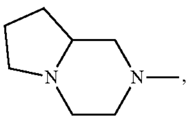, 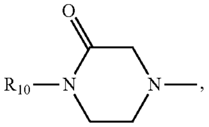,

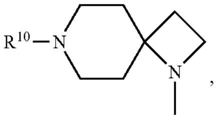, 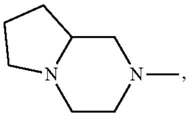, 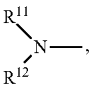,

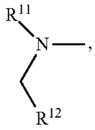, 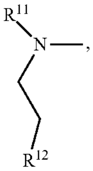, 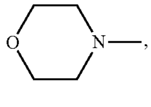,

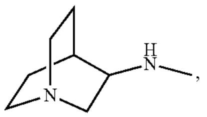, and 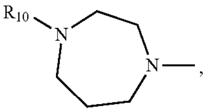, each of which may be substituted with 1 to 3 groups independently chosen from halogens, hydroxyl groups, $C_1$-$C_6$ alkyl groups, $C_1$-$C_6$ alkoxy groups, $C_3$-$C_8$ cycloalkyl groups, hydroxy $C_1$-$C_6$ alkyl groups, dimethylamino groups, and methoxy $C_1$-$C_6$ alkyl groups;

$R^2$, $R^3$, $R^4$, $R^5$, $R^6$, and $R^7$ are each independently chosen from hydrogen, hydroxyl groups, —O—$R^{10}$ groups, and $C_1$-$C_6$ alkyl groups;

$R^8$, $R^9$, and $R^{13}$ are each independently chosen from hydrogen and $C_1$-$C_6$ alkyl groups;

$R^{10}$ is chosen from hydrogen, $C_1$-$C_6$ alkyl groups, $C_1$-$C_6$ aminoalkyl groups, $C_1$-$C_6$ alkylamino groups, $C_1$-$C_6$ alkylcarboxylic acid groups, $C_3$-$C_8$ cycloalkyl groups, benzyl groups, $C_3$-$C_8$ heterocyclyl groups, —$CH_2$—$C_3$-$C_8$ heterocyclyl groups, —C(O)—$C_3$-$C_8$ heterocyclyl groups, acyl groups, hydroxy $C_1$-$C_6$ alkyl groups, methoxy $C_1$-$C_6$ alkyl groups, —$CD_3$, and —C(O)—$NR^{11}R^{12}$ groups;

$R^{11}$ and $R^{12}$ are independently chosen from hydrogen, $C_1$-$C_6$ alkyl groups, $C_1$-$C_6$ aminoalkyl groups, $C_1$-$C_6$ alkylamino groups, $C_3$-$C_8$ cycloalkyl groups, and $C_3$-$C_8$ heterocyclyl groups;

V is chosen from —$CH_2$— and —N($R^9$)—;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—; and each n is independently chosen from 0 to 4.

Also disclosed herein are pharmaceutical compositions comprising at least one compound chosen from compounds of Formula I (including Formulas IIa-e, IIIa, IVa, and Va) and pharmaceutically acceptable salts thereof. In some embodiments, the pharmaceutical compositions further comprise at least one pharmaceutically acceptable carrier.

Also disclosed herein are methods of treating a subject with cancer comprising administering to the subject a therapeutically effective amount of at least one compound chosen from compounds of Formula I (including Formulas IIa-e, IIIa, IVa, and Va) and/or pharmaceutically acceptable salts thereof. In some embodiments, the cancer is chosen from myelodysplastic syndrome, chronic lymphocytic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and/or lung cancer. In some embodiments, the cancer is chosen from cancers that test positive for one or more mutations in the Splicing factor 3B subunit 1 (SF3B1) gene or protein. In some embodiments, the cancer is chosen from cancers that test positive for one or more mutations in a spliceosome gene or protein, such as those listed in Table 1. In some embodiments, administration of at least one compound chosen from compounds of Formula I (including Formulas IIa-e, IIIa, IVa, and Va) and/or pharmaceutically acceptable salts thereof, induces at least one neoantigen and/or a T-cell response.

Also disclosed herein are the use of at least one compound chosen from compounds of Formula I (including Formulas IIa-e, IIIa, IVa, and Va) and pharmaceutically acceptable salts thereof in a method of therapeutic treatment, e.g., treatment for a cancer. In some embodiments, the cancer is chosen from myelodysplastic syndrome, chronic lymphocytic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and/or lung cancer. In some embodiments, the cancer is chosen from cancers that test positive for one or more mutations in the Splicing factor 3B subunit 1 (SF3B1) gene or protein. In some embodiments, the cancer is chosen from cancers that test positive for one or more mutations in a spliceosome gene or protein, such as those listed in Table 1. In some embodiments, administration of at least one compound chosen from compounds of Formula I (including Formulas IIa-e, IIIa, IVa, and Va) and/or pharmaceutically acceptable salts thereof, induces at least one neoantigen and/or a T-cell response.

Also disclosed herein are at least one compound chosen from compounds of Formula I (including Formulas IIa-e, IIIa, IVa, and Va) and pharmaceutically acceptable salts thereof for use in the preparation of a medicament. In some embodiments, the medicament is useful for the treatment of cancer. In some embodiments, the cancer is chosen from myelodysplastic syndrome, chronic lymphocytic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and/or lung cancer. In some embodiments, the cancer is chosen from cancers that test positive for one or more mutations in the Splicing factor 3B subunit 1 (SF3B1) gene or protein. In some embodiments, the cancer is chosen from cancers that test positive for one or more mutations in a spliceosome gene or protein, such as those listed in Table 1. In some embodiments, administration of at least one compound chosen from compounds of Formula I (including Formulas IIa-e, IIIa, IVa, and Va) and/or pharmaceutically acceptable salts thereof, induces at least one neoantigen and/or a T-cell response.

Also disclosed herein are uses of at least one compound chosen from compounds of Formula I (including Formulas IIa-e, IIIa, IVa, and Va) and/or pharmaceutically acceptable salts thereof, to target the spliceosome, e.g., subunit 1 of the SF3B spliceosome.

Also disclosed herein are methods of inducing at least one neoantigen, comprising contacting a neoplastic cell with an effective amount of at least one compound chosen from compounds of Formula I (including Formulas IIa-e, IIIa, IVa, and Va) and/or pharmaceutically acceptable salts thereof. In some embodiments, such contact may induce production of at least one neoantigen.

Also disclosed herein are methods of inducing at least one neoantigen and/or a T-cell response in a subject having or suspected of having a neoplastic disorder, comprising administering to the subject an effective amount of at least one compound chosen from compounds of Formula I (including Formulas IIa-e, IIIa, IVa, and Va) and/or pharmaceutically acceptable salts thereof.

Also disclosed herein are methods of treating a subject having or suspect of having a neoplastic disorder. In some embodiments, the method comprises administering to the subject an effective amount of at least one compound chosen from compounds of Formula I (including Formulas IIa-e, IIIa, IVa, and Va) and/or pharmaceutically acceptable salts thereof, wherein administration may result in inducing at least one neoantigen and/or a T-cell response. In some embodiments, the method may also comprise detecting one or more neoantigens and/or a T-cell response in the subject after administration of at least one compound chosen from compounds of Formula I (including Formulas IIa-e, IIIa, IVa, and Va) and/or pharmaceutically acceptable salts thereof. In some embodiments, the method may also comprise continuing administration of at least one compound chosen from compounds of Formula I (including Formulas IIa-e, IIIa, IVa, and Va) and/or pharmaceutically acceptable salts thereof, if one or more neoantigens and/or a T-cell response is detected.

Also provided herein are methods of treating a subject having or suspected of having a neoplastic disorder, comprising administering to the subject an effective amount of at least one compound chosen from compounds of Formula I (including Formulas IIa-e, IIIa, IVa, and Va) and/or pharmaceutically acceptable salts thereof.

Also provided herein are neoantigen vaccines comprising at least one neoantigen peptide. In some embodiments, the at least one neoantigen peptide comprises a modified or novel neoantigen sequence induced by contacting a neoplastic cell with an effective amount of at least one compound chosen from compounds of Formula I (including Formulas IIa-e, IIIa, IVa, and Va) and/or pharmaceutically acceptable salts thereof.

The methods and uses provided herein, in some embodiments, may further comprise administering at least one additional therapy. In some embodiments, the methods and uses provided herein may result in lower systemic toxicity and/or improved tolerance.

Also disclosed herein is a method of treating cancer in a subject in need thereof, comprising administering at least one compound chosen from compounds of Formula I (including Formulas IIa-e, IIIa, IVa, and Va) and/or pharmaceutically acceptable salts thereof, and at least one additional therapy.

Also disclosed herein is a method of treating a subject having or suspected of having a neoplastic disorder comprising administering at least one compound chosen from compounds of Formula I (including Formulas IIa-e, IIIa, IVa, and Va) and/or pharmaceutically acceptable salts thereof, and at least one additional therapy.

As used herein, the following definitions shall apply unless otherwise indicated.

As described herein, compounds may be substituted with one or more substituents, such as those illustrated generally herein, or as exemplified by particular classes, subclasses, and species of the disclosure. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

"Stable" refers to compounds that are not substantially altered chemically and/or physically when subjected to conditions to allow for their production, detection, and their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"Isomers" refers to compounds having the same number and kind of atoms, and hence the same molecular weight, but differing with respect to the arrangement or configuration of the atoms. "Stereoisomers" refers to compounds that have the same atomic connectivity but different arrangements of their atoms in space. "Diastereoisomers" or "diastereomers" refers to stereoisomers that are not enantiomers. "Enantiomers" refers to stereoisomers that are non-superimposable mirror images of one another. "Geometric isomers" refers to cis-trans isomers having different positions of groups with respect to a double bond or ring or central atom.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. In some embodiments, a stereomerically pure composition of a compound having two chiral centers will be substantially free of diastereomers, and substantially free of the opposite enantiomer, of the compound. In some embodiments, a stereomerically pure compound comprises greater than about 80% by weight of one stereoisomer of the compound and less than about 20% by weight of the other stereoisomers of the compound, such as greater than about 90% by weight of one stereoisomer of the compound and less than about 10% by weight of the other stereoisomers of the compound, further such as greater than about 95% by weight of one stereoisomer of the compound and less than about 5% by weight of the other stereoisomers of the compound, and further such as greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Amine oxide" or "amine-N-oxide" or "N-oxide" is a chemical compound that contains the functional group $R^3N^+—O^-$, an N—O bond with three additional hydrogen and/or hydrocarbon sidechains attached to N. Sometimes it is written as $R^3N \rightarrow O$.

"Ar" or "aryl" refer to an aromatic carbocyclic moiety having one or more closed rings. Examples include, without limitation, phenyl, naphthyl, anthracenyl, phenanthracenyl, biphenyl, and pyrenyl. In certain embodiments, aryl groups contain 6 carbon atoms ("$C_6$aryl").

"Alkyl" or "alkyl group," as used herein, means a straight-chain, branched, or cyclic hydrocarbon chain that is completely saturated. In certain embodiments, alkyl groups contain 1-8 carbon atoms ("$C_1$-$C_8$alkyl"). In certain embodiments, alkyl groups contain 1-6 carbon atoms ("$C_1$-$C_6$alkyl"). In certain embodiments, alkyl groups contain 1-3 carbon atoms. In still other embodiments, alkyl groups contain 2-3 carbon atoms, and in yet other embodiments alkyl groups contain 1-2 carbon atoms. In certain embodiments, the term "alkyl" or "alkyl group" refers to a cycloalkyl group. In certain embodiments, cycloalkyl groups contain 3-8 carbon atoms ("$C_3$-$C_8$cycloalkyl"). In certain embodiments, cycloalkyl groups contain 3-6 carbon atoms ("$C_3$-$C_6$cycloalkyl"). Non-limiting examples of exemplary alkyl groups include methyl, ethyl, propyl, isopropyl, butyl, cyclopropyl and cyclohexyl.

"Alkoxy", as used herein, refers to an alkyl group, as previously defined, attached to the principal carbon chain through an oxygen ("alkoxy") atom.

"Carbocycle," as used herein, includes both aromatic (e.g., aryl) and non-aromatic (e.g., cycloalkyl) groups. In certain embodiments, carbocycle groups contain 3-10 carbon atoms ("3 to 10 membered carbocycle"). In certain embodiments, carbocycle groups contain 3-8 carbon atoms ("3 to 8 membered carbocycle"). In certain embodiments, carbocycle groups contain 3-6 carbon atoms ("3 to 6 membered carbocycle"). In certain embodiments, carbocycle groups contain 3-5 carbon atoms ("3 to 5 membered carbocycle").

"Haloalkyl" refers to an alkyl group substituted with one or more halo atoms (F, Cl, Br, I). For example, "fluoromethyl" refers to a methyl group substituted with one or more fluoro atoms (e.g., monofluoromethyl, difluoromethyl, or trifluoromethyl).

"Heteroatom" refers to 0, S or N.

"Heteroaryl" refers to a cyclic moiety having one or more closed rings, with one or more heteroatoms (oxygen, nitrogen or sulfur) in at least one of the rings, wherein at least one of the rings is aromatic, and wherein the ring or rings may independently be fused, and/or bridged. Examples include without limitation thiophenyl, triazolyl, pyridinyl, pyrimidinyl, pyridazinyl, and pyrazinyl.

"Heterocyclyl" or "heterocyclic" as used herein, means a monocyclic heterocycle, a bicyclic heterocycle, or a tricyclic heterocycle containing at least one heteroatom in the ring. Hetercocyles may be aromatic (e.g., heteroaryl) or non-aromatic. In certain embodiments, heterocycle groups contain 2-10 carbon atoms, 3-10 carbon atoms, 2-8 carbon atoms, 3-8 carbon atoms, 2-6 carbon atoms, 3-6 carbon atoms, 2-4 carbon atoms, 3-4 carbon atoms, or 3 carbon atoms. In certain embodiments, the heterocycle may be a 3-10 membered ring, 3-8 membered ring, 3-6 membered ring, 3-4 membered ring, or 3 membered ring.

The monocyclic heterocycle is a 3-, 4-, 5-, 6-, 7, or 8-membered ring containing at least one heteroatom independently chosen from O, N, and S. In some embodiments, the heterocycle is a 3- or 4-membered ring containing one heteroatom chosen from O, N and S. In some embodiments, the heterocycle is a 5-membered ring containing zero or one double bond and one, two or three heteroatoms chosen from O, N and S. In some embodiments, the heterocycle is a 6-, 7-, or 8-membered ring containing zero, one or two double bonds and one, two or three heteroatoms chosen from O, N and S. Representative examples of monocyclic heterocycle include, but are not limited to, azetidinyl, azepanyl, aziridinyl, diazepanyl, 1,3-dioxanyl, 1,3-dioxolanyl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The bicyclic heterocycles of the present disclosure are exemplified by a monocyclic heterocycle fused to an aryl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, 3,4-dihydro-2H-pyranyl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

In some embodiments, the bicyclic heterocycle is a spiro heterocycle. As known in the art, a "spiro" heterocycle is a bicyclic moiety with rings connected through just one atom. The connecting atom is also called the spiro atom and most often is a quaternary atom such as carbon or nitrogen. Spiro compounds may be designated with the infix spiro followed by square brackets containing the number of atoms in the smaller ring and the number of atoms in the larger ring excluding the spiroatom itself, the numbers being separated by a dot. Example of such compounds include, but are not limited to, 2,6-diazaspiro[3.3]heptane.

The tricyclic heterocycle is a bicyclic heterocycle fused to an aryl group, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycles include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycle groups of the present disclosure are connected to the parent molecular moiety through any substitutable carbon atom or any substitutable nitrogen, oxygen or sulfur atom contained within the groups and may contain one or two alkylene bridges of 1, 2, 3, or 4 carbon atoms, each linking two non-adjacent carbon atoms of the groups. Examples of such "bridged" heterocycle groups include, but are not limited to, oxatricyclo[$3.3.1.1^{3,7}$] decyl (including 2-oxatricyclo [$3.3.1.1^{3,7}$] decyl), 2,4-dioxabicyclo[4.2.1]nonyl, oxabicyclo[2.2.1]heptyl (including 2-oxabicyclo[2.2.1]heptyl) and 2,5-diazabicyclo[2.2.1]heptane.

In the above heteroaryl and heterocycles the nitrogen or sulfur atoms can be optionally oxidized to various oxidation states. In a specific example, the group $S(O)_{0-2}$ refers to —S-(sulfide), —S(O)-(sulfoxide), and —$SO_2$-(sulfone) respectively. For convenience, nitrogens, particularly but not exclusively, those defined as annular aromatic nitrogens, are meant to include those corresponding N-oxide forms. Thus, for a compound of the disclosure having, for example, a pyridyl ring; the corresponding pyridyl-N-oxide is meant to be included as another compound of the disclosure.

"Treatment," "treat," or "treating" cancer refers to reversing (e.g., overcoming a differentiation blockage of the cells), alleviating (e.g., alleviating one or more symptoms, such as fatigue from anemia, low blood counts, etc.), and/or delaying the progression of (e.g., delaying the progression of the condition such as transformation to AML) a cancer as described herein.

"Subject", as used herein, means an animal subject, such as a mammalian subject, and particularly human beings.

The term "antibody" is used in the broadest sense to refer to an immunoglobulin molecule that recognizes and specifically binds to a target, such as a protein, polypeptide, carbohydrate, polynucleotide, lipid, or combinations of the foregoing through at least one antigen recognition site within the variable region of the immunoglobulin molecule. The heavy chain of an antibody is composed of a heavy chain variable domain ($V_H$) and a heavy chain constant region ($C_H$). The light chain is composed of a light chain variable domain ($V_L$) and a light chain constant domain ($C_L$). For the purposes of this application, the mature heavy chain and light chain variable domains each comprise three complementarity determining regions (CDR1, CDR2 and CDR3) within four framework regions (FR1, FR2, FR3, and FR4) arranged from N-terminus to C-terminus: FR1, CDR1, FR2, CDR2, FR3, CDR3, and FR4. An "antibody" can be naturally occurring or man-made, such as monoclonal antibodies produced by conventional hybridoma technology. The term "antibody" includes full-length monoclonal antibodies and full-length polyclonal antibodies, as well as antibody fragments such as Fab, Fab', $F(ab')_2$, Fv, and single chain antibodies. An antibody can be any one of the five major classes of immunoglobulins: IgA, IgD, IgE, IgG, and IgM, or subclasses thereof (e.g., isotypes IgG1, IgG2, IgG3, IgG4). The term further encompasses human antibodies, chimeric antibodies, humanized antibodies and any modified immunoglobulin molecule containing an antigen recognition site, so long as it demonstrates the desired biological activity (e.g., binds the target antigen, internalizes within a target-antigen expressing cell).

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al., "Commentary: Occurrence of Pharmaceutically Acceptable Anions and Cations in the Cambridge Structural Database," J. Pharmaceutical Sciences, vol. 94, no. 10 (2005), and Berge et al., "Pharmaceutical Salts", J. Pharmaceutical Sciences, vol. 66, no. 1 (1977), which are incorporated by reference herein.

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a chemical group is described by its chemical formula or structure having a terminal bond moiety indicated by "-", it will be understood that the "-" represents the point of attachment.

Unless otherwise stated, compounds depicted herein include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein include compounds that differ only by the presence of one or more isotopically enriched atoms. For example, compounds having the formulae disclosed herein except for the replacement of hydrogen by deuterium or tritium, or the replacement of a carbon by a $^{3}C$- or $^{14}C$-enriched carbon, are within the scope of this disclosure.

Provided herein according to some embodiments are compounds of Formula I:

I

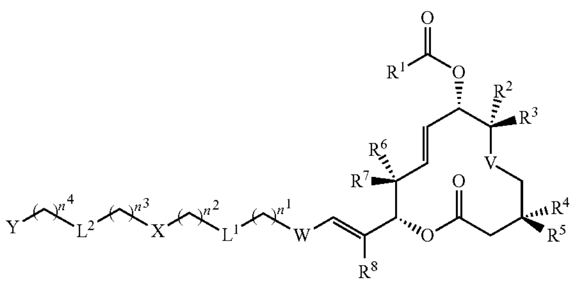

and pharmaceutically acceptable salts thereof, wherein:

$R^1$ is chosen from:

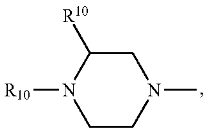, 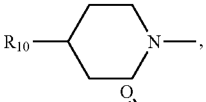, 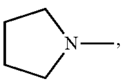, 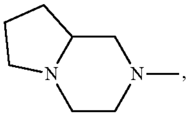, 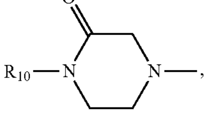, 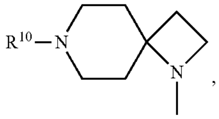, 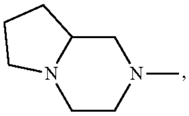, 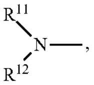, 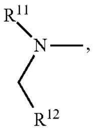, 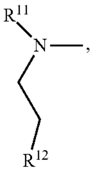, 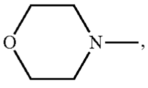, 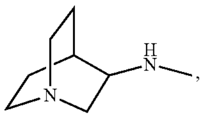, and 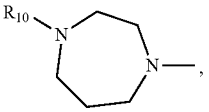, each of which may be substituted with 1 to 3 groups independently chosen from halogens, hydroxyl groups, $C_1$-$C_6$ alkyl groups, $C_1$-$C_6$ alkoxy groups, $C_3$-$C_8$ cycloalkyl groups, hydroxy $C_1$-$C_6$ alkyl groups, dimethylamino groups, and methoxy $C_1$-$C_6$ alkyl groups;

$R^2$, $R^3$, $R^4$, $R^1$, $R^6$, and $R^7$ are each independently chosen from hydrogen, hydroxyl groups, —O—$R^{10}$ groups, and $C_1$-$C_6$ alkyl groups;

$R^8$, $R^9$, and $R^{13}$ are each independently chosen from hydrogen and $C_1$-$C_6$ alkyl groups;

$R^{10}$ is chosen from hydrogen, $C_1$-$C_6$ alkyl groups, $C_1$-$C_6$ aminoalkyl groups, $C_1$-$C_6$ alkylamino groups, $C_1$-$C_6$ alkylcarboxylic acid groups, $C_3$-$C_8$ cycloalkyl groups, benzyl groups, $C_3$-$C_8$ heterocyclyl groups, —$CH_2$—$C_3$-$C_8$ heterocyclyl groups, —C(O)—$C_3$-$C_8$ heterocyclyl groups, acyl groups, hydroxy $C_1$-$C_6$ alkyl groups, methoxy $C_1$-$C_6$ alkyl groups, —$CD_3$, and —C(O)—$NR^{11}R^{12}$ groups;

$R^{11}$ and $R^{12}$ are independently chosen from hydrogen, $C_1$-$C_6$ alkyl groups, $C_1$-$C_6$ aminoalkyl groups, $C_1$-$C_6$ alkylamino groups, $C_3$-$C_8$ cycloalkyl groups, and $C_3$-$C_8$ heterocyclyl groups;

V is chosen from —$CH_2$— and —N($R^9$)—;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—; and each n is independently chosen from 0 to 4.

In some embodiments, $R^1$ in the compounds of Formula I is chosen from

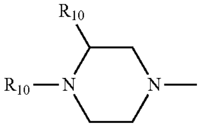, and 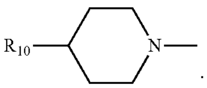.

In some embodiments, $R^1$ in the compounds of Formula I is substituted with one to three groups chosen from halogens and $C_1$-$C_6$ alkyl groups.

In some embodiments, $R^1$ in the compounds of Formula I is

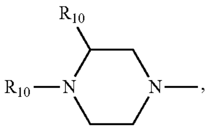, substituted with 1 to 3 groups chosen from $C_1$-$C_6$ alkyl groups, wherein $R^{10}$ is methyl. In some embodiments, $R^1$ in the compounds of Formula I is unsubstituted.

In some embodiments, $R^2$ and $R^3$ in the compounds of Formula I are methyl and hydrogen, respectively.

In some embodiments, R4 and R5 in the compounds of Formula I are hydrogen and hydroxyl, respectively.

In some embodiments, $R^6$ and $R^7$ in the compounds of Formula I are hydrogen and methyl, respectively In some embodiments, $R^8$ in the compounds of Formula I is methyl.

In some embodiments, V in the compounds of Formula I is —$CH_2$—.

In some embodiments, W in the compounds of Formula I is chosen from a benzene ring, pyridine ring, benzimidazole ring, benzotriazole ring, indazole ring, 1,2,3,6-tetrahydropyridine ring, and imidazopyridine ring, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups.

In some embodiments, W in the compounds of Formula I is a benzene ring, which may be substituted with 1 to 3 groups chosen from halogens and $C_1$-$C_6$ alkyl groups.

In some embodiments, X and Y in the compounds of Formula I are each independently chosen from a bond,

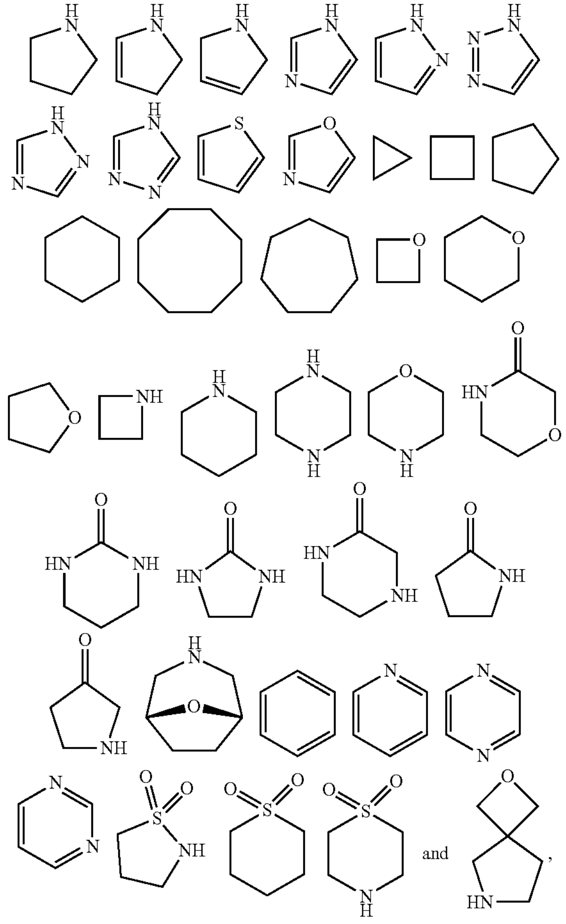

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and are each independently chosen from hydrogen and $C_1$-$C_6$ alkyl groups.

In some embodiments, Y in the compounds of Formula I is hydrogen, and X in the compounds of Formula I is chosen from:

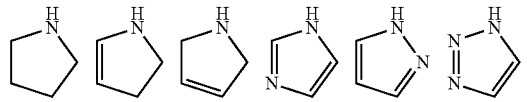

-continued

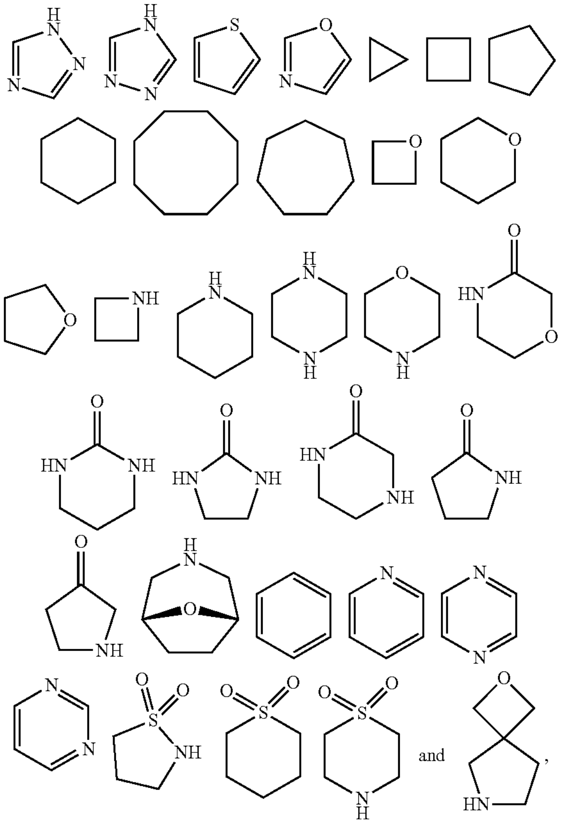

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$S(O_2)$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula I is hydrogen, and X in the compounds of Formula I is a bond.

In some embodiments, compounds of Formula I are chosen from compounds of Formula IIa:

IIa

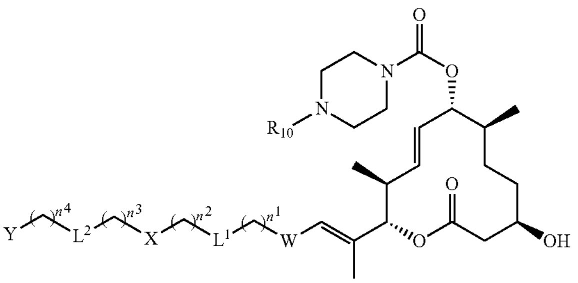

and pharmaceutically acceptable salts thereof, wherein:

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl-groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

In some embodiments, W in the compounds of Formula IIa is chosen from a benzene ring, pyridine ring, benzimidazole ring, benzotriazole ring, indazole ring, 1,2,3,6-tetrahydropyridine ring, and imidazopyridine ring, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups.

In some embodiments, W in the compounds of Formula IIa is a benzene ring, which may be substituted with 1 to 3 groups chosen from halogens and $C_1$-$C_6$ alkyl groups.

In some embodiments, X and Y in the compounds of Formula IIa are each independently chosen from a bond,

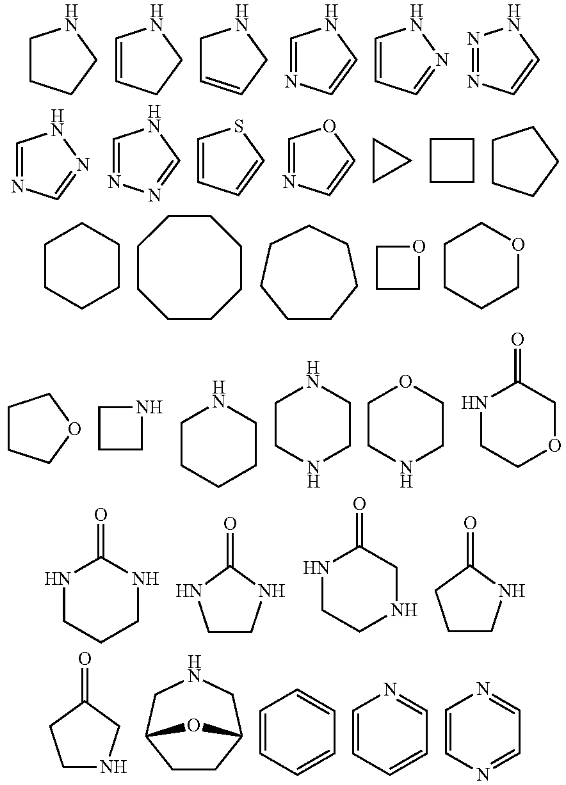

-continued

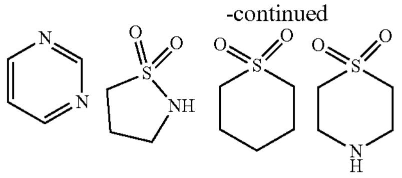

and

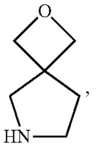

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula IIa is hydrogen, and X in the compounds of Formula IIa is chosen from:

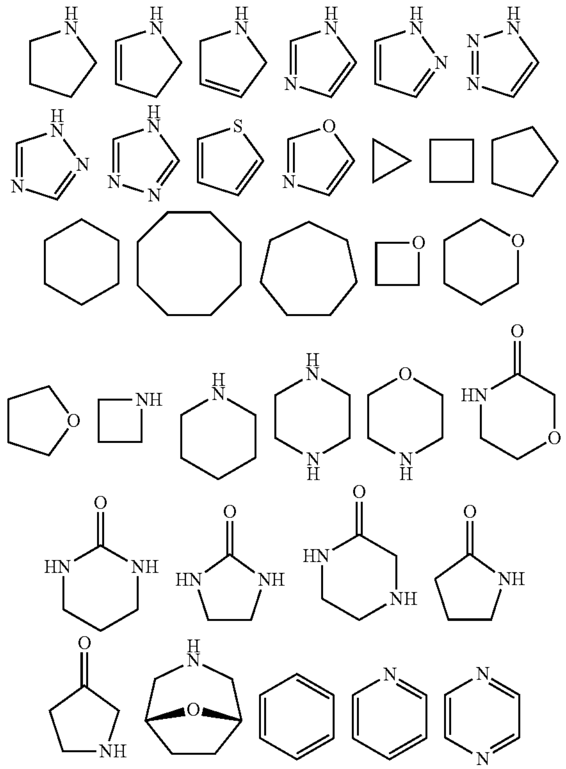

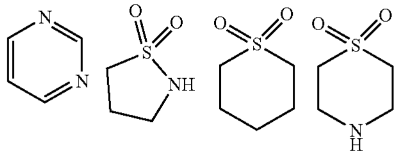

and

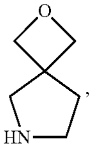

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —S($O_2$)—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula IIa is hydrogen, and X in the compounds of Formula IIa is a bond.

In some embodiments, compounds of Formula I are chosen from compounds of Formula IIb:

IIb

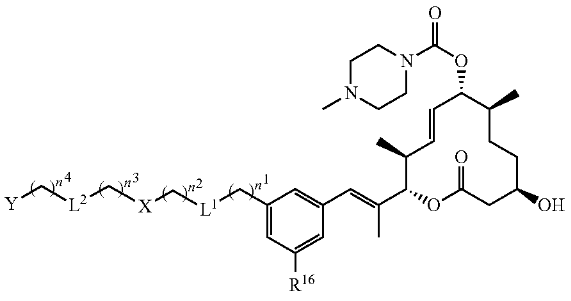

and pharmaceutically acceptable salts thereof, wherein:

$R^{16}$ is chosen from hydrogen and fluoro;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

In some embodiments, X and Y in the compounds of Formula IIb are each independently chosen from a bond,

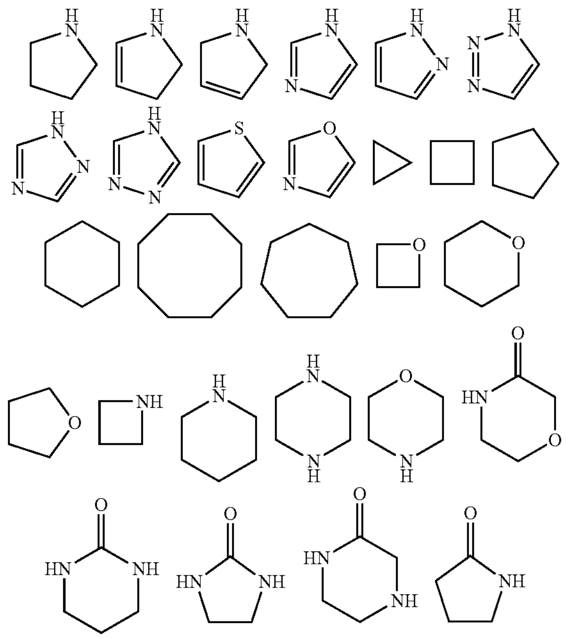

-continued

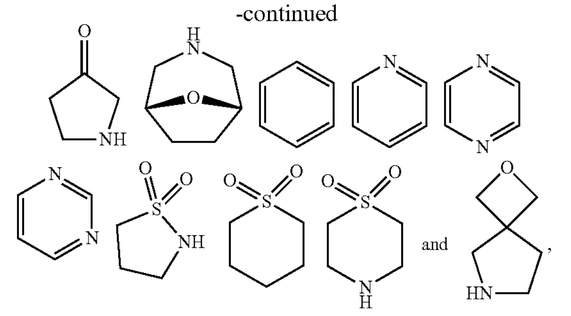

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula IIb is hydrogen, and X in the compounds of Formula IIb is chosen from:

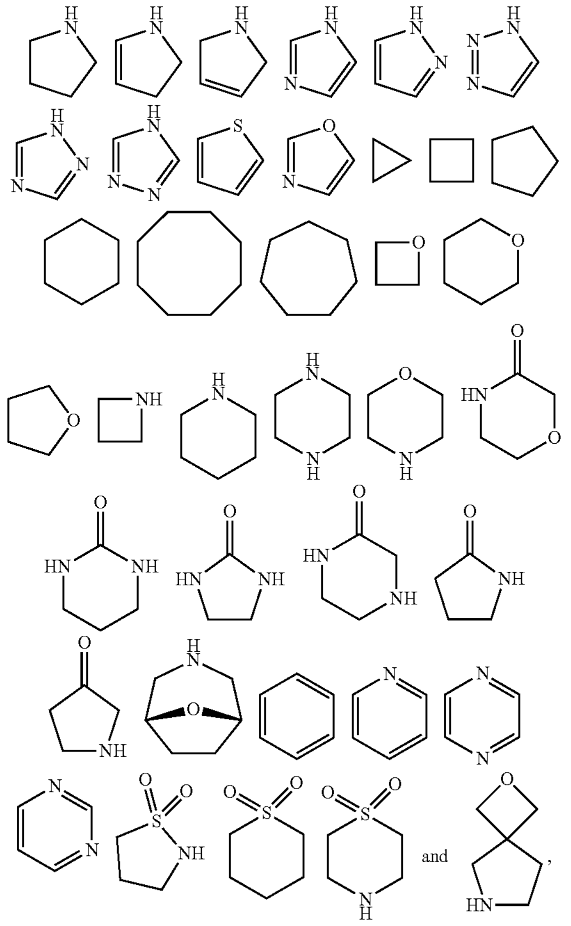

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —S($O_2$)—$C_1$-

$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula IIb is hydrogen, and X in the compounds of Formula IIb is a bond.

In some embodiments, $R^{16}$ in the compounds of Formula IIb is fluoro.

In some embodiments, compounds of Formula I are chosen from compounds of Formula IIc:

IIc

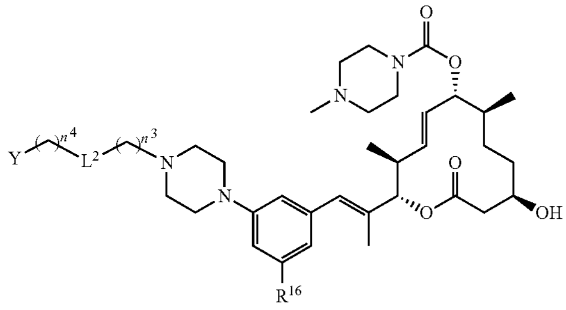

and pharmaceutically acceptable salts thereof, wherein:

$R^{16}$ is chosen from hydrogen and fluoro;

Y is chosen from hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy$C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^2$ is chosen from a bond, —O—, —C(O)—, —C(O)O—, —$N(R^{13})$—C(O)—, —C(O)—$N(R^{13})$—, —$N(R^{13})$—$S(O_2)$—, —$S(O_2)$—$N(R^{13})$—, —$S(O_2)$—, and —$N(R^{13})$—, wherein $R^{13}$ is chosen from hydrogen and $C_1$-$C_6$ alkyl groups;

$n^3$ is 0; and $n^4$ is chosen from 0 to 4.

In some embodiments, Y in the compounds of Formula IIc is chosen from hydrogen,

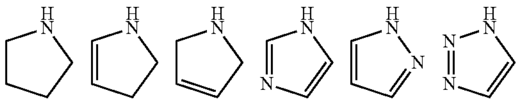

-continued

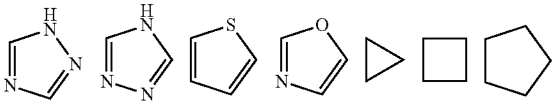

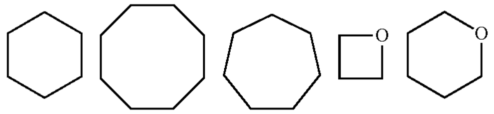

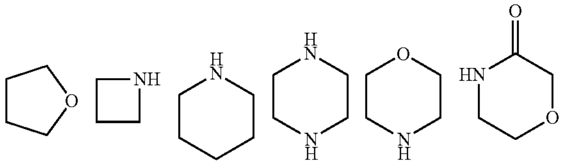

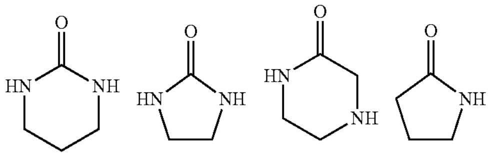

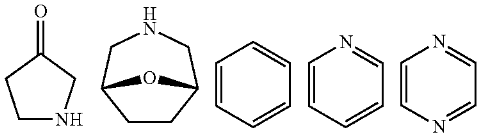

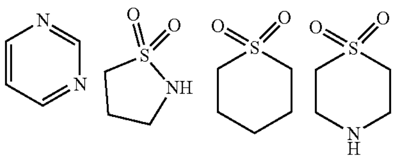

and

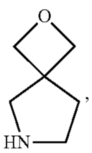, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, L2 in the compounds of Formula IIc is a bond.

In some embodiments, $R^{16}$ in the compounds of Formula IIc is fluoro.

In some embodiments, compounds of Formula I are chosen from compounds of Formula IId:

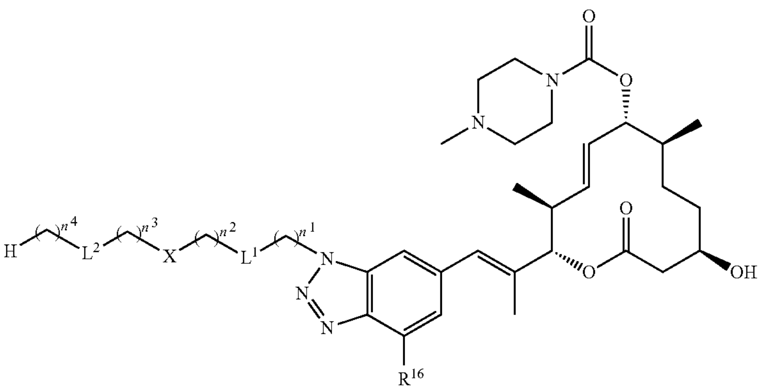

IId and pharmaceutically acceptable salts thereof, wherein:

$R^{16}$ is chosen from hydrogen and fluoro;

X is chosen from hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are independently chosen from a bond, —O—, —C(O)—, —C(O)O—, —$N(R^{13})$—C(O)—, —C(O)—$N(R^{13})$—, —$N(R^{13})$—$S(O_2)$—, —$S(O_2)$—$N(R^{13})$—, —$S(O_2)$—, and —$N(R^{13})$—, wherein $R^{13}$ is chosen from hydrogen and $C_1$-$C_6$ alkyl groups; and each n is independently chosen from 0 to 4.

In some embodiments, X in the compounds of Formula IId is chosen from a bond,

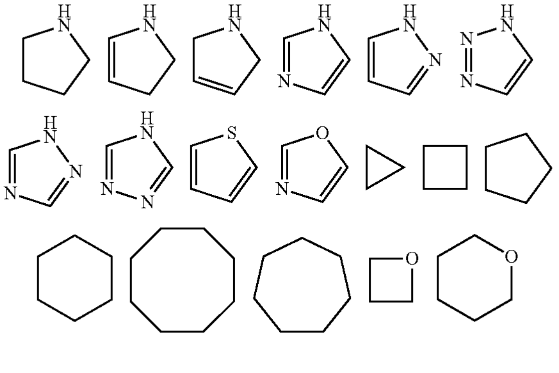

-continued

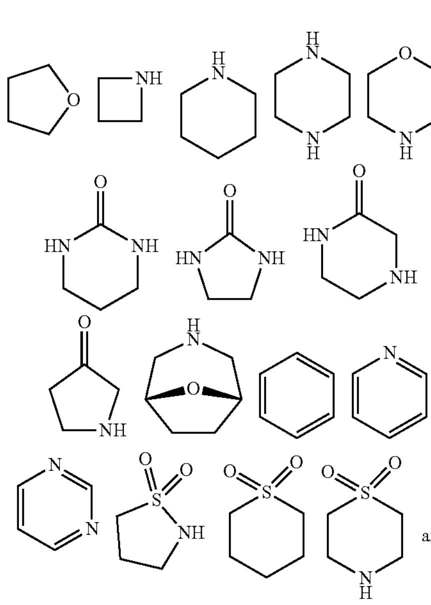

and

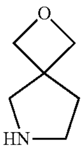

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, X in the compounds of Formula IId is a bond. In some embodiments, X, $L^1$, and $L^2$ in the compounds of Formula IId are bonds.

In some embodiments, $R^{16}$ in the compound of Formula IId is fluoro.

In some embodiments, compounds of Formula I are chosen from compounds of Formula IIe:

IIe

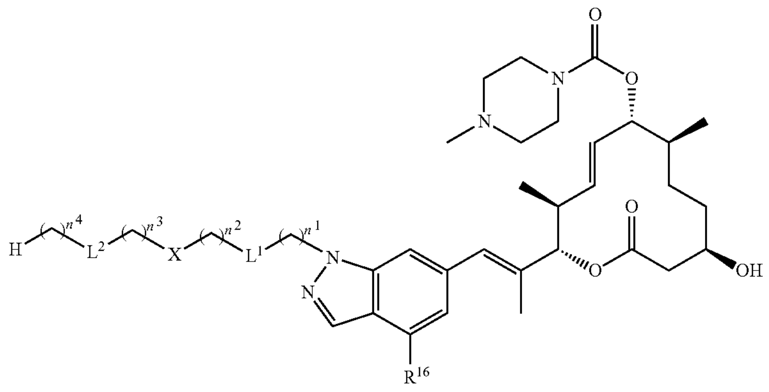

and pharmaceutically acceptable salts thereof, wherein:

$R^{16}$ is chosen from hydrogen and fluoro;

X is independently chosen from hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^5$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

In some embodiments, X in the compound of Formula IIe is chosen from a bond,

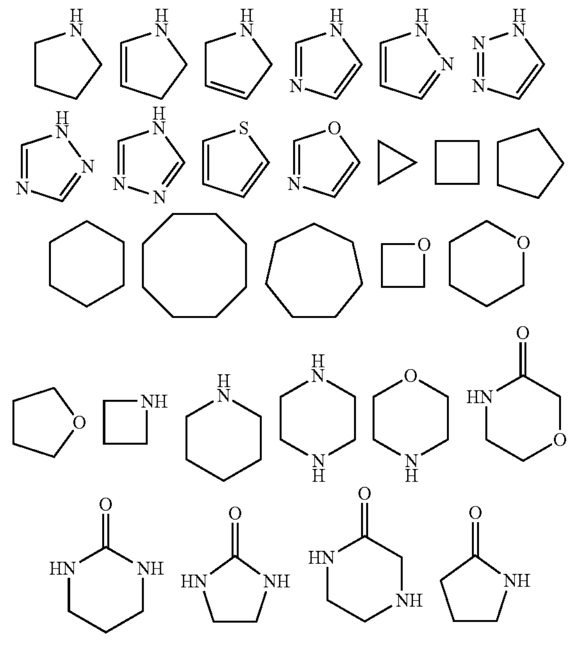

-continued

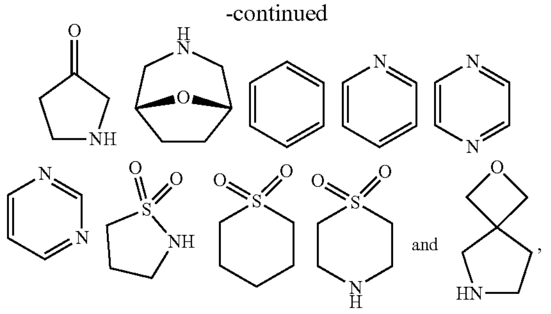

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^5$ are each independently chosen from hydrogen and $C_1$-$C_6$ alkyl groups.

In some embodiments, X in the compounds of Formula IIe is a bond. In some embodiments, X, $L^1$, and $L^2$ in the compounds of Formula IIe are bonds.

In some embodiments, $R^{16}$ in the compound of Formula IIe is fluoro.

In some embodiments, compounds of Formula I are chosen from compounds of Formula IIIa:

IIIa

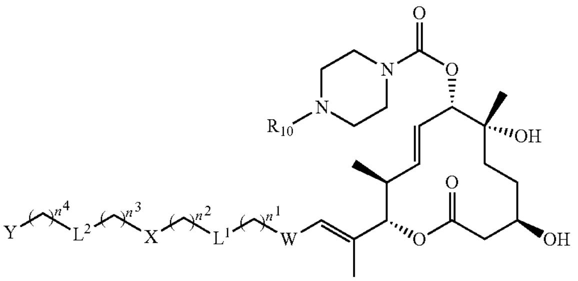

and pharmaceutically acceptable salts thereof, wherein:

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

In some embodiments, W in the compounds of Formula IIIa is chosen from a benzene ring, pyridine ring, benzimidazole ring, benzotriazole ring, indazole ring, 1,2,3,6-tetrahydropyridine ring, and imidazopyridine ring, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups.

In some embodiments, W in the compounds of Formula IIIa is a benzene ring, which may be substituted with 1 to 3 groups chosen from halogens and $C_1$-$C_6$ alkyl groups.

In some embodiments, X and Y in the compounds of Formula IIIa are each independently chosen from a bond,

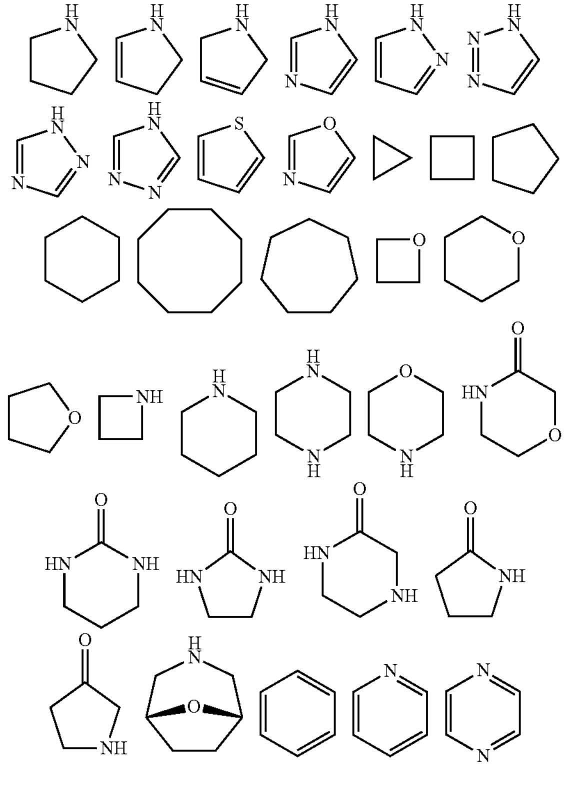

-continued

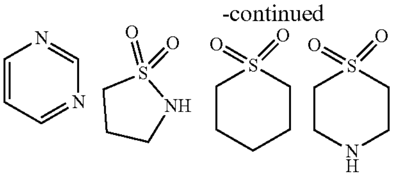

and

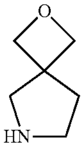

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula IIIa is hydrogen, and X in the compounds of Formula IIIa is chosen from:

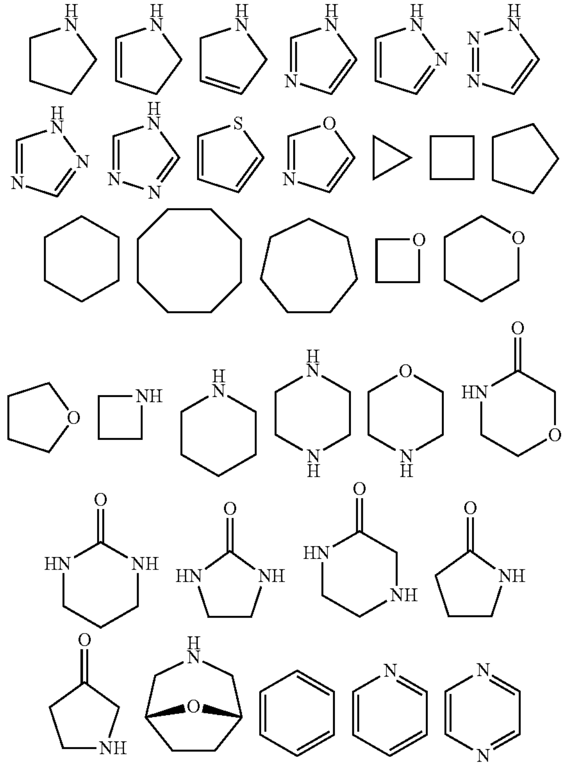

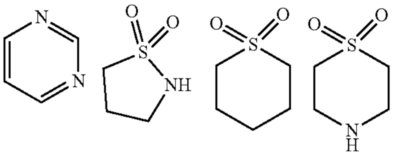

and

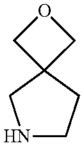

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —S($O_2$)—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula IIIa is hydrogen, and X in the compounds of Formula IIIa is a bond. In some embodiments, compounds of Formula I are chosen from compounds of Formula IVa:

IVa

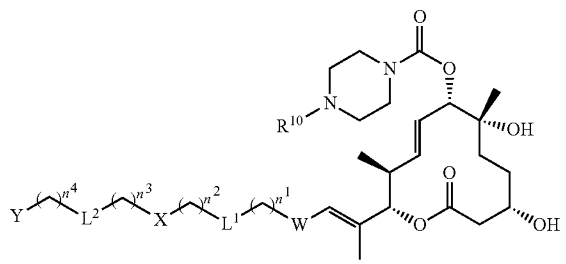

or a pharmaceutically acceptable salt thereof, wherein:

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl-groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

In some embodiments, W in the compounds of Formula IVa is chosen from a benzene ring, pyridine ring, benzimidazole ring, benzotriazole ring, indazole ring, 1,2,3,6-tetrahydropyridine ring, and imidazopyridine ring, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups.

In some embodiments, W in the compounds of Formula IVa is a benzene ring, which may be substituted with 1 to 3 groups chosen from halogens and $C_1$-$C_6$ alkyl groups.

In some embodiments, X and Y in the compounds of Formula IVa are each independently chosen from a bond,

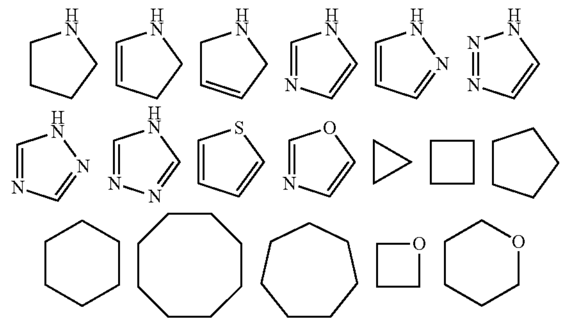

-continued

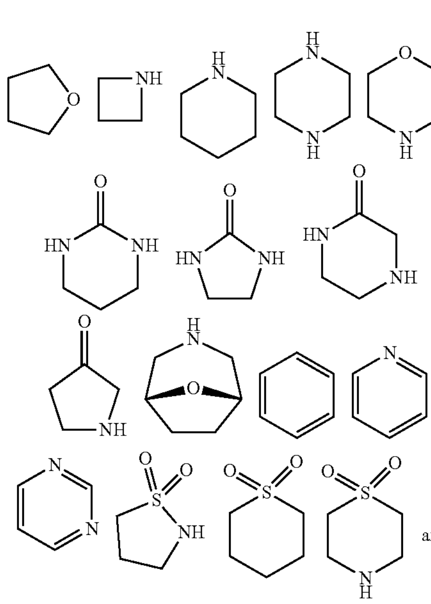

and

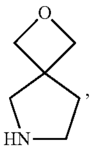

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^5$ are each independently chosen from hydrogen and $C_1$-$C_6$ alkyl groups.

In some embodiments, Y in the compounds of Formula IVa is hydrogen, and X in the compounds of Formula IVa is chosen from:

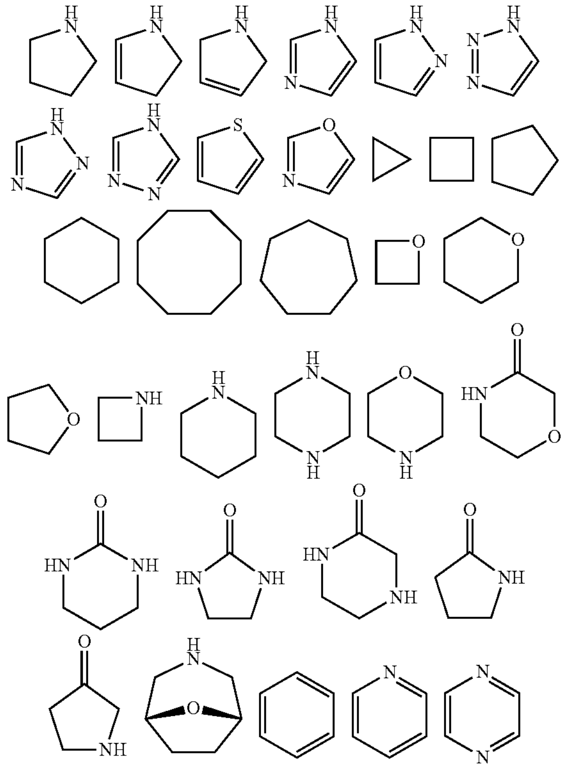

-continued

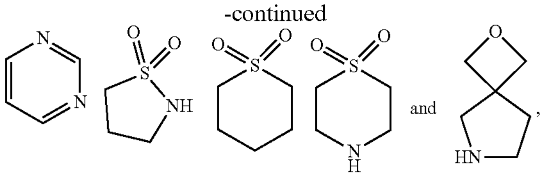

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$S(O_2)$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula IVa is hydrogen, and X in the compounds of Formula IVa is a bond.

In some embodiments, compounds of Formula I are chosen from compounds of Formula Va:

Va

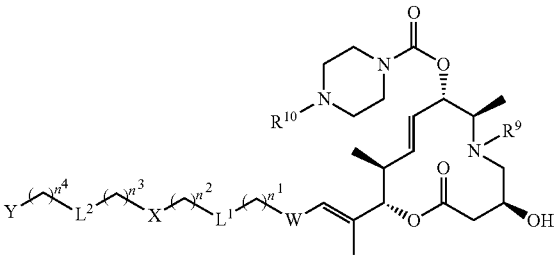

or a pharmaceutically acceptable salt thereof,
wherein:

$R^9$ is chosen from hydrogen and $C_1$-$C_6$ alkyl groups;

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl-groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —$N(R^{13})$—C(O)—, —C(O)—$N(R^{13})$—, —$N(R^{13})$—$S(O_2)$—, —$S(O_2)$—$N(R^{13})$—, —$S(O_2)$—, and —$N(R^{13})$—, wherein $R^{13}$ is chosen from hydrogen and $C_1$-$C_6$ alkyl groups; and each n is independently chosen from 0 to 4.

In some embodiments, W in the compounds of Formula Va is chosen from a benzene ring, pyridine ring, benzimidazole ring, benzotriazole ring, indazole ring, 1,2,3,6-tetrahydropyridine ring, and imidazopyridine ring, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups.

In some embodiments, W in the compounds of Formula Va is a benzene ring, which may be substituted with 1 to 3 groups chosen from halogens and $C_1$-$C_6$ alkyl groups.

In some embodiments, X and Y in the compounds of Formula Va are each independently chosen from a bond,

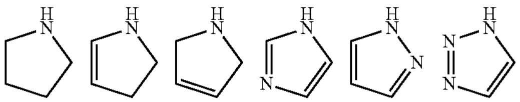

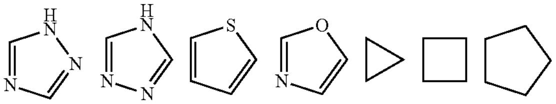

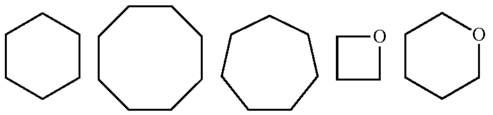

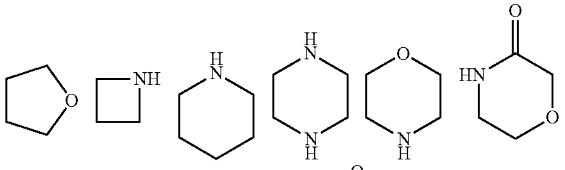

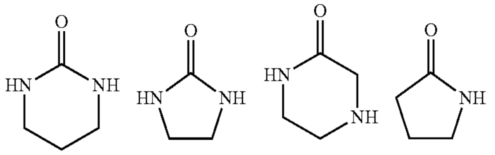

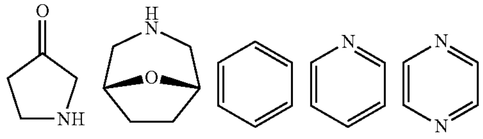

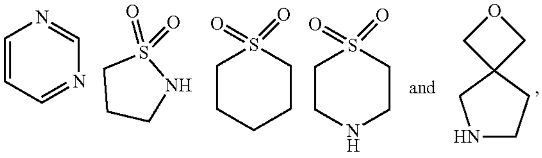

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula Va is hydrogen, and X in the compounds of Formula Va is chosen from:

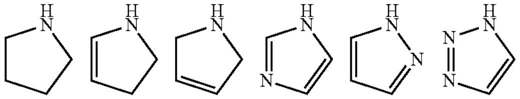

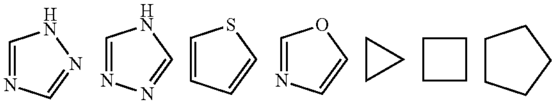

-continued

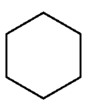 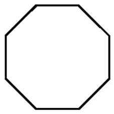 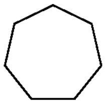 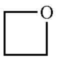 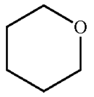

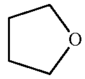 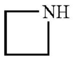 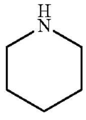 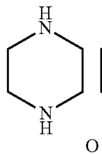 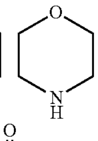 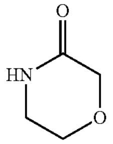

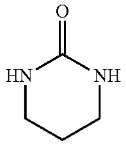 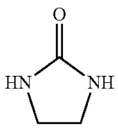 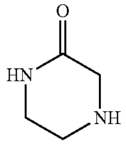 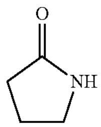

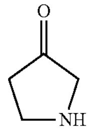 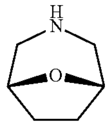 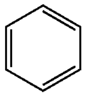 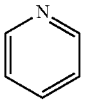 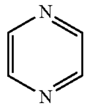

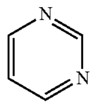 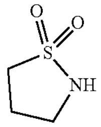 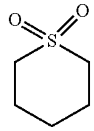 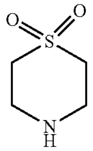 and 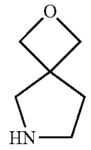, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$S(O_2)$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

In some embodiments, Y in the compounds of Formula Va is hydrogen, and X in the compounds of Formula Va is a bond.

In some embodiments, $R^9$ in the compounds of Formula Va is chosen from hydrogen and methyl.

Also disclosed herein are compounds chosen from:

[(2S,3S,4E,6R,7S,10R)-10-hydroxy-3,7-dimethyl-12-oxo-2-[(E)-1-(3-piperazin-1-ylphenyl)prop-1-en-2-yl]-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-(4-methylpiperazin-1-yl)phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-(1H-indazol-6-yl)prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-(1H-indazol-4-yl)prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(2-morpholin-4-ylpyridin-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-(2-fluoro-5-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(4-fluoro-3-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[(3R)-3-(methylamino)pyrrolidin-1-yl]phenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[(3 S)-3-(methylamino)pyrrolidin-1-yl]phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(2-fluoro-5-morpholin-4-ylphenyl)prop-1-en-2-yl]-10-hydroxy-3,7-dimethyl-12-oxo-1-oxacyclododec-4-en-6-yl]4-piperidin-1-ylpiperidine-1-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] 4-piperidin-1-ylpiperidine-1-carboxylate;

[(2S,3S,4E,6R,7S,10R)-2-[(E)-1-[3-fluoro-5-[(3R)-3-fluoropyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-(hydroxymethyl)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(2R,6S)-2,6-dimethylmorpholin-4-yl]-5-fluorophenyl]prop-1-en-2-yl]-10-hydroxy-3,7-dimethyl-12-oxo-1-oxacyclododec-4-en-6-yl] 4-piperidin-1-ylpiperidine-1-carboxylate;

[(2S,3S,4E,6R,7S,10R)-2-[(E)-1-[3-[(3 S)-3-(dimethylamino)pyrrolidin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(3-methyl-5-morpholin-4-ylphenyl)prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-morpholin-4-yl-5-(trifluoromethyl)phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(3-chloro-5-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(2-hydroxyethyl)piperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-methyl-N-(1-methylpiperidin-4-yl)carbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3R)-3,4-dimethylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-propan-2-ylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-tert-butylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-cyclobutylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-cyclopentylpiperazine-1-carboxylate;

[(2S,3S,4E,6R,7S,10R)-2-[(E)-1-(3,5-difluorophenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(dimethylamino)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(4-hydroxypiperidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-(1-methylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(1R,5S)-8-oxa-3-azabicyclo[3.2.1]octan-3-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-oxa-7-azaspiro[3.4]octan-7-yl)phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[(3R)-3-hydroxypyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-(3-oxopyrrolidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(oxan-4-yl)piperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-methyl-N-(1-methylpiperidin-3-yl)carbamate;

[(2S,3S,4E,6R,7S,10R)-2-[(E)-1-[3-fluoro-5-(3-fluoroazetidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-(methylamino)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]3-(dimethylamino)piperidine-1-carboxylate;

[(2S,3S,4E,6R,7S,10R)-2-[(E)-1-[3-fluoro-5-[(2R)-2-methylpyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-oxopyrrolidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-methylpyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2R)-2-(hydroxymethyl)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3R)-3-(methylamino)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(5-chloropyridin-3-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-methyl-N-(pyridin-4-ylmethyl)carbamate;

[(2S,3S,4E,6R,7S,10R)-2-[(E)-1-(3,5-dichlorophenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1,1-dioxo-1,2-thiazolidin-2-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(1,3-dimethylindazol-6-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1,1-dioxo-1,4-thiazinan-4-yl)-5-fluorophenyl]prop-1-en-2-yl]-10-hydroxy-3,7-dimethyl-12-oxo-1-oxacyclododec-4-en-6-yl]N,N-dimethylcarbamate;

[(2S,3S,4E,6R,7S,10R)-2-[(E)-1-[3-(1,1-dioxo-1,4-thiazinan-4-yl)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] morpholine-4-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] N-methyl-N-(1-methylpiperidin-4-yl)carbamate;

[(2S,3S,4E,6R,7S,10R)-10-hydroxy-3,7-dimethyl-2-[(E)-1-(1-methylindazol-6-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-fluoro-5-(3-oxomorpholin-4-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-(cyclopentylsulfamoyl)-2-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(4-methylsulfonylpiperazin-1-yl)phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-(4-fluoro-1H-indazol-6-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-imidazol-1-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6S,7R,10S)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-methylpiperazine-1-carboxylate;

[(2S,3S,4E,6S,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-piperidin-1-ylpiperidine-1-carboxylate;

[(2S,3S,4E,6S,7R,10S)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-piperidin-1-ylpiperidine-1-carboxylate;

[(2S,3S,4E,6R,7S,10R)-2-[(E)-1-[3-fluoro-5-(2-oxoimidazolidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[3-(2-hydroxyethyl)-2-oxoimidazolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[3-(2-fluoroethynyl)-2-oxoimidazolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[3-(2-morpholin-4-ylethyl)-2-oxoimidazolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[3-(cyclopropylmethyl)-2-oxoimidazolidin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-methylmorpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-methylmorpholin-4-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(2S,3 S)-3-hydroxy-2-methylpentyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(2R,3 S)-3-hydroxy-2-methylpentanoyl]piperazin-1-yl]phenyl] prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-morpholin-4-ylethylsulfonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(4-ethenylsulfonylpiperazin-1-yl)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3R)-3-methylmorpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-(hydroxymethyl)morpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-(hydroxymethyl)morpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2R)-2-(methylcarbamoyl)morpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-oxo-1,3-diazinan-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[3-(cyclopropylmethyl)-2-oxo-1,3-diazinan-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(2R)-2-hydroxypropanoyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]3,4,6,7,8,8a-hexahydro-1H-pyrrolo[1,2-a]pyrazine-2-carboxylate;

[(2S,3S,4E,6R,7S,10R)-2-[(E)-1-[3-fluoro-5-[(3 S)-3-methylmorpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(2-cyclopropyl-2-oxoethyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-oxo-2-pyrazin-2-ylethyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6S,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[1-(cyclopropylmethyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-imidazo[1,2-a]pyridin-6-ylprop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(7-methyl-1H-indazol-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[4-(cyclopropylsulfamoyl)-3-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[2-fluoro-5-(4-hydroxypiperidin-1-yl)sulfonylphenyl]prop-1-en-2-yl]-10-hydroxy- 3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(2,2,2-trifluoroethyl)piperazine-1-carboxylate;

[(2S,3S,4E,6R,7S,10R)-10-hydroxy-3,7-dimethyl-12-oxo-2-[(E)-1-(3-piperazin-1-ylsulfonylphenyl)prop-1-en-2-yl]-1-oxacyclododec-4-en-6-yl]4-methylpiperazine-1-carboxylate;

[(2S,3S,4E,6R,7S,10R)-2-[(E)-1-[3-(4-formylpiperazin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-(4-hydroxypiperidin-1-yl)sulfonylphenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(6-methyl-1H-indazol-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-(1,3-dimethylindazol-4-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-(1-azabicyclo[2.2.2]octan-3-yl)-N-methylcarbamate;

[(2S,3S,4E,6R,7S,10R)-2-[(E)-1-[2-(cyclopropylmethyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-(2-hydroxyethyl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(4-fluoro-1-methylindazol-6-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-[1-(pyridin-4-ylmethyl)pyrazol-4-yl]prop-1-en-2-yl]-1-oxacyclododec-4-en-6-yl]4-methylpiperazine-1-carboxylate;

[(2S,3S,4E,6R,7S,10R)-10-hydroxy-3,7-dimethyl-2-[(E)-1-(1-methylpyrazol-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyethyl)-3-oxopiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-methoxyethyl)-3-oxopiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[1-(1-methylpiperidin-4-yl)pyrazol-4-yl]prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2,2,2-trifluoroethyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-methoxyacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(cyclopropanecarbonyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(4-methoxyphenyl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylpyrazol-4-yl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(4-pyridin-3-ylsulfonylpiperazin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylimidazol-4-yl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(cyclohexanecarbonyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylindol-6-yl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-(oxan-4-yl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-2-(oxan-4-yl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxane-4-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-morpholin-4-ylacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylimidazole-4-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(2-cyclopropylacetyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1,3-oxazole-5-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyethylsulfonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxetan-3-ylsulfonyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[4-fluoro-1-(oxetan-3-ylsulfonyl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-(1-hydroxyisoquinolin-7-yl)prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-[2-(methylamino)-2-oxoethyl]indazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[4-fluoro-1-(2-oxo-2-pyrrolidin-1-ylethyl)indazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[4-fluoro-1-(2-morpholin-4-yl-2-oxoethyl)indazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[1-(cyanomethyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[1-[2-(dimethylamino)-2-oxoethyl]-4-fluoroindazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[1-(cyclopropylmethyl)-3-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(3-methoxypropanoyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(3-hydroxypropyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(cyclopropylmethyl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[2-(cyclopropylmethyl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[1-(cyclopropylmethyl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(oxan-4-yl) benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-2-(oxan-4-yl) benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(2-methoxyethyl)benzimidazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxolane-3-carbonyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[7-fluoro-3-[1-[(2-methylpropan-2-yl)oxycarbonyl]piperidin-4-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(4-chlorophenyl) methyl]-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1-acetylpiperidin-4-yl)-7-fluorobenzimidazol-5-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[7-fluoro-3-((1R,4S)-4-hydroxycyclohexyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(oxan-4-ylmethyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(2S)-1-hydroxypropan-2-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(2R)-1-hydroxypropan-2-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(3 S)-oxolane-3-carbonyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(3R)-oxolane-3-carbonyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxetane-3-carbonyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[4-(3-methyloxetane-3-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(3-hydroxypropanoyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(4-methyloxan-4-yl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(1-methylsulfonylpiperidin-4-yl)benzotriazol-5-yl]prop-1-en-2-yl]-

10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1,1-dioxothian-4-yl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(2-methoxyethyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1-acetylpiperidin-4-yl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(3R)-oxan-3-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(3 S)-oxan-3-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(3R,4S)-3-hydroxyoxan-4-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-cyclohexyl-7-fluorobenzotriazol-5-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(4-methoxyphenyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(4-methoxyphenyl)methyl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-chloro-5-fluorophenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl(oxan-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl(oxetan-3-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[methyl(oxan-4-yl)amino]phenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[methyl(oxetan-3-yl)amino]phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-[(1,1-dioxothian-4-yl)-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(1-methylsulfonylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-(1-methylsulfonylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[ethyl-(1-methylsulfonylpiperidin-4-yl)amino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(1-methylsulfonylpiperidin-4-yl)-propan-2-ylamino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-acetylpiperidin-4-yl)-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-(1-propanoylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[[1-(2-methoxyacetyl)piperidin-4-yl]-methylamino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-benzoylpiperidin-4-yl)-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(2,2,2-trifluoroacetyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-(1-propylsulfonylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-cyclopentylsulfonylpiperidin-4-yl)-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(1-methylimidazol-4-yl)sulfonylpiperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[[1-(benzenesulfonyl)piperidin-4-yl]-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-acetylpiperidin-4-yl)methyl-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[(1-methylsulfonylpiperidin-4-yl)methyl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(1,3-oxazole-5-carbonyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(pyrazine-2-carbonyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(1-methylimidazole-4-carbonyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(propan-2-ylcarbamoyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(propylcarbamoyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(phenylcarbamoyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(1-methylsulfonylpiperidin-4-yl)oxyphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[1-(4,4-difluorocyclohexyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-(1-methylsulfonylpiperidin-4-yl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-pyrrolidin-1-ylsulfonylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(azetidin-1-ylsulfonyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-[(3R)-3-hydroxypyrrolidin-1-yl]sulfonylphenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[(2R)-2-methylpyrrolidin-1-yl]sulfonylphenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-2-[(E)-1-[3-[(1-hydroxy-2-methylpropan-2-yl)sulfamoyl]phenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-[3-(4,4-difluoropiperidin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(4-methyl-3-pyrrolidin-1-ylsulfonylphenyl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-(3,3-difluoropyrrolidin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-(5-pyrrolidin-1-ylsulfonylpyridin-3-yl)prop-1-en-2-yl]-1-oxacyclododec-4-en-6-yl]4-methylpiperazine-1-carboxylate;

[(2S,3S,4E,6R,7S,10R)-2-[(E)-1-[3-(3,3-difluoroazetidin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[4-methyl-3-(2-oxopyrrolidin-1-yl)phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-(tert-butylsulfamoyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-[3-(propan-2-ylsulfamoyl)phenyl]prop-1-en-2-yl]-1-oxacyclododec-4-en-6-yl]4-methylpiperazine-1-carboxylate;

[(2S,3S,4E,6R,7S,10R)-2-[(E)-1-[3-(ethylsulfamoyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-(4-methylpiperazin-1-yl)sulfonylphenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-(methylsulfamoyl)phenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-(3-piperidin-1-ylsulfonylphenyl)prop-1-en-2-yl]-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-(3-pyrrolidin-1-ylsulfonylphenyl)prop-1-en-2-yl]-1-oxacyclododec-4-en-6-yl]4-methylpiperazine-1-carboxylate;

[(2S,3S,4E,6R,7S,10R)-2-[(E)-1-(3-cyclopropylsulfonylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(cyclopropylsulfonylamino)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-(methanesulfonamido)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-[(2-methoxyacetyl)amino]pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[1-[(2-methylpropan-2-yl)oxycarbonyl]-3,6-dihydro-2H-pyridin-5-yl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(trideuteriomethyl)piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl]N-(pyridin-4-ylmethyl)carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl]N-(pyrimidin-4-ylmethyl)carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] morpholine-4-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[2-(dimethylamino)ethyl]carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-methyl-1,4-diazepane-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[(4-methoxyphenyl)methyl]carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3R)-3-(dimethylamino)pyrrolidine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3S)-3-(dimethylamino)pyrrolidine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[(2R)-1-hydroxypropan-2-yl]carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 3-oxopiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3R)-3-fluoropyrrolidine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 3,3,4-trimethylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-methyl-N-(1-methylpiperidin-4-yl)carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-(2-hydroxyethyl)piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-cycloheptylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-pyridin-4-ylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-cyclohexylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[2-(4-hydroxyphenyl)ethyl]-N-methylcarbamate;

(2S,3S,6R,7S,10R,E)-2-((E)-1-(3-fluoro-5-morpholinophenyl)prop-1-en-2-yl)-10-hydroxy-3,7-dimethyl-12-oxo-1-oxacyclododec-4-en-6-yl 7-methyl-1,7-diazaspiro[3.5]nonane-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-(3-morpholin-4-yl-propyl)carbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-[2-(dimethylamino)ethyl]carbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3R)-3-(dimethylamino)pyrrolidine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3S)-3-(dimethylamino)pyrrolidine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-(2-cyanoethyl)-N-methylcarbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]3,3,4-trimethylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3R)-3-fluoropyrrolidine-1-carboxylate;

[(2S,3S,4E,6R,7S,10R)-2-[(E)-1-[3-(dimethylsulfamoylamino)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2-methoxyacetyl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(2-cyclopropylacetyl)amino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-[(3-hydroxyphenyl)methyl]piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-(pyridin-3-ylmethyl)piperazine-1-carboxylate;

[(2S,3S,4E,6R,7S,10R)-2-[(E)-1-[3-(1-acetylpiperidin-4-yl)-7-fluorobenzotriazol-5-yl]prop-1-en-2-yl]-10-hydroxy-3,7-dimethyl-12-oxo-1-oxacyclododec-4-en-6-yl] piperazine-1-carboxylate;

[(2S,3S,4E,6R,7S,10R)-10-hydroxy-2-[(E)-1-[3-[[(3R)-3-hydroxypyrrolidine-1-carbonyl]oxymethyl]phenyl]prop-1-en-2-yl]-3,7-dimethyl-12-oxo-1-oxacyclododec-4-en-6-yl]4-methylpiperazine-1-carboxylate;

[3-[(E)-2-[(2S,3 S,4E,6R,7S,10R)-10-hydroxy-3,7-dimethyl-6-(4-methylpiperazine-1-carbonyl)oxy-12-oxo-1-oxacyclododec-4-en-2-yl]prop-1-enyl]phenyl]methyl 2-oxa-7-azaspiro[3.4]octane-7-carboxylate;

[(2S,3S,4E,6R,7S,10R)-10-hydroxy-2-[(E)-1-[3-[[(3R)-3-fluoro-pyrrolidine-1-carbonyl]oxymethyl]phenyl]prop-1-en-2-yl]-3,7-dimethyl-12-oxo-1-oxacyclododec-4-en-6-yl]4-methylpiperazine-1-carboxylate;

[3-[(E)-2-[(2S,3 S,4E,6R,7S,10R)-10-hydroxy-3,7-dimethyl-6-(4-methylpiperazine-1-carbonyl)oxy-12-oxo-1-oxacyclododec-4-en-2-yl]prop-1-enyl]phenyl]methyl morpholine-4-carboxylate;

[(2S,3S,4E,6R,7S,10R)-2-[(E)-1-[3-(dimethylcarbamoyloxymethyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-[[(2S)-2-(hydroxymethyl)pyrrolidine-1-carbonyl]oxymethyl]phenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-[3-[[(3R)-3-fluoropyrrolidine-1-carbonyl]oxymethyl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-[(4-hydroxypiperidine-1-carbonyl)oxymethyl]phenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-piperidin-1-ylpiperidine-1-carboxylate;

[(2S,3S,4E,6R,7S,10R)-10-hydroxy-2-[(E)-1-[3-[4-(2-hydroxyethyl)piperazin-1-yl]phenyl]prop-1-en-2-yl]-3,7-dimethyl-12-oxo-1-oxacyclododec-4-en-6-yl]4-piperidin-1-ylpiperidine-1-carboxylate;

2-[4-[3-fluoro-5-[(E)-2-[(2S,3 S,4E,6R,7S,10R)-10-hydroxy-3,7-dimethyl-12-oxo-6-(piperazine-1-carbonyloxy)-1-oxacyclododec-4-en-2-yl]prop-1-enyl]phenyl] piperazin-1-yl]acetic acid;

(2S,3S,6R,7S,10R,E)-2-((E)-1-(3-(dimethylamino)phenyl) prop-1-en-2-yl)-10-hydroxy-3,7-dimethyl-12-oxooxacyclododec-4-en-6-yl 4-methylpiperazine-1-carboxylate;

(2S,3S,6R,7S,10R,E)-2-((E)-1-(3-(dimethylamino)phenyl) prop-1-en-2-yl)-10-hydroxy-3,7-dimethyl-12-oxooxacyclododec-4-en-6-yl piperazine-1-carboxylate;

(2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl piperazine-1-carboxylate;

(2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl piperazine-1-carboxylate;

and pharmaceutically acceptable salts thereof.

Disclosed herein are compositions comprising at least one compound of the present disclosure (e.g., compounds of Formulas I, IIa-e, IIIa, IVa, and Va and/or pharmaceutically acceptable salts thereof) and at least one pharmaceutically acceptable carrier. The at least one pharmaceutically acceptable carrier may be chosen according to the particular route of administration for which the composition is intended.

The pharmaceutical compositions of the present disclosure may be formulated for parenteral, oral, inhalation spray, topical, rectal, nasal, buccal, vaginal and/or implanted reservoir administration, etc. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered intravenously, orally, subcutaneously, or via intramuscular administration. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms, may also be used for the purposes of formulation.

For oral administration, a compound (e.g., a compound of Formulas I, IIa-e, IIIa, IVa, or Va or pharmaceutically acceptable salt thereof) may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient is combined with an emulsifying and/or suspending agent. If desired, certain sweetening, flavoring or coloring agents may also be added.

Compounds and compositions of the present disclosure may be used to treat various types of cancers, including those responsive to agents that target SF3B1. As noted above, the anti-tumor activity of pladienolide B is reported as being connected to its targeting of the SF3b complex, inhibiting splicing and altering the pattern of gene expression (Kotake et al., "Splicing factor SF3b as a target of the antitumor natural product pladienolide," Nature Chemical Biology 2007, 3, 570-575). Mutations in spliceosome genes such as the Splicing factor 3B subunit 1 (SF3B1) protein are known to be implicated in a number of cancers, such as hematologic malignancies and solid tumors. Scott et al., "Acquired mutations that affect pre-mRNA splicing in hematologic malignancies and solid tumors," JNCI 105, 20, 1540-1549.

Accordingly, the compounds (e.g., compounds of Formulas I, IIa-e, IIIa, IVa, and Va and pharmaceutically acceptable salts thereof) and compositions of the present disclosure may be used to treat hematological malignancies, such as, for example, cancers of the blood (leukemia) and cancers of the lymph nodes (lymphomas). Leukemias include acute lymphoblastic leukemia (ALL), acute myleogenous leukemia (AML), chronic lymphocytic leukemia (CLL), chronic myelogenous leukemia (CML), chronic myelomonocytic leukemia (CMML), acute monocytic leukemia (AMoL), etc. Lymphomas include Hodgkin's lymphoma and non-Hodgkin's lymphoma. Other hematologic malignancies may include myelodysplastic syndrome (MDS).

Solid tumors include carcinomas such as adenocarcinoma, e.g., breast cancer, pancreatic cancer, prostate cancer, colon or colorectal cancer, lung cancer, gastric cancer, cervical cancer, endometrial cancer, ovarian cancer, cholangiocarcinoma, glioma, melanoma, etc.

The compounds and compositions of the present disclosure (e.g., a compound of Formulas I, IIa-e, IIIa, IVa, or Va) may also be used to treat cancers that may be responsive to agents that target a spliceosome gene or protein other than SF3B1. The following are non-limiting examples of cancers that may be responsive to agents that target the spliceosome. Thus, compounds of the present disclosure may be administered to subjects to treat a variety of such cancers or conditions, such as patients or subjects afflicted with:

a) Myelodysplastic syndrome (MDS): See, e.g., "SF3B1 mutations in myelodysplastic syndromes: clinical associations and prognostic implications," Damm F. et al. Leukemia, 2011, 1-4; "Frequent pathway mutations in splicing machinery in myelodysplasia," Yoshida K. et al, Nature, 2011, 478, 64-69; "Clinical significance of SF3B1 mutations in myelodysplastic syndromes and myelodysplastic/myeloproliferative neoplasms," Malcovati L. et al., Blood, 2011, 118, 24, 6239-6246; "Mutations in the spliceosome machinery, a novel and ubiquitous pathway in leukemogenesis," Makishima et al, Blood, 2012, 119, 3203-3210; "Somatic SF3B1 mutation in myelodysplasia with ring sideroblasts," Pappaemannuil, E. et al, New England J. Med. 2011, DOI 10.1056/NEJMoa1103283.

b) Chronic lymphocytic leukemia (CLL): See, e.g., "Defects in the spliceosomal machinery: a new pathway of leukaemogenesis," Maciejewski, J. P., Padgett, R. A., Br. J. Haematology, 2012, 1-9; "Mutations in the SF3B1 splicing factor in chronic lymphocytic leukemia: associations with progression and fludarabine-refractoriness," Rossi et al, Blood, 2011, 118, 6904-6908; "Exome sequencing identifies recurrent mutations of the splicing factor SF3B1 gene in chronic lymphocytic leukemia," Quesada et al, Nature Genetics, 2011, 44, 47-52.

c) Chronic myelomonocytic leukemia (CMML): See, e.g., Yoshida et al, Nature 2011; "Spliceosomal gene mutations are frequent events in the diverse mutational spectrum of chronic myelomonocytic leukemia but largely absent in juvenile myelomonocytic leukemia," Kar S. A. et al, Haematologia, 2012, DOI: 10.3324/haematol.2012.064048; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105.

d) Acute myeloid leukemia (AML): See, e.g., Malcovati et al., Blood 2011; Yoshida et al, Nature 2011.

e) Breast cancer: See, e.g., "Whole genome analysis informs breast cancer response to aromatase inhibition," Ellis et al., Nature, 2012, 486, 353-360; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105; Maguire et al., "SF3B1 mutations constitute a novel therapeutic target in breast cancer," J Pathol 2015, 235, 571-580.

f) Uveal melanoma: See, e.g., "SF3B1 mutations are associated with alternative splicing in uveal melanoma," Furney et al., Cancer Disc. 2013, 10, 1122-1129; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105.

g) Endometrial cancer: See, e.g., Tefferi et al., "Myelodysplastic syndromes." N Engl J Med. 2009; 361:1872-85.

h) Gastric cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

i) Ovarian cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

j) Biliary Tract cancers such as Cholangiocarcinoma and Pancreatic cancer: See, e.g., Biankin et al., "Pancreatic cancer genomes reveal aberrations in axon guidance pathway genes," Nature 2012, 491, 399-405.

k) Lung cancer: See, e.g., "Exome sequencing identifies recurrent mutations of the splicing factor SF3B1 gene in chronic lymphocytic leukemia," Quesada et al., Nature Genetics 44, 47-52 (2012); Scott et al., "Acquired mutations that affect pre-mRNA splicing in hematologic malignancies and solid tumors," JNCI 105, 20, 1540-1549.

In addition, the Catalogue of somatic mutations in cancer (COSMIC) (Wellcome Trust Sanger Institute, Genome Research Limited, England) reports SF3B1 mutations have been found in various types of cancer samples.

A compound of the present disclosure (e.g., a compound of Formulas I, IIa-e, IIIa, IVa, or Va) may be administered to a subject in a treatment effective or therapeutically effective amount. The amount of a compound of the present disclosure that may be combined with a carrier material to produce a composition in a single dosage form will vary depending upon the subject treated and the particular route of administration. In some embodiments, a dose of 0.01 mg/kg to 100 mg/kg body weight/day of the at least one compound disclosed herein is administered. In some embodiments, the dose is 0.01 mg to 50 mg of the at least one compound disclosed herein. In some embodiments, 0.1 mg to 25 mg of the at least one compound disclosed herein is provided. In some embodiments, 5 mg to 40 mg of the at least one compound disclosed herein is provided.

One of ordinary skill will understand that a specific dosage and treatment regimen for a particular patient will depend upon a variety of factors, including the activity of the specific compound employed, the age, body weight, general health, sex, diet, time of administration, rate of excretion, drug combination, the judgment of the treating physician, and the severity of the particular disease being treated. The amount of the at least one compound disclosed herein will also depend upon the particular compound/salt being used.

In some embodiments, the cancer is tested for and/or is positive for one or more mutations in a spliceosome gene or protein, wherein the presence of the mutation(s) ("positive") may indicate the subject's cancer is responsive to a method of treatment comprising administration of a compound targeting this protein and/or the spliceosome. Examples of such spliceosome genes include, but are not limited to, those presented in Table 1.

TABLE 1

| Spliceosome genes and potential diseases affected | |
|---|---|
| Spliceosome gene | Disease(s) |
| Splicing factor 3B subunit 1 (SF3B1) | see listings above |
| U2 small nuclear RNA auxiliary factor 1 | MDS, AML, CMML, LUAD, UCEC |
| (U2AF1 ) | CMML, MDS, PMF, AML |
| Serine/arginine-rich splicing factor 2 (SRSF2) | MDS |
| Zinc finger (CCCH type), RNA-binding motif and serine/arginine rich 2 (ZRSR2) | Retinitis Pigmentosa |
| Pre-mRNA-processing-splicing factor 8 (PRPF8) | Myeloid neoplasms |
| U2 Small Nuclear RNA Auxiliary Factor 2 (U2AF2) | MDS, PRAD, COAD |
| Splicing Factor 1 (SF1) | myeloid neoplasms, OV, COAD |
| Splicing factor 3a subunit 1 (SF3A1) | MDS |
| PRP40 pre-mRNA processing factor 40 homolog B (PRPF40B) | LUAD |
| RNA Binding Motif Protein 10 (RBM10) | COAD |
| Poly(rC) binding protein 1 (PCBP1) | SKCM |
| Crooked neck pre-mRNA splicing factor 1 (CRNKL1) | LUSC |
| DEAH (Asp-Glu-Ala-His) box helicase 9 (DHX9) | STAD |
| Peptidyl-prolyl cis-trans isomerase-like 2 (PPIL2) | SKCM |
| RNA binding motif protein 22 (RBM22) | LUAD |
| Small nuclear ribonucleoprotein Sm D3 (SNRPD3) | GBM, LGG |
| Probable ATP-dependent RNA helicase DDX5 (DDX5) | LUAD |
| Pre-mRNA-splicing factor ATP-dependent RNA helicase DHX15 (DHX15) | DLBCL |
| Polyadenylate-binding protein 1 (PABPC1) | myeloid neoplasms |

Key:
MDS = Myelodysplastic syndrome
AML = Acute Myeloid Leukemia
CMML = chronic myelomonocytic leukemia
LUAD = Lung adenocarcinoma
UCEC = Uterine Corpus Endometrial Carcinoma
PMF = Progressive Massive Fibrosis
PRAD = Prostate adenocarcinoma
COAD = Colon adenocarcinoma
OV = Ovarian serous cystadenocarcinoma
SKCM = Skin Cutaneous Melanoma
LUSC = Lung squamous cell carcinoma
STAD = Stomach adenocarcinoma
GBM = Glioblastoma multiforme
LGG = Brain Lower Grade Glioma
DLBCL = Diffuse Large B-Cell Lymphoma In some embodiments, the subject's cancer may be responsive to a method of treatment comprising administration of a compound targeting this protein and/or the spliceosome even in the absence of such mutations in a spliceosome gene or protein.

Screening or testing for the mutations may be carried out by any known means, for example, genotyping, phenotyping, etc., by way of nucleic acid amplification, electrophoresis, microarrays, blot, functional assays, immunoassays, etc. Methods of screening may include, for example, collecting a biological sample from said subject containing the cancerous cells/tissue.

In some embodiments, a subject having cancer as described herein can be treated with at least one compound chosen from compounds of Formula I (including Formulas IIa-e, IIIa, IVa, and Va) and/or pharmaceutically acceptable salts thereof, and at least one additional therapy.

In some embodiments, the at least one additional therapy comprises a cytokine or cytokine analog therapy, e.g., any cytokine or cytokine analog therapy disclosed herein. Cytokines are a broad category of small proteins shown to be involved in autocrine signaling, paracrine signaling, and/or endocrine signaling as immunomodulating agents. Exemplary cytokines are disclosed herein, and include chemokines, interferons, interleukins, lymphokines, and tumor necrosis factors. As used herein, the term "cytokine" refers to a polypeptide secreted from a cell that influences the function of other cells to mediate an immune response, and the term "cytokine therapy" refers to the administration and/or induction of secretion of such a peptide. In some embodiments, the cytokine is a recombinant cytokine or an analog thereof. In some embodiments, the cytokine is a cytokine analog. The terms "cytokine analog" and "cytokine analog therapy" refer to a modified cytokine, wherein one or more amino acid residues of a native cytokine have been substituted with other natural or unnatural amino acid residues and/or wherein one or more natural or unnatural amino acid residues have been added to a native cytokine. In some embodiments, a cytokine or cytokine analog therapy comprises administering at least one cytokine or cytokine analog to a patient in need of such treatment.

In some embodiments, the at least one additional therapy comprises one or more engineered tumor-targeting T-cells (e.g., CAR-T or other cell-based therapy), e.g., any CAR-T therapy disclosed herein. The terms "CAR-T" and "CAR-T therapy" are used interchangeably to refer to a CAR-modified cell or cell population (e.g., a T-cell or T-cell population). In some embodiments, a chimeric T-cell receptor (CAR) can be engineered using antigen recognition sequences such that when the CAR is expressed on a cell (e.g., a T-cell), the CAR and/or cell is reactive with the target antigen. For instance, in some embodiments, a CAR may be engineered by first identifying antibodies that recognize a cell-surface expressed antigen protein domain. The antigen recognition sequences of such antibodies can then be fused to a T-cell receptor domain for selective targeting and activation. In some embodiments, the CAR sequences are cloned into patient-derived T-cell populations and expanded using currently available protocols. In some embodiments, the engineered T-cells are then transfused back into the patient's circulation, before, simultaneously with, or following treatment with at least one compound chosen from compounds of Formula I (including Formulas IIa-e, IIIa, IVa, and Va) and/or pharmaceutically acceptable salts thereof. After treatment with the at least one compound and/or pharmaceutically acceptable salt, in some embodiments, the tumor cells may begin to present an antigen, e.g., an antigen targeted by the engineered T-cell population. In some embodiments, the engineered T-cell population can engage with and kill antigen presenting tumor cells.

In some embodiments, the at least one additional therapy comprises a checkpoint inhibitor therapy, e.g., any checkpoint inhibitor therapy disclosed herein. Immune checkpoints are inhibitory pathways that slow down or stop immune reactions and prevent excessive tissue damage from uncontrolled activity of immune cells. As used herein, the terms "checkpoint inhibitor" and "checkpoint inhibitor therapy" are used interchangeably to refer to any therapeutic agent, including any small molecule chemical compound, antibody, nucleic acid molecule, or polypeptide, or any fragments thereof, that inhibits one or more of the inhibitory pathways, thereby allowing more extensive immune activity. In some embodiments, a checkpoint inhibitor therapy comprises administering at least one checkpoint inhibitor to a patient in need of such treatment.

In some embodiments, the at least one additional therapy comprises a neoantigen vaccine. In some embodiments, treatment comprises administering at least one compound chosen from compounds of Formula I (including Formulas IIa-e, IIIa, IVa, and Va) and/or pharmaceutically acceptable salts thereof and administering a neoantigen vaccine. In some embodiments, the neoantigen vaccine comprises a tumor neoantigen and/or a neoantigen induced by the at least one compound chosen from compounds of Formula I (including Formulas IIa-e, IIIa, IVa, and Va) and/or pharmaceutically acceptable salts thereof. In some embodiments, treatment further comprises administering a checkpoint inhibitor therapy. In some embodiments, the checkpoint inhibitor therapy is targeted at PD1/PDL1, CTLA4, OX40, CD40, LAG3, TIM3, GITR, and/or KIR. In some embodiments, the checkpoint inhibitor therapy is targeted at PD1/PDL1 (e.g., an anti-PD1 antibody or an anti-PDL1 antibody). In some embodiments, the checkpoint inhibitor therapy is targeted at CTLA4 (e.g., an anti-CTLA4 antibody). In some embodiments, treatment comprises administering a combination therapy comprising a neoantigen vaccine after first (i) administering at least one compound chosen from compounds of Formula I (including Formulas IIa-e, IIIa, IVa, and Va) and/or pharmaceutically acceptable salts thereof; and (ii) detecting the presence of a neoantigen (e.g., a neoantigen from the neoantigen vaccine). In some embodiments, neoantigen expression is monitored during the course of treatment. In some embodiments, treatment is discontinued if neoantigens are not detected.

Also disclosed herein, in some embodiments, are methods of treating a patient by inducing neoantigens in tumor cells that can be targeted by the patient's immune system for clearance. Without being bound by theory, in some embodiments, administering at least one compound chosen from compounds of Formula I (including Formulas IIa-e, IIIa, IVa, and Va) and/or pharmaceutically acceptable salts thereof, may produce neoantigens that induce an immune response, induce a double-stranded RNA immune response, e.g., as a result of re-expressed intron-resident endogenous retroviruses, and/or produce neoantigens that induce immunogenic cell death.

As used herein, the term "neoantigen" refers to any antigen to which the immune system has not previously been exposed that arises from one or more tumor-specific mutations and/or from exposing a tumor to at least one compound chosen from compounds of Formula I (including Formulas IIa-e, IIIa, IVa, and Va) and/or pharmaceutically acceptable salts thereof. Tumor-specific mutations can include missense mutations, frameshifts, translocations, and mRNA splicing variants, as well as mutations that influence posttranslational processing, such as phosphorylation and glycosylation. These exemplary mutations, in some embodiments, can be derived from non-synonymous coding changes and/or mutations that alter mRNA processing (e.g., splicing). All of these exemplary mutations, in some embodiments, can result in molecular changes that can be discriminated by an appropriate T-cell receptor. In various embodiments, an exemplary neoantigen is a neoantigen induced by delivery of at least one compound chosen from compounds of Formula I (including Formulas IIa-e, IIIa, IVa, and Va) and/or pharmaceutically acceptable salts thereof. In some embodiments, delivery of at least one compound chosen from compounds of Formula I (including Formulas IIa-e, IIIa, IVa, and Va) and/or pharmaceutically acceptable salts thereof can induce novel mRNA splicing that results in the translation of proteins containing one or more novel peptide domains to which the immune system has not previously been exposed. In some embodiments, tumor-specific mutations may be mRNA splicing variants resulting from delivery or administration of at least one compound chosen from compounds of Formula I (including Formulas IIa-e, IIIa, IVa, and Va) and/or pharmaceutically acceptable salts thereof.

Without being bound by theory, in some embodiments, the delivery of at least one compound chosen from compounds of Formula I (including Formulas IIa-e, IIIa, IVa, and Va) and/or pharmaceutically acceptable salts thereof may induce novel mRNA splicing (e.g., exon skipping, intron retention) that results in the alteration of the open reading frames and/or coding sequences of various genes. In some embodiments, these altered genes are translated into proteins containing one or more novel peptide domains recognized by the immune system as foreign. In some embodiments, the one or more novel peptide domains do not exist in the proteins or in any other part of the human proteome in the absence of compound treatment. In some embodiments, the proteins containing the one or more novel peptide domains can be degraded by the proteasome to create novel peptide fragments that act as substrates for the immunopeptide presentation machinery, e.g., via MHC presentation. In some embodiments, the novel peptide fragments representing neoantigens can be presented in the MHC1-bound peptidome, e.g., on tumor cells.

In some embodiments, the delivery of at least one compound chosen from compounds of Formula I (including Formulas IIa-e, IIIa, IVa, and Va) and/or pharmaceutically acceptable salts thereof may lead to one or more tumor cell-intrinsic events (e.g., cell growth arrest). In some embodiments, the tumor cell-intrinsic event(s) may lead to (1) enhanced engagement by phagocytic cells (Bracci et al. (2014) Cell Death Differ. 21(1):15-25); (2) the transport of novel peptide fragments to a tumor draining lymph node to engage with antigen-presenting cells; (3) antigen-presenting cells processing novel peptide fragments from a phagocytosed tumor cell and presenting the fragments as neoantigens to circulating naïve T-cell populations; (4) novel peptide fragments interacting with T-cells expressing receptors that recognize the fragments as neoantigens; (5) maturation and activation of effector T-cell responses (e.g., CD4+ and/or CD8+ T-cells; and/or (6) engagement of T-cells with additional tumor cells exposed to the compound treatment and presenting novel peptide fragments representing neoantigens on their surface MHC1 complexes. In some embodiments, the tumor cell-intrinsic event(s) may result, either directly or indirectly, in T-cell engagement of effector function and/or killing of neoantigen-presenting tumor cells.

Also, without being bound by theory, in some embodiments, the delivery of at least one compound chosen from compounds of Formula I (including Formulas IIa-e, IIIa, IVa, and Va) and/or pharmaceutically acceptable salts thereof may cause the re-expression of intron-resident endogenous retroviruses, leading to a double-stranded RNA immune response.

Further, without being bound by theory, in some embodiments, the delivery of at least one compound chosen from compounds of Formula I (including Formulas IIa-e, IIIa, IVa, and Va) and/or pharmaceutically acceptable salts thereof may lead to immunogenic cell death triggered by compound-induced release of mutationally-derived neoantigens. In some embodiments, the delivery of at least one compound chosen from compounds of Formula I (including Formulas IIa-e, IIIa, IVa, and Va) and/or pharmaceutically acceptable salts thereof may induce a double-stranded RNA immune response. In some embodiments, the double-stranded RNA immune response can result from the re-expression of intron-resident endogenous retroviruses. In some embodiments, the double-stranded RNA immune response can result in tumor cell death. In some embodiments, the delivery of at least one compound chosen from compounds of Formula I (including Formulas IIa-e, IIIa, IVa, and Va) and/or pharmaceutically acceptable salts thereof may induce immunogenic cell death. In some embodiments, the immunogenic cell death can result from release of mutational-derived neoantigens and/or a host immune response against tumor cells.

Accordingly, in some embodiments, methods of treatment are disclosed comprising inducing neoantigens by administering one or more compounds chosen from compounds of Formula I (including Formulas IIa-e, IIIa, IVa, and Va) and/or pharmaceutically acceptable salts thereof. In some embodiments, the method comprises administering a reduced dosage of the at least one compound chosen from compounds of Formula I (including Formulas IIa-e, IIIa, IVa, and Va) and/or pharmaceutically acceptable salts thereof than would be needed absent the induction of neoantigens. In some embodiments, the method comprises administering one or more initial induction doses to produce neoantigens and induce an immune response (e.g., converting naïve T-cells to memory cells), followed by a reduced dosage or administration frequency (i.e., because of the combinatorial effect of the at least one compound chosen from compounds of Formula I (including Formulas IIa-e, IIIa, IVa, and Va) and/or pharmaceutically acceptable salts thereof and of immune targeting of the neoantigens). In some embodiments, treatment can comprise a combination of administering the at least one compound chosen from compounds of Formula I (including Formulas IIa-e, IIIa, IVa, and Va) and/or pharmaceutically acceptable salts thereof to induce a neoantigen-based immune response and at least one additional therapy (e.g., a second anti-cancer therapy). For example, in some embodiments, treatment can comprise a combination of administering the at least one compound chosen from compounds of Formula I (including Formulas IIa-e, IIIa, IVa, and Va) and/or pharmaceutically acceptable salts thereof to induce a neoantigen-based immune response and one or more checkpoint inhibitors. In some embodiments, treatment can comprise a combination of administering the at least one compound chosen from compounds of Formula I (including Formulas IIa-e, IIIa, IVa, and Va) and/or pharmaceutically acceptable salts thereof to induce a neoantigen-based immune response and one or more cytokines or cytokine analogs. In some embodiments, treatment can comprise a combination of administering the at least one compound chosen from compounds of Formula I (including Formulas IIa-e, IIIa, IVa, and Va) and/or pharmaceutically acceptable salts thereof to induce a neoantigen-based immune response and one or more neoantigen vaccines. In some other embodiments, treatment can comprise a combination of administering the at least one compound chosen from compounds of Formula I (including Formulas IIa-e, IIIa, IVa, and Va) and/or pharmaceutically acceptable salts thereof to induce a neoantigen-based immune response and one or more engineered tumor-targeting T-cells (e.g., CAR-T).

In some embodiments, neoantigens can be used to monitor the effectiveness of treatment with at least one compound chosen from compounds of Formula I (including Formulas IIa-e, IIIa, IVa, and Va) and/or pharmaceutically acceptable salts thereof. For instance, after administration of at least one compound chosen from compounds of Formula I (including Formulas IIa-e, IIIa, IVa, and Va) and/or pharmaceutically acceptable salts thereof, a patient sample (e.g., a tumor biopsy) can be obtained and screened for neoantigens or for identifiers of an immune or inflammatory response. Further treatment can be provided, e.g., at reduced dosage, if a neoantigen and/or immune response is detected.

In some embodiments, methods of treatment are disclosed comprising inducing a double-stranded RNA immune response by administering one or more compounds chosen from compounds of Formula I (including Formulas IIa-e, IIIa, IVa, and Va) and/or pharmaceutically acceptable salts thereof.

In some embodiments, methods of treatment are disclosed comprising inducing immunogenic cell death by administering one or more compounds chosen from compounds of Formula I (including Formulas IIa-e, IIIa, IVa, and Va) and/or pharmaceutically acceptable salts thereof.

In some embodiments, administration of at least one compound chosen from compounds of Formula I (including Formulas IIa-e, IIIa, IVa, and Va) and/or pharmaceutically acceptable salts thereof can be combined with any known anti-cancer therapy. Examples of current immune activating strategies available for oncology treatment include, but are not limited to, treatment with immune checkpoint inhibitor (ICI) molecules, treatment with cytokines or cytokine analogs, vaccination with tumor-associated vaccines, and engineering tumor-targeting T-cells (e.g., expansion of tumor-infiltrating lymphocytes or CAR-T). These technologies are predominantly focused on enhancing or inducing an immune response to already existing tumor antigens (either mutations or aberrant expression of cell-surface proteins). One or more of these strategies may involve one or more mutations that are capable of inducing an antigenic T-cell response. For example, patient responses to checkpoint inhibition may correlate with non-synonymous mutational burden. In addition, cancer vaccine approaches may be used that rely on pre-existing mutations and the antigenicity of these mutations.

Compounds of Formula I (including Formulas IIa-e, IIIa, IVa, and Va) and/or pharmaceutically acceptable salts thereof may induce broad-ranging changes in the transcriptome that occur in multiple lineages. Translation of these mRNA changes may produce robust and reproducible protein changes that produce MHC1-bound neopeptides with high affinity across multiple HLA isotypes. Without being bound by theory, due to the large number of changes to the transcriptome and proteome, treatment with at least one compound chosen from compounds of Formula I (including Formulas IIa-e, IIIa, IVa, and Va) and/or pharmaceutically acceptable salts thereof may enrich the number of potentially reactive neoantigens for enhanced engagement of the adaptive immune response.

In some embodiments, the present disclosure provides a method of inducing at least one neoantigen by contacting a neoplastic cell with an effective amount of at least one compound chosen from compounds of Formula I (including Formulas IIa-e, IIIa, IVa, and Va) and/or pharmaceutically acceptable salts thereof. In some embodiments, the present disclosure provides a method of inducing a double-stranded RNA immune response by contacting a neoplastic cell with an effective amount of at least one compound chosen from compounds of Formula I (including Formulas IIa-e, IIIa, IVa, and Va) and/or pharmaceutically acceptable salts thereof. In some embodiments, the present disclosure provides a method of inducing immunogenic cell death by contacting a neoplastic cell with an effective amount of at least one compound chosen from compounds of Formula I (including Formulas IIa-e, IIIa, IVa, and Va) and/or pharmaceutically acceptable salts thereof.

In some embodiments, the neoplastic cell is present in an in vitro cell culture. In some embodiments, the neoplastic cell is obtained from a subject. In some embodiments, the neoplastic cell is present in a subject. In some embodiments, the neoplastic cell is derived from a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, and esophageal cancer. In some embodiments, the solid tumor is selected from HER2-positive breast cancer, gastric adenocarcinoma, and prostate cancer.

In some embodiments, the present disclosure further provides a method of inducing at least one neoantigen and/or a T-cell response in a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof. Also provided herein, in some embodiments, is a method of treating a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof, wherein administration of the at least one compound chosen from compounds of Formula I (including Formulas IIa-e, IIIa, IVa, and Va) and/or pharmaceutically acceptable salts thereof induces at least one neoantigen and/or a T-cell response.

In various other embodiments, the present disclosure provides a method of inducing a double-stranded RNA immune response in a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof. Also provided herein, in some embodiments, is a method of treating a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof, wherein administration of the at least one compound chosen from compounds of Formula I (including Formulas IIa-e, IIIa, IVa, and Va) and/or pharmaceutically acceptable salts thereof induces a double-stranded RNA immune response.

In still other embodiments, the present disclosure provides a method of inducing immunogenic cell death in a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof. Further provided herein, in some embodiments, is a method of treating a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof comprising at least one compound chosen from compounds of Formula I (including Formulas IIa-e, IIIa, IVa, and Va) and/or pharmaceutically acceptable salts thereof, wherein administration of the at least one compound chosen from compounds of Formula I (including Formulas IIa-e, IIIa, IVa, and Va) and/or pharmaceutically acceptable salts thereof induces immunogenic cell death.

In some embodiments, the present disclosure further provides a method of treating a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof, wherein administration of the at least one compound chosen from compounds of Formula I (including Formulas IIa-e, IIIa, IVa, and Va) and/or pharmaceutically acceptable salts thereof induces immunogenic cell death, in combination with one or more additional therapies comprising a second agent.

In some embodiments of the therapeutic methods described herein, the amount of the at least one compound chosen from compounds of Formula I (including Formulas IIa-e, IIIa, IVa, and Va) and/or pharmaceutically acceptable salts thereof, or second agent administered is reduced due to induction of at least one neoantigen and/or a T-cell response, as compared to a standard dosage of the at least one compound chosen from compounds of Formula I (including Formulas IIa-e, IIIa, IVa, and Va) and/or pharmaceutically acceptable salts thereof, or second agent. In some embodiments, the administered amount of the at least one compound chosen from compounds of Formula I (including Formulas IIa-e, IIIa, IVa, and Va) and/or pharmaceutically acceptable salts thereof, or second agent is reduced by 10%, 15%, 20%, 25%, 30%, 35%, 40%, 45%, 50%, 75%, or 90%, as compared to a standard dosage of the at least one compound chosen from compounds of Formula I (including Formulas IIa-e, IIIa, IVa, and Va) and/or pharmaceutically acceptable salts thereof, or second agent. In some embodiments, the at least one compound chosen from compounds of Formula I (including Formulas IIa-e, IIIa, IVa, and Va) and/or pharmaceutically acceptable salts thereof, or second agent is administered at least 10%, 15%, 20%, 25%, 30%, 35%, 40%, 45%, 50%, 75%, or 90% less frequently, as compared to a standard dosing regimen of the at least one compound chosen from compounds of Formula I (including Formulas IIa-e, IIIa, IVa, and Va) and/or pharmaceutically acceptable salts thereof, or second agent. In some embodiments, the administered amount and/or dosage of the at least one compound chosen from compounds of Formula I (including Formulas IIa-e, IIIa, IVa, and Va) and/or pharmaceutically acceptable salts thereof, or second agent results in lower systemic toxicity and/or improved tolerance.

As used herein, the term "standard dosage" or "standard dosing regimen" refers to any usual or routine dosing regimen for a therapeutic agent, e.g., a regimen proposed by the manufacturer, approved by regulatory authorities, or otherwise tested in human subjects to meet the average patient's needs. In some embodiments, the therapeutic agent is at least one compound chosen from compounds of Formula I (including Formulas IIa-e, IIIa, IVa, and Va) and/or pharmaceutically acceptable salts thereof with anti-cancer activity.

For instance, a standard dosing regimen for trastuzumab, an exemplary anti-HER2 antibody, may be 8 mg/kg administered intravenously over 90 min (week 1) followed by 6 mg/kg administered intravenously over 30-90 min every 3 weeks (week 4 through the end of the therapy cycle) (Herceptin® (trastuzumab) FDA Label Supplement, 2017).

As another example, a standard dosing regimen for ipilimumab, an exemplary anti-CTLA4 checkpoint inhibitor antibody, may be 3 mg/kg administered intravenously over 90 min every 3 weeks for 4 doses (Yervoy® (ipilimumab) FDA Label Supplement, 2018). Another standard dosing regimen for ipilimumab may be 10 mg/kg administered intravenously over 90 min every 3 weeks for 4 doses, followed by 10 mg/kg every 12 weeks for up to 3 years (Yervoy® (ipilimumab) FDA Label Supplement, 2018).

As another example, a standard dosing regimen for nivolumab, an exemplary anti-PD1 checkpoint inhibitor antibody, may be 3 mg/kg administered intravenously over 60 min every 2 weeks (Opdivo® (nivolumab) FDA Label, 2015).

As another example, a standard dosing regimen for atezolizumab, an exemplary anti-PDL1 checkpoint inhibitor antibody, may be 1200 mg administered intravenously over 60 min every 3 weeks (Tecentriq® (atezolizumab) FDA Label Supplement, 2018).

As yet another example, a standard dosing regimen for T-DM1, an exemplary anti-HER2 antibody-drug conjugate, may be 3.6 mg/kg administered intravenously over 90 min every 3 weeks (Kadcyla® (T-DM1) FDA Label Supplement, 2016).

In some embodiments, the methods described herein may further comprise administering at least one additional therapy (e.g., a checkpoint inhibitor, a neoantigen vaccine, a cytokine or cytokine analog, CAR-T, etc.). In some embodiments, the amount of the at least one compound chosen from compounds of Formula I (including Formulas IIa-e, IIIa, IVa, and Va) and/or pharmaceutically acceptable salts thereof, and/or the at least one additional therapy administered is reduced due to induction of at least one neoantigen and/or a T-cell response, as compared to a standard dosage of the at least one compound chosen from compounds of Formula I (including Formulas IIa-e, IIIa, IVa, and Va) and/or pharmaceutically acceptable salts thereof, and/or the at least one additional therapy. In some embodiments, the amount of the at least one compound chosen from compounds of Formula I (including Formulas IIa-e, IIIa, IVa, and Va) and/or pharmaceutically acceptable salts thereof, and/or the at least one additional therapy administered is reduced due to induction of a double-stranded RNA immune response, as compared to a standard dosage of the at least one compound chosen from compounds of Formula I (including Formulas IIa-e, IIIa, IVa, and Va) and/or pharmaceutically acceptable salts thereof, and/or the at least one additional therapy. In some embodiments, the amount of the at least one compound chosen from compounds of Formula I (including Formulas IIa-e, IIIa, IVa, and Va) and/or pharmaceutically acceptable salts thereof, and/or the at least one additional therapy administered is reduced due to induction of immunogenic cell death, as compared to a standard dosage of the at least one compound chosen from compounds of Formula I (including Formulas IIa-e, IIIa, IVa, and Va) and/or pharmaceutically acceptable salts thereof, and/or the at least one additional therapy. In some embodiments, the administered amount of the at least one compound chosen from compounds of Formula I (including Formulas IIa-e, IIIa, IVa, and Va) and/or pharmaceutically acceptable salts thereof, and/or the at least one additional therapy is reduced by 10%, 15%, 20%, 25%, 30%, 35%, 40%, 45%, 50%, 75%, or 90%, as compared to a standard dosage of the at least one compound chosen from compounds of Formula I (including Formulas IIa-e, IIIa, IVa, and Va) and/or pharmaceutically acceptable salts thereof, and/or the at least one additional therapy. In some embodiments, the at least one compound chosen from compounds of Formula I (including Formulas IIa-e, IIIa, IVa, and Va) and/or pharmaceutically acceptable salts thereof, and/or the at least one additional therapy is administered at least 10%, 15%, 20%, 25%, 30%, 35%, 40%, 45%, 50%, 75%, or 90% less frequently, as compared to a standard dosing regimen of the at least one compound chosen from compounds of Formula I (including Formulas IIa-e, IIIa, IVa, and Va) and/or pharmaceutically acceptable salts thereof, and/or the at least one additional therapy. In some embodiments, the administered amount and/or dosage of the at least one compound chosen from compounds of Formula I (including Formulas IIa-e, IIIa, IVa, and Va) and/or pharmaceutically acceptable salts thereof, and/or the at least one additional therapy results in lower systemic toxicity and/or improved tolerance.

In some embodiments, administration of the at least one compound chosen from compounds of Formula I (including Formulas IIa-e, IIIa, IVa, and Va) and/or pharmaceutically acceptable salts thereof is initiated before administration of the at least one additional therapy. In other embodiments, administration of the at least one compound chosen from compounds of Formula I (including Formulas IIa-e, IIIa, IVa, and Va) and/or pharmaceutically acceptable salts thereof is initiated after administration of the at least one additional therapy. In still other embodiments, administration of the at least one compound chosen from compounds of Formula I (including Formulas IIa-e, IIIa, IVa, and Va) and/or pharmaceutically acceptable salts thereof is initiated concurrently with administration of the at least one additional therapy.

In some embodiments, administration of the at least one compound chosen from compounds of Formula I (including Formulas IIa-e, IIIa, IVa, and Va) and/or pharmaceutically acceptable salts thereof is repeated at least once after initial administration. In some embodiments, the amount of the at least one compound chosen from compounds of Formula I (including Formulas IIa-e, IIIa, IVa, and Va) and/or pharmaceutically acceptable salts thereof used for repeated administration is reduced as compared to the amount used for initial administration. In some embodiments, the amount of the at least one compound chosen from compounds of Formula I (including Formulas IIa-e, IIIa, IVa, and Va) and/or pharmaceutically acceptable salts thereof used for repeated administration is reduced as compared to a standard dosage of the at least one compound chosen from compounds of Formula I (including Formulas IIa-e, IIIa, IVa, and Va) and/or pharmaceutically acceptable salts thereof. In some embodiments, the amount of the at least one compound chosen from compounds of Formula I (including Formulas IIa-e, IIIa, IVa, and Va) and/or pharmaceutically acceptable salts thereof used for repeated administration is reduced by 10%, 15%, 20%, 25%, 30%, 35%, 40%, 45%, 50%, 75%, or 90%, as compared to a standard dosage or initial dosage of the at least one compound chosen from compounds of Formula I (including Formulas IIa-e, IIIa, IVa, and Va) and/or pharmaceutically acceptable salts thereof.

In some embodiments, administration of the at least one additional therapy is repeated at least once after initial administration. In some embodiments, the amount of the at least one additional therapy used for repeated administration is reduced as compared to the amount used for initial administration. In some embodiments, the amount of the at least one additional therapy used for repeated administration is reduced as compared to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, as compared to a standard dosage or initial dosage of the at least one additional therapy.

In some embodiments, repeated administration of the at least one compound chosen from compounds of Formula I (including Formulas IIa-e, IIIa, IVa, and Va) and/or pharmaceutically acceptable salts thereof is concurrent with repeated administration of the at least one additional therapy. In some embodiments, administration of the at least one compound chosen from compounds of Formula I (including Formulas IIa-e, IIIa, IVa, and Va) and/or pharmaceutically acceptable salts thereof is sequential or staggered with repeated administration of the at least one additional therapy.

In some embodiments, the at least one additional therapy comprises administering a checkpoint inhibitor, e.g., any checkpoint inhibitor disclosed herein. In some embodiments, the subject is intolerant, non-responsive, or poorly responsive to the checkpoint inhibitor when administered alone. In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is an antibody having inhibitory or agonist activity to its target. In some embodiments, a checkpoint inhibitor is targeted with an inhibitory antibody or other similar inhibitory molecule. In other embodiments, a checkpoint inhibitor is targeted with an agonist antibody or other similar agonist molecule.

In some other embodiments, the at least one additional therapy comprises administering a neoantigen vaccine, e.g., any neoantigen vaccine disclosed herein. In some embodiments, the at least one compound chosen from compounds of Formula I (including Formulas IIa-e, IIIa, IVa, and Va) and/or pharmaceutically acceptable salts thereof is administered before administration of the neoantigen vaccine. In some embodiments, the at least one compound chosen from compounds of Formula I (including Formulas IIa-e, IIIa, IVa, and Va) and/or pharmaceutically acceptable salts thereof is administered after administration of the neoantigen vaccine. In some embodiments, the at least one compound chosen from compounds of Formula I (including Formulas IIa-e, IIIa, IVa, and Va) and/or pharmaceutically acceptable salts thereof is administered concurrently with administration of the neoantigen vaccine. In some embodiments, administration of the at least one compound chosen from compounds of Formula I (including Formulas IIa-e, IIIa, IVa, and Va) and/or pharmaceutically acceptable salts thereof is repeated at least once after initial administration. In some embodiments, the amount of the at least one compound chosen from compounds of Formula I (including Formulas IIa-e, IIIa, IVa, and Va) and/or pharmaceutically acceptable salts thereof used for repeated administration is reduced as compared to the amount used for initial administration.

In some embodiments, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length. In some embodiments, the at least one neoantigen peptide comprises one or more than one neoantigen sequence.

In some embodiments, the neoantigen sequence and/or antigenic portion ranges from about 10 to about 50 amino acids in length. In some embodiments, the at least one neoantigen peptide ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 3).

The term "antigenic portion" or "antigenic fragment" of a neoantigen sequence, as used herein, refers to one or more fragments of a neoantigen sequence that retain the ability to induce a T-cell response (e.g., antigen-specific expansion and/or maturation of effector T-cell population(s)). An antigenic portion, in some embodiments, may also retain the ability to be internalized, processed, and/or presented by antigen-presenting cells (e.g., dendritic cells). In some embodiments, an antigenic portion also retains T-cell priming function. In some embodiments, an antigenic portion of a neoantigen sequence ranges from about 10 to about 50 amino acids in length. In some embodiments, an antigenic portion of a neoantigen sequence ranges from about 10 to about 35 amino acids in length. In some embodiments, an antigenic portion of a neoantigen sequence ranges from about 15 to about 25 amino acids in length. In some embodiments, an antigenic portion of a neoantigen sequence ranges from about 10 to about 20 amino acids in length. In some embodiments, an antigenic portion of a neoantigen sequence (e.g., an antigenic portion of any one of SEQ ID NOs: 30-57), or its encoding mRNA, is formulated as a neoantigen vaccine.

An exemplary embodiment of an antigenic portion is the region(s) flanking amino acids 45-53 of SEQ ID NO: 30. Another exemplary embodiment of an antigenic portion is the region(s) flanking amino acids 82-90 of SEQ ID NO: 30. In some embodiments, the antigenic portion is capable of binding to at least one HLA allele expressed in a subject (e.g., HLA-A*02:01). In some other embodiments, the antigenic portion is capable of binding to at least one HLA allele expressed in at least 10%, at least 15%, at least 20%, at least 25%, at least 30%, at least 35%, at least 40%, or at least 45% of subjects in a population of subjects suffering from a neoplastic disorder. In some embodiments, the antigenic portion is capable of eliciting a T-cell response against a tumor present in at least 1%, at least 5%, or at least 10% of a population of subjects suffering from a neoplastic disorder.

In some embodiments, an antigenic portion does not exclusively overlap or consist of a canonical peptide sequence. The term "canonical peptide sequence," as used herein, refers to any contiguous peptide sequence present in the human proteome in the absence of contact with at least one compound chosen from compounds of Formula I (including Formulas IIa-e, IIIa, IVa, and Va) and/or pharmaceutically acceptable salts thereof (e.g., in the absence of contact with at least one compound chosen from compounds of Formula I (including Formulas IIa-e, IIIa, IVa, and Va) and/or pharmaceutically acceptable salts thereof), and/or to which the immune has previously been exposed. In some embodiments, the canonical peptide sequence is derived from and/or encoded by the canonical transcript open reading frame. Exemplary canonical peptide sequences are underlined in Table 3.

In some embodiments, when a compound chosen from compounds of Formula I (including Formulas IIa-e, IIIa, IVa, and Va) and/or pharmaceutically acceptable salts thereof is administered, a canonical peptide sequence may be derived from and/or encoded by the immediate 5' in-frame 24 nucleotides preceding an aberrant splicing event induced by the at least one compound chosen from compounds of Formula I (including Formulas IIa-e, IIIa, IVa, and Va) and/or pharmaceutically acceptable salts thereof. Thus, in some embodiments, the canonical peptide sequence comprises or consists of the 8 amino acids immediately N-terminal to the neoantigen sequence induced by the at least one compound chosen from compounds of Formula I (including Formulas IIa-e, IIIa, IVa, and Va) and/or pharmaceutically acceptable salts thereof. In some embodiments, when a 5' exon sequence terminates with a terminal nucleotide of a codon, the canonical peptide sequence terminates at the end of the exon. In some other embodiments, when a 5' exon sequence terminates with one or two of the three nucleotides of a codon, the canonical peptide sequence is derived from and/or encoded by the 24 nucleotides preceding the incomplete codon. In some embodiments, mRNA sequences 3' of the aberrant splicing event may be translated in the same open reading frame derived from the 5' exon until reaching a stop codon, whereupon translation may terminate. In some embodiments, when the aberrant splicing event (e.g., exon skipping) results in a conservation of the canonical transcript open reading frame, the C-terminal sequence may be translated for an additional 24 nucleotides, encoding 8 C-terminal amino acids. In this context, in some embodiments, only the region across the aberrant exon junction may encode a neoantigen sequence. In some embodiments, when the open reading frame is shifted (e.g., intron retention), the complete C-terminal sequence (encoded by the 3' mRNA) may encode a neoantigen sequence.

In some embodiments, an antigenic portion of a neoantigen sequence is chosen by comparing the neoantigen sequence to the canonical peptide sequence; and selecting a portion of the neoantigen sequence that does not exclusively overlap, consist of, and/or align with the canonical peptide sequence. An antigenic portion of a neoantigen sequence, in some embodiments, can be screened for antigenicity and/or T-cell priming function in the same manner as are full-length neoantigen sequences (e.g., the neoantigen sequence from which the antigenic portion is derived). In some embodiments, an antigenic portion of a neoantigen sequence is evaluated for antigenicity and/or T-cell priming function using a T-cell priming assay, such as the exemplary T-cell priming experiments described herein.

In some embodiments, the neoantigen sequence is a neoantigen sequence specific to the subject. In some embodiments, the neoantigen sequence is a personalized neoantigen vaccine for the subject. In some embodiments, the neoantigen sequence used to create a personalized neoantigen vaccine for a subject is capable of binding to at least one HLA allele expressed in the subject. In some embodiments, a personalized neoantigen vaccine is selected by identifying neoantigens expressed in a subject's tumor, e.g., after administration of at least one compound chosen from compounds of Formula I (including Formulas IIa-e, IIIa, IVa, and Va) and/or pharmaceutically acceptable salts thereof, and selecting a vaccine comprising a neoantigen sequence observed in the patient's tumor.

The term "personalized" when used to describe a neoantigen vaccine refers to a vaccine created by identifying one or more neoantigens produced in a patient, preferably one identified in the patient after an exposure to at least one compound chosen from compounds of Formula I (including Formulas IIa-e, IIIa, IVa, and Va) and/or pharmaceutically acceptable salts thereof, and then using one or more of those neoantigens as the basis of the vaccine for the same patient. Accordingly, in some embodiments, a patient is given at least one compound chosen from compounds of Formula I (including Formulas IIa-e, IIIa, IVa, and Va) and/or pharmaceutically acceptable salts thereof and screened for neoantigens produced by the treatment. In some embodiments, the selected neoantigen vaccine comprises a neoantigen peptide or mRNA disclosed herein and confirmed to be present in the patient after exposure to the at least one compound chosen from compounds of Formula I (including Formulas IIa-e, IIIa, IVa, and Va) and/or pharmaceutically acceptable salts thereof. In some embodiments, the at least one compound chosen from compounds of Formula I (including Formulas IIa-e, IIIa, IVa, and Va) and/or pharmaceutically acceptable salts thereof and/or peptide or mRNA vaccine may be administered to the patient once or repeatedly. Subsequently, in some embodiments, one or more of those neoantigens are used to create a personalized vaccine that is given to the patient. In some embodiments, the one or more neoantigens used to create a personalized vaccine possess binding affinity for one or more patient-specific HLA alleles. In some embodiments, the patient expresses one or more MHC1 alleles that bind to the one or more neoantigens. The prediction of whether a given neoantigen will bind to a specific MHC1 allele can be determined using any computational prediction method known in the art. Exemplary computational prediction methods are disclosed, e.g., in Meydan et al. (2013) BMC Bioinformatics 14(Suppl. 2):S13, which is incorporated herein by reference for such methods.

In some other embodiments, the neoantigen sequence is a universal neoantigen sequence. In some embodiments, the neoantigen sequence is a universal neoantigen vaccine.

The term "universal" when used to describe a neoantigen vaccine refers to a vaccine having a peptide or mRNA sequence that is based on common or known neoantigen(s) observed by sequencing neoantigens produced in multiple patients and/or patient tissue samples, preferably after an exposure to at least one compound chosen from compounds of Formula I (including Formulas IIa-e, IIIa, IVa, and Va) and/or pharmaceutically acceptable salts thereof. The peptide or mRNA sequence used in the vaccine need not be present in every patient but rather be observed in at least several patients or patient tissue samples. In some embodiments, the at least one compound chosen from compounds of Formula I (including Formulas IIa-e, IIIa, IVa, and Va) and/or pharmaceutically acceptable salts thereof and/or peptide or mRNA vaccine may be administered to the patient once or repeatedly. Subsequently, in some embodiments, that peptide or mRNA sequence is used for vaccinating further patients. In some embodiments, a patient is given at least one compound chosen from compounds of Formula I (including Formulas IIa-e, IIIa, IVa, and Va) and/or pharmaceutically acceptable salts thereof, and then given a peptide or mRNA vaccine of known neoantigen to enhance immune response to the neoantigens produced by the at least one compound chosen from compounds of Formula I (including Formulas IIa-e, IIIa, IVa, and Va) and/or pharmaceutically acceptable salts thereof. In some embodiments, a patient is given a universal peptide or mRNA vaccine and then given at least one compound chosen from compounds of Formula I (including Formulas IIa-e, IIIa, IVa, and Va) and/or pharmaceutically acceptable salts thereof once or repeatedly. In some embodiments, the neoantigen sequence (or sequences) used to create a universal neoantigen vaccine is selected based on overall MHC1 allele frequency in a given patient population (Maiers et al. (2007) Hum. Immunol. 68(9):779-88).

In some embodiments, the neoantigen (e.g., a universal neoantigen) sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide, or its encoding mRNA, induced in the subject by administering an effective amount of the at least one compound chosen from compounds of Formula I (including Formulas IIa-e, IIIa, IVa, and Va) and/or pharmaceutically acceptable salts thereof. In some embodiments, the at least one neoantigen peptide comprises a neoantigen sequence induced by contacting a neoplastic cell with an effective amount of the at least one compound chosen from compounds of Formula I (including Formulas IIa-e, IIIa, IVa, and Va) and/or pharmaceutically acceptable salts thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide and a pharmaceutically acceptable carrier (e.g., any of the exemplary carriers described herein). In some embodiments, the at least one neoantigen peptide is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen peptide and the pharmaceutically acceptable carrier are covalently attached via a linker. In some embodiments, the neoantigen peptide and the pharmaceutically acceptable carrier are expressed as a fusion protein. In some embodiments, the neoantigen vaccine comprises at least one neoantigen peptide and a pharmaceutically acceptable diluent. In some embodiments, the neoantigen vaccine comprises at least one neoantigen peptide and a pharmaceutically acceptable adjuvant.

In some embodiments, the neoantigen vaccine comprises at least one neoantigen mRNA. In some embodiments, the at least one neoantigen mRNA encodes one or more than one neoantigen sequence.

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing the protein sequence of at least one neoantigen. In some embodiments, the neoantigen sequence has been identified by sequencing at least one mRNA encoding a neoantigen induced in the subject by administering an effective amount of the at least one compound chosen from compounds of Formula I (including Formulas IIa-e, IIIa, IVa, and Va) and/or pharmaceutically acceptable salts thereof. In some embodiments, the at least one neoantigen mRNA encodes a neoantigen sequence induced by contacting a neoplastic cell with an effective amount of the at least one compound chosen from compounds of Formula I (including Formulas IIa-e, IIIa, IVa, and Va) and/or pharmaceutically acceptable salts thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier (e.g., any of the exemplary carriers described herein). In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant. In some embodiments, the neoantigen mRNA is encapsulated by an encapsulating agent. In some embodiments, the encapsulating agent is a liposome. In some embodiments, the encapsulating agent is a nanoparticle.

In some embodiments, the at least one additional therapy comprises administering a cytokine or cytokine analog, e.g., any cytokine or cytokine analog disclosed herein. In some embodiments, the subject is intolerant, non-responsive, or poorly responsive to the cytokine or cytokine analog when administered alone. In some embodiments, the cytokine or cytokine analog comprises a T-cell enhancer. In some embodiments, the cytokine or cytokine analog comprises IL-2, IL-10, IL-12, IL-15, IFN$\gamma$, and/or TNF$\alpha$. In some embodiments, the cytokine or cytokine analog comprises IL-2, IL-10, IL-12, and/or IL-15. In some embodiments, administering the cytokine or cytokine analog enhances T-cell priming following administration of at least one compound chosen from compounds of Formula I (including Formulas IIa-e, IIIa, IVa, and Va) and/or pharmaceutically acceptable salts thereof due to the induction and presentation of neoantigens.

In some embodiments, the at least one additional therapy comprises administering engineered tumor-targeting T-cells (i.e., CAR-T), e.g., any CAR-T therapy disclosed herein.

In some embodiments, the methods described herein may further comprise detecting one or more neoantigens and/or a T-cell response in the subject after administration of the at least one compound chosen from compounds of Formula I (including Formulas IIa-e, IIIa, IVa, and Va) and/or pharmaceutically acceptable salts thereof, and, optionally, continuing administration of the at least one compound chosen from compounds of Formula I (including Formulas IIa-e, IIIa, IVa, and Va) and/or pharmaceutically acceptable salts thereof if one or more neoantigens and/or a T-cell response is detected. In some embodiments, detecting one or more neoantigens and/or a T-cell response in the subject indicates efficacy of treatment with the at least one compound chosen from compounds of Formula I (including Formulas IIa-e, IIIa, IVa, and Va) and/or pharmaceutically acceptable salts thereof. In some embodiments, treatment with the additional therapy, along with the at least one compound chosen from compounds of Formula I (including Formulas IIa-e, IIIa, IVa, and Va) and/or pharmaceutically acceptable salts thereof, is continued if one or more neoantigens and/or a T-cell response is detected. In some embodiments, treatment is continued at a reduced dosage and/or frequency if one or more neoantigens and/or a T-cell response is detected.

In some embodiments, the methods described herein may further comprise detecting a double-stranded RNA immune response in the subject after administration of the at least one compound chosen from compounds of Formula I (including Formulas IIa-e, IIIa, IVa, and Va) and/or pharmaceutically acceptable salts thereof, and, optionally, continuing administration of the at least one compound chosen from compounds of Formula I (including Formulas IIa-e, IIIa, IVa, and Va) and/or pharmaceutically acceptable salts thereof if a double-stranded RNA immune response is detected. In some embodiments, detecting a double-stranded RNA immune response in the subject indicates efficacy of treatment with the at least one compound chosen from compounds of Formula I (including Formulas IIa-e, IIIa, IVa, and Va) and/or pharmaceutically acceptable salts thereof. In some embodiments, treatment with the additional therapy, along with the at least one compound chosen from compounds of Formula I (including Formulas IIa-e, IIIa, IVa, and Va) and/or pharmaceutically acceptable salts thereof, is continued if a double-stranded RNA immune response is detected. In some embodiments, treatment is continued at a reduced dosage and/or frequency if a double-stranded RNA immune response is detected.

In some embodiments, the methods described herein may further comprise detecting immunogenic cell death in the subject after administration of the at least one compound chosen from compounds of Formula I (including Formulas IIa-e, IIIa, IVa, and Va) and/or pharmaceutically acceptable salts thereof, and, optionally, continuing administration of the at least one compound chosen from compounds of Formula I (including Formulas IIa-e, IIIa, IVa, and Va) and/or pharmaceutically acceptable salts thereof if immunogenic cell death is detected. In some embodiments, detecting immunogenic cell death in the subject indicates efficacy of treatment with the at least one compound chosen from compounds of Formula I (including Formulas IIa-e, IIIa, IVa, and Va) and/or pharmaceutically acceptable salts thereof. In some embodiments, treatment with the additional therapy, along with the at least one compound chosen from compounds of Formula I (including Formulas IIa-e, IIIa, IVa, and Va) and/or pharmaceutically acceptable salts thereof, is continued if immunogenic cell death is detected. In some embodiments, treatment is continued at a reduced dosage and/or frequency if immunogenic cell death is detected.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, and esophageal cancer. In some embodiments, the solid tumor is selected from HER2-positive breast cancer, gastric adenocarcinoma, and prostate cancer.

In some embodiments, the present disclosure further provides a method of treating a subject having or suspected of having a neoplastic disorder, comprising: (a) administering to the subject an effective amount of at least one compound chosen from compounds of Formula I (including Formulas IIa-e, IIIa, IVa, and Va) and/or pharmaceutically acceptable salts thereof, wherein administration of the at least one compound chosen from compounds of Formula I (including Formulas IIa-e, IIIa, IVa, and Va) and/or pharmaceutically acceptable salts thereof induces at least one neoantigen and/or a T-cell response; (b) detecting one or more neoantigens and/or a T-cell response in the subject after administration of the at least one compound chosen from compounds of Formula I (including Formulas IIa-e, IIIa, IVa, and Va) and/or pharmaceutically acceptable salts thereof; and (c) continuing administration of the at least one compound chosen from compounds of Formula I (including Formulas IIa-e, IIIa, IVa, and Va) and/or pharmaceutically acceptable salts thereof if one or more neoantigens and/or a T-cell response is detected. In some embodiments, detecting one or more neoantigens and/or a T-cell response in the subject indicates efficacy of treatment with the at least one compound chosen from compounds of Formula I (including Formulas IIa-e, IIIa, IVa, and Va) and/or pharmaceutically acceptable salts thereof. In some embodiments, the one or more neoantigens comprise an amino acid sequence of any one of SEQ ID NOs: 1-29. In some embodiments, the one or more neoantigens comprise an amino acid sequence of SEQ ID NO: 1. In some embodiments, the one or more neoantigens comprise an amino acid sequence of SEQ ID NO: 3. In some embodiments, the one or more neoantigens comprise an amino acid sequence of any one of SEQ ID NOs: 10-13.

In some embodiments, a patient having a cancer as described herein can be treated with a combination of at least one compound chosen from compounds of Formula I (including Formulas IIa-e, IIIa, IVa, and Va) and/or pharmaceutically acceptable salts thereof and a checkpoint inhibitor therapy.

Treatment of patients with immune checkpoint inhibition has been shown to have robust efficacy in certain clinical indications. Recently, the FDA approved use of a checkpoint inhibitor in patients with tumors exhibiting high microsatellite instability, agnostic to the tissue lineage. This approval was based, in part, on the observation that response rates correlate positively with mutational burden (Rizvi et al. (2015) Science 348(6230):124-8; Hellmann et al. (2018) Cancer Cell 33(5):853-861). Estimates from the literature vary in absolute numbers and by lineage, but generally support that above a threshold of ~150-250 mutations, the probability of response rises. Analysis of TCGA data shows that a large percentage of adult-onset tumor lineages have comparatively low non-synonymous mutational burden (Vogelstein et al. (2013) Science 339:1549-58). Most lineages have median non-synonymous mutational rates of ~30-80 per patient, well below the thresholds for improved odds of response to checkpoint inhibitors.

For instance, HER2-positive breast cancer has been shown to have a median of ~60 non-synonymous mutations present per patient sample. However, the threshold for checkpoint inhibitor treatment efficacy, as mentioned above, is estimated to be in the range of ~150-250 non-synonymous mutations, i.e., patients above this threshold are more likely to show complete remission, partial remission, and/or stable disease, whereas patients below this threshold are more likely to exhibit progressive disease. Strategies to enhance the apparent number of non-synonymous mutations and/or neoantigens being presented on tumor cells are therefore desirable, and may enhance the overall probability of response, e.g., to checkpoint inhibitor therapies. As cytokines (and analogs thereof) act via a similar mechanism of action, such strategies may also enhance the overall probability of response to cytokine-based therapies.

Current response rates in HER2-positive breast cancer are ~15-25% (CTI NCT02129556). In some embodiments disclosed herein, treatment at least one compound chosen from compounds of Formula I (including Formulas IIa-e, IIIa, IVa, and Va) and/or pharmaceutically acceptable salts thereof, in combination with a checkpoint inhibitor and/or cytokine therapy may improve such response rates. In some embodiments, treatment with a therapeutically effective amount of at least one compound chosen from compounds of Formula I (including Formulas IIa-e, IIIa, IVa, and Va) and/or pharmaceutically acceptable salts thereof, in combination with a checkpoint inhibitor and/or cytokine therapy may apply to any adult-onset tumor, particularly those in which the median non-synonymous mutational rate is below the estimated ~150 mutations threshold. In some embodiments, exemplary cancer types suitable for treatment with a therapeutically effective amount of at least one compound chosen from compounds of Formula I (including Formulas IIa-e, IIIa, IVa, and Va) and/or pharmaceutically acceptable salts thereof, alone or in combination with an additional therapy (e.g., a checkpoint inhibitor therapy, a cytokine therapy) include but are not limited to esophageal cancer, non-Hodgkin's lymphoma, colorectal cancer, head and neck cancer, gastric cancer, endometrial cancer, pancreatic adenocarcinoma, ovarian cancer, prostate cancer, hepatocellular cancer, glioblastoma, breast cancer (e.g., HER2-positive breast cancer), lung cancer (e.g., non-small cell lung cancer), chronic lymphocytic leukemia, and acute myeloid leukemia. Other exemplary suitable cancer types are identified, e.g., in Vogelstein et al. (2013) Science 339:1549-58, which is incorporated herein by reference in its entirety.

As many checkpoint inhibitor therapies are based on chronic expression of tumor-associated antigens, regular treatment boosts are required for efficacy and for "reboosting" reactive T-cell populations. The inducible nature of at least one compound chosen from compounds of Formula I (including Formulas IIa-e, IIIa, IVa, and Va) and/or pharmaceutically acceptable salts thereof, derived neoantigens described herein provide for therapeutic dosing regimens that may be designed to enhance the immune response of neoantigen-reactive T-cells, while limiting T-cell exhaustion often caused by chronic antigen stimulation. For instance, in some embodiments, an initial dose of at least one compound chosen from compounds of Formula I (including Formulas IIa-e, IIIa, IVa, and Va) and/or pharmaceutically acceptable salts thereof, is administered to a subject to trigger aberrant splicing and production of neoantigen peptides. After a period of time to allow for protein production and antigen presentation, in some embodiments, the subject is then administered an initial dose of a checkpoint inhibitor to boost and/or enhance effector T-cell priming and expansion. In some embodiments, the wait period between doses of at least one compound chosen from compounds of Formula I (including Formulas IIa-e, IIIa, IVa, and Va) and/or pharmaceutically acceptable salts thereof, and checkpoint inhibitor is about 2, about 3, about 4, about 5, about 6, or about 7 days. In some embodiments, the wait period is between about 3 days and about 5 days.

In some embodiments, the checkpoint inhibitor is targeted at CTLA4, OX40, CD40, and/or GITR. In some embodiments, the combination therapeutic benefit of a therapeutically effective amount of at least one compound chosen from compounds of Formula I (including Formulas IIa-e, IIIa, IVa, and Va) and/or pharmaceutically acceptable salts thereof, and a checkpoint inhibitor may be additive or superadditive.

In some embodiments, administration of the therapeutically effective amount of at least one compound chosen from compounds of Formula I (including Formulas IIa-e, IIIa, IVa, and Va) and/or pharmaceutically acceptable salts thereof is initiated before administration of the checkpoint inhibitor.

In some embodiments, administration of the therapeutically effective amount of at least one compound chosen from compounds of Formula I (including Formulas IIa-e, IIIa, IVa, and Va) and/or pharmaceutically acceptable salts thereof is initiated after administration of the checkpoint inhibitor.

In some embodiments, administration of the therapeutically effective amount of at least one compound chosen from compounds of Formula I (including Formulas IIa-e, IIIa, IVa, and Va) and/or pharmaceutically acceptable salts thereof is initiated concurrently with administration of the checkpoint inhibitor, e.g., in a single formulated product or separate formulated products administered in a single procedure.

In some embodiments, after a period to allow for T-cell priming and expansion, the subject is then administered a second or subsequent dose of at least one compound chosen from compounds of Formula I (including Formulas IIa-e, IIIa, IVa, and Va) and/or pharmaceutically acceptable salts thereof, to trigger re-presentation of neoantigen peptides. In some embodiments, the wait period between an initial dose of a checkpoint inhibitor and a second or subsequent dose of a therapeutically effective amount of at least one compound chosen from compounds of Formula I (including Formulas IIa-e, IIIa, IVa, and Va) and/or pharmaceutically acceptable salts thereof is about 2, about 3, about 4, or about 5 weeks. In some embodiments, the wait period is about 3 weeks. Following a second or subsequent dose of at least one compound chosen from compounds of Formula I (including Formulas IIa-e, IIIa, IVa, and Va) and/or pharmaceutically acceptable salts thereof, in some embodiments, the immune system may engage with the neoantigen-presenting tumor cells and/or elicit tumor cell killing. In some embodiments, the subject is then administered a second or subsequent dose of the checkpoint inhibitor to further expand the memory effector T-cell population, after allowing for secondary T-cell priming and expansion.

In some embodiments, the wait period between an initial dose of a therapeutically effective amount of at least one compound chosen from compounds of Formula I (including Formulas IIa-e, IIIa, IVa, and Va) and/or pharmaceutically acceptable salts thereof and a second or subsequent dose of a checkpoint inhibitor is about 2, about 3, about 4, or about 5 weeks. In some embodiments, the wait period is about 3 weeks.

In some embodiments, dosing of a therapeutically effective amount of at least one compound chosen from compounds of Formula I (including Formulas IIa-e, IIIa, IVa, and Va) and/or pharmaceutically acceptable salts thereof, following this exemplary initial treatment regimen can be pulsatile, i.e., a therapeutically effective amount of at least one compound chosen from compounds of Formula I (including Formulas IIa-e, IIIa, IVa, and Va) and/or pharmaceutically acceptable salts thereof, may be dosed at prolonged intervals (e.g., about every 4 weeks, about every 5 weeks, about every 6 weeks) to allow for antigen presentation, T-cell engagement and/or tumor cell killing, and/or recovery of the memory T-cell population. At later timepoints, in some embodiments, a therapeutically effective amount of at least one compound chosen from compounds of Formula I (including Formulas IIa-e, IIIa, IVa, and Va) and/or pharmaceutically acceptable salts thereof, treatment may be combined with one or more checkpoint inhibitors targeted to restore effector functionality to exhausted T-cell populations. For example, in some embodiments, at later timepoints, the at least one compound chosen from compounds of Formula I (including Formulas IIa-e, IIIa, IVa, and Va) and/or pharmaceutically acceptable salts thereof, treatment may be combined with one or more checkpoint inhibitors targeted at PD1/PDL1, LAG3, and/or TIM3. In some embodiments, the pulsed nature of neoantigen presentation and priming may allow a checkpoint inhibitor and/or at least one compound chosen from compounds of Formula I (including Formulas IIa-e, IIIa, IVa, and Va) and/or pharmaceutically acceptable salts thereof, to be administered less frequently and/or at lower doses. In some embodiments, the pulsed nature of neoantigen presentation may provide one or more treatment benefits for a checkpoint inhibitor (e.g., an anti-CTLA4 antibody such as ipilimumab), relative to the checkpoint inhibitor when administered without concurrent administration of a therapeutically effective amount of at least one compound chosen from compounds of Formula I (including Formulas IIa-e, IIIa, IVa, and Va) and/or pharmaceutically acceptable salts thereof, for example, by lowering the potential risk of adverse reactions often observed with the checkpoint inhibitor's standard dosing regimen.

In certain embodiments, the checkpoint inhibitor is an inhibitor of the cytotoxic T-lymphocyte-associated antigen (CTLA4) pathway. CTLA4, also known as CD152, is a protein receptor that downregulates immune responses. CTLA4 is constitutively expressed in regulatory T-cells, but only upregulated in conventional T-cells after activation. As used herein, the term "CTLA4 inhibitor" is meant to refer to any inhibitor of CTLA4 and/or the CTLA4 pathway. Exemplary CTLA4 inhibitors include but are not limited to anti-CTLA4 antibodies. CTLA4 blocking antibodies for use in humans were developed based on the pre-clinical activity seen in mouse models of anti-tumor immunity. Exemplary anti-CTLA4 antibodies include but are not limited to ipilimumab (MDX-010) and tremelimumab (CP-675,206), both of which are fully human. Ipilimumab is an IgG1 with a plasma half-life of approximately 12-14 days; tremelimumab is an IgG2 with a plasma half-life of approximately 22 days. See, e.g., Phan et al. (2003) Proc Natl Acad Sci USA. 100:8372-7; Ribas et al. (2005) J Clin Oncol. 23:8968-77; Weber et al. (2008) J Clin Oncol. 26:5950-6. In some embodiments, the anti-CTLA4 antibody is ipilimumab.

In certain embodiments, the checkpoint inhibitor is an inhibitor of the programmed death-1 (PD1) pathway. The programmed cell death 1 (PD1) pathway represents a major immune control switch which may be engaged by tumor cells to overcome active T-cell immune surveillance. The ligands for PD1 (PDL1 and PDL2) are constitutively expressed or can be induced in various tumors. High expression of PDL1 on tumor cells (and to a lesser extent of PDL2) has been found to correlate with poor prognosis and survival in various other solid tumor types. Furthermore, PD1 has been suggested to regulate tumor-specific T-cell expansion in patients with malignant melanoma. These observations suggest that the PD1/PDL1 pathway plays a critical role in the tumor immune evasion and may be considered an attractive target for therapeutic intervention. As used herein, the term "PD1 inhibitor" is meant to refer to any inhibitor of PD1 and/or the PD1 pathway. Exemplary PD1 inhibitors include but are not limited to anti-PD1 and anti-PDL1 antibodies. In certain embodiments, the checkpoint inhibitor is an anti-PD1 antibody. Exemplary anti-PD1 antibodies include but are not limited to nivolumab and pembrolizumab (MK-3475). Nivolumab, for example, is a fully human immunoglobulin G4 (IgG4) PD1 immune checkpoint inhibitor antibody that disrupts the interaction of the PD1 receptor with its ligands PDL1 and PDL2, thereby inhibiting the cellular immune response (Guo et al. (2017) J Cancer 8(3):410-6). In some embodiments, the anti-PD1 antibody is nivolumab. Pembrolizumab, for example, is a potent and highly-selective humanized mAb of the IgG4/kappa isotype designed to directly block the interaction between PD1 and its ligands, PDL1 and PDL2. Pembrolizumab strongly enhances T lymphocyte immune responses in cultured blood cells from healthy human donors, cancer patients, and primates. Pembrolizumab has also been reported to modulate the level of interleukin-2 (IL-2), tumor necrosis factor alpha (TNFα), interferon gamma (IFNγ), and other cytokines. Exemplary anti-PDL1 antibodies include but are not limited to atezolizumab, avelumab, and durvalumab. Atezolizumab, for example, is an IgG1 humanized mAb that is reported to block the PD1/PDL1 interaction, by targeting the expressed PDL1 on numerous kinds of malignant cells. This blockage of the PD1/PDL1 pathway may stimulate the immune defense mechanisms against tumors (Abdin et al. (2018) Cancers (Basel) 10(2):32). In some embodiments, the anti-PDL1 antibody is atezolizumab.

In certain embodiments, the checkpoint inhibitor is targeted at PD1/PDL1, CTLA4, OX40, CD40, LAG3, TIM3, GITR, and/or KIR. In certain embodiments, the checkpoint inhibitor is targeted at CTLA4, OX40, CD40, and/or GITR. In certain embodiments, a checkpoint inhibitor is targeted with an inhibitory antibody or other similar inhibitory molecule (e.g., an inhibitory anti-CTLA4 or anti-PD1/PDL1 antibody). In certain other embodiments, a checkpoint inhibitor is targeted with an agonist for the target; examples of this class include the stimulatory targets OX40, CD40, and/or GITR. In some embodiments, the checkpoint inhibitor targeted at OX40, CD40, and/or GITR is an agonist antibody. Agonist antibodies directed against OX40 may have a dual role, inhibiting regulatory T-cell suppression, while enhancing effector T-cell functions. Agonist anti-GITR antibodies have also been shown to make effector T-cells more resistant to the inhibition induced by regulatory T-cells (Karaki et al. (2016) Vaccines (Basel) 4(4):37). Likewise, agonist CD40 antibodies demonstrate T-cell-dependent anti-tumor activity. Activation of CD40 on dendritic cells increases cross-presentation of tumor antigens and consequently the number of activated tumor-directed effector T-cells (Ellmark et al. (2015) Oncoimmunol. 4(7): e1011484).

In certain embodiments, the checkpoint inhibitor is targeted at CTLA4 (e.g., an anti-CTLA4 antibody). In certain embodiments, targeting CTLA4 facilitates priming and activation of naïve T-cells. In certain embodiments, the checkpoint inhibitor is targeted at OX40 (e.g., an anti-OX40 antibody). In certain embodiments, targeting OX40 enhances expansion of effector T-cells. In certain embodiments, the checkpoint inhibitor is targeted at CD40 (e.g., an anti-CD40 antibody). In certain embodiments, targeting CD40 inhibits "tolerogenic" priming of T-cells and/or formation of regulatory T-cells. In certain embodiments, the checkpoint inhibitor is targeted at GITR (e.g., an anti-GITR antibody). In certain embodiments, targeting GITR inhibits activity of regulatory T-cells. In certain embodiments, the benefit of combination therapy (e.g., the effect on at least one symptom or the risk/rate of disease progression) with a therapeutically effective amount of at least one compound chosen from compounds of Formula I (including Formulas IIa-e, IIIa, IVa, and Va) and/or pharmaceutically acceptable salts thereof, and a CTLA4-, OX40-, CD40-, and/or GITR-targeted agent is additive. In some embodiments, the benefit of combination therapy with a therapeutically effective amount of at least one compound chosen from compounds of Formula I (including Formulas IIa-e, IIIa, IVa, and Va) and/or pharmaceutically acceptable salts thereof, and a CTLA4-, OX40-, CD40-, and/or GITR-targeted agent is superadditive (i.e., synergistic).

Checkpoint inhibitor treatment strategies are based on the hypothesis that treatment facilitates and/or enhances priming of T-cell responses to weakly or poorly antigenic tumors (e.g., CTLA4) or that treatment restores and/or reinvigorates T-cells that respond to tumor antigens, but have become "exhausted" due to the chronic nature of the antigen presentation (e.g., PD1, PDL1) (Chen and Mellman (2013) Immunity 39(1):1-10). Examples of suitable checkpoint inhibition therapies and agents, e.g., anti-PD1, anti-PDL1, or anti-CTLA4 antibodies, are known in the art. See, e.g., WO 2001/014424 WO 2013/173223, WO 2016/007235.

Combining these primed T-cell responses following checkpoint inhibitor therapy with treatment to induce neoantigens in tumor cells (e.g., by administration of a therapeutically effective amount of at least one compound chosen from compounds of Formula I (including Formulas IIa-e, IIIa, IVa, and Va) and/or pharmaceutically acceptable salts thereof) to which the primer immune system can react may provide beneficial synergy. As compounds chosen from compounds of Formula I (including Formulas IIa-e, IIIa, IVa, and Va) and/or pharmaceutically acceptable salts thereof derived neoantigens have not yet been presented for T-cell priming, combination with a CTLA4 inhibitor may be particularly beneficial. In some embodiments, treatment comprises administering a therapeutically effective amount of at least one compound chosen from compounds of Formula I (including Formulas IIa-e, IIIa, IVa, and Va) and/or pharmaceutically acceptable salts thereof, to induce the production of neoantigens, followed before, concurrently, or thereafter by an initial administration of a CTLA4 inhibitor to stimulate CD8 T-cell priming. In some embodiments, additional administrations of an CTLA4 inhibitor are provided to the patient, e.g., to further stimulate priming and/or activation of neoantigen-reactive CD8 populations. In some embodiments, additional administrations of a therapeutically effective amount of at least one compound chosen from compounds of Formula I (including Formulas IIa-e, IIIa, IVa, and Va) and/or pharmaceutically acceptable salts thereof, can be given to the patient to increase neoantigen presentation by the tumor. Repeat administrations of a therapeutically effective amount of at least one compound chosen from compounds of Formula I (including Formulas IIa-e, IIIa, IVa, and Va) and/or pharmaceutically acceptable salts thereof, and checkpoint inhibitor therapy can occur concurrently or in staggered intervals. In some embodiments, treatment further comprises administering a PD1/PDL1 inhibitor co-treatment, e.g., to restore effector function of exhausted neoantigen-targeted T-cells within the tumor microenvironment.

The terms "combination" or "combination therapy," as used herein, refer to the administration of a therapeutically effective amount of at least one compound chosen from compounds of Formula I (including Formulas IIa-e, IIIa, IVa, and Va) and/or pharmaceutically acceptable salts thereof, together with an additional agent or therapy (e.g., a checkpoint inhibitor, a cytokine or cytokine analog, a neoantigen vaccine, CAR-T), as part of a treatment regimen intended to provide a beneficial (i.e., additive or synergistic) effect from the co-action of one or more of the administered agents. In some embodiments, the combination may also include one or more additional agents, including but not limited to chemotherapeutic agents, anti-angiogenesis agents, and agents that reduce immune-suppression (e.g., a second checkpoint inhibitor). The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks, depending upon the combination selected).

Administered "in combination" or "co-administration," as used herein, means that two or more different treatments are delivered to a subject during the subject's affliction with a medical condition (e.g., cancer or a neoplastic disorder), in any order. For example, in some embodiments, the two or more treatments are delivered after the subject has been diagnosed with a disease or disorder, and before the disease or disorder has been cured or eliminated, or when a subject is identified as being at risk but before the subject has developed symptoms of the disease. In some embodiments, the delivery of one treatment is still occurring when the delivery of the second treatment begins, so that there is overlap. In some embodiments, the first and second treatment are initiated at the same time. These types of delivery are sometimes referred to herein as "simultaneous," "concurrent," or "concomitant" delivery. In other embodiments, the delivery of one treatment ends before delivery of the second treatment begins. This type of delivery is sometimes referred to herein as "successive" or "sequential" delivery.

In some embodiments, the two treatments (e.g., at least one compound chosen from compounds of Formula I (including Formulas IIa-e, IIIa, IVa, and Va) and/or pharmaceutically acceptable salts thereof, and a checkpoint inhibitor) are comprised in the same composition. Such compositions may be administered in any appropriate form and by any suitable route. In other embodiments, the two treatments (e.g., at least one compound chosen from compounds of Formula I (including Formulas IIa-e, IIIa, IVa, and Va) and/or pharmaceutically acceptable salts thereof, and a checkpoint inhibitor) are administered in separate compositions, in any appropriate form and by any suitable route. For example, in some embodiments, a composition comprising a therapeutically effective amount of at least one compound chosen from compounds of Formula I (including Formulas IIa-e, IIIa, IVa, and Va) and/or pharmaceutically acceptable salts thereof, and a composition comprising a checkpoint inhibitor may be administered concurrently or sequentially, in any order at different points in time; in either case, they should be administered sufficiently close in time so as to provide the desired therapeutic or prophylactic effect.

In embodiments of either simultaneous or sequential delivery, treatment may be more effective because of combined administration. In some embodiments, the first treatment is more effective, e.g., an equivalent effect is seen with less of the first treatment (e.g., with a lower dose), than would be seen if the first treatment were administered in the absence of the second treatment. In some embodiments, the first treatment is more effective such that the reduction in a symptom, or other parameter associated with the disease or disorder, is greater than what would be observed with the first treatment delivered in the absence of the second treatment. In other embodiments, an analogous situation is observed with the second treatment. In some embodiments, the benefit of combination therapy (e.g., the effect on at least one symptom or the risk/rate of disease progression) is additive. In some embodiments, the benefit of combination therapy is superadditive.

In some embodiments, the present disclosure provides a method of treating cancer in a subject in need thereof and/or a subject having or suspected of having a neoplastic disorder by administering to the subject a therapeutically effective amount of at least one compound chosen from compounds of Formula I (including Formulas IIa-e, IIIa, IVa, and Va) and/or pharmaceutically acceptable salts thereof; and at least one additional therapy (e.g., a checkpoint inhibitor therapy, a cytokine or cytokine analog, a neoantigen vaccine, CAR-T). In some embodiments, administration of at least one compound chosen from compounds of Formula I (including Formulas IIa-e, IIIa, IVa, and Va) and/or pharmaceutically acceptable salts thereof, induces at least one neoantigen and/or a T-cell response. In some embodiments, administration of a therapeutically effective amount of at least one compound chosen from compounds of Formula I (including Formulas IIa-e, IIIa, IVa, and Va) and/or pharmaceutically acceptable salts thereof, induces a double-stranded RNA immune response. In some embodiments, administration of a therapeutically effective amount of at least one compound chosen from compounds of Formula I (including Formulas IIa-e, IIIa, IVa, and Va) and/or pharmaceutically acceptable salts thereof, induces immunogenic cell death. In some embodiments, the at least one additional therapy may comprise at least one, at least two, at least three, at least four, or at least five additional therapies. For example, in some embodiments, a therapeutically effective amount of at least one compound chosen from compounds of Formula I (including Formulas IIa-e, IIIa, IVa, and Va) and/or pharmaceutically acceptable salts thereof, may be administered in combination with two checkpoint therapies, i.e., using two different checkpoint inhibitors. In some other embodiments, at least one compound chosen from compounds of Formula I (including Formulas IIa-e, IIIa, IVa, and Va) and/or pharmaceutically acceptable salts thereof, may be administered in combination with a checkpoint inhibitor therapy and a neoantigen vaccine.

In some embodiments of combination therapy, the administered amount of at least one compound chosen from compounds of Formula I (including Formulas IIa-e, IIIa, IVa, and Va) and/or pharmaceutically acceptable salts thereof, and/or the at least one additional therapy is reduced by 10%, 15%, 20%, 25%, 30%, 35%, 40%, 45%, 50%, 75%, or 90%, relative to a standard dosage of at least one compound chosen from compounds of Formula I (including Formulas IIa-e, IIIa, IVa, and Va) and/or pharmaceutically acceptable salts thereof, and/or the at least one additional therapy. In some embodiments, the at least one compound chosen from compounds of Formula I (including Formulas IIa-e, IIIa, IVa, and Va) and/or pharmaceutically acceptable salts thereof, and/or the at least one additional therapy is administered at least 10%, 15%, 20%, 25%, 30%, 35%, 40%, 45%, 50%, 75%, or 90% less frequently, relative to a standard dosing regimen of the at least one compound chosen from compounds of Formula I (including Formulas IIa-e, IIIa, IVa, and Va) and/or pharmaceutically acceptable salts thereof, and/or the at least one additional therapy. In some embodiments, the administered amount and/or dosage of the at least one compound chosen from compounds of Formula I (including Formulas IIa-e, IIIa, IVa, and Va) and/or pharmaceutically acceptable salts thereof, and/or the at least one additional therapy results in lower systemic toxicity and/or improved tolerance.

In some embodiments, administration of a therapeutically effective amount of at least one compound chosen from compounds of Formula I (including Formulas IIa-e, IIIa, IVa, and Va) and/or pharmaceutically acceptable salts thereof, is initiated before administration of the at least one additional therapy. In some embodiments, administration of a therapeutically effective amount of at least one compound chosen from compounds of Formula I (including Formulas IIa-e, IIIa, IVa, and Va) and/or pharmaceutically acceptable salts thereof, is initiated after administration of the at least one additional therapy. In some embodiments, administration of a therapeutically effective amount of at least one compound chosen from compounds of Formula I (including Formulas IIa-e, IIIa, IVa, and Va) and/or pharmaceutically acceptable salts thereof, is initiated concurrently with administration of the at least one additional therapy.

In some embodiments, administration of a therapeutically effective amount of at least one compound chosen from compounds of Formula I (including Formulas IIa-e, IIIa, IVa, and Va) and/or pharmaceutically acceptable salts thereof, is repeated at least once after initial administration. In some embodiments, the amount of the at least one compound chosen from compounds of Formula I (including Formulas IIa-e, IIIa, IVa, and Va) and/or pharmaceutically acceptable salts thereof, used for repeated administration is reduced relative to the amount used for initial administration. In some embodiments, the amount of the at least one compound chosen from compounds of Formula I (including Formulas IIa-e, IIIa, IVa, and Va) and/or pharmaceutically acceptable salts thereof, used for repeated administration is reduced relative to a standard dosage of the at least one compound chosen from compounds of Formula I (including Formulas IIa-e, IIIa, IVa, and Va) and/or pharmaceutically acceptable salts thereof. In some embodiments, the amount of the at least one compound chosen from compounds of Formula I (including Formulas IIa-e, IIIa, IVa, and Va) and/or pharmaceutically acceptable salts thereof, used for repeated administration is reduced by 10%, 15%, 20%, 25%, 30%, 35%, 40%, 45%, 50%, 75%, or 90%, relative to a standard dosage of the at least one compound chosen from compounds of Formula I (including Formulas IIa-e, IIIa, IVa, and Va) and/or pharmaceutically acceptable salts thereof.

In some embodiments, administration of the at least one additional therapy is repeated at least once after initial administration. In some embodiments, the amount of the at least one additional therapy used for repeated administration is reduced relative to the amount used for initial administration. In some embodiments, the amount of the at least one additional therapy used for repeated administration is reduced relative to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, relative to a standard dosage of the at least one additional therapy.

In some embodiments, repeated administration of a therapeutically effective amount of at least one compound chosen from compounds of Formula I (including Formulas IIa-e, IIIa, IVa, and Va) and/or pharmaceutically acceptable salts thereof, is concurrent with repeated administration of the at least one additional therapy. In some embodiments, repeated administration of a therapeutically effective amount of at least one compound chosen from compounds of Formula I (including Formulas IIa-e, IIIa, IVa, and Va) and/or pharmaceutically acceptable salts thereof, is sequential or staggered with repeated administration of the at least one additional therapy.

In some embodiments, the present disclosure provides a method of treating cancer in a subject in need thereof and/or a subject having or suspected of having a neoplastic disorder by administering to the subject a therapeutically effective amount of at least one compound chosen from compounds of Formula I (including Formulas IIa-e, IIIa, IVa, and Va) and/or pharmaceutically acceptable salts thereof; and a checkpoint inhibitor therapy. In some embodiments, the checkpoint inhibitor therapy comprises administering at least one checkpoint inhibitor. In some embodiments, the subject is intolerant, non-responsive, or poorly responsive to the at least one checkpoint inhibitor when administered alone. In some embodiments, a subject may be considered non-responsive or poorly responsive to the at least one checkpoint inhibitor as determined using, e.g., the immune-related Response Criteria (irRC) and/or the immune-related Response Evaluation Criteria in Solid Tumors (irRECIST). See, e.g., Wolchok et al. (2009) Clin Cancer Res. 15(23): 7412-20; Bohnsack et al. "Adaptation of the Immune-Related Response Criteria:irRECIST" (Abstract 4958) ESMO 2014. Exemplary criteria may include those used in the art to define when tumors in cancer patients improve ("respond"), remain the same ("stabilize"), or worsen ("progress") during treatment, when the treatment being evaluated is an immune-oncology drug (e.g., a checkpoint inhibitor). In some embodiments, a subject may be considered intolerant to the at least one checkpoint inhibitor if the subject presents with one or more than one adverse (grade 2+) event identified for the respective checkpoint inhibitor (e.g., ipilimumab). In some embodiments, for example, a subject may be considered intolerant to ipilimumab treatment if the subject presents with one or more adverse events chosen from enterocolitis, hepatitis, dermatitis (including toxic epidermal necrolysis), neuropathy, and endocrinopathy (Yervoy® (ipilimumab) FDA Label Supplement, 2018).

In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is targeted with an inhibitory antibody or other similar inhibitory molecule. In some other embodiments, the checkpoint inhibitor is targeted with an agonist antibody or other similar agonist molecule. In some embodiments, the checkpoint inhibitor comprises a cytotoxic T-lymphocyte-associated antigen 4 pathway (CTLA4) inhibitor. In some embodiments, the CTLA4 inhibitor is an anti-CTLA4 antibody. In some embodiments, the anti-CTLA4 antibody is ipilimumab. In some embodiments, the checkpoint inhibitor comprises a programmed death-1 pathway (PD1) inhibitor. In some embodiments, the PD1 inhibitor is an anti-PD1 antibody. In some embodiments, the anti-PD1 antibody is nivolumab. In some embodiments, the PD1 inhibitor is an anti-PDL1 antibody. In some embodiments, the anti-PDL1 antibody is atezolizumab. In some embodiments, the checkpoint inhibitor comprises a CTLA4 inhibitor and a PD1 inhibitor. In some embodiments, the checkpoint inhibitor is targeted at OX40. In some embodiments, the checkpoint inhibitor is targeted at CD40. In some embodiments, the checkpoint inhibitor is targeted at GITR. In some embodiments, the benefit of combination therapy (e.g., the effect on at least one symptom or the risk/rate of disease progression) with a therapeutically effective amount of at least one compound chosen from compounds of Formula I (including Formulas IIa-e, IIIa, IVa, and Va) and/or pharmaceutically acceptable salts thereof, and a checkpoint inhibitor (e.g., a CTLA4-, PD1/PDL1-, OX40-, CD40-, and/or GITR-targeted antibody or molecule) is additive. In some embodiments, the benefit of combination therapy with a therapeutically effective amount of at least one compound chosen from compounds of Formula I (including Formulas IIa-e, IIIa, IVa, and Va) and/or pharmaceutically acceptable salts thereof, and a checkpoint inhibitor (e.g., a CTLA4-, PD1/PDL1, OX40-, CD40-, and/or GITR-targeted antibody or molecule) is superadditive (i.e., synergistic).

In some embodiments, the present disclosure provides a method of treating cancer in a subject in need thereof and/or a subject having or suspected of having a neoplastic disorder by administering to the subject a therapeutically effective amount of at least one compound chosen from compounds of Formula I (including Formulas IIa-e, IIIa, IVa, and Va) and/or pharmaceutically acceptable salts thereof; and a cytokine or cytokine analog therapy. In some embodiments, the cytokine or cytokine analog therapy comprises administering at least one cytokine or cytokine analog. In some embodiments, the subject is intolerant, non-responsive, or poorly responsive to the at least one cytokine or cytokine analog when administered alone.

In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of a therapeutically effective amount of at least one compound chosen from compounds of Formula I (including Formulas IIa-e, IIIa, IVa, and Va) and/or pharmaceutically acceptable salts thereof, due to induction and presentation of neoantigens.

In some embodiments, the cytokine or cytokine analog comprises IL-2. In some embodiments, IL-2 boosts signals to effector cells promoting their expansion (Rosenberg (2014) J Immunol. 192(12):5451-8). In some embodiments, the cytokine or cytokine analog comprises IL-10. In some embodiments, IL-10 boosts CD8+ T-cell priming and activation (Mumm et al. (2011) Cancer Cell 20(6):781-96). In some embodiments, the cytokine or cytokine analog comprises IL-12. In some embodiments, IL-12 links the innate and adaptive immune responses to boost antigen-specific priming and targeting (Tugues et al. (2015) Cell Death Differ. 22(2):237-46). In some embodiments, the cytokine or cytokine analog comprises IL-15. In some embodiments, IL-15 boosts T-effector (CD8) cell priming and/or activation. In some embodiments, the cytokine or cytokine analog comprises IFNγ. In some embodiments, IFNγ supplements T-effector cell secretion of IFNγ. In some embodiments, the cytokine or cytokine analog comprises TNFα. In some embodiments, TNFα supplements T-effector cell secretion of TNFα.

In some embodiments, an initial dose of a therapeutically effective amount of at least one compound chosen from compounds of Formula I (including Formulas IIa-e, IIIa, IVa, and Va) and/or pharmaceutically acceptable salts thereof, is administered to a subject to trigger aberrant splicing and production of neoantigen peptides. After a period of to allow for protein production and antigen presentation, in some embodiments, the subject is then administered an initial dose of a cytokine or cytokine analog to boost and/or enhance effector T-cell priming and expansion. In some embodiments, the wait period between doses of the at least one compound chosen from compounds of Formula I (including Formulas IIa-e, IIIa, IVa, and Va) and/or pharmaceutically acceptable salts thereof, and cytokine or cytokine analog is about 2, about 3, about 4, about 5, about 6, or about 7 days. In some embodiments, the wait period is between about 3 days and about 5 days. In some embodiments, the cytokine or cytokine analog is IL-2, IL-10, IL-12, IL-15, IFNγ, and/or TNFα. In some embodiments, the combination therapeutic benefit of the at least one compound chosen from compounds of Formula I (including Formulas IIa-e, IIIa, IVa, and Va) and/or pharmaceutically acceptable salts thereof, and a cytokine or cytokine analog may be additive or superadditive.

In some embodiments, after a period to allow for T-cell priming and expansion, the subject is then administered a second or subsequent dose of a therapeutically effective amount of at least one compound chosen from compounds of Formula I (including Formulas IIa-e, IIIa, IVa, and Va) and/or pharmaceutically acceptable salts thereof, to trigger re-presentation of neoantigen peptides. In some embodiments, the wait period between an initial dose of a cytokine or cytokine analog and a second or subsequent dose of a therapeutically effective amount of at least one compound chosen from compounds of Formula I (including Formulas IIa-e, IIIa, IVa, and Va) and/or pharmaceutically acceptable salts thereof, is about 2, about 3, about 4, or about 5 weeks. In some embodiments, the wait period is about 3 weeks. In some embodiments, subsequent doses of the cytokine or cytokine analog may be administered, e.g., interspersed between subsequent doses of a therapeutically effective amount of at least one compound chosen from compounds of Formula I (including Formulas IIa-e, IIIa, IVa, and Va) and/or pharmaceutically acceptable salts thereof. Following a second or subsequent dose of a therapeutically effective amount of at least one compound chosen from compounds of Formula I (including Formulas IIa-e, IIIa, IVa, and Va) and/or pharmaceutically acceptable salts thereof, in some embodiments, the immune system may engage with the neoantigen-presenting tumor cells and/or elicit tumor cell killing. In some embodiments, dosing of a therapeutically effective amount of at least one compound chosen from compounds of Formula I (including Formulas IIa-e, IIIa, IVa, and Va) and/or pharmaceutically acceptable salts thereof, following this exemplary initial treatment regimen can be pulsatile, i.e., the at least one compound chosen from compounds of Formula I (including Formulas IIa-e, IIIa, IVa, and Va) and/or pharmaceutically acceptable salts thereof, may be dosed at prolonged intervals (e.g., about every 4 weeks, about every 5 weeks, about every 6 weeks) to allow for antigen presentation, T-cell engagement and/or tumor cell killing, and/or recovery of the memory T-cell population.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is chosen from a B-cell malignancy, a leukemia, a lymphoma, and a myeloma. In some embodiments, the hematological malignancy is chosen from acute myeloid leukemia and multiple myeloma. In some embodiments, the solid tumor is chosen from breast cancer, gastric cancer, prostate cancer, ovarian cancer, lung cancer, uterine cancer, salivary duct carcinoma, melanoma, colon cancer, and esophageal cancer. In some embodiments, the solid tumor is chosen from HER2-positive breast cancer, gastric adenocarcinoma, and prostate cancer.

In some embodiments, the subject is in need of a method of treating cancer. In some embodiments, the cancer is a hematological malignancy or a solid tumor. In some embodiments, the hematological malignancy is chosen from a B-cell malignancy, a leukemia, a lymphoma, and a myeloma. In some embodiments, the hematological malignancy is chosen from acute myeloid leukemia and multiple myeloma. In some embodiments, the solid tumor is chosen from breast cancer, gastric cancer, prostate cancer, ovarian cancer, lung cancer, uterine cancer, salivary duct carcinoma, melanoma, colon cancer, and esophageal cancer. In some embodiments, the solid tumor is chosen from HER2-positive breast cancer, gastric adenocarcinoma, and prostate cancer. In some embodiments, a patient having a cancer as described herein can be treated with a combination of at least one compound chosen from compounds of Formula I (including Formulas IIa-e, IIIa, IVa, and Va) and/or pharmaceutically acceptable salts thereof and a neoantigen vaccine. Without being bound by theory, vaccines, used alone or in combination with immune checkpoint inhibitor (ICI) molecules, have shown promise in early trials (Ott et al. (2017) Nature 547(7662):217-21; Sahin et al. (2017) Nature 547(7662): 222-6), but generally require sequencing of patient tumor mutations (Ott et al. (2017) Nature 547(7662):217-21; Aldous and Dong (2018) Bioorg. Med. Chem. 26(10):2842-9). As such, vaccines are often dependent on sufficient numbers of non-synonymous mutations that are antigenic. In general, tumors with very low mutation burden provide few candidate antigens, and those with rapid growth provide limited time to identify and produce patient-specific vaccines.

To date, attempts to develop vaccines that would be broadly immunogenic across a large percentage of patients have focused on proteins that are either frequently mutated, ectopically overexpressed, or amplified, and/or that exist as "self" proteins within the organism. In addition, these proteins are often expressed in immunologically restricted tissues (e.g., neuronal markers expressed in neuroendocrine tumor types), while others may be normally expressed during embryogenesis (e.g., oncofetal antigens). Thus, utility of vaccines using such proteins as antigens is often limited to specific tumor lineages or subsets where one or more of the antigens are presented. Vaccine utility would also need to be confirmed by sequencing of patient tumor samples, which can be time-consuming.

Moreover, if these antigens exist as "self" proteins, the immune system would likely be primed to recognize these as "self" and thus, not respond. Or, alternatively, if the immune system is able to mount an effector response to these antigens, it may lead to on-target side effects in tissues where the antigen may be expressed. In both of these cases, one of the key challenges is that most antigenic peptides are derived from "passenger" genes (i.e., genes that are mutated or amplified in the course of tumorigenesis, but that do not play a critical role in the continued survival or proliferation of the tumor itself). As such, these genes may be silenced without significant consequence to the tumor progression, and thus would allow a tumor to "escape" an immune response against these antigens. Without wishing to be bound by theory, this mechanism may play a role in tumor evolution, where random mutations that are strongly antigenic are often "selected against" by the tumor during the early stages of tumorigenesis (Dunn et al. (2004) Annu. Rev. Immunol. 22:329-60).

In addition, certain evidence also indicates that chronic antigen presentation and immune stimulation may lead to immune cell anergy and exhaustion (Pardoll (2012) Nat. Rev. Cancer 12(4):252-64). These phenotypes underlie the therapeutic rationale behind current ICI treatments, as ICI has been shown to either repress the exhausted immune cell phenotype (α-PD1/PD-L1) or to facilitate additional immune cell responses (α-CTLA4). Notably, with α-CTLA4 therapy, a certain subset of patients have been reported to exhibit severe immune-related adverse events that may be ascribed to the promotion of T-cell activation and a break of the immune tolerance mechanisms that restrain self-reactive immune responses.

Both of these approaches (i.e., triggering or enhancing de novo immune responses to neoantigens or derepressing the anergy or exhaustion of existing immune responses) are linked to a chronic immune activation. As such, these approaches are sensitive to anergy, editing, and other tumor-mediated mechanisms designed to suppress immune engagement.

In contrast, treatment with at least one compound chosen from compounds of Formula I (including Formulas IIa-e, IIIa, IVa, and Va) and/or pharmaceutically acceptable salts thereof may induce an immune response to novel sequences representing neoantigens. In some embodiments, presentation of neoantigens provides the adaptive immune system with more divergent targets with which to engage and activate. In some embodiments, the ability of at least one compound chosen from compounds of Formula I (including Formulas IIa-e, IIIa, IVa, and Va) and/or pharmaceutically acceptable salts thereof to acutely induce alternative splicing and the resulting neoantigens may reduce the risk of immune system fatigue due to chronic exposure to mutation-driven neoantigens and/or limit the ability of tumor cells to adapt to evade therapy. In some embodiments, administering at least one compound chosen from compounds of Formula I (including Formulas IIa-e, IIIa, IVa, and Va) and/or pharmaceutically acceptable salts thereof in combination with a neoantigen vaccine enhances the immune response to the neoantigens produced by the at least one compound chosen from compounds of Formula I (including Formulas IIa-e, IIIa, IVa, and Va) and/or pharmaceutically acceptable salts thereof. In some embodiments, the at least one compound chosen from compounds of Formula I (including Formulas IIa-e, IIIa, IVa, and Va) and/or pharmaceutically acceptable salts thereof is administered before, during, or after vaccination. In some embodiments, the at least one compound chosen from compounds of Formula I (including Formulas IIa-e, IIIa, IVa, and Va) and/or pharmaceutically acceptable salts thereof and/or vaccine may be administered once or more than once during the course of treatment. In some embodiments, the vaccine is administered once and the at least one compound chosen from compounds of Formula I (including Formulas IIa-e, IIIa, IVa, and Va) and/or pharmaceutically acceptable salts thereof is administered more than once during the course of treatment. In some embodiments, the vaccine is administered once and then one or more boosters are administered during the course of treatment.

As used herein, the term "neoantigen vaccine" refers to a pooled sample of one or more immunogenic neoantigen peptides or mRNAs, for example at least two, at least three, at least four, at least five, or more neoantigen peptides. The term "vaccine" refers to a composition for generating immunity for the prophylaxis and/or treatment of a disease (e.g., a neoplastic disorder, e.g., a hematological malignancy or solid tumor). Accordingly, vaccines are medicaments which comprise immunogenic agents and are intended to be used in humans or animals for generating specific immune defenses and protective substances after vaccination. A neoantigen vaccine can additionally include a pharmaceutically acceptable carrier, diluent, excipient, and/or adjuvant.

As used herein, the term "immunogenic" refers to any agent or composition that can elicit an immune response, e.g., a T-cell response. The immune response can be antibody- or cell-mediated, or both.

In some embodiments, a patient is given at least one compound chosen from compounds of Formula I (including Formulas IIa-e, IIIa, IVa, and Va) and/or pharmaceutically acceptable salts thereof and then given a peptide or mRNA vaccine of known neoantigen to enhance immune response to the neoantigens produced by the at least one compound chosen from compounds of Formula I (including Formulas IIa-e, IIIa, IVa, and Va) and/or pharmaceutically acceptable salts thereof. In some other embodiments, a patient is given at least one compound chosen from compounds of Formula I (including Formulas IIa-e, IIIa, IVa, and Va) and/or pharmaceutically acceptable salts thereof and screened for neoantigens produced by the treatment. Subsequently, one or more of those neoantigens are used to create a personalized vaccine that is given to the patient. In either of these embodiments, the at least one compound chosen from compounds of Formula I (including Formulas IIa-e, IIIa, IVa, and Va) and/or pharmaceutically acceptable salts thereof and/or peptide or mRNA vaccine may be administered to the patient once or repeatedly.

In some embodiments, a suitable neoantigen for a vaccine can be identified by screening a panel of transcripts with altered splicing and robust expression from one or more tissue samples in a patient (e.g., from a tumor biopsy). In some embodiments, variant protein sequences are identified in the screened sample based on translation across the aberrantly spliced mRNA junction while retaining portions of the protein sequence (up to 12 amino acids) flanking the junction-spanning amino acid changes. In some embodiments, these junction-spanning peptide fragments are scanned for high affinity binding to MHC1 alleles, e.g., using a tool such as NetMHC1 (Nielsen et al. (2003) Protein Sci 12(5):1007-17; Andreatta and Neilsen (2016) Bioinformatics 32(4):511-7). These results allow for filtering of the neopeptides to those that are predicted high affinity binders for a unique patient HLA allele makeup as well as assembly of pools of neopeptides predicted to be broadly binding to HLA alleles that are present with high frequencies in different populations (Maiers et al. (2007) Hum Immunol 68(9):779-88). In some embodiments, the identified neopeptides are then formulated as a vaccine, e.g., by conjugation to a suitable carrier or adjuvant (Ott et al. (2017) Nature 547(7662):217-21), or for delivery as an mRNA (Sahin et al. (2017) Nature 547(7662):222-6).

In some embodiments, the selected neoantigen is based on a screen of an individual patent's tumor response to the at least one compound chosen from compounds of Formula I (including Formulas IIa-e, IIIa, IVa, and Va) and/or pharmaceutically acceptable salts thereof to identify one or more neoantigens resulting from treatment to use in subsequent vaccination. In other embodiments, a neoantigen is chosen, e.g., based on screening a panel of samples from different patients to identify common neoantigens produced by the at least one compound chosen from compounds of Formula I (including Formulas IIa-e, IIIa, IVa, and Va) and/or pharmaceutically acceptable salts thereof and then used as a universal vaccine for future patients.

Without being bound by theory, in some embodiments, use of a universal neoantigen vaccine would avoid the need to sequence and analyze the unique mutation status of each patient's tumor because the chosen neoantigens are not dependent on tumor mutation but rather mimic a neoantigen produced by at least one compound chosen from compounds of Formula I (including Formulas IIa-e, IIIa, IVa, and Va) and/or pharmaceutically acceptable salts thereof and generally recognized by the body as foreign. In addition, in some embodiments, use of a neoantigen vaccine may be particularly effective since a patient's tumor cells may be more likely to mutate away from producing one or more neoantigens that are dependent on tumor mutation, as compared to those that mimic a neoantigen produced by at least one compound chosen from compounds of Formula I (including Formulas IIa-e, IIIa, IVa, and Va) and/or pharmaceutically acceptable salts thereof. This may allow for the formulation of a bulk vaccine that would be broadly immunogenic across a large percentage of patients, expediting the initiation of a treatment regime. Patients may be vaccinated according to the schedules outlined herein and, prior to following completion of the vaccination, could be further treated with at least one compound chosen from compounds of Formula I (including Formulas IIa-e, IIIa, IVa, and Va) and/or pharmaceutically acceptable salts thereof, e.g., to induce expression of the neoantigen peptides. In some embodiments, patients may be administered at least one compound chosen from compounds of Formula I (including Formulas IIa-e, IIIa, IVa, and Va) and/or pharmaceutically acceptable salts thereof before, at the same time as, or after vaccination. In some embodiments, patients are administered at least one compound chosen from compounds of Formula I (including Formulas IIa-e, IIIa, IVa, and Va) and/or pharmaceutically acceptable salts thereof, screened for one or more neoantigens found in a panel of universal neoantigens, and vaccinated with a universal neoantigen vaccine comprising at least one universal neoantigen identified in the subject. In some embodiments, patients may be administered at least one compound chosen from compounds of Formula I (including Formulas IIa-e, IIIa, IVa, and Va) and/or pharmaceutically acceptable salts thereof once or more than once after vaccination. The compound(s) chosen from compounds of Formula I (including Formulas IIa-e, IIIa, IVa, and Va) and/or pharmaceutically acceptable salts thereof and/or the vaccine may be administered once or more than once during the course of treatment.

In some embodiments, a vaccine may comprise one or more than one neoantigen peptide or mRNA. In some embodiments, a vaccine may comprise one or more than one long neoantigen peptide. Such "long" neoantigen peptides, in some embodiments, undergo efficient internalization, processing, and cross-presentation in professional antigen-presenting cells such as dendritic cells. Similarly, long vaccine peptides have been shown, in other contexts, to induce cytotoxic T-cells in humans (Melief and van der Burg (2008) Nat Rev Cancer 8(5):351-60). In some embodiments, a neoantigen peptide is extended to comprise the neoantigen peptide sequence itself in addition to flanking amino acid sequences. In some embodiments, the extended peptide sequence facilitates the uptake of protein by antigen-presenting cells, e.g., dendritic cells. In some embodiments, the extended peptide sequence enables efficient antigen presentation and T-cell priming in models with different HLA isotypes. In some embodiments, a longer neoantigen peptide and/or extended peptide sequence exhibits increased uptake by antigen-presenting cells (e.g., dendritic cells), increased antigen presentation, and/or increased T-cell priming, as compared to a shorter neoantigen peptide and/or shorter peptide sequence (e.g., a peptide sequence less than about 10 or less than about 5 amino acids in length). In some embodiments, a long neoantigen peptide ranges from about 5 to about 50 amino acids in length. In some embodiments, a long neoantigen peptide ranges from about 10 to about 50 amino acids in length. In some embodiments, the at least one neoantigen peptide ranges from about 10 to about 35 amino acids in length. In some embodiments, a long neoantigen peptide ranges from about 15 to about 25 amino acids in length.

In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 3).

Amino acid sequences of exemplary long neoantigen peptides are set forth in Table 3.

These exemplary neoantigen peptides are generated after administration of ADCs containing pladienolide splicing modulators, however, given the similar mechanism of action (i.e., similar mechanisms of splicing modulation), similar neoantigen peptides may be produced by compounds chosen from compounds of Formula I (including Formulas IIa-e, IIIa, IVa, and Va) and/or pharmaceutically acceptable salts thereof.

TABLE 2

Neopeptides

| | Neopeptide | SEQ ID NO | Junction (HG19) | Gene | Event type | Observed in |
|---|---|---|---|---|---|---|
| 1 | SPTLPPRSL | 1 | chr12:49663470-49663610:+ | TUBA1C | Intron retention | H1568 |
| 2 | HPSIKRGLSSL | 2 | chr12:42729776-42781257:+ | PPHLN1 | Exon skipping | H1568 |
| 3 | LLLPHHVL | 3 | chr12:49663470-49663610:+ | TUBA1C | Intron retention | H1568 |

TABLE 2-continued

| Neopeptides | | | | | |
|---|---|---|---|---|---|
| Neopeptide | SEQ ID NO | Junction (HG19) | Gene | Event type | Observed in |
| 4 RTAPGVRPPF | 4 | chr14:35182767-35183743:- | CFL2 | Intron retention | H1568 |
| 5 RPQKSIQAL | 5 | chr10:28822963-28823162:+ | WAC | Intron retention | H1568 |
| 6 APAPPPLPA | 6 | chr17:80009840-80011149:+ | GPS1 | Intron retention | H1568 |
| 7 RPRPSFPVSL | 7 | chr7:55087058-55134942:+ | EGFR | Intron retention | H1568 |
| 8 RPKHGDGFSL | 8 | chr11:57472287-57472444:- | MED19 | Intron retention | H1568 |
| 9 GPAPGKTGL | 9 | chr7:75932393-75933118:+ | HSBP1 | Intron retention | H1568 |
| 10 EAARKGNSL | 10 | chr1:53480715-53504588:+ | SCP2 | Exon skipping | H1568 |
| 11 RIKEKIEEL | 11 | chr9:72897499-72912881:+ | SMC5 | Exon skipping | H1568 |
| 12 EIKKRFRQF | 12 | chr1:28531860-28541450:- | DNAJC8 | Exon skipping | H1568 |
| 13 HESAAMAET | 13 | chr11:102272937-102323254:- | TMEM123 | Exon skipping | HCC1954 |
| 14 ALKLKQVGV | 14 | chr1:153610924-153617539:+ | CHTOP | Exon skipping | H1568 |
| 15 DLKKRHITF | 15 | chr13:41323417-41331008:- | MRPS31 | Exon skipping | H1568 |
| 16 DVKRNDIAM | 16 | chr1:41213277-41218822:+ | NFYC | Exon skipping | H1568 |
| 17 IPSDHILTPA | 17 | chr6:149718900-149720239:+ | TAB2 | Exon skipping | H1568 |
| 18 TVFSTSSLK | 18 | chr11:61197654-61213412:+ | SDHAF2 | Exon skipping | H1568 |
| 19 ITSCLLNF | 19 | chr5:137892555-137893090:- | HSPA9 | Intron retention | H1568 |
| 20 RASPVRGQL | 20 | chr7:75677544-75677893:+ | MDH2 | Intron retention | H1568 |
| 21 VVRKPVIAL | 21 | chr1:36923582-36929406:- | MRPS15 | Exon skipping | H1568 |
| 22 LLSEKKKIS | 22 | chr6:31750622-31750872:- | VARS | Intron retention | H1568 |
| 23 APASKPRPRL | 23 | chr19:3573798-3574380:+ | HMG20B | Intron retention | H1568 |
| 24 RYGQLSEKF | 24 | chr19:33076813-33078158:+ | PDCD5 | Exon skipping | HCC1954 |
| 25 VYISNVSKL | 25 | chr3:53920961-53925796:- | SELK | Exon skipping | HCC1954 |
| 26 LPTKETPSF | 26 | chr2:85133241-85133394:+ | TMSB10 | Alt 3'ss | HCC1954 |
| 27 GEAPPPPPA | 27 | chr17:80223672-80231181:- | CSNK1D | Intron retention | HCC1954 |
| 28 LEEISKQEI | 28 | chr17:27804724-27807385:+ | TAOK1 | Exon skipping | HCC1954 |
| 29 IYNHITVKI | 29 | chr4:2886393-2896308:+ | ADD1 | Exon skipping | HCC1954 |

The protein sequences of the twenty nine neopeptides listed in Table 2 can be extended. The extended protein sequence incorporates both the neopeptide sequence itself in addition to flanking amino acid sequences. The extended protein sequence better facilitates the uptake of protein by dendritic cells and enables antigen presentation and T-cell priming in models with different HLA isotypes. Amino acid sequences of the twenty nine extended neopeptides are set forth in Table 3.

TABLE 3

| Amino acid sequences of extended neopeptides | | |
|---|---|---|
| Gene | SEQ ID NO | Extended neopeptide amino acid sequence* |
| TUBA1C | 30 | VDLEPTVIGELTSVTQVRSQGAGTGGLSWGGSAGHSPTLPPRSLSL LLLPHHVLQMKFALALTASSSTLSNSSQARKMLPITMPEGTTPLA RRSLTSCWTEFASWLTSAPVFRASWFSTALVGELVLGSPRCSWNV SQLIMARSPSWSSPFTRRPRFPQL |

TABLE 3-continued

Amino acid sequences of extended neopeptides

| Gene | SEQ ID NO | Extended neopeptide amino acid sequence* |
|---|---|---|
| PPHLN1 | 31 | APPRSHPSIKRGLSSL |
| CFL2 | 32 | MVRRARWPGGRGEARKAPRTAPGVRPPF |
| WAC | 33 | WVNCLFVSGRAAAGGGGGGAVPPYLELAGPPFLLLTLIRIGLGRR SGRAGGRAGTQCGGERGPGFAAFRPLRPFRRLRVCAVCVRGSAL GRSVGLPRGGAAGAPFSSSPAPHPRRVLCRCLLFLFFSCHDRRGDS QPYQVPAEAGVEGLEGAGGGREGLLLERRPQKSIQALRCNTSETS TADPLKIPGLVPLALSSKV |
| GPS1 | 34 | MPLPVQVFNLQVTSRGRPGPPRPRAPRHWGRAEVEQGRGACARS RSGTLRAGPPRAARVGGCRAEGASPPWLRAAIGGRRAAPAPPPLP AAHGRGSRPPRR |
| EGFR | 35 | QPAQPRTGAPARRPRPRPSFPVSLRSAAPPTGTAGGTGRFVLRPGE SGAGGGGDAWDTGLQARRGTAAGTSGAPNRSQLSSLTFPAQLRR IGVSGRKPGAGGRLGPGSRTCAPRCLPRARRGPGAHPRGGRCPPA ETALFREAEEGTQKYSLPSDPAGQAAF |
| MED19 | 36 | FRLHTGPVSPVGGRRQMGRPKHGDGFSLQVCSFIMEQNG |
| HSBP1 | 37 | GVVEITGEPPCSCRGEEEASRAGRAGGVRLKRGSRGPGELNVGPA PGKTGLLIPLLRNWECGSLLRALSAL |
| SCP2 | 38 | KMGFPEAARKGNSL |
| SMC5 | 39 | LEARIKEKIEELQQALI |
| DNAJC8 | 40 | EIKKRFRQFKQAVYKQ |
| TMEM123 | 41 | AHESAAMAETLQHVPS |
| CHTOP | 42 | NRPSVQAALKLKQVGV |
| MRPS31 | 43 | KTDDLKKRHITFTLGCGIC |
| NFYC | 44 | MKLDEDVKRNDIAMAI |
| TAB2 | 45 | NSISQIPSDHILTPALFITFMTILDL |
| SDHAF2 | 46 | TVFSTSSLKLNQPQKYLKMKSWPC |
| HSPA9 | 47 | AEEDRRKKVITSCLLNFNLSKAQS |
| MDH2 | 48 | RSFSTSAQVGQTRGGLQAEAPRPGPRASPVRGQL |
| MRPS15 | 49 | RGYVVRKPVIALSVKI |
| VARS | 50 | VDMDFGTGGQGAGPVGRGKDWSCTLAVHLLSEKKKISFSQIDRA WGGSQGTVLDKWGPGVVSELHPSAKEVSVGRNSVESLMTWAS |
| HMG20B | 51 | EKGSHEEEVRVPALSWGRPRAPAPASKPRPRLDLNCLWLRPQPIF LWKLRPRPVPAATPLTGPLPL |
| PDCD5 | 52 | RYGQLSEKFNRRKVMDS |
| SELK | 53 | MVYISNVSKLCFSKM |
| TMSB10 | 54 | NTLPTKETPSFLLNPHTSWVPRPHREAPRLRVGVAAPLQRPLPAL HSH |
| CSNK1D | 55 | FGDIYLGEAPPPPPAARRPGPCGCQDQARSRKEVVAPAGSPRKSR HRRIVARTQRPLG |
| TAOK1 | 56 | GSASDLLEEISKQEISF |
| ADD1 | 57 | QLIYNHITVKINLQGD |

*Underline indicates amino acids derived from the canonical transcript reading open frame (i.e., the canonical peptide sequence).

As used herein, a neoantigen peptide or mRNA vaccine encompasses using a fragment of a neoantigen peptide or its encoding mRNA, so long as that fragment retains immunogenic potential.

In some embodiments, a neoantigen vaccine comprises at least one neoantigen peptide. In some embodiments, a neoantigen vaccine comprises at least 2, at least 3, at least 4, at least 5, at least 6, at least 7, at least 8, at least 9, at least 10, at least 12, at least 15, or at least 20 neoantigen peptides. In some embodiments, the neoantigen peptide(s) range from about 5 to about 50 amino acids in length. In some embodiments, the neoantigen peptide(s) range from about 10 to about 50 amino acids in length. In some embodiments, the at least one neoantigen peptide ranges from about 10 to about 35 amino acids in length. In some embodiments, the neoantigen peptide(s) range from about 15 to about 25 amino acids in length.

In some embodiments, the present disclosure provides a method of treating a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof; and a neoantigen vaccine. A neoantigen vaccine may be, e.g., a peptide or mRNA neoantigen vaccine. In some embodiments, the at least one compound chosen from compounds of Formula I (including Formulas IIa-e, IIIa, IVa, and Va) and/or pharmaceutically acceptable salts thereof is administered before administration of the neoantigen vaccine. In some embodiments, the at least one compound chosen from compounds of Formula I (including Formulas IIa-e, IIIa, IVa, and Va) and/or pharmaceutically acceptable salts thereof is administered after administration of the neoantigen vaccine. In some embodiments, the at least one compound chosen from compounds of Formula I (including Formulas IIa-e, IIIa, IVa, and Va) and/or pharmaceutically acceptable salts thereof is administered concurrently with administration of the neoantigen vaccine. In some embodiments, administration of the at least one compound chosen from compounds of Formula I (including Formulas IIa-e, IIIa, IVa, and Va) and/or pharmaceutically acceptable salts thereof is repeated at least once after initial administration. In some embodiments, the amount of the at least one compound chosen from compounds of Formula I (including Formulas IIa-e, IIIa, IVa, and Va) and/or pharmaceutically acceptable salts thereof used for repeated administration is reduced as compared to the amount used for initial administration.

In some embodiments, the present disclosure further provides a combination comprising at least one compound chosen from compounds of Formula I (including Formulas IIa-e, IIIa, IVa, and Va) and/or pharmaceutically acceptable salts thereof; and a neoantigen vaccine (e.g., a universal neoantigen vaccine) for use in treating a subject having or suspected of having a neoplastic disorder. In some embodiments, the neoantigen vaccine is a peptide or mRNA neoantigen vaccine. In some embodiments, the combination further comprises at least one additional therapy. In some embodiments, the at least one additional therapy comprises at least one, at least two, at least three, at least four, or at least five additional therapies.

In some embodiments, the present disclosure further provides a method of treating a subject having or suspected of having a neoplastic disorder by (a) administering to the subject an effective amount of at least one compound chosen from compounds of Formula I (including Formulas IIa-e, IIIa, IVa, and Va) and/or pharmaceutically acceptable salts thereof; (b) detecting one or more neoantigens in the subject after administration of the at least one compound chosen from compounds of Formula I (including Formulas IIa-e, IIIa, IVa, and Va) and/or pharmaceutically acceptable salts thereof; (c) comparing the one or more neoantigens to a panel of universal neoantigens; and (d) administering to the subject a universal neoantigen vaccine comprising at least one universal neoantigen present in the subject. In some embodiments, the universal neoantigen vaccine is administered alone or in combination with at least one additional therapy. In some embodiments, the at least one additional therapy comprises at least one, at least two, at least three, at least four, or at least five additional therapies.

In some embodiments, the at least one additional therapy comprises repeated administration of the at least one compound chosen from compounds of Formula I (including Formulas IIa-e, IIIa, IVa, and Va) and/or pharmaceutically acceptable salts thereof. In some embodiments, repeated administration of the at least one compound chosen from compounds of Formula I (including Formulas IIa-e, IIIa, IVa, and Va) and/or pharmaceutically acceptable salts thereof is initiated before administration of the universal neoantigen vaccine. In some embodiments, repeated of the at least one compound chosen from compounds of Formula I (including Formulas IIa-e, IIIa, IVa, and Va) and/or pharmaceutically acceptable salts thereof is initiated after administration of the universal neoantigen vaccine. In some embodiments, repeated administration of the at least one compound chosen from compounds of Formula I (including Formulas IIa-e, IIIa, IVa, and Va) and/or pharmaceutically acceptable salts thereof is initiated concurrently with administration of the universal neoantigen vaccine. In some embodiments, the amount of the at least one compound chosen from compounds of Formula I (including Formulas IIa-e, IIIa, IVa, and Va) and/or pharmaceutically acceptable salts thereof used for repeated administration is reduced as compared to the amount used for initial administration. In some embodiments, the amount of the at least one compound chosen from compounds of Formula I (including Formulas IIa-e, IIIa, IVa, and Va) and/or pharmaceutically acceptable salts thereof used for the initial and/or repeated administration is reduced as compared to a standard dosage of the at least one compound chosen from compounds of Formula I (including Formulas IIa-e, IIIa, IVa, and Va) and/or pharmaceutically acceptable salts thereof when used without a vaccine treatment. In some embodiments, the amount of the at least one compound chosen from compounds of Formula I (including Formulas IIa-e, IIIa, IVa, and Va) and/or pharmaceutically acceptable salts thereof used for initial and/or repeated administration is reduced by 10%, 15%, 20%, 25%, 30%, 35%, 40%, 45%, 50%, 75%, or 90%, as compared to a standard dosage of the at least one compound chosen from compounds of Formula I (including Formulas IIa-e, IIIa, IVa, and Va) and/or pharmaceutically acceptable salts thereof.

In some embodiments, the at least one additional therapy comprises administering a checkpoint inhibitor (e.g., any of the exemplary checkpoint inhibitors described herein). In some embodiments, administration of the checkpoint inhibitor is initiated before administration of the universal neoantigen vaccine and/or repeated administration of the at least one compound chosen from compounds of Formula I (including Formulas IIa-e, IIIa, IVa, and Va) and/or pharmaceutically acceptable salts thereof. In some embodiments, administration of the checkpoint inhibitor is initiated after administration of the universal neoantigen vaccine and/or repeated of the at least one compound chosen from compounds of Formula I (including Formulas IIa-e, IIIa, IVa, and Va) and/or pharmaceutically acceptable salts thereof. In some embodiments, administration of the checkpoint inhibitor is initiated concurrently with administration of the universal neoantigen vaccine and/or repeated administration of the at least one compound chosen from compounds of Formula I (including Formulas IIa-e, IIIa, IVa, and Va) and/or pharmaceutically acceptable salts thereof. In some embodiments, administration of the checkpoint inhibitor is repeated at least once after initial administration. In some embodiments, the amount of the checkpoint inhibitor used for repeated administration is reduced as compared to the amount used for initial administration. In some embodiments, the amount of the checkpoint inhibitor used for repeated administration is reduced as compared to a standard dosage of the checkpoint inhibitor. In some embodiments, the amount of the checkpoint inhibitor used for repeated administration is reduced by 10%, 15%, 20%, 25%, 30%, 35%, 40%, 45%, 50%, 75%, or 90%, as compared to a standard dosage of the checkpoint inhibitor. In some embodiments, the subject is intolerant, non-responsive, or poorly responsive to the checkpoint inhibitor when administered alone.

Also provided herein, in some embodiments, are neoantigen vaccines comprising at least one neoantigen peptide or at least one neoantigen mRNA. In some embodiments, a neoantigen vaccine comprises at least one neoantigen peptide. In some other embodiments, a neoantigen vaccine comprises at least one neoantigen mRNA.

Also provided herein, in some embodiments, are kits comprising at least one compound chosen from compounds of Formula I (including Formulas IIa-e, IIIa, IVa, and Va) and/or pharmaceutically acceptable salts thereof; and a neoantigen vaccine (e.g., a universal neoantigen vaccine). In some embodiments, the neoantigen vaccine is a peptide or mRNA neoantigen vaccine. In some embodiments, the kit further comprises one or more additional components, including but not limited to: instructions for use; other agents, e.g., one or more additional therapeutic agents; devices, containers, or other materials for preparing the at least one compound chosen from compounds of Formula I (including Formulas IIa-e, IIIa, IVa, and Va) and/or pharmaceutically acceptable salts thereof, and/or neoantigen vaccine for therapeutic administration; pharmaceutically acceptable carriers; and devices, containers, or other materials for administering the at least one compound chosen from compounds of Formula I (including Formulas IIa-e, IIIa, IVa, and Va) and/or pharmaceutically acceptable salts thereof, and/or neoantigen vaccine to a patient. Instructions for use can include guidance for therapeutic applications including suggested dosages and/or modes of administration, e.g., in a patient having or suspected of having a neoplastic disorder. In some embodiments, the kit further contains instructions for therapeutic use, e.g., use of the at least one compound chosen from compounds of Formula I (including Formulas IIa-e, IIIa, IVa, and Va) and/or pharmaceutically acceptable salts thereof, and the neoantigen vaccine to treat or prevent a neoplastic disorder in a patient. In some embodiments, the kit further contains at least one additional therapeutic agent (e.g., for administering together with the at least one compound chosen from compounds of Formula I (including Formulas IIa-e, IIIa, IVa, and Va) and/or pharmaceutically acceptable salts thereof, and the neoantigen vaccine, e.g., a checkpoint inhibitor). In some embodiments, the at least one compound chosen from compounds of Formula I (including Formulas IIa-e, IIIa, IVa, and Va) and/or pharmaceutically acceptable salts thereof, and/or neoantigen vaccine is formulated as a pharmaceutical composition.

In some embodiments of the methods and compositions disclosed herein, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length.

In some embodiments, the at least one neoantigen peptide comprises one or more than one neoantigen sequence disclosed herein.

In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 3).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide induced in the subject by administering an effective amount of the at least one compound chosen from compounds of Formula I (including Formulas IIa-e, IIIa, IVa, and Va) and/or pharmaceutically acceptable salts thereof. In some embodiments, the at least one neoantigen peptide comprises a neoantigen sequence induced by contacting a neoplastic cell with an effective amount of the at least one compound chosen from compounds of Formula I (including Formulas IIa-e, IIIa, IVa, and Va) and/or pharmaceutically acceptable salts thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide or mRNA and a pharmaceutically acceptable carrier. In some embodiments, a neoantigen peptide or mRNA can be linked to a suitable carrier to help elicit an immune response. Exemplary carriers for linking to immunogenic agents (e.g., a neoantigen peptide or mRNA) include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers for stimulating or enhancing an immune response include cytokines such as IL-1, IL-1α and β peptides, IL-2, γINF, IL-10, GM-CSF, and chemokines, such as M1P1α and β and RANTES. Immunogenic agents can also be linked to peptides that enhance transport across tissues, as described, e.g., in WO 97/17613 and WO 97/17614. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen peptide or mRNA may be linked to the pharmaceutically acceptable carrier. Immunogenic agents can be linked to carriers by chemical crosslinking. Techniques for linking an immunogenic peptide to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described in Jansen et al. ((1982) Immun Rev. 62:185). Other bifunctional coupling agents form a thioether rather than a disulfide linkage. Many of these thioether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt. In some embodiments, the neoantigen peptide and the pharmaceutically acceptable carrier are covalently attached via a linker.

Neoantigen and other such immunogenic peptides can also be expressed as fusion proteins with carriers. The immunogenic peptide can be linked at the amino terminus, the carboxyl terminus, or at a site anywhere within the peptide (internally) to the carrier. In some embodiments, multiple repeats of the immunogenic peptide can be present in the fusion protein. In some embodiments, the neoantigen peptide and the pharmaceutically acceptable carrier are expressed as a fusion protein.

In some embodiments, the neoantigen vaccine comprises at least one neoantigen peptide or its encoding mRNA and a pharmaceutically acceptable diluent. In some embodiments, the neoantigen vaccine comprises at least one neoantigen peptide or its encoding mRNA and a pharmaceutically acceptable adjuvant (e.g., an adjuvant as described herein).

In some embodiments of the methods and compositions disclosed herein, the neoantigen vaccine comprises at least one neoantigen mRNA. In some embodiments, the at least one neoantigen mRNA encodes one or more than one neoantigen sequence.

In some embodiments, the neoantigen sequence and/or antigenic portion ranges from about 10 to about 50 amino acids in length. In some embodiments, the at least one neoantigen peptide ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 3).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen mRNA induced in the subject by administering an effective amount of the at least one compound chosen from compounds of Formula I (including Formulas IIa-e, IIIa, IVa, and Va) and/or pharmaceutically acceptable salts thereof. In some embodiments, the at least one neoantigen mRNA encodes a neoantigen sequence induced by contacting a neoplastic cell with an effective amount of the at least one compound chosen from compounds of Formula I (including Formulas IIa-e, IIIa, IVa, and Va) and/or pharmaceutically acceptable salts thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier. In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant (e.g., an adjuvant as described herein).

In some embodiments, the neoantigen mRNA is encapsulated by an encapsulating agent. In some embodiments, the encapsulating agent protects the neoantigen mRNA from degradation and improves vaccine delivery (McNamara et al. (2015) J Immunol Res. 2015:794528). In some embodiments, the encapsulating agent is a liposome. In some embodiments, the liposome is a cationic liposome such as N-[1-(2,3-dioleoloxy)propyl]-N,N,N-trimethyl ammonium chloride 1 (DOTAP). In some embodiments, the encapsulating agent is a nanoparticle. In some embodiments, the nanoparticle protects the neoantigen mRNA from nuclease degradation and/or enhances cell uptake and/or delivery efficiency. In some embodiments, the nanoparticle may be engineered to be fully degradable. In some embodiments, the nanoparticle is a biodegradable core-shell structured nanoparticle with a pH responsive poly-(b-amino ester) (PBAE) core enveloped by a phospholipid shell (Su et al. (2011) Mol Pharm. 8(3):774-87). In some embodiments, such nanoparticles are particularly efficient in delivering mRNA in vivo and eliciting an anti-tumor immune response.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, and esophageal cancer. In some embodiments, the solid tumor is selected from HER2-positive breast cancer, gastric adenocarcinoma, and prostate cancer.

As used herein, "adjuvant" refers to a substance that is capable of increasing, amplifying, or modulating an immune response to an accompanying immunogenic agent, e.g., a neoantigen peptide or mRNA. In certain embodiments, a neoantigen of the present disclosure can be administered in combination with adjuvants, i.e., substances that do not themselves cause adaptive immune responses, but amplify or modulate the response to an accompanying neoantigen. A variety of adjuvants can be used in combination with the disclosed neoantigens, in order to elicit an immune response. In some embodiments, the adjuvant(s) are chosen to augment the intrinsic response to the neoantigen without causing conformational changes in the neoantigen that would affect the qualitative form of the response. In some embodiments, the adjuvant(s) are chosen to enhance T-effector (e.g., CD8) cell priming and/or activation.

In certain embodiments, the adjuvant is an aluminum salt (alum), such as aluminum hydroxide, aluminum phosphate, and aluminum sulphate. Such adjuvants can be used with or without other specific immunostimulating agents, such as 3 de-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP)), or other bacterial cell wall components. Other adjuvants are oil-in-water emulsions and include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem) containing 2% squalene, 0.2% Tween 80, and one or more bacterial cell wall components from the group consisting of monophosphoryllipid A (MPL), trehalose dimycolate (TDM), and cell wall skeleton (CWS), for example MPL-FCWS (Detox™). In some embodiments, the adjuvant is a saponin, such as Stimulon™ (QS21) or particles generated therefrom such as ISCOMs (immunostimulating complexes) and ISCOMATRIX. Other adjuvants include Complete Freund's Adjuvant (CFA) and Incomplete Freund's Adjuvant (IFA), cytokines, such as interleukins (IL-1, IL-2, and IL-12), macrophage colony stimulating factor (M-CSF), and tumor necrosis factor (TNF).

An adjuvant can be administered with an immunogenic agent (e.g., a neoantigen peptide or mRNA) as a single composition, or can be administered before, concurrent with, or after administration of the immunogenic agent. In some embodiments, the immunogenic agent and adjuvant can be packaged and supplied in the same vial or can be packaged in separate vials and mixed before use. In some embodiments, the immunogenic agent and adjuvant can be packaged with a label, indicating the intended therapeutic application. In some embodiments, if the immunogenic agent and adjuvant are packaged separately, the packaging can include instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al. (1998) Adv Drug Deliv Rev. 32:173-186) alone or optionally in combination with any of alum, QS21, and MPL and all combinations thereof are suitable for human administration.

In some embodiments, the present disclosure further provides methods of screening for and identifying at least one neoantigen. More specifically, in some embodiments, the present disclosure provides a method of identifying at least one neoantigen by (a) contacting a neoplastic cell with an effective amount of at least one compound chosen from compounds of Formula I (including Formulas IIa-e, IIIa, IVa, and Va) and/or pharmaceutically acceptable salts thereof; (b) detecting at least one alternatively-spliced mRNA transcript after contacting the neoplastic cell with the at least one compound chosen from compounds of Formula I (including Formulas IIa-e, IIIa, IVa, and Va) and/or pharmaceutically acceptable salts thereof; (c) predicting translation of the at least one alternatively-spliced mRNA transcript into at least one peptide; and (d) comparing the at least one peptide to a reference proteome, wherein at least one neoantigen is identified if the at least one peptide does not match any peptides in the reference proteome. In some embodiments, the method further comprises contacting one or more additional neoplastic cells to identify at least one universal neoantigen. In some embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In various other embodiments, the present disclosure provides a method of identifying at least one neoantigen by (a) contacting a neoplastic cell with an effective amount of at least one compound chosen from compounds of Formula I (including Formulas IIa-e, IIIa, IVa, and Va) and/or pharmaceutically acceptable salts thereof; (b) detecting at least one peptide comprising a potential neoantigen sequence after contacting the neoplastic cell with the at least one compound chosen from compounds of Formula I (including Formulas IIa-e, IIIa, IVa, and Va) and/or pharmaceutically acceptable salts thereof; and (c) comparing the at least one peptide to a reference proteome, wherein at least one neoantigen is identified if the at least one peptide does not match any peptides in the reference proteome. In some embodiments, the method further comprises contacting one or more additional neoplastic cells to identify at least one universal neoantigen. In some embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In some embodiments of the neoantigen identification methods described herein, detecting at least one alternatively-spliced mRNA transcript comprises RNAseq. In some embodiments, predicting translation of the at least one alternatively-spliced mRNA transcript comprises quantifying the change in percent spliced in (dPSI) value for the at least one transcript. In some embodiments, predicting translation of the at least one alternatively-spliced mRNA transcript comprises RiboSeq and/or ribosomal profiling.

In some embodiments of the neoantigen identification methods described herein, the methods further comprise evaluating the at least one peptide for predicted major histocompatibility complex (MHC) binding. In some embodiments, predicted MHC binding is determined by measuring raw affinity predicted binding strength of the at least one peptide. In some embodiments, a raw affinity predicted binding strength of about 500 nM or higher indicates MHC binding. In some embodiments, predicted MHC binding is determined by identifying a distribution of predicted binding strengths for a series of random peptides; and comparing predicted binding strength of the at least one peptide to the distribution. In some embodiments, a predicted binding strength in the top 2% of the distribution indicates weak MHC binding. In some embodiments, a predicted binding strength in the top 0.5% of the distribution indicates strong MHC binding.

In some embodiments of the neoantigen identification methods described herein, the neoplastic cell is present in an in vitro cell culture. In some embodiments, the neoplastic cell is obtained from the subject. In some embodiments, the neoplastic cell is present in the subject.

Also provided herein, in some embodiments, are methods of making a neoantigen vaccine by (a) identifying at least one neoantigen (e.g., at least one neoantigen peptide or its encoding mRNA) using any of the exemplary identification methods disclosed herein; and (b) formulating the at least one neoantigen together with a pharmaceutically acceptable carrier, diluent, or adjuvant (e.g., any of the pharmaceutically acceptable carriers, diluents, or adjuvants described herein).

In some embodiments, the at least one neoantigen and/or antigenic portion ranges from about 10 to about 50 amino acids in length. In some embodiments, the at least one neoantigen peptide ranges from about 10 to about 35 amino acids in length. In some embodiments, the at least one neoantigen and/or antigenic portion ranges from about 15 to about 25 amino acids in length. In some embodiments, the at least one neoantigen and/or antigenic portion ranges from about 10 to about 20 amino acids in length. In some embodiments, the at least one neoantigen and/or antigenic portion does not exclusively overlap or consist of the canonical peptide sequence (e.g., any of the exemplary canonical peptide sequences underlined in Table 3).

In some embodiments, the at least one neoantigen used in the vaccine is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, a patient having a cancer as described herein can be treated with a combination of at least one compound chosen from compounds of Formula I (including Formulas IIa-e, IIIa, IVa, and Va) and/or pharmaceutically acceptable salts thereof and one or more engineered tumor-targeting T-cells (i.e., CAR-T). Thus, in some embodiments, the present disclosure provides a method of treating a subject having or suspected of having a neoplastic disorder by administering to the subject an effective amount of at least one compound chosen from compounds of Formula I (including Formulas IIa-e, IIIa, IVa, and Va) and/or pharmaceutically acceptable salts thereof; and engineered tumor-targeting T-cells (i.e., CAR-T). In some embodiments, a chimeric T-cell receptor can be engineered using antigen recognition sequences that are reactive with an identified neoantigen.

For instance, in some embodiments, in order to target changes in the extracellular domains of cell surface proteins induced by at least one compound chosen from compounds of Formula I (including Formulas IIa-e, IIIa, IVa, and Va) and/or pharmaceutically acceptable salts thereof, a chimeric antigen-reactive T-cell receptor (CAR) may be engineered by first identifying antibodies that recognize a cell surface-expressed neoantigen protein domain. The antigen recognition sequences of such antibodies can then be fused to a T-cell receptor domain for selective targeting and activation.

In various other embodiments, a strategy integrating the antigen presentation machinery of tumor cells together with neoantigens derived from at least one compound chosen from compounds of Formula I (including Formulas IIa-e, IIIa, IVa, and Va) and/or pharmaceutically acceptable salts thereof is employed. In some embodiments, cells containing known and frequently represented HLA alleles (e.g., HLA-A*02:01) can be treated with at least one compound chosen from compounds of Formula I (including Formulas IIa-e, IIIa, IVa, and Va) and/or pharmaceutically acceptable salts thereof and MHC1-bound neoantigens are identified by ligandomics. In some embodiments, these peptides can be used to prime and/or expand T-cells from healthy donors expressing the same HLA allele. Such T-cells, in some embodiments, can be isolated and the T-cell receptor (TCR) $\alpha$ and $\beta$ chains sequenced to identify the cognate antigen recognition/variable regions. In some embodiments, a cognate CAR can then be engineered.

In some embodiments, the CAR sequences are cloned into patient-derived T-cell populations and expanded using currently available protocols. In some embodiments, the engineered T-cells are then transfused back into the patient's circulation, before, simultaneously with, or following treatment with at least one compound chosen from compounds of Formula I (including Formulas IIa-e, IIIa, IVa, and Va) and/or pharmaceutically acceptable salts thereof. After treatment with the at least one compound chosen from compounds of Formula I (including Formulas IIa-e, IIIa, IVa, and Va) and/or pharmaceutically acceptable salts thereof, in some embodiments, the tumor cells may begin to present an antigen, e.g., an antigen targeted by the engineered T-cell population. In some embodiments, the engineered T-cell population can engage with and kill antigen presenting tumor cells.

In order that the disclosure described herein may be more fully understood, the following examples are set forth. It should be understood that these examples are for illustrative purposes only and are not to be construed as limiting this disclosure in any manner.

EXAMPLES 1-268

General:

Microwave heating was done using a Biotage Emrys Liberator or Initiator microwave. Column chromatography was carried out using a Combiflash Rf200d (Teledyne ISCO). Solvent removal was carried out using either a Buchi rotary evaporator or a Genevac centrifugal evaporator. Preparative LC/MS was conducted using a Waters autopurifier and 19×100 mm XTerra 5-micron MS C18 column under acidic mobile phase condition. NMR spectra were recorded using a Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

General methods and experimentals for preparing compounds of the present disclosure are set forth below.

The following abbreviations are used herein:

MeOH: Methanol
DMF: Dimethylformamide
LHMDS: Lithium hexamethyldisilazide
KHMDS: Potassium bis(trimethylsilyl)amide
LCMS: Liquid chromatography-mass spectrometry
MS: Mass spectrometry
HPLC: High pressure liquid chromatography
UPLC: Ultra performance liquid chromatography
LC: Liquid chromatography
$^1$H NMR: Proton nuclear magnetic resonance
TBSCl: tert-Butyldimethylsilyl chloride
THF: Tetrahydrofuran
TLC: Thin-layer chromatography
HBTU: Hexafluorophosphate benzotriazole tetramethyl uronium
TEA: Triethylamine
DCM: Dichloromethane
DMSO: Dimethylsulfoxide
ISCO: Automated chromatography (Combiflash RF200d)
Hex: Hexanes
EtOAc: Ethyl acetate
DMAP: Dimethylaminopyridine
NaOH: Sodium hydroxide
$MgSO_4$: Magnesium Sulfate
HCl: Hydrochloric acid
AcOH: Acetic acid
AIBN: 2,2'-azobisisobutyronitrile
NBS: N-bromosuccinimide
Boc: N-tert-butoxycarbonyl
TBDMS: t-butyldimethylsilyl
TBAF: Tetrabutylammonium fluoride
mCPBA: m-chloroperoxybenzoic acid Materials: The following compounds are commercially available and/or can be prepared in a number of ways well known to one skilled in the art of organic synthesis. More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions are apparent to one skilled in the art, and alternate methods are therefore indicated. The starting materials for the examples are either commercially available or are readily prepared by standard methods from known materials.

LCMS Information

Mobile phases: A (0.1% formic acid in $H_2O$) and B (0.1% formic acid in acetonitrile).

Gradient: B 5%→95% in 1.8 minutes.

Column: Acquity BEH C18 column (1.7 um, 2.1×50 mm).

U.S. Pat. Nos. 7,884,128 and 7,816,401, both entitled: Process for Total Synthesis of Pladienolide B and Pladienolide D, describe methods for synthesis of Pladienolide B and D. Synthesis of Pladienolide B and D may also be performed using methods known in the art and described in Kanada et al., "Total Synthesis of the Potent Antitumor Macrolides Pladienolide B and D," *Angew. Chem. Int. Ed.* 46:4350-4355 (2007). Kanada et al. and PCT application publication WO 2003/099813, entitled: Novel Physiologically Active Substances, describe methods for the synthesis of E7107 (Compound 45 of WO '813) from Pladienolide D (11107D of WO '813). A corresponding U.S. Pat. No. 7,550,503 to Kotake et al.

EXEMPLIFIED SYNTHESIS OF COMPOUNDS

The exemplified compounds were prepared according to either General Scheme A, involving intermediates without a hydroxyl group at the C6 position, or General Scheme B, involving intermediates with a hydroxyl group at the C6 position.

General Scheme A.

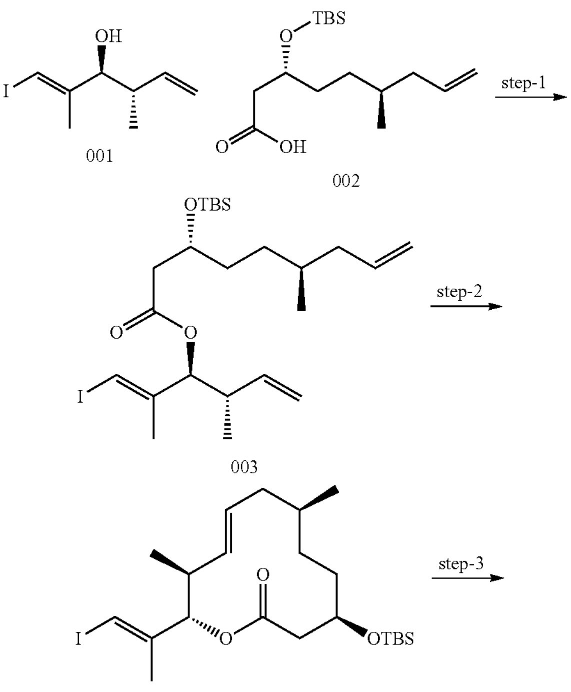

001 002 003 004

-continued

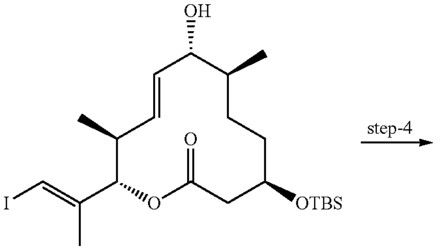

005

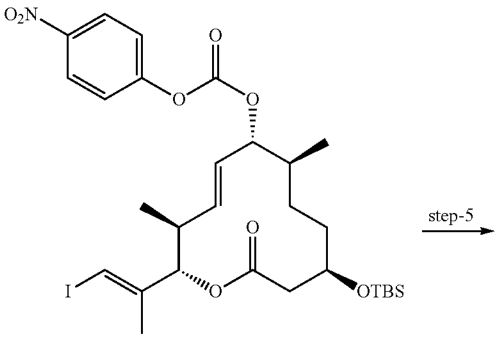

006

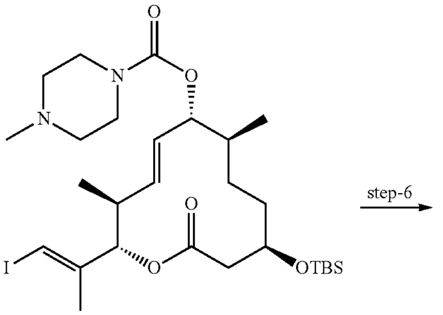

007

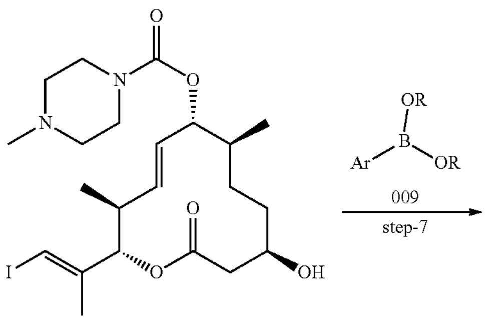

008

-continued

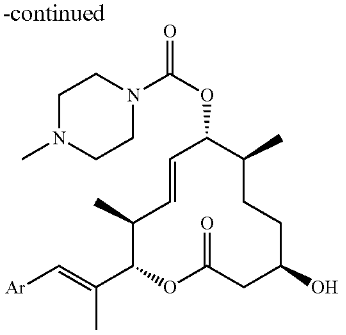

010

Step-1: To a solution of (3S,4S,E)-1-iodo-2,4-dimethylhexa-1,5-dien-3-ol (001, 5.03 g, 19.966 mmol) and (3R,6S)-3-((tert-butyldimethylsilyl)oxy)-6-methylnon-8-enoic acid (002, 5.0 g, 16.638 mmol) in dry DCM (84 ml, 1297.798 mmol), was added EDC (8.29 g, 43.26 mmol), DMAP (0.407 g, 3.328 mmol), and followed by TEA (6.96 ml, 49.915 mmol). The reaction solution was stirred at room temperature overnight. LCMS suggested full conversion of acid. The reaction was quenched with water and then extracted by DCM (3×100 ml). Combined organic layer was dried over sodium sulfate, filtered, and concentrated in vacuum. Purified crude product via ISCO on a 0-20% gradient to give product (3R,6S)-(3S,4S,E)-1-iodo-2,4-dimethylhexa-1,5-dien-3-yl 3-((tert-butyldimethylsilyl)oxy)-6-methylnon-8-enoate (003, 7.5 g, 14.03 mmol, 84% yield) as colorless oil.

Step-2: A solution of (3R,6S)-(3S,4S,E)-1-iodo-2,4-dimethylhexa-1,5-dien-3-yl 3-((tert-butyldimethylsilyl)oxy)-6-methylnon-8-enoate (002, 6.5 g, 12.159 mmol) and benzoquinone (0.066 g, 0.608 mmol) in TOLUENE (1296 ml, 9.38 mM) was degassed for 15 minutes. Then added Hoveyda-Grubbs II catalyst (0.762 g, 1.216 mmol)) and stirred at 50° C. under nitrogen for 6 hours. Reaction mixture was filtered through a celite pad, washed with excess toluene, and then concentrated. The crude reaction mixture was purified via ISCO on a 0-20% Hex:EtOAc to give product (4R,7S,11S,12S,E)-4-((tert-butyldimethylsilyl)oxy)-12-((E)-1-iodoprop-1-en-2-yl)-7,11-dimethyloxacyclododec-9-en-2-one (004, 5.71 g, 11.27 mmol, 93% yield) as off-white oil.

Step-3: (4R,7S,11S,12S,E)-4-((tert-butyldimethylsilyl)oxy)-12-((E)-1-iodoprop-1-en-2-yl)-7,11-dimethyloxacyclododec-9-en-2-one (004, 6.15 g, 11.27 mmol) was dissolved in Dioxane (520 mL) and degassed, selenium dioxide (4.05 g, 36.477 mmol) was added. The mixture was warmed to 80° C. and stirred for 5 hrs. LCMS suggested completion of reaction. The reaction mixture was diluted with ethyl acetate and washed by saturated $NaHCO_3$. Dried with Na2SO4, filtered, and concentrated in vacuo. The reaction mixture was purified via ISCO on a 0-30% Hex:EtOAc gradient to give (4R,7S,8R,11S,12S,E)-4-((tert-butyldimethylsilyl)oxy)-8-hydroxy-12-((E)-1-iodoprop-1-en-2-yl)-7,11-dimethyloxacyclododec-9-en-2-one (005, 5.5 g, 10.53 mmol).

Step-4: To a solution of (4R,7S,8R,11S,12S,E)-4-((tert-butyldimethylsilyl)oxy)-8-hydroxy-12-((E)-1-iodoprop-1-en-2-yl)-7,11-dimethyloxacyclododec-9-en-2-one (005, 2.5 g, 4.784 mmol) in DCM (0.406 g, 4.784 mmol) was added DMAP (0.117 g, 0.957 mmol), triethylamine (2.046 ml, 14.353 mmol) and 4-Nitrophenyl chloroformate (1.447 g, 7.177 mmol). The resulting yellowish suspension was stirred for 5 h. Reaction mixture was concentrated and purified via ISCO on a 0-15% Hex:EtOAc gradient to give the product (2S,3S,6R,7S,10R,E)-10-((tert-butyldimethylsilyl)oxy)-2-((E)-1-iodoprop-1-en-2-yl)-3,7-dimethyl-12-oxooxacyclododec-4-en-6-yl (4-nitrophenyl) carbonate (006, 3.15 g, 4.58 mmol, 96% yield).

Step-5: To a solution of (2S,3S,6R,7S,10R,E)-10-((tert-butyldimethylsilyl)oxy)-2-((E)-1-iodoprop-1-en-2-yl)-3,7-dimethyl-12-oxooxacyclododec-4-en-6-yl (4-nitrophenyl) carbonate (006, 2.1 g, 3.054 mmol) in DCM (0.259 g, 3.054 mmol) was added DMAP (0.373 g, 3.054 mmol) and 1-methylpiperazine (0.459 g, 4.581 mmol). The resulting yellowish suspension was stirred for 3 hrs. Reaction mixture was concentrated and applied to ISCO on a 0-15% DCM: MeOH to give the product (2S,3S,6R,7S,10R,E)-10-((tert-butyldimethylsilyl)oxy)-2-((E)-1-iodoprop-1-en-2-yl)-3,7-dimethyl-12-oxooxacyclododec-4-en-6-yl 4-methylpiperazine-1-carboxylate (007, 1.89 g, 2.91 mmol, 95% yield).

Step-6: To a solution of (2S,3S,6R,7S,10R,E)-10-((tert-butyldimethylsilyl)oxy)-2-((E)-1-iodoprop-1-en-2-yl)-3,7-dimethyl-12-oxooxacyclododec-4-en-6-yl 4-methylpiperazine-1-carboxylate (007, 1.8 g, 2.775 mmol) in methanol (0.089 g, 2.775 mmol), was added 4-methylbenzenesulfonic acid hydrate (0.528 g, 2.775 mmol) at room temperature After 2 h, the reaction was quenched with TEA (0.560 g, 5.55 mmol). Concentrate the reaction mixture and diluted in DCM 300 mL then wash by brine (3×50 mL). The organic extraction was concentrated and applied to ISCO on a 0-15% DCM:MeOH to give the product (2S,3S,6R,7S,10R,E)-10-hydroxy-2-((E)-1-iodoprop-1-en-2-yl)-3,7-dimethyl-12-oxooxacyclododec-4-en-6-yl 4-methylpiperazine-1-carboxylate (008, 1.4 g, 2.62 mmol, 94% yield).

Step-7: To a solution of (2S,3S,6R,7S,10R,E)-10-hydroxy-2-((E)-1-iodoprop-1-en-2-yl)-3,7-dimethyl-12-oxooxacyclododec-4-en-6-yl 4-methylpiperazine-1-carboxylate (009, 15.0 mg, 0.029 mmol) and aryl boronic acid (010, 0.035 mmol) was added silver oxide (19 mg, 0.086 mmol) and Pd(0) (3.3 mg, 0.003 mmol). The mixture was heated to 60° C. for 5 h. LCMS suggested full conversion of 009. The mixture was cooled, filtered through a short plug of celite and concentrated. The crude reaction mixture was applied to ISCO on a 0-10% DCM:MeOH to give products (010, 0.019 mmol, 68.4% yield).

General Scheme B.

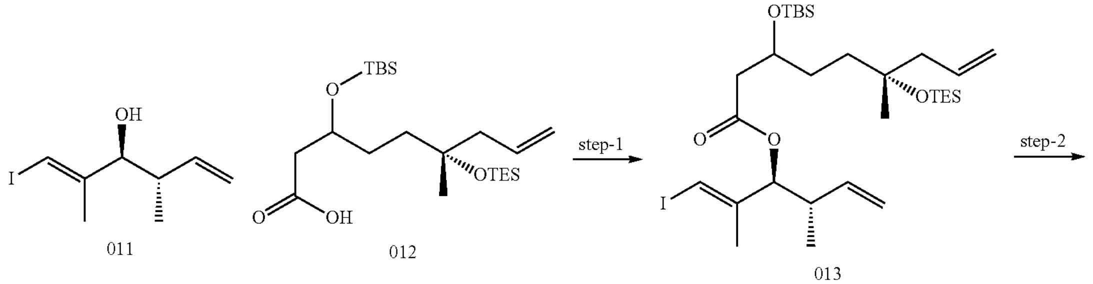

011 012 013

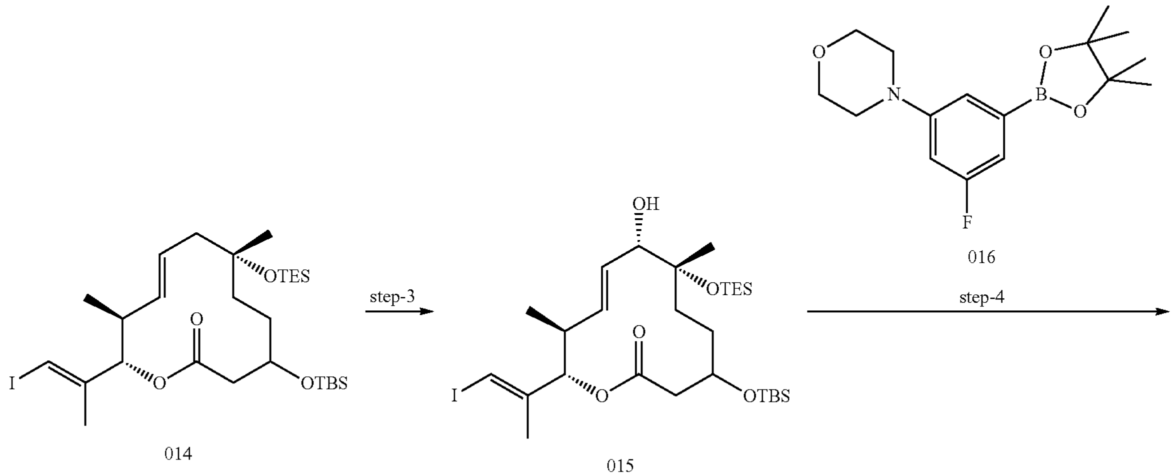

014 015 016

-continued

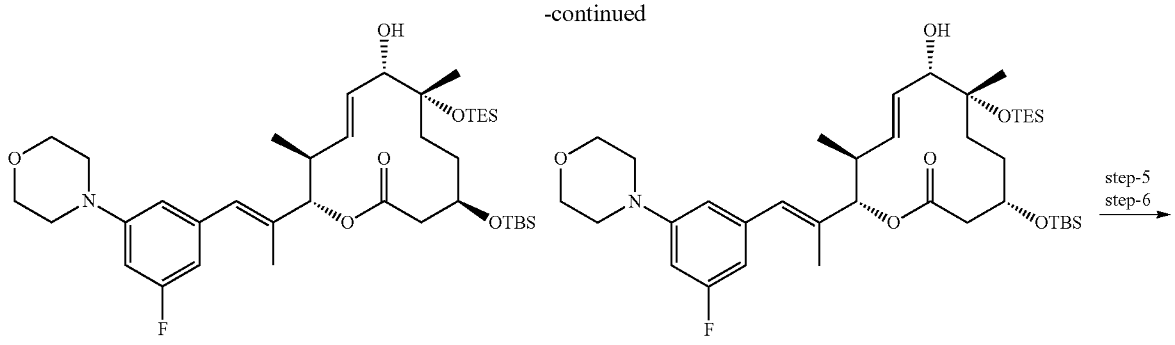

A B

017

Two diastereomers isolated

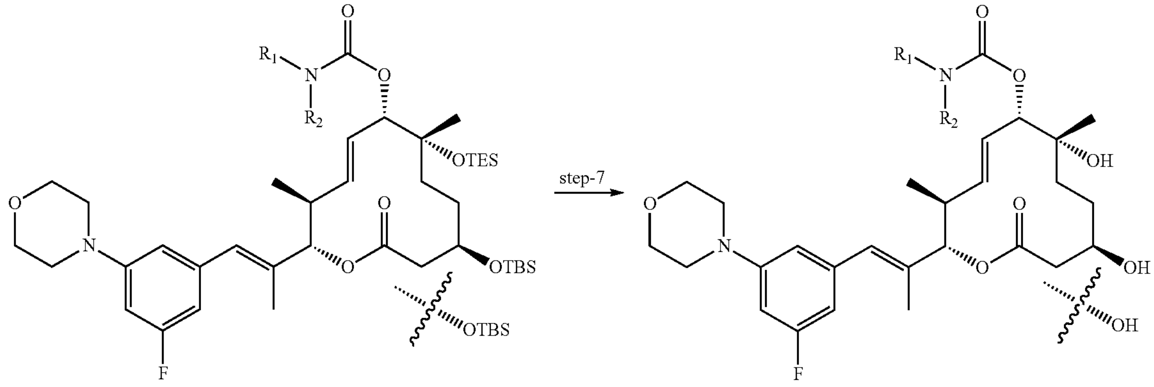

018 019

Steps 1-3 follow steps 1-3 from Scheme 1, respectively.

Step-4: To a stirred solution of 015 and 016 in 1,4-dioxane/water (3:1) were added 3.0 eq $Ag_2O$ and 0.1 eq tetrakis(triphenylphosphine)palladium(0). The mixture was degassed and heated to 100° C. for 2 hrs. Upon completion by UPLC, the mixture was cooled to room temperature and filtered to afford compound 017 as a mixture of two diastereomers (isomers A and B). Isomers A and B were separately isolated by column chromatography eluting with a 0-100% EtOAc/hexanes gradient then a 0-20% MeOH/DCM gradient.

Steps 5 and 6 follow steps 4 and 5 from Scheme 1, respectively.

Step-7: To a solution of 018 in methanol, p-toluenesulfonic acid monohydrate was added at room temperature. After 2 hours, the reaction was quenched with excess $Et_3N$ and concentrated. The solution was extracted with EtOAc, washed with $NaHCO_3$ and brine, dried with $Na_2SO_4$, filtered, and concentrated. The crude product mixture was purified via column chromatography on silica gel to afford compound 019.

Compounds 1-85 (Table 4) were prepared by the general methods of Procedures 1-10.

Synthesis of Brominated Aryl Intermediates:
Procedure 1.

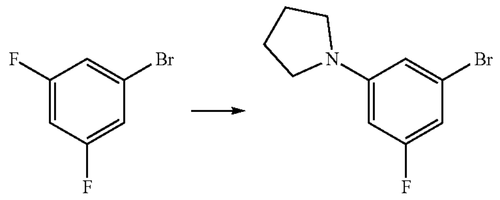 [SMILES: Fc1cc(F)cc(Br)c1 ; Fc1cc(Br)cc(N2CCCC2)c1]

To 1-bromo-3,5-difluorobenzene in DMSO was added $Cs_2CO_3$ or Hunig's base (2.5 eq) and amine (1.5 eq). The mixture was microwave heated in a sealed tube at the desired temperature for 1.5 h. The reaction was diluted with EtOAc, filtered, and concentrated in vacuo to give the crude product. The crude product was purified via column chromatography on silica gel.
Procedure 2.

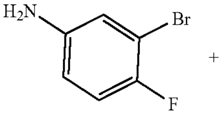

-continued

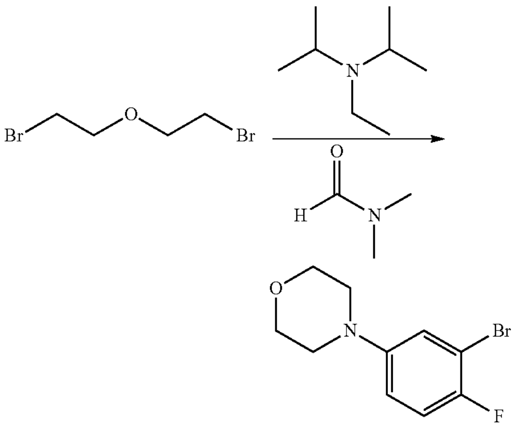

To a solution of amine in DMF at rt was added 2-bromoethylether (1.2 eq.) and Hunig's base (3.0 eq.). The mixture was microwave heated to 140° C. in a sealed tube for 24 h. The reaction was cooled, quenched with aqueous $NaHCO_3$, extracted with EtOAc, washed with brine, dried with Na2SO4, filtered and concentrated in vacuo to give the crude product. The crude product was purified via column chromatography on silica gel.

Synthesis of Pinacol Boronate Intermediates:

Procedure 3.

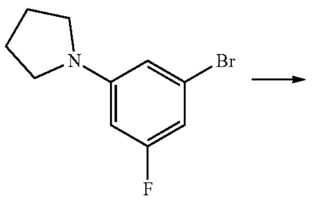

1-(3-bromo-5-fluorophenyl)pyrrolidine

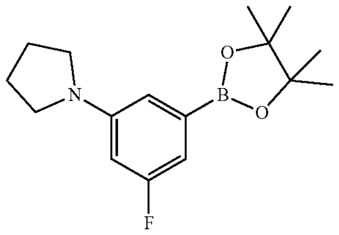

1-(3-fluoro-5-(4,4,5,5-tetramethyl-1,3,2-dioxaborolan-2-yl)phenyl)pyrrolidine

To a degassed solution of 1-(3-bromo-5-fluorophenyl) pyrrolidine in 1,4-dioxane (0.1 M) was added potassium acetate (2.0 eq), diborolane(1.2 eq) and $PdCl_2(dppf)_2$ (0.05 eq). The mixture was heated to reflux while the reaction was monitored by LC. After 5 h, aqueous workup resulted in the crude product. Column chromatography on silica gel afforded 1-(3-fluoro-5-(4,4,5,5-tetramethyl-1,3,2-dioxaborolan-2-yl)phenyl)pyrrolidine.

Synthesis of Suzuki Coupling Intermediates:

Procedure 4.

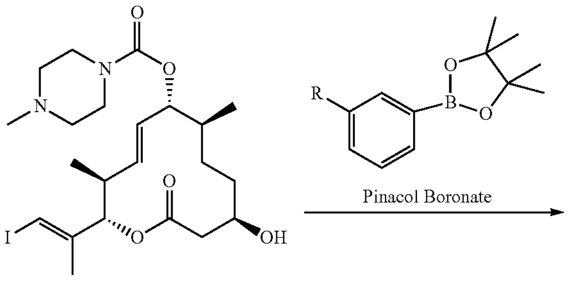

Iodide 1

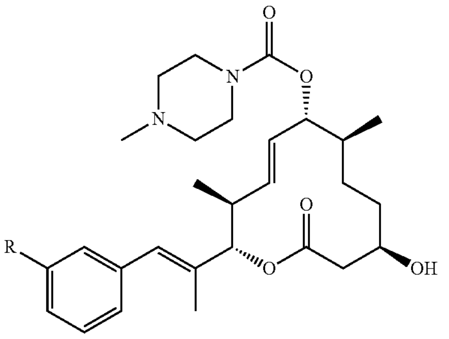

Aryl Pladienolide

To a stirred solution of Iodide 1 and Pinacol Boronate in p-dioxane were added 3.0 eq silver oxide (or $K_2CO_3$) and 0.1 eq tetrakis(triphenylphosphine)palladium(0). The mixture was degassed and heated to 80° C. for 90 minutes. Upon completion by UPLC, the reaction mixture was cooled to room temperature, filtered, and concentrated. Purification by column chromatography eluting with a 0-20% MeOH/DCM gradient afforded the Aryl Pladienolide coupling product.

Procedure 5:

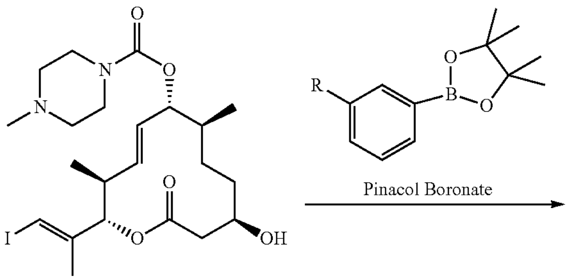

Iodide 1

-continued

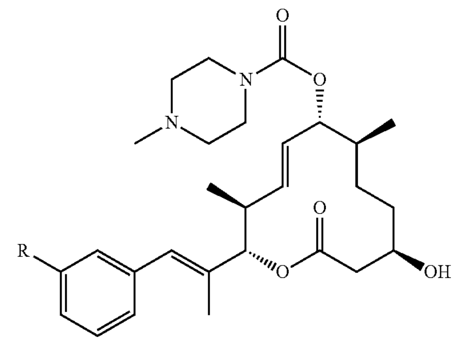

Aryl Pladienolide

To a stirred solution of Iodide 1 and Pinacol Boronate in p-dioxane/$H_2O$ (3:1) were added 2.0 eq $K_2CO_3$ and 0.1 eq Pd(dppf)$Cl_2$. The mixture was degassed and heated to 80° C. for 1 h. Upon completion by UPLC, the reaction mixture was cooled to room temperature, filtered, and concentrated. Purification by column chromatography eluting with a 0-20% MeOH/DCM gradient afforded the Aryl Pladienolide coupling product.

Procedure 6.

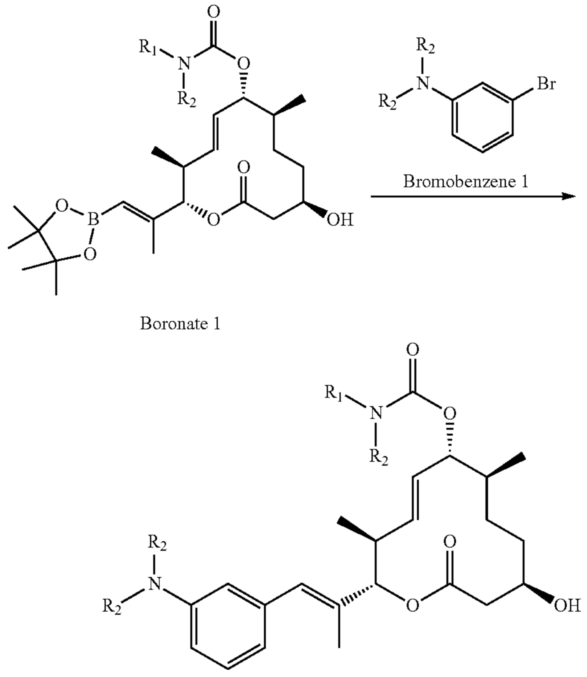

Boronate 1

Aryl Pladienolide

To a stirred solution of boronate (e.g., Boronate 1, above) and Bromobenzene 1 in 1,4-dioxane/water (3:1) were added 3.0 eq potassium carbonate (or $Ag_2O$) and 0.1 eq $Pd(PPh_3)_4$(or Pddppf$Cl_2$). The mixture was degassed and heated to 100° C. for 2 hrs. Upon completion by UPLC, the mixture was cooled to room temperature, filtered, and purified by column chromatography eluting with a 0-100% EtOAc/hexanes gradient then a 0-20% MeOH/DCM gradient afforded the Aryl Pladienolide coupling product.

Procedure 7.

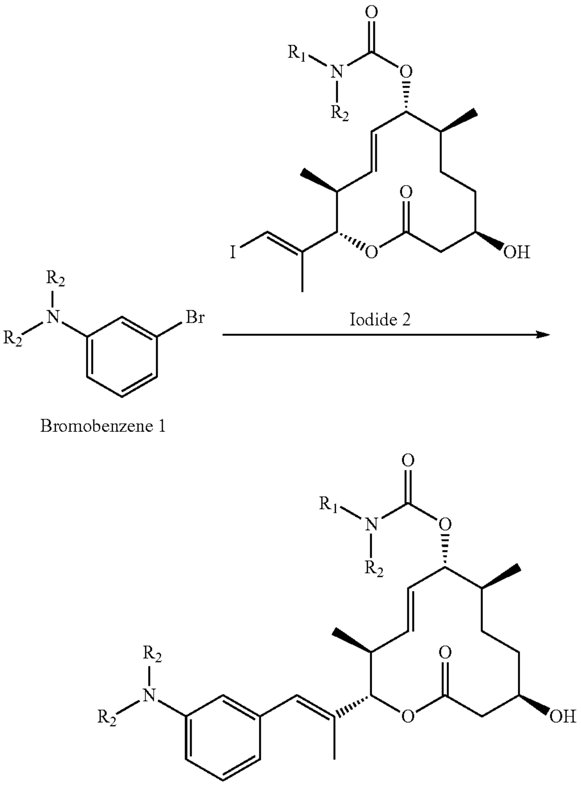

Bromobenzene 1

Aryl Pladienolide

To a degassed solution of 1.5 eq Bromobenzene 1 in 1,4-dioxane were added 3.0 eq potassium acetate, 2.0 eq diborolane and 0.2 eq Pd(dppf)$Cl_2$. The mixture was heated to reflux while the reaction was monitored by LC. After 5 h, the reaction was cooled. 3.0 eq $Ag_2O$, 0.2 eq $Pd(PPh_3)_4$ and a solution of 1.0 eq Iodide 2 were added. The mixture was degassed and heated to 80° C. for 2 h. The mixture was cooled, and direct column chromatography on silica gel afforded the Aryl Pladienolide coupling product.

Synthesis of Amidization Products:

Procedure 8.

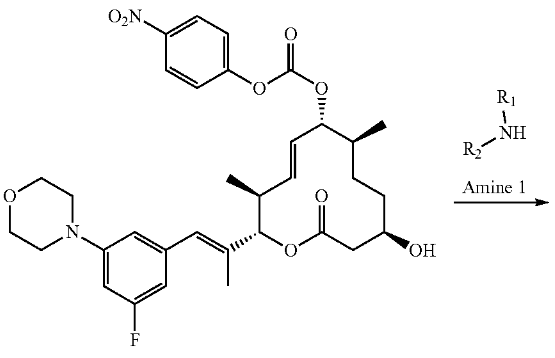

Carbonate 1

-continued

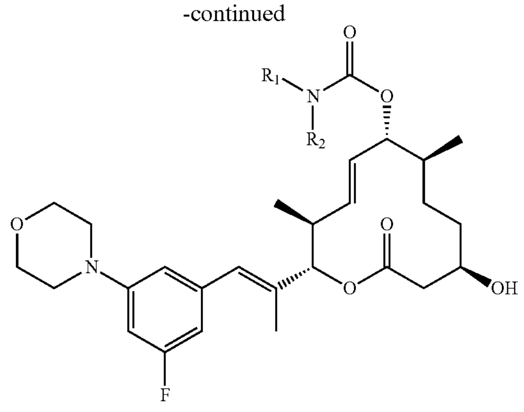

Aryl Pladienolide Carbamate

To a solution of Carbonate 1 in DCM was 3.0 eq triethylamine and 2.0 eq Amine 1. The resulting yellowish suspension was stirred for 12 hours until Carbonate 1 had disappeared. The reaction mixture was concentrated to give the crude product, and the Aryl Pladienolide Carbamate product was isolated via liquid chromatography.

Procedure 9.

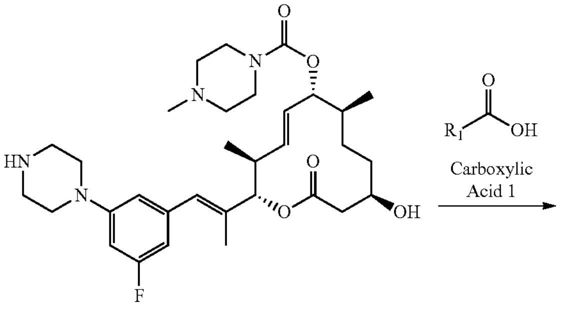

Amine 2

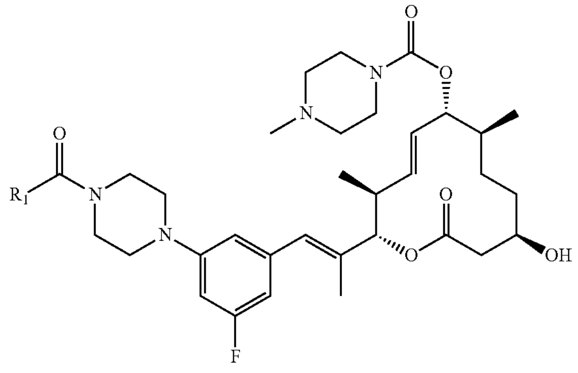

Aryl Pladienolide Amide

To a solution of Amine 2 and Carboxylic Acid 1 (1.2 eq) in DMSO at room temperature was added HBTU (1.2 eq) and triethylamine (1.5 eq). The solution was stirred for 5 hours at room temperature. Water was added in to quench the reaction, which was then extracted with EtOAc, washed with brine, and concentrated in vacuo to give the crude product. The resulting Aryl Pladienolide Amide product was purified via column chromatography on silica gel.

Procedure 10.

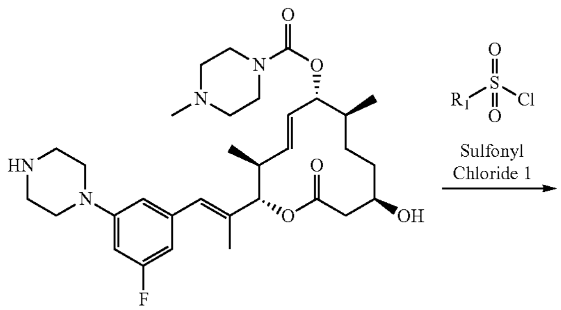

Amine 2

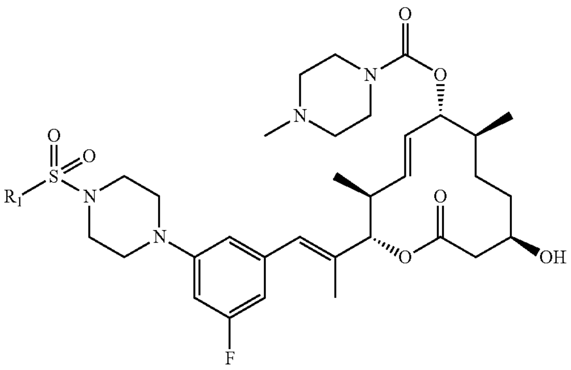

Aryl Pladienolide Sulfonamide

To a solution of the Amine 2 in DCM were added 1.2 eq Sulfonyl Chloride 1, 3.0 eq Hunig's base, and 0.1 eq DMAP. The mixture was stirred at room temperature until Amine 2 was consumed. The reaction was quenched with water, extracted with EtOAc, washed with brine, dried over $Na_2SO_4$, filtered, and concentrated to give the crude product. The Aryl Pladienolide Sulfonamide product was purified via column chromatography on silica gel.

TABLE 4

| Characterization of Compounds 1-85 and 265-267 | | |
|---|---|---|
| Ex. | Structure and IUPAC Chemical Name | Characterization |
| 1 | 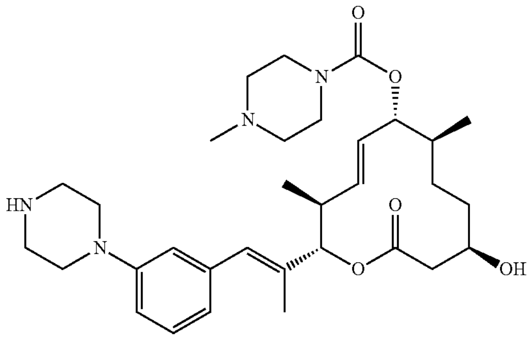 [(2S,3S,4E,6R,7S,10R)-10-hydroxy-3,7-dimethyl-12-oxo-2-[(E)-1-(3-piperazin-1-ylphenyl)prop-1-en-2-yl]-1-oxacyclo-dodec-4-en-6-yl] 4-methylpiperazine-1-carboxylate | LCMS (ESI, m/z), 569.6 $[M + H]^+$. $^1H$ NMR (400 MHz, $CDCl_3$) δ 1.04 (t, J = 6.53 Hz, 6 H) 1.15-1.29 (m, 2 H) 1.49-1.58 (m, 1 H) 1.80-1.89 (m, 1 H) 1.92 (d, J = 1.13 Hz, 3 H) 1.94-2.01 (m, 1 H) 2.34 (s, 3 H) 2.40 (br s, 4 H) 2.55-2.64 (m, 2 H) 2.65-2.73 (m, 1 H) 2.97-3.12 (m, 4 H) 3.14-3.28 (m, 4 H) 3.48-5.28 (m, 5 H) 3.71-3.85 (m, 1 H) 4.90 (t, J = 10.10 Hz, 1 H) 5.29 (d, J = 10.67 Hz, 1 H) 5.40 (dd, J = 15.00, 9.60 Hz, 1 H) 5.61 (dd, J = 14.93, 9.91 Hz, 1 H) 6.57 (s, 1 H) 6.77-6.87 (m, 3 H) 7.24 (t, J = 8.09 Hz, 1 H) |
| 2 | 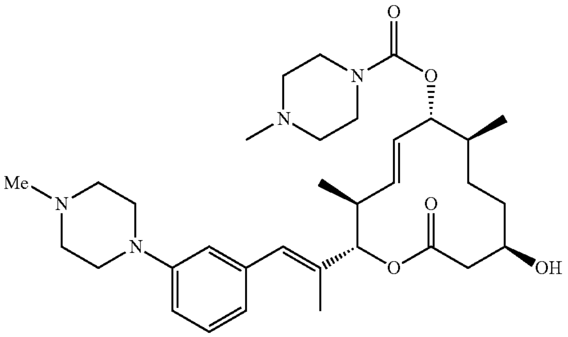 [(2S,3S,4E,6R,7S,10R)-10-hydroxy-3,7-dimethyl-2-[(E)-1-[3-(4-methylpiperazin-1-yl)phenyl]prop-1-en-2-yl]-12-oxo-1-oxacyclododec-4-en-6-yl] 4-methylpiperazine-1-carboxylate | LCMS (ESI, m/z), 583.4 $[M + H]^+$. $^1H$ NMR (400 MHz, $CD_3OD$) δ ppm 0.92 (d, J = 6.78 Hz, 3 H) 0.97 (d, J = 6.78 Hz, 3 H) 1.21-1.39 (m, 2 H) 1.49-1.67 (m, 2 H) 1.81 (d, J = 1.13 Hz, 3 H) 1.89-2.02 (m, 1 H) 2.41 (dd, J = 14.05, 5.40 Hz, 1 H) 2.52-2.65 (m, 2 H) 2.85 (s, 3 H) 2.91 (s, 3 H) 3.10-3.28 (m, 12 H) 3.32-3.50 (m, 4 H) 3.70-3.85 (m, 1 H) 4.78-4.84 (m, 1 H), 5.09 (d, J = 10.54 Hz, 1 H) 5.39-5.62 (m, 2 H) 6.48-6.56 (m, 1 H) 6.80-6.93 (m, 3 H) 7.16-7.26 (m, 1 H) |
| 3 | 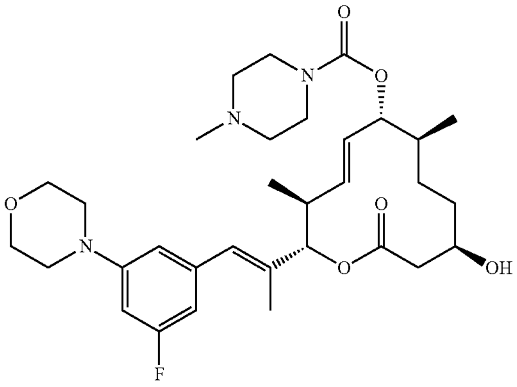 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 588.4 $[M + H]^+$. $^1H$ NMR (400 MHz, $CDCl_3$) δ ppm 0.92 (d, J = 6.90 Hz, 3 H) 0.95 (d, J = 6.90 Hz, 3 H) 1.15-1.29 (m, 2 H) 1.43 (ddd, J = 13.52, 9.69, 3.76 Hz, 1 H) 1.74 (br d, J = 3.51 Hz, 2 H) 1.81 (s, 3 H) 1.83-1.92 (m, 1 H) 2.24 (s, 3 H) 2.30 (br s, 4 H) 2.41-2.67 (m, 3 H) 3.00-3.17 (m, 4 H) 3.42 (br s, 4 H) 3.66 (br s, 1 H) 3.77-3.83 (m, 4 H) 4.82 (t, J = 10.04 Hz, 1 H) 5.20 (d, J = 10.54 Hz, 1 H) 5.34 (dd, J = 14.93, 9.66 Hz, 1 H) 5.53 (dd, J = 15.06, 9.91 Hz, 1 H) 6.32-6.60 (m, 4 H) |

TABLE 4-continued

Characterization of Compounds 1-85 and 265-267

| Ex. | Structure and IUPAC Chemical Name | Characterization |
|---|---|---|
| 4 | 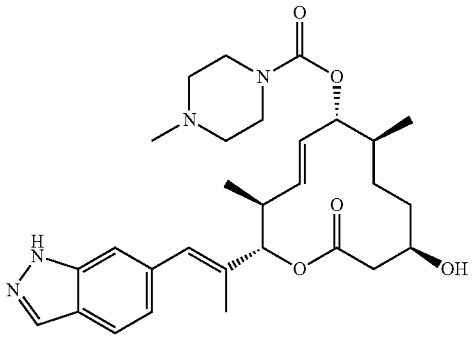 [(2S,3S,4E,6R,7S,10R)-10-hydroxy-2-[(E)-1-(1H-indazol-6-yl)prop-1-en-2-yl]-3,7-dimethyl-12-oxo-1-oxacyclododec-4-en-6-yl] 4-methylpiperazine-1-carboxylate | LCMS (ESI, m/z), 525.4 $[M + H]^+$. $^1H$ NMR (400 MHz, $CDCl_3$) δ ppm 0.94 (d, J = 2.76 Hz, 3 H) 0.96 (d, J = 2.76 Hz, 3 H) 1.15-1.29 (m, 2 H) 1.40-1.50 (m, 1 H) 1.68-1.80 (m, 1 H) 1.83-1.93 (m, 1 H) 1.86 (d, J = 1.13 Hz, 3 H) 2.24 (s, 3 H) 2.27-2.39 (m, 4 H) 2.46-2.64 (m, 3 H) 3.43 (br s, 4 H) 3.60-3.98 (m, 2 H) 4.84 (t, J = 10.04 Hz, 1 H) 5.26 (d, J = 10.67 Hz, 1 H) 5.31-5.41 (m, 1 H) 5.56 (dd, J = 15.06, 9.91 Hz, 1 H) 6.67 (s, 1 H) 7.04 (d, J = 8.41 Hz, 1 H) 7.33 (s, 1 H) 7.65 (d, J = 8.28 Hz, 1 H) 1.99 (s, 1 H) 9.91-10.32 (m, 1 H) |
| 5 | 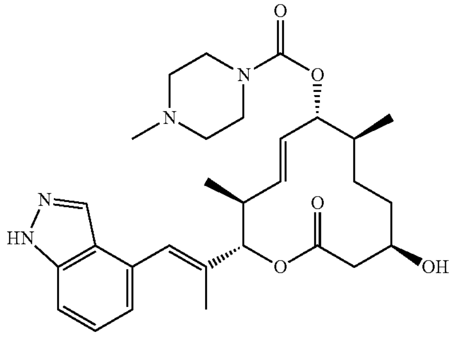 [(2S,3S,4E,6R,7S,10R)-10-hydroxy-2-[(E)-1-(1H-indazol-4-yl)prop-1-en-2-yl)]-3,7-dimethyl-12-oxo-1-oxacyclododec-4-en-6-yl] 4-methylpiperazine-1-carboxylate | LCMS (ESI, m/z), 525.5 $[M + H]^+$. $^1H$ NMR (400 MHz, $CDCl_3$) δ ppm 1.02 (d, J = 6.90 Hz, 3 H) 1.06 (d, J = 6.78 Hz, 3 H) 1.22-1.36 (m, 2 H) 1.47-1.56 (m, 1 H) 1.77-1.84 (m, 1 H) 1.87 (d, J = 1.13 Hz, 3 H) 1.90-2.01 (m, 1 H) 2.30 (s, 3 H) 2.37 (br s, 4 H) 2.53-2.73 (m, 3 H) 3.31-3.61 (m, 4 H) 3.75 (br s, 2 H) 4.91 (t, J = 10.04 Hz, 1 H) 5.38-5.49 (m, 2 H) 5.63 (dd, J = 15.06, 9.91 Hz, 1 H) 6.92 (s, 1 H) 7.06 (d, J = 6.65 Hz, 1 H) 7.34-7.46 (m, 2 H) 8.03 (s, 1 H) 9.95-10.34 (m, 1 H) |
| 6 | 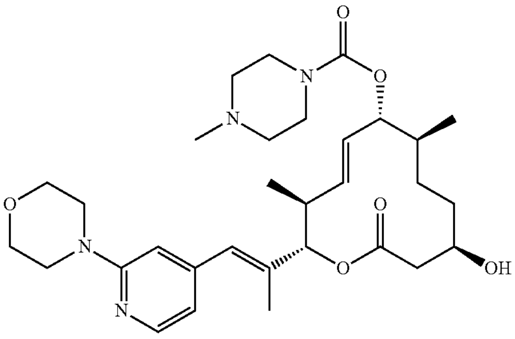 [(2S,3S,4E,6R,7S,10R)-10-hydroxy-3,7-dimethyl-2-[(E)-1-(2-morpholin-4-ylpyridin-4-yl)prop-1-en-2-yl]-12-oxo-1-oxacyclododec-4-en-6-yl] 4-methylpiperazine-1-carboxylate | LCMS (ESI, m/z), 571.5 $[M + H]^+$. $^1H$ NMR (400 MHz, $CDCl_3$) δ ppm 1.00 (t, J = 6.84 Hz, 6 H) 1.19-1.31 (m, 2 H) 1.42-1.55 (m, 1 H) 1.74-1.84 (m, 1 H) 1.87 (d, J = 1.00 Hz, 3 H) 1.88-1.97 (m, 1 H) 2.31 (s, 3 H) 2.38 (br s, 4 H) 2.50-2.70 (m, 3 H) 3.40-3.60 (m, 8 H) 3.69-3.78 (m, 1 H) 3.79-3.88 (m, 4 H) 4.88 (t, J = 10.10 Hz, 1 H) 5.26 (d, J = 10.67 Hz, 1 H) 5.35-5.46 (m, 1 H) 5.59 (dd, J = 15.00, 9.85 Hz, 1 H) 6.46 (s, 2 H) 6.57 (d, J = 5.27 Hz, 1 H) 8.15 (d, J = 5.14 Hz, 1 H) |

TABLE 4-continued

| Characterization of Compounds 1-85 and 265-267 | | |
|---|---|---|
| Ex. | Structure and IUPAC Chemical Name | Characterization |
| 7 | 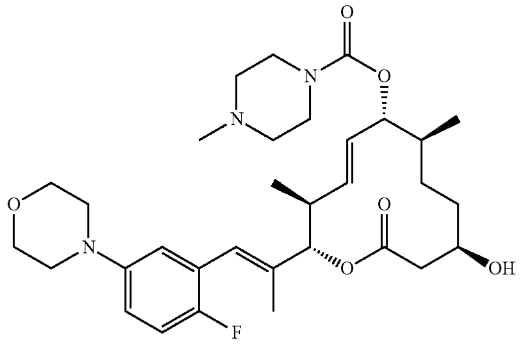 [(2S,3S,4E,6R,7S,10R)-2-[(E)-1-(2-fluoro-5-morpholin-4-ylphenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 588.5 $[M + H]^+$. $^1H$ NMR (400 MHz, $CDCl_3$) δ ppm 1.00 (d, J = 1.76 Hz, 3 H) 1.02 (d, J = 1.76 Hz, 3 H) 1.21-1.32 (m, 2 H) 1.43-1.55 (m, 1 H) 1.76 (s, 3 H) 1.78-1.86 (m, 1 H) 1.89-1.98 (m, 1 H) 2.30 (s, 3 H) 2.36 (br s, 4 H) 2.48-2.70 (m, 3 H) 3.02-3.12 (m, 4 H) 3.41-3.56 (m, 5 H) 3.67-3.77 (m, 1 H) 3.84-3.89 (m, 4 H) 4.89 (t, J = 10.04 Hz, 1 H) 5.31 (d, J = 10.92 Hz, 1 H) 5.40 (dd, J = 15.00, 9.72 Hz, 1 H) 5.60 (dd, J = 14.93, 10.04 Hz, 1 H) 6.50 (s, 1 H) 6.73 (dd, J = 6.09, 2.95 Hz, 1 H) 6.76-6.82 (m, 1 H) 6.97 (t, J = 9.10 Hz, 1 H) |
| 8 | 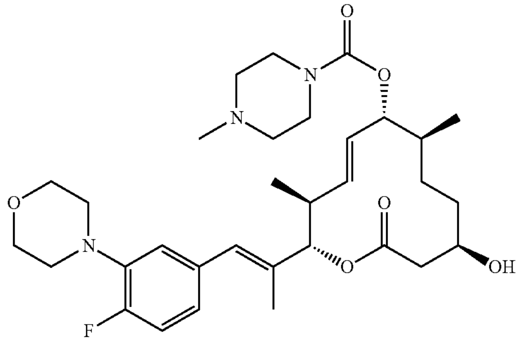 [(2S,3S,4E,6R,7S,10R)-2-[(E)-1-(4-fluoro-3-morpholin-4-ylphenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 588.5 $[M + H]^+$. $^1H$ NMR (400 MHz, $CDCl_3$) δ ppm 0.99 (d, J = 4.02 Hz, 3 H) 1.01 (d, J = 3.89 Hz, 3 H) 1.16-1.35 (m, 2 H) 1.43-1.55 (m, 1 H) 1.75-1.84 (m, 1 H) 1.86 (s, 3 H) 1.90-2.00 (m, 2 H) 2.51 (s, 3 H) 2.50-2.88 (m, 3 H) 2.64-2.76 (m, 4 H) 3.05-3.11 (m, 4 H) 3.58-3.76 (m, 5 H) 3.84-3.91 (m, 4 H) 4.89 (t, J = 10.10 Hz, 1 H) 5.27 (d, J = 10.54 Hz, 1 H) 5.39 (dd, J = 14.93, 9.54 Hz, 1 H) 5.61 (dd, J = 14.93, 9.91 Hz, 1 H) 6.52 (s, 1 H) 6.78-6.83 (m, 1 H) 6.85-6.90 (m, 1 H) 6.96-7.04 (m, 1 H) |
| 9 | 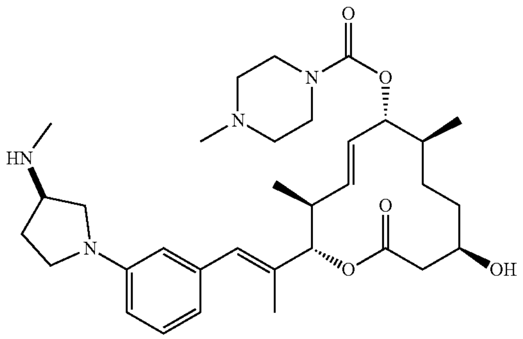 [(2S,3S,4E,6R,7R,10S)-10-hydroxy-3,7-dimethyl-2-[(E)-1-[3-(3S)-3-(methylamino)pyrrolidin-1-yl]phenyl]prop-1-en-2-yl]-12-oxo-1-oxacyclododec-4-en-6-yl] 4-methylpiperazine-1-carboxylate | LCMS (ESI, m/z), 583.6 $[M + H]^+$. $^1H$ NMR (400 MHz, $CDCl_3$) δ ppm 1.00 (t, J = 6.21 Hz, 6 H) 1.20-1.35 (m, 2 H) 1.41-1.57 (m, 1 H) 1.72-1.84 (m, 1 H) 1.88 (d, J = 1.25 Hz, 3 H) 1.90-1.98 (m, 1 H) 2.23 (td, J = 13.11, 6.15 Hz, 2 H) 2.30 (s, 3 H) 2.37 (br s, 4 H) 2.50 (s, 3 H) 2.52-2.70 (m, 3 H) 3.08-3.20 (m, 1 H) 3.23-3.34 (m, 1 H) 3.37-3.45 (m, 2 H) 3.45-3.57 (m, 5 H) 3.67-3.75 (m, 1 H) 4.89 (t, J = 10.04 Hz, 1 H) 5.28 (d, J = 10.67 Hz, 1 H) 5.39 (dd, J = 15.00, 9.72 Hz, 1 H) 5.61 (dd, J = 15.00, 9.98 Hz, 1 H) 6.39-6.49 (m, 2 H) 6.56 (s, 1 H) 6.62 (d, J = 7.65 Hz, 1 H) 7.18 (t, J = 7.78 Hz, 1 H) |

TABLE 4-continued

| Characterization of Compounds 1-85 and 265-267 | | |
|---|---|---|
| Ex. | Structure and IUPAC Chemical Name | Characterization |
| 10 | 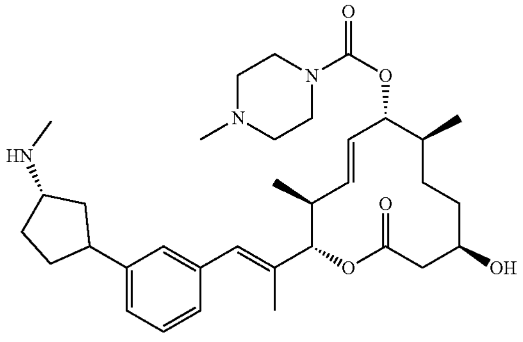 [(2S,3S,4E,6R,7R,10S)-10-hydroxy-3,7-dimethyl-2-[(E)-1-[3-(3S)-3(methylamino)pyrrolidin-1-yl]phenyl]prop-1-en-2-yl]-12-oxo-1-oxacyclododec-4-en-6-yl] 4-methyl-piperazine-1-carboxylate | LCMS (ESI, m/z), 583.6 $[M + H]^+$ |
| 11 | 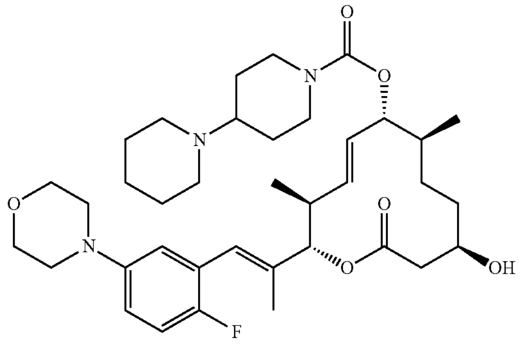 [(2S,3S,4E,6R,7S,10R)-2-[(E)-1-(2-fluoro-5-morpholin-4-ylphenyl)prop-1-en-2-yl]-10-hydroxy-3,7-dimethyl-12-oxo-1-oxacyclododec-4-en-6-yl] 4-piperidin-1-ylpiperidine-1-carboxylate | LCMS (ESI, m/z), 656.5 $[M + H]^+$. $^1H$ NMR (400 MHz, $CDCl_3$) δ ppm 0.99 (d, J = 5.02 Hz, 3 H) 1.01 (d, J = 5.02 Hz, 3 H) 1.18-1.36 (m, 2 H) 1.41-1.69 (m, 6 H) 1.76 (s, 3 H) 1.77-1.84 (m, 1 H) 1.85-2.22 (m, 6 H) 2.45-2.60 (m, 2 H) 2.62-2.69 (m, 1 H) 2.72-3.00 (m, 6 H) 3.02-3.12 (m, 4 H) 3.34-3.44 (m, 1 H) 3.69-3.77 (m, 1 H) 3.80-3.89 (m, 4 H) 4.20-4.36 (m, 2 H) 4.86 (t, J = 10.10 Hz, 1 H) 5.31 (d, J = 10.54 Hz, 1 H) 5.39 (dd, J = 15.12, 9.72 Hz, 1 H) 5.60 (dd, J = 15.06, 9.91 Hz, 1 H) 6.50 (s, 1 H) 6.73 (dd, J = 6.15, 3.01 Hz, 1 H) 6.76-6.83 (m, 1 H) 6.92-7.00 (m, 1 H) |
| 12 | 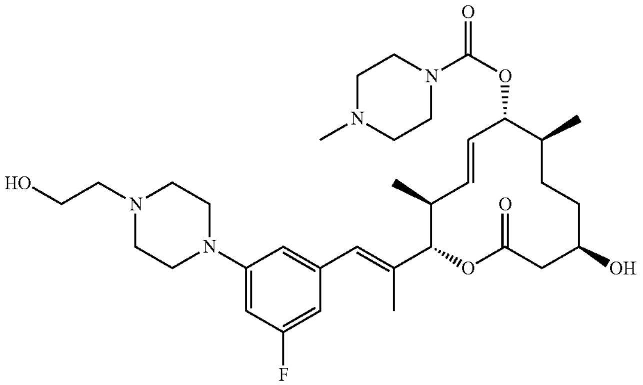 [(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 631.7 $[M + H]^+$. $^1H$ NMR (400 MHz, $CDCl_3$) δ ppm 0.98 (d, J = 6.65 Hz, 3 H) 1.01 (d, J = 6.78 Hz, 3 H) 1.21-1.46 (m, 2 H) 1.54-1.70 (m, 2 H) 1.86 (d, J = 1.13 Hz, 3 H) 1.89-2.02 (m, 1 H) 2.30 (s, 3 H) 2.36-2.43 (m, 4 H) 2.44-2.51 (m, 1 H) 2.56-2.68 (m, 4 H) 2.69-2.76 (m, 4 H) 3.20-3.26 (m, 4 H) 3.44-3.57 (m, 4 H) 3.73 (t, J = 5.90 Hz, 2 H) 3.77-3.84 (m, 1 H) 4.78-4.83 (m, 1 H) 5.13 (d, J = 10.67 Hz, 1 H) 5.43-5.60 (m, 2 H) 6.48 (br d, J = 9.29 Hz, 1 H) 6.52-6.66 (m, 3 H) |

TABLE 4-continued

| Characterization of Compounds 1-85 and 265-267 | | |
|---|---|---|
| Ex. | Structure and IUPAC Chemical Name | Characterization |
| 13 | 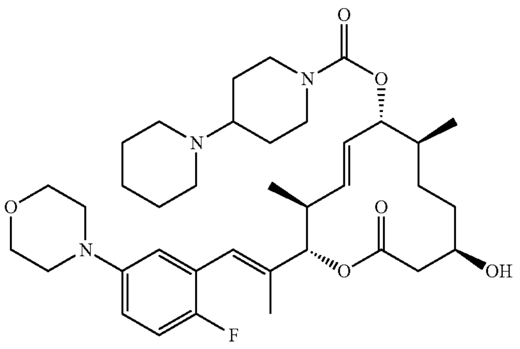 [(2S,3S,4E,6R,7S,10R)-2-[(E)-1-(2-fluoro-5-morpholin-4-ylphenyl)prop-1-en-2-yl]-10-hydroxy-3,7-dimethyl-12-oxo-1-oxacyclododec-4-en-6-yl] 4-piperidin-1-ylpiperidine-1-carboxylate | LCMS (ESI, m/z), 699.5 $[M + H]^+$. $^1H$ NMR (400 MHz, $CDCl_3$) δ ppm 0.98 (d, J = 6.78 Hz, 3 H) 1.01 (br d, J = 6.78 Hz, 3 H) 1.24-1.55 (m, 6 H) 1.56-1.72 (m, 6 H) 1.86 (d, J = 1.13 Hz, 3 H) 1.87-2.01 (m, 3 H) 2.39-2.52 (m, 1 H) 2.54-2.71 (m, 13 H) 2.72-2.88 (m, 2 H) 3.16-3.27 (m, 4 H) 3.72 (t, J = 6.02 Hz, 2 H) 3.77-3.87 (m, 1 H) 4.07-4.29 (m, 2 H) 4.76-4.83 (m, 1 H) 5.13 (d, J = 10.67 Hz, 1 H) 5.42-5.64 (m, 2 H) 6.47 (br d, J = 9.03 Hz, 1 H) 6.52-6.68 (m, 3 H) |
| 14 | 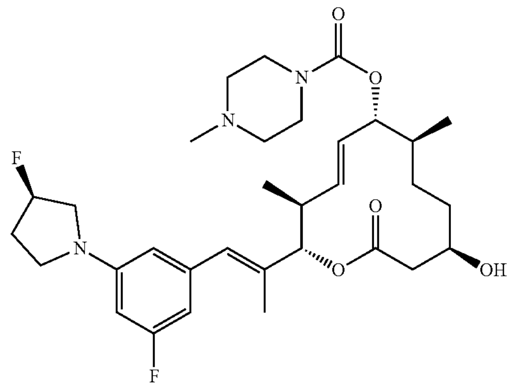 [(2S,3S,4E,6R,7S,10R)-2-[(E)-1-[3-fluoro-5-[(3R)-3-fluoropyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 590.6 $[M + H]^+$. $^1H$ NMR (400 MHz, $CDCl_3$) δ ppm 0.99 (d, J = 3.89 Hz, 3 H) 1.00 (d, J = 3.89 Hz, 3 H) 1.15-1.33 (m, 2 H) 1.45-1.54 (m, 1 H) 1.75-1.84 (m, 1 H) 1.88 (d, J = 1.13 Hz, 3 H) 1.93 1.90-1.99 (m, 1 H) 2.07-2.27 (m, 1 H) 2.32-2.44 (m, 4 H) 2.52 (s, 3 H) 2.54-2.60 (m, 2 H) 2.62-2.68 (m, 1 H) 2.73 (br s, 4 H) 3.36-3.63 (m, 5 H) 3.64-3.76 (m, 5 H) 4.89 (t, J = 10.10 Hz, 1 H) 5.27 (d, J = 10.67 Hz, 1 H) 5.39 (dd, J = 14.93, 9.79 Hz, 1 H) 5.61 (dd, J = 15.00, 9.98 Hz, 1 H) 6.12-6.22 (m, 2 H) 6.31-6.39 (m, 1 H) 6.49-5.54 (m, 1 H) |
| 15 | 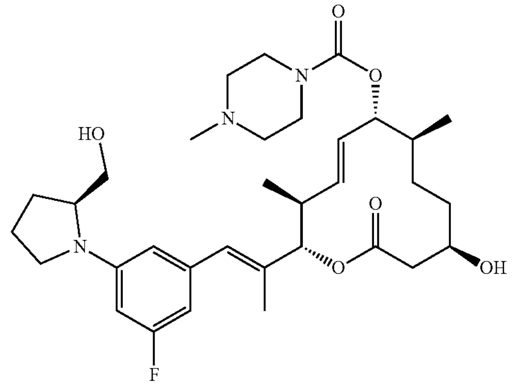 [(2S,3S,4E,6R,7S,10R)-2-[(E)-1-[3-fluoro-5-[(2R)-2-hydroxymethyl)pyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.4 $[M + H]^+$. $^1H$ NMR (400 MHz, $CDCl_3$) 0.90 (d, J = 6.65 Hz, 3 H) 1.00 (d, J = 6.78 Hz, 3 H) 1.16-1.32 (m, 2 H) 1.45-1.54 (m, 1 H) 1.70-1.84 (m, 1 H) 1.88 (d, J = 1.13 Hz, 3 H) 1.90-1.96 (m, 1 H) 1.98-2.14 (m, 2 H) 2.31 (s, 3 H) 2.39 (br s, 4 H) 2.50-2.61 (m, 2 H) 2.62-2.71 (m, 1 H) 3.07-3.22 (m, 1 H) 3.34-3.57 (m, 6 H) 3.58-3.69 (m, 3 H) 3.69-3.77 (m, 1 H) 3.79-3.86 (m, 1 H) 4.89 (t, J = 10.10 Hz, 1 H) 5.26 (d, J = 10.67 Hz, 1 H) 5.39 (dd, J = 15.06, 9.66 Hz, 1 H) 5.60 (dd, J = 15.00, 9.98 Hz, 1 H) 6.24-6.42 (m, 3 H) 6.50 (s, 1 H) |

TABLE 4-continued

| Characterization of Compounds 1-85 and 265-267 | | |
|---|---|---|
| Ex. | Structure and IUPAC Chemical Name | Characterization |
| 16 | 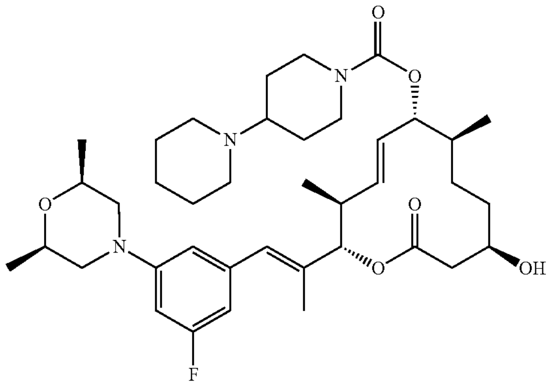 [(2S,3S,4E,6R,7R,10S)-2-[(E)-1-[3-[(2R,6S)-2,6-dimethymorpholin-4-yl]-5-fluorophenyl]prop-1-en-2-yl]-10-hydroxy-3,7-dimethyl-12-oxo-1-oxacyclododec-4-en-6-yl] 4-piperidin-1-ylpiperazine-1-carboxylate | LCMS (ESI, m/z), 684.7 [M + H]$^+$. $^1$H NMR (400 MHz, $CDCl_3$) 0.98 (d, J = 3.39 Hz, 3 H) 1.00 (d, J = 3.26 Hz, 3 H) 1.07-1.17 (m, 1 H) 1.18-1.33 (m, 10 H) 1.42-1.54 (m, 1 H) 1.54-1.71 (m, 5 H) 1.74-1.83(m, 1 H) 1.87 (s, 3 H) 1.89-1.97 (m, 1 H) 1.98-2.12 (m, 2 H) 2.32-2.46 (m, 2 H) 2.51-2.69 (m, 3 H) 2.70-2.84 (m, 2 H) 2.85-3.18 (m, 5 H) 3.33-3.44 (m, 2 H) 3.70-3.85 (m, 3 H) 4.22-4.40 (m, 2 H) 4.86 (t, J = 10.04 Hz, 1 H) 5.25 (d, J = 10.54 Hz, 1 H) 5.39 (dd, J = 15.06, 9.66 Hz, 1 H) 5.59 (dd, J = 15.00, 9.85 Hz, 1 H) 6.41-6.54 (m, 4 H) |
| 17 | 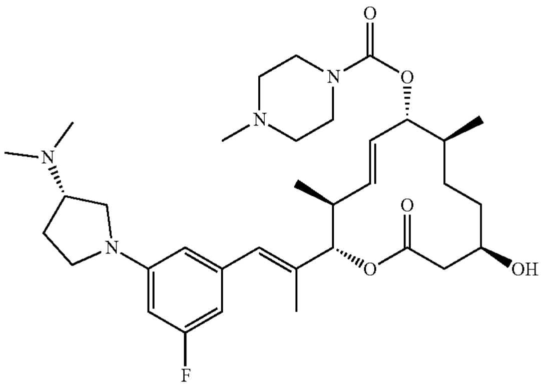 [(2S,3S,4E,6R,7S,10R)-2-[(E)-1-[3-[(3S)-3-(dimethylamino)pyrrolidin-1-yl]-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 615.7 [M + H]$^+$. $^1$H NMR (400 MHz, $CDCl_3$) 0.95-1.05 (m, 6 H) 1.18-1.31 (m, 2 H) 1.42-1.54 (m, 1 H) 1.70-1.84 (m, 1 H) 1.88 (d, J = 1.13 Hz, 3 H) 1.90-1.96 (m, 1 H) 2.17-2.25 (m, 2 H) 2.30 (s, 3 H) 2.32 (s, 6 H) 2.33-2.43 (m, 5 H) 2.48-2.70 (m, 3 H) 2.80-2.97 (m, 1 H) 3.15 (t, J = 8.53 Hz, 1 H) 3.29 (td, J = 9.44, 6.84 Hz, 1 H) 3.36-3.44 (m, 2 H) 3.45-3.56 (m, 4 H) 3.67-3.75 (m, 1 H) 4.86 (t, J = 10.04 Hz, 1 H) 5.25 (d, J = 10.54 Hz, 1 H) 5.39 (dd, J = 15.06, 9.66 Hz, 1 H) 5.59 (dd, J = 15.00, 9.85 Hz, 1 H) 6.08-6.16 (m, 2 H) 6.32 (br d, J = 9.66 Hz, 1 H) 6.47-6.54 (m, 1 H) |
| 18 | 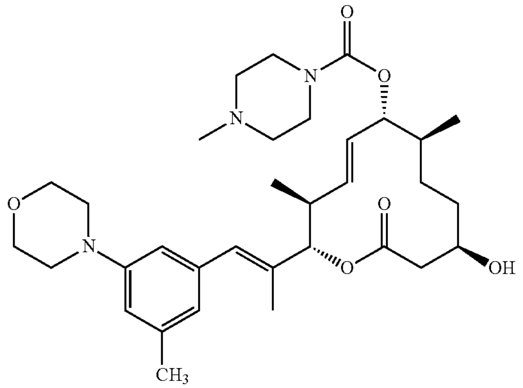 [(2S,3S,4E,6R,7S,10R)-10-hydroxy-3,7-dimethyl-2-[(E)-1-(3methyl-5-morpholin-4-ylphenyl)prop-1-en-2-yl]-12-oxo-1-oxacyclododec-4-en-6-yl] 4-methylpiperazine-1-carboxylate | LCMS (ESI, m/z), 584.6 [M + H]$^+$. $^1$H NMR (400 MHz, DMSO-$d_6$) 0.87-0.92 (m, 6 H) 1.09-1.34 (m, 3 H) 1.40-1.56 (m, 2 H) 1.80 (s, 3 H) 1.95-2.05 (m, 2 H) 2.14-2.37 (m, 8 H) 2.50 (s, 3 H) 3.05-3.10 (m, 4 H) 3.30-3.39 (m, 4 H) 3.69-3.75 (m, 5 H) 4.61 (d, J = 5.40 Hz, 1 H) 4.66-4.77 (m, 1 H) 4.99 (d, J = 10.29 Hz, 1 H) 5.37-5.50 (m, 2 H) 6.45 (s, 1 H) 6.51-6.71 (m, 3 H) |

TABLE 4-continued

| Ex. | Structure and IUPAC Chemical Name | Characterization |
|---|---|---|
| | Characterization of Compounds 1-85 and 265-267 | |
| 19 | 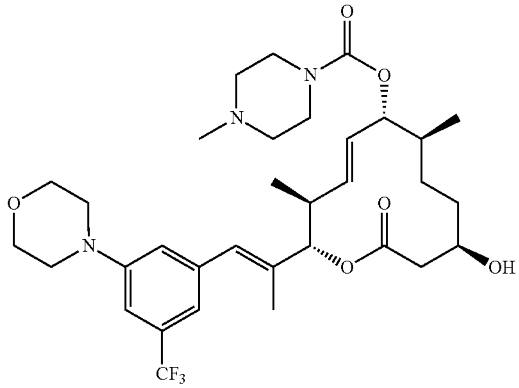 [(2S,3S,4E,6R,7S,10R)-10-hydroxy-3,7-dimethyl-2-[(E)-1-[3-morpholin-4-yl-5-(trifluoromethyl)phenyl]prop-1-en-2-yl]-12-oxo-1-oxacyclododec-4-en-6-yl] 4-methyl-piperazine-1-carboxylate | LCMS (ESI, m/z), 584.6 $[M + H]^+$ |
| 20 | 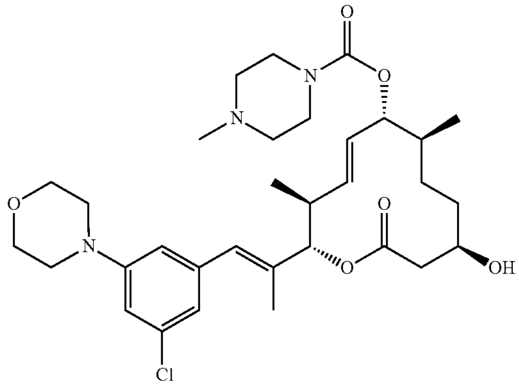 [(2S,3S,4E,6R,7S,10R)-2-[(E)-1-(3-chloro-5-morpholin-4-ylphenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 604.5 $[M + H]^+$. $^1H$ NMR (400 MHz, DMSO-$d_6$) 0.89 (d, J = 6.65 Hz, 6 H) 1.16-1.33 (m, 3 H) 1.38-1.55 (m, 2 H) 1.81 (s, 3 H) 2.16 (s, 3 H) 2.20-2.35 (m, 7 H) 3.07-3.17 (m, 4 H) 3.32-3.53 (m, 4 H) 3.68-3.78 (m, 5 H) 4.64 (d, J = 5.14 Hz, 1 H) 4.69 (t, J = 9.47 Hz, 1 H) 4.99 (d, J = 10.54 Hz, 1 H) 5.31-5.54 (m, 2 H) 6.46 (s, 1 H) 6.72-6.80 (m, 2 H) 6.86 (s, 1 H) |
| 21 | 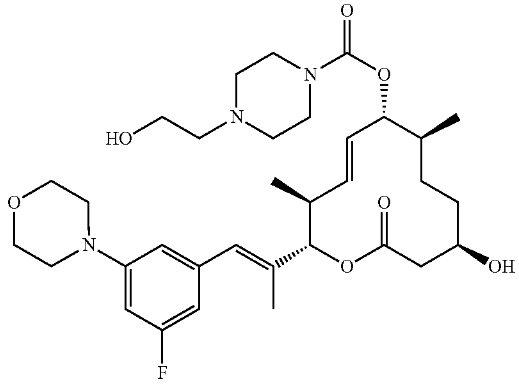 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-(2-hydroxyethyl)piperazine-1-carboxylate | LCMS (ESI, m/z), 618.6 $[M + H]^+$. $^1H$ NMR (400 MHz, DMSO-$d_6$) 0.89 (dd, J = 6.59, 2.07 Hz, 6 H) 1.13-1.33 (m, 3 H) 1.40-1.51 (m, 2 H) 1.82 (s, 3 H) 2.23-2.44 (m, 9 H) 3.08-3.18 (m, 4 H) 3.26-3.56 (m, 6 H) 3.66-3.77 (m, 5 H) 4.40-4.49 (m, 1 H) 4.63 (d, J = 5.02 Hz, 1 H) 4.69 (t, J = 9.47 Hz, 1 H) 4.98 (d, J = 10.67 Hz, 1 H) 5.34-5.51 (m, 2 H) 6.43-6.56 (m, 2 H) 6.60-6.70 (m, 2 H) |

TABLE 4-continued

| Characterization of Compounds 1-85 and 265-267 | | |
|---|---|---|
| Ex. | Structure and IUPAC Chemical Name | Characterization |
| 22 | 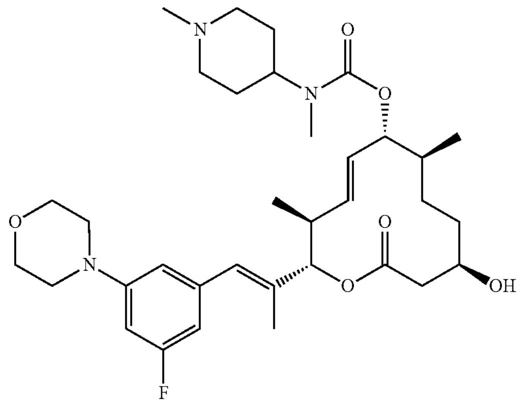 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] N-methyl-N-(1-methylpiperidin-4-yl)carbamate | LCMS (ESI, m/z), 616.6 $[M + H]^+$. $^1H$ NMR (400 MHz, DMSO-$d_6$) 0.88 (dd, J = 6.53, 2.89 Hz, 6 H) 1.16-1.30 (m, 4 H) 1.38-1.52 (m, 4 H) 1.63-1.74 (m, 1 H) 1.82 (s, 3 H) 1.90-2.05 (m, 2 H) 2.17 (s, 3 H) 2.25-2.38 (m, 1 H) 2.48-2.52 (m, 3 H) 2.69 (s, 3 H) 2.79-2.87 (m, 2 H) 3.09-3.17 (m, 4 H) 3.66-3.76 (m, 5 H) 4.64 (br s, 1 H) 4.66-4.73 (m, 1 H) 4.98 (d, J = 10.92 Hz, 1 H) 5.42 (dd, J = 16.12, 8.47 Hz, 2 H) 6.36-6.57 (m, 2 H) 6.59-6.74 (m, 2 H) |
| 23 | 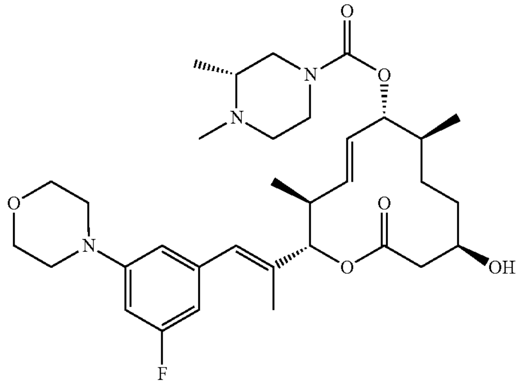 [(2R,3R,4E,6R,7S,10S)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] (3S)-3,4-dimethylpiperazine-1-carboxylate | LCMS (ESI, m/z), 602.6 $[M + H]^+$. $^1H$ NMR (400 MHz, DMSO-$d_6$) 0.88 (dd, J = 6.65, 3.89 Hz, 6 H) 0.96 (d, J = 6.40 Hz, 3 H) 1.16-1.30 (m, 3 H) 1.37-1.54 (m, 2 H) 1.81 (s, 3 H) 1.92-2.04 (m, 1 H) 2.22-2.34 (m, 2 H) 2.35-2.46 (m, 3 H) 2.50 (s, 3 H) 3.06-3.21 (m, 4 H) 3.29-3.41 (m, 4 H) 3.67-3.80 (m, 5 H) 4.64-4.72 (m, 2 H) 4.97 (d, J = 10.29 Hz, 1 H) 5.32-5.53 (m, 2 H) 6.39-6.56 (m, 2 H) 6.59-6.74 (m, 2 H) |
| 24 | 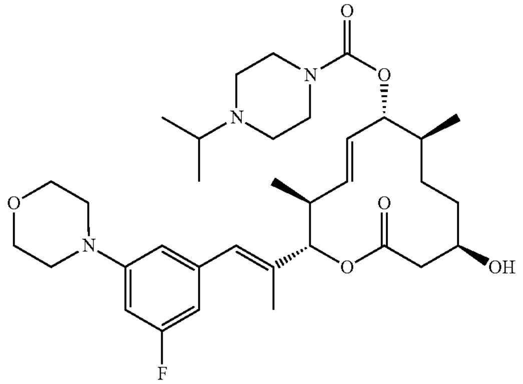 [(2R,3R,4E,6R,7S,10S)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-propan-2-ylpiperazine-1-carboxylate | LCMS (ESI, m/z), 616.6 $[M + H]^+$. $^1H$ NMR (400 MHz, DMSO-$d_6$) 0.88 (dd, J = 6.40, 3.89 Hz, 6 H) 1.00 (s, 6 H) 1.17-1.32 (m, 3 H) 1.41-1.52 (m, 2 H) 1.81 (s, 3 H) 1.93-2.07 (m, 1 H) 2.20-2.37 (m, 2 H) 2.41-2.47 (m, 5 H) 3.09-3.15 (m, 4 H) 3.27-3.39 (m, 4 H) 3.68-3.77 (m, 5 H) 4.64-4.72 (m, 2 H) 4.97 (d, J = 10.54 Hz, 1 H) 5.35-5.51 (m, 2 H) 6.40-6.59 (m, 2 H) 6.59-6.72 (m, 2 H) |

TABLE 4-continued

| Characterization of Compounds 1-85 and 265-267 | | |
|---|---|---|
| Ex. | Structure and IUPAC Chemical Name | Characterization |
| 25 | 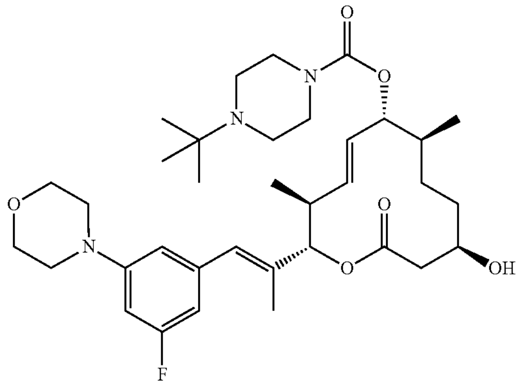 [(2R,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-tert-butylpiperazine-1-carboxylate | LCMS (ESI, m/z), 630.6 $[M + H]^+$. $^1H$ NMR (400 MHz, DMSO-$d_6$) 0.08 (s, 9 H) 0.89 (dd, J = 6.71, 3.70 Hz, 6 H) 1.17-1.32 (m, 2 H) 1.41-1.52 (m, 2 H) 1.55-1.68 (m, 1 H) 1.81 (s, 3 H) 1.95-2.12 (m, 1 H) 2.24-2.35 (m, 2 H) 2.41-2.48 (m, 4 H) 3.03-3.17 (m, 4 H) 3.24-3.35 (m, 4 H) 3.68-3.82 (m, 5 H) 4.58-4.75 (m, 2 H) 4.98 (d, J = 10.04 Hz, 1 H) 5.35-5.55 (m, 2 H) 6.44-6.55 (s, 2 H) 6.60-6.75 (m, 2 H) |
| 26 | 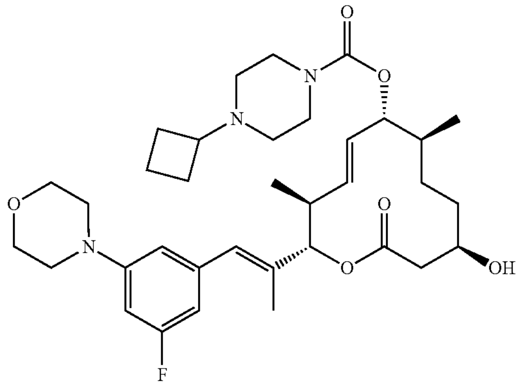 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-cyclobutylpiperazine-1-carboxylate | LCMS (ESI, m/z), 628.6 $[M + H]^+$. $^1H$ NMR (400 MHz, DMSO-$d_6$) 0.85-0.90 (m, 6 H) 1.14-1.35 (m, 5 H) 1.39-1.51 (m, 4 H) 1.52-1.63 (m, 1 H) 1.70-1.76 (m, 1 H) 1.80 (s, 3 H) 1.93-2.05 (m, 1 H) 2.22-2.47 (m, 7 H) 3.08-3.15 (m, 4 H) 3.23-3.38 (m, 4 H) 3.67-3.80 (m, 5 H) 4.50-4.81 (m, 2 H) 4.97 (d, J = 10.67 Hz, 1 H) 5.34-5.54 (m, 2 H) 6.46 (s, 2 H) 6.62 (s, 2 H) |
| 27 | 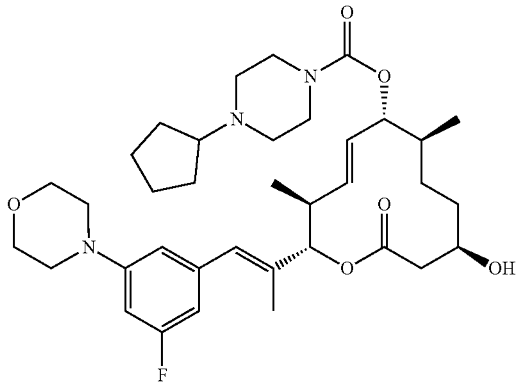 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-cyclopentylpiperazine-1-carboxylate | LCMS (ESI, m/z), 642.7 $[M + H]^+$. $^1H$ NMR (400 MHz, DMSO-$d_6$) 0.85-0.95 (m, 6 H) 1.14-1.33 (m, 4 H) 1.38-1.52 (m, 6 H) 1.53-1.65 (m, 2 H) 1.67-1.76 (m, 1 H) 1.80 (s, 3 H) 1.89-2.08 (m, 1 H) 2.19-2.36 (m, 2 H) 2.39-2.50 (m, 5 H) 3.08-3.15 (m, 4 H) 3.36-3.52 (m, 4 H) 3.68-3.76 (m, 5 H) 4.61-4.77 (m, 2 H) 4.97 (d, J = 10.79 Hz, 1 H) 5.35-5.50 (m, 2 H) 6.42-6.56 (m, 2 H) 6.60-6.70 (m, 2 H) |

TABLE 4-continued

| Characterization of Compounds 1-85 and 265-267 | | |
|---|---|---|
| Ex. | Structure and IUPAC Chemical Name | Characterization |
| 28 | 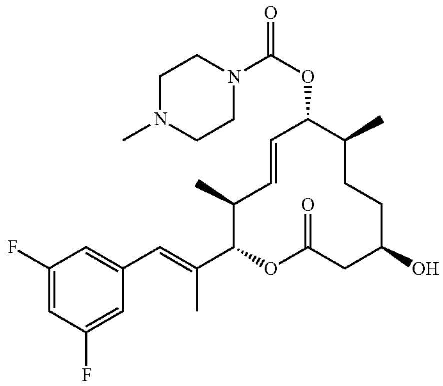 [(2S,3S,4E,6R,7S,10R)-2-[(E)-1-(3,5-difluorophenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 521.5 $[M + H]^+$. $^1H$ NMR (400 MHz, $CDCl_3$) 0.98 (d, J = 6.78 Hz, 3 H) 1.01 (d, J = 6.78 Hz, 3 H) 1.20-1.32 (m, 2 H) 1.42-1.56 (m, 1 H) 1.75-1.84 (m, 1 H) 1.87 (d, J = 1.13 Hz, 3 H) 1.89-1.98 (m, 1 H) 2.30 (s, 3 H) 2.36 (br s, 4 H) 2.49-2.70 (m, 3 H) 3.34 (br s, 1 H) 3.49 (br s, 4 H) 3.71 (s, 1 H) 4.88 (t, J = 10.04 Hz, 1 H) 5.25 (d, J = 10.54 Hz, 1 H) 5.40 (dd, J = 15.06, 9.66 Hz, 1 H) 5.53-5.65 (m, 1 H) 6.49 (s, 1 H) 6.62-6.73 (m, 1 H) 6.74-6.82 (m, 2 H) |
| 29 | 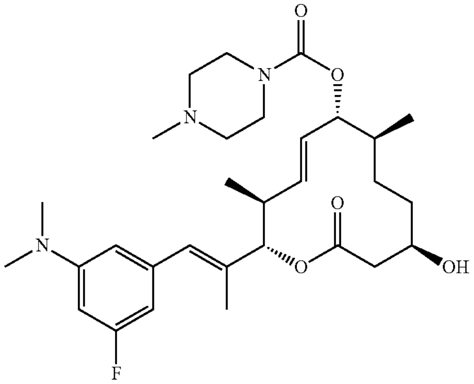 [(2S,3S,4E,6R,7S,10R)-2-[(E)-1-[3-(dimethylamino)-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 546.5 $[M + H]^+$. $^1H$ NMR (400 MHz, $CDCl_3$) 0.99 (t, J = 6.84 Hz, 6 H) 1.21-1.30 (m, 2 H) 1.43-1.55 (m, 1 H) 1.70-1.82 (m, 1 H) 1.88 (br d, J = 1.25 Hz, 3 H) 1.90-1.97 (m, 1 H) 2.35 (s, 3 H) 2.46 (br s, 4 H) 2.51-2.68 (m, 3 H) 2.94 (s, 6 H) 3.50-3.61 (m, 4 H) 3.68-3.78 (m, 1 H) 4.88 (t, J = 10.04 Hz, 1 H) 5.26 (m, t, J = 10.67 Hz, 1 H) 5.39 (dd, J = 14.93, 9.66 Hz, 1 H) 5.60 (dd, J = 15.00, 9.85 Hz, 1 H) 6.18-6.43 (m, 3 H) 6.51 (s, 1 H) |
| 30 | 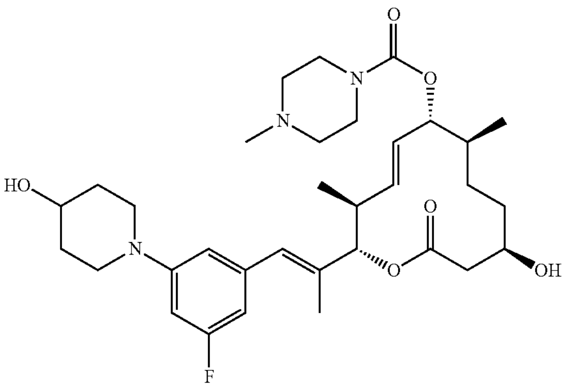 [(2S,3S,4E,6R,7S,10R)-2-[(E)-1-[3-fluoro-5-(4-hydroxypiperidin-1-yl)phenyl]prop-1-en-2-yl]-10-hydroxy-3,7-dimethyl-12-oxo-1-oxacyclododec-4-en-6-yl] 4-methylpiperizine-1-carboxylate | LCMS (ESI, m/z), 602.5 $[M + H]^+$. $^1H$ NMR (400 MHz, $CDCl_3$) 0.99 (t, J = 6.71 Hz, 6 H) 1.19-1.31 (m, 2 H) 1.42-1.55 (m, 1 H) 1.59-1.72 (m, 2 H) 1.75-1.84 (m, 1 H) 1.87 (d, J = 1.25 Hz, 3 H) 1.89-2.02 (m, 3 H) 2.44 (s, 3 H) 2.49-2.70 (m, 8 H) 2.92-3.01 (m, 2 H) 3.50-3.67 (m, 6 H) 3.67-3.78 (m, 1 H) 3.88 (tt, J = 8.56, 4.05 Hz, 1 H) 4.88 (t, J = 10.04 Hz, 1 H) 5.25 (d, J = 10.54 Hz, 1 H) 5.39 (dd, J = 15.00, 9.72 Hz, 1 H) 5.60 (dd, J = 15.06, 9.91 Hz, 1 H) 6.41-6.52 (m, 3 H) 6.54 (s, 1 H) |

TABLE 4-continued

Characterization of Compounds 1-85 and 265-267

| Ex. | Structure and IUPAC Chemical Name | Characterization |
|---|---|---|
| 31 | 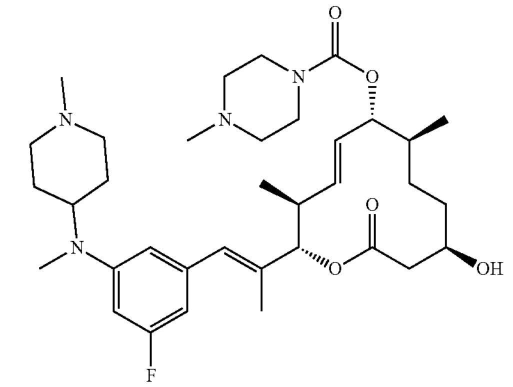 [(2S,3S,4E,6R,7S,10R)-2-[(E)-1-[3-fluoro-5-[methyl-(1-methylpiperidin-4-yl)amino]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 629.6 $[M + H]^+$. $^1H$ NMR (400 MHz, $CDCl_3$) 1.02 (t, J = 6.78 Hz, 6 H) 1.18-1.36 (m, 2 H) 1.46-1.57 (m, 1 H) 1.76-1.92 (m, 6 H) 1.91-2.00 (m, 1 H) 2.22-2.39 (m, 2 H) 2.50 (s, 3 H) 2.54-2.66 (m, 3 H) 2.66-2.77 (m, 8 H) 2.81 (s, 3 H) 3.53-3.89 (m, 9 H) 4.91 (t, J = 10.10 Hz, 1 H) 5.28 (d, J = 10.54 Hz, 1 H) 5.42 (dd, J = 15.00, 9.72 Hz, 1 H) 5.62 (dd, J = 14.81, 9.91 Hz, 1 H) 6.31-6.47 (m, 3 H) 6.52 (s, 1 H) |
| 32 | 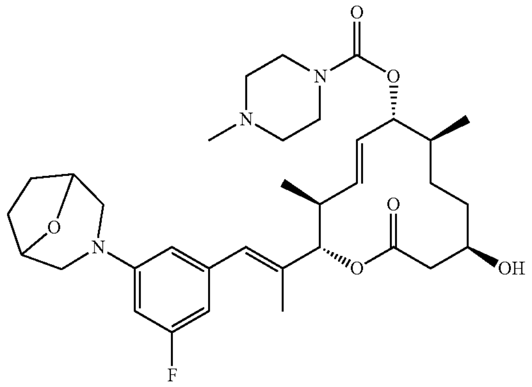 [(2S,3S,4E,6R,7S,10R)-2-[(E)-1-[3-fluoro-5-[(1R,5S)-8-oxa-3-azabicyclo[3.2.1]octan-3-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 614.6 $[M + H]^+$. $^1H$ NMR (400 MHz, $CDCl_3$) 0.99 (t, J = 6.15 Hz, 6 H) 1.18-1.32 (m, 2 H) 1.46-1.57 (m, 1 H) 1.73-1.84 (m, 1 H) 1.86 (s, 3 H) 1.88-2.04 (m, 5 H) 2.45-2.70 (m, 6 H) 2.76-2.93 (m, 4 H) 2.99-3.10 (m, 2 H) 3.16-3.36 (m, 2 H) 3.55-3.77 (m, 5 H) 4.39-4.55 (m, 2 H) 4.88 (t, J = 10.10 Hz, 1 H) 5.25 (d, J = 10.67 Hz, 1 H) 5.38 (dd, J = 14.87, 9.72 Hz, 1 H) 5.60 (dd, J = 15.00, 9.98 Hz, 1 H) 6.35-6.42 (m, 2 H) 6.45 (br d, J = 9.03 Hz, 1 H) 6.50 (s, 1 H) |
| 33 | 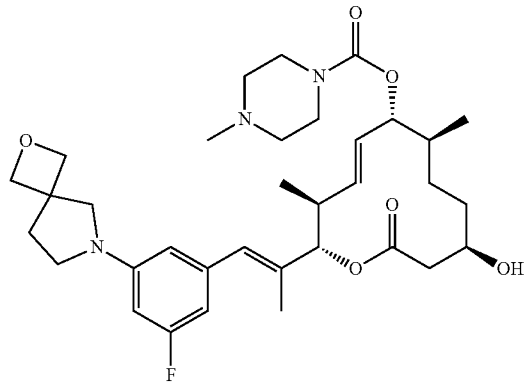 [(2S,3S,4E,6R,7S,10R)-2-[(E)-1-[3-fluoro-5-(2-oxa-7-azaspiro[3.4]octan-7-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 614.5 $[M + H]^+$. $^1H$ NMR (400 MHz, $CDCl_3$) 0.99 (d, J = 6.78 Hz, 6 H) 1.19-1.34 (m, 2 H) 1.43-1.55 (m, 1 H) 1.70-1.82 (m, 1 H) 1.88 (br d, J = 1.25 Hz, 3 H) 1.91-1.99 (m, 1 H) 2.31 (t, J = 6.90 Hz, 2 H) 2.49-2.70 (m, 3 H) 2.78 (s, 3 H) 2.89-3.22 (m, 4 H) 3.30 (t, J = 6.90 Hz, 3 H) 3.53 (s, 2 H) 3.68-3.78 (m, 1 H) 3.80-4.10 (m, 4 H) 4.61-4.67 (m, 2 H) 4.67-4.76 (m, 2 H) 4.89 (t, J = 10.16 Hz, 1 H) 5.26 (d, J = 10.67 Hz, 1 H) 5.38 (dd, J = 15.06, 9.79 Hz, 1 H) 5.61 (dd, J = 15.00, 9.98 Hz, 1 H) 6.09-6.18 (m, 2 H) 6.30-6.37 (m, 1 H) 6.50 (s, 1 H) |

TABLE 4-continued

| Ex. | Structure and IUPAC Chemical Name | Characterization |
| --- | --- | --- |
| | Characterization of Compounds 1-85 and 265-267 | |
| 34 | 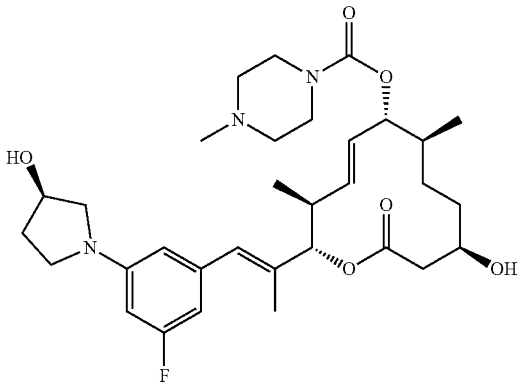 [(2S,3S,4E,6R,7S,10R)-2-[(E)-1-[3-fluoro-5-[(3R)-3-hydroxypyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 588.5 [M + H]$^+$. $^1$H NMR (400 MHz, $CDCl_3$) 0.98 (d, J = 5.52 Hz, 3 H) 1.00 (d, J = 5.52 Hz, 3 H) 1.19-1.34 (m, 2 H) 1.43-1.55 (m, 1 H) 1.73-1.84 (m, 1 H) 1.87 (d, J = 1.25 Hz, 3 H) 1.90-1.97 (m, 1 H) 2.05-2.19 (m, 2 H) 2.46 (s, 3 H) 2.51-2.59 (m, 3 H) 2.60-2.68 (m, 4 H) 3.25 (d, J = 10.54 Hz, 1 H) 3.34 (td, J = 8.91, 3.26 Hz, 1 H) 3.43-3.53 (m, 2 H) 3.62 (br s, 4 H) 3.70-3.79 (m, 1 H) 4.54-4.66 (m, 1 H) 4.88 (t, J = 10.10 Hz, 1 H) 5.26 (d, J = 10.67 Hz, 1 H) 5.39 (dd, J = 14.93, 9.54 Hz, 1 H) 5.60 (dd, J = 14.93, 9.91 Hz, 1 H) 6.10-6.22 (m, 2 H) 6.29-6.37 (m, 1 H) 6.51 (s, 1 H) |
| 35 | 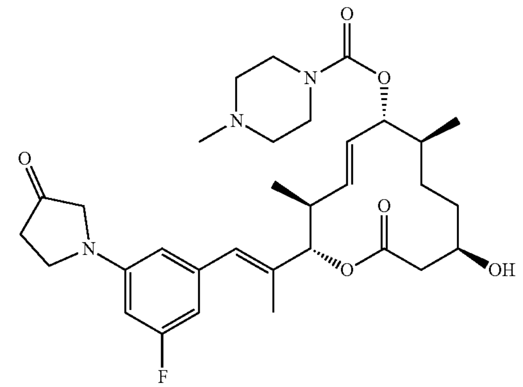 [(2S,3S,4E,6R,7S,10R)-2-[(E)-1-[3-fluoro-5-(3-oxopyrrolidin-1-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 586.5 [M + H]$^+$. $^1$H NMR (400 MHz, $CDCl_3$) 0.88-1.06 (m, 6 H) 1.19-1.34 (m, 2 H) 1.41-1.56 (m, 1 H) 1.73-1.85 (m, 1 H) 1.87 (d, J = 1.25 Hz, 3 H) 1.91-2.01 (m, 1 H) 2.49-2.90 (m, 10 H) 3.35-3.56 (m, 2 H) 3.59-3.82 (m, 7 H) 4.10-4.35 (m, 2 H) 4.89 (br t, J = 10.10 Hz, 1 H) 5.27 (d, J = 10.79 Hz, 1 H) 5.34-5.43 (m, 1 H) 5.62 (br dd, J = 14.56, 9.79 Hz, 1 H) 6.17-6.32 (m, 1 H) 6.47 (br d, J = 9.41 Hz, 1 H) 6.53 (s, 1 H) |
| 36 | 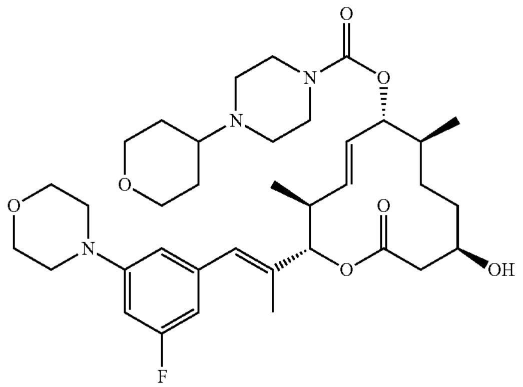 [(2S,3S,4E,6R,7S,10R)-2-[(E)-1-[3-fluoro-5-morpholin-4-ylphenyl)prop-1-en-2-yl]-10-hydroxy-3,7-dimethyl-12-oxo-1-oxacyclododec-4-en-6-yl] 4-(oxan-4-yl)piperazine-1-carboxylate | LCMS (ESI, m/z), 658.6 [M + H]$^+$. $^1$H NMR (400 MHz, $CDCl_3$) 0.99 (d, J = 6.78 Hz, 6 H) 1.17-1.32 (m, 2 H) 1.41-1.58 (m, 1 H) 1.71-1.85 (m, 3 H) 1.87 (d, J = 1.13 Hz, 3 H) 1.89-1.97 (m, 1 H) 1.99-2.14 (m, 2 H) 2.48-2.60 (m, 3 H) 2.60-2.69 (m, 1 H) 3.02 (br s, 4 H) 3.12-3.24 (m, 5 H) 3.41 (br t, J = 11.42 Hz, 2 H) 3.63-3.78 (m, 1 H) 3.81-3.87 (m, 4 H) 3.92 (br s, 4 H) 4.05-4.16 (m, 2 H) 4.88 (t, J = 10.10 Hz, 1 H) 5.25 (d, J = 10.67 Hz, 1 H) 5.38 (dd, J = 15.00, 9.73 Hz, 1 H) 5.60 (dd, J = 15.00, 9.98 Hz, 1 H) 6.44-6.60 (m, 4 H) |

TABLE 4-continued

| Characterization of Compounds 1-85 and 265-267 | | |
|---|---|---|
| Ex. | Structure and IUPAC Chemical Name | Characterization |
| 37 | 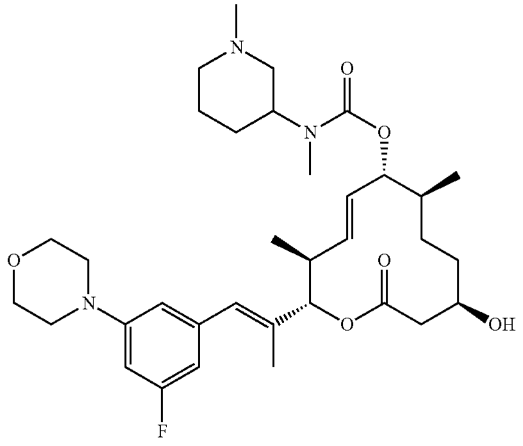 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] N-methyl-N-(1-methylpiperidin-3-yl)carbamate | LCMS (ESI, m/z), 616.5 $[M + H]^+$. $^1H$ NMR (400 MHz, $CDCl_3$) 0.89-1.09 (m, 6 H) 1.17-1.35 (m, 2 H) 1.40-1.60 (m, 3 H) 1.71-1.86 (m, 2 H) 1.87 (s, 3 H) 1.88-2.00 (m, 2 H) 2.25-2.45 (m, 2 H) 2.49-2.67 (m, 4 H) 2.71 (s, 3 H) 2.82 (s, 3 H) 2.88-3.03 (m, 2 H) 3.13-3.20 (m, 4 H) 3.67-3.77 (m, 1 H) 3.81-3.91 (m, 4 H) 4.21-4.63 (m, 1 H) 4.80-4.93 (m, 1 H) 5.25 (d, J = 10.67 Hz, 1 H) 5.35-5.45 (m, 1 H) 5.58 (dd, J = 14.93, 10.04 Hz, 1 H) 6.36-6.66 (m, 4 H) |
| 38 | 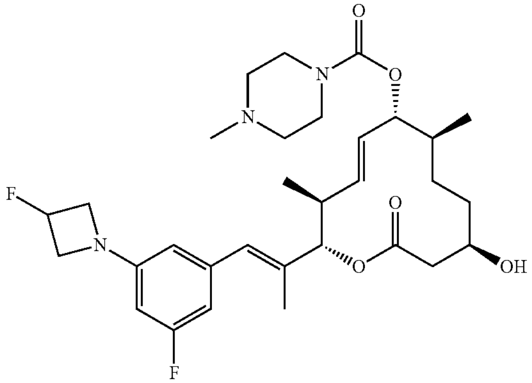 [(2S,3S,4E,6R,7S,10R)-2-[(E)-1-(3-fluoro-5-(3-flouroazetidin-1-yl)phenyl]prop-1-en-2-yl]-10-hydroxy-3,7-dimethyl-12-oxo-1-oxacyclododec-4-en-6-yl] 4-methylpiperidin-1-yl)carboxylate | LCMS (ESI, m/z), 576.5 $[M + H]^+$. $^1H$ NMR (400 MHz, $CDCl_3$) 0.98 (d, J = 6.65 Hz, 3 H) 1.01 (d, J = 6.78 Hz, 3 H) 1.27-1.47 (m, 2 H) 1.56-1.73 (m, 2 H) 1.86 (d, J = 1.00 Hz, 3 H) 1.91-2.03 (m, 1 H) 2.30 (s, 3 H) 2.36-2.43 (m, 4 H) 2.43-2.53 (m, 1 H) 2.58-2.70 (m, 2 H) 3.38-3.57 (m, 6 H) 3.73-3.98 (m, 3 H) 4.17 (m, 2 H) 4.82 (m, 1 H) 5.13 (d, J = 10.54 Hz, 1 H) 5.43-5.62 (m, 2 H) 6.07-6.19 (m, 2 H) 6.34-6.42 (m, 1 H) 6.49-6.54 (m, 1 H) |
| 39 | 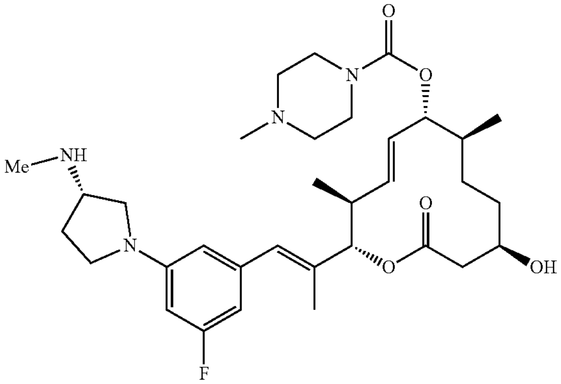 [(2S,3S,4E,6R,7S,10S)-2-[(E)-1-(3-fluoro-5-[(3S)-3-(methylamino)pyrrolidin)phenyl]prop-1-en-2-yl]-10-hydroxy-3,7-dimethyl-12-oxo-1-oxacyclododec-4-en-6-yl] 4-methylpiperidin-1-yl)carboxylate | LCMS (ESI, m/z), 601.6 $[M + H]^+$. $^1H$ NMR (400 MHz, $CDCl_3$) 0.98 (d, J = 6.78 Hz, 3 H) 1.01 (d, J = 6.78 Hz, 3 H) 1.27-1.47 (m, 2 H) 1.64 (br s, 2 H) 1.87 (d, J = 1.00 Hz, 3 H) 1.90-2.01 (m, 2 H) 2.02-2.16 (m, 1 H) 2.31 (s, 3 H) 2.35-2.52 (m, 6 H) 2.56-2.70 (m, 4 H) 3.33-3.38 (m, 2 H) 3.45-3.59 (m, 6 H) 3.66-3.75 (m, 1 H) 3.76-3.85 (m, 1 H) 479-4.84 (m, 1 H) 5.13 (d, J = 10.67 Hz, 1 H) 5.44-5.62 (m, 2 H) 6.19-6.32 (m, 2 H) 6.33-6.39 (m, 1 H) 6.53 (s, 1 H) |

TABLE 4-continued

| Characterization of Compounds 1-85 and 265-267 | | |
|---|---|---|
| Ex. | Structure and IUPAC Chemical Name | Characterization |
| 40 | 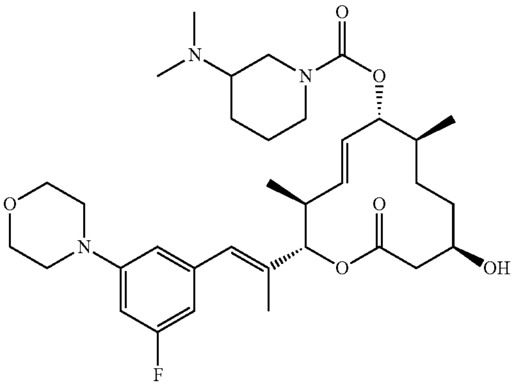 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 3-(dimethylamino)piperidin-1-carboxylate | LCMS (ESI, m/z), 616.5 [M + H]+. 1H NMR (400 MHz, $CDCl_3$) 0.91-1.05 (m, 6 H) 1.17-1.35 (m, 3 H) 1.42-1.61 (m, 3 H) 1.73-1.83 (m, 2 H) 1.87 (s, 3 H) 1.86-2.03 (m, 1 H) 2.29-2.46 (m, 1 H) 2.50-2.68 (m, 3 H) 2.78 (br s, 6 H) 2.87-2.98 (m, 1 H) 3.01-3.11 (m, 1 H) 3.12-3.21 (m, 4 H) 3.59-3.78 (m, 1 H) 3.80-3.91 (m, 3 H) 3.99-4.23 (m, 1 H) 4.36-4.66 (m, 1 H) 4.73-5.00 (m, 1 H) 5.25 (d, J = 10.67 Hz, 1 H) 5.33-5.47 (m, 1 H) 5.52-5.73 (m, 1 H) 6.31-6.58 (m, 4 H) |
| 41 | 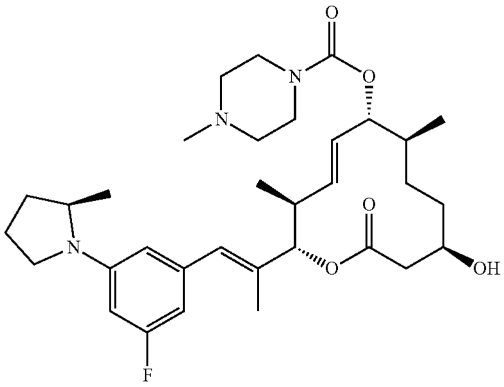 [(2S,3S,4E,6R,7R,10S)-2-[(E)-1-[3-fluoro-5-[(2S)-2-methylpyrrolidin-1-yl]phenyl]prop-1-en-2-yl]-10-hydroxy-3,7-dimethyl-12-oxo-1-oxocyclododec-4-en-6-yl] 4-methylpiperazine-1-carboxylate | LCMS (ESI, m/z), 586.6 [M + H]+. 1H NMR (400 MHz, $CDCl_3$) 0.95-1.03 (m, 6 H) 1.16 (d, J = 6.27 Hz, 3 H) 1.21-1.33 (m, 2 H) 1.40-1.56 (m, 1 H) 1.67-1.746 (m, 1 H) 1.74-1.84 (m, 1 H) 1.89 (s, 3 H) 1.92-1.99 (m, 1 H) 1.99-2.13 (m, 3 H) 2.48-2.60 (m, 2 H) 2.62-2.70 (m, 1 H) 2.76 (s, 3 H) 2.90-3.10 (m, 4 H) 3.10-3.24 (m, 1 H) 3.32-3.44 (m, 1 H) 3.67-3.77 (m, 1 H) 3.79-3.86 (m, 1 H) 3.86-4.05 (m, 4 H) 4.89 (br t, J = 10.10 Hz, 1 H) 5.27 (d, J = 10.54 Hz, 1 H) 5.32-5.44 (m, 1 H) 5.55-5.68 (m, 1 H) 6.09-6.22 (m, 2 H) 6.28 (br d, J = 9.54 Hz, 1 H) 6.50 (s, 1 H) |
| 42 | 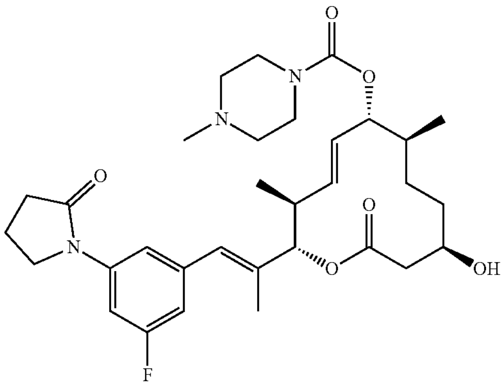 [(2S,3S,4E,6R,7S,10R)-2-[(E)-1-[3-fluoro-5-(2-oxo-pyrrolidin-1-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 586.5 [M + H]+. 1H NMR (400 MHz, $CDCl_3$) 0.98 (d, J = 6.78 Hz, 3 H) 1.00 (d, J = 6.78 Hz, 3 H) 1.16-1.32 (m, 2 H) 1.40-1.54 (m, 1 H) 1.74-1.82 (m, 1 H) 1.89 (d, J = 1.25 Hz, 3 H) 1.90-1.97 (m, 1 H) 2.09-2.22 (m, 2 H) 2.29 (s, 3 H) 2.24-2.33 (m, 4 H) 2.50-2.70 (m, 5 H) 3.24-3.35 (m, 1 H) 3.35-3.50 (m, 4 H) 3.60-3.70 (m, 1 H) 3.84 (t, J = 7.03 Hz, 2 H) 4.88 (t, J = 10.10 Hz, 1 H) 5.26 (d, J = 10.67 Hz, 1 H) 5.36-5.45 (m, 1 H) 5.52 (dd, J = 15.00, 9.98 Hz, 1 H) 6.53 (s, 1 H) 6.72-6.83 (m, 1 H) 7.27-7.30 (m, 1 H) 7.35-7.41 (m, 1 H) |

TABLE 4-continued

Characterization of Compounds 1-85 and 265-267

| Ex. | Structure and IUPAC Chemical Name | Characterization |
|---|---|---|
| 43 | 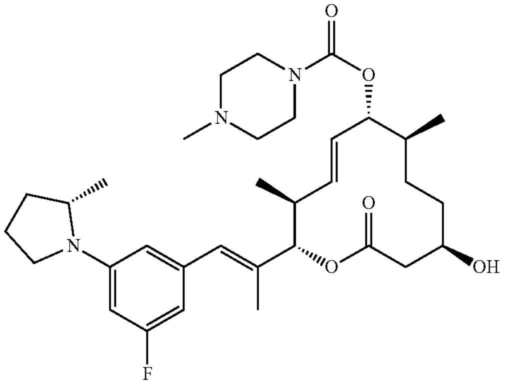 [(2S,3S,4E,6R,7S,10S)-2-[(E)-1-[3-fluoro-5-(2-methyl pyrrolidin-1-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), x586.5 [M + H]$^+$. $^1$H NMR (400 MHz, $CDCl_3$) 0.99 (br d, J = 5.27 Hz, 6 H) 1.17 (d, J = 6.27 Hz, 3 H) 1.21-1.33 (m, 2 H) 1.40-1.56 (m, 1 H) 1.67-1.746 (m, 1 H) 1.74-1.84 (m, 1 H) 1.89 (s, 3 H) 1.92-1.99 (m, 1 H) 1.99-2.13 (m, 3 H) 2.48-2.60 (m, 2 H) 2.62-2.70 (m, 1 H) 2.76 (s, 3 H) 2.90-3.10 (m, 4 H) 3.10-3.24 (m, 1 H) 3.32-3.44 (m, 1 H) 3.67-3.77 (m, 1 H) 3.79-3.86 (m, 1 H) 3.86-4.05 (m, 4 H) 4.89 (br t, J = 10.10 Hz, 1 H) 5.27 (d, J = 10.54 Hz, 1 H) 5.39 (dd, J = 14.93, 9.54 Hz, 1 H) 5.60 (dd, J = 14.93, 9.91 Hz, 1 H) 6.10-6.23 (m, 2 H) 6.28 (br d, J = 9.54 Hz, 1 H) 6.50 (s, 1 H) |
| 44 | 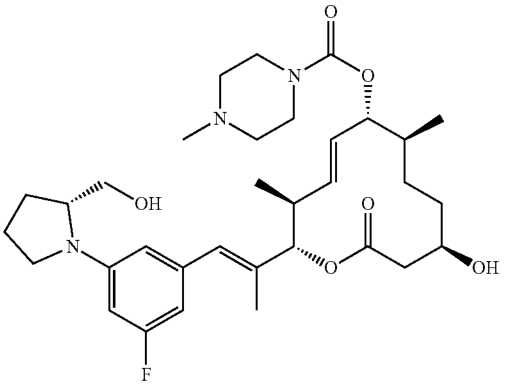 [(2S,3S,4E,6R,7S,10R)-2-[(E)-1-[3-fluoro-5-[(2R)-2-(hydroxymethyl)pyrrolidin-1-yl]phenyl]prop-1-en-2-yl]-10-hydroxy-3,7-dimethyl-12-oxo-1-oxacyclodeodec-4-en-6-yl] 4-methylpiperazine-1-carboxylate | LCMS (ESI, m/z), 602.5 [M + H]$^+$. $^1$H NMR (400 MHz, $CDCl_3$) 0.99 (d, J = 6.65 Hz, 5 H) 1.18-1.35 (m, 2 H) 1.42-1.51 (m, 1 H) 1.72-1.84 (m, 1 H) 1.88 (s, 3 H) 1.91-1.97 (m, 1 H) 1.97-2.19 (m, 4 H) 2.47-2.68 (m, 3 H) 2.71-2.88 (m, 5 H) 3.12-3.22 (m, 1 H) 3.34-3.55 (m, 4 H) 3.62-3.79 (m, 5 H) 3.80-3.90 (m, 1 H) 4.10-4.34 (m, 2 H) 4.89 (br t, J = 10.04 Hz, 1 H) 5.26 (d, J = 10.54 Hz, 1 H) 5.38 (br dd, J = 14.62, 9.60 Hz, 1 H) 5.61 (dd, J = 14.81, 9.91 Hz, 1 H) 6.29-6.44 (m, 3 H) 6.51 (s, 1 H) |
| 45 | 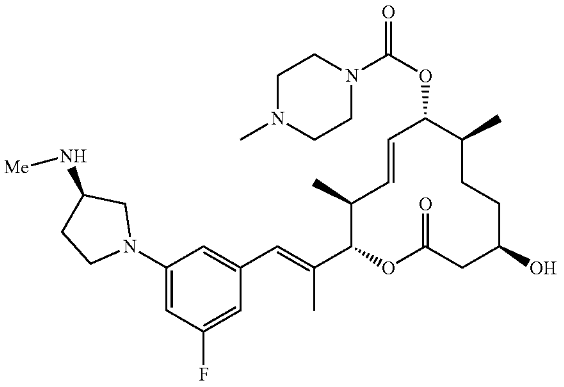 [(2S,3S,4E,6R,7S,10S)-2-[(E)-1-[3-fluoro-5-[(3S)-3-(methylamino)pyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 601.5 [M + H]$^+$. $^1$H NMR (400 MHz, $CDCl_3$) 0.98 (d, J = 6.90 Hz, 3 H) 1.00 (d, J = 7.03 Hz, 3 H) 1.17-1.32 (m, 2 H) 1.43-1.55 (m, 1 H) 1.72-1.84 (m, 1 H) 1.87 (d, J = 1.13 Hz, 3 H) 1.88-1.97 (m, 2 H) 2.18-2.28 (m, 1 H) 2.30 (s, 3 H) 2.38 (br s, 4 H) 2.49 (s, 3 H) 2.51-2.60 (m, 2 H) 2.60-2.69 (m, 1 H) 2.94-3.18 (m, 5 H) 3.24-3.35 (m, 1 H) 3.37-3.59 (m, 5 H) 3.67-3.79 (m, 1 H) 4.88 (t, J = 10.10 Hz, 1 H) 5.25 (d, J = 10.67 Hz, 1 H) 5.39 (dd, J = 15.06, 9.66 Hz, 2 H) 5.59 (dd, J = 15.06, 9.91 Hz, 2 H) 6.06-6.21 (m, 2 H) 6.28-6.37 (m, 1 H) 6.50 (s, 1 H) |

TABLE 4-continued

| Characterization of Compounds 1-85 and 265-267 | | |
|---|---|---|
| Ex. | Structure and IUPAC Chemical Name | Characterization |
| 46 | 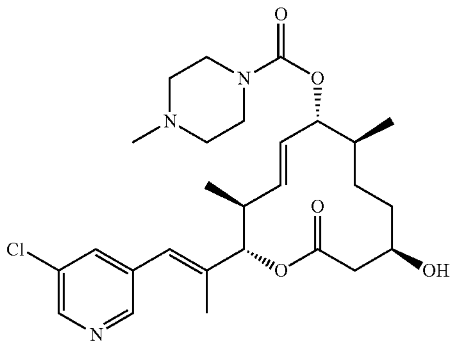 [(2S,3S,4E,6R,7S,10R)-2-[(E)-1-(5-chloropyridin-3-yl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 520.5 $[M + H]^+$. $^1H$ NMR (400 MHz, $CDCl_3$) 0.99 (d, J = 5.40 Hz, 3 H) 1.01 (d, J = 5.27 Hz, 3 H) 1.17-1.33 (m, 2 H) 1.42-1.55 (m, 1 H) 1.74-1.85 (m, 1 H) 1.89 (s, 3 H) 1.90-1.98 (m, 1 H) 2.32 (s, 3 H) 2.39 (br s, 4 H) 2.50-2.78 (m, 3 H) 3.25-3.37 (m, 1 H) 3.50 (br s, 4 H) 3.73 (br s, 1 H) 4.88 (t, J = 10.04 Hz, 1 H) 5.28 (d, J = 10.67 Hz, 1 H) 5.41 (dd, J = 15.06, 9.66 Hz, 1 H) 5.59 (dd, J = 15.00, 9.85 Hz, 1 H) 6.35-6.64 (m, 1 H) 7.49-7.68 (m, 1 H) 8.40 (d, J = 1.38 Hz, 1 H) 8.44 (d, J = 2.13 Hz, 1 H) |
| 47 | 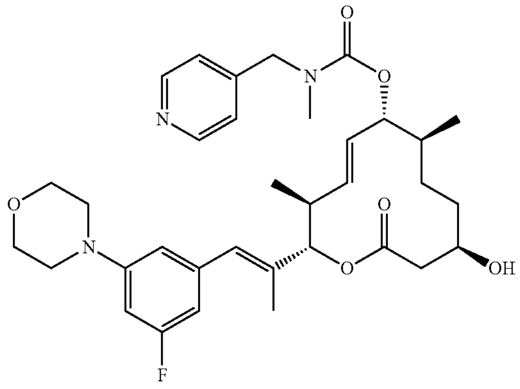 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] N-methyl-N-(pyridin-4-ylmethyl)carbamate | LCMS (ESI, m/z), 610.5 $[M + H]^+$. $^1H$ NMR (400 MHz, $CDCl_3$) 0.83-1.11 (m, 6 H) 1.14-1.35 (m, 1 H) 1.35-1.60 (m, 1 H) 1.67-1.84 (m, 1 H) 1.87 (s, 3 H) 1.94-2.07 (m, 1 H) 2.49-2.75 (m, 3 H) 2.86-3.05 (m, 3 H) 3.08-3.25 (m, 4 H) 3.63-3.78 (m, 1 H) 3.81-3.94 (m, 4 H) 4.45-4.69 (m, 2 H) 4.92 (t, J = 9.91 Hz, 1 H) 5.19-5.53 (m, 2 H) 5.57-5.70 (m, 1 H) 6.41-6.59 (m, 4 H) 7.28-7.49 (m, 2 H) 8.49-8.78 (m, 2 H) |
| 48 | 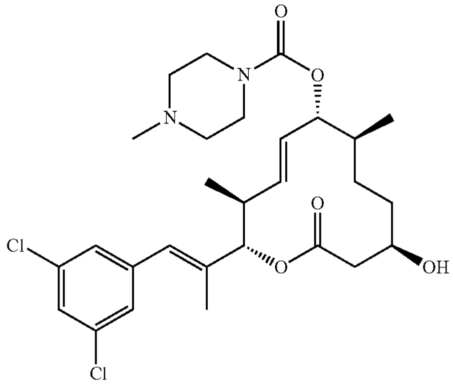 [(2S,3S,4E,6R,7S,10R)-2-[(E)-1-(3,5-dichlorophenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 553.4 $[M + H]^+$. $^1H$ NMR (400 MHz, $CDCl_3$) 0.98 (d, J = 6.78 Hz, 3 H) 1.00 (d, J = 6.78 Hz, 3 H) 1.18-1.32 (m, 2 H) 1.40-1.54 (m, 1 H) 1.74-1.83 (m, 1 H) 1.85 (d, J = 1.13 Hz, 3 H) 1.89-1.97 (m, 1 H) 2.29 (s, 3 H) 2.36 (br s, 4 H) 2.47-2.71 (m, 3 H) 3.26-3.40 (m, 1 H) 3.48 (br s, 4 H) 3.63-3.80 (m, 1 H) 4.87 (t, J = 10.10 Hz, 1 H) 5.40 (dd, J = 15.06, 9.66 Hz, 1 H) 5.58 (dd, J = 15.00, 9.85 Hz, 1 H) 6.46 (s, 1 H) 7.13 (d, J = 1.76 Hz, 2 H) 7.24 (t, J = 1.82 Hz, 1 H) |

TABLE 4-continued

| Characterization of Compounds 1-85 and 265-267 | | |
|---|---|---|
| Ex. | Structure and IUPAC Chemical Name | Characterization |
| 49 | 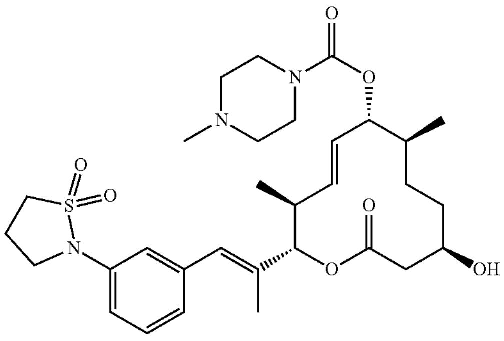 [(2S,3S,4E,6R,7S,10R)-2-[(E)-1-(1,1-dioxo-1,2-thiazolidin-2-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 604.5 $[M + H]^+$. $^1H$ NMR (400 MHz, $CDCl_3$) 1.00 (t, J = 6.71 Hz, 6 H) 1.18-1.32(m, 2 H) 1.44-1.55 (m, 1 H) 1.73-1.84 (m, 1 H) 1.88 (d, J = 1.25 Hz, 3 H) 1.90-2.00 (m, 1 H) 2.30 (s, 3 H) 2.37 (br s, 4 H) 2.49-2.60 (m, 4 H) 2.61-2.74 (m, 1 H) 3.39 (t, J = 7.53 Hz, 2 H) 3.49 (br s, 4 H) 3.67-3.75 (m, 1 H) 3.78 (t, J = 6.59 Hz, 2 H) 4.89 (t, J = 10.04 Hz, 1 H) 5.28 (d, J = 10.54 Hz, 1 H) 5.40 (dd, J = 15.06, 9.66 Hz, 1 H) 5.60 (dd, J = 15.00, 9.85 Hz, 1 H) 6.56 (s, 1 H) 7.03-7.09 (m, 1 H) 7.12-7.22 (m, 2 H) 7.29-7.37 (m, 1 H) |
| 50 | 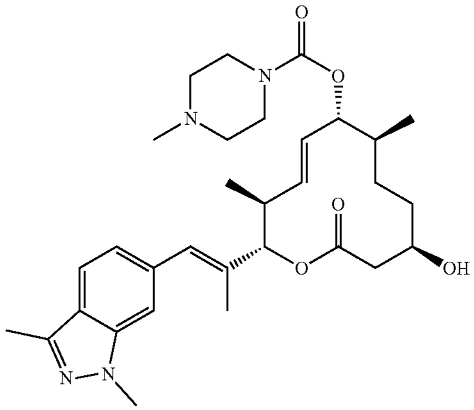 [(2S,3S,4E,6R,7S,10R)-2-[(E)-1-(1,3-dimethylindazol-6-yl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 553.5 $[M + H]^+$. $^1H$ NMR (400 MHz, $CDCl_3$) 1.04 (d, J = 7.03 Hz, 3 H) 1.06 (d, J = 6.90 Hz, 3 H) 1.22-1.36 (m, 2 H) 1.47-1.55 (m, 1 H) 1.75-1.89 (m, 1 H) 1.93-2.01 (m, 4 H) 2.33 (s, 3 H) 2.39 (br s, 4 H) 2.54-2.74 (m, 6 H) 3.44 (br d, J = 10.79 Hz, 1 H) 3.52 (br s, 4 H) 3.69-3.82 (m, 1 H) 4.01 (s, 3 H) 4.92 (t, J = 10.04 Hz, 1 H) 5.35 (d, J = 10.67 Hz, 1 H) 5.44 (dd, J = 14.93, 9.66 Hz, 1 H) 5.65 (dd, J = 15.06, 9.91 Hz, 1 H) 6.77 (s, 1 H) 7.06 (dd, J = 8.41, 1.13 Hz, 1 H) 7.21 (s, 1 H) 7.61 (d, J = 8.28 Hz, 1 H) |
| 51 | 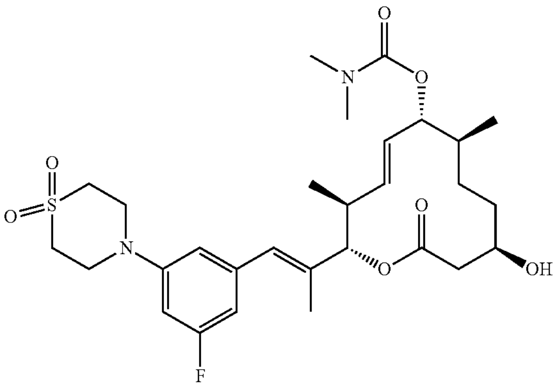 [(2S,3S,4E,6R,7S,10R)-2-[(E)-1-[3-(1,1-dioxo-1,4-thiazinan-4-yl)-5-fluorophenyl]prop-1-en-2-yl]-10-hydroxy-3,7-dimethyl-12-oxo-1-oxacyclododec-4-en-6-yl] N,N-dimethylcarbamate | LCMS (ESI, m/z), 581.5 $[M + H]^+$. $^1H$ NMR (400 MHz, $CDCl_3$) 0.98 (d, J = 6.78 Hz, 3 H) 1.01 (d, J = 6.90 Hz, 3 H) 1.15-1.33 (m, 2 H) 1.40-1.56 (m, 1 H) 1.72-1.84 (m, 1 H) 1.86 (d, J = 1.13 Hz, 3 H) 1.89-2.06 (m, 1 H) 2.48-2.68 (m, 3 H) 2.90 (s, 6 H) 3.02-3.17 (m, 4 H) 3.69-3.78 (m, 1 H) 3.82-3.95 (m, 4 H) 4.85 (t, J = 10.04 Hz, 1 H) 5.24 (d, J = 10.54 Hz, 1 H) 5.40 (dd, J = 15.06, 9.66 Hz, 1 H) 5.58 (dd, J = 15.00, 9.85 Hz, 1 H) 6.43-6.53 (m, 3 H) 6.57 (br d, J = 9.29 Hz, 1 H) |

TABLE 4-continued

Characterization of Compounds 1-85 and 265-267

| Ex. | Structure and IUPAC Chemical Name | Characterization |
|---|---|---|
| 52 | 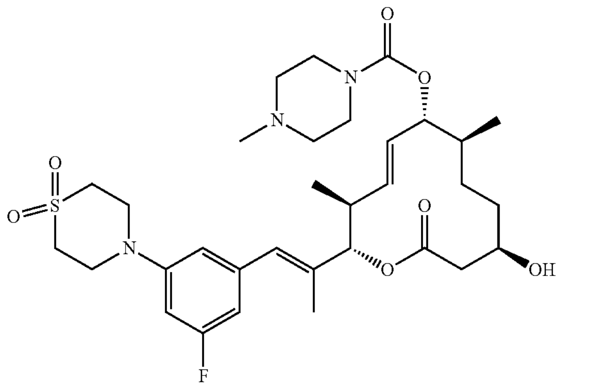<br>[(2S,3S,4E,6R,7S,10R)-2-[(E)-1-[3-(1,1-dioxo-1,4-thiazinan-4-yl)-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 636.6 $[M + H]^+$. $^1H$ NMR (400 MHz, $CDCl_3$) 1.00 (t, J = 6.84 Hz, 6 H) 1.21-1.31 (m, 2 H) 1.45-1.55 (m, 1 H) 1.72-1.84 (m, 1 H) 1.87 (s, 3 H) 1.90-1.99 (m, 1 H) 2.40 (s, 3 H) 2.48-2.70 (m, 7 H) 3.04-3.16 (m, 4 H) 3.50-3.66 (m, 5 H) 3.69-3.79 (m, 1 H) 3.81-3.88 (m, 4 H) 4.88 (t, J = 10.10 Hz, 1 H) 5.25 (d, J = 10.29 Hz, 1 H)) 5.40 (dd, J = 15.06, 9.66 Hz, 1 H) 5.59 (dd, J = 14.87, 10.10 Hz, 1 H) 6.46-6.52 (m, 3 H) 6.54-6.62 (m, 1 H) |
| 53 | 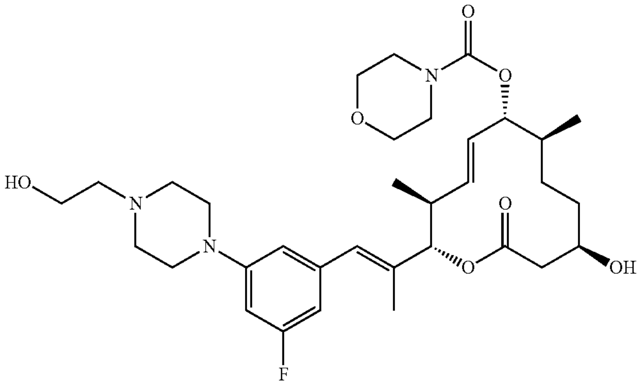<br>[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] morpholine-4-carboxylate | LCMS (ESI, m/z), 618.6 $[M + H]^+$. $^1H$ NMR (400 MHz, $CDCl_3$) 0.98 (d, J = 6.90 Hz, 3 H) 1.01 (d, J = 6.90 Hz, 3 H) 1.17-1.33 (m, 2 H) 1.41-1.55 (m, 1 H) 1.74-1.84 (m, 1 H) 1.86 (d, J = 1.00 Hz, 3 H) 1.90-2.03 (m, 1 H) 2.49-2.59 (m, 2 H) 2.60-2.66 (m, 3 H) 2.66-2.74 (m, 4 H) 3.16-3.28 (m, 4 H) 3.39-3.52 (m, 4 H) 3.60-3.78 (m, 7 H) 4.89 (t, J = 10.10 Hz, 1 H) 5.25 (d, J = 10.67 Hz, 1 H) 5.40 (dd, J = 15.06, 9.66 Hz, 1 H) 5.60 (dd, J = 15.06, 9.91 Hz, 1 H) 6.40-6.63 (m, 4 H) |
| 54 | 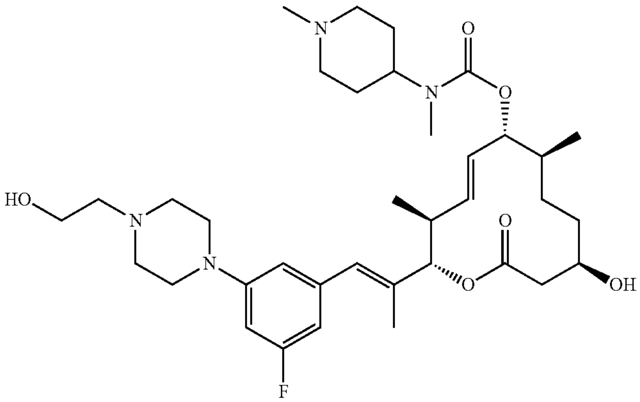<br>[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] N-methyl-N-(1-methylpiperidin-4-yl)carbamate | LCMS (ESI, m/z), 659.8 $[M + H]^+$. $^1H$ NMR (400 MHz, $CDCl_3$) 0.97 (d, J = 6.78 Hz, 3 H) 1.00 (d, J = 6.78 Hz, 3 H) 1.14-1.31 (m, 2 H) 1.43-1.55 (m, 1 H) 1.56-1.69 (m, 2 H) 1.72-1.84 (m, 3 H) 1.86 (d, J = 1.25 Hz, 3 H) 1.89-1.99 (m, 1 H) 2.02 (s, 3 H) 2.05-2.17 (m, 2 H) 2.30 (s, 3 H) 2.45-2.58 (m, 2 H) 2.59-2.63 (m, 3 H) 2.64-2.70 (m, 4 H) 2.77 (s, 3 H) 2.92-3.00 (m, 2 H) 3.16-3.26 (m, 4 H) 3.63-3.69 (m, 2 H) 3.70-3.77 (m, 1 H) 4.88 (t, J = 9.98 Hz, 1 H) 5.25 (d, J = 10.54 Hz, 1 H) 5.40 (dd, J = 15.06, 9.66 Hz, 1 H) 5.58 (dd, J = 14.93, 9.91 Hz, 1 H) 6.37-6.58 (m, 4 H) |

TABLE 4-continued

| Characterization of Compounds 1-85 and 265-267 | | |
|---|---|---|
| Ex. | Structure and IUPAC Chemical Name | Characterization |
| 55 | 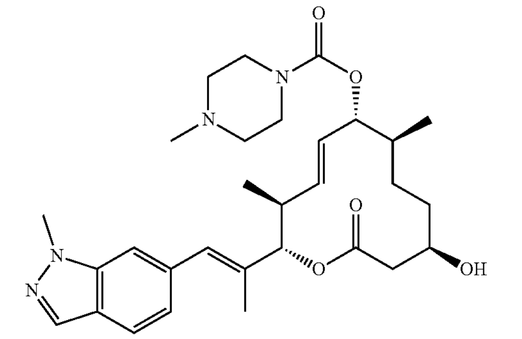 [(2S,3S,4E,6R,7S,10R)-10-hydroxy-3,7-dimethyl-2-[(E)-1-(1-methylindazol-6-yl)prop-1-en-2-yl]-12-oxo-1-oxacyclododec-4-en-6-yl] 4-methylpiperazine-1-carboxylate | LCMS (ESI, m/z), 539.5 [M + H]$^+$. $^1$H NMR (400 MHz, $CDCl_3$) 1.01 (d, J = 6.78 Hz, 3 H) 1.03-1.06 (m, 3 H) 1.23-1.30 (m, 2 H) 1.46-1.57 (m, 1 H) 1.75-1.86 (m, 2 H) 1.98-1.98 (m, 4 H) 2.36 (s, 3 H) 2.40-2.51 (m, 4 H) 2.53-2.71 (m, 3 H) 3.44-3.61 (m, 4 H) 3.70-3.78 (m, 1 H) 4.06 (s, 3 H) 4.90 (t, J = 10.16 Hz, 1 H) 5.33 (d, J = 10.54 Hz, 1 H) 5.41 (dd, J = 15.00, 9.72 Hz, 1 H) 5.63 (dd, J = 15.06, 9.91 Hz, 1 H) 6.75 (s, 1 H) 7.07 (dd, J = 8.41, 1.13 Hz, 1 H) 7.67 (d, J = 8.91 Hz, 1 H) 7.94 (d, J = 1.00 Hz, 1 H) |
| 56 | 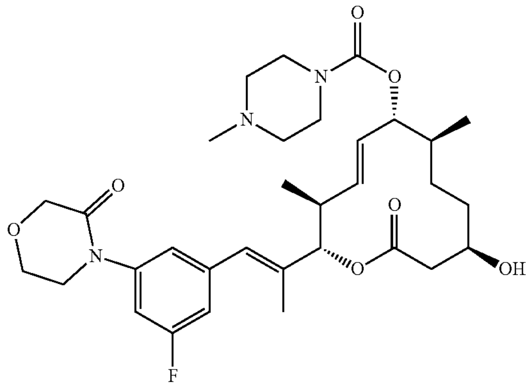 [(2S,3S,4E,6R,7S,10R)-2-[(E)-1-[3-fluoro-5-(3-oxomorpholin-4-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.6 [M + H]$^+$. $^1$H NMR (400 MHz, $CDCl_3$) 0.98 (d, J = 6.78 Hz, 3 H) 1.00 (d, J = 6.90 Hz, 3 H) 1.17-1.32 (m, 2 H) 1.41-1.52 (m, 1 H) 1.75-1.85 (m, H) 1.88 (d, J = 1.38 Hz, 3 H) 1.93 (br s, 1 H) 2.39 (br s, 3 H) 2.43-2.72 (m, 7 H) 3.50-3.62 (m, 4 H) 3.63-3.68 (m, 1 H) 3.70-3.80 (m, 3 H) 4.01-4.06 (m, 2 H) 4.54 (s, 2 H) 4.88 (t, J = 10.10 Hz, 1 H) 5.25 (d, J = 10.54 Hz, 1 H) 5.40 (dd, J = 15.06, 9.66 Hz, 1 H) 5.59 (dd, J = 14.93, 9.91 Hz, 1 H) 6.53 (s, 1 H) 6.87-6.95 (m, 1 H) 6.97-7.02 (m, 1 H) 7.05 (s, 1 H) |
| 57 | 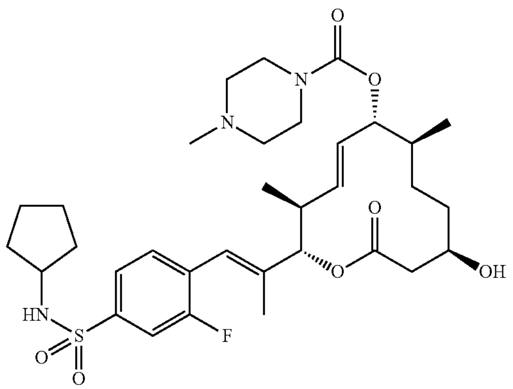 [(2S,3S,4E,6R,7S,10R)-2-[(E)-1-[4-(cyclopentylsulfamoyl)-2-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 650.5 [M + H]$^+$. $^1$H NMR (400 MHz, $CDCl_3$) 0.99 (d, J = 4.64 Hz, 3 H) 1.01 (d, J = 4.64 Hz, 3 H) 1.18-1.31 (m, 3 H) 1.32-1.43 (m, 2 H) 1.44-1.56 (m, 3 H) 1.57-1.70 (m, 2 H) 1.72-1.85 (m, 3 H) 1.90 (d, J = 1.13 Hz, 3 H) 1.92-1.98 (m, 1 H) 2.40 (s, 3 H) 2.44-2.73 (m, 7 H) 3.47-3.69 (m, 5 H) 3.69-3.80 (m, 1 H) 4.71 (d, J = 7.53 Hz, 1 H) 4.88 (t, J = 10.04 Hz, 1 H) 5.26 (d, J = 10.54 Hz, 1 H) 5.40 (dd, J = 15.06, 9.66 Hz, 1 H) 5.59 (dd, J = 15.00, 9.85 Hz, 1 H) 6.56 (s, 1 H) 7.00-7.19 (m, 2 H) 7.86 (s, 1 H) |

TABLE 4-continued

| Characterization of Compounds 1-85 and 265-267 | | |
|---|---|---|
| Ex. | Structure and IUPAC Chemical Name | Characterization |
| 58 | 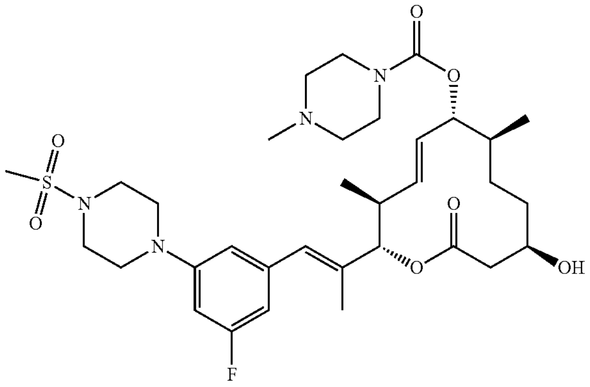 [(2S,3S,4E,6R,7S,10R)-2-[(E)-1-[3-fluoro-5-(4-methylsulfonylpiperazin-1-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 665.6 [M + H]$^+$. $^1$H NMR (400 MHz, $CDCl_3$) 0.99 (t, J = 6.71 Hz, 6 H) 1.26 (br t, J = 7.15 Hz, 6 H) 1.17-1.32 (m, 2 H) 1.44-1.54 (m, 1 H) 1.71-1.84 (m, 1 H) 1.86 (d, J = 1.13 Hz, 3 H) 1.89-1.99 (m, 1 H) 2.43 (br s, 3 H) 2.49-2.68 (m, 7 H) 2.83 (s, 3 H) 3.23-3.32 (m, 4 H) 3.34-3.45 (m, 4 H) 3.52-3.68 (m, 4 H) 3.68-3.79 (m, 1 H) 4.88 (t, J = 10.04 Hz, 1 H) 5.25 (d, J = 10.54 Hz, 1 H) 5.39 (dd, J = 14.93, 9.66 Hz, 1 H) 5.59 (dd, J = 15.06, 9.91 Hz, 1 H) 6.44-6.65 (m, 4 H) |
| 59 | 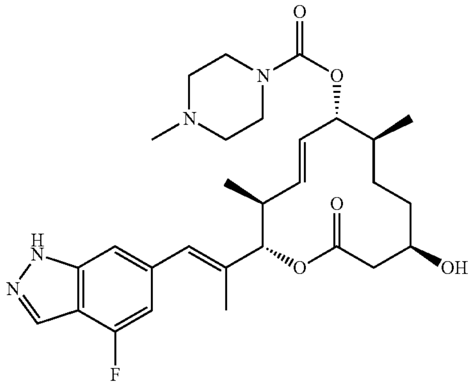 [(2S,3S,4E,6R,7S,10R)-2-[(E)-1-(4-fluoro-1H-indazol-6-yl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 543.5 [M + H]$^+$. $^1$H NMR (400 MHz, $CDCl_3$) 1.00 (d, J = 5.02 Hz, 3 H) 1.02 (br d, J = 4.89 Hz, 3 H) 1.19-1.36 (m, 2 H) 1.41-1.59 (m, 1 H) 1.75-1.86 (m, 1 H) 1.92 (d, J = 1.13 Hz, 3 H) 1.93-1.98 (m, 1 H) 2.47-2.87 (m, 10 H) 3.30-3.45 (m, 1 H) 3.62-3.98 (m, 5 H) 4.89 (t, J = 10.10 Hz, 1 H) 5.29 (d, J = 10.54 Hz, 1 H) 55.39 (dd, J = 14.93, 9.66 Hz, 1 H) 5.62 (dd, J = 14.93, 9.91 Hz, 1 H) 6.66 (s, 1 H) 6.76 (d, J = 10.67 Hz, 1 H) 7.16 (s, 1 H) 8.11 (s, 1 H) |
| 60 | 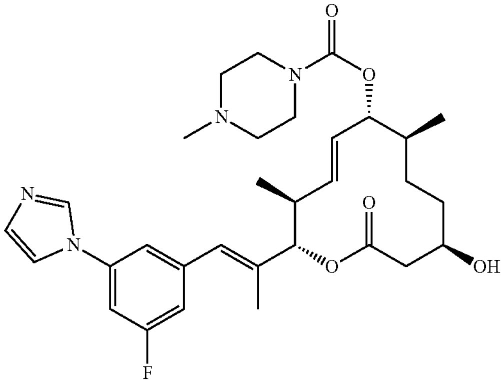 [(2S,3S,4E,6R,7S,10R)-2-[(E)-1-(3-fluoro-5-imidazol-1-ylphenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 569.5 [M + H]$^+$. $^1$H NMR (400 MHz, $CDCl_3$) 1.01 (dd, J = J = 6.84,1.19 Hz, 6 H) 1.19-1.34 (m, 2 H) 1.44-1.55 (m, 1 H) 1.72-1.85 (m, 1 H) 1.91 (d, J = 1.25 Hz, 3 H) 1.92-1.98 (m, 1 H) 2.37 (br s, 3 H) 2.47 (br s, 4 H) 2.53-2.71 (m, 3 H) 3.33 (br s, 1 H) 3.45-3.67 (m, 4 H) 3.73 (br s, 1 H) 4.88 (t, J = 10.04 Hz, 1 H) 5.28 (d, J = 10.67 Hz, 1 H) 5.41 (dd, J = 14.93, 9.66 Hz, 1 H) 5.60 (dd, J = 14.93, 9.91 Hz, 1 H) 6.57 (s, 1 H) 6.96-7.04 (m, 2 H) 7.06-7.11 (m, 1 H) 7.19-7.24 (m, 1 H) 7.26 (s, 1 H) 7.81-7.92 (m, 1 H) |

TABLE 4-continued

| Ex. | Structure and IUPAC Chemical Name | Characterization |
|---|---|---|
| | Characterization of Compounds 1-85 and 265-267 | |
| 61 | 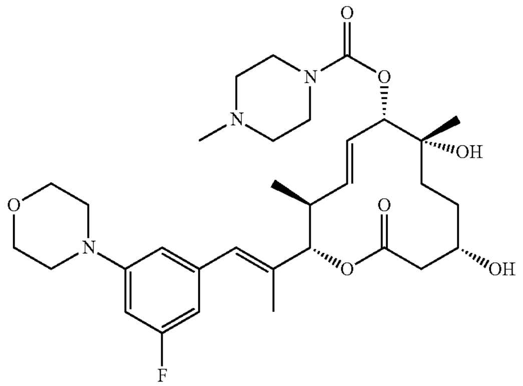 [(2S,3S,4E,6R,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl] 4-methylpiperazine-1-carboxylate | LCMS (ESI, m/z), 604.5 $[M + H]^+$. $^1H$ NMR (400 MHz, $CDCl_3$) 0.98 (br d, J = 6.78 Hz, 3 H) 1.08-1.18 (m, 2 H) 1.23 (br s, 3 H) 1.41-1.48 (m, 1 H) 1.73-1.79 (m, 1 H) 1.86 (s, 3 H) 2.45-2.69 (m, 7 H) 2.70-2.93 (m, 3 H) 3.11-3.27 (m, 4 H) 3.63-4.02 (m, 8 H) 4.34-4.52 (m, 1 H) 5.00 (br d, J = 9.66 Hz, 1 H) 5.15 (br d, J = 10.16 Hz, 1 H) 5.50-5.65 (m, 1 H) 5.69-5.81 (m, 1 H) 6.39-6.61 (m, 4 H) |
| 62 | 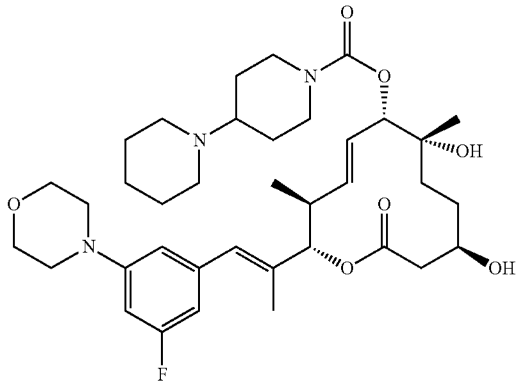 [(2S,3S,4E,6R,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl] 4-piperidin-1-ylpiperidine-1-carboxylate | LCMS (ESI, m/z), 672.7 $[M + H]^+$. $^1H$ NMR (400 MHz, $CDCl_3$) 0.97 (d, J = 6.78 Hz, 3 H) 1.16-1.30 (m, 5 H) 1.32-1.41 (m, 2 H) 1.50-1.61 (m, 1 H) 1.64-1.74 (m, 5 H) 1.81-1.88 (m, 5 H) 2.02-2.08 (m, 2 H) 2.36-2.48 (m, 2 H) 2.52-2.67 (m, 3 H) 2.67-2.92 (m, 2 H) 3.08-3.22 (m, 5 H) 3.36-3.52 (m, 3 H) 3.59-3.68 (m, 1 H) 3.71-3.78 (m, 1 H) 3.80-3.86 (m, 4 H) 4.31 (s, 1 H) 4.99 (d, J = 9.41 Hz, 1 H) 5.25 (d, J = 10.79 Hz, 1 H) 5.56-5.79 (m, 3 H) 6.41-6.57 (m, 4 H) |
| 63 | 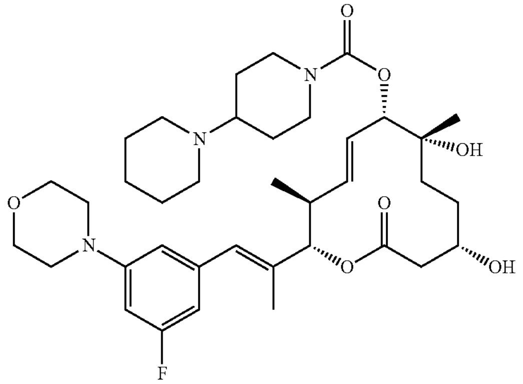 [(2S,3S,4E,6R,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl] 4-piperidin-1-ylpiperidine-1-carboxylate | LCMS (ESI, m/z), 672.8 $[M + H]^+$. $^1H$ NMR (400 MHz, $CDCl_3$) 0.95 (d, J = 6.78 Hz, 3 H) 1.11-1.30 (m, 5 H) 1.37-1.51 (m, 3 H) 1.55-1.75 (s, 5 H) 1.79-1.82 (m, 1 H) 1.84 (br d, J = 1.00 Hz, 3 H) 1.87-1.92 (m, 1 H) 2.02-2.08 (m, 2 H) 2.46-2.66 (m, 5 H) 2.71-2.91 (m, 3 H) 3.07-3.18 (m, 4 H) 3.34-3.50 (m, 3 H) 3.78-3.89 (m, 4 H) 4.25-4.43 (m, 2 H) 4.95 (d, J = 9.79 Hz, 1 H) 5.12 (d, J = 10.79 Hz, 1 H) 5.55 (dd, J = 15.06, 9.91 Hz, 1 H) 5.74 (dd, J = 15.62, 9.98 Hz, 1 H) 6.35-6.56 (m, 4 H) |

TABLE 4-continued

| Ex. | Structure and IUPAC Chemical Name | Characterization |
|---|---|---|
| | Characterization of Compounds 1-85 and 265-267 | |
| 64 | 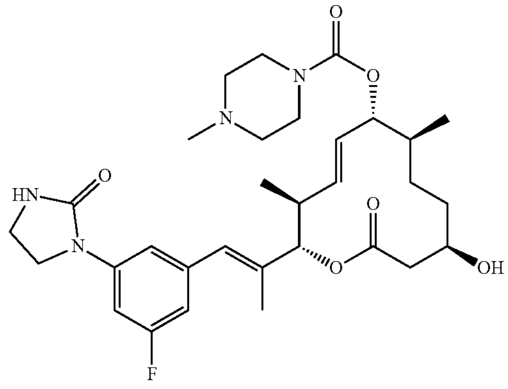 [(2S,3S,4E,6R,7S,10R)-2-[(E)-1-[3-fluoro-5-(2-oxo-imidazolidin-1-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 587.5 $[M + H]^+$. $^1H$ NMR (400 MHz, $CDCl_3$) 0.96 (d, J = 5.02 Hz, 3 H) 0.98 (d, J = 5.02 Hz, 4 H) 1.16-1.29 (m, 2 H) 1.41-1.54 (m, 1 H) 1.82-1.85 (m, 1 H) 1.87 (d, J = 1.25 Hz, 3 H) 1.89-1.94 (m, 1 H) 2.52 (br s, 3 H) 2.50-2.68 (m, 7 H) 3.52-3.78 (m, 7 H) 3.84-4.00 (m, 2 H) 4.72 (s, 1 H) 4.86 (t, J = 10.10 Hz, 1 H) 5.24 (d, J = 10.67 Hz, 1 H) 5.37 (dd, J = 15.00, 9.72 Hz, 1 H) 5.57 (dd, J = 15.00, 9.85 Hz, 1 H) 6.51 (s, 1 H) 6.60-6.70 (m, 1 H) 7.15 (s, 1 H) 7.29-7.32 (m, 1 H) |
| 65 | 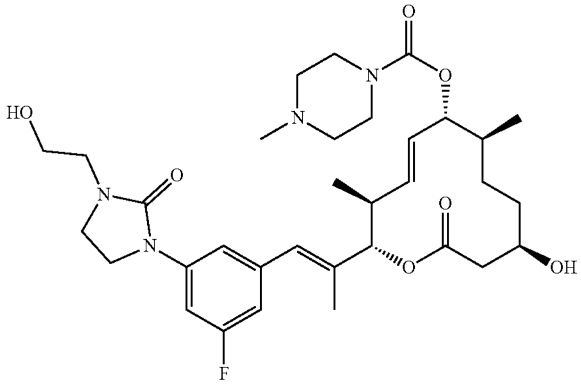 [(2S,3S,4E,6R,7S,10R)-2-[(E)-1-[3-fluoro-5-[3-(2-hydroxyethyl)-2-oxoimidazolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 631.6 $[M + H]^+$. $^1H$ NMR (400 MHz, $CDCl_3$) 0.97 (d, J = 6.65 Hz, 6 H) 1.16-1.29 (m, 2 H) 1.41-1.56 (m, 1 H) 1.81-1.84 (m, 1 H) 1.87 (br d, J = 1.25 Hz, 8 H) 1.89-1.95 (m, 1 H) 2.45-2.70 (m, 3 H) 2.72-2.84 (m, 7 H) 3.38-3.47 (m, 4 H) 3.58-3.65 (m, 2 H) 3.66-3.75 (m, 1 H) 3.77-3.91 (m, 4 H) 4.08-4.30 (m, 2 H) 4.86 (t, J = 9.85 Hz, 1 H) 5.24 (d, J = 10.79 Hz, 1 H) 5.36 (dd, J = 14.68, 9.54 Hz, 1 H) 5.58 (dd, J = 14.93,10.04 Hz, 1 H) 6.50 (s, 1 H) 6.56-6.68 (m, 1 H) 7.14-7.24 (m, 2 H) |
| 66 | 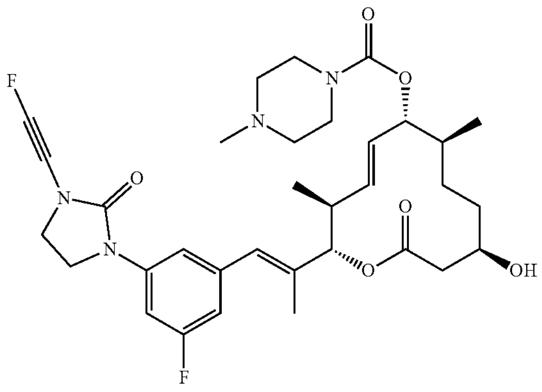 [(2S,3S,4E,6R,7S,10R)-2-[(E)-1-[3-fluoro-5-[3-(2-fluoroethynyl)-2-oxoimidazolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 629.6 $[M + H]^+$. $^1H$ NMR (400 MHz, $CDCl_3$) 0.96 (d, J = 2.64 Hz, 3 H) 0.98 (d, J = 2.51 Hz, 3 H) 1.16-1.32 (m, 2 H) 1.44-1.57(m, 1 H) 1.75-1.83 (m, 1 H) 1.87 (br d, J = 1.25 Hz, 3 H) 1.91-1.96 (m, 1 H) 2.48-2.57 (m, 5 H) 2.59-2.69 (m, 2 H) 2.77 (s, 3 H) 3.63-3.79 (m, 2 H) 3.82-3.90 (m, 4 H) 3.91-4.00 (m, 4 H) 4.86 (t, J = 10.04 Hz, 1 H) 5.24 (d, J = 10.54 Hz, 1 H) 5.37 (dd, J = 14.87, 9.72 Hz, 1 H) 5.58 (dd, J = 15.00, 9.98 Hz, 1 H) 6.52 (s, 1 H) 6.71-6.81 (m, 1 H) 7.18 (s, 1 H) 7.27-7.31 (m, 1 H) |

TABLE 4-continued

| Characterization of Compounds 1-85 and 265-267 | | |
|---|---|---|
| Ex. | Structure and IUPAC Chemical Name | Characterization |
| 67 | 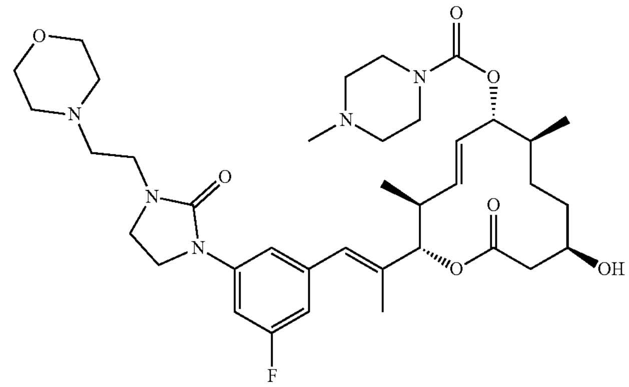 [(2S,3S,4E,6R,7S,10R)-2-[(E)-1-[3-fluoro-5-[3-(2-morpholin-4-ylethyl)-2-oxoimidazolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 700.7 $[M + H]^+$. $^1H$ NMR (400 MHz, $CDCl_3$) 0.97 (t, J = 7.09 Hz, 6 H) 1.13-1.28 (m, 2 H) 1.40-1.54 (m, 1 H) 1.81-1.84 (m, 1 H) 1.86 (d, J = 1.13 Hz, 3 H) 1.89-1.93 (m, 1 H) 2.37 (br s, 3 H) 2.44-2.67 (m, 13 H) 3.33-3.48 (m, 3 H) 3.50-3.64 (m, 6 H) 3.66-3.74 (m, 5 H) 3.76-3.82 (m, 2 H) 4.86 (t, J = 10.04 Hz, 1 H) 5.23 (d, J = 10.54 Hz, 1 H) 5.37 (dd, J = 14.87, 9.72 Hz, 1 H) 5.57 (dd, J = 15.06, 9.91 Hz, 1 H) 6.50 (s, 1 H) 6.57-6.67 (m, 1 H) 7.19 (s, 1 H) 7.22-7.25 (m, 1 H) |
| 68 | 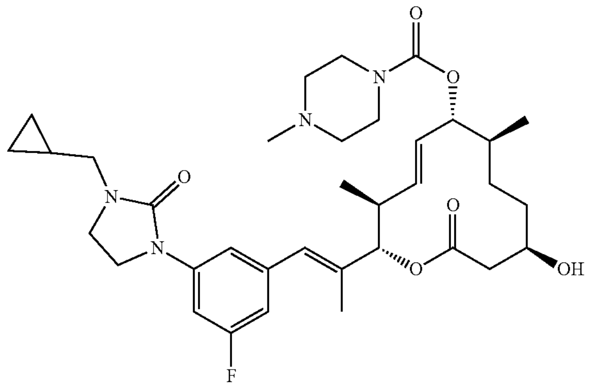 [(2S,3S,4E,6R,7S,10R)-2-[(E)-1-[3-[3-(cyclopropylmethyl)-2-oxoimidazolidin-1-yl]-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 641.7 $[M + H]^+$. $^1H$ NMR (400 MHz, $CDCl_3$) 0.16-0.28 (m, 2 H) 0.48-0.57 (m, 2 H) 0.89-0.94 (m, 1 H) 0.97 (t, J = 7.03 Hz, 6 H) 1.18-1.29 (m, 2 H) 1.42-1.53 (m, 1 H) 1.73-1.83 (m, 1 H) 1.87 (d, J = 1.13 Hz, 3 H) 1.90-1.94 (m, 1 H) 2.37 (s, 3 H) 2.44-2.69 (m, 7 H) 3.15 (d, J = 7.03 Hz, 2 H) 3.49-3.64 (m, 5 H) 3.66-3.74 (m, 1 H) 3.78 (d, J = 8.91 Hz, 2 H) 4.86 (t, J = 10.10 Hz, 1 H) 5.23 (d, J = 10.54 Hz, 1 H) 5.37 (dd, J = 14.87, 9.72 Hz, 1 H) 5.57 (dd, J = 15.06, 9.91 Hz, 1 H) 6.45-6.54 (m, 1 H) 6.57-6.67 (m, 1 H) 7.20-7.26 (m, 2 H) |
| 69 | 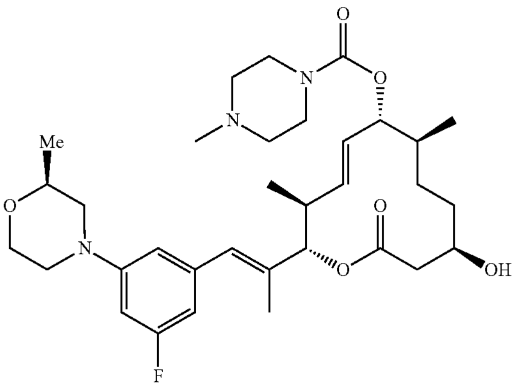 [(2S,3S,4E,6R,7R,10S)-2-[(E)-1-[3-fluoro-5-[(2S)-2-methylmorpholin-4-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.5 $[M + H]^+$ |

TABLE 4-continued

| Characterization of Compounds 1-85 and 265-267 | | |
|---|---|---|
| Ex. | Structure and IUPAC Chemical Name | Characterization |
| 70 | 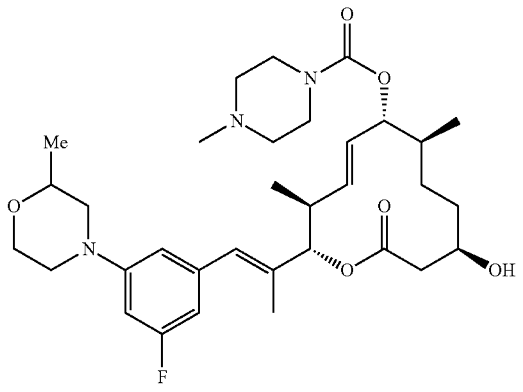 [(2S,3S,4E,6R,7R,10S)-2-[(E)-1-[3-fluoro-5-(2-methyl-morpholin-4-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.5 [M + H]$^+$ |
| 71 | 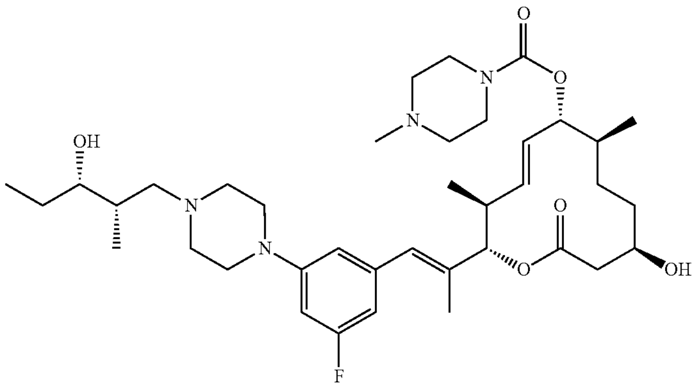 [(2S,3S,4E,6R,7R,10S)-2-[(E)-1-[3-fluoro-5-[4-[(2S,3R)-3-hydroxy-2-methylpentyl]piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 687.7 [M + H]$^+$. $^1$H NMR (400 MHz, $CDCl_3$) 0.83 (d, J = 7.03 Hz, 3 H) 0.91-1.04 (m, 11 H) 1.17-1.28 (m, 2 H) 1.30-1.40 (m, 1 H) 1.42-1.52 (m, 1 H) 1.76-1.80 (m, 1 H) 1.83 (s, 3 H) 1.86-1.91 (m, 1 H) 2.38 (s, 3 H) 2.46-2.72 (m, 7 H) 2.76-2.86 (m, 2 H) 2.89-3.33 (m, 8 H) 3.46-3.64 (m, 5 H) 3.69 (br s, 1 H) 4.85 (t, J = 9.85 Hz, 1 H) 5.22 (d, J = 10.67 Hz, 1 H) 5.37 (dd, J = 14.87, 9.72 Hz, 1 H) 5.57 (dd, J = 15.06, 9.91 Hz, 1 H) 6.36-6.57 (m, 4 H) |
| 72 | 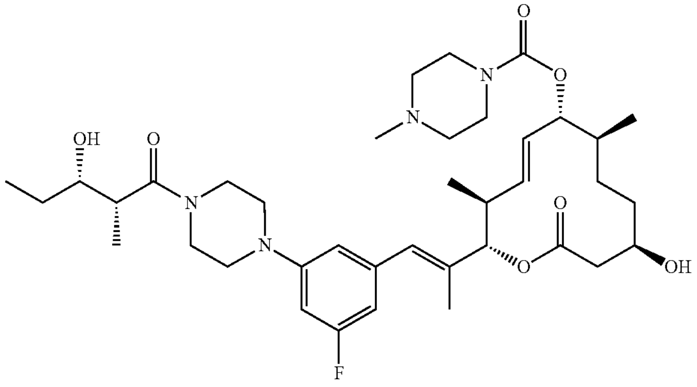 [(2S,3S,4E,6R,7R,10S)-2-[(E)-1-[3-fluoro-5-[4-[(2R,3R)-3-hydroxy-2-methylpentanoyl]piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 701.7 [M + H]$^+$. $^1$H NMR (400 MHz, $CDCl_3$) 0.89-1.03 (m, 9 H) 1.15 (d, J = 7.15 Hz, 3 H) 1.20-1.33 (m, 2 H) 1.36-1.63 (m, 3 H) 1.70-1.81 (m, 1 H) 1.84 (d, J = 1.13 Hz, 3 H) 1.86-1.91 (m, 1 H) 2.30 (s, 3 H) 2.37 (br s, 4 H) 2.48-2.57 (m, 2 H) 2.60-2.71 (m, 2 H) 3.08-3.26 (m, 4 H) 3.48 (br s, 4 H) 3.57-3.66 (m, 2 H) 3.68-3.75 (m, 2 H) 3.75-3.85 (m, 2 H) 4.12-4.29 (m, 1 H) 4.85 (t, J = 10.04 Hz, 1 H) 5.22 (d, J = 10.54 Hz, 1 H) 5.38 (dd, J = 15.06, 9.66 Hz, 1 H) 5.56 (dd, J = 14.93, 9.91 Hz, 1 H) 6.22-6.76 (m, 4 H) |

TABLE 4-continued

| Characterization of Compounds 1-85 and 265-267 | | |
|---|---|---|
| Ex. | Structure and IUPAC Chemical Name | Characterization |
| 73 | 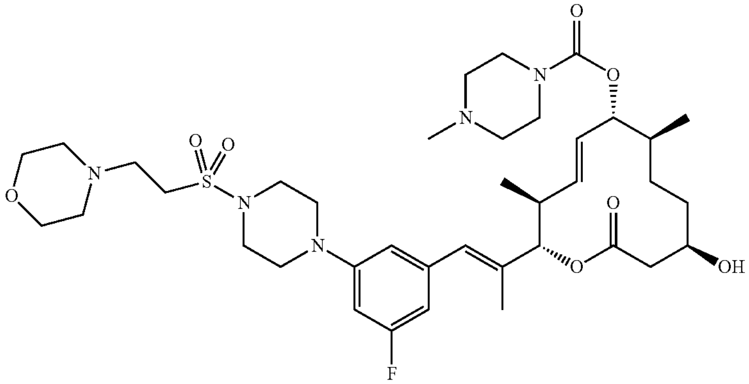 [(2S,3S,4E,6R,7S,10R)-2-[(E)-1-[3-fluoro-5-[4-(2-morpholin-4-ylethylsulfonyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 764.8 $[M + H]^+$. $^1H$ NMR (400 MHz, $CDCl_3$) 0.97 (t, J = 6.40 Hz, 6 H) 1.15-1.28 (m, 2 H) 1.41-1.55 (m, 1 H) 1.72-1.81 (m, 1 H) 1.84 (d, J = 1.13 Hz, 3 H) 1.87-1.95 (m, 1 H) 2.44 (s, 3 H) 2.46-2.68 (m, 11 H) 2.80-2.89 (m, 3 H) 3.11-3.18 (m, 2 H) 3.20-3.32 (m, 4 H) 3.39-3.45 (m, 4 H) 3.59 (br s, 4 H) 3.65-3.75 (m, 5 H) 4.85 (t, J = 10.10 Hz, 1 H) 5.22 (d, J = 10.67 Hz, 1 H) 5.37 (dd, J = 15.00, 9.60 Hz, 1 H) 5.57 (dd, J = 15.00, 9.85 Hz, 1 H) 6.45-6.58 (m, 4 H) |
| 74 | 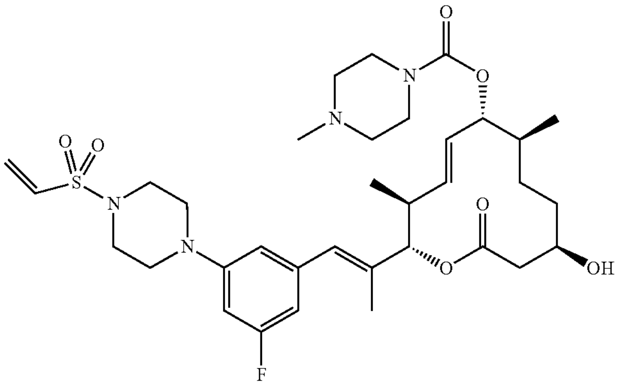 [(2S,3S,4E,6R,7S,10R)-2-[(E)-1-[3-(4-ethenylsulfonylpiperazin-1-yl)-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 677.6 $[M + H]^+$. $^1H$ NMR (400 MHz, $CDCl_3$) 0.96 (t, J = 6.65 Hz, 6 H) 1.17-1.31 (m, 2 H) 1.40-1.54 (m, 1 H) 1.70-1.81 (m, 1 H) 1.84 (d, J = 1.13 Hz, 3 H) 1.88-1.95 (m, 1 H) 2.47 (s, 3 H) 2.49-2.64 (m, 3 H) 2.68 (br s, 4 H) 3.32-3.53 (m, 8 H) 3.55-3.67 (m, 4 H) 3.68-3.76 (m, 1 H) 4.76-4.91 (m, 1 H) 4.85 (t, J = 10.10 Hz, 1 H) 5.22 (d, J = 10.67 Hz, 1 H) 5.56 (dd, J = 15.00, 9.85 Hz, 1 H) 6.07 (d, J = 9.91 Hz, 1 H) 6.20-6.31 (m, 1 H) 6.39-6.58 (m, 5 H) |
| 75 | 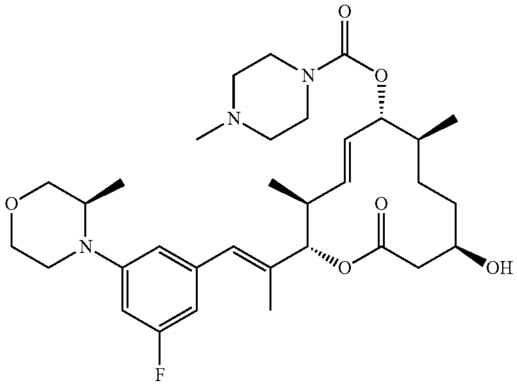 [(2S,3S,4E,6R,7R,10S)-2-[(E)-1-[3-fluoro-5-[(3S)-3-methylmorpholin-4-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.5 $[M + H]^+$. $^1H$ NMR (400 MHz, $CDCl_3$) 0.99 (br t, J = 6.71 Hz, 6 H) 1.12 (br d, J = 6.40 Hz, 3 H) 1.17-1.31 (m, 2 H) 1.42-1.56 (m, 1 H) 1.74-1.83 (m, 1 H) 1.87 (s, 3 H) 1.89-1.98 (m, 1 H) 2.46 (br s, 3 H) 2.51-2.79 (m, 7 H) 3.06-3.24 (m, 2 H) 3.50-3.69 (m, 5 H) 3.70-3.78 (m, 3 H) 3.80-3.87 (m, 1 H) 3.95-4.04 (m, 1 H) 4.88 (br t, J = 10.23 Hz, 1 H) 5.39 (dd, J = 15.00, 9.60 Hz, 1 H) 5.60 (dd, J = 15.00, 9.85 Hz, 1 H) 6.40-6.54 (m, 4 H) |

TABLE 4-continued

| Characterization of Compounds 1-85 and 265-267 | | |
|---|---|---|
| Ex. | Structure and IUPAC Chemical Name | Characterization |
| 76 | 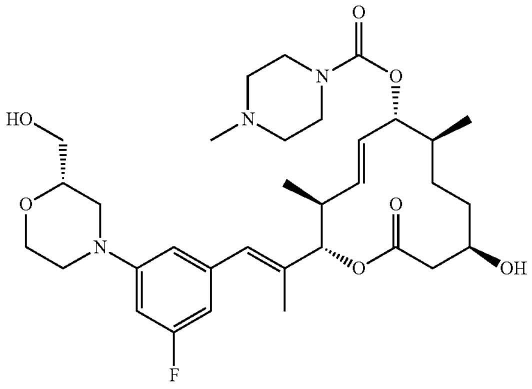 [(2S,3S,4E,6R,7S,10R)-2-[(E)-1-[3-fluoro-5-[(2R)-2-(hydroxymethyl)morpholin-4-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 618.5 $[M + H]^+$. $^1H$ NMR (400 MHz, $CDCl_3$) 0.98 (d, J = 6.78 Hz, 3 H) 1.01 (d, J = 6.90 Hz, 3 H) 1.19-1.33 (m, 2 H) 1.44-1.55 (m, 1 H) 1.75-1.84 (m, 1 H) 1.86 (d, J = 1.00 Hz, 3 H) 1.88-1.98 (m, 1 H) 2.30 (s, 3 H) 2.36 (br s, 4 H) 2.50-2.59 (m, 2 H) 2.60-2.74 (m, 2 H) 2.86 (td, J = 11.92, 3.51 Hz, 1 H) 3.32-3.58 (m, 6 H) 3.64-3.88 (m, 5 H) 4.05 (br d, J = 2.01 Hz, 1 H) 4.88 (t, J = 10.10 Hz, 1 H) 5.25 (d, J = 10.67 Hz, 1 H) 5.40 (dd, J = 15.06, 9.66 Hz, 1 H) 5.59 (dd, J = 15.06, 9.91 Hz, 1 H) 6.39-6.57 (m, 4 H) |
| 77 | 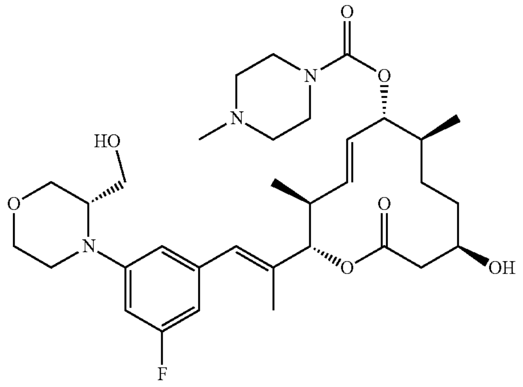 [(2S,3S,4E,6R,7S,10R)-2-[(E)-1-[3-fluoro-5-[(3S)-3-(hydroxymethyl)morpholin-4-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 618.5 $[M + H]^+$. $^1H$ NMR (400 MHz, $CDCl_3$) 0.98 (d, J = 7.03 Hz, 3 H) 1.01 (d, J = 6.78 Hz, 3 H) 1.19-1.33 (m, 2 H) .44-1.55 (m, 1 H) 1.75-1.84 (m, 1 H) 1.87 (d, J = 1.13 Hz, 3 H) 1.88-1.98 (m, 1 H) 2.19-2.43 (m, 7 H) 2.44-2.71 (m, 3 H) 3.12-3.28 (m, 2 H) 3.31-3.42 (m, 1 H) 3.42-3.57 (m, 2 H) 3.59-3.84 (m, 7 H) 3.90-4.04 (m, 2 H) 4.10-4.17 (m, 1 H) 4.88 (t, J = 10.10 Hz, 1 H) 5.25 (d, J = 10.67 Hz, 1 H) 5.40 (dd, J = 14.93, 9.54 Hz, 1 H) 5.59 (dd, J = 14.93, 9.91 Hz, 1 H) 6.28-6.59 (m, 4 H) |
| 78 | 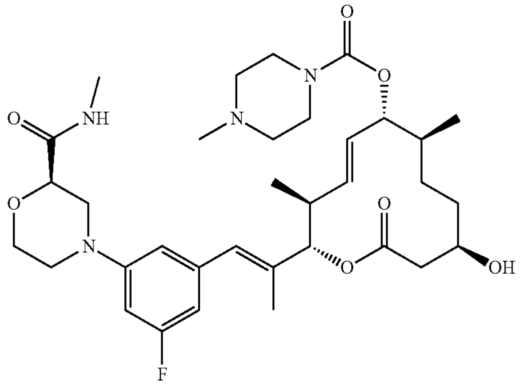 [(2S,3S,4E,6R,7R,10S)-2-[(E)-1-[3-fluoro-5-[(2R)-2-(methylcarbamoyl)morpholin-4-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 645.6 $[M + H]^+$. $^1H$ NMR (400 MHz, $CDCl_3$) 1.00 (t, J = 6.84 Hz, 6 H) 1.21-1.27 (m, 2 H) 1.36-1.54 (m, 1 H) 1.80-1.84 (m, 1 H) 1.86 (br d, J = 1.13 Hz, 3 H) 1.88-1.91 (m, 1 H) 2.37 (s, 3 H) 2.41-2.60 (m, 6 H) 2.62-2.70 (m, 2 H) 2.80-2.91 (m, 4 H) 3.37-3.45 (m, 1 H) 3.51-3.62 (m, 4 H) 3.68-3.76 (m, 1 H) 3.77-3.87 (m, 1 H) 3.92-4.01 (m, 1 H) 4.04-4.12 (m, 1 H) 4.89 (t, J = 10.04 Hz, 1 H) 5.25 (d, J = 10.67 Hz, 1 H) 5.39 (dd, J = 15.00, 9.47 Hz, 1 H) 5.60 (dd, J = 15.06, 9.79 Hz, 1 H) 6.44-6.64 (m, 5 H) |

TABLE 4-continued

| Characterization of Compounds 1-85 and 265-267 | | |
|---|---|---|
| Ex. | Structure and IUPAC Chemical Name | Characterization |
| 79 | 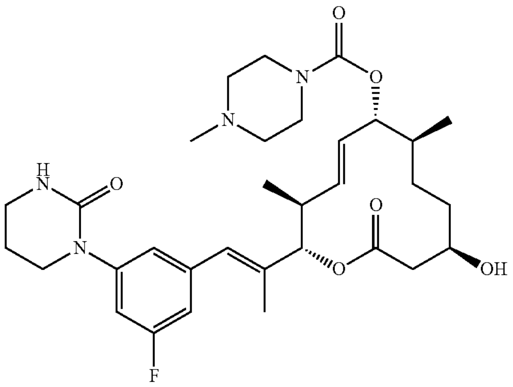 [(2S,3S,4E,6R,7S,10R)-2-[(E)-1-[3-fluoro-5-(2-oxo-1,3-diazinan-1-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 601.5 $[M + H]^+$. $^1H$ NMR (400 MHz, $CD_3OD$) 0.98 (d, J = 6.78 Hz, 3 H) 1.01 (d, J = 6.78 Hz, 3 H) 1.23-1.46 (m, 2 H) 1.61-1.69 (m, 2 H) 1.89 (d, J = 1.25 Hz, 3 H) 1.94-2.00 (m, 1 H) 2.05-2.14 (m, 2 H) 2.36 (s, 3 H) 2.42-2.54 (m, 5 H) 2.55-2.70 (m, 2 H) 3.36-3.41 (m, 2 H) 3.44-3.59 (m, 4 H) 3.71 (t, J = 5.83 Hz, 2 H) 3.79-3.89 (m, 1 H) 4.90-4.96 (m, 1 H) 5.14 (d, J = 10.92 Hz, 2 H) 5.43-5.63 (m, 2 H) 6.56-6.59 (m, 1 H) 6.81-6.92 (m, 1 H) 6.93-7.03 (m, 1 H) 7.04-7.06 (m, 1 H) |
| 80 | 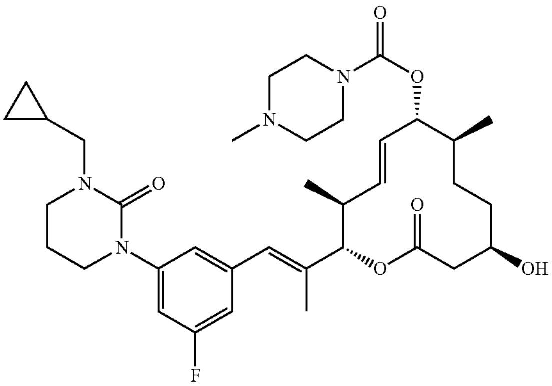 [(2S,3S,4E,6R,7S,10R)-2-[(E)-1-[3-[3-(cyclopropylmethyl)-2-oxo-1,3-diazinan-1-yl]-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 655.6 $[M + H]^+$. $^1H$ NMR (400 MHz, $CDCl_3$) 0.19-0.30 (m, 2 H) 0.46-0.58 (m, 2 H) 0.91-1.09 (m, 7 H) 1.19-1.33 (m, 2 H) 1.44-1.53 (m, 1 H) 1.74-1.84 (m, 1 H) 1.87 (d, J = 1.13 Hz, 3 H) 1.89-1.99 (m, 1 H) 2.08-2.20 (m, 2 H) 2.30 (s, 3 H) 2.36 (br s, 4 H) 2.49-2.58 (m, 2 H) 2.60-2.70 (m, 1 H) 3.29 (d, J = 6.90 Hz, 2 H) 3.35-3.42 (m, 1 H) 3.43-3.57 (m, 6 H) 3.63-3.78 (m, 3 H) 4.88 (t, J = 10.10 Hz, 1 H) 5.25 (d, J = 10.54 Hz, 1 H) 5.39 (dd, J = 15.06, 9.66 Hz, 1 H) 5.59 (dd, J = 15.00, 9.85 Hz, 1 H) 6.39-6.57 (m, 1 H) 6.70-6.86 (m, 1 H) 6.92-7.01 (s, 2 H) |
| 81 | 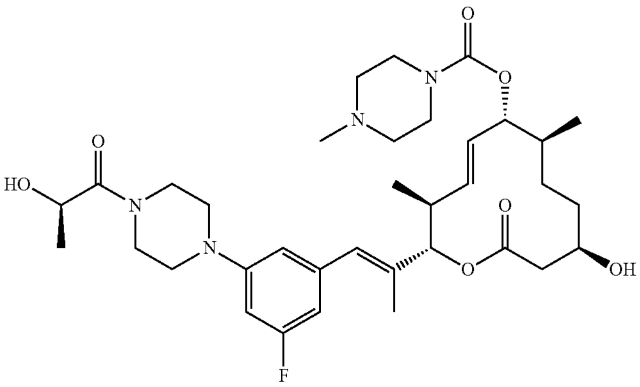 [(2S,3S,4E,6R,7R,10S)-2-[(E)-1-[3-fluoro-5-[4-[(2R)-2-hydroxypropanoyl]piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 659.5 $[M + H]^+$. $^1H$ NMR (400 MHz, $CDCl_3$) 0.98 (d, J = 6.78 Hz, 3 H) 1.01 (d, J = 6.78 Hz, 3 H) 1.19-1.31 (m, 2 H) 1.36 (d, J = 6.65 Hz, 3 H) 1.43-1.55 (m, 1 H) 1.73-1.84 (m, 1 H) 1.87 (d, J = 1.13 Hz, 3 H) 1.89-1.99 (m, 1 H) 2.32 (s, 3 H) 2.39 (br s, 4 H) 2.48-2.68 (m, 3 H) 3.20 (t, J = 5.14 Hz, 4 H) 3.42-3.63 (m, 6 H) 3.68-3.95 (m, 3 H) 4.50 (q, J = 6.65 Hz, 1 H) 4.88 (t, J = 10.04 Hz, 1 H) 5.25 (d, J = 10.67 Hz, 1 H) 5.40 (dd, J = 14.93, 9.66 Hz, 1 H) 5.59 (dd, J = 15.06, 9.91 Hz, 1 H) 6.38-6.67 (m, 4 H) |

TABLE 4-continued

| Ex. | Structure and IUPAC Chemical Name | Characterization |
|---|---|---|
| | Characterization of Compounds 1-85 and 265-267 | |
| 82 | 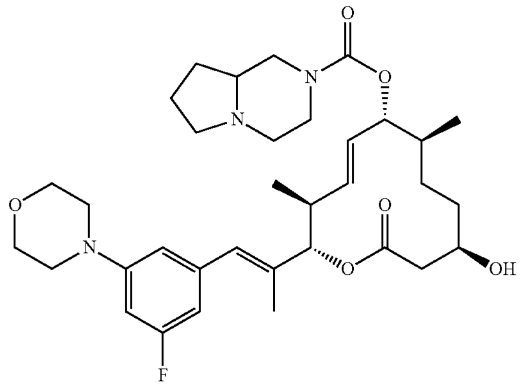 [(2S,3S,4E,6R,7S,10R)-2-[(E)-1-[3-fluoro-5-morpholin-4-ylphenyl)prop-1-en-2-yl]-10-hydroxy-3,7-dimethyl-12-oxo-1-oxacyclododec-4-en-6-yl] 3,4,6,7,8,8a-hexanehydro-1H-pyrrolo[1,2-a]pyrazine-2-carboxylate | LCMS (ESI, m/z), 614.8 $[M + H]^+$. $^1H$ NMR (400 MHz, $CDCl_3$) δ ppm 0.99 (br d, J = 4.39 Hz, 3 H) 1.00 (d, J = 4.27 Hz, 3 H) 1.18-1.35 (m, 4 H) 1.42-1.50 (m, 3 H) 1.75-1.84 (m, 1 H) 1.87 (d, J = 1.00 Hz, 3 H) 1.90-1.99 (m, 1 H) 2.48-2.70 (m, 7 H) 2.95-3.08 (m, 1 H) 3.10-3.18 (m, 4 H) 3.38 (br d, J = 10.67 Hz, 2 H) 3.67-3.78 (m, 2 H) 3.80-3.91 (m, 5 H) 4.89 (br t, J = 9.79 Hz, 1 H) 5.26 (d, J = 10.54 Hz, 1 H) 5.39 (dd, J = 15.06, 9.79 Hz, 1 H) 5.60 (dd, J = 15.06, 9.66 Hz, 1 H) 6.43-6.55 (m, 4 H) |
| 83 | 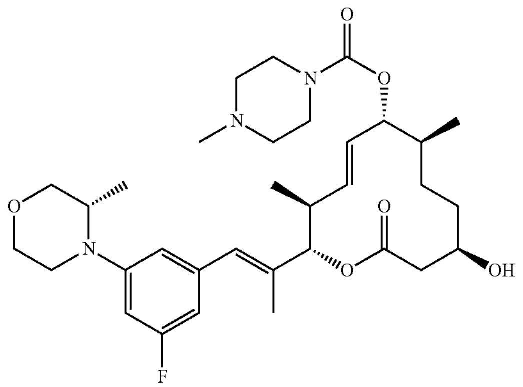 [(2S,3S,4E,6R,7R,10S)-2-[(E)-1-[3-fluoro-5-[(3S)-3-methylmorpholin-4-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.6 $[M + H]^+$. $^1H$ NMR (400 MHz, $CDCl_3$) δ ppm 0.92 (br t, J = 5.90 Hz, 6 H) 1.05 (br d, J = 6.53 Hz, 3 H) 1.10-1.28 (m, 2 H) 1.45-1.56 (m, 1 H) 1.75-1.85 (m, 1 H) 1.80 (s, 3 H) 1.83-1.93 (m, 1 H) 2.38 (s, 3 H) 2.42-2.70 (m, 7 H) 2.97-3.18 (m, 2 H) 3.40-3.70 (m, 8 H) 3.71-3.80 (m, 1 H) 3.84-3.97 (m, 1 H) 4.88 (br t, J = 10.10 Hz, 1 H) 5.26 (br d, J = 10.54 Hz, 1 H) 5.39 (dd, J = 15.00, 9.85 Hz, 1 H) 5.60 (br dd, J = 15.12, 9.85 Hz, 1 H) 6.34-6.56 (m, 4 H) |
| 84 | 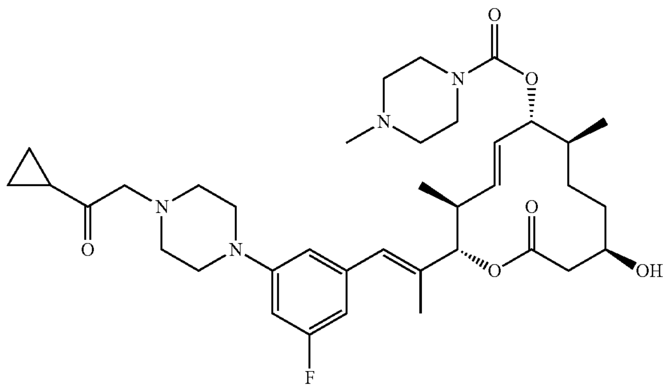 [(2S,3S,4E,6R,7S,10R)-2-[(E)-1-[3-[4-(2-cyclopropyl-2-oxoethyl)piperazin-1-yl]-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 669.7 $[M + H]^+$. $^1H$ NMR (400 MHz, $CDCl_3$) δ ppm 0.88-0.95 (m, 2 H) 0.98 (d, J = 6.90 Hz, 3 H) 1.00 (d, J = 6.90 Hz, 3 H) 1.04-1.13 (m, 2 H) 1.21-1.31 (m, 2 H) 1.42-1.51 (m, 1 H) 1.73-1.82 (m, 1 H) 1.83-1.87 (m, 3 H) 1.89-1.96 (m, 1 H) 2.10-2.23 (m, 1 H) 2.28-2.48 (m, 7 H) 2.49-2.63 (m, 3 H) 2.64-2.76 (m, 4 H) 3.15-3.29 (m, 4 H) 3.40 (s, 2 H) 3.63-3.69 (m, 4 H) 3.69-3.81 (m, 1 H) 4.88 (t, J = 10.10 Hz, 1 H) 5.25 (d, J = 10.79 Hz, 1 H) 5.41 (d, J = 9.79 Hz, 1 H) 5.58 (d, J = 9.91 Hz, 1 H) 6.42-6.59 (m, 4 H) |

TABLE 4-continued

Characterization of Compounds 1-85 and 265-267

| Ex. | Structure and IUPAC Chemical Name | Characterization |
| --- | --- | --- |
| 85 | 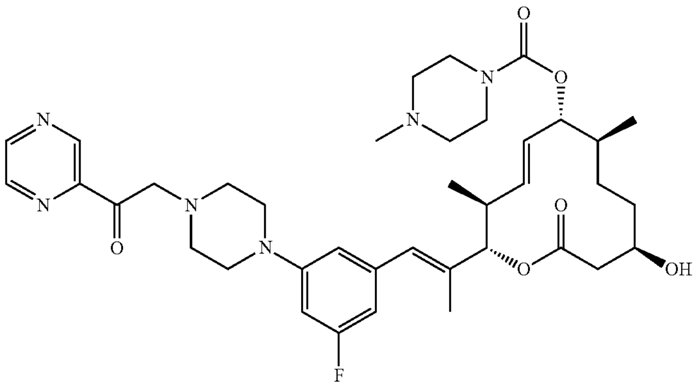 [(2S,3S,4E,6R,7S,10R)-2-[(E)-1-[3-fluoro-5-[4-(2-oxo-2-pyrazin-2-ylethyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 707.6 $[M + H]^+$. $^1H$ NMR (400 MHz, $CDCl_3$) δ ppm 0.96-1.04 (m, 6 H) 1.20-1.32 (m, 2 H) 1.40-1.54 (m, 1 H) 1.75-1.84 (m, 1 H) 1.87 (s, 3 H) 1.90-1.98 (m, 1 H) 2.25-2.50 (m, 7 H) 2.52-2.70 (m, 3 H) 2.78-2.85 (m, 4 H) 3.26-3.34 (m, 4 H) 3.49-3.75 (m, 5 H) 4.19 (s, 2 H) 4.78-4.97 (m, 1 H) 5.26 (d, J = 10.54 Hz, 1 H) 5.36-5.45 (m, 1 H) 5.55-5.64 (m, 1 H) 6.45-6.57 (m, 4 H) 8.50-8.66 (m, 1 H) 8.79 (d, J = 2.38 Hz, 1 H) 9.25 (d, J = 1.51 Hz, 1 H) |
| 265 | 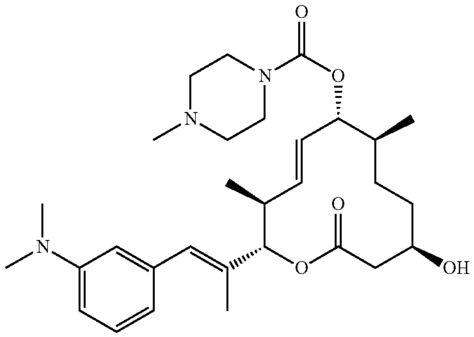 (2S,3S,6R,7S,10R,E)-2-((E)-1-(3-(dimethylamino)phenyl)prop-1-en-2-yl)-10-hydroxy-3,7-dimethyl-12-oxooxacyclododec-4-en-6-yl 4-methylpiperazine-1-carboxylate | LCMS (ESI, m/z), 528.5 $[M + H]^+$. $^1H$ NMR (400 MHz, $CDCl_3$) δ ppm 1.02 (d, J = 6.78 Hz, 6 H) 1.23-1.32 (m, 2 H) 1.45-1.59 (m, 1 H) 1.76-1.86 (m, 1 H) 1.91 (d, J = 1.25 Hz, 4 H) 2.50-2.73 (m, 9 H) 2.97 (s, 6 H) 3.44-3.50 (m, 1 H) 3.65-3.80 (m, 5 H) 4.86-4.95 (m, 1 H) 5.27-5.33 (m, 1 H) 5.36-5.45 (m, 1 H) 5.58-5.69 (m, 1 H) 6.56-6.71 (m, 4 H) 7.22 (t, J = 7.91 Hz, 1 H). |
| 266 | 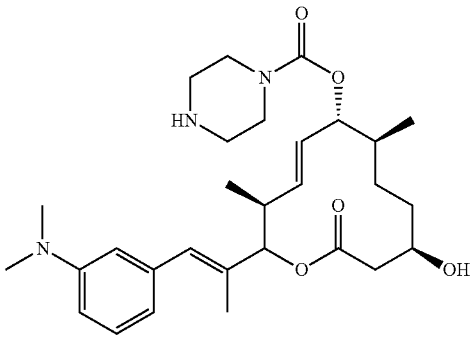 (2S,3S,6R,7S,10R,E)-2-((E)-1-(3-(dimethylamino)phenyl)prop-1-en-2-yl)-10-hydroxy-3,7-dimethyl-12-oxooxacyclododec-4-en-6-yl piperazine-1-carboxylate | LCMS (ESI, m/z), 514.4 $[M + H]^+$. |

TABLE 4-continued

| Characterization of Compounds 1-85 and 265-267 | | |
|---|---|---|
| Ex. | Structure and IUPAC Chemical Name | Characterization |
| 267 | 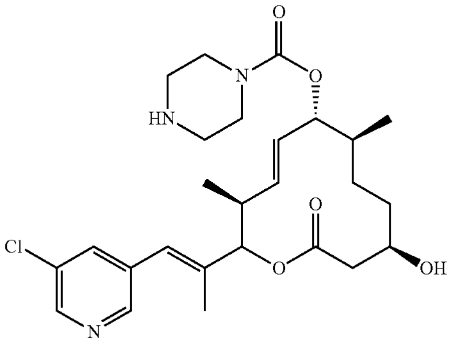 (2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl piperazine-1-carboxylate | LCMS (ESI, m/z), 506.3 [M + H]$^+$. |

Compounds 86-166 and 264 (Table 5) were prepared by following Procedures 11-19.

Synthesis of Indazole Intermediates:

Procedures 11 and 12 were used to synthesize indazole intermediates of the following general formulas:

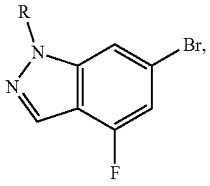
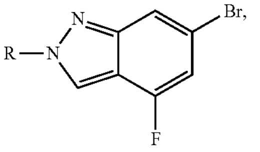

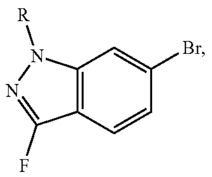
and
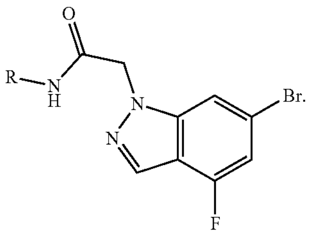

Procedure 11.

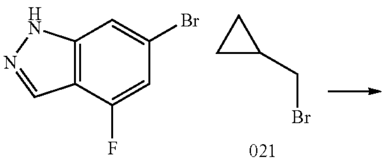

020 021

-continued

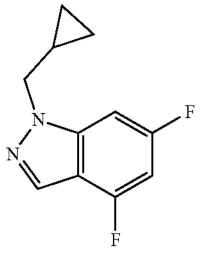
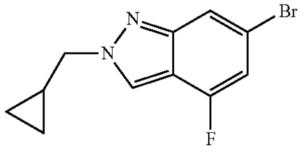

022 023

To a solution of 6-bromo-4-fluoro-1H-indazole (020, 100 mg, 0.465 mmol) in THF (3.0 mL, 0.15 M) were added cesium carbonate (303 mg, 0.93 mmol) and (bromomethyl) cyclopropane (021, 126 mg, 0.93 mmol). At room temperature, the reaction mixture was stirred overnight. Then the reaction mixture was diluted by EtOAc (100 mL) and washed by brine. The combined organic layer was concentrated and applied to ISCO on a gradient 0-30% Hex:EtOAc to give both isomers, 6-bromo-1-(cyclopropylmethyl)-4-fluoro-1H-indazole (022, 62 mg, 0.233 mmol, 50% yield) and 6-bromo-2-(cyclopropylmethyl)-4-fluoro-1H-indazole (023, 20 mg, 0.078 mmol, 17% yield) were collected.

(022) LCMS (ESI, m/z), 269.0 [M+H]$^+$. $^1$H NMR (400 MHz, $CDCl_3$) δ 0.40-0.50 (m, 2H), 0.57-0.66 (m, 2H), 1.30-1.41 (m, 1H), 1.59 (s, 1H), 4.24 (d, J=6.90 Hz, 2H), 6.96 (dd, J=9.16, 1.25 Hz, 1H), 7.43 (t, J=1.07 Hz, 1H), 8.04 (d, J=0.75 Hz, 1H).

(023) LCMS (ESI, m/z), 269.0 [M+H]$^+$. $^1$H NMR (400 MHz, $CDCl_3$) δ 0.45-0.56 (m, 2H), 0.71-0.80 (m, 2H), 1.38-1.60 (m, 1H), 4.29 (d, J=7.15 Hz, 2H), 6.87 (dd, J=9.54, 1.25 Hz, 1H), 7.70 (t, J=1.13 Hz, 1H), 8.12 (s, 1H).

Procedure 12.

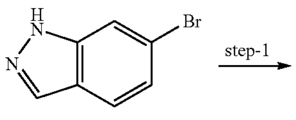

024

-continued

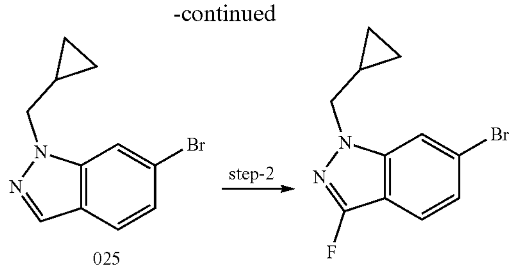

025 026

-continued

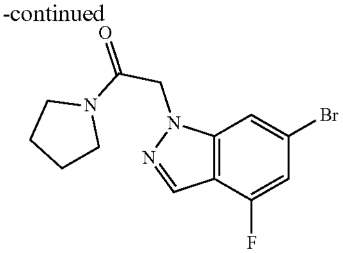

028

Step-1: To a solution of 6-bromo-1H-indazole (024, 900 mg, 3.688 mmol) of THF (30 mL, 0.12 M) was added NaH (66%, 221 mg, 5.532 mmol). The solution was stirred for 30 mins and then (bromomethyl)cyclopropane (597 mg, 4.426 mmol) was added. The resulting solution was stirred under $N_2$ for 12 hours at room temperature. The reaction mixture was diluted by EtOAc (200 mL) and washed with brine. The combined organic layer was concentrated and applied to ISCO on a gradient 0-20% Hex:EtOAc to give 1-(cyclopropylmethyl)-6-bromo-1H-indazole (025, 450 mg, 1.509 mmol, 40.9% yield).

Step-2: To a solution of 1-(cyclopropylmethyl)-6-bromo-1H-indazole (025, 350 mg, 1.174 mmol) in ACN (1.5 ml, 0.78 M) at room temperature was added acetic acid (200 μL, 3.5 mmol) and SELECTFLUOR (832 mg, 2.348 mmol). The resulting solution was stirred under N2 for 12 hours at 50° C. Then the reaction mixture was diluted by EtOAc (100 mL) and washed by brine. The combined organic layer was concentrated and applied to ISCO on a gradient 0-30% Hex:EtOAc to give 1-(cyclopropylmethyl)-3-fluoro-6-bromo-1H-indazole (026, 41 mg, 0.130 mmol, 11.05% yield). LCMS (ESI, m/z), 269.0 $[M+H]^+$. $^1H$ NMR (400 MHz, $CDCl_3$) δ 0.33-0.51 (m, 1H), 0.34-0.39 (m, 2H), 0.45-0.51 (m, 1H), 1.14-1.37 (m, 2H), 1.49 (s, 1H), 4.31 (d, J=7.03 Hz, 2H), 7.16-7.17 (m, 1H), 7.16-7.20 (m, 1H), 7.30 (dd, J=8.41, 4.89 Hz, 1H), 7.89 (d, J=2.26 Hz, 1H).

Procedure 13.

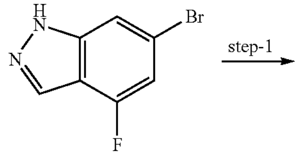

020

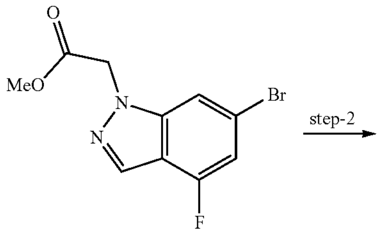

027

Step-1: To a solution of 6-bromo-4-fluoro-1H-indazole (020, 100 mg, 0.465 mmol) in THE (3.0 mL, 0.15 M) were added cesium carbonate (303 mg, 0.93 mmol) and methyl 2-bromoacetate (142 mg, 0.93 mmol). At room temperature, the reaction mixture was stirred overnight. The reaction mixture was diluted with EtOAc (100 mL) and washed with brine. The combined organic layer was concentrated and applied to ISCO on a gradient 0-30% Hex:EtOAc to give methyl 2-(6-bromo-4-fluoro-1H-indazol-1-yl)acetate (027, 100 mg, 0.349 mmol, 75% yield).

Step-2: To a solution of methyl 2-(6-bromo-4-fluoro-1H-indazol-1-yl)acetate (027, 13 mg, 0.045 mmol) in dichloromethane (0.3 mL, 0.15 M) at room temperature was added pyrrolidine (32.2 mg, 0.453 mmol). The reaction mixture was stirred at room temperature overnight. LCMS suggested full conversion of reaction. The reaction mixture was diluted with EtOAc (100 mL) and washed with brine. The combined organic layer was concentrated and applied to ISCO on a gradient 0-30% Hex:EtOAc to give 2-(6-bromo-4-fluoro-1H-indazol-1-yl)-1-(pyrrolidin-1-yl)ethanone (028, 10 mg, 0.031 mmol, 67.7% yield).

Synthesis of Benzotriazole Intermediates:

Procedures 14 and 15 were used to synthesize benzotriazole intermediates of the following general formulas:

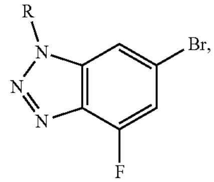
,
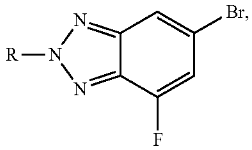
,
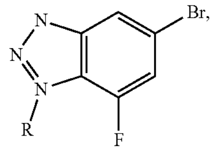
, and
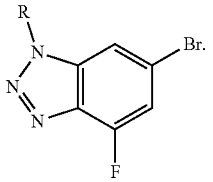
.

Procedure 14.

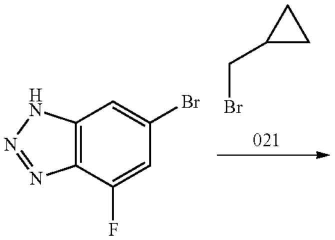

029

021

-continued

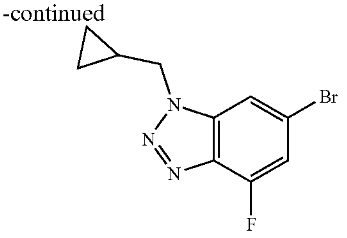

030

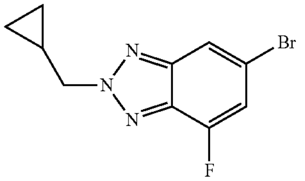

031

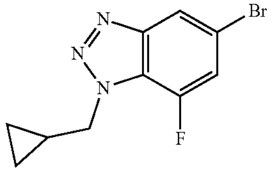

032

To a solution of 6-bromo-4-fluoro-1H-benzo[d][1,2,3]triazole (029, 100 mg, 0.463 mmol) in THE (3.0 mL, 0.15 M) were added cesium carbonate (303 mg, 0.93 mmol) and (bromomethyl)cyclopropane (021, 187 mg, 0.93 mmol). At room temperature, the reaction mixture was stirred overnight. The reaction mixture was diluted with EtOAc (100 mL) and washed with brine. The combined organic layer was concentrated and applied to ISCO on a gradient 0-30% Hex:EtOAc to give 5-bromo-1-(cyclopropylmethyl)-7-fluoro-1H-benzo[d][1,2,3]triazole (030, 40 mg, 0.148 mmol, 32% yield), 6-bromo-2-(cyclopropylmethyl)-4-fluoro-2H-benzo[d][1,2,3]triazole (031, 20 mg, 0.074 mmol, 16% yield) and 6-bromo-1-(cyclopropylmethyl)-4-fluoro-1H-benzo[d][1,2,3]triazole (032, 16 mg, 0.059 mmol, 12% yield). (030) LCMS (ESI, m/z), 270.0 $[M+H]^+$. $^1H$ NMR (400 MHz, $CDCl_3$) δ 0.38-0.61 (m, 4H), 1.31-1.45 (m, 1H), 4.53 (d, J=7.28 Hz, 2H), 7.18-7.27 (m, 1H), 7.95 (d, J=1.38 Hz, 1H). (031) LCMS (ESI, m/z), 270.0 $[M+H]^+$. $^1H$ NMR (400 MHz, $CDCl_3$) δ 0.40-0.51 (m, 2H), 0.55-0.67 (m, 2H), 1.48 (quint, J=7.72, 7.72, 7.72, 7.72, 4.77, 4.77 Hz, 1H), 4.49 (d, J=7.40 Hz, 2H), 7.08 (dd, J=9.54, 1.38 Hz, 1H), 7.77 (d, J=1.38 Hz, 1H). (032) LCMS (ESI, m/z), 270.0 $[M+H]^+$. $^1H$ NMR (400 MHz, $CDCl_3$) δ 0.45-0.57 (m, 2H), 0.64-0.76 (m, 2H), 1.35-1.46 (m, 1H), 4.49 (d, J=7.15 Hz, 2H), 7.19 (dd, J=9.22, 1.32 Hz, 1H), 7.58 (d, J=1.38 Hz, 1H).

Procedure 15.

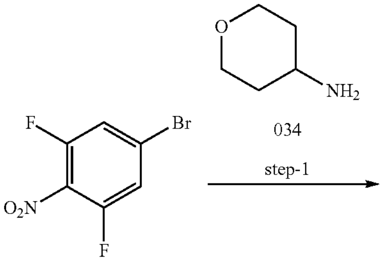

033

-continued

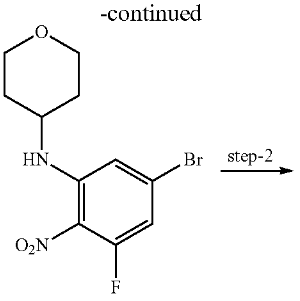

035

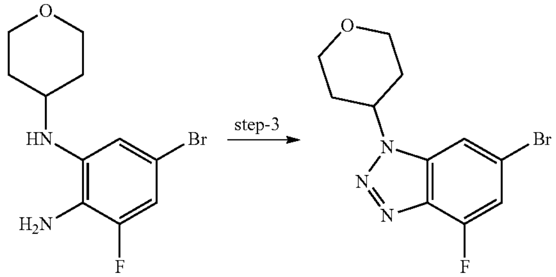

036

037

Step-1: To a solution of 5-bromo-1,3-difluoro-2-nitrobenzene (033, 500 mg, 2.101 mmol) in THE (10 mL, 0.2 M) at rt were added tetrahydro-2H-pyran-4-amine (034, 202 mg, 1.996 mmol) and triethylamine (0.359 ml, 2.521 mmol). The reaction mixture was stirred at 80° C. for 4 hrs. The reaction mixture was concentrated and applied to ISCO on a gradient 0-20% Hex:EtOAc to give N-(5-bromo-3-fluoro-2-nitrophenyl)tetrahydro-2H-pyran-4-amine (035, 540 mg, 1.692 mmol, 81% yield).

Step-2: To a solution of N-(5-bromo-3-fluoro-2-nitrophenyl)tetrahydro-2H-pyran-4-amine (035, 80 mg, 0.251 mmol) in HCl (1M) MeOH (2.5 mL) was added iron (280 mg, 5.014 mmol). Under N2, the reaction mixture was stirred at room temperature for 2 hours. LCMS suggested full conversion of the reaction. Filter through a pad of silica gel, then evaporate the solvent. Re-dissolve the reaction mixture in EtOAc (50 mL) and filter again through a pad of silica gel. The crude product 5-bromo-3-fluoro-N1-(tetrahydro-2H-pyran-4-yl)benzene-1,2-diamine (036, 60 mg, 0.208 mmol, 83% yield) was used directly for next step.

Step-3: To a solution of 5-bromo-3-fluoro-N1-(tetrahydro-2H-pyran-4-yl)benzene-1,2-diamine (036, 60 mg, 0.208 mmol) in acetic acid (1 mL, 0.2 M) at room temperature was added sodium nitrite (35.8 mg, 0.519 mmol). The reaction mixture was stirred at 60° C. for 2 hrs. LC/MS suggested the completion of the reaction. The reaction mixture was vacuumed and re-suspended in EtOAc (50 mL) then washed by brine. The reaction mixture was concentrated and applied to ISCO on a gradient 0-40% Hex:EtOAc to give 6-bromo-4-fluoro-1-(tetrahydro-2H-pyran-4-yl)-1H-benzo[d][1,2,3]triazole (037, 42 mg, 0.140 mmol, 67.4% yield). LCMS (ESI, m/z), 300.3 $[M+H]^+$. $^1H$ NMR (400 MHz, $CDCl_3$) δ 2.06-2.13 (m, 2H), 2.42 (qd, J=12.09, 4.39 Hz, 2H), 3.57 (td, J=11.92, 2.01 Hz, 2H), 4.06-4.16 (m, 2H), 4.97 (tt, J=11.50, 4.19 Hz, 1H), 7.19-7.27 (m, 1H), 7.96 (d, J=1.38 Hz, 1H).

Synthesis of Benzimidazole Intermediates:

Procedure 16 was used to synthesize benzotriazole intermediates of the following general formula:

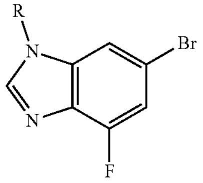

Procedure 16.

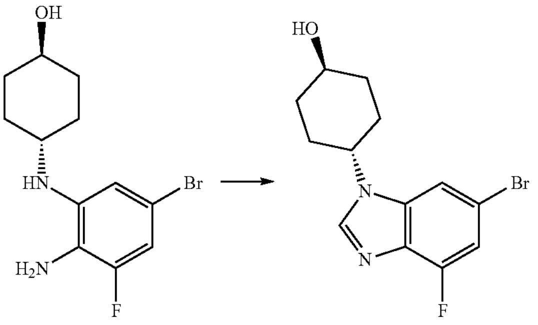

038 039

To a solution of (1r,4r)-4-((2-amino-5-bromo-3-fluorophenyl)amino)cyclohexanol (038, 100 mg, 0.33 mmol) in formic acid (3 mL, 0.11 M) at room temperature was added a few drops of concentrated HCl. The reaction mixture was stirred at 60° C. for 2 hrs. LC/MS suggested the completion of the reaction. The reaction mixture was vacuumed and re-suspended in EtOAc (50 mL) then washed by brine. The reaction mixture was concentrated and applied to ISCO on a gradient 0-10% DCM:MeOH to give (1r,4r)-4-(6-bromo-4-fluoro-1H-benzo[d]imidazol-1-yl)cyclohexanol (039, 80 mg, 0.256 mmol, 79% yield). LCMS (ESI, m/z), 313.3 $[M+H]^+$. $^1H$ NMR (400 MHz, $CDCl_3$) δ 1.55-1.67 (m, 2H), 1.84-1.99 (m, 2H), 2.20-2.30 (m, 4H), 3.84 (tt, J=10.89, 4.05 Hz, 1H), 4.10-4.22 (m, 1H), 7.15 (dd, J=9.66, 1.51 Hz, 1H), 7.39 (d, J=1.51 Hz, 1H).

Synthesis of Phenylpiperazine Intermediates:

Procedure 17 was used to synthesize phenylpiperazine intermediates of the following general formula:

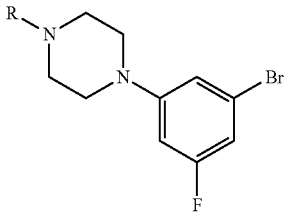

Procedure 17.

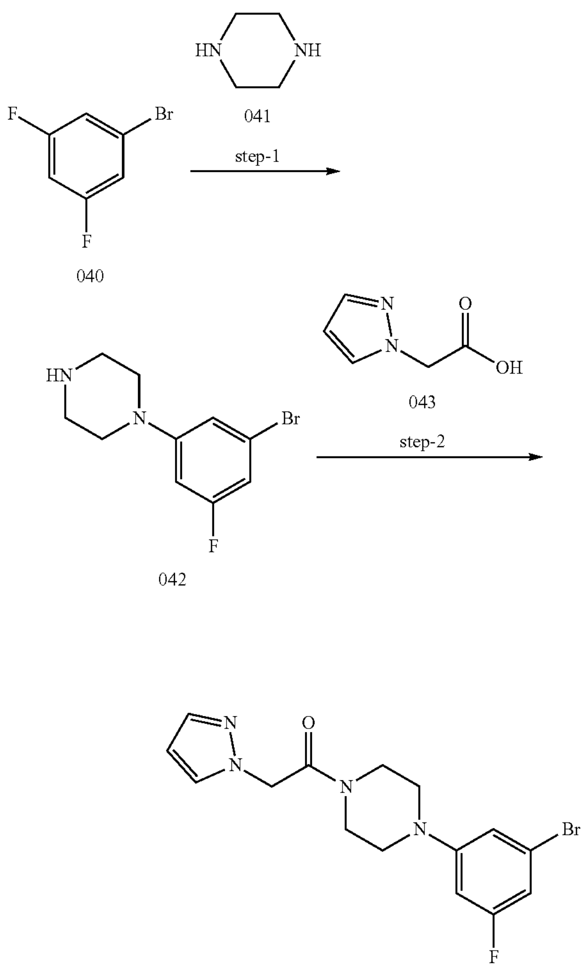

044

Step-1: To a solution of 1-bromo-3,5-difluorobenzene (040, 218 mg, 1.13 mmol) in DMSO (5.0 mL, 0.23 M) added $K_2CO_3$ (187 mg, 1.356 mmol) and piperazine (041, 146 mg, 1.694 mmol). The reaction mixture was heated to 140° C. in sealed tube for 24 h. The reaction mixture was cooled and diluted by EtOAc (200 mL) then washed with brine and dried with $Na_2SO_4$. The organic layer was concentrated and applied to ISCO on a gradient 0-30% DCM:MeOH to give 1-(3-bromo-5-fluorophenyl)piperazine (042, 234 mg, 0.903 mmol, 80% yield).

Step-2: To a solution of 1-(3-bromo-5-fluorophenyl)piperazine (042, 45 mg, 0.174 mmol) and 2-(1H-pyrazol-1-yl) acetic acid (043, 32.9 mg, 0.26 mmol) in DMSO (1 ml, 0.17 M) at room temperature was added HBTU (231 mg, 0.608 mmol) and TEA (0.087 ml, 0.608 mmol). The reaction was stirred overnight. The reaction mixture was diluted in EtOAc (50 ml) and washed by brine. The combined organic layer was concentrated and applied to ISCO on a gradient 0-10% DCM:MeOH to give 1-(4-(3-bromo-5-fluorophenyl)piperazin-1-yl)-2-(1H-pyrazol-1-yl)ethanone (044, 60 mg, 0.163 mmol, 94% yield). LCMS (ESI, m/z), 367.0 $[M+H]^+$. $^1H$ NMR (400 MHz, $CDCl_3$) δ 2.80 (s, 2H), 3.08-3.21 (m, 4H), 3.64-3.80 (m, 4H), 5.05 (s, 2H), 6.27-6.40 (m, 1H), 6.43-6.540 (m, 1H), 6.69-6.82 (m, 2H), 7.45-7.63 (m, 2H).

Procedure 18.

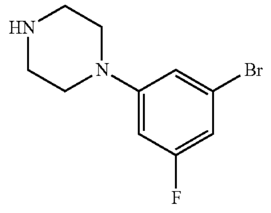

042

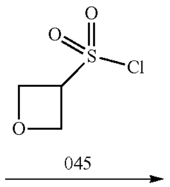

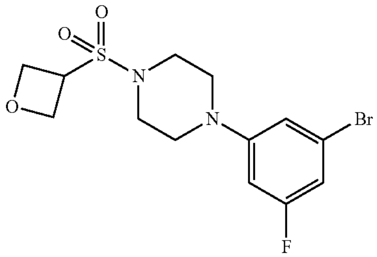

046

To a solution of 1-(3-bromo-5-fluorophenyl)piperazine (042, 40 mg, 0.154 mmol) in DCM (1.5 mL, 0.1 mmol) at room temperature was added TEA (31.2 mg, 0.309 mmol) and and oxetane-3-sulfonyl chloride (045, 25 mg, 0.15 mmol) and stir for 5 mins. Then add DMAP (0.943 mg, 7.718 μmol). The reaction mixture was stirred for 4 hrs. Dilute the reaction mixture into DCM (50 mL) and washed by brine. The combined organic layer was concentrated and applied to ISCO on a gradient 0-100% Hex:EtOAc to give 1-(3-bromo-5-fluorophenyl)-4-(oxetan-3-ylsulfonyl)piperazine (046, 40 mg, 0.11 mmol, 68.3% yield).

Synthesis of Boronate Coupling Products:

Procedure 19.

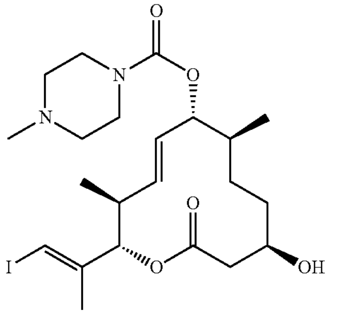

008

-continued

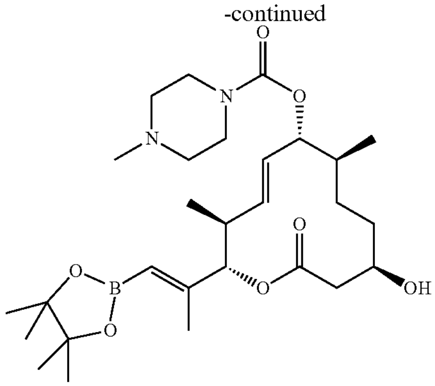

Boronate 1

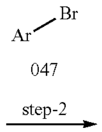

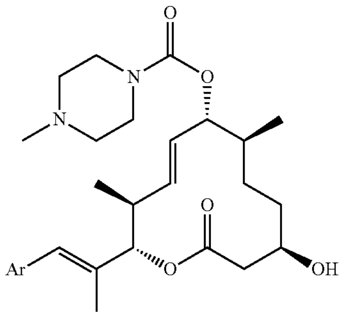

010

Step-1: To a solution of (2S,3S,6R,7S,10R,E)-10-hydroxy-2-((E)-1-iodoprop-1-en-2-yl)-3,7-dimethyl-12-oxooxacyclododec-4-en-6-yl 4-methylpiperazine-1-carboxylate (008, 500 mg, 0.936 mmol) in DMSO (9.0 ml, 0.1 M) were added Pd(0) (108 mg, 0.094 mmol), 4,4,4',4',5,5,5',5'-octamethyl-2,2'-bi(1,3,2-dioxaborolane) (475 mg, 1.871 mmol) and potassium acetate (184 mg, 1.871 mmol). The reaction mixture was flushed by $N_2$, before heated up to 80° C. and stirred for 30 min. The reaction was cooled down to room temperature and $H_2O$ (50 mL) was added in. The reaction mixture was extracted by EtOAc (4×100 mL). The combined organic extracts were dried over MgSO4, filtered and concentrated under vacuum. The crude reaction mixture was applied to ISCO on a 0-10% DCM:MeOH to give (2S,3S,6R,7S,10R,E)-10-hydroxy-3,7-dimethyl-12-oxo-2-((E)-1-(4,4,5,5-tetramethyl-1,3,2-dioxaborolan-2-yl)prop-1-en-2-yl)oxacyclododec-4-en-6-yl 4-methylpiperazine-1-carboxylate (Boronate 1, 360 mg, 0.674 mmol, 72.0% yield) as a yellowish solid. LCMS (ESI, m/z), 536.4 $[M+H]^+$. $^1H$ NMR (400 MHz, $CDCl_3$) δ ppm 0.87-1.08 (m, 6H), 1.19-1.35 (m, 3H), 1.28 (s, 12H), 1.42-1.55 (m, 1H), 1.73-1.85 (m, 1H), 1.88-1.96 (m, 1H), 1.98 (s, 3H), 2.31 (s, 3H), 2.35-2.49 (m, 5H), 2.50-2.65 (m, 2H), 3.39-3.58 (m, 4H), 3.66-3.77 (m, 1H), 4.87 (t, J=10.10 Hz, 1H), 5.14 (d, J=10.54 Hz, 1H), 5.33-5.47 (m, 2H), 5.56 (dd, J=15.00, 9.98 Hz, 1H).

Step-2: To a solution of (2S,3S,6R,7S,10R,E)-10-hydroxy-3,7-dimethyl-12-oxo-2-((E)-1-(4,4,5,5-tetramethyl-1,3,2-dioxaborolan-2-yl)prop-1-en-2-yl)oxacyclododec-4-en-6-yl 4-methylpiperazine-1-carboxylate) (Boronate 1, 15 mg, 0.029 mmol) and arylbromide (047, 0.035 mmol) were added silver oxide (19 mg, 0.086 mmol) and Pd(0) (3.3 mg, 0.003 mmol). The reaction mixture was heated to 60° C. for 5 h. LCMS suggested full conversion of boronate. The mixture was cooled, filtered through a short plug of celite and concentrated. The crude reaction mixture was applied to ISCO on a 0-10% DCM:MeOH to give product 010.

TABLE 5

| Characterization of Compounds 86-166 and 264 | | |
|---|---|---|
| Ex. | Structure and IUPAC Chemical Name | Characterization |
| 86 | 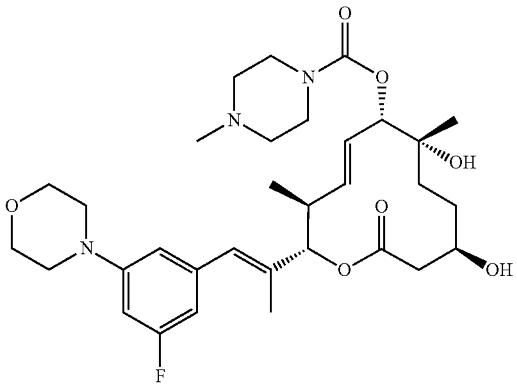 [(2S,3S,4E,6R,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl] 4-methylpiperazine-1-carboxylate | LCMS (ESI, m/z), 604.6 [M + H]. $^1$H NMR (400 MHz, $CDCl_3$) δ ppm 1.00 (br d, J = 6.78 Hz, 3 H) 1.09-1.21 (m, 2 H) 1.26 (hr s, 3H) 1.40-1.48 (m, 1 H) 1.76-1.80 (m, 1H) 1.87 (s, 3 H) 2.49-2.74 (m, 3H) 2.82 (s, 3H) 2.97-3.08 (m, 4H) 3.12-3.21 (m, 4H) 3.75-3.82 (m, 1H) 3.83-3.91 (m, 8 H) 5.01-5.06 (m, 1H) 5.27-5.31(m, 1H) 5.35 (d, J = 10.29 Hz, 1H) 5.65-5.75 (m, 1H) 6.44-6.62 (m, 3H) 6.66-6.75 (m, 1H) |
| 87 | 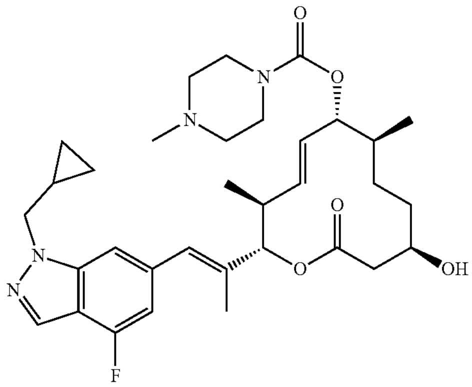 [(2S,3S,4E,6R,7S,10R)-2-[(E)-1-[1-(cyclopropylmethyl)-4-fluoroindazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 597.7 [M + H]$^+$. $^1$H NMR (400 MHz, $CDCl_3$) δ 0.41-0.62 (m, 2H), 0.68-0.91 (m, 2H), 1.03 (d, J = 6.78 Hz, 6H), 1.19-1.39 (m, 3H), 1.39-1.87 (m, 4H), 1.93-2.00 (m, 1H), 1.95 (s, 3H), 2.33-2.42 (m, 3H), 2.42-2.55 (m, 3H), 2.55-2.75 (m, 3H), 3.35-3.50 (m, 1H), 3.50-3.65 (m, 4H), 3.65-3.71 (m, 1H), 3.71-3.82 (m, 1H), 4.23-4.38 (m, 2H), 4.92 (t, J = 10.10 Hz, 1H), 5.30-5.36 (m, 1H), 5.38-5.48 (m, 1H), 5.64 (dd, J = 15.00, 9.98 Hz, 1H), 6.61-6.68 (m, 2H), 7.41 (s, 1H), 8.10 (s, 1H) |
| 88 | 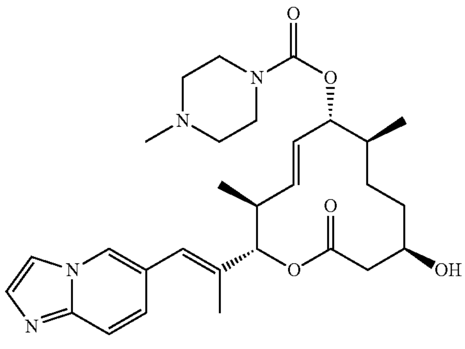 [(2S,3S,4E,6R,7S,10R)-10-hydroxy-2-[(E)-1-imidazo[1,2-a]pyridin-6-ylprop-1-en-2-yl]-3,7-dimethyl-12-oxo-l-oxacyclododec-4-en-6-yl] 4-methylpiperazine-1-carboxylate | LCMS (ESI, m/z), 525.6 [M + H]$^+$. $^1$H NMR (400 MHz, $CDCl_3$) δ 0.97-1.07 (m, 6H), 1.20-1.35 (m, 3H), 1.45-1.59 (m, 1H), 1.92 (d, J = 1.13 Hz, 5H), 2.29-2.35 (m, 3H), 2.35-2.48 (m, 4H), 2.52-2.72 (m, 3H), 3.41-3.61 (m, 4H), 3.69-3.81 (m, 3H), 4.91 (t, J = 10.10 Hz, 1H), 5.23-5.38 (m, 1H), 5.43 (dd, J = 15.00, 9.73 Hz, 1H), 5.62 (dd, J = 14.93, 9.91 Hz, 1H), 6.52 (s, 1H), 7.14 (dd, J = 9.35, 1.57 Hz, 1H), 7.49-7.73 (m, 1H), 7.63-7.68 (m, 1H), 7.63-7.67 (m, 1H), 8.07 (s, 1H) |

TABLE 5-continued

| Ex. | Structure and IUPAC Chemical Name | Characterization |
| --- | --- | --- |
| | Characterization of Compounds 86-166 and 264 | |
| 89 | 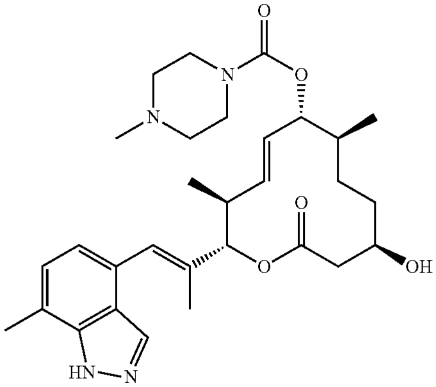 [(2S,3S,4E,6R,7S,10R)-10-hydroxy-3,7-dimethyl-2-[(E)-1-(7-methyl-1H-indazol-4-yl)prop-1-en-2-yl]-12-oxo-1-oxacyclododec-4-en-6-yl] 4-methylpiperazine-1-carboxylate | LCMS (ESI, m/z), 539.3 [M + H]$^+$. $^1$H NMR (400 MHz, $CDCl_3$) δ 0.89-1.05 (m, 6H), 1.10-1.29 (m, 5H), 1.34-1.54 (m, 1H), 1.71-1.82 (m, 4H), 1.82-1.91 (m, 1H), 2.25-2.42 (m, 3H), 2.42-2.63 (m, 10H), 3.51 (hr s, 6H), 3.57-3.76 (m, 3H), 4.84 (t, J = 10.10 Hz, 1H), 5.29-5.39 (m, 3H), 5.57 (dd, J = 15.00, 9.98 Hz, 1H), 6.82 (s, 1H), 6.92 (d, J = 7.15 Hz, 1H), 7.07 (d, J = 7.15 Hz, 1H), 7.95 (s, 1H), 8.20 (hr s, 1H) |
| 90 | 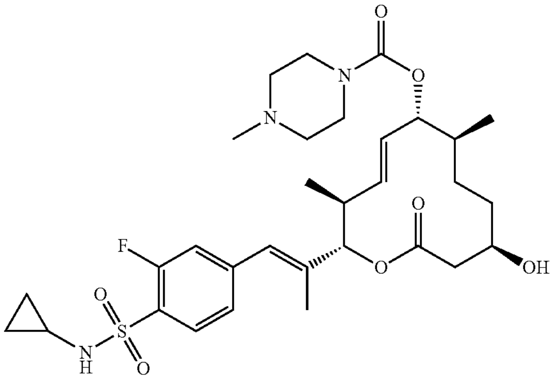 [(2S,3S,4E,6R,7S,10R)-2-[(E)-1-[4-(cyclopropylsulfamoyl)-3-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 622.3 [M + H]$^+$. $^1$H NMR (400 MHz, $CDCl_3$) δ 0.57-0.66 (m, 2H), 0.66-0.73 (m, 2H), 0.97-1.07 (m, 6H), 1.20-1.38 (m, 2H), 1.47-1.58 (m, 1H), 1.76-1.87 (m, 1H), 1.87-2.02 (m, 3H), 2.25-2.32 (m, 1H), 2.39 (s, 3H), 2.42-2.93 (m, 8H), 3.45-3.66 (m, 4H), 3.66-3.79 (m, 1H), 4.90 (t, J = 10.04 Hz, 1H), 5.15 (br s, 1H), 5.29 (d, J = 10.54 Hz, 1H), 5.43 (dd, J = 15.06, 9.66 Hz, 1H), 5.61 (dd, J = 14.93, 9.91 Hz, 1H), 6.59 (s, 1H), 7.12-7.22 (m, 1H), 7.18-7.23 (m, 1H), 7.92 (t, J = 7.84 Hz, 1H), 8.24-8.30 (m, 1H) |
| 91 | 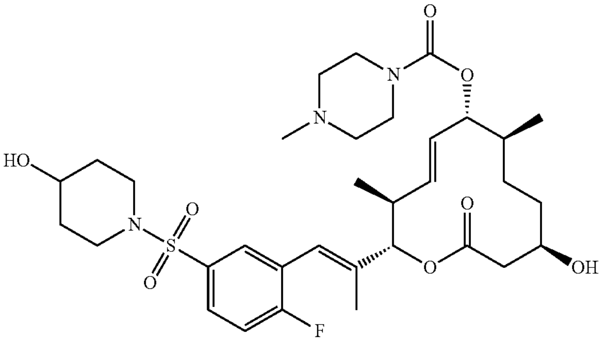 [(2S,3S,4E,6R,7S,10R)-2-[(E)-1-[2-fluoro-5-(4-hydroxypiperidin-1-yl)sulfonylphenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 666.3 [M + H]$^+$. $^1$H NMR (400 MHz, $CDCl_3$) δ 0.87-1.00 (m, 6H), 1.13-1.27 (m, 4H), 1.31-1.49 (m, 2H), 1.54-1.66 (m, 2H), 1.66-1.80 (m, 3H), 1.81-1.93 (m, 3H), 2.23-2.32 (s, 3H), 2.32-2.44 (m, 3H), 2.44-2.55 (m, 2H), 2.55-2.65 (m, 1H), 2.81-2.92 (m, 2H), 3.16-3.28 (m, 2H), 3.46 (br s, 4H), 3.56-3.70 (m, 2H), 3.71-3.81 (m, 1H), 4.77-4.86 (m, 1H), 5.22-5.28 (m, 1H), 5.29-5.41 (m, 1H), 5.48-5.57 (m, 1H), 6.47 (s, 1H), 7.10-7.17 (m, 1H), 7.60 (m, 2H) |

TABLE 5-continued

Characterization of Compounds 86-166 and 264

| Ex. | Structure and IUPAC Chemical Name | Characterization |
|---|---|---|
| 92 | 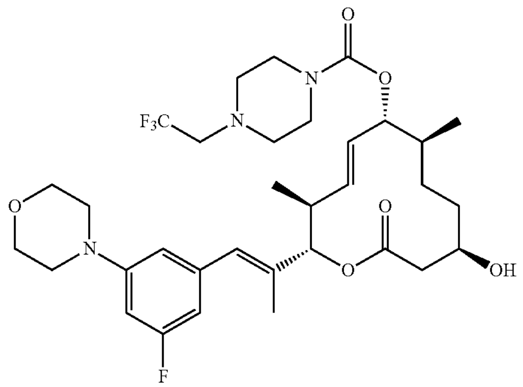 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-(2,2,2-trifluoroethyl)piperazine-1-carboxylate | LCMS (ESI, m/z), 656.3 $[M + H]^+$. $^1H$ NMR (400 MHz, $CDCl_3$) δ 0.96-1.06 (m, 6H), 1.18-1.36 (m, 2H), 1.45-1.71 (m, 1H), 1.76-1.86 (m, 1H), 1.90 (s, 3H), 1.91-2.00 (m, 1H), 2.50-2.72 (m, 6H), 2.95-3.07 (m, 2H), 3.13-3.24 (m, 4H), 3.36-3.45 (m, 1H), 3.45-3.61 (m, 3H), 3.70-3.80 (m, 1H), 3.82-3.91 (m, 4H), 4.86-4.95 (m, 1H), 5.24-5.31 (m, 1H), 5.37-5.47 (m, 1H), 5.56-5.67 (m, 1H), 5.58-5.62 (m, 1H), 5.62-5.62 (m, 1H), 5.62-5.62 (m, 1H), 6.46-6.57 (m, 4H) |
| 93 | 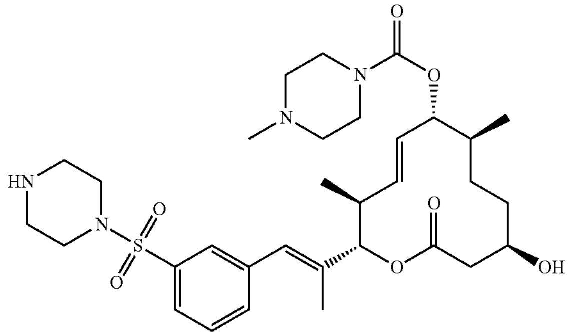 [(2S,3S,4E,6R,7S,10R)-10-hydroxy-3,7-dimethyl-12-oxo-2-[(E)-1-(3-piperazin-1-ylsulfonylphenyl)prop-1-en-2-yl]-1-oxacyclododec-4-en-6-yl] 4-methylpiperazine-1-carboxylate | LCMS (ESI, m/z), 633.3 $[M + H]^+$. $^1H$ NMR (400 MHz, $CDCl_3$) δ 0.89-0.99 (m, 6H), 1.09-1.30 (m, 6H), 1.66-1.93 (m, 4H), 2.31 (s, 3H), 2.35-2.63 (m, 7H), 2.83-3.07 (m, 6H), 3.19-3.29 (m, 1H), 3.37-3.73 (m, 6H), 4.77-4.86 (m, 1H), 5.17-5.25 (m, 1H), 5.29-5.39 (m, 1H), 5.47-5.59 (m, 1H), 6.50-6.58 (m, 1H), 7.38-7.61 (m, 4H) |
| 94 | 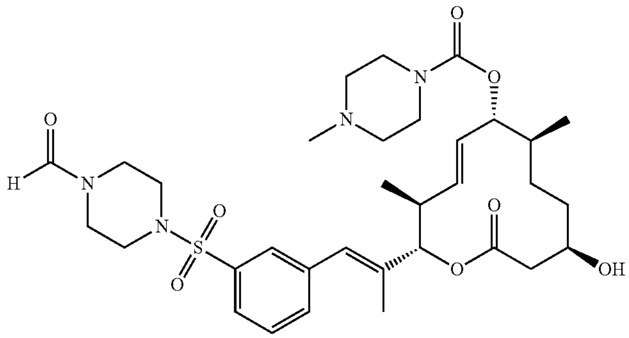 [(2S,3S,4E,6R,7S,10R)-[(E)-1-[3-(4-formylpiperazine-1-yl)sulfonylphenyl] prop-1-en-2-yl]-10-hydroxy-3,7-dimethyl-12-oxo-1-oxacyclododec-4-en-6-yl] 4-methylpiperazine-1-carboxylate | LCMS (ESI, m/z), 661.3 $[M + H]^+$. $^1H$ NMR (400 MHz, $CDCl_3$) δ 0.89-0.99 (m, 6H), 1.12-1.28 (m, 4H), 1.38-1.48 (m, 1H), 1.66-1.78 (m, 2H), 1.81 (d, J = 1.25 Hz, 3H),1.84-1.93 (m, 1H), 2.24-2.63 (m, 9H), 2.91-3.05 (m, 4H), 3.37-3.62 (m, 7H), 3.63-3.73 (m, 1H), 4.78-4.86 (m, 1H), 5.18-5.25 (m, 1H), 5.29-5.39 (m, 1H), 5.48-5.59 (m, 1H), 6.51-6.56 (m, 1H), 7.42-7.49 (m, 2H), 7.51-7.58 (m, 2H), 7.89-7.94 (m, 1H) |

TABLE 5-continued

| Characterization of Compounds 86-166 and 264 | | |
|---|---|---|
| Ex. | Structure and IUPAC Chemical Name | Characterization |
| 95 | 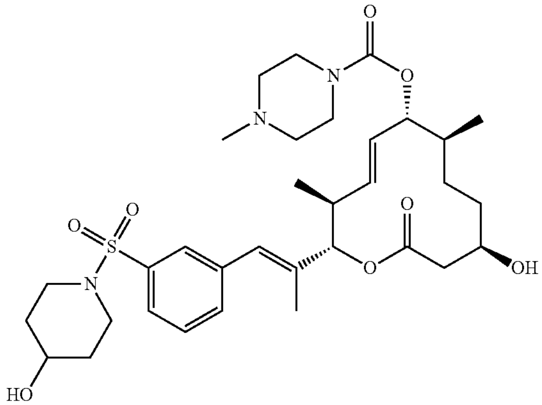 [(2S,3S,4E,6R,7S,10R)-10-hydroxy-2-[(E)-1-[3-(4-hydroxypiperidin-1-yl)sulfonylphenyl]prop-1-en-2-yl]-3,7-dimethyl-12-oxo-1-oxacyclododec-4-en-6-yl] 4-methylpiperazine-1-carboxylate | LCMS (ESI, m/z), 648.3 $[M + H]^+$. $^1H$ NMR (400 MHz, CDCl3) δ 0.98-1.07 (m, 6H), 1.22-1.35 (m, 2H), 1.46-1.57 (m, 1H), 1.60-1.73 (m, 2H), 1.75-1.86 (m, 1H), 1.86-2.01 (m, 6H), 2.41 (s, 3H), 2.47-2.73 (m, 7H), 2.84-2.99 (m, 2H), 3.27-3.47 (m, 3H), 3.50-3.86 (m, 7H), 4.86-4.95 (m, 1H), 5.27-5.34 (m, 1H), 5.38-5.47 (m, 1H), 5.57-5.67 (m, 1H), 6.61-6.66 (m, 1H), 7.47-7.55 (m, 2H), 7.63-7.69 (m, 2H) |
| 96 | 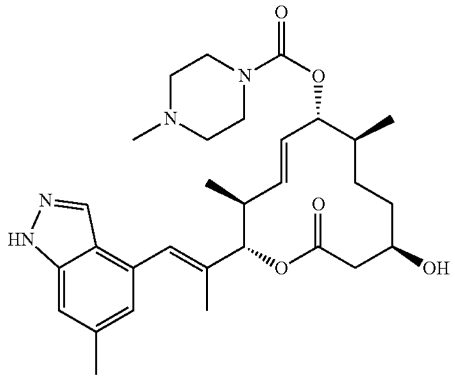 [(2S,3S,4E,6R,7S,10R)-10-hydroxy-3,7-dimethyl-2-[(E)-1-(6-methyl-1H-indazol-4-yl)prop-1-en-2-yl]-12-oxo-1-oxacyclododec-4-en-6-yl] 4-methylpiperazine-1-carboxylate | LCMS (ESI, m/z), 539.5 $[M + H]^+$. $^1H$ NMR (400 MHz, $CD_3OD$) δ 0.98-1.08 (m, 7H), 1.30-1.49 (m, 4H), 1.62-1.70 (m, 2H), 1.82-1.89 (m, 3H), 1.91-2.01 (m, 1H), 2.29-2.35 (m, 3H), 2.38-2.53 (m, 6H), 2.53-2.58 (m, 3H), 2.58-2.75 (m, 2H), 3.42-3.57 (m, 5H), 3.76-3.88 (m, 1H), 5.22-5.30 (m, 1H), 5.44-5.66 (m, 2H), 6.91 (s, 1H), 6.94-7.02 (m, 1H), 7.10-7.17 (m, 1H), 7.97 (s, 1H) |
| 97 | 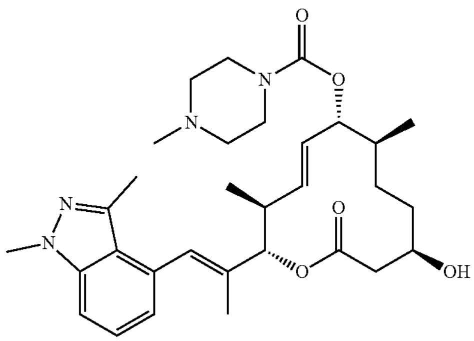 [(2S,3S,4E,6R,7S,10R)-2-[(E)-1-(1,3-dimethylindazol-4-yl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 553.3 $[M + H]^+$. $^1H$ NMR (400 MHz, $CDCl_3$) δ 1.04 (d, J = 6.78 Hz, 3H),1.06-1.13 (m, 3H), 1.25-1.33 (m, 2H), 1.50-1.61 (m, 1H), 1.73-1.89 (m, 4H), 1.90-2.02 (m, 1H), 2.33-2.38 (m, 3H), 2.38-2.50 (m, 4H), 2.56-2.71 (m, 7H), 3.44-3.65 (m, 4H), 3.73-3.81 (m, 2H), 4.02 (s, 3H), 4.88-4.96 (m, 1H), 5.37-5.50 (m, 2H), 5.61-5.70 (m, 1H), 6.87-6.93 (m, 1H), 7.07-7.11 (m, 1H), 7.21-7.26 (m, 1H), 7.29-7.36 (m, 1H) |

TABLE 5-continued

| Characterization of Compounds 86-166 and 264 | | |
|---|---|---|
| Ex. | Structure and IUPAC Chemical Name | Characterization |
| 98 | 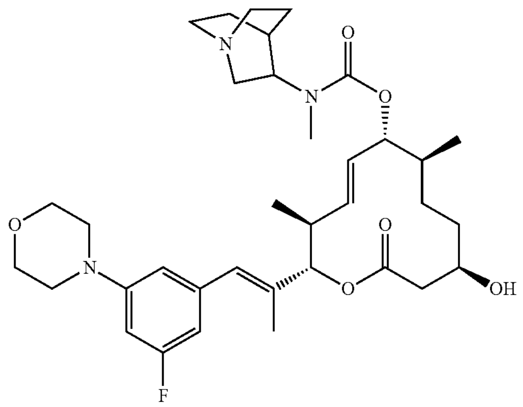 [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] N-(1-azabicyclo[2.2.2]octan-3-yl)-N-methylcarbamate | LCMS (ESI, m/z), 628.5 $[M + H]^+$. $^1H$ NMR (400 MHz, $CD_3OD$) δ 0.86-0.96 (m, 1H), 0.96-1.02 (m, 3H), 1.02-1.08 (m, 3H), 1.24-1.46 (m, 6H), 1.60-1.70 (m, 1H), 1.85-1.93 (m, 3H), 1.96-2.08 (m, 3H), 2.10-2.25 (m, 1H), 2.28-2.34 (m, 1H), 2.45-2.55 (m, 1H), 2.60-2.73 (m, 2H), 3.05 (s, 3H), 3.14-3.20 (m, 3H), 3.20-3.31 (m, 3H), 3.44-3.58 (m, 2H), 3.58-3.72 (m, 1H), 3.80-3.87 (m, 4H), 4.20-4.32 (m, 1H), 5.16 (d, J = 10.54 Hz, 1H), 5.56 (d, J = 8.78 Hz, 2H), 6.49-6.66 (m, 3H), 8.42-8.69 (m, 2H) |
| 99 | 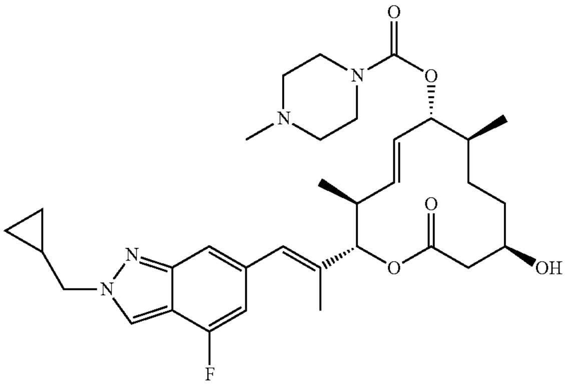 [(2S,3S,4E,6R,7S,10R)-2-[(E)-1-[2-(cyclopropylmethyl)-4-fluoroindazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 597.3 $[M + H]^+$. $^1H$ NMR (400 MHz, $CDCl_3$) δ 0.28-0.40 (m, 2H), 0.47-0.67 (m, 2H), 0.67-0.91 (m, 2H), 0.68-0.73 (m, 1H), 0.95 (t, J = 6.84 Hz,6H), 1.09-1.33 (m, 1H), 1.40-1.50 (m, 1H), 1.68-1.79 (m, 1H), 1.82-1.92 (m, 2H), 2.36-2.45 (m, 3H), 2.45-2.67 (m, 4H), 2.67-2.99 (m, 4H), 3.51-3.60 (m, 4H), 3.65 (m, 1H), 4.17 (d, J = 6.90 Hz, 2H), 4.82 (t, J = 10.10 Hz, 1H), 5.19-5.29 (m, 1H), 5.34 (dd, J = 15.00, 9.72 Hz, 1H), 5.55 (dd, J = 14.93, 9.91 Hz, 1H), 6.60-6.68 (m, 2H), 6.99 (s, 1H), 7.95 (d, J = 0.75 Hz, 1H), 8.16 (s, 1H) |
| 100 | 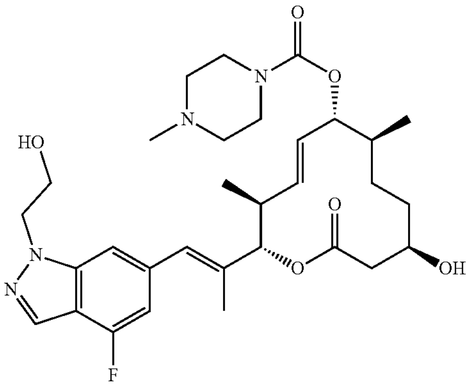 [(2S,3S,4E,6R,7S,10R)-2-[(E)-1-[4-fluoro-1-(2-hydroxyethyl)indazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 597.3 $[M + H]^+$. $^1H$ NMR (400 MHz, $CDCl_3$) δ 0.73-0.87 (m, 1H), 0.87-0.97 (m, 6H), 1.11-1.26 (m, 1H), 1.26-1.35 (m, 1H), 1.37-1.50 (m, 1H), 1.67-1.78 (m, 2H), 1.80-1.91 (m, 4H), 2.34 (s, 3H), 2.37-2.64 (m, 6H), 3.38-3.60 (m, 4H), 3.61-3.77 (m, 1H), 4.01-4.09 (m, 2H), 4.35-4.42 (m, 2H), 4.82 (t, J = 10.10 Hz, 1H), 5.23 (d, J = 10.67 Hz, 1H), 5.34 (dd, J = 15 .00, 9.73 Hz, 1H), 5.54 (dd, J = 14.93, 9.91 Hz, 1H), 6.61 (s, 1H), 6.68 (d, J = 10.79 Hz, 1H), 7.02 (s, 2H), 7.97-8.02 (m, 1H) |

TABLE 5-continued

| Characterization of Compounds 86-166 and 264 | | |
|---|---|---|
| Ex. | Structure and IUPAC Chemical Name | Characterization |
| 101 | 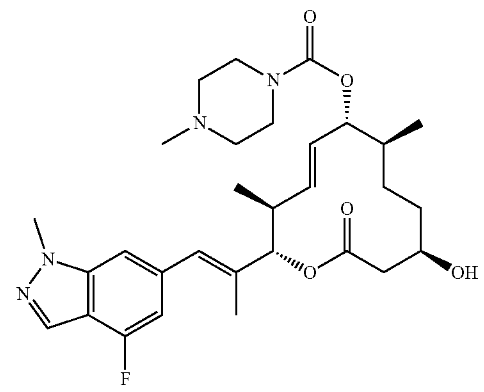 [(2S,3S,4E,6R,7S,10R)-2-[(E)-1-(4-fluoro-1-methylindazol-6-yl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 557.3 [M + H]$^+$. $^1$H NMR (400 MHz, $CDCl_3$) δ 0.85-0.99 (m, 6H), 1.09-1.30 (m, 2H), 1.44 (br dd, J = 13.30, 9.66 Hz, 2H), 1.57-1.79 (m, 2H), 1.80-1.92 (m, 4H), 2.21-2.30 (m, 3H), 2.33 (hr s, 1H), 2.42-2.61 (m, 2H), 3.16-3.57 (m, 6H), 3.60-3.72 (m, 1H), 3.99 (s, 3H), 4.82 (t, J = 10.10 Hz, 1H), 5.24 (d, J = 10.54 Hz, 1H), 5.35 (dd, J = 15.00, 9.72 Hz, 1H), 5.55 (dd, J = 15.00, 9.98 Hz, 1H), 6.60-6.69 (m, 2H), 6.96 (s, 1H), 7.93 (s, 1H) |
| 102 | 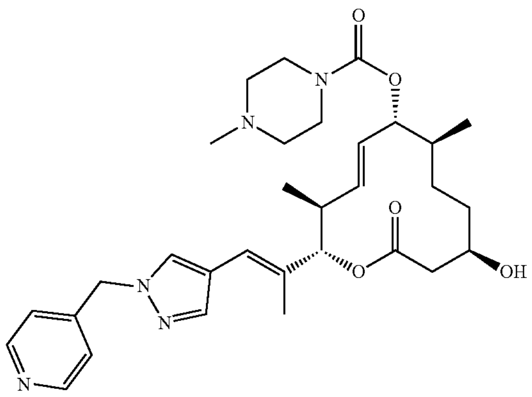 [(2S,3S,4E,6R,7S,10R)-10-hydroxy-3,7-dimethyl-12-oxo-2-[(E)-1-[1-(pyridin-4-ylmethyl)pyrazol-4-yl]prop-1-en-2-yl]-1-oxacyclododec-4-en-6-yl] 4-methylpiperazine-1-carboxylate | LCMS (ESI, m/z), 566.3 [M + H]$^+$. $^1$H NMR (400 MHz, $CDCl_3$) δ 0.77-0.97 (m, 6H), 1.07-1.28 (m, 3H), 1.32-1.55 (m, 1H), 1.66-1.78 (m, 1H), 1.78-1.82 (m, 3H), 1.82-1.91 (m, 1H), 2.19-2.27 (m, 3H), 2.27-2.39 (m, 4H), 2.36-2.56 (m, 2H), 3.18-3.55 (m, 5H), 3.64 (br s, 1H), 4.81 (t, J = 10.04 Hz, 1H), 5.13-5.21 (m, 1H), 5.21-5.27 (m, 2H), 5.27-5.38 (m, 1H), 5.45-5.58 (m, 1H), 6.31 (s, 1H), 6.93-7.02 (m, 2H), 7.36-7.42 (m, 1H), 7.56 (s, 1H), 8.47-8.53 (m, 2H) |
| 103 | 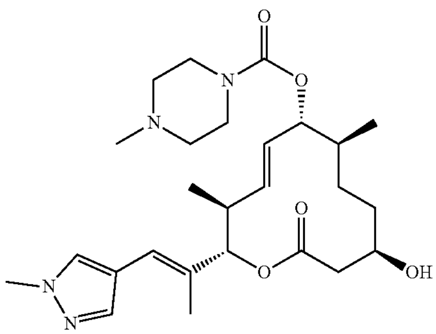 [(2S,3S,4E,6R,7S,10R)-10-hydroxy-3,7-dimethyl-2-[(E)-1-(1-methylpyrazol-4-yl)prop-1-en-2-yl]-12-oxo-1-oxacyclododec-4-en-6-yl] 4-methylpiperazine-1-carboxylate | LCMS (ESI, m/z), 489.3 [M + H]$^+$. $^1$H NMR (400 MHz, $CDCl_3$) δ 0.78-0.90 (m, 3H), 0.93 (d, J = 6.90 Hz, 3H), 1.09-1.29 (m, 2H), 1.35-1.77 (m, 2H), 1.79 (s, 3H), 1.82-1.93 (m, 3H), 2.30-2.37 (m, 1H), 2.37-2.57 (m, 7H), 3.34 (br d, J = 5.27 Hz,1H), 3.46-3.54 (m, 3H), 3.54-3.72 (m, 2H), 3.83 (s, 3H), 4.81 (t, J = 10.10 Hz, 1H), 5.14-5.23 (m, 1H), 5.31 (dd, J = 15.00, 9.73 Hz, 1H), 5.52 (dd, J = 15.00, 9.98 Hz, 1H), 6.29 (s, 1H), 7.31 (s, 1H), 7.46 (s, 1H) |

TABLE 5-continued

| Characterization of Compounds 86-166 and 264 | | |
|---|---|---|
| Ex. | Structure and IUPAC Chemical Name | Characterization |
| 104 | 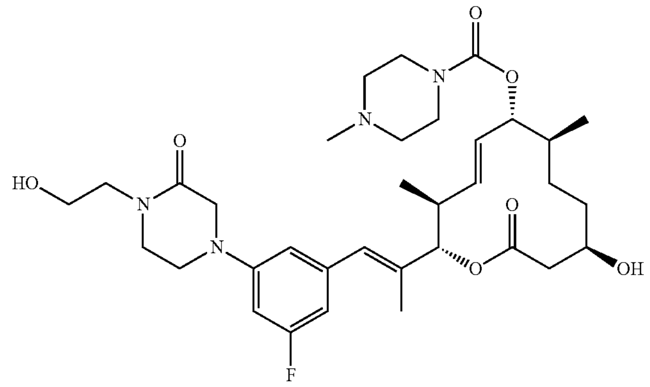 [(2S,3S,4E,6R,7S,10R)-2-[(E)-1-[3-fluoro-5-[4-(2-hydroxyethyl)-3-oxopiperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 645.3 [M + H]$^+$. $^1$H NMR (400 MHz, $CDCl_3$) δ 0.92-1.01 (m, 6H), 1.11-1.17 (m, 2H), 1.22-1.42 (m, 2H), 1.60 (hr s, 2H), 1.81-1.86 (m, 3H), 1.87-1.98 (m, 1H), 2.27 (s, 3H), 2.33-2.48 (m, 4H), 2.50-2.65 (m, 2H), 3.25-3.31 (m, 3H), 3.48 (hr dd, J = 6.59, 4.08 Hz, 2H), 3.52-3.62 (m, 6H), 3.73-3.80 (m, 1H), 3.80-3.85 (m, 2H), 4.74-4.79 (m, 1H), 5.06-5.15 (m, 1H), 5.48 (dd, J = 15.12, 9.10 Hz, 2H), 6.45-6.58 (m, 4H) |
| 105 | 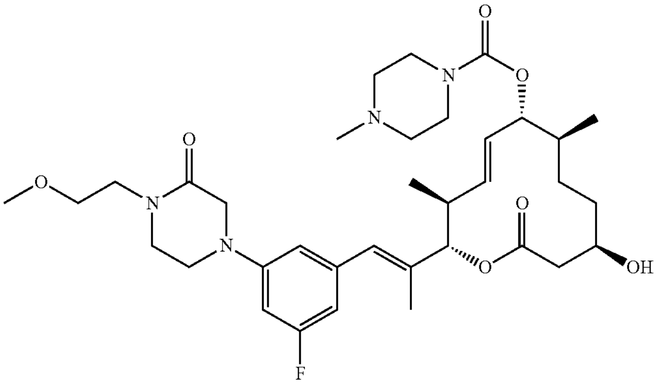 [(2S,3S,4E,6R,7S,10R)-2-[(E)-1-[3-fluoro-5-[4-(2-methoxyethyl)-3-oxopiperazin-1-yl]phenyl]prop-1-en-2-yl]-10-hydrozy-3,7-dimethyl-12-oxo-1-oxacyclododec-4-en-6-yl] 4-methylpiperazine-1-carboxylate | LCMS (ESI, m/z), 658.3 [M + H]$^+$. $^1$H NMR (400 MHz, DMSO-d6) δ 0.00 (dd, J = 9.54, 6.78 Hz, 6H), 0.25-0.45 (m, 3H), 0.65 (br s, 2H), 0.89 (d, J = 1.25 Hz, 4H), 1.31 (s, 3H), 1.36-1.52 (m, 5H), 1.58-1.71 (m, 4H), 2.44-2.70 (m, 11H), 2.71-2.77 (m, 2H), 2.77-2.85 (m, 1H), 2.85-2.92 (m, 2H), 3.79-3.87 (m, 1H), 4.09-4.19 (m, 1H), 4.45-4.61 (m, 2H), 5.47-5.66 (m, 4H) |
| 106 | 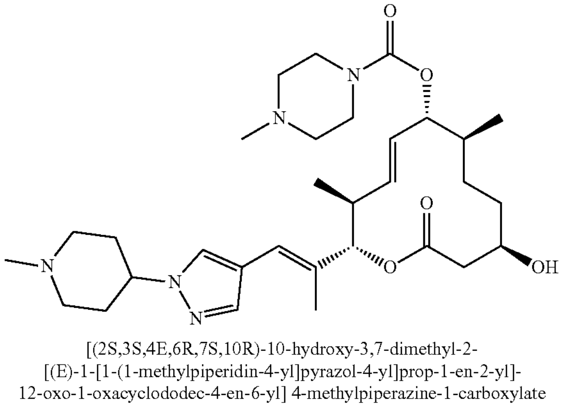 [SMILES: C/C(=C\c1cnn(C2CCN(C)CC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-2-[(E)-1-[1-(1-methylpiperidin-4-yl]pyrazol-4-yl]prop-1-en-2-yl]-12-oxo-1-oxacyclododec-4-en-6-yl] 4-methylpiperazine-1-carboxylate | LCMS (ESI, m/z), 572.3 [M + H]$^+$. $^1$H NMR (400 MHz, $CDCl_3$) δ 0.78-0.90 (m, 3H), 0.93 (d, J = 6.78 Hz, 3H), 1.08-1.27 (m, 2H), 1.42 (ddd, J = 13.87, 9.85, 3.89 Hz, 1H), 1.66-1.77 (m, 1H), 1.80 (s, 3H), 1.82-1.91 (m, 2H), 1.92-2.13 (m, 6H), 2.19-2.33 (m, 8H), 2.34-2.57 (m, 4H), 2.91 (br d, J = 11.54 Hz, 2H), 3.41 (br s, 4H), 3.49-3.68 (m, 2H), 4.05 (tt, J = 11.26, 4.11 Hz, 1H), 4.81 (t, J = 10.10 Hz, 1H), 5.17 (d, J = 10.67 Hz, 1H), 5.31 (dd, J = 15.06, 9.66 Hz, 1H), 5.51 (dd, J = 14.93, 9.91 Hz, 1H), 6.30 (s, 1H), 7.38 (s, 1H), 7.48 (s, 1H) |

TABLE 5-continued

| Characterization of Compounds 86-166 and 264 | | |
|---|---|---|
| Ex. | Structure and IUPAC Chemical Name | Characterization |
| 107 | 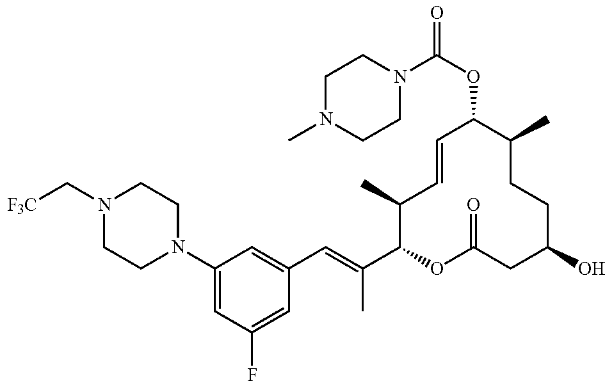 [(2S,3S,4E,6R,7S,10R)-2-[(E)-1-[3-fluoro-5-[4-(2,2,2-trifluoroethyl) piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 669.3 $[M + H]^+$. $^1H$ NMR (400 MHz, $CDCl_3$) δ 0.84-0.94 (m, 6H), 1.44-1.68 (m, 3H), 1.68-2.01 (m, 6H), 2.31-2.37 (m, 3H), 2.37-2.48 (m, 4H), 2.51-2.71 (m, 3H), 2.77-2.90 (m, 4H), 3.05 (d, J = 9.54 Hz, 2H), 3.17-3.29 (m, 4H), 3.46-3.62 (m, 5H), 3.70-3.80 (m, 1H), 4.90 (s, 1H), 5.24-5.30 (m, 1H), 5.42 (s, 1H), 5.57-5.65 (m, 1H), 6.47-6.56 (m, 3H) |
| 108 | 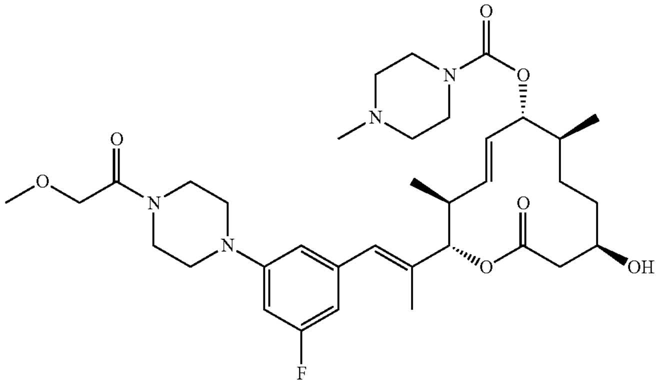 [(2S,3S,4E,6R,7S,10R)-2-[(E)-1-[3-fluoro-5-[4-(2-methoxyacetyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 659.3 $[M + H]^+$. $^1H$ NMR (400 MHz, $CDCl_3$) δ 1.02 (dd, J = 8.53, 6.90 Hz, 6H), 1.42-1.60 (m, 1H), 1.76-1.87 (m, 1H), 1.90 (s, 3H), 1.90-2.00 (m, 2H), 2.30-2.38 (m, 3H), 2.42 (br s, 4H), 2.48-2.68 (m, 4H), 3.12-3.28 (m, 4H), 3.42-3.47 (m, 4H), 3.47-3.59 (m, 4H), 3.59-3.71 (m, 2H), 3.71-3.84 (m, 3H), 4.15-4.19 (m, 2H), 4.90 (t, J = 10.10 Hz, 1H), 5.27 (d, J = 10.54 Hz, 1H), 5.42 (dd, J = 15.00, 9.73 Hz, 1H), 5.61 (dd, J = 15.00, 9.85 Hz, 1H), 6.48-6.59 (m, 4H) |
| 109 | 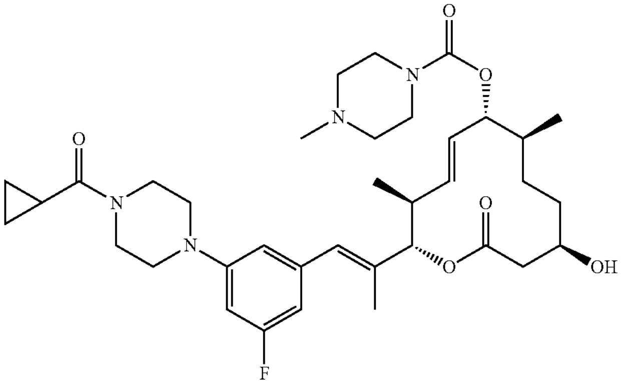 [(2S,3S,4E,6R,7S,10R)-2-[(E)-1-[3-[4-(cyclopropanecarbonyl) piperazin-1-yl]-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 655.3 $[M + H]^+$. $^1H$ NMR (400 MHz, $CDCl_3$) δ 0.79-0.92 (m, 2H), 0.94-1.08 (m, 8H), 1.42-1.65 (m, 1H), 1.72-1.86 (m, 2H), 1.89 (s, 3H), 1.90-2.01 (m, 1H), 2.31-2.37 (m, 3H), 2.37-2.48 (m, 4H), 2.52-2.71 (m, 4H), 3.10-3.33 (m, 5H), 3.53 (br s, 4H), 3.70-3.89 (m, 5H), 4.90 (t, J = 10.10 Hz, 1H), 5.27 (d, J = 10.67 Hz, 1H), 5.42 (dd, J = 14.93, 9.66 Hz, 1H), 5.61 (dd, J = 15.06, 9.91 Hz, 1H), 6.49-6.57 (m, 4H) |

TABLE 5-continued

| Ex. | Structure and IUPAC Chemical Name | Characterization |
| --- | --- | --- |
| | Characterization of Compounds 86-166 and 264 | |
| 110 | 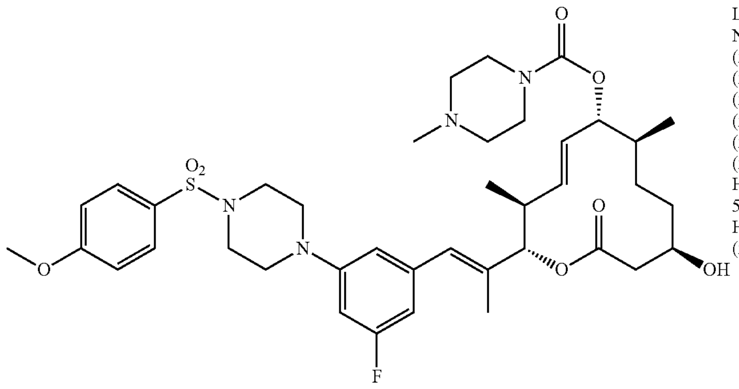 [(2S,3S,4E,6R,7S,10R)-2-[(E)-1-[3-fluoro-5-[4-(4-methoxyphenyl) sulfonylpiperazin-1-yl]phenyl]prop-1-en-2-yl]-10-hydrozy-3,7-dimethyl-12-oxo-1-oxacyclododec-4-en-6-yl] 4-methylpiperazine-1-carboxylate | LCMS (ESI, m/z), 757.3 $[M + H]^+$. $^1H$ NMR (400 MHz, $CDCl_3$) δ 0.94-1.07 (m, 6H), 1.40-1.58 (m, 1H), 1.76-1.88 (m, 4H), 1.88-2.00 (m, 1H), 2.32-2.37 (m, 3H), 2.37-2.48 (m, 5H), 2.50-2.70 (m, 4H), 3.10-3.21 (m, 4H), 3.21-3.32 (m, 4H), 3.40-3.64 (m, 4H), 3.63-3.89 (m, 2H), 3.90 (s, 3H), 4.89 (t, J = 10.04 Hz, 1H), 5.25 (d, J = 10.67 Hz, 1H), 5.37-5.46 (m, 1H), 5.60 (dd, J = 15.06, 9.91 Hz, 1H), 6.42-6.54 (m, 4H), 7.01-7.06 (m, 2H), 7.72-7.77 (m, 2H) |
| 111 | 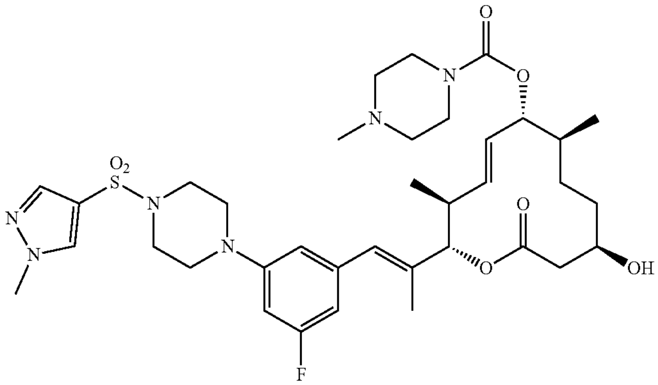 [(2S,3S,4E,6R,7S,10R)-2-[(E)-1-[3-fluoro-5-[4-(1-methylpyrazol-4-yl) sulfonylpiperazin-1-yl]phenyl]prop-1-en-2-yl]-10-hydrozy-3,7-dimethyl-12-oxo-1-oxacyclododec-4-en-6-yl] 4-methylpiperazine-1-carboxylate | LCMS (ESI, m/z), 757.3 $[M + H]^+$. $^1H$ NMR (400 MHz, $CDCl_3$) δ 0.88-1.00 (m, 6H), 1.41 (br d, J = 9.41 Hz, 2H), 1.78 (d, J = 1.13 Hz, 4H), 1.80-1.89 (m, 2H), 2.25-2.31 (m, 3H), 2.33-2.43 (m, 3H), 2.43-2.63 (m, 4H), 2.99-3.15 (m, 4H), 3.16-3.30 (m, 4H), 3.40-3.58 (m, 4H), 3.61-3.78 (m, 2H), 3.90 (s, 3H), 4.81 (t, J = 10.10 Hz, 1H), 5.17 (d, J = 10.54 Hz, 1H), 5.32 (dd, J = 15 .06, 9.66 Hz, 1H), 5.52 (dd, J = 15.00, 9.85 Hz, 1H), 6.34-6.49 (m, 4H), 7.64-7.68 (m, 1H), 7.68-7.73 (m, 1H) |
| 112 | 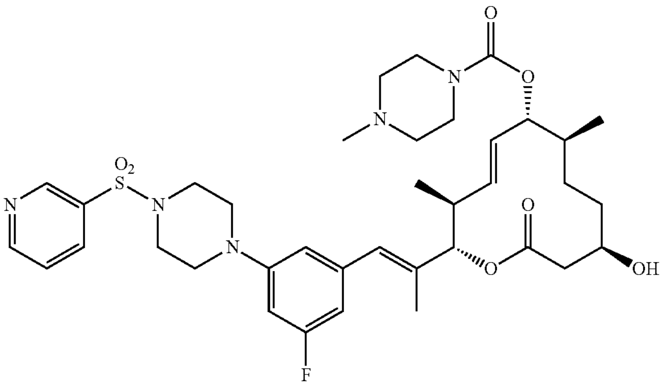 [(2S,3S,4E,6R,7S,10R)-2-[(E)-1-[3-fluoro-5-(4-pyridin-3-ylsulfonylpiperazin-1-yl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 737.3 $[M + H]^+$. $^1H$ NMR (400 MHz, $CDCl_3$) δ 0.95-1.07 (m, 6H), 1.42-1.56 (m, 1H), 1.74-1.88 (m, 5H), 1.88-1.99 (m, 2H), 2.32-2.38 (m, 3H), 2.38-2.49 (m, 4H), 2.49-2.70 (m, 4H), 3.26 (br dd, J = 17.07, 5.52 Hz, 8H), 3.46-3.63 (m, 4H), 3.70-3.86 (m, 1H), 4.90 (t, J = 10.04 Hz, 1H), 5.25 (d, J = 10.67 Hz, 1H), 5.41 (dd, J = 14.93, 9.66 Hz, 1H), 5.60 (dd, J = 14.93, 9.91 Hz, 1H), 6.43-6.57 (m, 4H), 7.54 (ddd, J = 8.00, 4.86, 0.69 Hz, 1H), 8.10 (dt, J = 8.03, 2.01 Hz, 1H), 8.88 (dd, J = 4.83, 1.44 Hz, 1H), 9.03-9.06 (m, 1H) |

TABLE 5-continued

| Characterization of Compounds 86-166 and 264 | | |
|---|---|---|
| Ex. | Structure and IUPAC Chemical Name | Characterization |
| 113 | 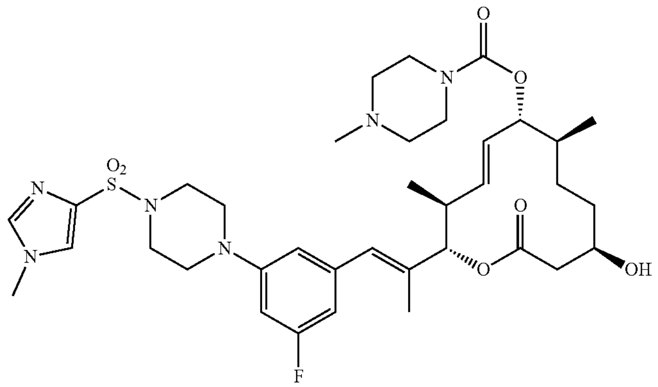 [(2S,3S,4E,6R,7S,10R)-2-[(E)-1-[3-fluoro-5-[4-(1-methylimidazol-4-yl)sulfonylpiperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 757.3 $[M + H]^+$. $^1H$ NMR (400 MHz, $CDCl_3$) δ 1.01 (dd, J = 11.54, 6.78 Hz, 6H), 1.44-1.58 (m, 1H), 1.74-1.90 (m, 4H), 1.90-2.02 (m, 3H), 2.33-2.39 (m, 3H), 2.39-2.50 (m, 4H), 2.52-2.70 (m, 4H), 3.25-3.32 (m, 4H), 3.32-3.41 (m, 4H), 3.47-3.63 (m, 4H), 3.70-3.78 (m, 1H), 3.78-3.82 (m, 3H), 4.90 (t, J = 10.10 Hz, 1H), 5.26 (d, J = 10.67 Hz, 1H), 5.41 (dd, J = 15.06, 9.66 Hz, 1H), 5.61 (dd, J = 14.93, 9.91 Hz, 1H), 6.45-6.56 (m, 4H), 7.46-7.50 (m, 1H), 7.50-7.53 (m, 1H) |
| 114 | 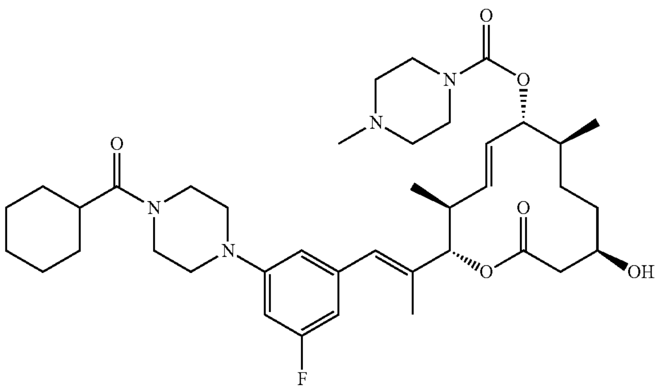 [(2S,3S,4E,6R,7S,10R)-2-[(E)-1-[3-[4-(cyclohexanecarbonyl) piperazin-1-yl)-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 697.3 $[M + H]^+$. $^1H$ NMR (400 MHz, $CDCl_3$) δ 1.02 (dd, J = 8.41, 6.90 Hz, 6H), 1.19-1.37 (m, 4H), 1.44-1.68 (m, 4H), 1.68-1.87 (m, 6H), 1.89 (d, J = 1.00 Hz, 3H), 1.91-2.00 (m, 2H), 2.32-2.41 (m, 4H), 2.41-2.68 (m, 6H), 3.19 (br s, 4H), 3.55 (br s, 4H), 3.61-3.70 (m, 2H), 3.75 (br d, J = 17.19 Hz, 4H), 4.90 (t, J = 10.10 Hz, 1H), 5.27 (d, J = 10.67 Hz, 1H), 5.42 (dd, J = 14.93, 9.66 Hz, 1H), 5.61 (dd, J = 15.06, 9.91 Hz, 1H), 6.49-6.57 (m, 4H) |
| 115 | 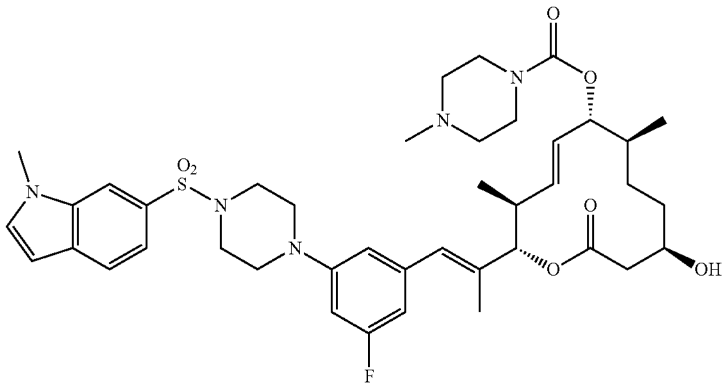 [(2S,3S,4E,6R,7S,10R)-2-[(E)-1-[3-fluoro-5-[4-(1-methylindol-6-yl) sulfonylpiperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 780.3 $[M + H]^+$. $^1H$ NMR (400 MHz, $CDCl_3$) δ 1.00 (dd, J = 17.82, 6.78 Hz, 6H), 1.77-1.87 (m, 4H), 1.87-2.00 (m, 2H), 2.35-2.38 (m, 3H), 2.38-2.50 (m, 5H), 2.50-2.69 (m, 4H), 3.13-3.21 (m, 4H), 3.21-3.30 (m, 4H), 3.41-3.67 (m, 5H), 3.70-3.79 (m, 1H), 3.88 (s, 3H), 4.89 (t, J = 10.10 Hz, 1H), 5.24 (d, J = 10.67 Hz, 1H), 5.36-5.48 (m, 1H), 5.60 (dd, J = 15.00, 9.85 Hz, 1H), 6.39-6.52 (m, 4H), 6.66 (dd, J = 3.20, 0.69 Hz, 1H), 7.22 (d, J = 3.14 Hz, 1H), 7.45 (d, J = 8.66 Hz, 1H), 7.64 (dd, J = 8.66, 1.76 Hz, 1H), 8.14 (d, J = 1.38 Hz, 1H) |

TABLE 5-continued

| Characterization of Compounds 86-166 and 264 | | |
|---|---|---|
| Ex. | Structure and IUPAC Chemical Name | Characterization |
| 116 | 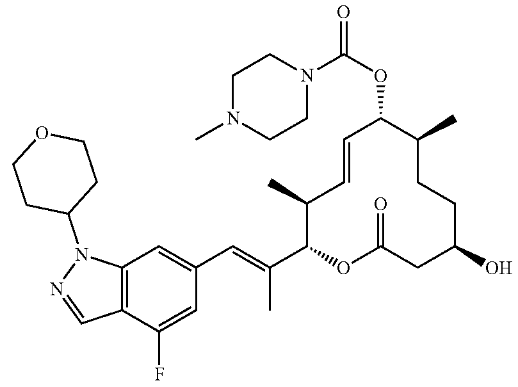 [(2S,3S,4E,6R,7S,10R)-2-[(E)-1-[4-fluoro-1-(oxan-4-yl)indazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 627.3 [M + H]$^+$. $^1$H NMR (400 MHz, $CDCl_3$) δ 0.89-0.98 (m, 6H), 1.10-1.25 (m, 2H), 1.42 (br d, J = 9.41 Hz, 1H), 1.68-1.94 (m, 7H), 2.17-2.41 (m, 9H), 2.44-2.61 (m, 3H), 3.32-3.47 (m, 4H), 3.47-3.59 (m, 3H), 3.66 (br d, J = 2.89 Hz, 1H), 4.09 (br s, 2H), 4.47-4.56 (m, 1H), 4.82 (t, J = 10.04 Hz, 1H), 5.22 (d, J = 10.54 Hz, 1H), 5.36 (br s, 1H), 5.54 (dd, J = 14.93, 9.91 Hz, 1H), 6.60-6.70 (m, 2H), 7.00 (s, 1H), 7.96 (s, 1H) |
| 117 | 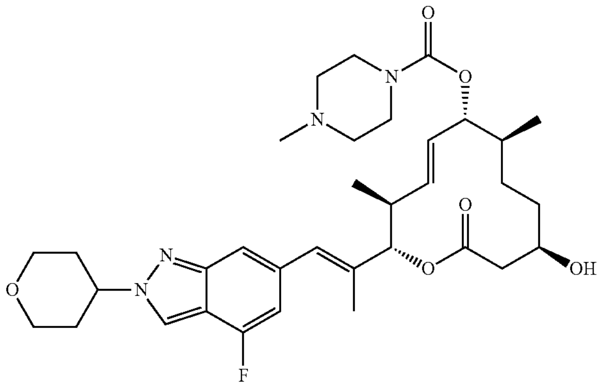 [(2S,3S,4E,6R,7S,10R)-2-[(E)-1-[4-fluoro-2-(oxan-4-yl)indazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 627.3 [M + H]$^+$. $^1$H NMR (400 MHz, $CDCl_3$) δ 0.93 (dd, J = 6.78, J = 6.78, 1.88 Hz, 6H), 1.18 (br d, J = 8.91 Hz, 2H), 1.32-1.58 (m, 2H), 1.58-1.80 (m, 2H), 1.85 (d, J = 1.13 Hz, 3H), 2.10-2.22 (m, 4H), 2.24 (s, 3H), 2.30 (br s, 4H), 2.42-2.61 (m, 4H), 3.33-3.46 (m, 4H), 3.46-3.58 (m, 3H), 3.65 (br d, J = 2.26 Hz, 1H), 4.10 (dt, J = 11 .67, 3.07 Hz, 2H), 4.51-4.61 (m, 1H), 4.82 (t, J = 10.10 Hz, 1H), 5.23 (d, J = 10.54 Hz, 1H), 5.32 (dd, J = 15.00, 9.72 Hz, 1H), 5.53 (dd, J = 15.00, 9.98 Hz, 1H), 6.51-6.58 (m, 2H), 7.31 (s, 1H), 7.93 (s, 1H) |
| 118 | 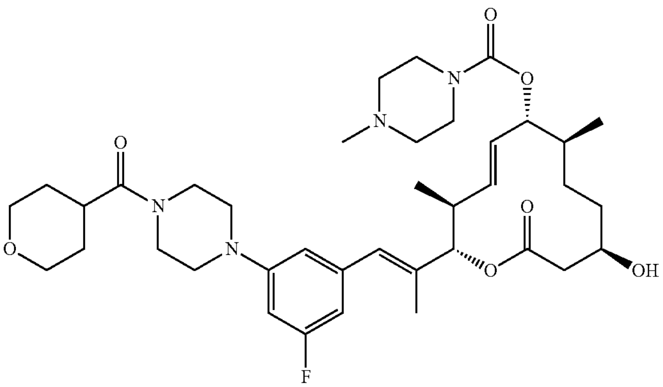 [(2S,3S,4E,6R,7S,10R)-2-[(E)-1-[3-fluoro-5-[4-(oxane-4-carbonyl) piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 699.3 [M + H]$^+$. $^1$H NMR (400 MHz, $CDCl_3$) δ 1.01 (dd, J = 9.35, 6.84 Hz, 6H), 1.47-1.56 (m, 1H), 1.60-1.72 (m, 2H), 1.73-1.87 (m, 2H), 1.89 (s, 3H), 1.90-2.03 (m, 2H), 2.32 (s, 3H), 2.41 (br s, 4H), 2.52-2.69 (m, 3H), 2.79 (tt, J = 11.26, 3.80 Hz, 2H), 3.20 (br s, 4H), 3.39-3.60 (m, 7H), 3.63-3.85 (m, 6H), 4.01-4.10 (m, 2H), 4.90 (t, J = 10.10 Hz, 1H), 5.27 (d, J = 10.54 Hz, 1H), 5.42 (dd, J = 15.06, 9.66 Hz, 1H), 5.61 (dd, J = 14.93, 9.91 Hz, 1H), 6.49-6.57 (m, 4H) |

TABLE 5-continued

Characterization of Compounds 86-166 and 264

| Ex. | Structure and IUPAC Chemical Name | Characterization |
|---|---|---|
| 119 | 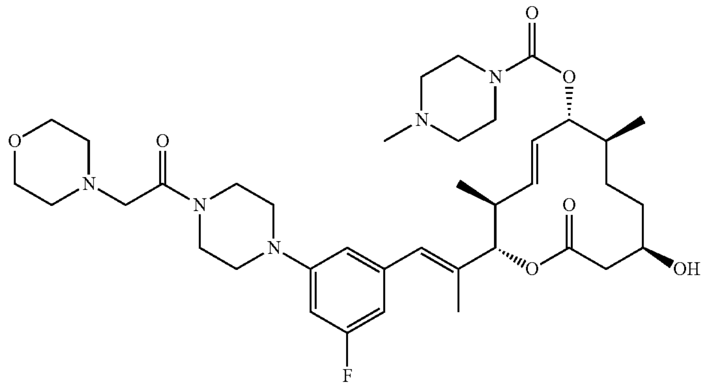 [(2S,3S,4E,6R,7S,10R)-2-[(E)-1-[3-fluoro-5-[4-(2-morpholin-4-ylacetyl) piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 714.3 [M + H]+. $^{1}$H NMR (400 MHz, $CDCl_3$) δ 0.93 (dd, J = 8.53, 6.90 Hz, 6H), 1.48-1.77 (m, 5H), 1.75-1.88 (m, 6H), 1.83-1.90 (m, 1H), 2.21-2.29 (m, 4H), 2.33 (hr s, 4H), 2.39-2.59 (m, 6H), 3.05-3.22 (m, 5H), 3.31-3.51 (m, 5H), 3.51-3.72 (m, 6H), 4.81 (t, J = 10.04 Hz, 1H), 5.18 (d, J = 10.67 Hz, 1H), 5.29-5.39 (m, 1H), 5.47-5.58 (m, 1H), 6.39-6.51 (m, 4H) |
| 120 | 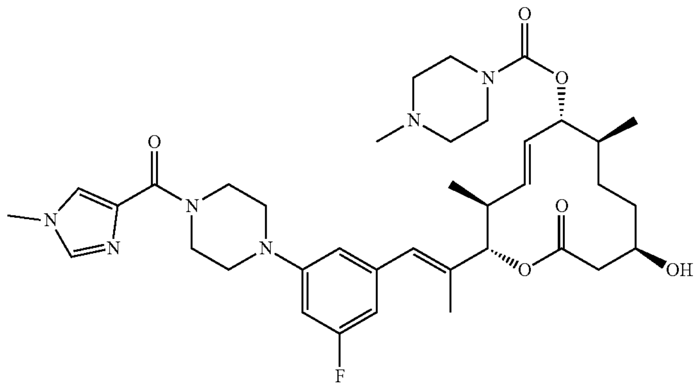 [(2S,3S,4E,6R,7S,10R)-2-[(E)-1-[3-fluoro-5-[4-(1-methylimidazole-4-carbonyl) piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 695.3 [M + H]+. $^{1}$H NMR (400 MHz, $CDCl_3$) δ 0.93 (dd, J = 8.78, 6.90 Hz, 6H), 1.37-1.48 (m, 2H), 1.48-1.77 (m, 3H), 1.77-1.82 (m, 3H), 1.82-1.92 (m, 1H), 2.20-2.27 (m, 4H), 2.31 (hr s, 4H), 2.42-2.62 (m, 3H), 3.09-3.27 (m, 5H), 3.42 (br s, 5H), 3.56-3.70 (m, 5H), 4.81 (t, J = 10.10 Hz, 1H), 5.19 (d, J = 10.67 Hz, 1H), 5.33 (dd, J = 15.06, 9.66 Hz, 1H), 5.52 (dd, J = 14.93, 9.91 Hz, 1H), 6.41-6.49 (m, 4H), 7.32 (d, J = 1.25 Hz, 1H), 7.49 (d, J = 1.38 Hz, 1H) |
| 121 | 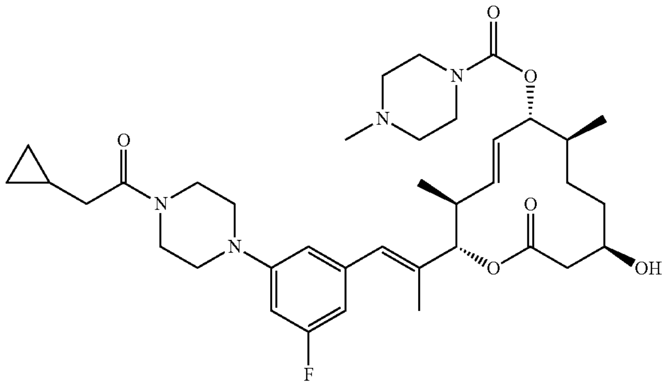 [(2S,3S,4E,6R,7S,10R)-2-[(E)-1-[3-[4-(2-cyclopropylacetyl) piperazin-1-yl]-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 669.3 [M + H]+. $^{1}$H NMR (400 MHz, $CDCl_3$) δ −0.04-0.02 (m, 2H), 0.35-0.41 (m, 2H), 0.72-0.90 (m, 8H), 1.20-1.41 (m, 1H), 1.54-1.65 (m, 2H), 1.65-1.68 (m, 3H), 1.68-1.78 (m, 2H), 2.06-2.10 (m, 4H), 2.13-2.21 (m, 4H), 2.24-2.46 (m, 3H), 2.97 (br s, 4H), 3.15-3.34 (m, 4H), 3.34-3.46 (m, 3H), 3.48-3.61 (m, 3H), 4.68 (t, J = 10.10 Hz, 1H), 5.00-5.10 (m, 1H), 5.19 (dd, J = 14.93, 9.66 Hz, 1H), 5.39 (dd, J = 15.06, 9.91 Hz, 1H), 6.26-6.34 (m, 4H) |

TABLE 5-continued

| Characterization of Compounds 86-166 and 264 | | |
|---|---|---|
| Ex. | Structure and IUPAC Chemical Name | Characterization |
| 122 | 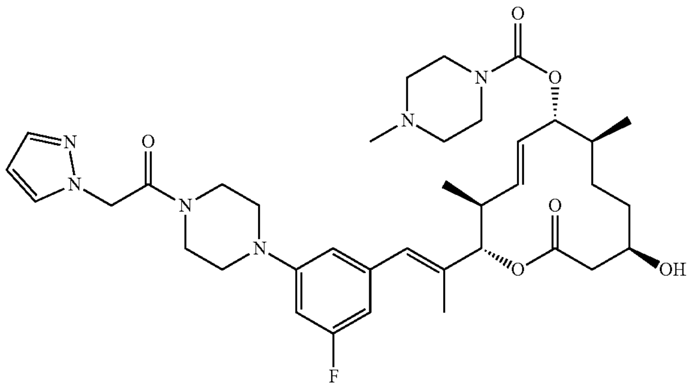 [(2S,3S,4E,6R,7S,10R)-2-[(E)-1-[3-fluoro-5-[4-(2-pyrazol-1-ylacetyl)) piperazin-1-yl]phenyl]prop-1-en-2-yl]- 10-hydroxy-3,7-dimethyl-12-oxo-1- oxacyclododec-4-en-6-yl] 4-methylpiperazine-1-carboxylate | LCMS (ESI, m/z), 695.3 $[M + H]^+$. $^1H$ NMR (400 MHz, $CDCl_3$) δ 0.89-0.93 (m, 3H), 0.94 (br d, J = 6.90 Hz, 3H), 1.33-1.54 (m, 1H), 1.63-1.78 (m, 3H), 1.7 (s, 3H), 1.80-1.91 (m, 2H), 2.20-2.26 (m, 5H), 2.29 (br s, 3H), 2.39-2.59 (m, 3H), 3.00-3.13 (m, 5H), 3.42 (br s, 4H), 3.61-3.73 (m, 5H), 4.81 (t, J = 10.04 Hz, 1H), 4.98 (s, 2H), 5.15-5.23 (m, 1H), 5.33 (dd, J = 15.06, 9.66 Hz, 1H), 5.52 (dd, J = 15.00, 9.85 Hz, 1H), 6.26 (t, J = 2.13 Hz,1H), 6.37-6.48 (m, 4H), 7.47 (d, J = 2.26 Hz, 2H) |
| 123 | 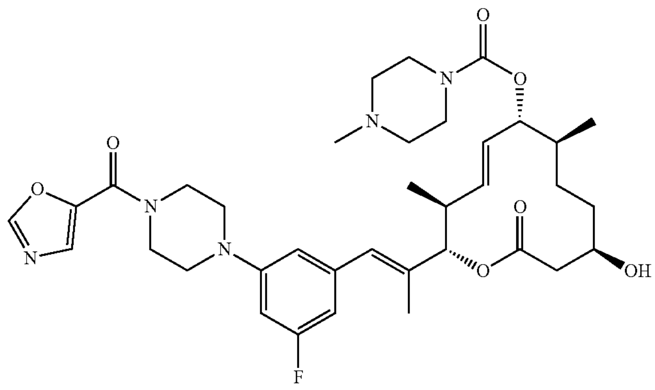 [(2S,3S,4E,6R,7S,10R)-2-[(E)-1-[3-fluoro-5-[4-(1,3-oxazole-5-carbonyl) piperazin-1-yl]phenyl]prop-1-en-2-yl]- 10-hydroxy-3,7-dimethyl-12-oxo-1- oxacyclododec-4-en-6-yl] 4-methylpiperazine-1-carboxylate | LCMS (ESI, m/z), 682.3 $[M + H]^+$. $^1H$ NMR (400 MHz, $CDCl_3$) δ 0.93 (dd, J = 8.91, 6.78 Hz, 6H), 1.38-1.48 (m, 2H), 1.68-1.78 (m, 2H), 1.78-1.83 (m, 3H), 1.83-1.91 (m, 1H), 2.20-2.24 (m, 3H), 2.24-2.35 (m, 4H), 2.44-2.59 (m, 3H), 3.16-3.24 (m, 4H), 3.24-3.34 (m, 1H), 3.34-3.52 (m, 4H), 3.62-3.71 (m, 1H), 3.81-3.92 (m, 4H), 4.81 (t, J = 10.10 Hz, 1H), 5.19 (d, J = 10.54 Hz, 1H), 5.33 (dd, J = 15.00 , 9.60 Hz, 1H), 5.52 (dd, J = 14.93, 9.91 Hz, 1H), 6.41-6.50 (m, 4H), 7.58 (s, 1H), 7.90 (s, 1H) |
| 124 | 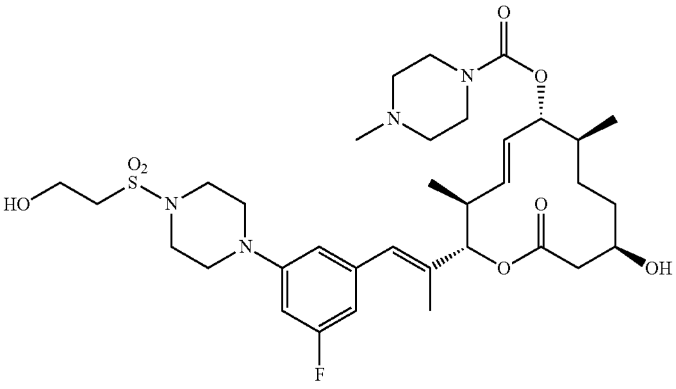 [(2S,3S,4E,6R,7S,10R)-2-[(E)-1-[3-fluoro-5-[4-(2-hydroxyethylsulfonyl) piperazin-1-yl]phenyl]prop-1-en-2-yl]- 10-hydroxy-3,7-dimethyl-12-oxo-1- oxacyclododec-4-en-6-yl] 4-methylpiperazine-1-carboxylate | LCMS(ESI, m/z), 682.3 $[M + H]^+$. $^1H$ NMR (400 MHz, $CDCl_3$) δ 0.97-1.05 (m, 6H), 1.26-1.29 (m, 1H), 1.45-1.57 (m, 1H), 1.77-1.86 (m, 1H), 1.89 (s, 3H), 1.91-2.01 (m, 1H), 2.29-2.34 (m, 3H), 2.34-2.46 (m, 4H), 2.51-2.72 (m, 3H), 3.18-3.26 (m, 2H), 3.26-3.34 (m, 4H), 3.42-3.56 (m, 8H), 3.71-3.79 (m, 1H), 4.08-4.17 (m, 3H), 4.90 (t, J = 10.04 Hz, 1H), 5.27 (d, J = 10.67 Hz, 1H), 5.42 (dd, J = 14.93, 9.66 Hz, 1H), 5.61 (dd, J = 15.00, 9.85 Hz, 1H), 6.49-6.59 (m, 4H) |

TABLE 5-continued

| Characterization of Compounds 86-166 and 264 | | |
|---|---|---|
| Ex. | Structure and IUPAC Chemical Name | Characterization |
| 125 | 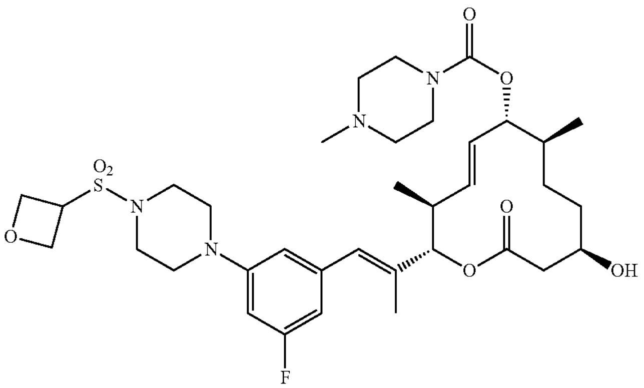 [(2S,3S,4E,6R,7S,10R)-2-[(E)-1-[3-fluoro-5-[4-(oxetan-3-ylsulfonyl) piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 707.3 $[M + H]^+$. $^1H$ NMR (400 MHz, $CDCl_3$) δ 0.89-0.98 (m, 6H), 1.12-1.25 (m, 2H), 1.37-1.48 (m, 1H), 1.69-1.77 (m, 1H), 1.79 (s, 3H), 1.81-1.91 (m, 1H), 2.20-2.25 (m, 3H), 2.28 (br s, 4H), 2.39-2.59 (m, 3H), 3.10-3.23 (m, 4H), 3.23-3.32 (m, 1H), 3.33-3.47 (m, 8H), 3.65 (q, J = 6.99 Hz, 1H), 4.38 (tt, J = 8.14, 6.48 Hz, 1H), 4.77-4.85 (m, 3H), 4.86-4.94 (m, 2H), 5.18 (d, J = 10.54 Hz, 1H), 5.33 (dd, J = 14.93, 9.66 Hz, 1H), 5.52 (dd, J = 14.93, 9.91 Hz, 1H), 6.39-6.50 (m, 4H) |
| 126 | 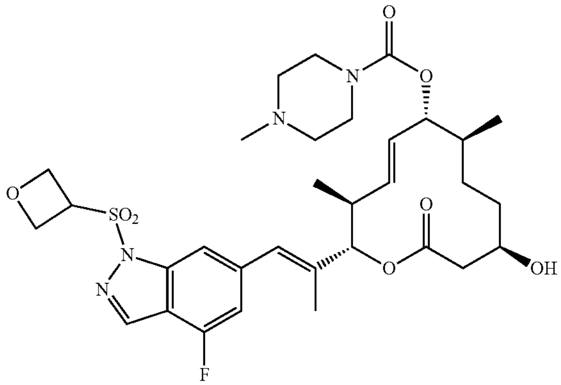 [(2S,3S,4E,6R,7S,10R)-2-[(E)-1-[4-fluoro-1-(oxetan-3-ylsulfonyl)indazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 663.3 $[M + H]^+$. $^1H$ NMR (400 MHz, $CDCl_3$) δ 0.94 (dd, J = 6 .7 8, 2.89 Hz, 6H), 1.09-1.26 (m, 2H), 1.38-1.49 (m, 2H), 1.67-1.78 (m, 2H), 1.85 (d, J = 1.13 Hz, 5H), 2.42-2.55 (m, 5H), 2.55-2.78 (m, 4H), 3.57-3.73 (m, 6H), 4.77-4.90 (m, 4H), 5.18-5.28 (m, 1H), 5.34 (dd, J = 15.00, 9.72 Hz, 1H), 5.55 (dd, J = 15.00, 9.98 Hz, 1H), 6.59 (s, 1H), 6.69 (d, J = 10.92 Hz, 1H), 7.10 (s, 1H), 8.02-8.06 (m, 1H) |
| 127 | 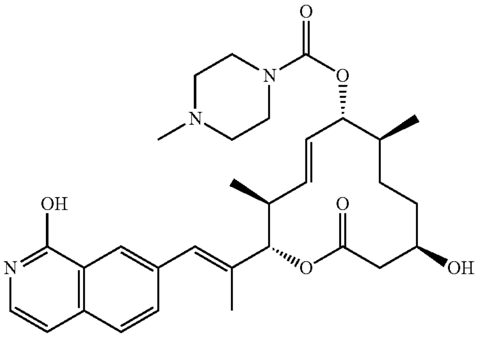 [(2S,3S,4E,6R,7S,10R)-10-hydroxy-2-[(E)-1-(1-hydroxyisoquinolin-7-yl)prop-1-en-2-yl]-3,7-dimethyl-12-oxo-1-oxacyclododec-4-en-6-yl] 4-methylpiperazine-1-carboxylate | LCMS (ESI, m/z), 552.3 $[M + H]^+$. $^1H$ NMR (400 MHz, $CDCl_3$) δ 0.86-1.03 (m, 6H), 1.38-1.49 (m, 1H), 1.68-1.80 (m, 2H), 1.81-1.93 (m, 5H), 2.18-2.27 (m, 3H), 2.30 (hr s, 3H), 2.41-2.62 (m, 4H), 3.32-3.49 (m, 4H), 3.55-3.72 (m, 2H), 4.83 (t, J = 10.10 Hz, 1H), 5.25 (d, J = 10.67 Hz, 1H), 5.30-5.38 (m, 1H), 5.55 (dd, J = 15.00, 9.85 Hz, 1H), 6.46 (d, J = 7.15 Hz, 1H), 6.61 (s, 1H), 7.01 (br s, 1H), 7.42-7.53 (m, 2H), 8.26 (s, 1H), 9.91 (br s, 1H) |

TABLE 5-continued

| Characterization of Compounds 86-166 and 264 | | |
|---|---|---|
| Ex. | Structure and IUPAC Chemical Name | Characterization |
| 128 | 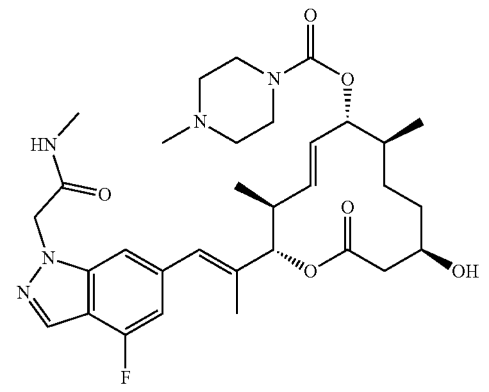 [(2S,3S,4E,6R,7S,10R)-2-[(E)-1-[4-fluoro-1-[2-(methylamino)-2-oxoethyl]indazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 614.3 $[M + H]^+$. $^1H$ NMR (400 MHz, $CDCl_3$) δ 0.94 (d, J = 6.78 Hz, 6H), 1.15-1.24 (m, 1H), 1.34-1.56 (m, 1H), 1.66-1.77 (m, 1H), 1.89 (s, 3H), 2.20-2.26 (m, 3H), 2.26-2.40 (m, 3H), 2.43-2.62 (m, 2H), 2.69 (d, J = 4.77 Hz, 3H), 3.42 (hr s, 3H), 3.65 (br s, 1H), 4.81 (t, J = 10.04 Hz, 1H), 4.96 (d, J = 9.66 Hz, 3H), 5.21 (d, J = 10.54 Hz, 1H), 5.34 (dd, J = 15.06, 9.66 Hz, 1H), 5.53 (dd, J = 15.00, 9.85 Hz, 1H), 5.76 (br d, J = 4.64 Hz, 2H), 6.58 (s, 1H), 6.68-6.75 (m, 1H), 6.75-6.84 (m, 1H), 6.97 (s, 1H), 7.12 (d, J = 8.41 Hz, 1H), 7.30 (td, J = 8.06, 4.96 Hz, 1H), 8.03-8.08 (m, 1H), 8.08-8.15 (m, 1H) |
| 129 | 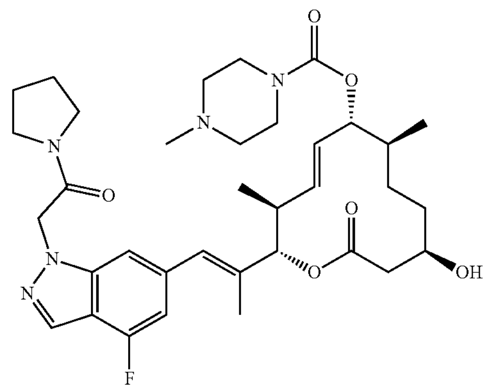 [(2S,3S,4E,6R,7S,10R)-2-[(E)-1-[4-fluoro-1-(2-oxo-2-pyrrolidin-1-ylethyl)indazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 654.3 $[M + H]^+$. $^1H$ NMR (400 MHz, $CDCl_3$) δ 0.93 (d, J = 6.78 Hz, 6H), 1.08-1.24 (m, 2H), 1.42 (ddd, J = 13.71, 9.82, 3.95 Hz, 1H), 1.68-1.82 (m, 4H), 1.82-1.85 (m, 2H), 1.89 (s, 3H), 2.19-2.28 (m, 3H), 2.32 (br s, 4H), 2.39-2.61 (m, 4H), 3.42 (br t, J = 6.90 Hz, 9H), 3.54-3.70 (m, 1H), 4.81 (t, J = 10.04 Hz, 1H), 5.05 (s, 2H), 5.20 (d, J = 10.67 Hz, 1H), 5.33 (dd, J = 15.06, 9.66 Hz, 1H), 5.52 (dd, J = 14.93, 9.91 Hz, 1H), 6.58 (s, 1H), 6.67 (d, J = 10.92 Hz, 1H), 7.03 (s, 1H), 7.97 (d, J = 0.75 Hz, 1H) |
| 130 | 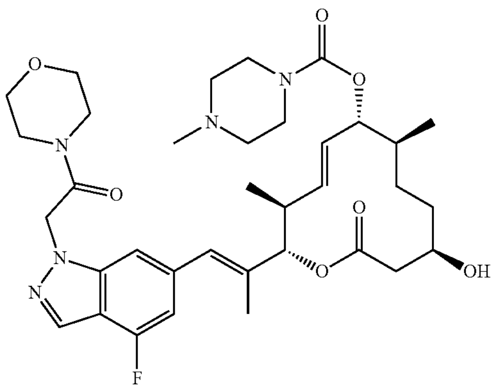 [(2S,3S,4E,6R,7S,10R)-2-[(E)-1-[4-fluoro-1-(2-morpholin-4-yl-2-oxoethyl)indazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 670.3 $[M + H]^+$. $^1H$ NMR (400 MHz, $CDCl_3$) δ 0.93 (d, J = 6 .78 Hz, 6H), 1.07-1.29 (m, 2H), 1.34-1.60 (m, 1H), 1.60-1.80 (m, 2H), 1.83 (d, J = 1.13 Hz, 3H), 2.20-2.28 (m, 4H), 2.32 (hr s, 3H), 2.38-2.63 (m, 3H), 3.31-3.45 (m, 4H), 3.45-3.57 (m, 9H), 3.60-3.71 (m, 1H), 4.81 (t, J = 10.10 Hz, 1H), 5.11 (s, 2H), 5.10-5.23 (m, 2H), 5.33 (dd, J = 15.00, 9.72 Hz, 1H), 5.53 (dd, J = 15.00, 9.85 Hz, 1H), 6.58 (s, 1H), 6.69 (d, J = 10.79 Hz, 1H), 7.05 (s, 1H), 7.96-8.02 (m, 1H) |

TABLE 5-continued

| Characterization of Compounds 86-166 and 264 | | |
|---|---|---|
| Ex. | Structure and IUPAC Chemical Name | Characterization |
| 131 | 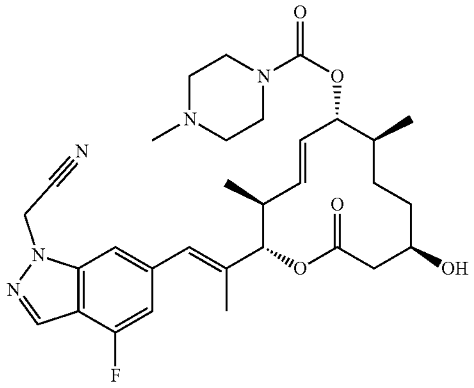 [(2S,3S,4E,6R,7S,10R)-2-[(E)-1-[1-(cyanomethyl)-4-fluoroindazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 582.3 [M + H]$^+$. $^1$H NMR (400 MHz, $CDCl_3$) δ 0.94 (t, J = 6.21 Hz, 6H), 1.19 (br d, J = 8.78 Hz, 2H), 1.34-1.59 (m, 2H), 1.59-1.81 (m, 1H), 1.85 (d, J = 1.13 Hz, 4H), 2.18-2.28 (m, 3H), 2.32 (hr s, 4H), 2.44-2.61 (m, 3H), 3.31-3.54 (m, 4H), 3.66 (hr d, J = 6.27 Hz, 1H), 4.82 (t, J = 10.04 Hz, 1H), 5.20-5.25 (m, 3H), 5.31-5.39 (m, 1H), 5.53 (dd, J = 14.93, 9.91 Hz, 1H), 6.62 (s, 1H), 6.76 (d, J = 10.67 Hz, 1H), 7.04 (s, 1H), 8.03 (d, J = 0.88 Hz, 1H) |
| 132 | 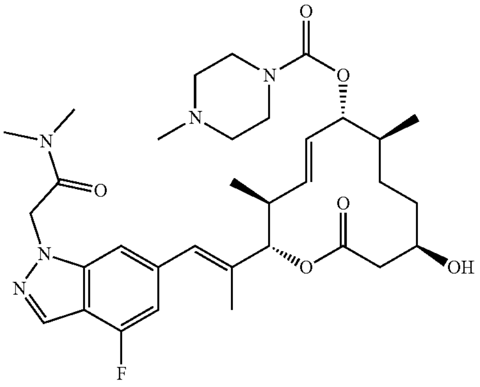 [(2S,3S,4E,6R,7S,10R)-2-[(E)-1-[1-[2-(dimethylamino)-2-oxoethyl]-4-fluoroindazol-6-yl] prop-1-en-2-yl]-10-hydroxy-3,7-dimethyl-12-oxo-1-oxacyclododec-4-en-6-yl] 4-methylpiperazine-1-carboxylate | LCMS (ESI, m/z), 628.3 [M + H]$^+$. $^1$H NMR (400 MHz, $CDCl_3$) δ 0.93 (dd, J = 6.78, 0.88 Hz, 6H), 1.07-1.28 (m, 1H), 1.42 (ddd, J = 13.71, 9.76, 3.76 Hz, 1H), 1.63-1.78 (m, 1H), 1.80-1.84 (m, 4H), 1.84-1.91 (m, 1H), 2.19-2.27 (m, 2H), 2.30 (hr s, 3H), 2.43-2.62 (m, 4H), 2.80-2.99 (m, 4H), 3.01-3.07 (m, 4H), 3.32-3.51 (m, 3H), 3.61-3.70 (m, 1H), 4.81 (t, J = 10.10 Hz, 1H), 5.12 (s, 2H), 5.16-5.24 (m, 1H), 5.33 (dd, J = 15.00, 9.72 Hz, 1H), 5.52 (dd, J = 15.06, 9.91 Hz, 1H), 6.58 (s, 1H), 6.65-6.74 (m, 2H), 7.00 (s, 1H), 7.96-8.02 (m, 1H) |
| 133 | 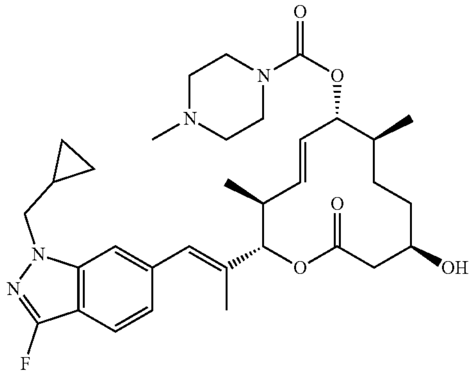 [(2S,3S,4E,6R,7S,10R)-2-[(E)-1-[1-(cyclopropylmethyl)-3-fluoroindazol-6-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 597.3 [M + H]$^+$. $^1$H NMR (400 MHz, $CDCl_3$) δ 0.32-0.48 (m, 4H), 0.93 (dd, J = 6.78, 0.88 Hz, 6H), 1.11-1.34 (m, 2H), 1.12-1.24 (m, 1H), 1.37-1.65 (m, 2H), 1.65-1.80 (m, 4H), 1.86 (td, J = 6.68, 3.58 Hz, 3H), 2.23 (s, 3H), 2.31 (br s, 4H), 2.40-2.62 (m, 2H), 3.43 (br s, 3H), 3.55-3.70 (m, 1H), 4.27-4.37 (m, 2H), 4.82 (t, J = 10.10 Hz, 1H), 5.27-5.37 (m, 2H), 5.55 (dd, J = 14.93, 9.91 Hz, 1H), 6.58 (s, 1H), 6.87 (dd, J = 8.28, 5.77 Hz, 1H), 7.34 (d, J = 8.28 Hz, 1H), 7.88 (d, J = 2.38 Hz, 1H) |

TABLE 5-continued

| Ex. | Structure and IUPAC Chemical Name | Characterization |
|---|---|---|
| | Characterization of Compounds 86-166 and 264 | |
| 134 | 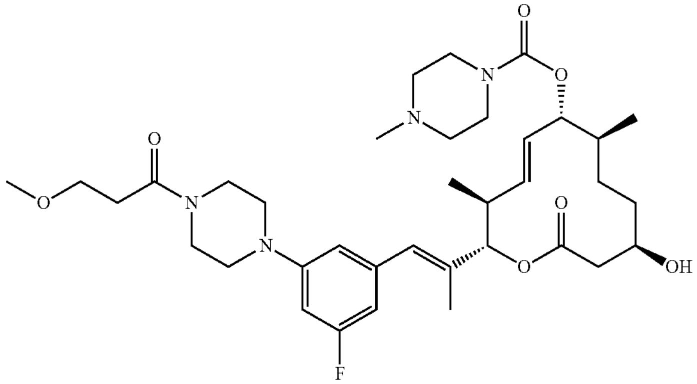 [(2S,3S,4E,6R,7R,10S)-2-[(E)-1-[3-fluoro-5-[4-(3-methoxypropanoyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 673.3 [M + H]+. $^{1}H$ NMR (400 MHz, $CDCl_3$) δ 0.88-0.92 (d, J = 6.90, 3H), 0.93 (br d, J = 6.90 Hz, 3H), 1.18 (br d, J = 8.41 Hz, 2H), 1.33-1.57 (m, 1H), 1.64-1.75 (m, 2H), 1.78 (s, 3H), 1.80-1.92 (m, 2H), 2.17-2.27 (m, 4H), 2.30 (br s, 4H), 2.43-2.59 (m, 5H), 3.03-3.27 (m, 5H), 3.29 (s, 3H), 3.35-3.51 (m, 4H), 3.53-3.60 (m, 2H), 3.62-3.68 (m, 3H), 3.68-3.76 (m, 2H), 4.80 (t, J = 10.10 Hz, 1H), 5.17 (d, J = 10.67 Hz, 1H), 5.32 (dd, J = 15.06, 9.66 Hz, 1H), 5.51 (dd, J = 15.06, 9.91 Hz, 1H), 6.38-6.47 (m, 4H) |
| 135 | 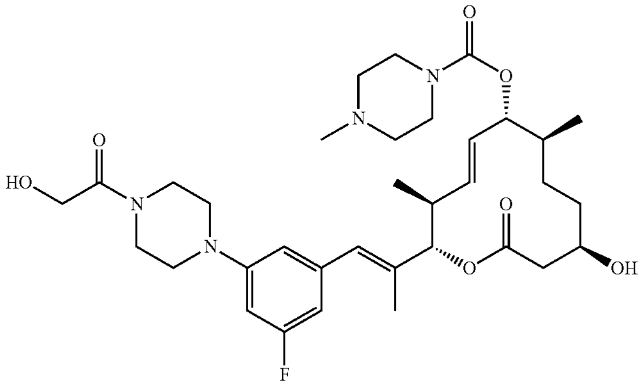 [(2S,3S,4E,6R,7S,10R)-2-[(E)-1-[3-fluoro-5-[4-(2-hydroxyacetyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 645.3 [M + H]+. $^{1}H$ NMR (400 MHz, $CDCl_3$) δ 0.87-0.92 (d, J = 6.78 Hz, 3H), 0.93 (d, J = 6.78 Hz, 3H), 1.10-1.24 (m, 2H), 1.34-1.48 (m, 1H), 1.67-1.77 (m, 1H), 1.79 (s, 3H), 1.80-1.92 (m, 1H), 2.26 (s, 3H), 2.35 (br s, 4H), 2.42-2.60 (m, 4H), 3.07-3.17 (m, 4H), 3.28-3.40 (m, 3H), 3.44 (br s, 4H), 3.55-3.69 (m, 1H), 3.69-3.78 (m, 2H), 4.13 (s, 2H), 4.80 (t, J = 10.04 Hz, 1H), 5.17 (d, J = 10.54 Hz, 1H), 5.32 (dd, J = 14.93, 9.66 Hz, 1H), 5.51 (dd, J = 15.06, 9.91 Hz, 1H), 6.39-6.50 (m, 4H) |
| 136 | 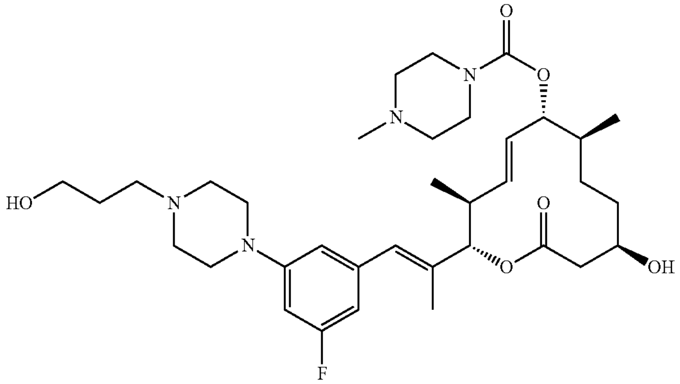 [(2S,3S,4E,6R,7S,10R)-2-[(E)-1-[3-fluoro-5-[4-(3-hydroxypropyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 645.3 [M + H]+. $^{1}H$ NMR (400 MHz, $CDCl_3$) δ 0.85-0.92 (d, J = 6.78 Hz, 3H), 0.93 (d, J = 6.78 Hz, 3H), 1.11-1.37 (m, 3H), 1.37-1.47 (m, 1H), 1.64-1.75 (m, 3H), 1.79 (s, 3H), 1.81-1.90 (m, 1H), 2.20-2.24 (m, 3H), 2.24-2.34 (m, 4H), 2.40-2.56 (m, 3H), 2.57-2.67 (m, 5H), 3.03-3.20 (m, 4H), 3.41 (br s, 5H), 3.60-3.69 (m, 1H), 3.61-3.77 (m, 3H), 4.80 (t, J = 9.98 Hz, 1H), 5.17 (d, J = 10.67 Hz, 1H), 5.32 (dd, J = 15.06, 9.66 Hz, 1H), 5.51 (dd, J = 15.00, 9.85 Hz, 1H), 6.37-6.45 (m, 4H) |

TABLE 5-continued

| Characterization of Compounds 86-166 and 264 | | |
|---|---|---|
| Ex. | Structure and IUPAC Chemical Name | Characterization |
| 137 | 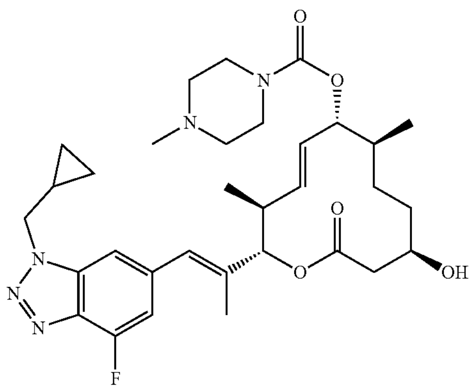 [(2S,3S,4E,6R,7S,10R)-2-[(E)-1-[3-(cyclopropylmethyl)-7-fluorobenzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 598.3 $[M + H]^+$. $^1H$ NMR (400 MHz, $CDCl_3$) δ 0.37-0.45 (m, 2H), 0.54-0.63 (m, 2H), 0.90-0.94 (m, 3H), 0.95 (br d, J = 4.02 Hz, 3H), 1.12-1.24 (m, 2H), 1.24-1.47 (m, 1H), 1.38-1.51 (m, 1H), 1.67-1.78 (m, 1H), 1.78-1.93 (m, 4H), 2.22-2.26 (m, 3H), 2.26-2.39 (m, 4H), 2.38-2.61 (m, 4H), 3.32-3.52 (m, 4H), 3.66 (hr d, J = 3.39 Hz, 1H), 4.42 (dd, J = 7.09, 1.32 Hz, 2H), 4.81 (t, J = 10.10 Hz, 1H), 5.23 (d, J = 10.67 Hz, 1H), 5.34 (dd, J = 14.93, 9.66 Hz, 1H), 5.53 (dd, J = 15.00, 9.85 Hz, 1H), 6.62 (s, 1H), 6.90 (d, J = 10.92 Hz, 1H), 7.11 (s, 1H) |
| 138 | 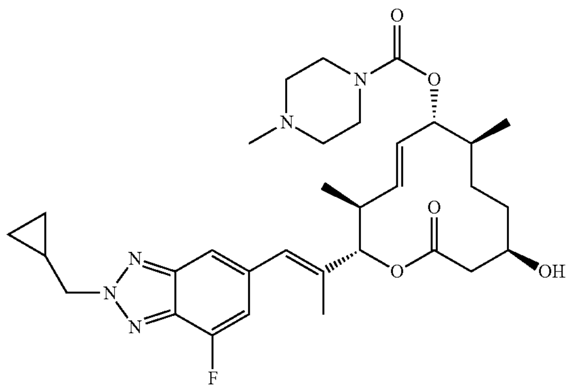 [(2S,3S,4E,6R,7S,10R)-2-[(E)-1-[2-(cyclopropylmethyl)-7-fluorobenzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS(ESI, m/z), 598.3 $[M + H]^+$. $^1H$ NMR (400 MHz, $CDCl_3$) δ 0.37-0.55 (m, 2H), 0.55-0.64 (m, 2H), 0.90-0.96 (m, 6H), 1.15-1.24 (m, 2H), 1.36-1.56 (m, 2H), 1.68-1.78 (m, 2H), 1.80-1.90 (m, 4H), 2.21-2.26 (m, 3H), 2.26-2.38 (m, 4H), 2.44-2.64 (m, 3H), 3.34-3.52 (m, 4H), 3.61-3.72 (m, 1H), 4.50 (d, J = 7.28 Hz, 2H), 4.82 (t, J = 10.04 Hz, 1H), 5.23 (d, J = 10.54 Hz, 1H), 5.33 (dd, J = 15.00, 9.72 Hz, 1H), 5.53 (dd, J = 14.93, 9.91 Hz, 1H), 6.57 (s, 1H), 6.88 (dd, J = 11.42, 0.88 Hz, 1H), 7.46 (s, 1H) |
| 139 | 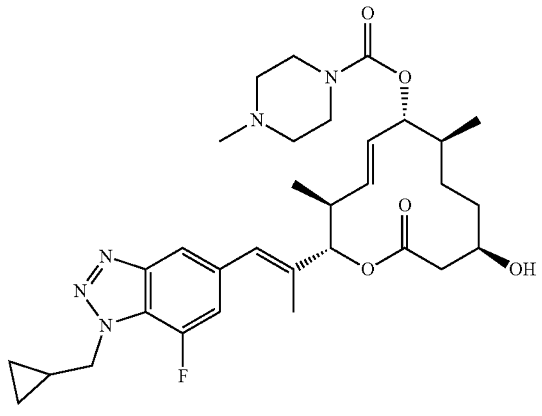 [(2S,3S,4E,6R,7S,10R)-2-[(E)-1-[1-(cyclopropylmethyl)-7-fluorobenzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 598.3 $[M + H]^+$. $^1H$ NMR (400 MHz, $CDCl_3$) δ 0.40-0.49 (m, 2H), 0.51-0.61 (m, 2H), 0.94 (d, J = 6.65 Hz, 6H), 1.09-1.35 (m, 2H), 1.35-1.49 (m, 2H), 1.67-1.80 (m, 2H), 1.80-1.91 (m, 4H), 2.22-2.26 (m, 3H), 2.27-2.38 (m, 4H), 2.44-2.63 (m, 3H), 3.35-3.53 (m, 4H), 3.61-3.72 (m, 1H), 4.53 (d, J = 7.28 Hz, 2H), 4.82 (t, J = 10.04 Hz, 1H), 5.23 (d, J = 10.67 Hz, 1H), 5.30-5.38 (m, 1H), 5.53 (dd, J = 15.00, 9.85 Hz, 1H), 6.58 (s, 1H), 6.98 (d, J = 11.67 Hz, 1H), 7.66 (s, 1H) |

TABLE 5-continued

Characterization of Compounds 86-166 and 264

| Ex. | Structure and IUPAC Chemical Name | Characterization |
|---|---|---|
| 140 | 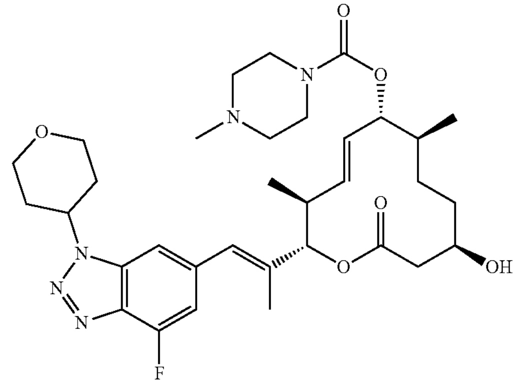 [(2S,3S,4E,6R,7S,10R)-2-[(E)-1-[7-fluoro-3-(oxan-4-yl) benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 628.3 [M + H]+. $^1$H NMR (400 MHz, $CDCl_3$) δ 0.89-0.98 (m, 6H), 1.13-1.26 (m, 2H), 1.38-1.49 (m, 1H), 1.66-1.79 (m, 2H), 1.79 (s, 3H), 1.96-2.22 (m, 3H), 2.22-2.26 (m, 3H), 2.26-2.35 (m, 4H), 2.36-2.63 (m, 5H), 3.33-3.50 (m, 4H), 3.57 (br t, J = 11.67 3.33-3.50 2H), 3.63-3.71 (m, 1H), 4.14 (br d, J = 11.54 Hz, 2H), 4.77-4.85 (m, 2H), 5.22 (d, J = 10.67 Hz, 1H), 5.31-5.39 (m, 1H), 5.53 (dd, J = 14.93, 9.91 Hz, 1H), 6.62 (s, 1H), 6.90 (d, J = 10.92 Hz, 1H), 7.11 (s, 1H) |
| 141 | 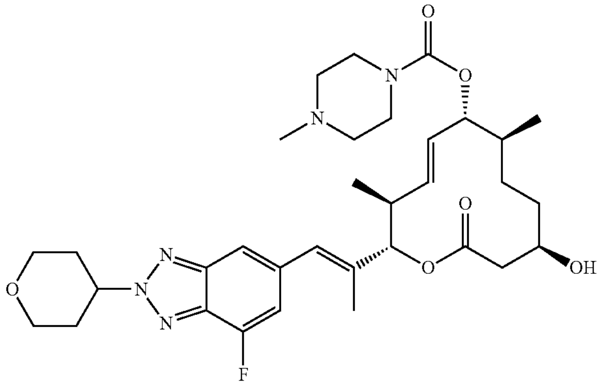 [(2S,3S,4E,6R,7S,10R)-2-[(E)-1-[7-fluoro-2-(oxan-4-yl) benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 628.3 [M + H]+. $^1$H NMR (400 MHz, $CDCl_3$) δ 0.94 (d, J = 6.78 Hz, 6H), 1.10-1.25 (m, 2H), 1.42 (ddd, J = 13.90, 9.94, 3.76 Hz, 1H), 1.67-1.78 (m, 1H), 1.79-1.91 (m, 4H), 2.17-2.25 (m, 5H), 2.25-2.43 (m, 5H), 2.45-2.62 (m, 3H), 3.33-3.50 (m, 4H), 3.50-3.61 (m, 2H), 3.61-3.72 (m, 1H), 4.05-4.12 (m, 2H), 4.82 (t, J = 10.10 Hz, 1H), 4.87-4.98 (m, 1H), 5.23 (d, J = 10.67 Hz, 1H), 5.33 (dd, J = 14.93, 9.66 Hz, 1H), 5.53 (dd, J = 14.93, 9.91 Hz, 1H), 6.56 (s, 1H), 6.88 (dd, J = 11.29, 0.88 Hz, 1H), 7.46 (s, 1H) |
| 142 | 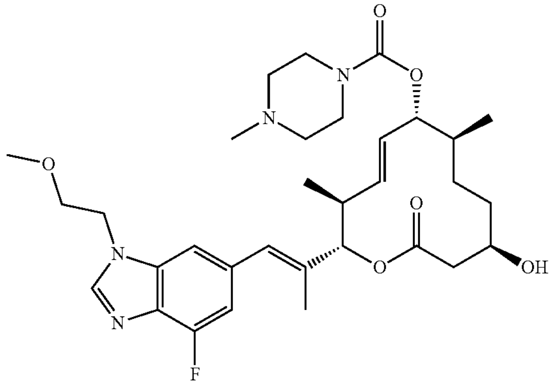 [(2S,3S,4E,6R,7S,10R)-2-[(E)-1-[7-fluoro-3-(2-methoxyethyl)benzimidazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 601.3 [M + H]+. $^1$H NMR (400 MHz, $CDCl_3$) δ 0.94 (dd, J = 6 .78, 1.51 Hz, 6H), 1.08-1.29 (m, 2H), 1.33-1.60 (m, 1H), 1.60-1.81 (m, 2H), 1.81-1.92 (m, 4H), 2.20-2.29 (m, 4H), 2.33 (br s, 4H), 2.44-2.62 (m, 3H), 3.24 (s, 3H), 3.34-3.54 (m, 3H), 3.63 (t, J = 5.08 Hz, 3H),4.22 (t, J = 5.02 Hz, 2H), 4.82 (t, J = 10.10 Hz, 1H), 5.22 (d, J = 10.67 Hz, 1H), 5.33 (dd, J = 14.93, 9.66 Hz, 1H), 5.54 (dd, J = 14.93, 9.91 Hz, 1H), 6.61 (s, 1H), 6.87 (d, J = 11.42 Hz, 1H), 6.99 (s, 1H), 7.86 (s, 1H) |

TABLE 5-continued

| Characterization of Compounds 86-166 and 264 | | |
|---|---|---|
| Ex. | Structure and IUPAC Chemical Name | Characterization |
| 143 | 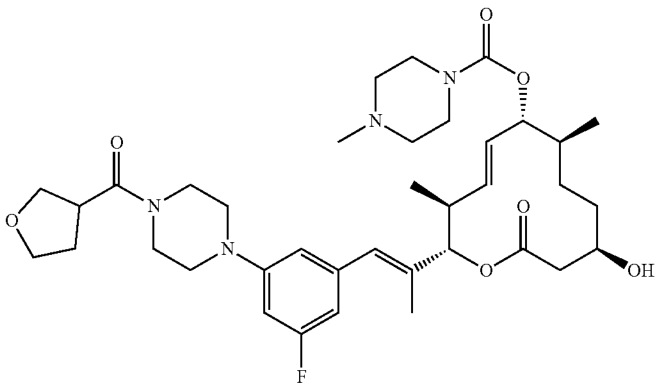 [(2S,3S,4E,6R,7S,10R)-2-[(E)-1-[3-fluoro-5-[4-(oxolane-3-carbonyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 685.7 [M + H]$^+$. $^1$H NMR (400 MHz, $CDCl_3$) δ ppm 0.92 (dd, J = 9.10, 6.84 Hz, 6H), 1.14-1.24 (m, 2H), 1.37-1.45 (m, 1H), 1.66-1.74 (m, 1H), 1.79 (d, J = 1.13 Hz, 3H), 1.82-1.90 (m, 2H), 1.97-2.08 (m, 2H), 2.14-2.21 (m, 1H), 2.23-2.27 (m, 1H), 2.26-2.35 (m, 3H), 2.42-2.60 (m, 3H), 3.05-3.14 (m, 4H), 3.14-3.24 (m, 1H), 3.35-3.49 (m, 4H), 3.55-3.62 (m, 2H), 3.62-3.67 (m, 1H), 3.67-3.74 (m, 2H), 3.75-3.86 (m, 3H), 3.92-4.00 (m, 1H), 4.76-4.86 (m, 1H), 5.13-5.22 (m, 1H), 5.26-5.37 (m, 1H), 5.44-5.56 (m, 1H), 6.37-6.48 (m, 4H) |
| 144 | 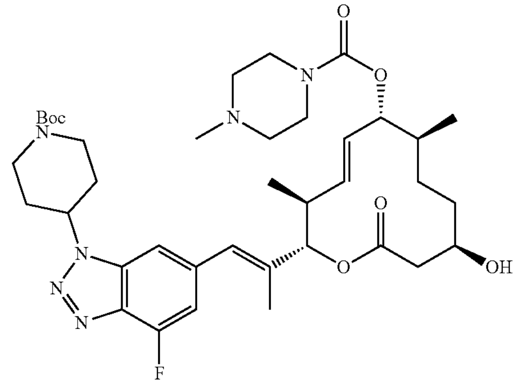 [(2S,3S,4E,6R,7S,10R)-2-[(E)-1-[7-fluoro-3-[1-[2-methylpropan-2-yl)oxocarbonyl]piperidin-4-yl]benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 727.8 [M + H]$^+$. $^1$H NMR (400 MHz, $CDCl_3$) δ ppm 0.92-0.98 (m, 6H), 1.14-1.21 (m, 2H), 1.42 (s, 10H), 1.69-1.77 (m, 1H), 1.83 (d, J = 1.25 Hz, 4H), 2.04-2.14 (m, 2H), 2.24 (s, 9H), 2.46-2.61 (m, 3H), 2.89-3.00 (m, 2H), 3.34-3.52 (m, 4H), 3.62-3.70 (m, 1H), 4.19-4.32 (m, 2H), 4.65-4.75 (m, 1H), 4.75-4.86 (m, 1H), 5.18-5.27 (m, 1H), 5.29-5.41 (m, 1H), 5.48-5.58 (m, 1H), 6.58-6.64 (m, 1H), 6.86-6.94 (m, 1H), 7.07 (s, 1H) |
| 145 | 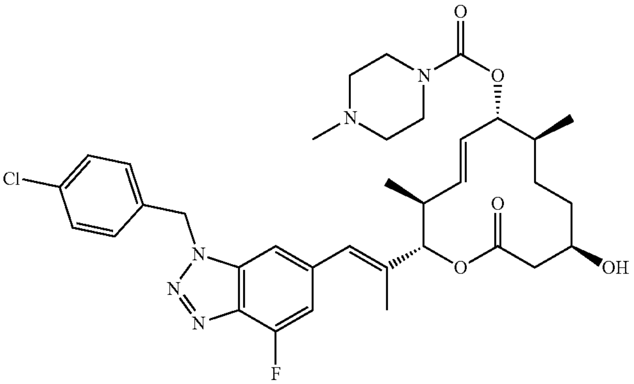 [(2S,3S,4E,6R,7S,10R)-2-[(E)-1-[3-[4-chlorophenyl)methyl]-7-fluorobenzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 668.6 [M + H]$^+$. $^1$H NMR (400 MHz, $CDCl_3$) δ ppm 0.92 (dd, J = 10.48, 6.84 Hz, 6H), 1.11-1.22 (m, 3H), 1.36-1.45 (m, 1H), 1.72-1.73 (m, 3H), 1.81-1.87 (m, 2H), 2.27 (s, 3H), 2.30-2.41 (m, 4H), 2.43-2.61 (m, 3H), 3.33-3.53 (m, 4H), 3.60-3.71 (m, 1H), 4.80 (t, J = 10.10 Hz, 1H), 5.18 (d, J = 10.67 Hz, 1H), 5.27-5.38 (m, 1H), 5.51 (dd, J = 15.00, 9.85 Hz, 1H), 5.71 (d, J = 1.00 Hz, 2H),6.49-6.57 (m, 1H), 6.83-6.92 (m, 2H), 7.13 (d, J = 8.53 Hz, 2H), 7.24-7.28 (m, 2H) |

TABLE 5-continued

| Characterization of Compounds 86-166 and 264 | | |
|---|---|---|
| Ex. | Structure and IUPAC Chemical Name | Characterization |
| 146 | 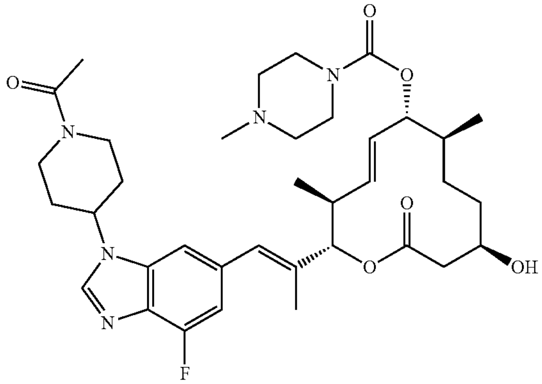 [(2S,3S,4E,6R,7S,10R)-2-[(E)-1-[3-(1-acetylpiperidin-4-yl)-7-fluorobenzimidazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 668.9 [M + H]+. $^1$H NMR (400 MHz, $CDCl_3$) δ (m, 3H), 0.95 (br d, J = 3.76 Hz, 3H), 1.19 (br d, J = 8.66 Hz, 2H), 1.37-1.51 (m, 1H), 1.67-1.79 (m, 2H), 1.80-2.01 (m, 5H), 2.08-2.12 (m, 1H), 2.08-2.27 (m, 6H), 2.20-2.22 (m, 1H), 2.22-2.27 (m, 1H), 2.32 (s, 3H), 2.40-2.60 (m, 3H), 2.68 (br t, J = 12.99 Hz, 1H), 3.08-3.31 (m, 2H), 3.31-3.54 (m, 4H), 3.62-3.71 (m, 1H), 3.98 (br d, J = 12.67 Hz, 1H), 4.27-4.35 (m, 1H), 4.78-4.88 (m, 2H), 5.22 (d, J = 10.67 Hz, 1H), 5.34 (dd, J = 14.93, 9.66 Hz, 1H), 5.53 (dd, J = 15.00, 9.85 Hz, 1H), 6.62 (s, 1H), 6.90 (d, J = 11.42 Hz, 1H), 6.97 (s, 1H), 7.85 (s, 1H). |
| 147 | 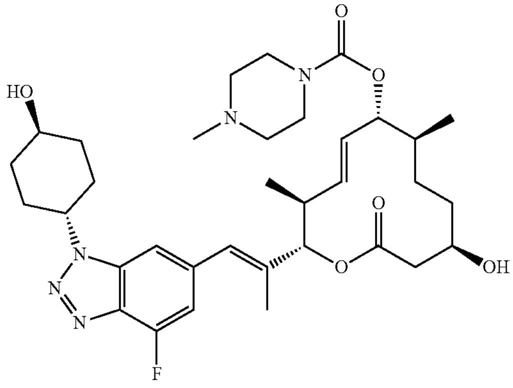 [(2S,3S,4E,6R,7S,10R)-2-[(E)-1-[7-fluoro-3-(4-hydroxycyclohexyl)benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 642.8 [M + H]+. $^1$H NMR (400 MHz, $CDCl_3$) δ 0.91-0.95 (m, 3H), 0.95 (d, J = 5.52 Hz, 3H), 1.10-1.26 (m, 2H), 1.36-1.63 (m, 3H), 1.66-1.80 (m, 1H), 1.80-1.89 (m, 4H), 2.11-2.27 (m, 9H), 2.30 (hr s, 4H), 2.43-2.62 (m, 4H), 3.30-3.54 (m, 4H), 3.54-3.71 (m, 1H), 3.77-3.86 (m, 1H), 4.48-4.57 (m, 1H), 4.81 (t, J = 10.04 Hz, 1H), 5.22 (d, J = 10.54 Hz, 1H), 5.31-5.40 (m, 1H), 5.53 (dd, J = 15.00, 9.85 Hz, 1H), 6.62 (s, 1H), 6.87-6.95 (m, 1H), 7.06-7.11 (m, 1H) |
| 148 | 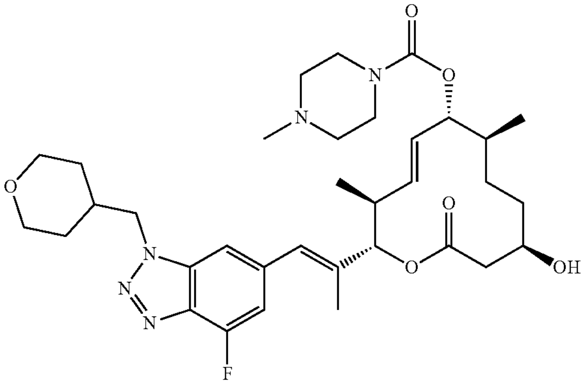 [(2S,3S,4E,6R,7S,10R)-2-[(E)-1-[7-fluoro-3-(oxan-4-ylmethyl)benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 641.6 [M + H]+. $^1$H NMR (400 MHz, $CDCl_3$) δ 0.91-0.94 (m, 3H), 0.95 (d, J = 4.89 Hz, 3H), 1.10-1.34 (m, 2H), 1.34-1.49 (m, 6H), 1.68-1.79 (m, 1H), 1.82-1.91 (m, 4H), 2.21-2.28 (m, 4H), 2.28-2.42 (m, 4H), 2.41-2.60 (m, 3H), 3.18-3.34 (m, 3H), 3.34-3.55 (m, 4H), 3.66 (hr s, 1H), 3.86-3.93 (m, 2H), 4.41 (d, J = 7.15 Hz, 2H), 4.81 (t, J = 10.10 Hz, 1H), 5.20-5.25 (m, 1H), 5.35 (dd, J = 14.93, 9.66 Hz, 1H), 5.53 (dd, J = 14.93, 9.91 Hz, 1H), 6.62 (s, 1H), 6.91 (d, J = 10.54 Hz, 1H), 7.04 (s, 1H) |

TABLE 5-continued

| Characterization of Compounds 86-166 and 264 | | |
|---|---|---|
| Ex. | Structure and IUPAC Chemical Name | Characterization |
| 149 | 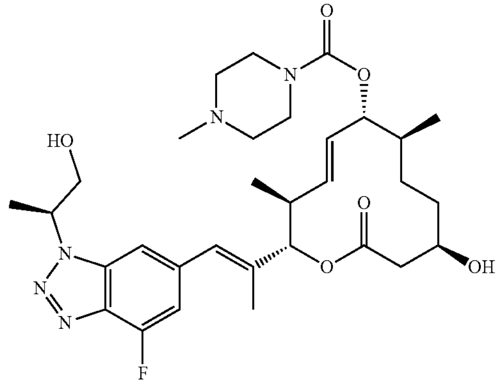 [(2S,3S,4E,6R,7R,10S)-2-[(E)-1-[7-fluoro-3-[(2S)-1-hydroxypropan-2-yl]benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.6 [M + H]+. $^1$H NMR (400 MHz, $CDCl_3$) δ 0.94 (dd, J = 6.78, 3.39 Hz, 6H), 1.13-1.25 (m, 2H), 1.37-1.51 (m, 1H), 1.59-1.65 (m, 3H), 1.67-1.77 (m, 1H), 1.79-1.91 (m, 5H), 2.20-2.28 (m, 4H), 2.28-2.42 (m, 4H), 2.45-2.62 (m, 3H), 3.35-3.55 (m, 4H), 3.62-3.72 (m, 1H), 4.04-4.12 (m, 1H), 4.18 (dd, J = 11.86, 7.47 Hz, 1H), 4.78-4.89 (m, 2H), 5.22 (d, J = 10.54 Hz, 1H), 5.34 (dd, J = 15.00, 9.72 Hz, 1H), 5.53 (dd, J = 15.00, 9.85 Hz, 1H), 6.61 (s, 1H), 6.89 (d, J = 11.04 Hz, 1H), 7.13 (s, 1H) |
| 150 | 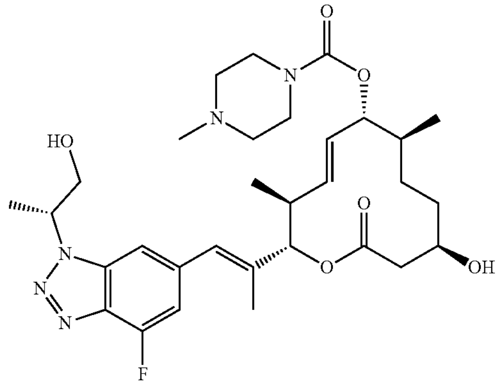 [(2S,3S,4E,6R,7R,10S)-2-[(E)-1-[7-fluoro-3-[(2S)-1-hydroxypropan-2-yl]benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.6 [M + H]+. $^1$H NMR (400 MHz, $CDCl_3$) δ 0.90-0.97 (m, 6H), 1.19 (br d, J = 8.03 Hz, 2H), 1.38-1.51 (m, 1H), 1.57-1.68 (m, 3H), 1.68-1.79 (m, 1H), 1.79-1.91 (m, 5H), 2.18-2.26 (m, 4H), 2.26-2.41 (m, 4H), 2.43-2.63 (m, 3H), 3.34-3.53 (m, 4H), 3.61-3.72 (m, 1H), 4.04-4.10 (m, 1H), 4.14-4.21 (m, 1H), 4.78-4.89 (m, 2H), 5.19-5.25 (m, 1H), 5.30-5.39 (m, 1H), 5.53 (dd, J = 15.00, 9.85 Hz, 1H), 6.61 (s, 1H), 6.89 (d, J = 10.92 Hz, 1H), 7.13 (s, 1H) |
| 151 | 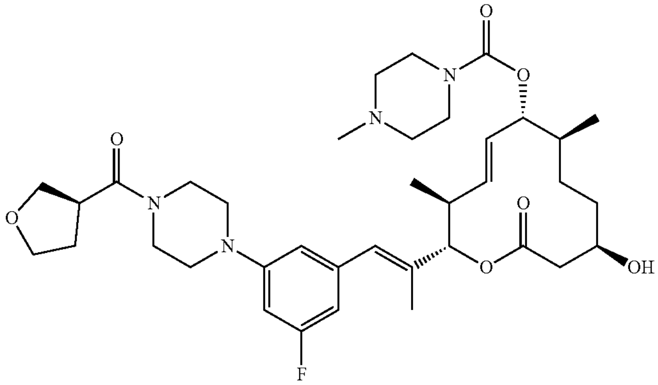 [(2S,3S,4E,6R,7S,10R)-2-[(E)-1-[3-fluoro-5-[4-[(3S)-oxolane-3-carbonyl]piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 685.4 [M + H]+. $^1$H NMR (400 MHz, $CDCl_3$) δ 0.88-0.92 (d, J = 6.90 Hz, 3H), 0.93 (d, J = 6.90 Hz, 3H), 1.06-1.29 (m, 2H), 1.34-1.49 (m, 1H), 1.68-1.77 (m, 1H), 1.77-1.81 (m, 4H), 1.81-1.91 (m, 2H), 1.95-2.13 (m, 1H), 2.13-2.22 (m, 1H), 2.22-2.26 (m, 3H), 2.32 (hr s, 4H), 2.37-2.62 (m, 4H), 3.05-3.23 (m, 5H), 3.37-3.52 (m, 4H), 3.67-3.87 (m, 5H), 3.68-3.75 (m, 1H), 3.90-4.00 (m, 1H), 4.80 (t, J = 10.04 Hz, 1H), 5.17 (d, J = 10.54 Hz, 1H), 5.32 (dd, J = 14.93, 9.66 Hz, 1H), 5.51 (dd, J = 14.93, 9.91 Hz, 1H), 6.39-6.48 (m, 4H) |

TABLE 5-continued

| Characterization of Compounds 86-166 and 264 | | |
|---|---|---|
| Ex. | Structure and IUPAC Chemical Name | Characterization |
| 152 | 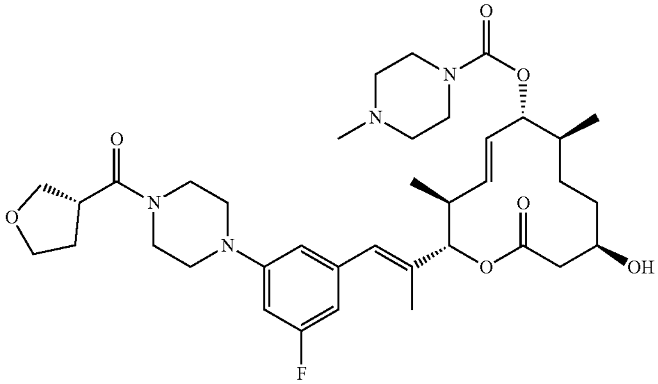 [(2S,3S,4E,6R,7S,10R)-2-[(E)-1-[3-fluoro-5-[4-[(3S)-oxolane-3-carbonyl]piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 685.4 [M + H]+. $^1H$ NMR (400 MHz, $CDCl_3$) δ 0.86-0.97 (m, 6H), 1.10-1.24 (m, 2H), 1.34-1.49 (m, 1H), 1.68-1.89 (m, 6H), 1.94-2.12 (m, 1H), 2.12-2.29 (m, 2H), 2.33 (s, 4H), 2.38-2.61 (m, 7H), 3.05-3.23 (m, 4H), 3.47 (br s, 3H), 3.53-3.62 (m, 2H), 3.62-3.86 (m, 6H), 3.93-3.98 (m, 1H), 4.80 (t, J = 10.10 Hz, 1H), 5.15-5.23 (m, 1H), 5.32 (dd, J = 15.06, 9.66 Hz, 1H), 5.51 (dd, J = 14.93, 9.91 Hz, 1H), 6.39-6.51 (m, 4H) |
| 153 | 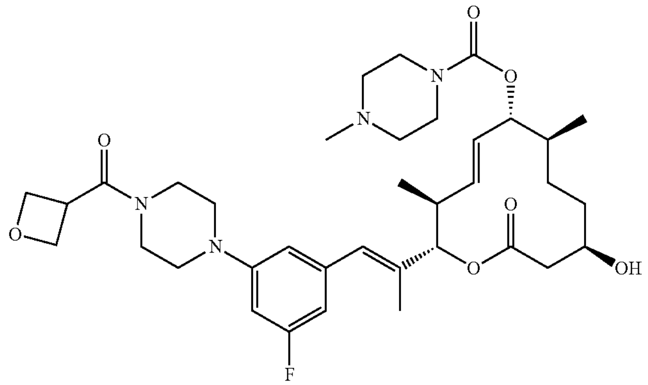 [(2S,3S,4E,6R,7S,10R)-2-[(E)-1-[3-fluoro-5-[4-(oxetane-3-carbonyl]piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 671.4 [M + H]+. $^1H$ NMR (400 MHz, $CDCl_3$) δ 0.83-0.97 (m, 6H), 1.12-1.22 (m, 2H), 1.34-1.48 (m, 1H), 1.67-1.81 (m, 1H), 1.81-1.96 (m, 4H), 2.19-2.26 (m, 2H), 2.26-2.32 (m, 3H), 2.32-2.57 (m, 3H), 3.07 (dt, J = 18.16, 5.10 Hz, 4H), 3.18-3.33 (m, 3H), 3.41 (hr s, 5H), 3.53-3.67 (m, 2H), 3.67-3.76 (m, 2H), 3.91-4.00 (m, 1H), 4.70-4.89 (m, 2H), 4.89-5.09 (m, 1H), 5.17 (d, J = 10.67 Hz, 1H), 5.23-5.37 (m, 2H), 5.40-5.55 (m, 2H), 6.37-6.48 (m, 4H) |
| 154 | 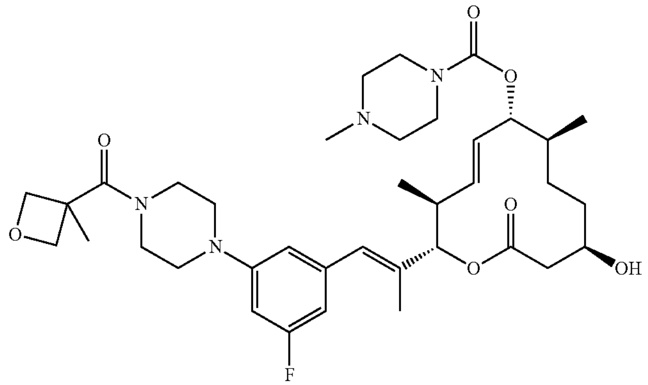 [(2S,3S,4E,6R,7S,10R)-2-[(E)-1-[3-fluoro-5-[4-[(3-methyloxetane-3-carbonyl]piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 685.4 [M + H]+. $^1H$ NMR (400 MHz,$CDCl_3$) δ 0.90 (br d, J = 6.78 Hz, 3H), 0.92-0.95 (m, 3H), 1.06-1.28 (m, 2H), 1.33-1.60 (m, 1H), 1.62 (s, 3H), 1.67-1.77 (m, 1H), 1.77-1.80 (m, 3H), 1.80-1.90 (m, 1H), 2.20-2.27 (m, 4H), 2.30 (hr s, 4H), 2.36-2.61 (m, 4H), 3.08 (br s, 5H), 3.31-3.53 (m, 4H), 3.53-3.73 (m, 3H), 4.29 (d, J = 6.02 Hz, 2H), 4.80 (t, J = 10.04 Hz, 1H), 4.93 (d, J = 6.02 Hz, 2H), 5.17 (d, J = 10 .54 Hz, 1H), 5.32 (dd, J = 14.93, 9.66 Hz, 1H), 5.51 (dd, J = 15.06, 9.91 Hz, 1H), 6.38-6.49 (m, 4H) |

TABLE 5-continued

Characterization of Compounds 86-166 and 264

| Ex. | Structure and IUPAC Chemical Name | Characterization |
|---|---|---|
| 155 | 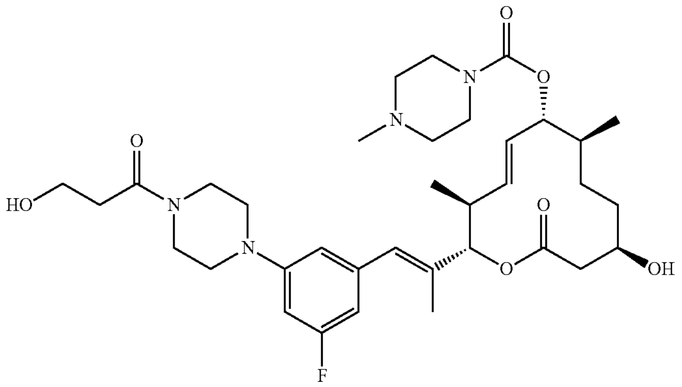 [(2S,3S,4E,6R,7S,10R)-2-[(E)-1-[3-fluoro-5-[4-(3-hydroxypropanoyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 659.4 $[M + H]^+$. $^1H$ NMR (400 MHz, $CDCl_3$) δ 0.92 (dd, J = 9.16, 6.90 Hz, 6H), 1.06-1.28 (m, 2H), 1.33-1.49 (m, 1H), 1.66-1.76 (m, 1H), 1.76-1.80 (m, 3H), 1.80-1.91 (m, 1H), 2.18-2.27 (m, 4H), 2.31 (hr s, 4H), 2.36-2.58 (m, 5H), 3.03-3.16 (m, 4H), 3.31-3.47 (m, 4H), 3.47-3.58 (m, 3H), 3.60-3.74 (m, 3H), 3.83 (t, J = 5.21 Hz, 2H), 4.80 (t, J = 10.10 Hz, 1H), 5.17 (d, J = 10 .67 Hz, 1H), 5.32 (dd, J = 14.93, 9.66 Hz, 1H), 5.51 (dd, J = 15.06, 9.91 Hz, 1H), 6.38-6.48 (m, 4H) |
| 156 | 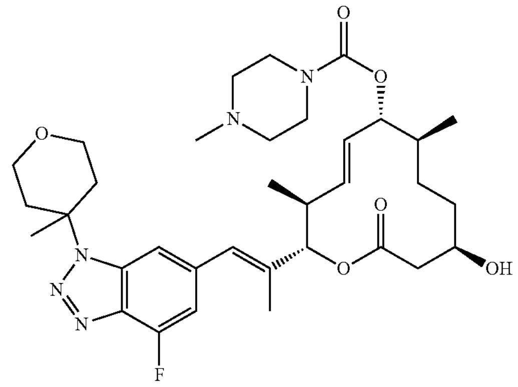 [(2S,3S,4E,6R,7S,10R)-2-[(E)-1-[7-fluoro-3-[4-methyloxan-4-yl)benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 642.3 $[M + H]^+$. $^1H$ NMR (400 MHz, $CDCl_3$) δ 0.94 (dd, J = 6 .7 1, 3.07 Hz, 6H), 1.10-1.26 (m, 2H), 1.36-1.64 (m, 2H), 1.64-1.77 (m, 4H), 1.84 (d, J = 1.13 Hz, 3H), 2.00-2.21 (m, 3H), 2.21-2.28 (m, 4H), 2.32 (br s, 4H), 2.39-2.62 (m, 4H), 2.66-2.91 (m, 2H), 3.32-3.51 (m, 3H), 3.51-3.70 (m, 2H), 3.74-3.83 (m, 2H), 4.81 (t, J = 10.10 Hz, 1H), 5.22 (d, J = 10.67 Hz, 1H), 5.30-5.40 (m, 1H), 5.53 (dd, J = 15.06, 9.91 Hz, 1H), 6.61 (s, 1H), 6.92 (d, J = 10.79 Hz, 1H), 7.18 (s, 1H) |
| 157 | 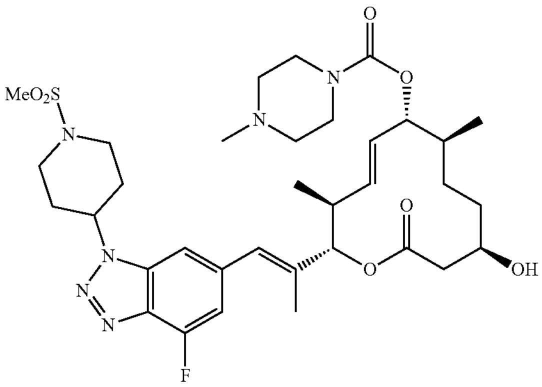 [(2S,3S,4E,6R,7S,10R)-2-[(E)-1-[7-fluoro-3-(1-methylsulfonylpiperidin-4-yl)benzotriazol-5-yl] prop-1-en-2-yl]-10-hydroxy-3,7-dimethyl-12-oxo-1-oxacyclododec-4-en-6-yl] 4-methylpiperazine-1-carboxylate | LCMS (ESI, m/z), 705.3 $[M + H]^+$. $^1H$ NMR (400 MHz, $CDCl_3$) δ 0.94 (t, J = 6.27 Hz, 6H), 1.08-1.29 (m, 3H), 1.34-1.58 (m, 1H), 1.58-1.80 (m, 3H), 1.84 (d, J = 1.25 Hz, 5H), 2.20-2.29 (m, 4H), 2.29-2.35 (m, 3H), 2.35-2.60 (m, 4H), 2.82 (s, 3H), 2.98-3.14 (m, 2H), 3.31-3.55 (m, 4H), 3.55-3.71 (m, 1H), 3.84-3.92 (m, 2H), 4.73-4.84 (m, 2H), 5.22 (d, J = 10.54 Hz, 1H), 5.31-5.39 (m, 1H), 5.53 (dd, J = 15.00, 9.85 Hz, 1H), 6.62 (s, 1H), 6.92 (d, J = 10.79 Hz, 1H), 7.08 (s, 1H) |

TABLE 5-continued

| Ex. | Structure and IUPAC Chemical Name | Characterization |
|---|---|---|
| | Characterization of Compounds 86-166 and 264 | |
| 158 | 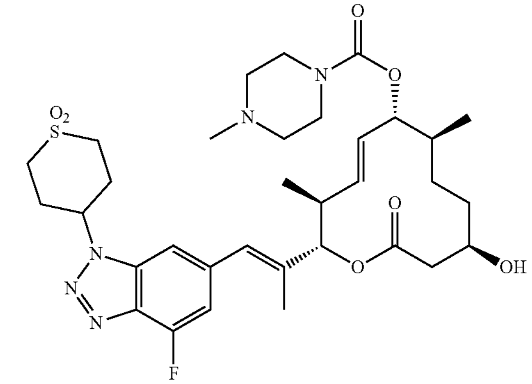 [(2S,3S,4E,6R,7S,10R)-2-[(E)-1-[3-(1,1-dioxothian-4-yl)-7-fluorobenzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 676.3 [M + H]$^+$. $^1$H NMR (400 MHz, $CDCl_3$) δ 0.91-0.94 (m, 3H), 0.95 (br d, J = 3.51 Hz, 3H), 1.08-1.29 (m, 2H), 1.35-1.60 (m, 1H), 1.61-1.81 (m, 1H), 1.81-1.92 (m, 4H), 2.19-2.29 (m, 4H), 2.33 (hr s, 4H), 2.45-2.69 (m, 6H), 2.73-2.95 (m, 3H), 3.12 (td, J = 8.72, 3.26 Hz, 3H), 3.33-3.55 (m, 5H), 3.57-3.76 (m, 1H), 4.81 (t, J = 10.04 Hz, 1H), 4.86-5.00 (m, 1H), 5.22 (d, J = 10.67 Hz, 1H), 5.35 (dd, J = 14.93, 9.66 Hz, 1H), 5.53 (dd, J = 15.00, 9.85 Hz, 1H), 6.62 (s, 1H), 6.92-7.04 (m, 1H), 7.08 (s, 1H) |
| 159 | 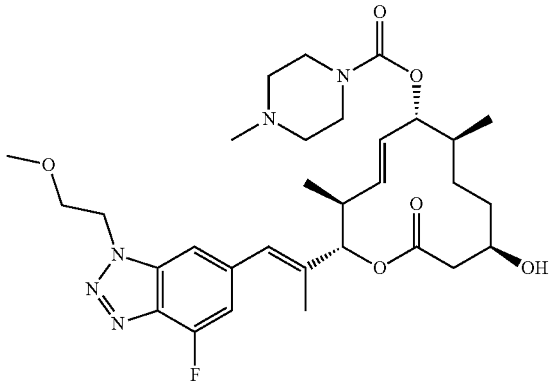 [(2S,3S,4E,6R,7R,10S)-2-[(E)-1-[7-fluoro-3-(2-methoxyethyl)benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 602.3 [M + H]$^+$. $^1$H NMR (400 MHz, $CDCl_3$) δ 0.94 (dd, J = 6.71, 3.07 Hz, 6H), 1.08-1.29 (m, 2H), 1.34-1.60 (m, 1H), 1.60-1.80 (m, 1H), 1.84 (d, J = 1.13 Hz, 4H), 2.20-2.28 (m, 3H), 2.32 (br s, 4H), 2.39-2.64 (m, 4H), 3.22 (s, 3H), 3.32-3.53 (m, 4H), 3.54-3.73 (m, 1H), 3.80 (t, J = 5.14 Hz, 2H), 4.70 (t, J = 5.14 Hz, 2H), 4.81 (t, J = 10.10 Hz, 1H), 5.23 (d, J = 10.67 Hz, 1H), 5.34 (dd, J = 15.06, 9.66 Hz, 1H), 5.53 (dd, J = 15.06, 9.91 Hz, 1H), 6.61 (s, 1H), 6.87 (d, J = 10.92 Hz, 1H), 7.17-7.20 (m, 1H) |
| 160 | 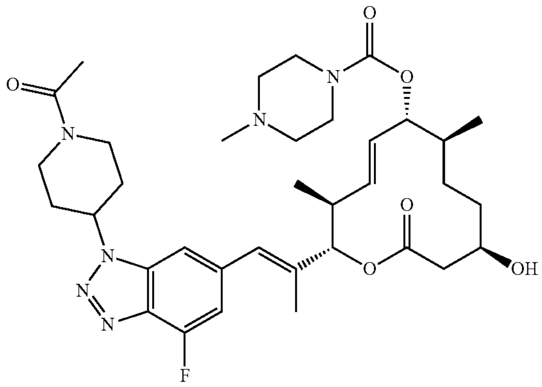 [(2S,3S,4E,6R,7S,10R)-2-[(E)-1-[3-(1-acetylpiperidin-4-yl)-7-fluorobenzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 669.9 [M + H]$^+$. $^1$H NMR (400 MHz, $CDCl_3$) δ 0.89-0.99 (m, 6H), 1.10-1.25 (m, 2H), 1.38-1.67 (m, 1H), 1.67-1.90 (m, 6H), 2.09-2.26 (m, 9H), 2.27-2.40 (m, 4H), 2.42-2.63 (m, 4H), 2.89 (br t, J = 10.92 Hz, 1H), 3.24-3.51 (m, 5H), 3.67 (br dd, J = 6.90, 3.51 Hz, 1H), 4.01 (br d, J = 13.80 Hz, 1H), 4.63-4.84 (m, 3H), 5.22 (d, J = 10.54 Hz, 1H), 5.29-5.44 (m, 1H), 5.47-5.59 (m, 1H), 6.62 (s, 1H), 6.92 (d, J = 10.92 Hz, 1H), 7.07 (s, 1H) |

TABLE 5-continued

| Characterization of Compounds 86-166 and 264 | | |
|---|---|---|
| Ex. | Structure and IUPAC Chemical Name | Characterization |
| 161 | 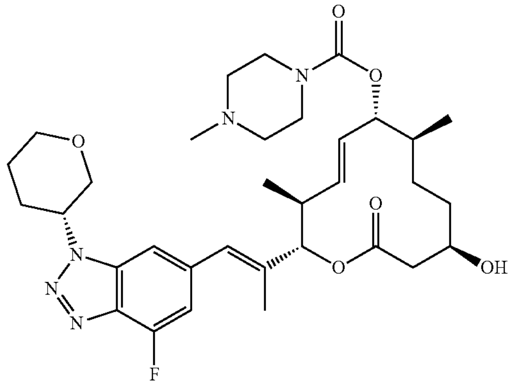 [(2S,3S,4E,6R,7S,10R)-2-[(E)-1-[7-fluoro-3-[(3S)-oxan-3-yl]benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 628.7 [M + H]$^+$. $^1$H NMR (400 MHz, $CDCl_3$) δ 0.92-0.99 (m, 6H), 1.11-1.27 (m, 5H), 1.34-1.49 (m, 2H), 1.69-1.94 (m, 4H), 2.20-2.25 (m, 4H), 2.25-2.37 (m, 4H), 2.37-2.61 (m, 3H), 3.25-3.45 (m, 4H), 3.52 (td, J = 10.95, 3.83 Hz, 1H), 3.61-3.71 (m, 1H), 3.79-3.94 (m, 1H), 3.98 (br d, J = 11.29 Hz, 1H), 4.07-4.14 (m, 1H), 4.62-4.74 (m, 1H), 4.75-4.85 (m, 2H), 5.23 (br s, 1H), 5.30-5.40 (m, 2H), 5.48-5.59 (m, 1H), 6.61 (s, 1H), 6.90 (d, J = 10.92 Hz, 1H), 7.12 (s, 1H) |
| 162 | 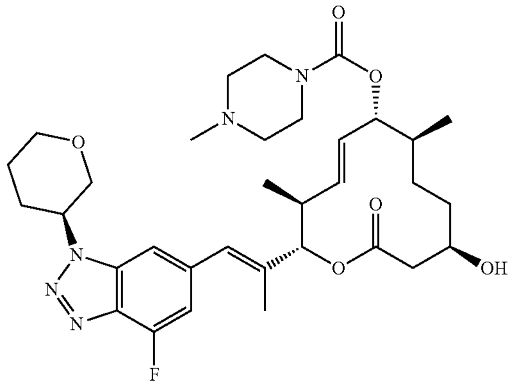 [(2S,3S,4E,6R,7S,10R)-2-[(E)-1-[7-fluoro-3-[(3S)-oxan-3-yl]benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 628.7 [M + H]$^+$. $^1$H NMR (400 MHz, $CDCl_3$) δ 0.89-0.98 (m, 6H), 1.10-1.38 (m, 2H), 1.38-1.50 (m, 1H), 1.67-1.91 (m, 8H), 2.20-2.27 (m, 4H), 2.30 (hr s, 4H), 2.35-2.61 (m, 4H), 3.39-3.45 (m, 3H), 3.52 (td, J = 10.98, 3.89 Hz, 2H), 3.67 (br dd, J = 6.53, 3.39 Hz, 1H), 3.85 (dd, J = 11.04, 10.29 Hz, 1H), 3.98 (hr d, J = 11.54 Hz, 1H), 4.07-4.13 (m, 1H), 4.66 (ddd, J = 10.63, 6.31, 4.39 Hz, 1H), 4.81 (t, J = 10.04 Hz, 1H), 5.22 (d, J = 10.67 Hz, 1H), 5.35 (dd, J = 14.93, 9.66 Hz, 1H), 5.53 (dd, J = 15.00, 9.85 Hz, 1H), 6.61 (s, 1H), 6.89 (d, J = 10.92 Hz, 1H), 7.12 (s, 1H) |
| 163 | 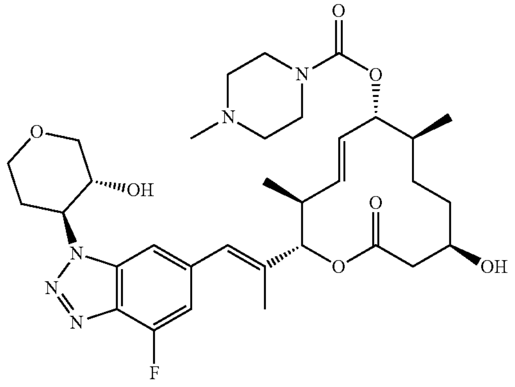 [(2S,3S,4E,6R,7S,10R)-2-[(E)-1-[7-fluoro-3-[(3R,4S)-3-hydroxyoxan-4-yl]benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 644.4 [M + H]$^+$. $^1$H NMR (400 MHz, $CDCl_3$) δ 0.94 (dd, J = 6.65, 5.14 Hz, 6H), 1.13-1.24 (m, 2H), 1.39-1.48 (m, 1H), 1.67-1.97 (m, 4H), 2.06-2.17 (m, 2H), 2.17-2.25 (m, 4H), 2.31 (br s, 4H), 2.39-2.63 (m, 5H), 3.30-3.60 (m, 6H), 3.61-3.74 (m, 1H), 4.05-4.26 (m, 2H), 4.35-4.44 (m, 1H), 4.44-4.56 (m, 1H), 4.81 (t, J = 10.04 Hz, 1H), 5.22 (d, J = 10.54 Hz, 1H), 5.35 (dd, J = 15 .00 , 9.60 Hz, 1H), 5.44-5.58 (m, 1H), 6.60 (s, 1H), 6.85 (d, J = 10.29 Hz, 1H), 7.11-7.17 (m, 1H) |

TABLE 5-continued

| Characterization of Compounds 86-166 and 264 | | |
|---|---|---|
| Ex. | Structure and IUPAC Chemical Name | Characterization |
| 164 | 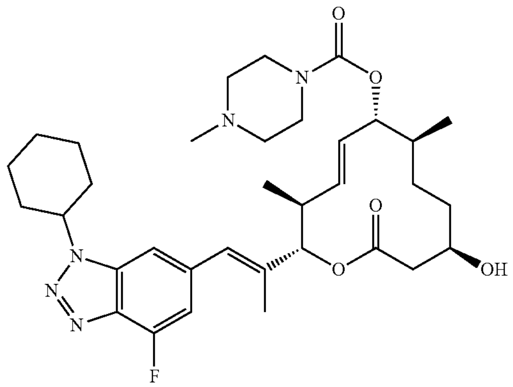 [(2S,3S,4E,6R,7S,10R)-2-[(E)-1-(3-cyclohexyl-7-fluorobenzotriazol-5-yl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 626.4 $[M + H]^+$. $^1H$ NMR (400 MHz, $CDCl_3$) δ 0.94 (t, J = 6.46 Hz,6H), 1.10-1.26 (m, 2H), 1.26-1.51 (m, 3H), 1.61-1.81 (m, 2H), 1.84 (d, J = 1.13 Hz, 4H), 1.94 (br d, J = 13.80 Hz, 3H), 2.00-2.22 (m, 4H), 2.23-2.32 (m, 3H), 2.37 (br s, 3H), 2.42-2.60 (m, 3H), 3.37-3.58 (m, 4H), 3.61-3.71 (m, 1H), 4.48-4.57 (m, 1H), 4.81 (t, J = 10.10 Hz, 1H), 5.23 (d, J = 10.67 Hz, 1H), 5.34 (dd, J = 15.06, 9.66 Hz, 1H), 5.53 (dd, J = 15.00, 9.98 Hz, 1H), 6.62 (s, 1H), 6.89 (d, J = 10.92 Hz, 1H), 7.09 (s, 1H) |
| 165 | 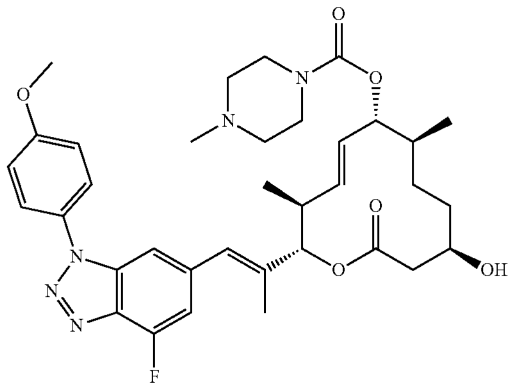 [(2S,3S,4E,6R,7R,10S)-2-[(E)-1-[7-fluoro-4-(4-methoxyphenyl)benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 650.4 $[M + H]^+$. $^1H$ NMR (400 MHz, $CDCl_3$) δ 0.93 (d, J = 6.65 Hz, 6H), 1.18 (hr d, J = 8.28 Hz, 2H), 1.38-1.46 1H), 1.57-1.91 (m, 3H), 2.18-2.29 (m, 4H), 2.34 (br s, 4H), 2.42-2.59 (m, 4H), 3.31-3.56 (m, 6H), 3.61-3.71 (m, 1H), 3.84 (s, 4H), 4.80 (s, 1H), 5.21 (d, J = 10.67 Hz, 1H), 5.35 (br d, J = 9.66 Hz, 1H), 5.50 (br d, J = 9.91 Hz, 1H), 6.60 (s, 1H), 6.95 (d, J = 10.92 Hz, 1H), 7.05 (d, J = 8.91 Hz, 2H), 7.55 (d, J = 8.91 Hz, 2H) |
| 166 | 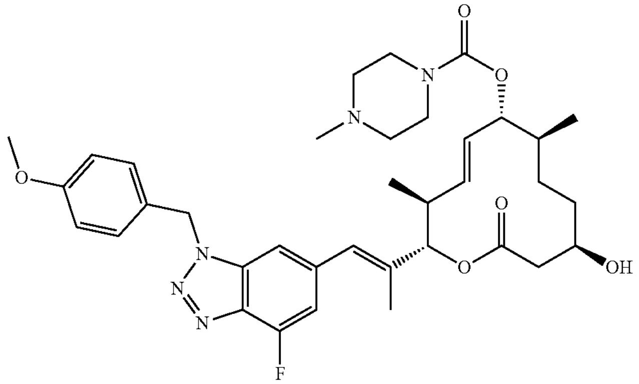 [(2S,3S,4E,6R,7R,10S)-2-[(E)-1-[7-fluoro-3-[4-methoxyphenyl)methyl]benzotriazol-5-yl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 664.4 $[M + H]^+$. $^1H$ NMR (400 MHz, $CDCl_3$) δ 0.88-0.93 (m, 6H), 1.15-1.22 (m, 2H), 1.37-1.45 (m, 2H), 1.70-1.74 (m, 5H), 1.81-1.91 (m, 2H), 2.22-2.28 (m, 3H), 2.28-2.40 (m, 4H), 2.41-2.63 (m, 3H), 3.34-3.53 (m, 4H), 3.61-3.68 (m, 1H), 3.70 (s, 4H), 4.80 (s, 1H), 5.14-5.20 (m, 1H), 5.28-5.38 (m, 1H), 5.46-5.55 (m, 1H), 5.68 (d, J = 2.13 Hz, 2H),6.79 (d, J = 8.78 Hz, 2H), 6.83-6.90 (m, 2H), 7.10-7.17 (m, 2H) |

TABLE 5-continued

| Characterization of Compounds 86-166 and 264 | | |
|---|---|---|
| Ex. | Structure and IUPAC Chemical Name | Characterization |
| 264 | 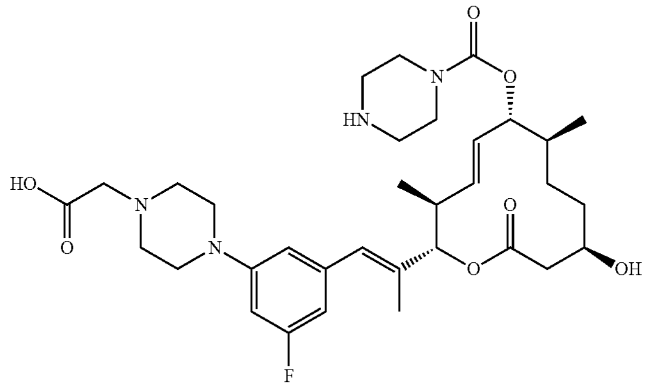 2-[4-[3-fluoro-5-[(E)-2-[(2S,3S,4E,6R,7S,10R)-10-hydrozy-3,7-dimethyl-12-oxo-6-(piperazine-1-carbonyloxy)-1-oxacyclododec-4-en-2-yl]prop-1-enyl]phenyl]piperazin-1-yl]acetic acid | LC/MS (ESI, m/z), 631.4 [M + H]$^+$. $^1$H NMR (400 MHz, $CHCl_3$-d): δ ppm 0.85 -1.16 (m, 2H) 1.23-1.52 (m, 1H) 1.57-1.77 (m, 1H) 1.87 (s, 1H) 1.92-2.13 (1H, 1 H) 2.35-2.55 (m, 1H) 2.50-2.74 (m, 1H) 3.11 (br s, 1H) 3.36-3.54 (m, 2H) 3.64 (br d, J = 10.42 Hz, 2H) 3.77-3.90 (m, 1 H) 4.76 (hr s, 4 H) 5.07-5.19 (m, 1H) 5.38-5.68 (m, 1H) 6.40-6.76 (m, 1H) 8.02-8.66 (m, 1H). |

Compounds 167-196 (Tables 5, 6, 8, 10, 12, and 14) and intermediates thereof (Tables 4, 7, 9, 11, and 13) were prepared by the following general methods of Procedures 20-29.

Synthesis of Boronate Intermediates:

Procedure 20.

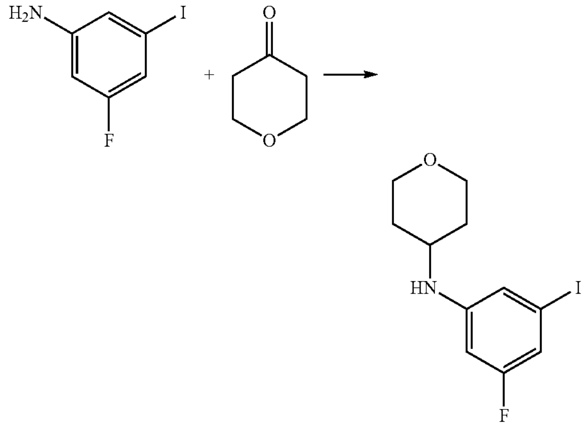

047

A solution of 3-fluoro-5-iodoaniline (250 mg, 1.055 mmol) and dihydro-2H-pyran-4(3H)-one (264 mg, 2.637 mmol) in methanol (5 mL) was charged into a 25 mL round bottom flask with a magnetic stir bar. Acetic acid (0.121 mL, 2.11 mmol) was added and the resulting solution was stirred for 30 minutes at room temperature. Sodium cyanoborohydride (133 mg, 2.11 mmol) was added, the resulting solution was stirred overnight at room temperature. The reaction was quenched with 10 mL 1M aqueous NaOH, stirred for 15 minutes. The solution was extracted with EtOAc (3×15 mL), the combined organic layers were washed with brine (15 mL), dried with $MgSO_4$, filtered, and evaporated under vacuum. The crude product was dry loaded onto 3 g. silica and purified by column chromatography (ISCO normal phase, 24 g. gold column, 0-60% EtOAc/hexanes gradient) to isolate N-(3-fluoro-5-iodophenyl)tetrahydro-2H-pyran-4-amine (047) (208 mg, 0.648 mmol, 61%). $^1$H NMR (400 MHz, $CDCl_3$) δ ppm 1.41-1.55 (m, 2H) 1.95-2.09 (m, 2H) 3.38-3.48 (m, 1H) 3.53 (td, J=11.61, 2.13 Hz, 2H) 3.65-3.80 (m, 1H) 4.02 (br d, J=11.54 Hz, 2H) 6.20-6.30 (m, 1H) 6.73 (br d, J=1.76 Hz, 2H). LCMS: 322.6 [M+H]$^+$.

Procedure 21.

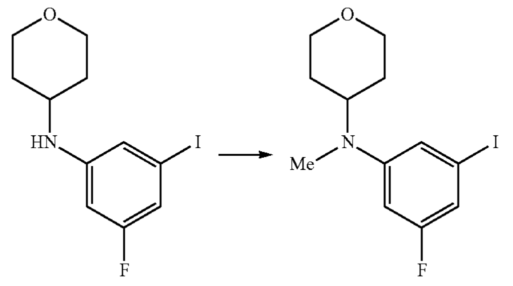

047 048

A solution of N-(3-fluoro-5-iodophenyl)tetrahydro-2H-pyran-4-amine (047) (208 mg, 0.648 mmol) in acetonitrile (4 mL) was charged into a 10 mL vial with a magnetic stir bar. Cesium carbonate (422 mg, 1.295 mmol) and iodomethane (0.203 mL, 3.239 mmol) were added. The vial was sealed and heated to 80° C. with stirring overnight. The reaction was cooled to room temperature. The solids were filtered off, washed with 20 mL EtOAc, and solvents evaporated under vacuum. The crude material was dry loaded onto 3 g. silica and purified by column chromatography (ISCO normal phase, 24 g. gold column, 0-60% EtOAc/hexanes gradient) to isolate N-(3-fluoro-5-iodophenyl)-N-methyltetrahydro-2H-pyran-4-amine (048) (143 mg, 0.427 mmol, 66%). $^1$H NMR (400 MHz, $CDCl_3$) δ ppm 1.62-1.72 (m, 2H) 1.80-1.94 (m, 2H) 2.79 (s, 3H) 3.46-3.56 (m, 2H) 3.68-3.78 (m, 1H) 4.05-4.14 (m, 2H) 6.38-6.47 (m, 1H) 6.74-6.81 (m, 1H) 6.85-6.90 (m, 1H). LCMS: 336.1 [M+H]$^+$.

Procedure 22.

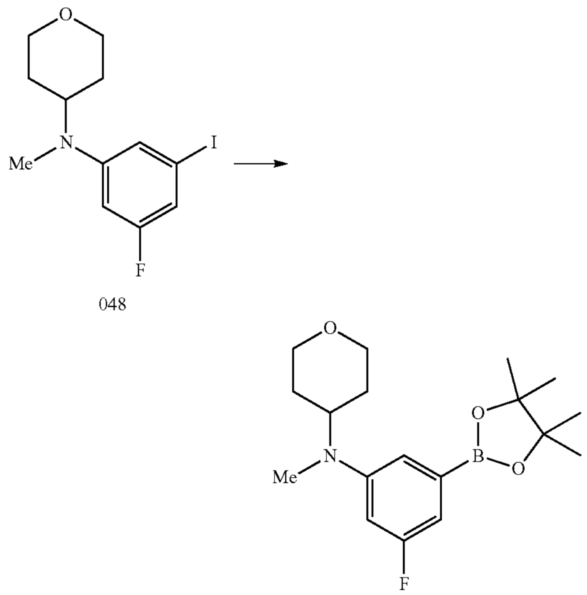

048

049

Bis(pinacolato)diboron (130 mg, 0.512 mmol), potassium acetate (126 mg, 1.28 mmol) and $Pd(dppf)Cl_2$ (38.8 mg, 0.043 mmol) were charged into a 10 mL vial with a magnetic stir bar. A solution of N-(3-fluoro-5-iodophenyl)-N-methyl-tetrahydro-2H-pyran-4-amine (048) (143 mg, 0.427 mmol) in DMF (4 mL) was added. The vial was sealed and heated to 100° C. and stirred for 20 hours. The vial was cooled to room temperature, diluted with 5 mL EtOAc, filtered through a plug of celite, washed with 10 mL EtOAc, and evaporated under vacuum. The crude material was dry loaded onto a 2 g. silica column and purified by column chromatography (ISCO normal phase, 12 g. gold column, 0-50% EtOAc/hexanes gradient) to obtain N-(3-fluoro-5-(4,4,5,5-tetramethyl-1,3,2-dioxaborolan-2-yl)phenyl)-N-methyltetrahydro-2H-pyran-4-amine (049) (82 mg, 0.245 mmol, 57%). $^1H$ NMR (400 MHz, $CDCl_3$) δ ppm 1.33-1.40 (m, 12H) 1.64-1.73 (m, 2H) 1.80-1.94 (m, 2H) 2.79-2.85 (m, 3H) 3.48-3.61 (m, 2H) 3.79-3.90 (m, 1H) 4.04-4.13 (m, 2H) 6.54-6.63 (m, 1H) 6.82-6.89 (m, 1H) 6.98-7.04 (m, 1H). LCMS: 336.3 $[M+H]^+$.

The following intermediates were also synthesized according to the general methods of Procedures 20-22.

TABLE 6

Characterization of intermediates synthesized according to Procedures 20-22

| Intermediate | Characterization |
|---|---|
| 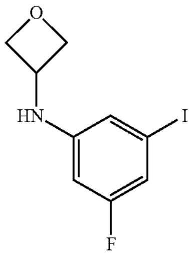 N-(3-fluoro-5-iodophenyl)oxetan-3-amine | $^1H$ NMR (400 MHz, $CDCl_3$) δ ppm 3.16-3.21 (m, 1 H) 4.49-4.54 (m, 2 H) 4.81-4.86 (m, 1 H) 5.01 (t, J = 6.53 Hz, 2 H) 6.12-6.18 (m, 1 H) 6.62-6.66 (m, 1 H) 6.81-6.86 (m, 1 H). LCMS: 294.1 $[M + H]^+$. |
| 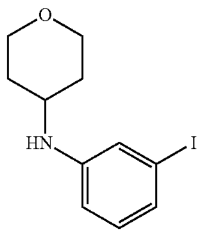 N-(3-iodophenyl)tetrahydro-2H-pyran-4-amine | $^1H$ NMR (400 MHz, $CDCl_3$) δ ppm 1.41-1.55 (m, 2 H) 1.98-2.09 (m, 2 H) 3.42-3.62 (m, 4 H) 3.97-4.07 (m, 2 H) 6.54-6.60 (m, 1 H) 6.85-6.92 (m, 1 H) 6.94-6.99 (m, 1 H) 7.00-7.07 (m, 1 H). LCMS: 304.1 $[M + H]^+$. |

TABLE 6-continued

| Characterization of intermediates synthesized according to Procedures 20-22 | |
|---|---|
| Intermediate | Characterization |
| 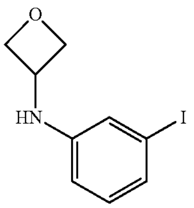 N-(3-iodophenyl)oxetan-3-amine | $^1$H NMR (400 MHz, $CDCl_3$) δ ppm 4.10-4.24 (m, 1 H) 4.52 (s, 2 H) 4.57-4.65 (m, 1 H) 5.01 (t, J = 6.65 Hz, 2 H) 6.43-6.51 (m, 1 H) 6.82-6.87 (m, 1 H) 6.88-6.94 (m, 1 H) 7.08-7.15 (m, 1 H). LCMS: 276.1 $[M + H]^+$. |
| 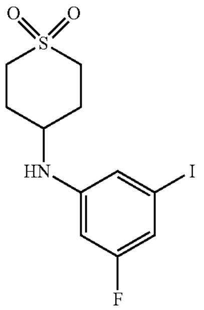 4-((3-fluoro-5-iodophenyl)amino)tetrahydro-2H-thiopyran 1,1-dioxide | $^1$H NMR (400 MHz, $CDCl_3$) δ ppm 2.10-2.26 (m, 2 H) 2.36-2.55 (m, 2 H) 3.04-3.28 (m, 4 H) 3.46-3.65 (m, 1 H) 3.69-3.89 (m, 1 H) 6.27 (d, J = 11.04 Hz, 1 H) 6.74 (s, 1 H) 6.79-6.89 (m, 1 H). LCMS: 370.1 $[M + H]^+$. |
| 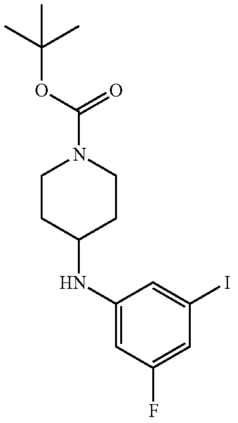 tert-butyl 4-((3-fluoro-5-iodophenyl)amino)piperidine-1-carboxylate | $^1$H NMR (400 MHz, $CDCl_3$) δ ppm 1.31-1.40 (m, 2 H) 1.49 (s, 9 H) 1.96-2.06 (m, 2 H) 2.87-3.02 (m, 2 H) 3.31-3.45 (m, 1 H) 3.65-3.80 (m, 1 H) 3.99-4.12 (m, 2 H) 6.25 (br d, J = 11.29 Hz, 1 H) 6.72 (s, 1 H) 6.74-6.79 (m, 1 H). |

TABLE 6-continued

| Characterization of intermediates synthesized according to Procedures 20-22 | |
|---|---|
| Intermediate | Characterization |
| 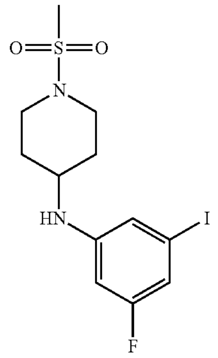 N-(3-fluoro-5-iodo-phenyl)-1-(methyl-sulfonyl)piperidin-4-amine | $^1$H NMR (400 MHz, $CDCl_3$) δ ppm 1.50-1.66 (m, 2 H) 2.16 (br dd, J = 13.24, 3.45 Hz, 2 H) 2.84 (s, 3 H) 2.87-2.97 (m, 2 H) 3.30-3.43 (m, 1 H) 3.72 (br d, J = 2.13 Hz, 1 H) 3.75-3.85 (m, 2 H) 6.25 (dt, J = 11.17, 2.13 Hz, 1 H) 6.73 (s, 1 H) 6.75-6.82 (m, 1 H). LCMS: 399.2 $[M + H]^+$. |
| 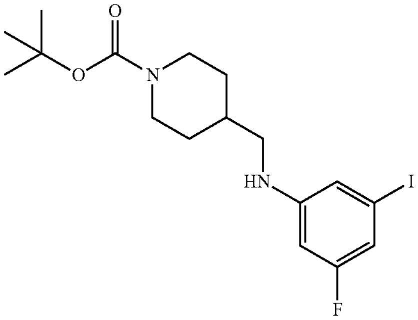 tert-butyl 4-(((3-fluoro-5-iodophenyl)amino)methyl)piperidine-1-carboxylate | $^1$H NMR (400 MHz, $CDCl_3$) δ ppm 1.18 (br dd, J = 12.30, 3.14 Hz, 2 H) 1.48 (s, 9 H) 1.64-1.82 (m, 3 H) 2.72 (br t, J = 12.36 Hz, 2 H) 3.00 (d, J = 6.27 Hz, 2 H) 4.15 (q, J = 7.07 Hz, 3 H) 6.27 (br d, J = 11.17 Hz, 1 H) 6.70-6.80 (m, 2 H). |
| 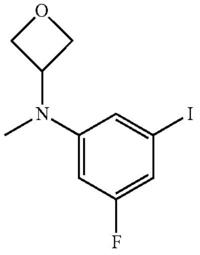 N-(3-fluoro-5-iodophenyl)-N-methyloxetan-3-amine | $^1$H NMR (400 MHz, $CDCl_3$) δ ppm 2.97 (s, 3 H) 4.66-4.79 (m, 3 H) 4.88 (d, J = 6.40 Hz, 2 H) 6.23-6.29 (m, 1 H) 6.71-6.76 (m, 1 H) 6.82-6.90 (m, 1 H). LCMS: 308.1 $[M + H]^+$. |
| 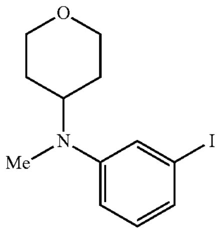 N-(3-iodophenyl)-N-methyltetrahydro-2H-pyran-4-amine | $^1$H NMR (400 MHz, $CDCl_3$) δ ppm 1.63-1.74 (m, 2 H) 1.80-1.93 (m, 2 H) 2.79 (s, 3 H) 3.44-4.31 (m, 2 H) 3.51 (d, J = 1.88 Hz, 1 H) 3.72-3.84 (m, 1 H) 4.04-4.13 (m, 1 H) 6.74-6.81 (m, 1 H) 6.91-6.99 (m, 1 H) 7.04-7.09 (m, 1 H) 7.10-7.16 (m, 1 H). LCMS: 318.2 $[M + H]^+$. |

TABLE 6-continued

| Characterization of intermediates synthesized according to Procedures 20-22 | |
|---|---|
| Intermediate | Characterization |
| 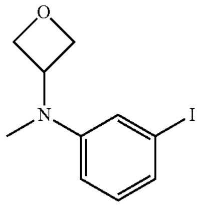 N-(3-iodophenyl)-N-methyloxetan-3-amine | $^1$H NMR (400 MHz, $CDCl_3$) δ ppm 2.94 (s, 3 H) 4.63-4.72 (m, 1 H) 4.72-4.78 (m, 2 H) 4.81-4.92 (m, 2 H) 6.53-6.64 (m, 1 H) 6.90-7.02 (m, 2 H) 7.12-7.19 (m, 1 H). LCMS: 290.3 $[M + H]^+$. |
| 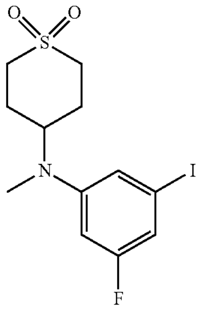 4-((3-fluoro-5-iodophenyl)(methyl)amino)tetrahydro-2H-thiopyran 1,1-dioxide | LCMS: 384.1 $[M + H]^+$. |
| 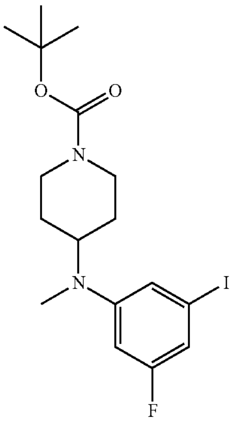 tert-butyl 4-((3-fluoro-5-iodophenyl)(methyl)amino) piperidine-1-carboxylate: | $^1$H NMR (400 MHz, $CDCl_3$) δ ppm 1.50 (s, 9 H) 1.60-1.78 (m, 4 H) 2.76 (s, 3 H) 2.77-2.88 (m, 2 H) 3.58-3.70 (m, 1 H) 4.18-4.37 (m, 2 H) 6.38-6.47 (m, 1 H) 6.76-6.82 (m, 1 H) 6.85-6.90 (m, 1 H). |

TABLE 6-continued

| Characterization of intermediates synthesized according to Procedures 20-22 | |
|---|---|
| Intermediate | Characterization |
| 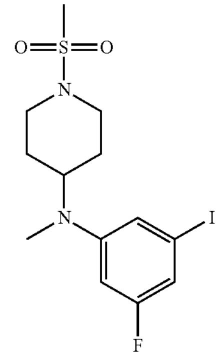 N-(3-fluoro-5-iodo-phenyl)-N-methyl-1-(methylsulfonyl) piperidin-4-amine | LCMS: 413.2 [M + H]$^+$. |
| 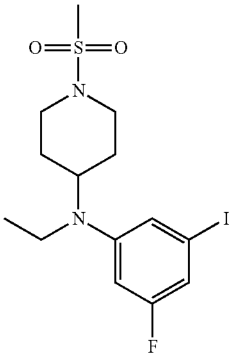 N-ethyl-N-(3-fluoro-5-iodophenyl)-1-(methylsulfonyl) piperidin-4-amine | $^1$H NMR (400 MHz, $CDCl_3$) δ ppm 1.18 (t, J = 7.03 Hz, 3 H) 1.80-1.98 (m, 4 H) 2.73-2.83 (m, 2 H) 2.85 (s, 3 H) 3.27 (q, J = 7.07 Hz, 2 H) 3.54-3.67 (m, 1 H) 3.93-4.03 (m, 2 H) 6.37 (dt, J = 12.89, 2.02 Hz, 1 H) 6.78 (br d, J = 7.53 Hz, 1 H) 6.81 (s, 1 H). LCMS: 427.7 [M + H]$^+$. |
| 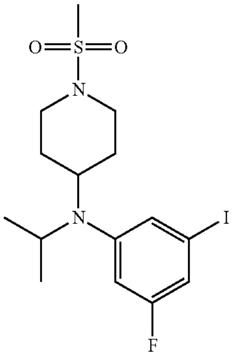 N-(3-fluoro-5-iodophenyl)-N-isopropyl-1-(methyl-sulfonyl)piperidin-4-amine | LCMS: 441.8 [M + H]$^+$. |

TABLE 6-continued

Characterization of intermediates synthesized according to Procedures 20-22

| Intermediate | Characterization |
|---|---|
| 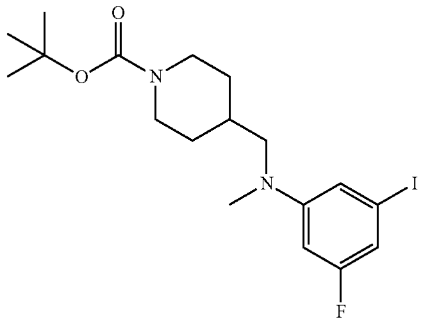 tert-butyl 4-(((3-fluoro-5-iodophenyl)(methyl) amino)methyl)piperidine-1-carboxylate | $^1$H NMR (400 MHz, $CDCl_3$) δ ppm 1.08-1.24 (m, 2 H) 1.48 (s, 9 H) 1.66 (br d, J = 14.56 Hz, 2 H) 1.87 (ddd, J = 11.45, 7.69, 3.83 Hz, 1 H) 2.67 (br t, J = 12.61 Hz, 2 H) 2.96 (s, 3 H) 3.17 (d, J = 7.28 Hz, 2 H) 4.15 (m, 2 H) 6.31 (dt, J = 12.67, 2.26 Hz, 1 H) 6.73-6.80 (m, 2 H). |
| 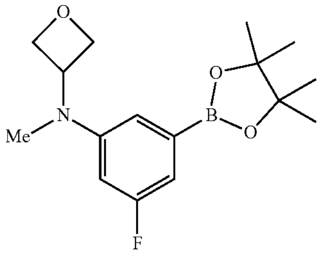 N-(3-fluoro-5-(4,4,5,5-tetramethyl-1,3,2-dioxaborolan-2-yl)phenyl)-N-methyloxetan-3-amine | $^1$H NMR (400 MHz, $CDCl_3$) δ ppm 1.36 (s, 12 H) 2.95-2.99 (m, 3 H) 4.72-4.82 (m, 3 H) 4.85-4.95 (m, 2 H) 6.35-6.46 (m, 1 H) 6.84-6.89 (m, 1 H) 6.91-6.97 (m, 1 H). LCMS: 308.3 $[M + H]^+$. |
| 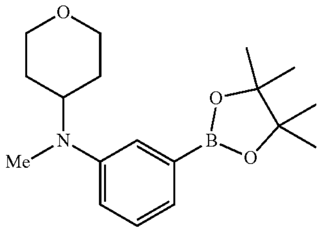 N-methyl-N-(3-(4,4,5,5-tetramethyl-1,3,2-dioxaborolan-2-yl)phenyl)tetrahydro-2H-pyran-4-amine | $^1$H NMR (400 MHz, $CDCl_3$) δ ppm 1.37 (s, 12 H) 1.64-1.75 (m, 2 H) 1.80-1.94 (m, 2 H) 2.83 (s, 3 H) 3.46-3.61 (m, 2 H) 3.79-3.91 (m, 1 H) 4.04-4.11 (m, 2 H) 6.92-6.99 (m, 1 H) 7.19-7.28 (m, 2 H) 7.29-7.31 (m, 1 H). LCMS: 318.2 $[M + H]^+$. |
| 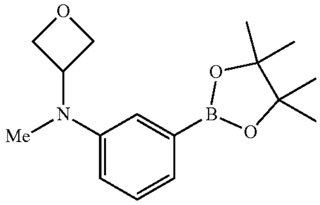 N-methyl-N-(3-(4,4,5,5-tetramethyl-1,3,2-dioxaborolan-2-yl)phenyl)oxetan-3-amine | $^1$H NMR (400 MHz, $CDCl_3$) δ ppm 1.36 (s, 12 H) 2.93-2.96 (m, 3 H) 4.71-4.79 (m, 3 H) 4.86-4.92 (m, 2 H) 6.73-6.79 (m, 1 H) 7.11-7.17 (m, 1 H) 7.23-7.28 (m, 1 H) 7.29-7.34 (m, 1 H). LCMS: 290.8 $[M + H]^+$. |
| N-methyl-N-(3-(4,4,5,5-tetramethyl-1,3,2-dioxaborolan-2-yl)phenyl)oxetan-3-amine: | |

Synthesis of Boronate Coupling Products: Procedure 23.

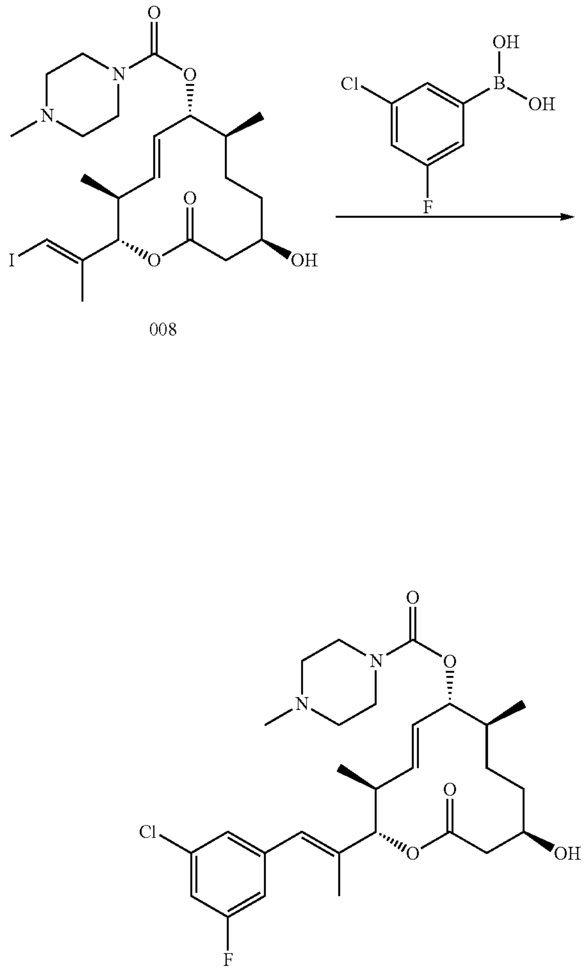

008

Ex. 167

A solution of iodide (008) (39 mg, 0.073 mmol) and (3-chloro-5-fluorophenyl)boronic acid (15.27 mg, 0.088 mmol) in 1,4-dioxane (1.0 ml) was charged into a 4 mL vial with a magnetic stir bar. The vial was de-gassed with argon for 5 minutes. Silver(I) oxide (50.7 mg, 0.219 mmol) and palladium tetrakis (8.43 mg., 0.007 mmol) were added, heated to 80° C., and stirred for 1 hour. The solution was cooled to room temperature, filtered through a plug of celite, washed with 15 mL EtOAc, and concentrated under vacuum. The crude material was dry loaded onto 1 g. silica and purified by column chromatography (ISCO normal phase, 12 g. gold column, 0-20% MeOH/DCM gradient) to provide the product Example 167 (15.2 mg, 0.028 mmol, 39% yield).

Procedure 24.

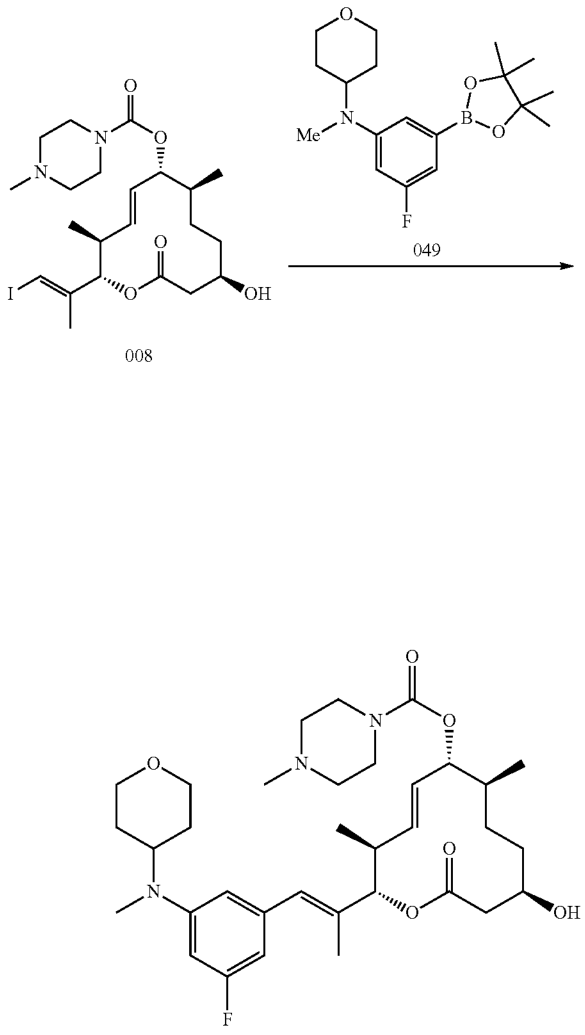

008

049

Ex. 168

A solution of iodide (008) (30 mg, 0.056 mmol) and N-(3-fluoro-5-(4,4,5,5-tetramethyl-1,3,2-dioxaborolan-2-yl)phenyl)-N-methyltetrahydro-2H-pyran-4-amine (049) (28.2 mg, 0.084 mmol) in 1,4-dioxane (1.0 mL) was charged into a 4 mL vial with a magnetic stir bar. The solution was degassed for 5 minutes. silver(I) oxide (39.0 mg, 0.168 mmol) and palladium tetrakis (6.49 mg, 0.0056 mmol) were added. The resulting dispersion was heated to 80° C. and stirred for 3 hours. The vial was cooled to room temperature, filtered through a plug of celite, washed with 15 mL EtOAc, and concentrated under vacuum. The crude product was purified by reverse phase chromatography (MeCN/$H_2O$ w/ 0.100 formic acid) and lyophilized, yielding Example 168 (2.3 mg, 0.0037 mmol, 79).

Compounds 167-171 were synthesized according to the general methods of Procedures 23 and 24:

TABLE 7

| Characterization of Compounds 167-171 | | |
|---|---|---|
| Ex. | Structure and IUPAC Chemical Name | Characterization |
| 167 | 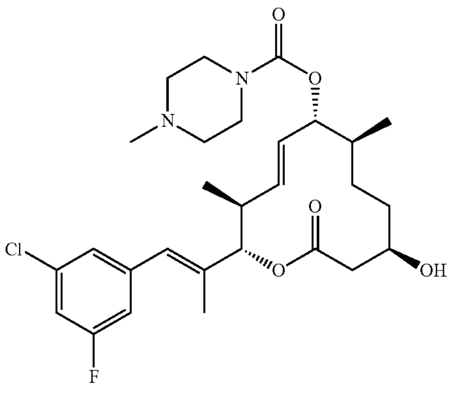 [(2S,3S,4E,6R,7S,10R)-2-[(E)-1-(3-chloro-5-fluorophenyl)prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 1.02 (dd, J = 10.04, 6.78 Hz, 6 H) 1.30-1.36 (m, 1 H) 1.45-1.56 (m, 2 H) 1.76-1.87 (m, 1 H) 1.89 (d, J = 1.25 Hz, 3 H) 1.95 (br dd, J = 7.34, 3.45 Hz, 1 H) 2.32 (s, 3 H) 2.38 (br s, 4 H) 2.51-2.72 (m, 3 H) 3.30-3.40 (m, 1 H) 3.51 (br s, 4 H) 3.76 (br s, 1 H) 4.91 (t, J = 10.10 Hz, 1 H) 5.27 (d, J = 10.67 Hz, 1 H) 5.43 (dd, J = 15.06, 9.66 Hz, 1 H) 5.61 (dd, J = 15.00, 9.85 Hz, 1 H) 6.51 (s, 1 H) 6.90 (d, J = 9.41 Hz, 1 H) 7.00 (dt, J = 8.41, 2.07 Hz, 1 H) 7.07 (s, 1 H). LCMS: 538.5 $[M + H]^+$ |
| 168 | 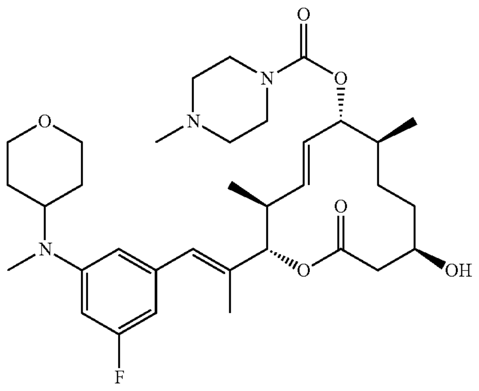 [(2S,3S,4E,6R,7S,10R)-2-[(E)-1-[3-fluoro-5-[methyl(oxan-4-yl)amino]phenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, DMSO-$d_6$) δ ppm 0.90 (dd, J = 6.71, 2.45 Hz, 6 H) 1.19-1.34 (m, 3 H) 1.42-1.60 (m, 4 H) 1.66-1.78 (m, 2 H) 1.84 (d, J = 1.00 Hz, 4 H) 2.17 (s, 3 H) 2.20-2.38 (m, 5 H) 2.73 (s, 3 H) 3.29 (s, 2 H) 3.34-3.40 (m, 3 H) 3.47 (br t, J = 11.11 Hz, 2 H) 3.68-3.78 (m, 1 H) 3.84-3.97 (m, 3 H) 4.61 (d, J = 5.02 Hz, 1 H) 4.70 (t, J = 9.41 Hz, 1 H) 5.01 (d, J = 10.29 Hz, 1 H) 5.35-5.56 (m, 2 H) 6.34-6.42 (m, 1 H) 6.45-6.52 (m, 2 H) 6.52-6.58 (m, 1 H). LCMS: 616.6 $[M + H]^+$ |
| 169 | 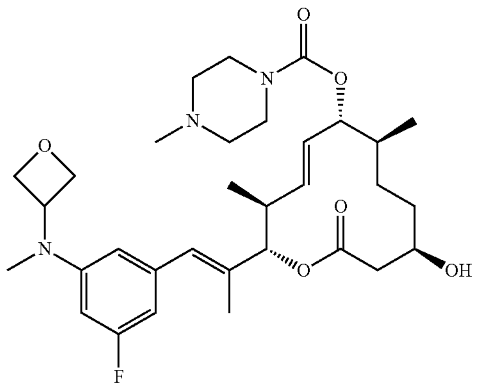 [(2S,3S,4E,6R,7S,10R)-2-[(E)-1-[3-fluoro-5-[methyl(oxetan-3-yl)amino]phenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.91 (t, J = 6.53 Hz, 6 H) 1.12-1.23 (m, 3 H) 1.37-1.45 (m, 2 H) 1.67-1.76 (m, 3 H) 1.68-1.74 (m, 2 H) 1.78 (d, J = 1.25 Hz, 3 H) 1.81-1.91 (m, 1 H) 2.43-2.50 (m, 4 H) 2.51-2.60 (m, 2 H) 2.85 (s, 3 H) 3.57-3.69 (m, 4 H) 4.53-4.63 (m, 1 H) 4.66 (t, J = 6.27 Hz, 2 H) 4.73-4.85 (m, 3 H) 5.17 (d, J = 10.54 Hz, 1 H) 5.25-5.36 (m, 1 H) 5.52 (dd, J = 14.93, 10.04 Hz, 1 H) 6.08-6.17 (m, 2 H) 6.36 (d, J = 9.03 Hz, 1 H) 6.40 (s, 1 H). LCMS: 588.6 $[M + H]^+$ |

TABLE 7-continued

Characterization of Compounds 167-171

| Ex. | Structure and IUPAC Chemical Name | Characterization |
|---|---|---|
| 170 | 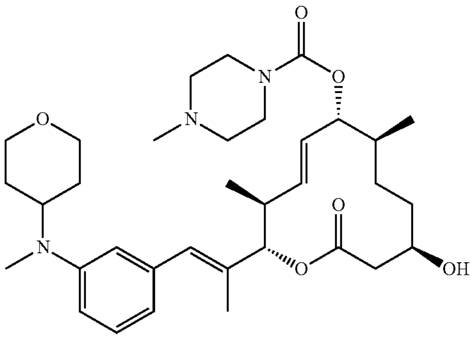 [(2S,3S,4E,6R,7S,10R)-10-hydroxy-3,7-dimethyl-2-[(E)-1-[3-[methyl(oxan-4-yl)amino]phenyl]prop-1-en-2-yl]-12-oxo-1-oxacyclododec-4-en-6-yl] 4-methylpiperazine-1-carboxylate | $^1$H NMR (400 MHz, DMSO-$d_6$) δ ppm 0.83 (d, J = 6.65 Hz, 6 H) 1.08-1.29 (m, 3 H) 1.33-1.52 (m, 5 H) 1.63-1.70 (m, 2 H) 1.76 (d, J = 1.13 Hz, 4 H) 2.09 (s, 5 H) 2.20-2.30 (m, 2 H) 2.46-2.56 (m, 2 H) 2.65 (s, 3 H) 3.32-3.43 (m, 3 H) 3.57-3.70 (m, 1 H) 3.74-3.90 (m, 3 H) 4.53 (d, J = 5.15 Hz, 1 H) 4.62 (d, J = 9.54 Hz, 1 H) 4.58-4.71 (m, 1 H) 4.93 (d, J = 3.01 Hz, 1 H) 5.27-5.45 (m, 3 H) 6.41 (s, 1 H) 6.55 (d, J = 8.03 Hz, 1 H) 6.62 (s, 1 H) 6.68 (dd, J = 8.53, 2.26 Hz, 1 H) 7.09 (t, J = 7.91 Hz, 1 H). LCMS: 598.7 [M + H]$^+$ |
| 171 | 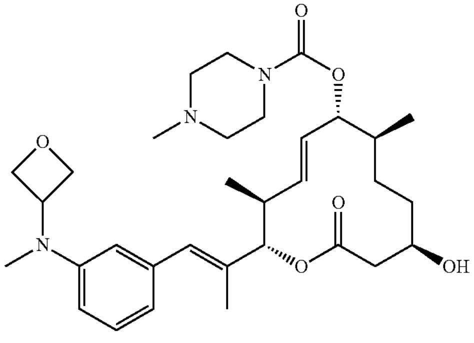 [(2S,3S,4E,6R,7S,10R)-10-hydroxy-3,7-dimethyl-2-[(E)-1-[3-[methyl(oxetan-3-yl)amino]phenyl]prop-1-en-2-yl]-12-oxo-1-oxacyclododec-4-en-6-yl] 4-methylpiperazine-1-carboxylate | $^1$H NMR (400 MHz, $CDCl_3$) δ ppm 1.02 (t, J = 7.22 Hz, 6 H) 1.24-1.31 (m, 2 H) 1.45-1.55 (m, 3 H) 1.77-1.86 (m, 1 H) 1.90 (d, J = 1.13 Hz, 3 H) 1.93-2.00 (m, 1 H) 2.27-2.46 (m, 6 H) 2.53-2.70 (m, 3 H) 2.92 (s, 3 H) 3.40-3.60 (m, 4 H) 3.67-3.81 (m, 1 H) 4.60-4.70 (m, 1 H) 4.76 (t, J = 6.15 Hz, 2 H) 4.83-5.03 (m, 3 H) 5.30 (d, J = 10.67 Hz, 1 H) 5.42 (dd, J = 15.00, 9.85 Hz, 1 H) 5.63 (dd, J = 14.81, 10.16 Hz, 1 H) 6.55 (d, J = 7.03 Hz, 3 H) 6.79 (d, J = 7.65 Hz, 1 H) 7.19-7.26 (m, 1 H). LCMS: 570.6 [M + H]$^+$ |

Procedure 25.

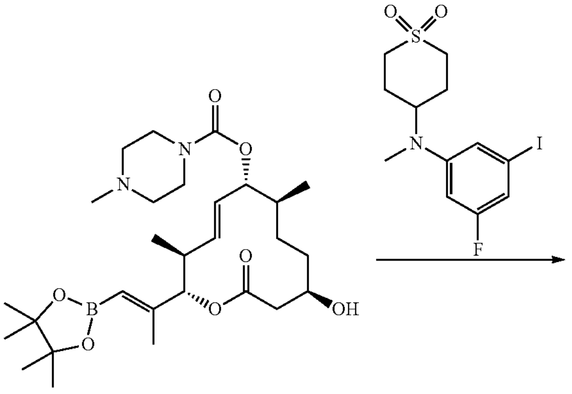

Boronate 1

-continued

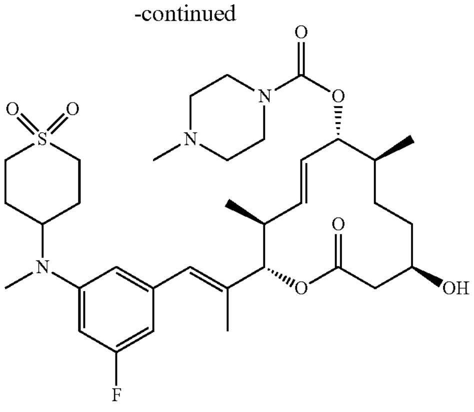

Ex. 172

A solution of Boronate 1 (11 mg, 0.021 mmol) and 4-((3-fluoro-5-iodophenyl)(methyl)amino)tetrahydro-2H-thiopyran 1,1-dioxide (11.83 mg, 0.031 mmol)) in 1,4-dioxane (1.0 mL) was charged into a 4 mL vial with a magnetic stir bar. The solution was degassed for 5 minutes. Silver(N) oxide (14.31 mg, 0.062 mmol) and palladium tetrakis (2.38 mg, 0.0021 mmol) were added. The resulting dispersion was heated to 80° C. and stirred for 3 hours. The vial was cooled to room temperature, filtered through a plug of celite, washed with 15 mL EtOAc, and concentrated under vacuum. The crude product was purified by reverse phase chromatography (MeCN/$H_2O$ w/ 0.100 formic acid) and lyophilized to obtain Example 172 (5.1 mg, 0.0077 mmol, 3722).

Compounds 172-176 were synthesized according to the general methods of Procedure 25:

TABLE 8

Characterization of Compounds 172-176

| Ex. | Structure and IUPAC Chemical Name | Characterization |
| --- | --- | --- |
| 172 | 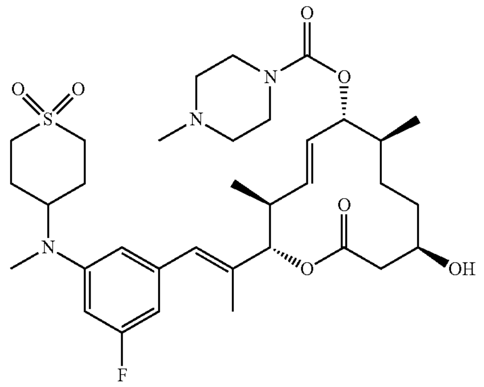 [(2S,3S,4E,6R,7S,10R)-2-[(E)-1-[3-[(1,1-dioxothian-4-yl)-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.96-1.08 (m, 6 H) 1.19-1.34 (m, 2 H) 1.43-1.52 (m, 1 H) 1.71-1.88 (m, 2 H) 1.90 (d, J =1.00 Hz, 3 H) 1.92-2.02 (m, 1 H) 2.06-2.18 (m, 2 H) 2.25-2.75 (m, 12 H) 2.82 (s, 3 H) 3.10-3.24 (m, 4 H) 3.28-3.45 (m, 1 H) 3.45-3.68 (m, 3 H) 3.68-3.88 (m, 2 H) 4.83-4.96 (m, 1 H) 5.20-5.34 (m, 1 H) 5.35-5.49 (m, 1 H) 5.54-5.68 (m, 1 H) 6.31-6.59 (m, 4 H). LCMS: 664.6 [M + H]$^+$ |
| 173 | 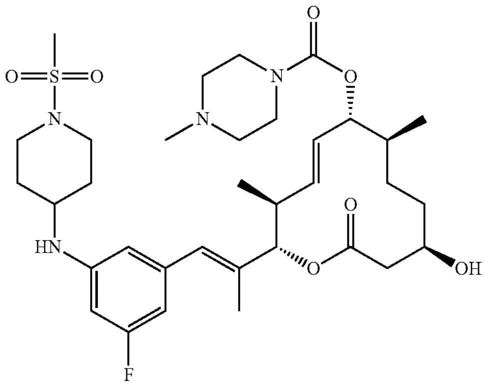 [(2S,3S,4E,6R,7S,10R)-2-[(E)-1-[3-fluoro-5-[(1-methylsulfonylpiperidin-4-yl)amino]phenyl]prop-1-en-2-yl]-10-hydroxy-3,7-dimethyl-12-oxo-1-oxacyclododec-4-en-6-yl] 4-methylpiperazine-1-carboxylate | LCMS: 679.6 [M +H]$^+$ |

TABLE 8-continued

| Characterization of Compounds 172-176 | | |
|---|---|---|
| Ex. | Structure and IUPAC Chemical Name | Characterization |
| 174 | 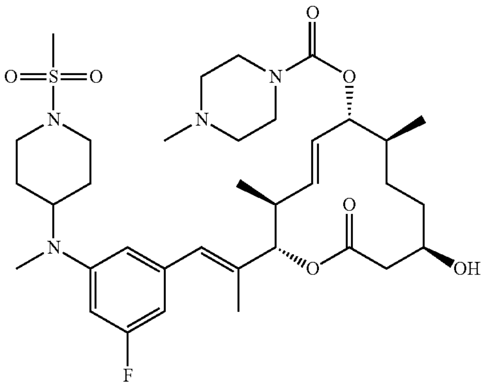 [(2S,3S,4E,6R,7S,10R)-2-[(E)-1-[3-fluoro-5-[methyl-(1-methylsulfonylpiperidin-4-yl)amino]phenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 1.02 (t, J = 7.40 Hz, 6 H) 1.24-1.32 (m, 2 H) 1.46-1.53 (m, 2 H) 1.84-1.89 (m, 3 H) 1.90 (s, 4 H) 1.93-1.96 (m, 1 H) 2.30-2.47 (m, 5 H) 2.52-2.72 (m, 5 H) 2.80 (s, 5 H) 2.85 (s, 3 H) 3.33-3.42 (m, 1 H) 3.47-3.60 (m, 3 H) 3.61-3.81 (m, 3 H) 3.98 (br d, J = 10.54 Hz, 2 H) 4.91 (t, J = 9.79 Hz, 1 H) 5.28 (d, J = 10.54 Hz, 1 H) 5.42 (dd, J = 15.18, 9.41 Hz, 1 H) 5.62 (dd, J = 14.74, 9.60 Hz, 1 H) 6.35-6.47 (m, 3 H) 6.53 (s, 1 H). LCMS: 693.7 [M + H]$^+$ |
| 175 | 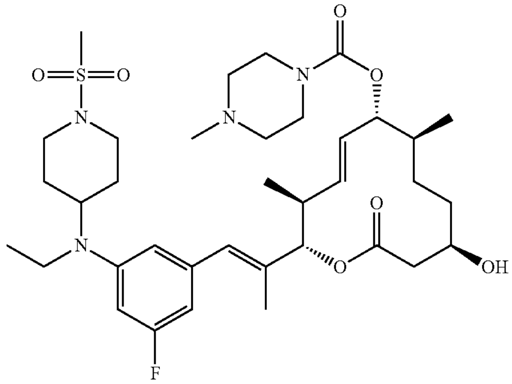 [(2S,3S,4E,6R,7R,10S)-2-[(E)-1-[3-[ethyl-(1-methylsulfonylpiperidin-4-yl)amino]-5-fluorophenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.91 (dd, J = 8.85, 6.84 Hz, 6 H) 1.08 (t, J = 7.03 Hz, 3 H) 1.13-1.22 (m, 2 H) 1.35-1.46 (m, 2 H) 1.64-1.79 (m, 5 H) 1.79-1.89 (m, 6 H) 2.32 (br dd, J = 3.58, 1.57 Hz, 3 H) 2.41-2.61 (m, 5 H) 2.69 (br d, J = 11.04 Hz, 2 H) 2.74 (s, 3 H) 3.18 (q, J = 7.07 Hz, 2 H) 3.40-3.59 (m, 5 H) 3.61-3.71 (m, 1 H) 3.82-3.92 (m, 2 H) 4.81 (t, J = 10.04 Hz, 1 H) 5.18 (d, J = 10.54 Hz, 1 H) 5.31 (dd, J = 15.25, 9.47 Hz, 1 H) 5.52 (dd, J = 14.93, 10.04 Hz, 1 H) 6.19-6.33 (m, 3 H) 6.41 (s, 1 H). LCMS: 707.5 [M + H]$^+$ |
| 176 | 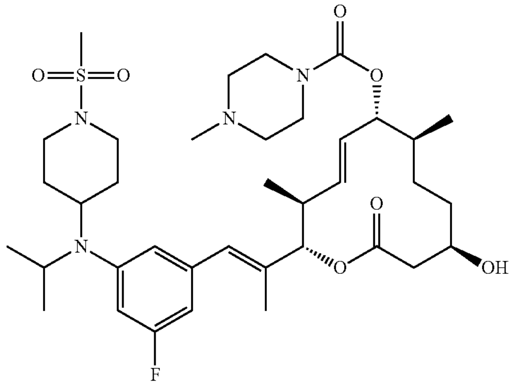 [(2S,3S,4E,6R,7R,10S)-2-[(E)-1-[3-fluoro-5-[(1-methylsulfonylpiperidin-4-yl)-propan-2-ylamino]phenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.92 (t, J = 6.46 Hz, 6 H) 1.12 (d, J = 6.65 Hz, 6 H) 1.15-1.22 (m, 2 H) 1.35-1.44 (m, 2 H) 1.65-1.79 (m, 4 H) 1.81 (d, J = 1.13 Hz, 3 H) 1.82-1.90 (m, 2 H) 2.33-2.60 (m, 8 H) 2.68 (s, 3 H) 2.72 (s, 3 H) 3.23-3.33 (m, 2 H) 3.46-3.71 (m, 6 H) 3.76 (br d, J = 11.29 Hz, 2 H) 4.81 (t, J = 10.10 Hz, 1 H) 5.18 (d, J = 10.79 Hz, 1 H) 5.31 (dd, J = 14.93, 9.66 Hz, 1 H) 5.52 (dd, J = 15.00, 9.98 Hz, 1 H) 6.34-6.56 (m, 4 H). LCMS: 721.7 [M + H]$^+$ |

Synthesis of Piperidine Intermediates: Procedure 26.

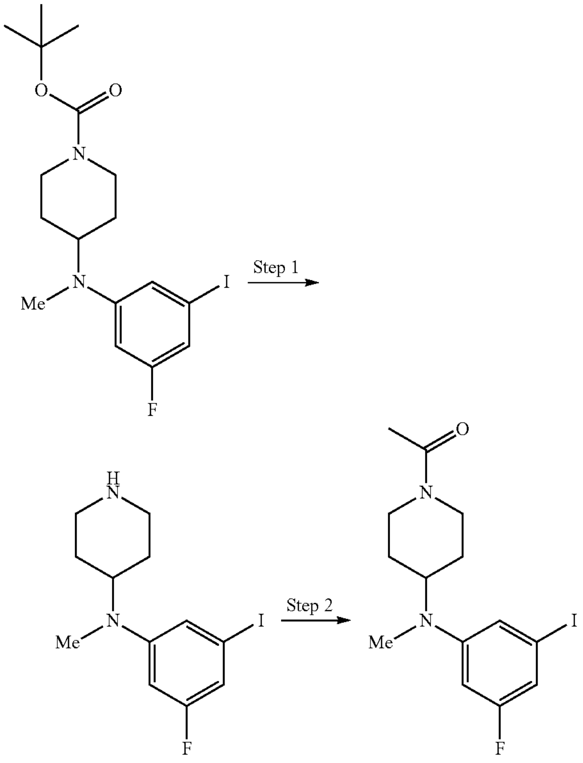

050

051

Step 1: A solution of tert-butyl 4-((3-fluoro-5-iodophenyl)(methyl)amino)piperidine-1-carboxyl ate (590 mg, 1.359 mmol) in methanol (15 mL, 370.765 mmol) was charged into a 50 mL round bottom flask with a magnetic stir bar. HCl (4.0M in dioxane, 1.698 mL, 6.793 mmol) was added, the resulting solution was stirred overnight at room temperature. Solvents were evaporated under vacuum to obtain N-(3-fluoro-5-iodophenyl)-N-methylpiperidin-4-amine HCl (050) (500 mg, 1.349 mmol, 99%). LCMS: 335.1 $[M+H]^+$.

Step 2: A solution of N-(3-fluoro-5-iodophenyl)-N-methylpiperidin-4-amine HCl (050) (50 mg, 0.135 mmol) in dichloromethane (2 mL) was charged into a 5 mL vial with a magnetic stir bar. N-ethyl-N-isopropylpropan-2-amine (0.059 mL, 0.337 mmol) was added then acetyl chloride (0.014 mL, 0.202 mmol). The resulting solution was stirred overnight at room temperature. The solution was partitioned between water (10 mL) and DCM (10 mL), extracted with DCM (3x10 mL), and the combined organic layers were washed with water (10 mL), dried with MgSO4, filtered and evaporated under vacuum. The crude product was dry loaded onto 2 g silica and purified by column chromatography (ISCO normal phase, 24 g. gold column, 0-100% EtOAc/hexanes gradient) to obtain 1-(4-((3-fluoro-5-iodophenyl)(methyl)amino)piperidin-1-yl)ethan-1-one (051) (24 mg, 0.064 mmol, 47%). $^1H$ NMR (400 MHz, $CDCl_3$) δ ppm 1.61-1.73 (m, 2H) 1.74-1.90 (m, 2H) 2.15 (s, 3H) 2.62 (td, J=12.77, 2.45 Hz, 1H) 2.75 (s, 3H) 3.11-3.24 (m, 1H) 3.63-3.80 (m, 1H) 3.95 (br dd, J=13.55, 2.38 Hz, 1H) 4.76-4.87 (m, 1H) 6.44 (dt, J=12.58, 2.18 Hz, 1H) 6.82 (dt, J=7.53, 1.69 Hz, 1H) 6.89 (s, 1H). LCMS: 377.2 $[M+H]^+$.

The following intermediates were also synthesized according to the general methods in Procedure 26:

TABLE 9

Characterization of intermediates synthesized according to Procedure 26

| Intermediate | Characterization |
|---|---|
| 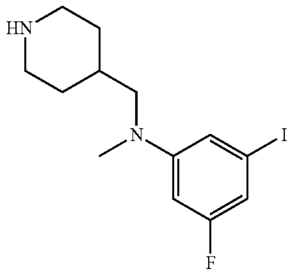 3-fluoro-5-iodo-N-methyl-N-(piperidin-4-ylmethyl)aniline | Carried forward without further purification. LCMS: 349.0 $[M + H]^+$. |

TABLE 9-continued

| Characterization of intermediates synthesized according to Procedure 26 | |
|---|---|
| Intermediate | Characterization |
| 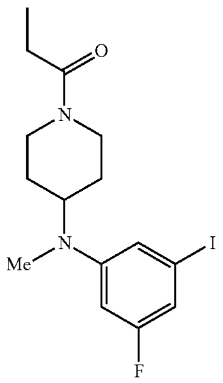 1-(4-((3-fluoro-5-iodophenyl)(methyl)amino)piperidin-1-yl)propan-1-one | $^1$H NMR (400 MHz, $CDCl_3$) δ ppm 1.19 (t, J = 7.47 Hz, 3 H) 1.59-1.72 (m, 2 H) 1.73-1.89 (m, 2 H) 2.40 (q, J = 7.40 Hz, 2 H) 2.52-2.68 (m, 1 H) 2.75 (s, 3 H) 3.13 (br t, J = 13.05 Hz, 1 H) 3.62-3.79 (m, 1 H) 3.92-4.10 (m, 1 H) 4.77-4.95 (m, 1 H) 6.44 (br d, J = 12.55 Hz, 1 H) 6.81 (d, J = 7.65 Hz, 1 H) 6.89 (s, 1 H). LCMS: 391.2 $[M + H]^+$. |
| 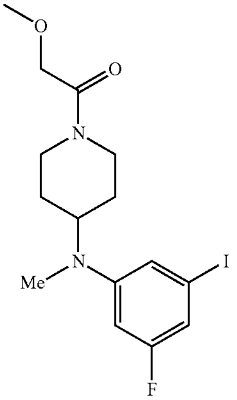 1-(4-((3-fluoro-5-iodephenyl)(methyl)amino)piperidin-1-yl)-2-methoxyethan-1-one | $^1$H NMR (400 MHz, $CDCl_3$) δ ppm 1.69 (qd, J = 12.42, 4.39 Hz, 2 H) 1.76-1.88 (m, 2 H) 2.67 (br t, J = 12.42 Hz, 1 H) 2.75 (s, 3 H) 3.12 (br s, 1 H) 3.47 (s, 3 H) 3.66-3.81 (m, 1 H) 4.01-4.22 (m, 3 H) 4.78 (br d, J = 13.30 Hz, 1 H) 6.43 (dt, J = 12.58, 2.24 Hz, 1 H) 6.77-6.84 (m, 1 H) 6.88 (s, 1 H). LCMS: 407.2 $[M + H]^+$. |
| 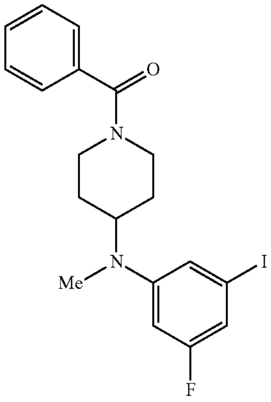 (4-((3-fluoro-5-iodophenyl)(methyl)amino)piperidin-1-yl)(phenyl)methanone | $^1$H NMR (400 MHz, $CDCl_3$) δ ppm 1.64-1.97 (m, 4 H) 2.79 (s, 3 H) 2.83-3.26 (m, 2 H) 3.68-3.83 (m, 1 H) 3.84-4.05 (m, 1 H) 4.78-5.05 (m, 1 H) 6.46 (br d, J = 12.55 Hz, 1 H) 6.83 (d, J = 7.53 Hz, 1 H) 6.91 (s, 1 H) 7.45 (s, 5 H). LCMS: 439.7 $[M + H]^+$. |

TABLE 9-continued

| Characterization of intermediates synthesized according to Procedure 26 | |
|---|---|
| Intermediate | Characterization |
| 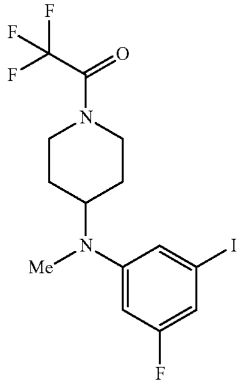 2,2,2-trifluoro-1-(4-((3-fluoro-5-iodophenyl)(methyl)amino)piperidin-1-yl)ethan-1-one | $^1$H NMR (400 MHz, $CDCl_3$) δ ppm 1.68-1.83 (m, 2 H) 1.85-1.96 (m, 2 H) 2.76 (s, 3 H) 2.86 (br t, J = 12.30 Hz, 1 H) 3.17-3.33 (m, 1 H) 3.73-3.87 (m, 1 H) 4.17 (br dd, J = 13.87, 1.94 Hz, 1 H) 4.74 (ddt, J = 13.52, 4.39, 2.34, 2.34 Hz, 1 H) 6.44 (d, J = 12.42 Hz, 1 H) 6.79-6.87 (m, 1 H) 6.89 (s, 1 H). LCMS: 431.7 [M + H]$^+$. |
| 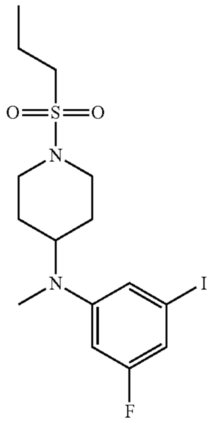 N-(3-fluoro-5-iodophenyl)-N-methyl-1-(propysulfonyl)piperidin-4-amine | $^1$H NMR (400 MHz, $CDCl_3$) δ ppm 1.10 (t, J = 7.47 Hz, 3 H) 1.77-1.96 (m, 6 H) 2.78 (s, 3 H) 2.84-2.98 (m, 4 H) 3.56-3.67 (m, 1 H) 3.98 (dt, J = 12.45, 2.12 Hz, 2 H) 6.41 (dt, J = 12.61, 2.16 Hz, 1 H) 6.80 (dt, J = 7.53, 1.69 Hz, 1 H) 6.86 (s, 1 H). LCMS: 441.7 [M + H]$^+$. |
| 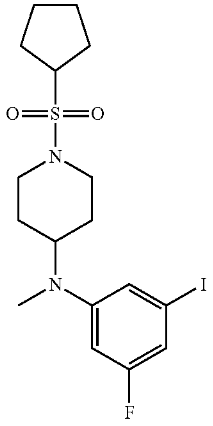 1-(cyclopentylsufonyl)-N-(3-fluoro-5-iodophenyl)-N-methylpiperidin-4-amine | $^1$H NMR (400 MHz, $CDCl_3$) δ ppm 1.59-1.73 (m, 2 H) 1.77-1.94 (m, 6 H) 1.98-2.08 (m, 4 H) 2.78 (s, 3 H) 2.88-3.01 (m, 2 H) 3.47 (quin, J = 8.16 Hz, 1 H) 3.55-3.68 (m, 1 H) 4.00 (dt, J = 12.61, 2.16 Hz, 2 H) 6.42 (dt, J = 12.55, 2.26 Hz, 1 H) 6.78-6.83 (m, 1 H) 6.87 (s, 1 H). LCMS: 467.2 [M + H]$^+$. |

TABLE 9-continued

| Characterization of intermediates synthesized according to Procedure 26 | |
|---|---|
| Intermediate | Characterization |
| 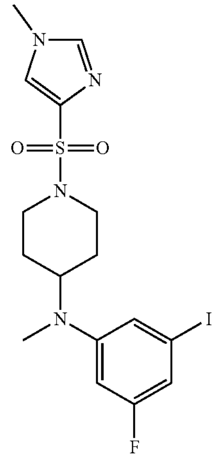 N-(3-fluoro-5-iodophenyl)-N-methyl-1-((1-methyl-1H-imidazol-4-yl)sulfonyl)piperidin-4-amine | $^1$H NMR (400 MHz, $CDCl_3$) δ ppm 1.72-1.82 (m, 2 H) 1.92 (qd, J = 12.36, 4.20 Hz, 2 H) 2.69-2.82 (m, 5 H) 3.50 (tt, J = 11.75, 3.87 Hz, 1 H) 3.81 (s, 3 H) 4.03 (dt, J = 12.20, 2.12 Hz, 2 H) 6.36 (dt, J = 12.67, 2.26 Hz, 1 H) 6.75-6.79 (m, 1 H) 6.82 (s, 1 H) 7.48 (d, J = 1.38 Hz, 1 H) 7.55 (d, J = 1.13 Hz, 1 H). LCMS: 479.2 $[M + H]^+$. |
| 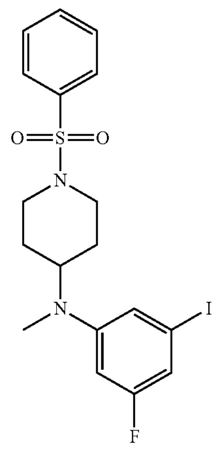 N-(3-fluoro-5-iodophenyl)-N-methyl-1-(phenylsulfonyl)piperidin-4-amine | $^1$H NMR (400 MHz, $CDCl_3$) δ ppm 1.73-1.82 (m, 2 H) 1.91 (qd, J = 12.36, 4.33 Hz, 2 H) 2.39 (td, J = 12.14, 2.57 Hz, 2 H) 2.75 (s, 3 H) 3.42 (tt, J = 11.70, 3.86 Hz, 1 H) 3.99 (dt, J = 11.89, 2.15 Hz, 2 H) 6.34 (dt, J = 12.55, 2.26 Hz, 1 H) 6.73-6.82 (m, 2 H) 7.55-7.63 (m, 2 H) 7.64-7.71 (m, 1 H) 7.78-7.85 (m, 2 H). LCMS: 475.1 $[M + H]^+$. |
| 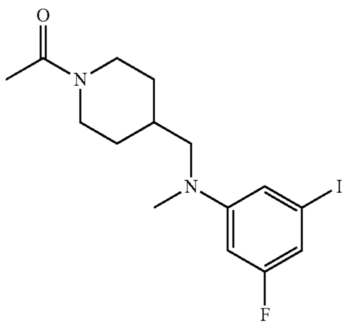 1-(4-(((3-fluoro-5-iodophenyl)(methyl)amino)methyl)piperidin-1-yl)ethan-1-one | $^1$H NMR (400 MHz, $CDCl_3$) δ ppm 1.09-1.25 (m, 2 H) 1.74 (br s, 2 H) 1.97 (ddd, J = 11.48, 7.72, 4.02 Hz, 1 H) 2.11 (s, 3 H) 2.52 (br t, J = 11.98 Hz, 1 H) 2.96 (s, 3 H) 2.98-3.13 (m, 1 H) 3.18 (d, J = 7.28 Hz, 2 H) 3.86 (br d, J = 13.43 Hz, 1 H) 4.69 (br d, J = 12.42 Hz, 1 H) 6.30 (dt, J = 12.67, 2.26 Hz, 1 H) 6.73-6.81 (m, 2 H). LCMS: 391.0 $[M + H]^+$. |

TABLE 9-continued

| Characterization of intermediates synthesized according to Procedure 26 | |
|---|---|
| Intermediate | Characterization |
| 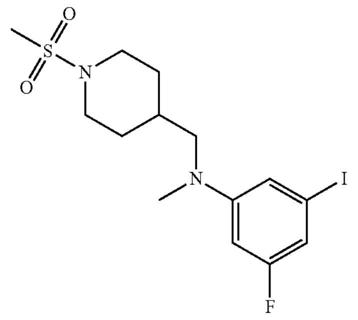 3-fluoro-5-iodo-N-methyl-N-((1-(methylsulfonyl)piperidin-4-yl)methyl)aniline | $^1H$ NMR (400 MHz, $CDCl_3$) δ ppm 1.33-1.49 (m, 2 H) 1.73-1.92 (m, 3 H) 2.64 (td, J = 12.11, 2.38 Hz, 2 H) 2.79 (s, 3 H) 2.97 (s, 3 H) 3.21 (d, J = 7.03 Hz, 2 H) 3.80-3.94 (m, 2 H) 6.30 (dt, J = 12.52, 2.21 Hz, 1 H) 6.71-6.80 (m, 2 H). LCMS: 427.0 $[M + H]^+$. |

Compounds 177-187 were generated from the above intermediates using the general methods of Procedures 23, 24, and 25:

TABLE 10

| Characterization of Compounds 177-187 | | |
|---|---|---|
| Ex. | Structure and IUPAC Chemical Name | Characterization |
| 177 | 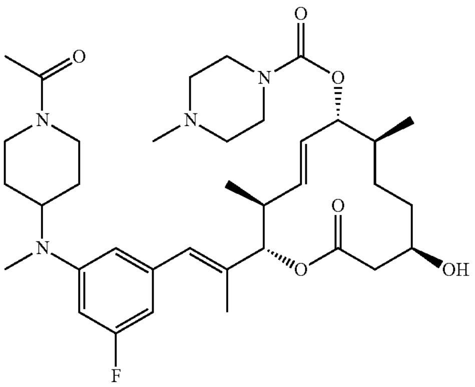 [(2S,3S,4E,6R,7S,10R)-2-[(E)-1-[3-[(1-acetylpiperidin-4-yl)-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate | $^1H$ NMR (400 MHz, $CDCl_3$) δ ppm 0.92 (t, J = 6.59 Hz, 6 H) 1.15-1.21 (m, 2 H) 1.37-1.43 (m, 2 H) 1.51-1.65 (m, 4 H) 1.66-1.77 (m, 4 H) 1.80 (d, J = 1.00 Hz, 3 H) 1.83-1.91 (m, 1 H) 2.05 (s, 3 H) 2.21-2.38 (m, 4 H) 2.42-2.60 (m, 6 H) 2.66 (s, 3 H) 3.01-3.14 (m, 1 H) 3.29 (br d, J = 10.29 Hz, 1 H) 3.59-3.74 (m, 3 H) 3.80-3.90 (m, 1 H) 4.71 (br dd, J = 14.93, 2.64 Hz, 1 H) 4.81 (t, J = 10.16 Hz, 1 H) 5.18 (d, J = 10.67 Hz, 1 H) 5.31 (dd, J = 15.06, 9.79 Hz, 1 H) 5.52 (dd, J = 15.00, 10.10 Hz, 1 H) 6.24-6.35 (m, 3 H) 6.43 (s, 1 H). LCMS: 657.5 $[M + H]^+$ |

TABLE 10-continued

| Characterization of Compounds 177-187 | | |
|---|---|---|
| Ex. | Structure and IUPAC Chemical Name | Characterization |
| 178 | 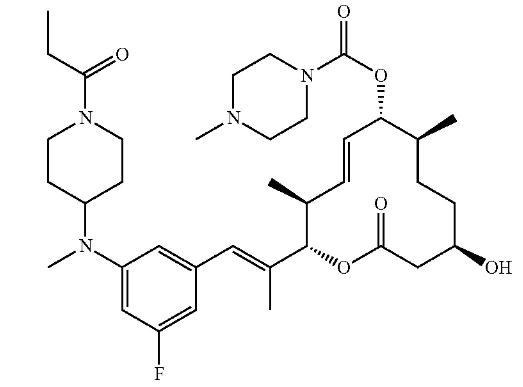 [(2S,3S,4E,6R,7R,10S)-2-[(E)-1-[3-fluoro-5-[methyl-(1-propanoylpiperidin-4-yl)amino]phenyl]prop-1-en-2-yl]-10-hydroxy-3,7-dimethyl-12-oxo-1-oxacyclododec-4-en-6-yl] 4-methylpiperazine-1-carboxylate | $^{1}$H NMR (400 MHz, $CDCl_3$) δ ppm 0.91 (t, J = 6.96 Hz, 6 H) 1.09 (t, J = 7.47 Hz, 3 H) 1.13-1.22 (m, 2 H) 1.34-1.46 (m, 2 H) 1.57-1.63 (m, 2 H) 1.64-1.76 (m, 4 H) 1.80 (d, J = 1.13 Hz, 3 H) 1.82-1.90 (m, 1 H) 2.30 (br d, J = 7.40 Hz, 7 H) 2.41-2.60 (m, 6 H) 2.66 (s, 3 H) 2.97-3.09 (m, 1 H) 3.38-3.58 (m, 3 H) 3.58-3.73 (m, 2 H) 3.85-3.95 (m, 1 H) 4.73 (br dd, J = 13.18, 2.13 Hz, 1 H) 4.80 (t, J = 10.04 Hz, 1 H) 5.18 (d, J = 10.67 Hz, 1 H) 5.31 (dd, J = 14.93, 9.66 Hz, 1 H) 5.52 (dd, J = 14.93, 10.04 Hz, 1 H) 6.25-6.34 (m, 3 H) 6.42 (s, 1 H). LCMS: 671.6 $[M + H]^+$ |
| 179 | 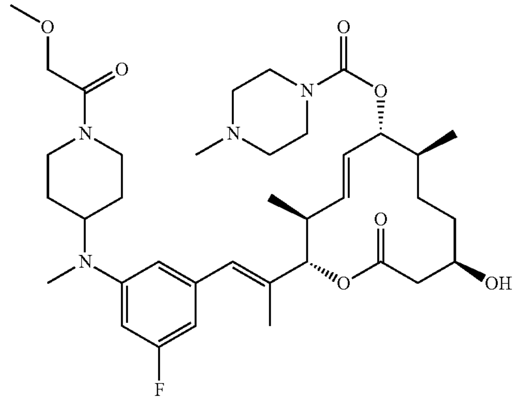 [(2S,3S,4E,6R,7R,10S)-2-[(E)-1-[3-fluoro-5-[[1-(2-methoxyacetyl)piperidin-4-yl]-methylamino]phenyl]prop-1-en-2-yl]-10-hydroxy-3,7-dimethyl-12-oxo-1-oxacyclododec-4-en-6-yl] 4-methylpiperazine-1-carboxylate | $^{1}$H NMR (400 MHz, $CDCl_3$) δ ppm 0.92 (t, J = 6.90 Hz, 6 H) 1.17 (br s, 2 H) 1.37-1.45 (m, 2 H) 1.56-1.65 (m, 4 H) 1.67-1.77 (m, 4 H) 1.80 (d, J = 1.00 Hz, 3 H) 1.82-1.91 (m, 1 H) 2.29-2.35 (m, 2 H) 2.43-2.61 (m, 6 H) 2.66 (s, 3 H) 2.93-3.10 (m, 1 H) 3.37 (s, 3 H) 3.38-3.59 (m, 3 H) 3.59-3.76 (m, 3 H) 3.87-3.97 (m, 1 H) 3.98-4.13 (m, 2 H) 4.63-4.72 (m, 1 H) 4.81 (t, J = 10.10 Hz, 1 H) 5.18 (d, J = 10.67 Hz, 1 H) 5.32 (dd, J = 15.00, 9.47 Hz, 1 H) 5.52 (dd, J = 15.12, 9.98 Hz, 1 H) 6.25-6.34 (m, 3 H) 6.43 (s, 1 H). LCMS: 687.6 $[M + H]^+$ |
| 180 | 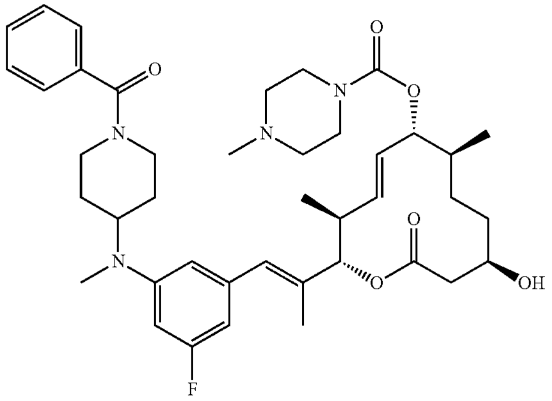 [(2S,3S,4E,6R,7S,10R)-2-[(E)-1-[3-[(1-benzoylpiperidin-4-yl)-methylamino]-5-fluorophenyl]prop-1-en-2-yl]-10-hydroxy-3,7-dimethyl-12-oxo-1-oxacyclododec-4-en-6-yl] 4-methyl-piperazine-1-carboxylate | $^{1}$H NMR (400 MHz, $CDCl_3$) δ ppm 0.92 (t, J = 7.47 Hz, 6 H) 1.12-1.23 (m, 2 H) 1.35-1.46 (m, 2 H) 1.55-1.77 (m, 6 H) 1.80 (s, 3 H) 1.82-1.92 (m, 1 H) 2.18-2.41 (m, 6 H) 2.41-2.63 (m, 4 H) 2.70 (s, 3 H) 2.94-3.11 (m, 1 H) 3.20-3.34 (m, 1 H) 3.35-3.55 (m, 3 H) 3.60-3.92 (m, 3 H) 4.81 (t, J = 10.04 Hz, 2 H) 5.18 (d, J = 10.54 Hz, 1 H) 5.31 (dd, J = 15.12, 9.60 Hz, 1 H) 5.52 (dd, J = 15.06, 10.16 Hz, 1 H) 6.25-6.35 (m, 3 H) 6.43 (s, 1 H) 7.34 (s, 5 H). LCMS: 719.8 $[M + H]^+$ |

TABLE 10-continued

| Characterization of Compounds 177-187 | | |
|---|---|---|
| Ex. | Structure and IUPAC Chemical Name | Characterization |
| 181 | 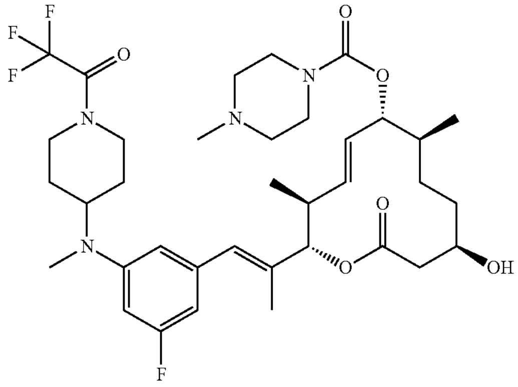 [(2S,3S,4E,6R,7S,10R)-2-[(E)-1-[3-fluoro-5-[methyl-[1-(2,2,2-trifluoroacetyl)piperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | $^1H$ NMR (400 MHz, $CDCl_3$) δ ppm 0.92 (t, J = 6.96 Hz, 6 H) 1.14-1.24 (m, 2 H) 1.37-1.46 (m, 1 H) 1.64-1.75 (m, 4 H) 1.80 (d, J = 1.25 Hz, 5 H) 1.84-1.89 (m, 1 H) 2.31 (br s, 3 H) 2.36-2.62 (m, 7 H) 2.67 (s, 3 H) 2.70-2.82 (m, 1 H) 3.14 (br t, J = 12.42 Hz, 1 H) 3.50 (br dd, J = 5.83, 2.95 Hz, 4 H) 3.61-3.67 (m, 1 H) 3.68-3.79 (m, 1 H) 3.99-4.14 (m, 1 H) 4.63 (br d, J = 13.55 Hz, 1 H) 4.81 (t, J = 10.10 Hz, 1 H) 5.18 (d, J = 10.67 Hz, 1 H) 5.32 (dd, J = 14.93, 9.66 Hz, 1 H) 5.52 (dd, J = 15.00, 9.85 Hz, 1 H) 6.26-6.37 (m, 3 H) 6.43 (s, 1 H). LCMS: 711.7 $[M + H]^+$ |
| 182 | 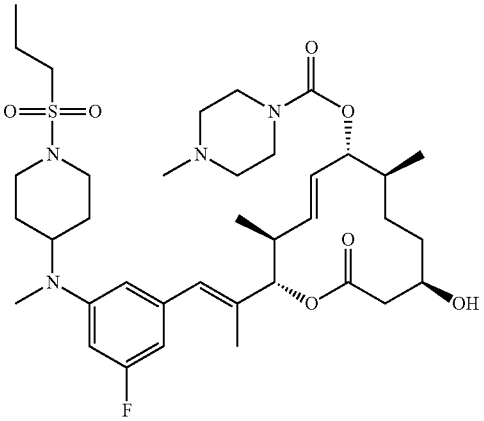 [(2S,3S,4E,6R,7R,10S)-2-[(E)-1-[3-fluoro-5-[methyl-(1-propylsulfonylpiperidin-4-yl)amino]phenyl]prop-1-en-2-yl]-10-hydroxy-3,7-dimethyl-12-oxo-1-oxacyclododec-4-en-6-yl] 4-methylpiperazine-1-carboxylate | $^1H$ NMR (400 MHz, $CDCl_3$) δ ppm 0.92 (dd, J = 8.34, 6.84 Hz, 6 H) 1.00 (t, J = 7.47 Hz, 3 H) 1.15-1.20 (m, 2 H) 1.37-1.47 (m, 2 H) 1.69-1.78 (m, 7 H) 1.80 (s, 5 H) 1.82-1.90 (m, 1 H) 2.24-2.30 (m, 1 H) 2.32-2.40 (m, 3 H) 2.44-2.61 (m, 4 H) 2.69 (s, 3 H) 2.82 (s, 5 H) 3.43-3.51 (m, 3 H) 3.54-3.60 (m, 1 H) 3.61-3.70 (m, 1 H) 3.87 (br d, J = 11.17 Hz, 2 H) 4.81 (t, J = 10.10 Hz, 1 H) 5.18 (d, J = 10.67 Hz, 1 H) 5.32 (dd, J = 15.06, 9.66 Hz, 1 H) 5.52 (dd, J = 15.00, 9.98 Hz, 1 H) 6.23-6.34 (m, 3 H) 6.42 (s, 1 H). LCMS: 721.7 $[M + H]^+$ |
| 183 | 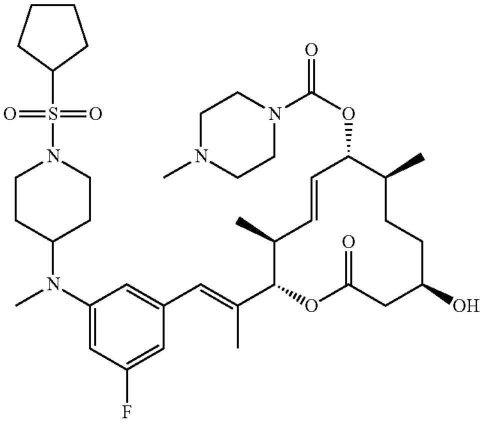 [(2S,3S,4E,6R,7S,10R)-2-[(E)-1-[3-[(1-cyclopentylsulfonylpiperidin-4-yl)-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate | $^1H$ NMR (400 MHz, $CDCl_3$) δ ppm 1.02 (dd, J = 6.59, 5.21 Hz, 6 H) 1.27-1.31 (m, 2 H) 1.44-1.50 (m, 2 H) 1.78-1.86 (m, 8 H) 1.90 (s, 3 H) 1.93-1.97 (m, 1 H) 2.00-2.07 (m, 4 H) 2.52-2.63 (m, 5 H) 2.64-2.75 (m, 3 H) 2.79 (s, 3 H) 2.88-3.02 (m, 2 H) 3.33-3.56 (m, 4 H) 3.73 (s, 6 H) 3.96-4.05 (m, 2 H) 4.91 (t, J = 9.98 Hz, 1 H) 5.29 (d, J = 10.67 Hz, 1 H) 5.37-5.46 (m, 1 H) 5.63 (dd, J = 15.12, 10.10 Hz, 1 H) 6.34-6.44 (m, 3 H) 6.53 (s, 1 H). LCMS: 747.7 $[M + H]^+$ |

TABLE 10-continued

| Characterization of Compounds 177-187 | | |
|---|---|---|
| Ex. | Structure and IUPAC Chemical Name | Characterization |
| 184 | 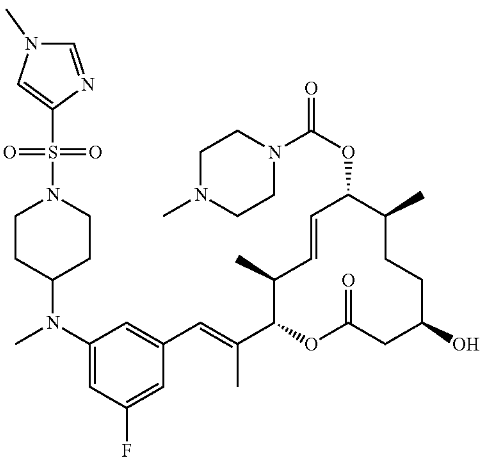 [(2S,3S,4E,6R,7S,10R)-2-[(E)-1-[3-fluoro-5-[methyl-[1-(1-methylimidazol-4-yl)sulfonylpiperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.91 (dd, J = 10.98, 6.84 Hz, 6 H) 1.12-1.21 (m, 2 H) 1.35-1.45 (m, 2 H) 1.61-1.75 (m, 4 H) 1.78 (d, J = 1.00 Hz, 3 H) 1.80-1.90 (m, 2 H) 2.22-2.38 (m, 3 H) 2.44-2.65 (m, 6 H) 2.68 (s, 3 H) 3.25-3.37 (m, 1 H) 3.39-3.57 (m, 4 H) 3.39-3.53 (m, 3 H) 3.60-3.66 (m, 1 H) 3.70 (s, 3 H) 3.88-3.98 (m, 2 H) 4.81 (t, J = 10.04 Hz, 1 H) 5.16 (d, J = 10.54 Hz, 1 H) 5.31 (dd, J = 15.12, 9.47 Hz, 1 H) 5.46-5.56 (m, 1 H) 6.19-6.32 (m, 3 H) 6.39 (s, 1 H) 7.37 (d, J = 1.25 Hz, 1 H) 7.45 (s, 1 H). LCMS: 759.5 $[M + H]^+$ |
| 185 | 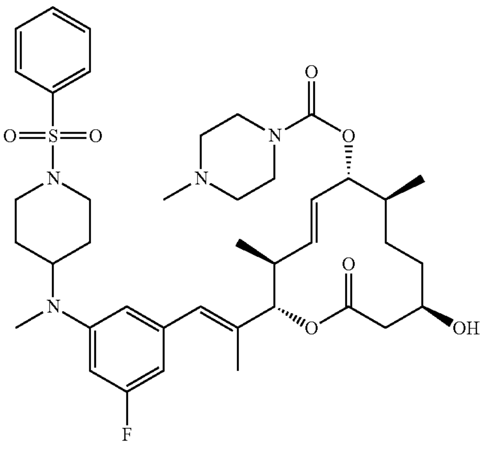 [(2S,3S,4E,6R,7S,10R)-2-[(E)-1-[3-[[1-(benzenesulfonyl)piperidin-4-yl]-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.90 (dd, J = 17.07, 6.78 Hz, 6 H) 1.17 (br d, J = 8.41 Hz, 2 H) 1.35-1.45 (m, 2 H) 1.65-1.73 (m, 4 H) 1.77 (d, J = 1.13 Hz, 3 H) 1.78-1.87 (m, 3 H) 2.20-2.38 (m, 7 H) 2.47 (m, 4 H) 2.66 (s, 3 H) 3.31-3.57 (m, 5 H) 3.59-3.70 (m, 1 H) 3.88 (br d, J = 10.54 Hz, 2 H) 4.80 (t, J = 9.98 Hz, 1 H) 5.15 (d, J = 10.67 Hz, 1 H) 5.30 (dd, J = 15.18, 9.66 Hz, 1 H) 5.44-5.57 (m, 1 H) 6.14-6.31 (m, 3 H) 6.37 (s, 1 H) 7.43-7.61 (m, 3 H) 7.67-7.76 (m, 2 H). LCMS: 755.6 $[M + H]^+$ |

TABLE 10-continued

| Characterization of Compounds 177-187 | | |
|---|---|---|
| Ex. | Structure and IUPAC Chemical Name | Characterization |
| 186 | 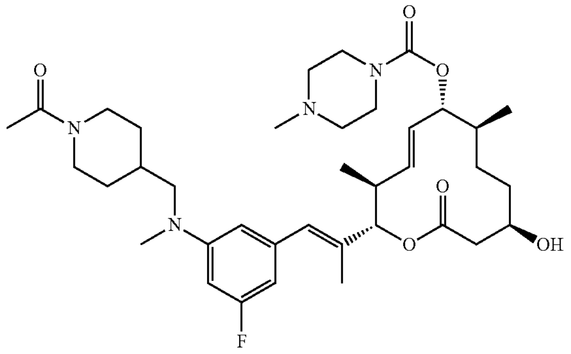 [(2S,3S,4E,6R,7S,10R)-2-[(E)-1-[3-[(1-acetylpiperidin-4-yl)methyl-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.91 (t, J = 6.27 Hz, 6 H) 1.18 (br d, J = 7.91 Hz, 2 H) 1.64-1.77 (m, 6 H) 1.80 (s, 3 H) 1.85 (br d, J = 3.01 Hz, 2 H) 2.01 (s, 3 H) 2.32-2.61 (m, 12 H) 2.87 (s, 3 H) 2.90-2.99 (m, 1 H) 3.10 (br d, J = 7.03 Hz, 2 H) 3.48-3.69 (m, 5 H) 3.70-3.81 (m, 1 H) 4.54-4.63 (m, 1 H) 4.81 (t, J = 9.91 Hz, 1 H) 5.18 (d, J = 10.79 Hz, 1 H) 5.31 (dd, J = 15.12, 9.60 Hz, 1 H) 5.52 (dd, J = 14.87, 9.98 Hz, 1 H) 6.11-6.20 (m, 2 H) 6.27 (br d, J = 8.78 Hz, 1 H) 6.42 (s, 1 H). LCMS: 671.8 $[M + H]^+$ |
| 187 | 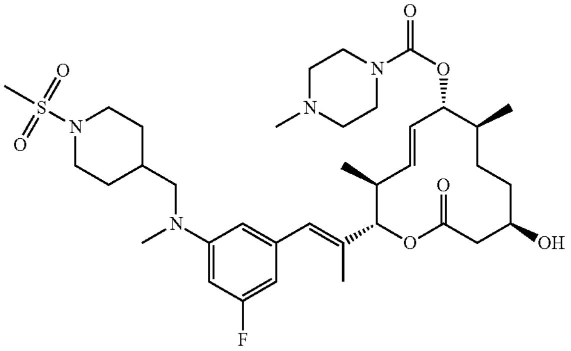 [(2S,3S,4E,6R,7S,10R)-2-[(E)-1-[3-fluoro-5-[methyl-[(1-methylsulfonylpiperidin-4-yl)methyl]amino]phenyl]prop-1-en-2-yl]-10-hydroxy-3,7-dimethyl-12-oxo-1-oxacyclododec-4-en-6-yl] 4-methylpiperazine-1-carboxylate | LCMS: 707.7 $[M + H]^+$ |

Synthesis of Piperidine Intermediates:

Procedure 27.

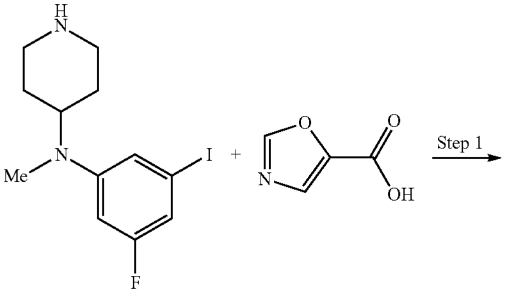

050

-continued

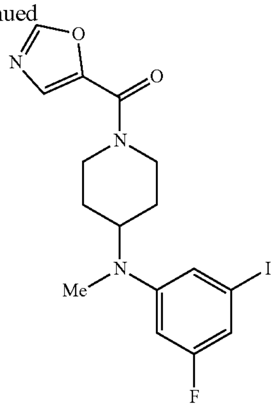

052

A solution of piperidine (050) (50 mg, 0.15 mmol) and oxazole-5-carboxylic acid (25.4 mg, 0.224 mmol) in DMF (2 mL) was charged into a 4 mL vial with a magnetic stir bar. Hunig's Base (0.078 mL, 0.449 mmol), EDC (60.2 mg, 0.314 mmol) and HOBT (48.1 mg, 0.314 mmol) were added. The resulting solution was stirred overnight at room temperature and partitioned between water (10 mL) and EtOAc (10 mL). The solution was extracted with EtOAc (3×10 mL), washed with water (10 mL), dried with $MgSO_4$, filtered, and evaporated under vacuum. The crude material was dry loaded onto 2 g. silica and purified by column chromatography (ISCO normal phase, 12 g. gold column, 0-20% MeOH/DCM gradient) to isolate (4-((3-fluoro-5-iodophenyl)(methyl)amino)piperidin-1-yl)(oxazol-5-yl)methanone (052) (24 mg, 0.056 mmol, 37%). $^1$H NMR (400 MHz, $CDCl_3$) δ ppm 1.68-1.85 (m, 2H) 1.85-1.96 (m, 2H) 2.77 (s, 3H) 2.99-3.51 (m, 2H) 3.82 (tt, J=11.56, 4.06 Hz, 1H) 4.37-5.02 (m, 2H) 6.45 (dt, J=12.55, 2.26 Hz, 1H) 6.81-6.87 (i, 1H) 6.91 (s, 1H) 7.64 (s, 1H) 7.96-8.00 (in, 1H). LCMS: 430.3 $[M+H]^+$.

The following intermediates were also synthesized according to the general methods of Procedure 27:

TABLE 11

Characterization of intermediates synthesized according to Procedure 27.

| Intermediate | Characterization |
|---|---|
| 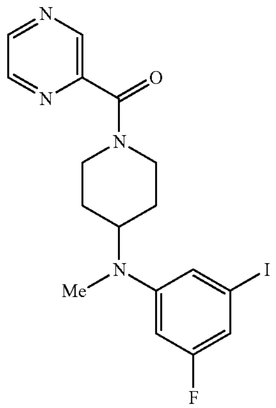 (4-((3-fluoro-5-iodophenyl)(methyl)amino)piperidin-1-yl)(pyrazin-2-yl)methanone | $^1$H NMR (400 MHz, $CDCl_3$) δ ppm 1.62-1.93 (m, 4 H) 2.70 (s, 3 H) 2.77-2.85 (m, 1 H) 3.04-3.20 (m, 1 H) 3.64-3.80 (m, 1 H) 4.03-4.16 (m, 1 H) 4.85 (br dd, J = 13.24, 2.07 Hz, 1 H) 6.36 (dt, J = 12.58, 2.24 Hz, 1 H) 6.69-6.75 (m, 1 H) 6.81 (s, 1 H) 8.49 (dd, J = 2.51, 1.51 Hz, 1 H) 8.58 (d, J = 2.64 Hz, 1 H) 8.89 (d, J = 1.51 Hz, 1 H). LCMS: 441.3 $[M + H]^+$. |

TABLE 11-continued

Characterization of intermediates synthesized according to Procedure 27.

| Intermediate | Characterization |
|---|---|
| 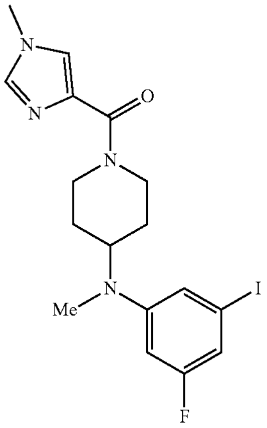 (4-((3-fluoro-5-iodophenyl)(methyl)amino)piperidin-1-yl)(1-methyl-1H-imidazol-4-yl)methanone | $^1$H NMR (400 MHz, $CDCl_3$) δ ppm 1.73-1.92 (m, 4 H) 2.76 (s, 3 H) 2.78-2.88 (m, 1 H) 3.01-3.24 (m, 1 H) 3.76 (s, 3 H) 3.77-3.84 (m, 1 H) 4.78-5.01 (m, 1 H) 5.36-5.55 (m, 1 H) 6.44 (dt, J = 12.77, 2.21 Hz, 1 H) 6.76-6.83 (m, 1 H) 6.89 (s, 1 H) 7.42-7.47 (m, 1 H) 7.55 (d, J = 1.38 Hz, 1 H). LCMS: 443.3 $[M + H]^+$. |

Compounds 188-190 were generated from the above intermediates using the general methods of Procedure 25.

TABLE 12

Characterization of Compounds 188-190

| Ex. | Structure and IUPAC Chemical Name | Characterization |
|---|---|---|
| 188 | 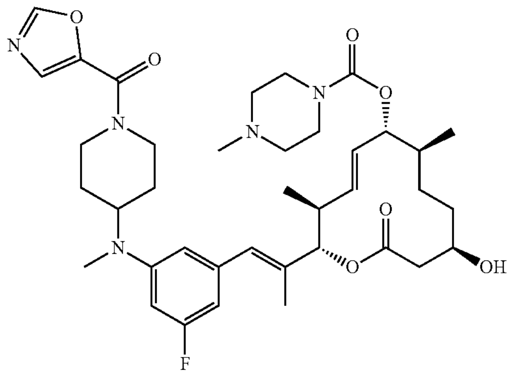 [(2S,3S,4E,6R,7S,10R)-2-[(E)-1-[3-fluoro-5-[methyl-[1-(1,3-oxazole-5-carbonyl)piperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.92 (t, J = 6.65 Hz, 7 H) 1.15-1.21 (m, 2 H) 1.38-1.44 (m, 2 H) 1.65-1.74 (m, 4 H) 1.74-1.83 (m, 6 H) 1.83-1.89 (m, 1 H) 2.25-2.43 (m, 6 H) 2.44-2.65 (m, 5 H) 2.68 (s, 3 H) 3.40-3.57 (m, 4 H) 3.58-3.70 (m, 2 H) 3.71-3.82 (m, 1 H) 4.81 (t, J = 9.91 Hz, 1 H) 5.19 (d, J = 10.79 Hz, 1 H) 5.32 (dd, J = 15.12, 9.60 Hz, 1 H) 5.44-5.59 (m, 1 H) 6.27-6.36 (m, 3 H) 6.43 (s, 1 H) 7.53 (s, 1 H) 7.88 (s, 1 H). LCMS: 710.6 $[M + H]^+$ |

TABLE 12-continued

| Characterization of Compounds 188-190 | | |
|---|---|---|
| Ex. | Structure and IUPAC Chemical Name | Characterization |
| 189 | 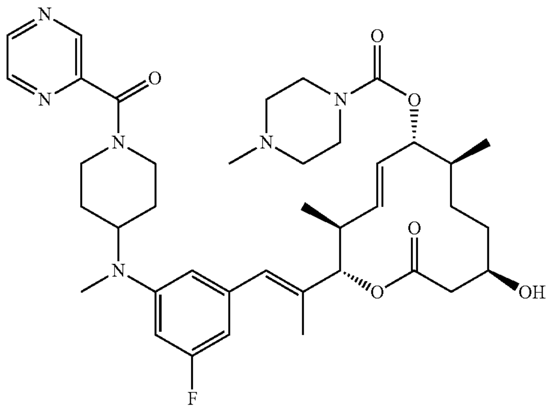 [(2S,3S,4E,6R,7S,10R)-2-[(E)-1-[3-fluoro-5-[methyl-[1-(pyrazine-2-carbonyl)piperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | $^{1}$H NMR (400 MHz, $CDCl_3$) δ ppm 0.92 (dd, J = 6.65, 4.89 Hz, 6 H) 1.14-1.21 (m, 2 H) 1.37-1.49 (m, 2 H) 1.69-1.77 (m, 4 H) 1.80 (d, J = 1.13 Hz, 5 H) 2.34-2.49 (m, 6 H) 2.52-2.63 (m, 4 H) 2.71 (s, 3 H) 2.74-2.86 (m, 1 H) 3.05-3.19 (m, 1 H) 3.50-3.69 (m, 5 H) 3.76 (s, 1 H) 4.05 (br d, J = 13.18 Hz, 1 H) 4.68-4.90 (m, 2 H) 5.18 (d, J = 10.67 Hz, 1 H) 5.31 (dd, J = 14.87, 9.60 Hz, 1 H) 5.52 (dd, J = 15.12, 10.10 Hz, 1 H) 6.33 (s, 3 H) 6.43 (s, 1 H) 8.48 (dd, J = 2.51, 1.51 Hz, 1 H) 8.57 (d, J = 2.51 Hz, 1 H) 8.88 (d, J = 1.51 Hz, 1 H). LCMS: 721.7 $[M + H]^+$ |
| 190 | 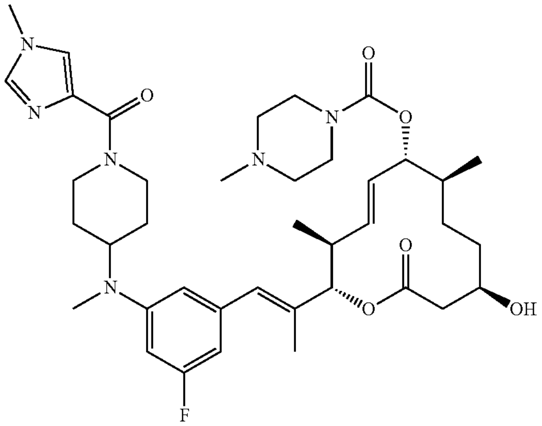 [(2S,3S,4E,6R,7S,10R)-2-[(E)-1-[3-fluoro-5-[methyl-[1-(1-methylimidazole-4-carbonyl)piperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | LCMS: 723.6 $[M + H]^+$ |

Synthesis of Piperidine Intermediates: Procedure 28.

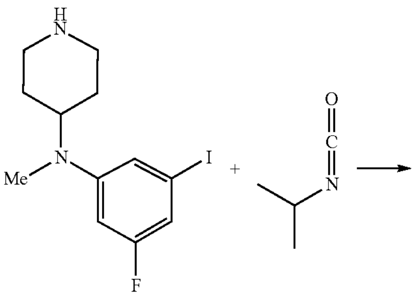

050

-continued

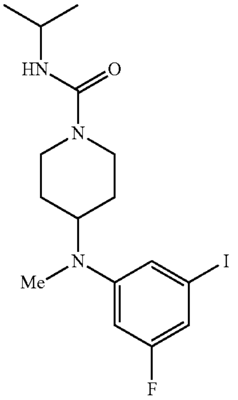

053

A solution of N-(3-fluoro-5-iodophenyl)-N-methylpiperidin-4-amine HCl (050) (50 mg, 0.135 mmol) in dichloromethane (2 mL) was charged into a 5 mL vial with a magnetic stir bar. N-ethyl-N-isopropylpropan-2-amine (0.035 mL, 0.202 mmol) then 2-isocyanatopropane (17.22 mg, 0.202 mmol) were added. The resulting solution was stirred overnight at room temperature and evaporated under vacuum. The crude product was dry loaded onto 2 g silica and purified by column chromatography (ISCO normal phase, 24 g. gold column, 0-100% EtOAc/hexanes gradient) to obtain 4-((3-fluoro-5-iodophenyl)(methyl)amino)-N-isopropylpiperidine-1-carboxamide (053) (45 mg, 0.107 mmol, 80%). $^1H$ NMR (400 MHz, $CDCl_3$) δ ppm 1.19 (d, J=6.53 Hz, 6H) 1.66-1.80 (m, 4H) 2.75 (s, 3H) 2.81-2.92 (m, 2H) 3.57-3.73 (m, 1H) 4.00 (dd, J=13.49, 6.59 Hz, 1H) 4.08 (dt, J=13.40, 2.09 Hz, 2H) 4.27 (br d, J=7.03 Hz, 1H) 6.41 (dt, J=12.67, 2.26 Hz, 1H) 6.75-6.82 (m, 1H) 6.86 (s, 1H). LCMS: 420.7 $[M+H]^+$.

The following intermediates were also synthesized according to the general methods of Procedure 28:

TABLE 13

Characterization of intermediates synthesized according to Procedure 28

| Intermediate | Characterization |
|---|---|
| 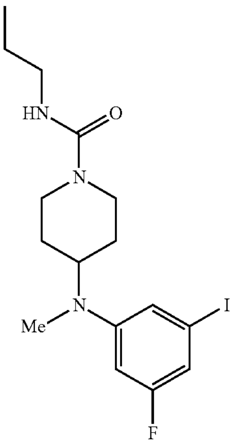 4-((3-fluoro-5-iodophenyl)(methyl)amino)-N-propylpiperidine-1-carboxamide | $^1H$ NMR (400 MHz, $CDCl_3$) δ ppm 0.96 (t, J = 7.40 Hz, 3 H) 1.53-1.60 (m, 2 H) 1.66-1.83 (m, 4 H) 2.75 (s, 3 H) 2.82-2.94 (m, 2 H) 3.19-3.30 (m, 2 H) 3.54-3.75 (m, 1 H) 4.02-4.19 (m, 2 H) 4.50 (br s, 1 H) 6.43 (dt, J = 12.64, 2.21 Hz, 1 H) 6.76-6.82 (m, 1 H) 6.87 (s, 1 H). LCMS: 420.7 $[M + H]^+$. |
| 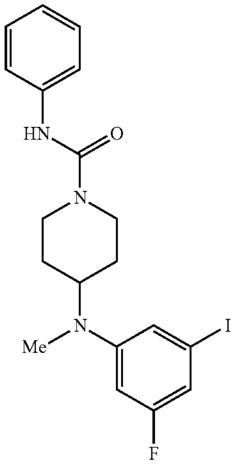 4-((3-fluoro-5-iodophenyl)(methyl)amino)-N-phenylpiperidine-1-carboxamide | $^1H$ NMR (400 MHz, $CDCl_3$) δ ppm 1.70-1.91 (m, 4 H) 2.77 (s, 3 H) 2.95-3.07 (m, 2 H) 3.65-3.79 (m, 1 H) 4.21-4.30 (m, 2 H) 6.42-6.49 (m, 1 H) 6.79-6.85 (m, 1 H) 6.90 (s, 1 H) 7.05-7.10 (m, 1 H) 7.30-7.41 (m, 5 H). LCMS: 454.2 $[M + H]^+$. |

Compounds 191-193 were generated from the above intermediates using the general methods of Procedure 25.

TABLE 14

| Characterization of Compounds 191-193 | | |
|---|---|---|
| Ex. | Structure and IUPAC Chemical Name | Characterization |
| 191 | 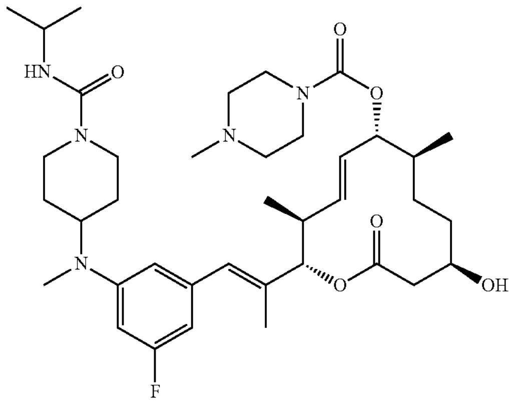 [(2S,3S,4E,6R,7R,10S)-2-[(E)-1-[3-fluoro-5-[methyl-[1-(propan-2-ylcarbamoyl)piperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | $^{1}$H NMR (400 MHz, $CDCl_3$) δ ppm 0.92 (t, J = 7.03 Hz, 6 H) 1.09 (d, J = 6.53 Hz, 6 H) 1.14-1.21 (m, 2 H) 1.33-1.45 (m, 2 H) 1.57-1.76 (m, 6 H) 1.80 (d, J = 1.13 Hz, 3 H) 1.81-1.89 (m, 1 H) 2.19-2.38 (m, 4 H) 2.44-2.60 (m, 4 H) 2.67 (s, 3 H) 2.71-2.82 (m, 2 H) 3.24-3.33 (m, 1 H) 3.37-3.53 (m, 3 H) 3.54-3.73 (m, 3 H) 3.90 (dd, J = 13.68, 6.53 Hz, 1 H) 3.98 (br d, J = 13.43 Hz, 2 H) 4.15 (br d, J = 7.40 Hz, 1 H) 4.81 (t, J = 10.10 Hz, 1 H) 5.18 (d, J = 10.54 Hz, 1 H) 5.31 (dd, J = 15.00, 9.72 Hz, 1 H) 5.52 (dd, J = 15.00. 9.98 Hz, 1 H) 6.25-6.34 (m, 3 H) 6.43 (s, 1 H). LCMS: 700.7 $[M + H]^+$ |
| 192 | 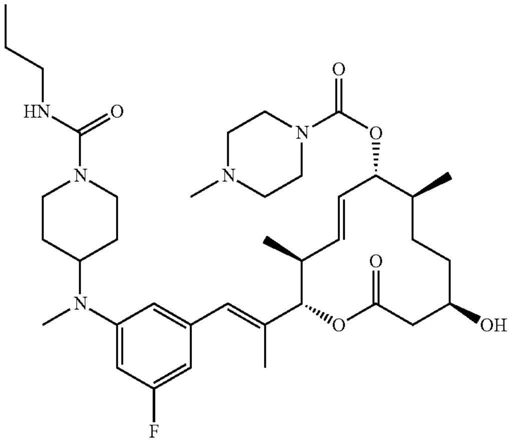 [(2S,3S,4E,6R,7R,10S)-2-[(E)-1-[3-fluoro-5-[methyl-[1-(propylcarbamoyl)piperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | $^{1}$H NMR (400 MHz, $CDCl_3$) δ ppm 0.86 (t, J = 7.40 Hz, 3 H) 0.92 (t, J = 6.90 Hz, 6 H) 1.18 (br d, J = 8.66 Hz, 2 H) 1.46 (br d, J = 7.28 Hz, 6 H) 1.61-1.71 (m, 4 H) 1.80 (d, J = 1.25 Hz, 3 H) 1.82-1.90 (m, 1 H) 2.18-2.41 (m, 4 H) 2.45-2.60 (m, 4 H) 2.67 (s, 3 H) 2.73-2.84 (m, 2 H) 3.09-3.18 (m, 2 H) 3.30 (br d, J = 10.92 Hz, 1 H) 3.36-3.54 (m, 3 H) 3.54-3.70 (m, 3 H) 3.99 (br d, J = 13.05 Hz, 2 H) 4.38 (br t, J = 5.46 Hz, 1 H) 4.81 (t, J = 10.10 Hz, 1 H) 5.18 (d, J = 10.54 Hz, 1 H) 5.31 (dd, J = 15.00, 9.60 Hz, 1 H) 5.52 (dd, J = 15.00, 9.98 Hz, 1 H) 6.25-6.33 (m, 3 H) 6.43 (s, 1 H). LCMS: 700.7 $[M + H]^+$ |

TABLE 14-continued

Characterization of Compounds 191-193

| Ex. | Structure and IUPAC Chemical Name | Characterization |
|---|---|---|
| 193 | 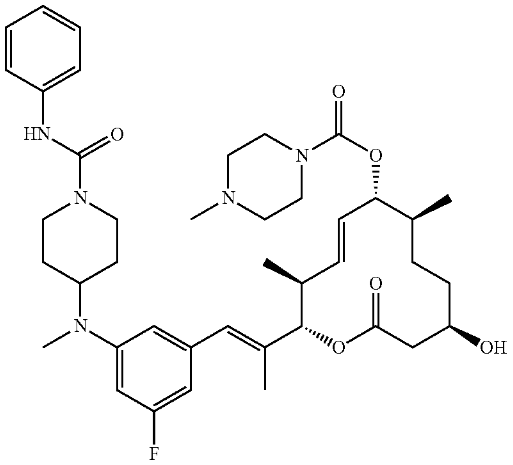 [(2S,3S,4E,6R,7S,10R)-2-[(E)-1-[3-fluoro-5-[methyl-[1-(phenylcarbamoyl)piperidin-4-yl]amino]phenyl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.92 (dd, J = 6.71, 1.44 Hz, 6 H) 1.15-1.23 (m, 2 H) 1.34-1.42 (m, 2 H) 1.64-1.77 (m, 6 H) 1.81 (d, J = 1.13 Hz, 3 H) 1.83-1.91 (m, 1 H) 2.32-2.66 (m, 8 H) 2.69 (s, 3 H) 2.87-2.98 (m, 2 H) 3.27-3.33 (m, 1 H) 3.62 (s, 5 H) 4.10-4.20 (m, 2 H) 4.81 (t, J = 9.85 Hz, 1 H) 5.19 (d, J = 10.42 Hz, 1 H) 5.31 (dd, J = 15.12, 9.72 Hz, 1 H) 5.53 (dd, J = 14.93, 9.66 Hz, 1 H) 6.25-6.36 (m, 4 H) 6.44 (s, 1 H) 6.94-7.01 (m, 1 H) 7.20-7.32 (m, 5 H). LCMS: 734.7 $[M + H]^+$ |

Synthesis of Piperidine Intermediates: Procedure 29.

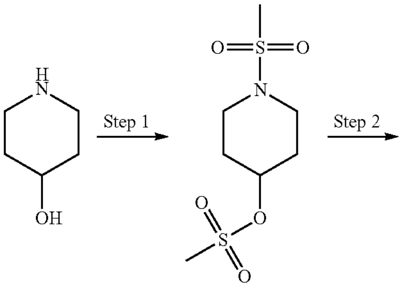

054

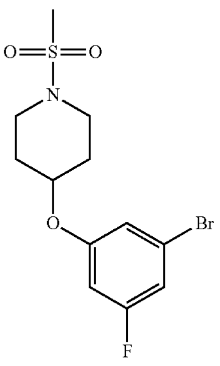

055

Step 1: A solution of piperidin-4-ol (200 mg, 1.977 mmol) in DCM (5 mL) was charged into a 25 mL round bottom flask with a magnetic stir bar. Hunig's Base (1.036 mL, 5.932 mmol) then methanesulfonyl chloride (0.339 mL, 4.35 mmol) were added. The resulting solution was stirred overnight at room temperature, and the reaction was quenched with water (10 mL). The resulting solution was extracted with DCM (3×10 mL), washed with brine (10 mL), dried with $MgSO_4$, filtered and evaporated under vacuum to yield 1-(methylsulfonyl)piperidin-4-yl methanesulfonate (054) (404 mg, 1.571 mmol).

Step 2: A solution of 3-bromo-5-fluorophenol (200 mg, 1.047 mmol) and 1-(methylsulfonyl)piperidin-4-yl methanesulfonate (054) (404 mg, 1.571 mmol) in DMF (5 mL) was charged into a 10 mL vial with a magnetic stir bar. Cesium carbonate (682 mg, 2.094 mmol) was added. The resulting dispersion was heated to 70° C. and stirred overnight. The reaction was cooled to room temperature and partitioned between EtOAc (10 mL) and water (10 mL). The solution was extract with EtOAc (3×10 mL), washed with brine (10 mL), dried with $MgSO_4$, filtered, and evaporated under vacuum. The crude product was dry loaded onto 2 g. silica and purified by column chromatography (ISCO normal phase, 24 g. gold column, 0-60% EtOAc/hexanes gradient) to isolate 4-(3-bromo-5-fluorophenoxy)-1-(methylsulfonyl) piperidine (055) (108 mg, 0.307 mmol, 29%). $^1$H NMR (400 MHz, $CDCl_3$) δ ppm 1.97-2.08 (m, 4H) 2.84 (s, 3H) 3.36-3.43 (m, 4H) 4.48-4.58 (m, 1H) 6.59 (dt, J=10.45, 2.24 Hz, 1H) 6.87-6.93 (m, 2H). LCMS: 353.1 $[M+H]^+$.

The following intermediate was also synthesized according to the general methods of Procedure 29:

TABLE 15

| Characterization of intermediate synthesized according to Procedure 29 | |
|---|---|
| Intermediate | Characterization |
| 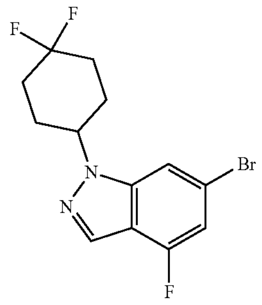<br>6-bromo-1-(4,4-difluorocyclohexyl)-4-fluoro-1H-indazole | $^1H$ NMR (400 MHz, $CDCl_3$) δ ppm 1.91-2.08 (m, 2 H) 2.08-2.18 (m, 2 H) 2.26-2.52 (m, 4 H) 4.49 (dt, J = 10.16, 5.08 Hz, 1 H) 6.99 (dd, J = 9.10, 1.19 Hz, 1 H) 7.43 (t, J = 1.00 Hz, 1 H) 8.05 (s, 1 H). LCMS: 334.1 $[M + H]^+$. |

Compounds 194-196 were generated from the above intermediates using the general methods of Procedure 25.

TABLE 16

| Characterization of Compounds 194-196 | | |
|---|---|---|
| Ex. | Structure and IUPAC Chemical Name | Characterization |
| 194 | 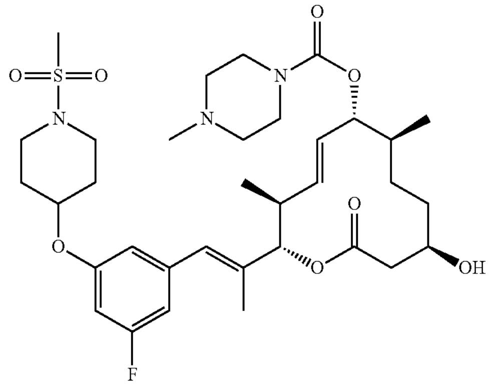<br>[(2S,3S,4E,6R,7S,10R)-2-[(E)-1-[3-fluoro-5-(1-methylsulfonylpiperidin-4-yl)oxyphenyl]prop-1-en-2-yl]-10-hydroxy-3,7-dimethyl-12-oxo-1-oxacyclododec-4-en-6-yl] 4-methylpiperazine-1-carboxylate | $^1H$ NMR (400 MHz, $CDCl_3$) δ ppm 0.91 (dd, J = 6.84, 1.44 Hz, 6 H) 1.15-1.22 (m, 2 H) 1.31-1.40 (m, 2 H) 1.65-1.77 (m, 2 H) 1.79 (d, J = 1.13 Hz, 3 H) 1.83-2.02 (m, 5 H) 2.32-2.72 (m, 8 H) 2.74 (s, 3 H) 3.10-3.38 (m, 7 H) 3.53-3.79 (m, 3 H) 4.42 (br dd, J = 5.71, 2.70 Hz, 1 H) 4.80 (t, J = 10.04 Hz, 1 H) 5.17 (d, J = 10.42 Hz, 1 H) 5.30 (dd, J = 15.25, 9.85 Hz, 1 H) 5.47-5.58 (m, 1 H) 6.38-6.46 (m, 2 H) 6.49 (s, 1 H) 6.54 (br d, J = 8.91 Hz, 1 H). LCMS: 680.6 $[M + H]^+$ |

TABLE 16-continued

| Characterization of Compounds 194-196 | | |
| --- | --- | --- |
| Ex. | Structure and IUPAC Chemical Name | Characterization |
| 195 | 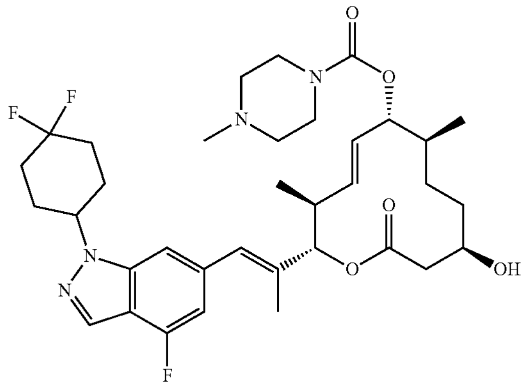<br>[(2S,3S,4E,6R,7S,10R)-2-[(E)-1-[1-(4,4-difluorocyclohexyl)-4-fluoroindazol-6-yl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.94 (dd, J = 9.22, 6.84 Hz, 6 H) 1.15-1.21 (m, 2 H) 1.36-1.45 (m, 2 H) 1.51-1.61 (m, 2 H) 1.66-1.77 (m, 2 H) 1.84 (d, J = 1.13 Hz, 3 H) 1.88-2.12 (m, 4 H) 2.17-2.42 (m, 6 H) 2.43-2.66 (m, 6 H) 3.20-3.39 (m, 1 H) 3.41-3.79 (m, 4 H) 4.43 (br d, J = 4.39 Hz, 1 H) 4.82 (t, J = 10.16 Hz, 1 H) 5.23 (d, J = 10.79 Hz, 1 H) 5.33 (dd, J = 15.12, 9.60 Hz, 1 H) 5.55 (dd, J = 15.00, 9.98 Hz, 1 H) 6.61 (s, 1 H) 6.68 (d, J = 10.67 Hz, 1 H) 6.96 (s, 1 H) 7.95 (s, 1 H). LCMS: 661.0 $[M + H]^+$ |
| 196 | 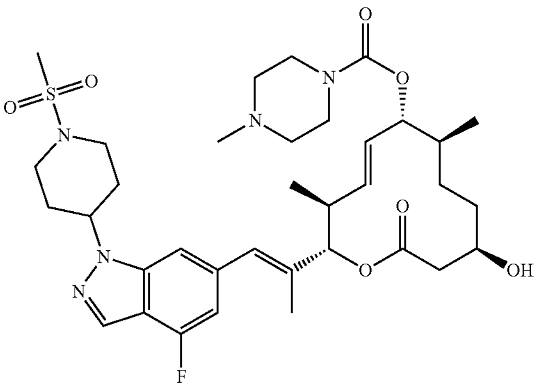<br>[(2S,3S,4E,6R,7S,10R)-2-[(E)-1-[4-fluoro-1-(1-methylsulfonylpiperidin-4-yl)indazol-6-yl]prop-1-en-2-yl]-10-hydroxy-3,7-dimethyl-12-oxo-1-oxacyclododec-4-en-6-yl] 4-methylpiperazine-1-carboxylate | $^1$H NMR (400 MHz, $CDCl_3$) δ ppm 0.94 (t, J = 7.03 Hz, 6 H) 1.15-1.26 (m, 2 H) 1.33-1.42 (m, 2 H) 1.48-1.58 (m, 2 H) 1.65 (br d, J = 5.27 Hz, 1 H) 1.84 (d, J = 1.13 Hz, 3 H) 1.86-1.91 (m, 1 H) 2.01-2.16 (m, 2 H) 2.22-2.40 (m, 5 H) 2.42-2.66 (m, 5 H) 2.80 (s, 3 H) 2.99 (br t, J = 11.73 Hz, 2 H) 3.22-3.30 (m, 1 H) 3.38-3.57 (m, 2 H) 3.60-3.77 (m, 2 H) 3.82-3.95 (m, 2 H) 4.35-4.52 (m, 1 H) 4.81 (t, J = 10.16 Hz, 1 H) 5.16-5.25 (m, 1 H) 5.34 (dd, J = 15.06, 9.66 Hz, 1 H) 5.54 (dd, J = 15.00, 9.98 Hz, 1 H) 6.56-6.76 (m, 2 H) 6.96 (s, 1 H) 7.95 (s, 1 H). LCMS: 704.6 $[M + H]^+$ |

Compounds 197-207 were prepared according to the general methods of Procedures 30 and 31.

Synthesis of sulfonylpyrrolidine intermediate: Procedure 30.

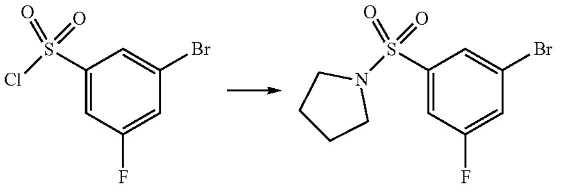

056

To a stirred solution of 3-bromo-5-fluorobenzene-1-sulfonyl chloride (40 mg, 0.146 mmol) in dichloromethane (471 μl) was added pyrrolidine (30.2 μl, 0.366 mmol). The reaction solution was stirred at room temperature overnight. The reaction solution was purified by column chromatography, eluting with a 0-100% EtOAc/hexanes gradient. This afforded 1-((3-bromo-5-fluorophenyl)sulfonyl)pyrrolidine (53.2 mg, 118%) as a white solid. LCMS (ESI, m/z), 308.0, 310.0 $[M+H]^+$. $^1H$ NMR (400 MHz, $CDCl_3$) δ 1.81-1.89 (m, 4H), 3.27-3.34 (m, 4H), 7.50 (tdd, J=7.53, 7.53, 2.38, 1.51 Hz, 2H), 7.76-7.83 (m, 1H).

Synthesis of Boronate Coupling Products:

Procedure 31.

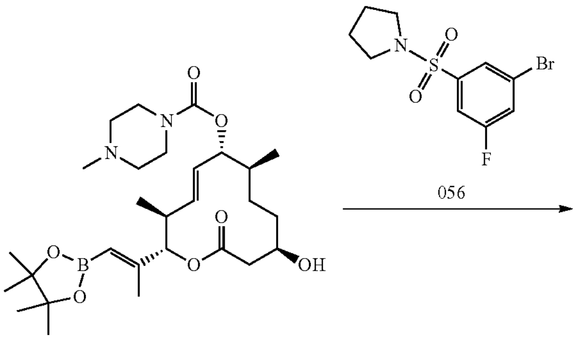

Boronate 1

-continued

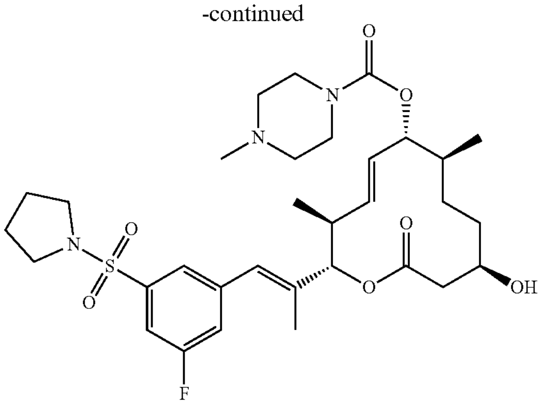

Ex. 197

To a stirred solution of Boronate 1 (15 mg, 0.028 mmol) and H-((3-bromo-5-fluorophenyl)sulfonyl)pyrrolidine (056) (12.11 mg, 0.039 mmol) in 480 μl of 1,4-dioxane and 10.11 μl water were added potassium carbonate (23.27 mg, 0.168 mmol) and tetrakis palladium triphenylphosphine (16.21 mg, 0.014 mmol). The mixture was degassed and heated to 95° C. for 2 hrs. Upon completion by UPLC, the mixture was cooled to room temperature, filtered, and purified by column chromatography eluting with a 0-100% EtOAc/hexanes gradient then a 0-20% MeOH/DCM gradient. This afforded Example 197 (8.1 mg, 45%) as a colorless oil.

TABLE 17

Characterization of Compounds 197-207

| Ex. | Structure and IUPAC Chemical Name | Characterization |
| --- | --- | --- |
| 197 | 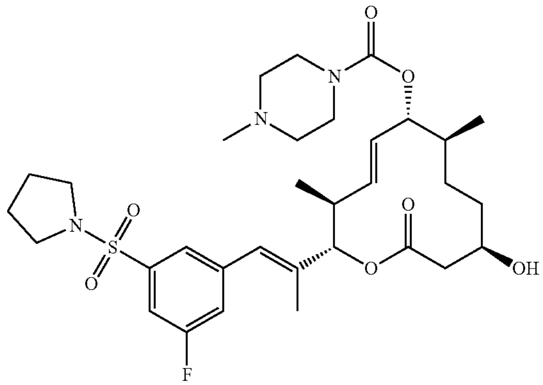 [SMILES: C/C(=C\c1cc(F)cc(S(=O)(=O)N2CCCC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-(3-fluoro-5-pyrrolidin-1-ylsulfonylphenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 636.3 [M + H]+. $^1H$ NMR (400 MHz, $CDCl_3$): δ 0.84-0.93 (m, 3H), 1.03 (d, J = 6.65 Hz, 6H), 1.21-1.32 (m, 11H), 1.47-1.52 (m, 2H), 1.79-1.85 (m, 5H), 1.91 (d, J = 1.25 Hz, 3H), 1.94-2.00 (m, 1H), 2.07 (s, 1H), 2.52-2.74 (m, 7H), 3.27-3.34 (m, 4H), 3.62-3.82 (m, 4H), 4.15 (q, J = 7.15 Hz, 1H), 4.91 (t, J = 10.10 Hz, 1H), 5.30 (d, J = 10.67 Hz, 1H), 5.43 (dd, J = 15.00, 9.60 Hz, 1H), 5.62 (dd, J = 15.00, 9.98 Hz, 1H), 6.60 (s, 1H), 7.18-7.23 (m, 1H), 7.44 (dt, J = 7.47, 2.04 Hz, 1H), 7.54 (s, 1H). |

TABLE 17-continued

| Characterization of Compounds 197-207 | | |
|---|---|---|
| Ex. | Structure and IUPAC Chemical Name | Characterization |
| 198 | 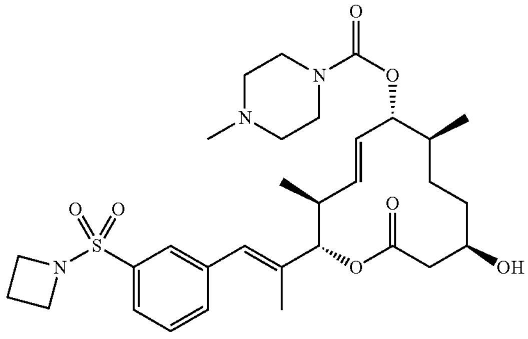 [SMILES: C/C(=C\c1cccc(S(=O)(=O)N2CCC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-(azetidin-1-ylsulfonyl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 604.6 [M + H]+. $^{1}$H NMR (400 MHz, $CDCl_3$) δ 0.87-0.97 (m, 6H), 1.10-1.25 (m, 3H), 1.29-1.46 (m, 1H), 1.33-1.45 (m, 3H), 1.68-1.78 (m, 1H), 1.78-1.90 (m, 4H), 1.95-2.08 (m, 2H), 2.43-2.60 (m, 6H), 2.43-2.63 (m, 6H), 3.22-3.31 (m, 1H), 3.60-3.78 (m, 7H), 4.76-4.85 (m, 1H), 5.17-5.26 (m, 1H), 5.28-5.38 (m, 1H), 5.47-5.58 (m, 1H), 6.52-6.59 (m, 1H), 7.40-7.52 (m, 2H), 7.60-7.69 (m, 2H), 7.70-7.70 (m, 1H) |
| 199 | 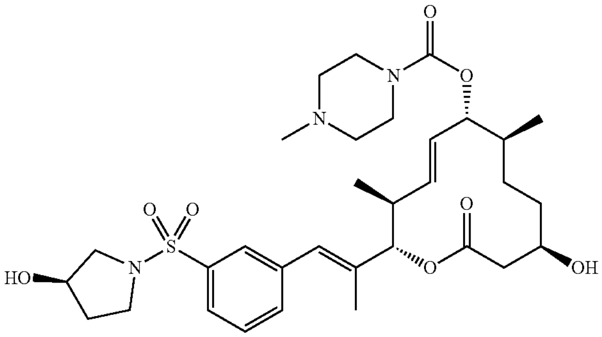 [SMILES: C/C(=C\c1cccc(S(=O)(=O)N2CC[C@@H](O)C2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-2-[(E)-1-[3-[(3R)-3-hydroxypyrrolidin-1-yl]sulfonylphenyl]prop-1-en-2-yl]-3,7-dimethyl-12-oxo-1-oxacyclododec-4-en-6-yl] 4-methylpiperazine-1-carboxylate | LCMS (ESI, m/z), 634.5 [M + H]+. $^{1}$H NMR (400 MHz, $CDCl_3$) δ 0.93 (br d, J = 6.78 Hz, 6H), 1.13-1.23 (m, 2H), 1.38-1.47 (m, 1H), 1.67-1.77 (m, 2H), 1.80 (s, 4H), 1.84-1.91 (m, 2H), 2.36-2.44 (m, 3H), 2.44-2.62 (m, 7H), 3.18 (br d, J = 11.17 Hz, 1H), 3.28-3.40 (m, 3H), 3.52-3.70 (m, 5H), 4.29-4.36 (m, 1H), 4.76-4.85 (m, 1H), 5.21 (br d, J = 10.67 Hz, 1H), 5.33 (br dd, J = 15.00, 9.72 Hz, 1H), 5.53 (br dd, J = 14.87, 9.73 Hz, 1H), 6.54 (s, 1H), 7.36-7.46 (m, 2H), 7.62-7.69 (m, 2H) |
| 200 | 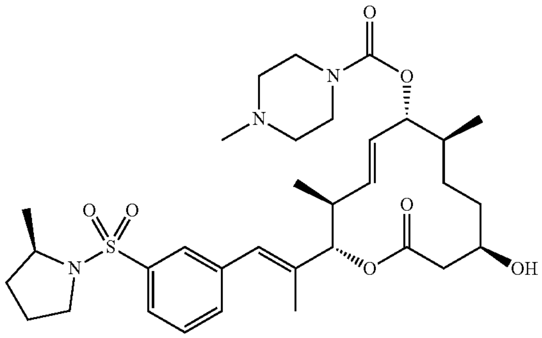 [SMILES: C/C(=C\c1cccc(S(=O)(=O)N2CCC[C@H]2C)c1)[C@H]1OC(=O)C[C@H](O)CC[C@H](C)[C@@H](OC(=O)N2CCN(C)CC2)/C=C/[C@@H]1C] [(2S,3S,4E,6R,7R,10S)-10-hydroxy-3,7-dimethyl-2-[(E)-1-[3-[(2S)-2-methylpyrrolidin-1-yl]sulfonylphenyl]prop-1-en-2-yl]-12-oxo-1-oxacyclododec-4-en-6-yl] 4-methylpiperazine-1-carboxylate | LCMS (ESI, m/z), 632.6 [M + H]+. 1H NMR (400 MHz, $CDCl_3$) δ 0.93 (d, J = 5.77 Hz, 7H), 1.07-1.21 (m, 3H), 1.24 (d, J = 6.40 Hz, 3H), 1.39-1.52 (m, 3H), 1.58-1.77 (m, 4H), 1.80 (s, 4H), 1.83-1.91 (m, 2H), 2.40-2.68 (m, 10H), 2.40-2.67 (m, 9H), 2.53-2.54 (m, 1H), 3.03-3.13 (m, 1H), 3.33-3.43 (m, 1H), 3.55-3.72 (m, 6H), 4.76-4.86 (m, 1H), 5.16-5.26 (m, 1H), 5.26-5.37 (m, 1H), 5.47-5.58 (m, 1H), 6.50-6.57 (m, 1H), 7.33-7.46 (m, 2H), 7.60-7.70 (m, 2H) |

TABLE 17-continued

| Characterization of Compounds 197-207 | | |
|---|---|---|
| Ex. | Structure and IUPAC Chemical Name | Characterization |
| 201 | 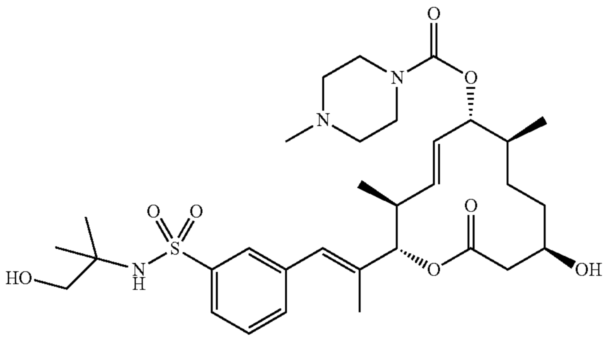 [SMILES: C/C(=C\c1cccc(S(=O)(=O)NC(C)(C)CO)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-2-[(E)-1-[3-[(1-hydroxy-2-methylpropan-2-yl)sulfamoyl]phenyl]prop-1-en-2-yl]-3,7-dimethyl-12-oxo-1-oxacyclododec-4-en-6-yl] 4-methylpiperazine-1-carboxylate | LCMS (ESI, m/z), 636.6 [M + H]+. $^1H$ NMR (400 MHz, $CDCl_3$) δ 0.88-0.96 (m, 6H), 1.04-1.10 (m, 6H), 1.15-1.23 (m, 2H), 1.36-1.45 (m, 2H), 1.68-1.77 (m, 2H), 1.77-1.83 (m, 3H), 1.84-1.91 (m, 1H), 2.44-2.62 (m, 6H), 2.67-2.86 (m, 2H), 3.36-3.43 (m, 2H), 3.62-3.78 (m, 4H), 4.77-4.86 (m, 2H), 5.18-5.23 (m, 1H), 5.27-5.36 (m, 1H), 5.48-5.57 (m, 1H), 6.49-6.57 (m, 1H), 7.32-7.45 (m, 2H), 7.67-7.75 (m, 2H) |
| 202 | 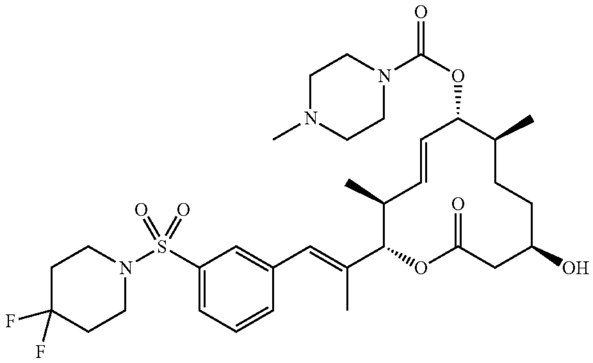 [SMILES: C/C(=C\c1cccc(S(=O)(=O)N2CCC(F)(F)CC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-(4,4-difluoropiperidin-1-yl)sulfonylphenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 668.6 [M + H]+. $^1H$ NMR (400 MHz, $CDCl_3$) δ 1.00-1.06 (m, 6H), 1.20-1.34 (m, 3H), 1.43-1.56 (m, 6H), 1.77-1.86 (m, 1H), 1.86-1.92 (m, 3H), 1.92-2.03 (m, 1H), 2.03-2.17 (m, 4H), 2.53-2.72 (m, 4H), 2.72-2.83 (m, 3H), 3.20-3.29 (m, 4H), 3.32-3.40 (m, 1H), 3.70-3.81 (m, 2H), 4.87-4.95 (m, 1H), 5.29-5.35 (m, 1H), 5.37-5.47 (m, 1H), 5.59-5.69 (m, 1H), 6.60-6.67 (m, 1H), 7.49-7.59 (m, 2H), 7.63-7.69 (m, 2H) |
| 203 | 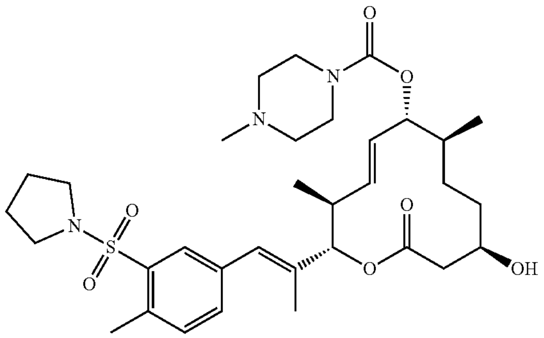 [SMILES: C/C(=C\c1ccc(C)c(S(=O)(=O)N2CCCC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-2-[(E)-1-(4-methyl-3-pyrrolidin-1-ylsulfonylphenyl)prop-1-en-2-yl]-12-oxo-1-oxacyclododec-4-en-6-yl] 4-methylpiperazine-1-carboxylate | LCMS (ESI, m/z), 632.6 [M + H]+. $^1H$ NMR (400 MHz, $CDCl_3$) δ 0.92 (dd, J = 6.78, 1.88 Hz, 6H), 1.12-1.24 (m, 3H), 1.37-1.46 (m, 3H), 1.67-1.75 (m, 2H), 1.78-1.89 (m, 8H), 2.44-2.61 (m, 10H), 3.16-3.27 (m, 5H), 3.27-3.36 (m, 1H), 3.58-3.72 (m, 5H), 4.76-4.85 (m, 1H), 5.17-5.23 (m, 1H), 5.28-5.36 (m, 1H), 5.48-5.58 (m, 1H), 6.44-6.51 (m, 1H), 7.20-7.27 (m, 2H), 7.77 (d, J = 1.51 Hz, 1H) |

TABLE 17-continued

Characterization of Compounds 197-207

| Ex. | Structure and IUPAC Chemical Name | Characterization |
| --- | --- | --- |
| 204 | 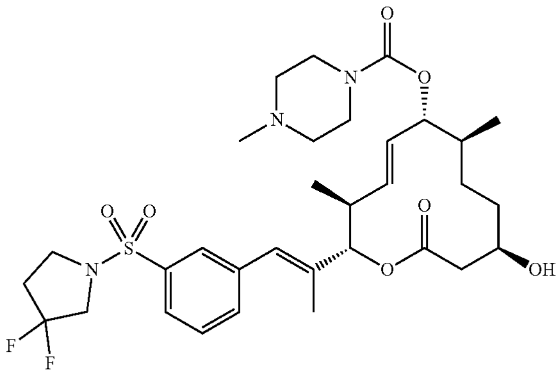 [(2S,3S,4E,6R,7S,10R)-2-[(E)-1-[3-(3,3-difluoropyrrolidin-1-yl)sulfonylphenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 354.6 [M + H]+. $^1$H NMR (400 MHz, $CDCl_3$) δ 0.88-0.96 (m, 6H), 1.11-1.29 (m, 5H), 1.64-1.76 (m, 2H), 1.77-1.82 (m, 3H), 1.84-1.94 (m, 1H), 2.14-2.29 (m, 2H), 2.42-2.62 (m, 3H), 2.65-2.78 (m, 4H), 3.33-3.42 (m, 4H), 3.45-3.57 (m, 2H), 3.59-3.73 (m, 2H), 4.07-4.20 (m, 1H), 4.74-4.87 (m, 1H), 5.17-5.27 (m, 1H), 5.27-5.39 (m, 1H), 5.49-5.61 (m, 1H), 6.51-6.59 (m, 1H), 7.40-7.51 (m, 2H), 7.58-7.67 (m, 2H), 7.85-7.95 (m, 1H) |
| 205 | 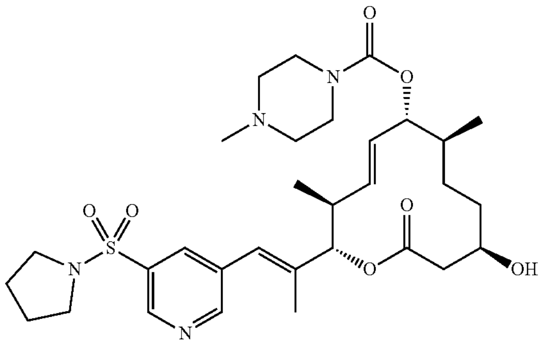 [SMILES: C/C(=C\c1cncc(S(=O)(=O)N2CCCC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-12-oxo-2-[(E)-1-(5-pyrrolidin-1-ylsulfonylpyridin-3-yl)prop-1-en-2-yl]-1-oxacyclododec-4-en-6-yl] 4-methylpiperazine-1-carboxylate | LCMS (ESI, m/z), 619.6 [M + H]+. $^1$H NMR (400 MHz, $CDCl_3$) δ 0.82-0.93 (m, 1H), 1.01-1.07 (m, 6H), 1.17-1.38 (m, 5H), 1.46-1.52 (m, 1H), 1.75-1.88 (m, 6H), 1.91-2.03 (m, 4H), 2.53-2.87 (m, 9H), 3.28-3.37 (m, 5H), 3.41-3.51 (m, 2H), 3.68-3.83 (m, 3H), 4.15-4.32 (m, 2H), 4.86-4.95 (m, 1H), 5.27-5.35 (m, 1H), 5.37-5.49 (m, 1H), 5.57-5.70 (m, 1H), 6.61 (s, 1H), 8.02 (s, 1H), 8.73 (d, J = 2.01 Hz, 1H), 8.89-8.98 (m, 1H) |
| 206 | 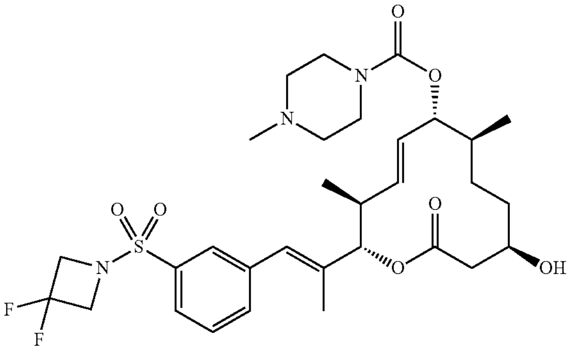 [SMILES: C/C(=C\c1cccc(S(=O)(=O)N2CC(F)(F)C2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-(3,3-difluoroazetidin-1-yl)sulfonylphenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 640.6 [M + H]+. $^1$H NMR (400 MHz, $CDCl_3$) δ 0.93 (dd, J = 9.22, 6.84 Hz, 7H), 0.94-0.95 (m, 1H), 1.03-1.28 (m, 6H), 1.25-1.39 (m, 4H), 1.51-1.56 (m, 2H), 1.68-1.89 (m, 4H), 2.44-2.62 (m, 3H), 2.62-2.72 (m, 2H), 2.72-2.76 (m, 3H), 3.34-3.42 (m, 2H), 3.57-3.72 (m, 3H), 4.04-4.21 (m, 7H), 4.76-4.85 (m, 1H), 5.18-5.26 (m, 1H), 5.26-5.37 (m, 1H), 5.49-5.59 (m, 1H), 6.53-6.58 (m, 1H), 7.45-7.53 (m, 2H), 7.63-7.70 (m, 2H) |

TABLE 17-continued

| Characterization of Compounds 197-207 | | |
|---|---|---|
| Ex. | Structure and IUPAC Chemical Name | Characterization |
| 207 | 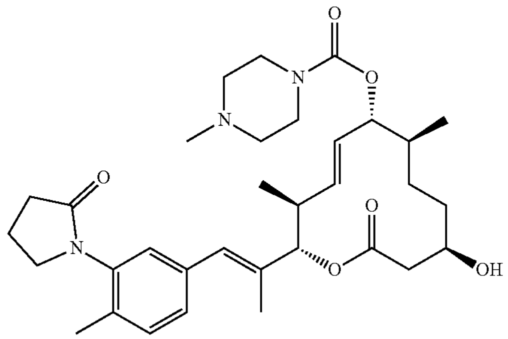 [SMILES: C/C(=C\c1ccc(C)c(N2CCCC2=O)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-2-[(E)-1-[4-methyl-3-(2-oxopyrrolidin-1-yl)phenyl]prop-1-en-2-yl]-12-oxo-1-oxacyclododec-4-en-6-yl] 4-methylpiperazine-1-carboxylate | LCMS (ESI, m/z), 582.6 [M + H]+. $^1$H NMR (400 MHz, $CDCl_3$) δ 0.86-0.95 (m, 6H), 1.10-1.26 (m, 2H), 1.35-1.42 (m, 2H), 1.64-1.76 (m, 1H), 1.76-1.80 (m, 3H), 1.81-1.89 (m, 1H), 2.10-2.20 (m, 5H), 2.41-2.60 (m, 6H), 2.62-2.72 (m, 3H), 3.32 (br d, J = 10.92 Hz, 1H), 3.59-3.69 (m, 4H), 4.81 (t, J = 10.04 Hz, 1H), 5.18 (d, J = 10.54 Hz, 1H), 5.29 (dd, J = 14.93, 9.66 Hz, 1H), 5.53 (dd, J = 15.00, 9.98 Hz, 1H), 6.41-6.48 (m, 1H), 6.94-6.99 (m, 1H), 7.03-7.09 (m, 1H), 7.13-7.17 (m, 1H) |

Compounds 208-218 were prepared according to the general methods of Procedure 32.

Synthesis of Boronate Coupling Products:

Procedure 32.

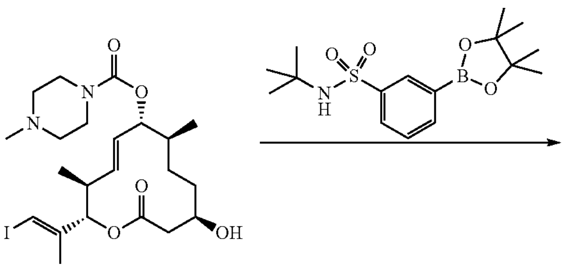

008

-continued

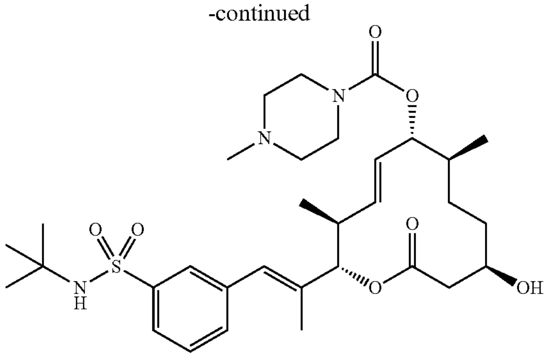

Ex. 208

To a stirred solution of iodide (008) (15 mg, 0.028 mmol) and N-(tert-butyl)-3-(4,4,5,5-tetramethyl-1,3,2-dioxaborolan-2-yl)benzenesulfonamide (11.43 mg, 0.034 mmol) in 426 μl of p-dioxane was added silver oxide (19.51 mg, 0.084 mmol) and tetrakis(triphenylphosphine)palladium(O) (3.24 mg, 2.807 μmol). The mixture was degassed and heated to 80° C. for 90 minutes. Upon completion by UPLC, the reaction mixture was cooled to room temperature, filtered, and concentrated. Purification by column chromatography eluting with a 0-20% MeOH/DCM gradient afforded Example 208 (23.3 mg, ~100%) as a colorless oil.

TABLE 18

Characterization of Compounds 208-218 and 268

| Ex. | Structure and IUPAC Chemical Name | Characterization |
|---|---|---|
| 208 | 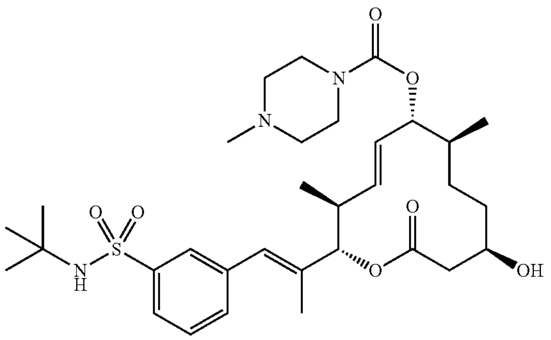 [SMILES: C/C(=C\c1cccc(S(=O)(=O)NC(C)(C)C)c1)[C@H]1OC(=O)C[C@H](O)CC[C@H](C)[C@@H](OC(=O)N2CCN(C)CC2)/C=C/[C@@H]1C]<br>[(2S,3S,4E,6R,7S,10R)-2-[(E)-1-[3-(tert-butylsulfamoyl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 620.8 [M + H]+. 1H NMR (400 MHz, $CDCl_3$) δ 0.84-0.93 (m, 1H), 0.99-1.05 (m, 6H), 1.22-1.29 (m, 13H), 1.48-1.56 (m, 1H), 1.79-1.87 (m, 1H), 1.88-1.92 (m, 3H), 1.93-1.99 (m, 1H), 2.39 (s, 3H), 2.48 (br s, 2H), 2.60 (br d, J = 3.14 Hz, 3H), 3.31-3.41 (m, 1H), 3.55-3.59 (m, 2H), 3.71-3.81 (m, 1H), 4.53 (s, 1H), 4.85-4.95 (m, 1H), 5.32 (s, 2H), 5.38-5.47 (m, 1H), 5.58-5.67 (m, 1H), 6.63 (s, 1H), 7.39-7.52 (m, 2H), 7.74-7.85 (m, 2H). |
| 209 | 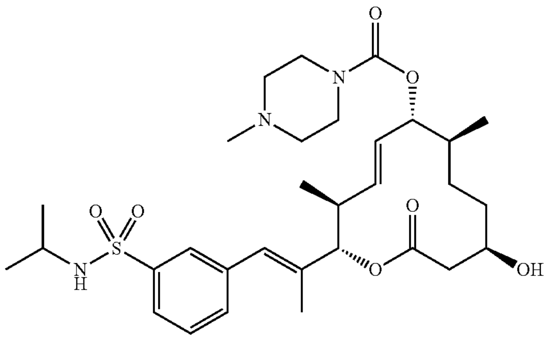 [SMILES: C/C(=C\c1cccc(S(=O)(=O)NC(C)C)c1)[C@H]1OC(=O)C[C@H](O)CC[C@H](C)[C@@H](OC(=O)N2CCN(C)CC2)/C=C/[C@@H]1C]<br>[(2S,3S,4E,6R,7R,10S)-10-hydroxy-3,7-dimethyl-12-oxo-2-[(E)-1-[3-(propan-2-ylsulfamoyl)phenyl]prop-1-en-2-yl]-1-oxacyclododec-4-en-6-yl] 4-methylpiperazine-1-carboxylate | LCMS (ESI, m/z), 606.6 [M + H]+. $^1H$ NMR (400 MHz, $CDCl_3$) δ 0.89-0.96 (m, 6H), 0.99-1.05 (m, 6H), 1.12-1.23 (m, 2H), 1.37-1.44 (m, 3H), 1.67-1.76 (m, 1H), 1.77-1.83 (m, 3H), 1.83-1.91 (m, 1H), 2.39-2.50 (m, 1H), 2.43-2.46 (m, 1H), 2.53-2.66 (m, 4H), 3.23-3.30 (m, 1H), 3.27-3.28 (m, 1H), 3.36-3.48 (m, 1H), 3.60-3.70 (m, 2H), 4.17-4.24 (m, 1H), 4.76-4.85 (m, 1H), 5.17-5.24 (m, 1H), 5.28-5.39 (m, 1H), 5.54 (dd, J = 15.00, 9.98 Hz, 1H), 6.50-6.56 (m, 1H), 7.32-7.45 (m, 2H), 7.64-7.72 (m, 2H) |
| 210 | 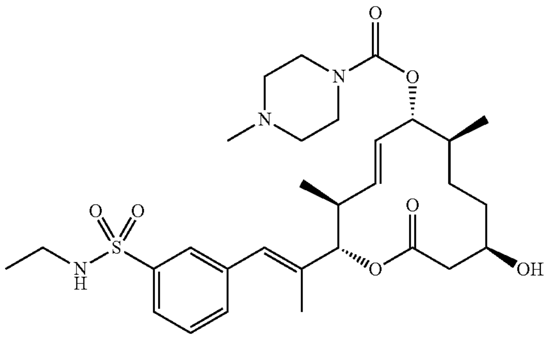 [SMILES: CCNS(=O)(=O)c1cccc(/C=C(\C)[C@H]2OC(=O)C[C@H](O)CC[C@H](C)[C@@H](OC(=O)N3CCN(C)CC3)/C=C/[C@@H]2C)c1]<br>[(2S,3S,4E,6R,7R,10S)-2-[(E)-1-[3-(ethylsulfamoyl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 592.6 [M + H]+. $^1H$ NMR (400 MHz, $CDCl_3$) δ 1.00-1.06 (m, 6H), 1.13-1.18 (m, 3H), 1.29-1.32 (m, 2H), 1.47-1.56 (m, 2H), 1.74-1.88 (m, 2H), 1.88-1.92 (m, 3H), 1.92-2.00 (m, 1H), 2.46 (br s, 3H), 2.56-2.70 (m, 5H), 2.99-3.11 (m, 2H), 3.32-3.40 (m, 1H), 3.54-3.81 (m, 5H), 4.32-4.41 (m, 1H), 4.86-4.96 (m, 1H), 5.27-5.35 (m, 1H), 5.37-5.48 (m, 1H), 5.56-5.68 (m, 1H), 6.60-6.66 (m, 1H), 7.44-7.55 (m, 2H), 7.73-7.82 (m, 2H) |

TABLE 18-continued

Characterization of Compounds 208-218 and 268

| Ex. | Structure and IUPAC Chemical Name | Characterization |
|---|---|---|
| 211 | 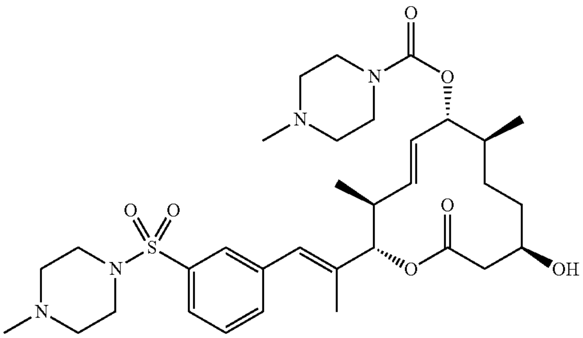 [SMILES: C/C(=C\c1cccc(S(=O)(=O)N2CCN(C)CC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-2-[(E)-1-[3-(4-methylpiperazin-1-yl)sulfonylphenyl]prop-1-en-2-yl]-12-oxo-1-oxacyclododec-4-en-6-yl] 4-methylpiperazine-1-carboxylate | LCMS (ESI, m/z), 647.7 [M + H]+. $^1$H NMR (400 MHz, $CDCl_3$) δ ppm 0.72-0.86 (m, 3H), 0.89-0.97 (m, 7H), 1.08-1.26 (m, 12H), 1.66-1.77 (m, 1H), 1.67-1.78 (m, 1H), 1.78-1.84 (m, 3H), 1.84-1.92 (m, 1H), 1.85-1.95 (m, 1H), 2.44-2.73 (m, 8H), 3.08-3.16 (m, 1H), 3.21-3.30 (m, 2H), 3.59-3.71 (m, 2H), 4.76 (s, 1H), 5.16-5.25 (m, 1H), 5.27-5.36 (m, 1H), 5.49-5.60 (m, 1H), 6.49-6.57 (m, 1H), 7.40-7.50 (m, 2H), 7.52-7.58 (m, 2H) |
| 212 | 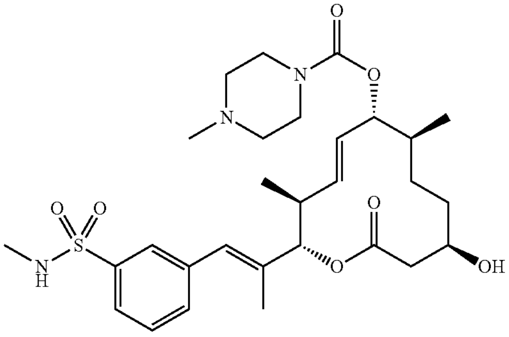 [SMILES: CNS(=O)(=O)c1cccc(/C=C(\C)[C@H]2OC(=O)C[C@H](O)CC[C@H](C)[C@@H](OC(=O)N3CCN(C)CC3)/C=C/[C@@H]2C)c1] [(2S,3S,4E,6R,7R,10S)-10-hydroxy-3,7-dimethyl-2-[(E)-1-[3-(methylsulfamoyl)phenyl]prop-1-en-2-yl]-12-oxo-1-oxacyclododec-4-en-6-yl] 4-methylpiperazine-1-carboxylate | LCMS (ESI, m/z), 578.5 [M + H]+. $^1$H NMR (400 MHz, $CDCl_3$) δ 0.93 (dd, J = 6.71, 2.07 Hz, 5H), 0.93-0.95 (m, 1H), 1.13-1.24 (m, 3H), 1.68-1.76 (m, 1H), 1.79-1.84 (m, 4H), 1.84-1.91 (m, 1H), 2.41-2.64 (m, 12H), 3.06 (s, 1H), 3.22-3.29 (m, 1H), 3.52-3.75 (m, 5H), 4.24-4.33 (m, 1H), 4.81 (t, J = 10.04 Hz, 1H), 5.21 (d, J = 10.54 Hz, 1H), 5.34 (d, J = 9.66 Hz, 1H), 5.53 (dd, J = 15.00, 9.85 Hz, 1H), 6.51-6.55 (m, 1H), 7.36-7.46 (m, 2H), 7.49-7.53 (m, 1H), 7.64-7.70 (m, 2H) |
| 213 | 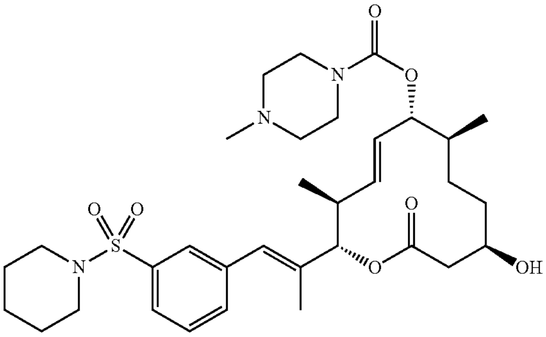 [SMILES: C/C(=C\c1cccc(S(=O)(=O)N2CCCCC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-12-oxo-2-[(E)-1-(3-piperidin-1-ylsulfonylphenyl)prop-1-en-2-yl]-1-oxacyclododec-4-en-6-yl] 4-methylpiperazine-1-carboxylate | LCMS (ESI, m/z), 632.6 [M + H]+. $^1$H NMR (400 MHz, $CDCl_3$) δ 1.03 (dd, J = 6.65, 2.89 Hz, 6H), 1.20-1.35 (m, 2H), 1.39-1.72 (m, 10H), 1.75-1.86 (m, 1H), 1.91 (d, J = 1.00 Hz, 3H), 1.93-2.00 (m, 1H), 2.51-2.82 (m, 7H), 3.02 (br d, J = 5.40 Hz, 4H), 3.31-3.42 (m, 1H), 3.59-3.94 (m, 4H), 4.88-4.98 (m, 1H), 5.26-5.35 (m, 1H), 5.37-5.48 (m, 1H), 5.62 (br d, J = 9.91 Hz, 1H), 6.59-6.67 (m, 1H), 7.51 (br d, J = 11.67 Hz, 2H), 7.68 (s, 2H) |

TABLE 18-continued

| Characterization of Compounds 208-218 and 268 | | |
|---|---|---|
| Ex. | Structure and IUPAC Chemical Name | Characterization |
| 214 | 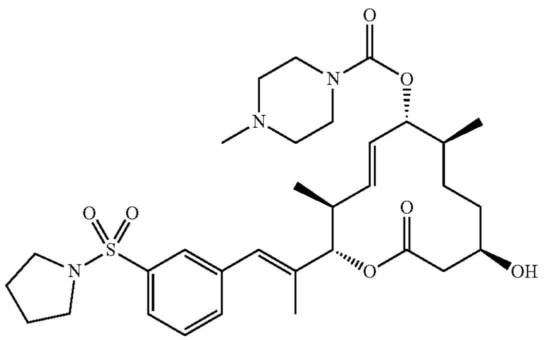 [SMILES: C/C(=C\c1cccc(S(=O)(=O)N2CCCC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-12-oxo-2-[(E)-1-(3-pyrrolidin-1-ylsulfonylphenyl)prop-1-en-2-yl]-1-oxacyclododec-4-en-6-yl] 4-methylpiperazine-1-carboxylate | LCMS (ESI, m/z), 618.5 [M + H]+. $^1H$ NMR (400 MHz, $CDCl_3$) δ 0.98-1.08 (m, 6H), 1.21-1.37 (m, 2H), 1.46-1.67 (m, 4H), 1.75-1.86 (m, 5H), 1.89-1.94 (m, 3H), 1.94-2.02 (m, 1H), 2.52-2.82 (m, 7H), 3.25-3.32 (m, 4H), 3.33-3.42 (m, 1H), 3.66-3.84 (m, 3H), 4.85-4.96 (m, 1H), 5.28-5.35 (m, 1H), 5.37-5.47 (m, 1H), 5.58-5.70 (m, 1H), 6.60-6.68 (m, 1H), 7.44-7.57 (m, 2H), 7.68-7.81 (m, 2H) |
| 215 | 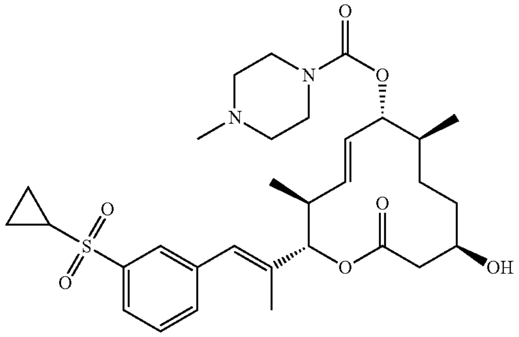 [SMILES: C/C(=C\c1cccc(S(=O)(=O)C2CC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-(3-cyclopropylsulfonylphenyl)prop-1-en-2-yl]-10-hydroxy-3,7-dimethyl-12-oxo-1-oxacyclododec-4-en-6-yl] 4-methylpiperazine-1-carboxylate | LCMS (ESI, m/z), 589.5 [M + H]+. $^1H$ NMR (400 MHz, $CDCl_3$) δ 0.97-1.10 (m, 9H), 1.21-1.33 (m, 2H), 1.35-1.43 (m, 2H), 1.47-1.57 (m, 2H), 1.77-1.87 (m, 1H), 1.91 (d, J = 1.25 Hz, 3H), 1.93-2.02 (m, 1H), 2.42-2.54 (m, 2H), 2.54-2.85 (m, 7H), 3.32-3.41 (m, 1H), 3.63-3.92 (m, 4H), 4.86-4.96 (m, 1H), 5.25-5.35 (m, 1H), 5.38-5.49 (m, 1H), 5.58-5.68 (m, 1H), 6.61-6.68 (m, 1H), 7.54 (br d, J = 0.75 Hz, 2H), 7.76-7.87 (m, 2H) |
| 216 | 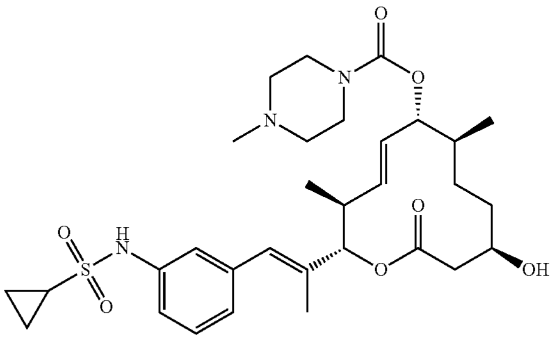 [SMILES: C/C(=C\c1cccc(NS(=O)(=O)C2CC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-(cyclopropylsulfonylamino)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 604.6 [M + H]+. $^1H$ NMR (400 MHz, $CDCl_3$) δ 0.93-1.07 (m, 8H), 0.98-0.98 (m, 1H), 1.15-1.22 (m, 2H), 1.23-1.36 (m, 2H), 1.46-1.57 (m, 2H), 1.76-1.87 (m, 1H), 1.88-1.92 (m, 3H), 1.96 (td, J = 6.74, 3.70 Hz, 1H), 2.44-2.73 (m, 8H), 3.41 (d, J = 10.79 Hz, 1H), 3.59-4.00 (m, 3H), 3.67-3.68 (m, 1H), 4.91 (t, J = 10.10 Hz, 1H), 5.25-5.34 (m, 1H), 5.35-5.48 (m, 1H), 5.63 (dd, J = 15.06, 9.91 Hz, 1H), 6.52-6.62 (m, 2H), 7.08-7.20 (m, 2H), 7.21-7.26 (m, 1H), 7.30-7.36 (m, 1H) |

TABLE 18-continued

| Characterization of Compounds 208-218 and 268 | | |
|---|---|---|
| Ex. | Structure and IUPAC Chemical Name | Characterization |
| 217 | 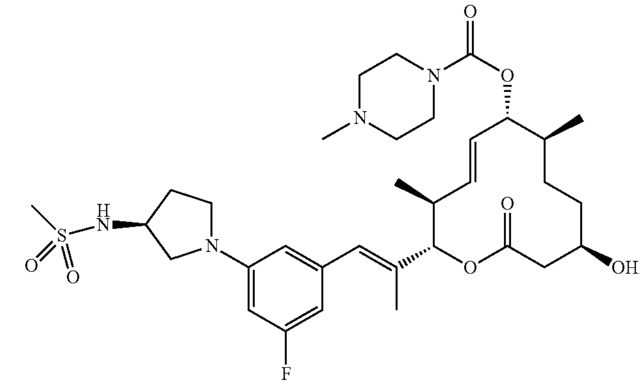 [SMILES: C/C(=C\c1cc(F)cc(N2CC[C@H](NS(C)(=O)=O)C2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-fluoro-5-[(3S)-3-(methanesulfonamido)pyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 665.5 [M + H] 1H NMR (400 MHz, $CDCl_3$) d ppm 0.97-1.05 (m, 6 H) 1.22-1.31 (m, 2 H) 1.45-1.53 (m, 2 H) 1.75-1.85 (m, 1 H) 1.92-1.99 (m, 1H) 2.04-2.12 (m, 1 H) 2.31 (br s, 8 H) 2.50-2.69 (m, 3 H) 3.04 (s, 3 H) 3.21-3.29 (m, 1 H) 3.31-3.49 (m, 4 H) 3.58-3.65 (m, 1 H) 3.69-3.77 (m, 1 H) 4.17-4.27 (m, 1 H) 4.36-4.47 (m, 1 H) 4.88-4.94 (m, 1 H) 5.23-5.29 (m, 1 H) 5.37-5.45 (m, 1 H) 5.56-5.65 (m, 1 H) 6.12-6.20 (m, 2 H) 6.34-6.41 (m, 1 H) 6.48-6.53 (m, 1 H) |
| 218 | 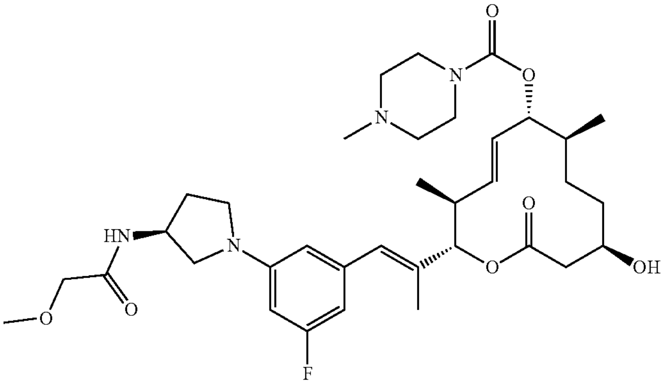 [SMILES: COCC(=O)N[C@H]1CCN(c2cc(F)cc(/C=C(\C)[C@H]3OC(=O)C[C@H](O)CC[C@H](C)[C@@H](OC(=O)N4CCN(C)CC4)/C=C/[C@@H]3C)c2)C1] [(2S,3S,4E,6R,7R,10S)-2-[(E)-1-[3-fluoro-5-[(3S)-3-[(2-methoxyacetyl)amino]pyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 659.7 [M + H]. |
| 268 | 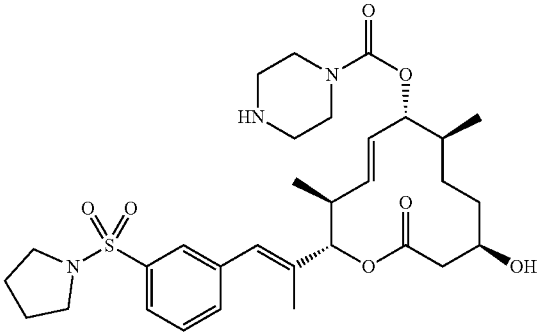 [SMILES: C/C(=C\c1cccc(S(=O)(=O)N2CCCC2)c1)[C@H]1OC(=O)C[C@H](O)CC[C@H](C)[C@@H](OC(=O)N2CCNCC2)/C=C/[C@@H]1C] (2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl piperazine-1-carboxylate | LCMS (ESI, m/z), 604.5 [M + H]. |

Compounds 219 and 220 (Tables 17 and 18) were synthesized according to the general methods of Procedures 33 and 34.

Procedure 33.

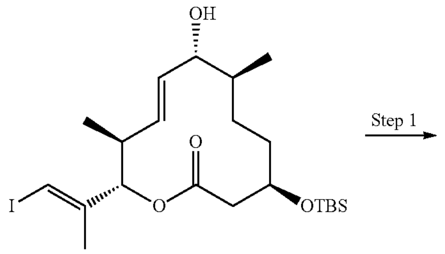

005

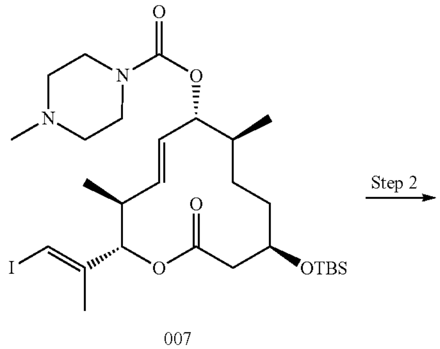

007

-continued

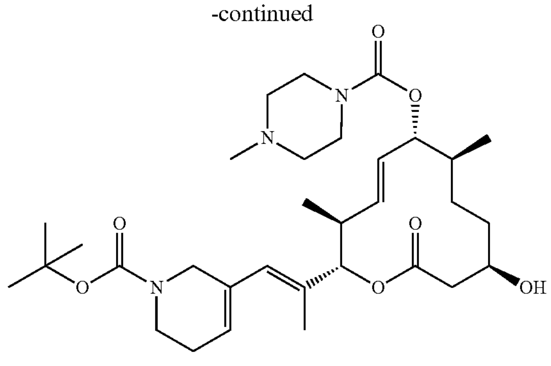

Ex. 219

Step 1. A vial was charged with DMAP (0.117 g, 0.957 mmol), DCM (4.78 ml, 0.957 mmol) (4R,7S,8R,11S,12S,E)-4-((tert-butyldimethylsilyl)oxy)-8-hydroxy-12-((E)-1-iodoprop-1-en-2-yl)-7,11-dimethyloxacyclododec-9-en-2-one (005) (0.5 g, 0.957 mmol), 4-nitrophenyl chloroformate (0.193 g, 0.957 mmol) were combined and stirred overnight. 1-Methyl piperazine (0.191 ml, 1.722 mmol) was added and and then the reaction stirred for 1 hr. The reaction mixture was directly loaded into a silica gel column and chromatographed to afford to afford (2S,3S,6R,7S,10R,E)-10-((tert-butyldimethylsilyl)oxy)-2-((E)-1-iodoprop-1-en-2-yl)-3,7-dimethyl-12-oxooxacyclododec-4-en-6-yl 4-methylpiperazine-1-carboxylate (007) (0.567 g, 0.874 mmol, 91% yield). LCMS (ESI, m/z), 649.4 [M+H]$^+$.

Step 2. Silver oxide (0.098 g, 0.421 mmol), tert-butyl 3-(4,4,5,5-tetramethyl-1,3,2-dioxaborolan-2-yl)-5,6-dihydropyridine-1(2H)-carboxylate (0.052 g, 0.168 mmol), (2S,3S,6R,7S,10R,E)-10-hydroxy-2-((E)-1-iodoprop-1-en-2-yl)-3,7-dimethyl-12-oxooxacyclododec-4-en-6-yl 4-methylpiperazine-1-carboxylate (007) (0.045 g, 0.084 mmol), 1,4-dioxane (0.842 ml, 0.084 mmol), were combined and sparged with nitrogen for 10 minutes after which tetrakis(triphenylphosphine)palladium(0) (0.019 g, 0.017 mmol) was added and sparged with nitrogen for 10 minutes and stirred at 90° C. for 1.5 hr. The reaction mix was filtered, concentrated and chromatographed to afford Example 219 (2S,3S,6R,7S,10R,E)-2-((E)-1-(1-(tert-butoxycarbonyl)-1,2,5,6-tetrahydropyridin-3-yl)prop-1-en-2-yl)-10-hydroxy-3,7-dimethyl-12-oxooxacyclododec-4-en-6-yl 4-methylpiperazine-1-carboxylate (12 mg, 0.020 mmol, 24.16% yield).

TABLE 19

Characterization of Compound 219

| Ex. | Structure and IUPAC Chemical Name | Characterization |
| --- | --- | --- |
| 219 | 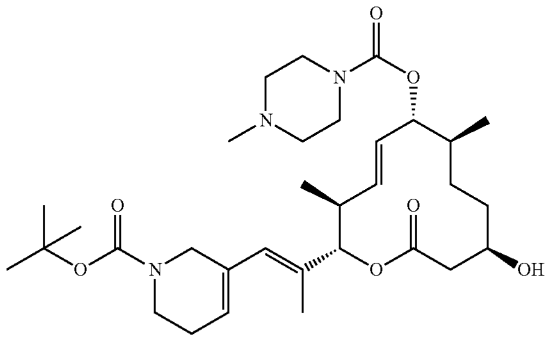 [SMILES: C/C(=C\C1=CCCN(C(=O)OC(C)(C)C)C1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-3,7-dimethyl-2-[(E)-1-[1-[(2-methylpropan-2-yl)oxycarbonyl]-3,6-dihydro-2H-pyridin-5-yl]prop-1-en-2-yl]-12-oxo-1-oxacyclododec-4-en-6-yl] 4-methylpiperazine-1-carboxylate | LCMS (ESI, m/z), 591.7 [M + H]+. 1H NMR (400 MHz, $CDCl_3$) □ ppm 0.87-0.97 (m, 3 H) 1.02 (d, J = 6.78 Hz, 3 H) 1.19-1.31 (m, 2 H) 1.42-1.59 (m, 9 H) 1.82 (s, 4H) 1.86-1.98 (m, 1 H) 2.18-2.27 (m, 2 H) 2.31 (s, 3 H) 2.37 (br s, 4 H) 2.45-2.69 (m, 3 H) 3.50 (br d, J = 5.52 Hz, 6 H) 3.66-3.80 (m, 1 H) 3.81-4.06 (m, 2 H) 4.82-4.92 (m, 1 H) 5.11-5.19 (m, 1 H) 5.33-5.43 (m, 1 H) 5.52-5.62 (m, 1 H) 5.73-5.93 (m, 2 H). |

Procedure 34.

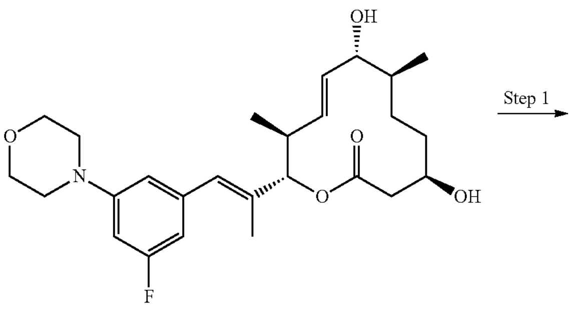

057

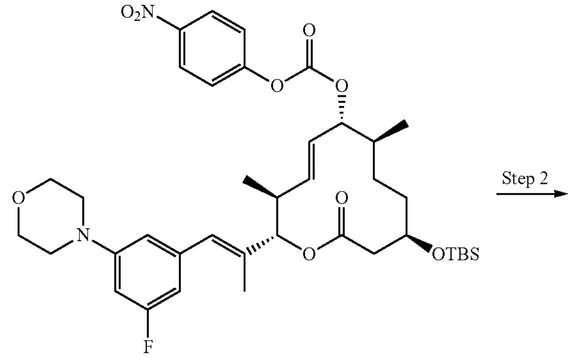

058

-continued

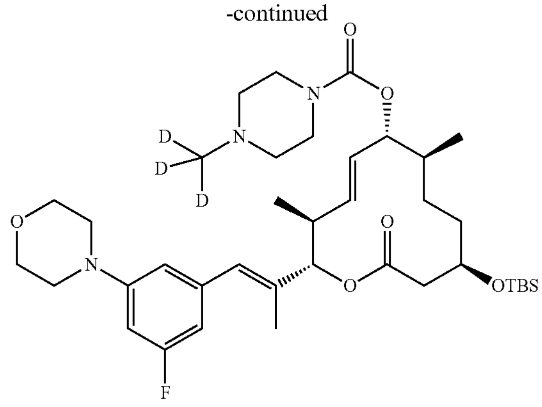

059

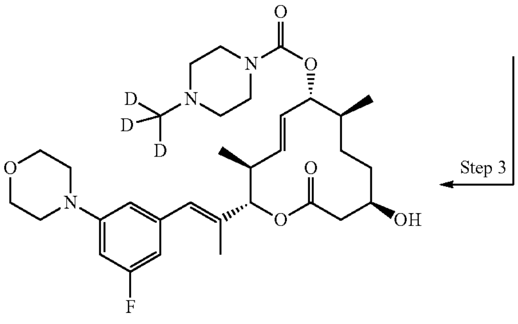

Ex. 220

Step 1. To a solution of alcohol (057) (265 mg, 0.423 mmol, 89% yield) in DCM (2.388 ml, 0.478 mmol) was added DMAP (0.058 g, 0.478 mmol), Hunig's Base (0.417 ml, 2.388 mmol),4-Nitrophenyl chloroformate (0.173 g, 0.86 mmol). The resulting yellowish suspension was stirred for 12 h till SM was gone, Reaction mixture was concentrated and chromatographed to afford the carbonate. The product was then taken up in methanol (4.78 ml, 0.478 mmol), added to sic acid (0.182 g, 0.955 mmol) and stirred for 1 hour. TEA (1 mL) was added and stirred for 10 minutes. The reaction mix was then concentrated to dryness and added DCM (6 mL) and sat'd $NaHCO_3$ (2 mL) and stirred and extracted. The aqueous layer was then back extracted with DCM (3×). The organic layers were combined, dried over anhydrous Na2SO4 and concentrated to dryness to afford (058) (265 mg, 0.423 mmol, 89% yield). LCMS (ESI, m/z), 627.3 [M+H]1H NMR (400 MHz, $CDCl_3$) δ ppm 0.06-0.12 (m, 6H) 0.41-0.42 (m, 1H) 0.85-0.89 (m, 4H) 0.91 (s, 10H) 0.97-1.05 (m, 6H) 1.09-1.14 (m, 3H) 1.59-1.66 (m, 2H) 1.68-1.77 (m, 1H) 1.84-1.89 (m, 3H) 1.95-2.02 (m, 1H) 2.04 (s, 2H) 2.36-2.44 (m, 1H) 2.51-2.65 (m, 2H) 3.10-3.18 (m, 4H) 3.79-3.88 (m, 4H) 3.88-3.95 (m, 1H) 4.79-4.88 (m, 1H) 5.07-5.14 (m, 1H) 5.45-5.57 (m, 1H) 5.63-5.74 (m, 1H) 6.42-6.55 (m, 4H) 7.38 (d, J=9.29 Hz, 2H) 8.24-8.30 (m, 2H).

Step 2. To a solution of carbonate (058) (50 mg, 0.087 mmol) in DCM (0.434 ml, 0.087 mmol) was added DMAP (10.61 mg, 0.087 mmol), Hunig's Base (0.076 ml, 0.434 mmol), 4-Nitrophenyl chloroformate (0.032 g, 0.156 mmol). The resulting yellowish suspension was stirred for 5 h and, d3-N-Methylpiperizine (0.027 g, 0.26 mmol) was added and stirred till the completion of the reaction (1 hr). Reaction mixture was concentrated and chromatographed to afford (059) (58 mg, 0.082 mmol, 95% yield). LCMS (ESI, m/z), 705.7 [M+H $_1$H NMR (400 MHz, $CDCl_3$) δ ppm 1.01 (s, 6H) 1.23-1.32 (m, 2H) 1.55 (s, 11H) 1.75-1.84 (m, 1H) 1.88 (d, J=1.25 Hz, 3H) 1.91-2.02 (m, 1H) 2.02-2.14 (m, 1H) 2.20-2.46 (m, 8H) 2.48-2.70 (m, 3H) 3.19-3.56 (m, 11H) 3.57-3.66 (m, 1H) 3.68-3.80 (m, 1H) 4.16-4.27 (m, 1H) 4.39-4.49 (m, 1H) 4.82-4.94 (m, 1H) 5.24-5.29 (m, 1H) 5.36-5.46 (m, 1H) 5.55-5.66 (m, 1H) 6.10-6.21 (m, 2H) 6.34-6.42 (m, 1H) 6.47-6.55 (m, 1H).

Step 3. Carbamate (059) (58 mg, 0.082 mmol), methanol (823 μl, 0.082 mmol), Tosic acid (46.9 mg, 0.247 mmol) was combined and stirred overnight. The reaction mix was then stirred with TEA (1 mL), concentrated to dryness and extracted with sat'd $NaHCO_3$. The organic layer was separated, dried over an. Na2SO4 and concentrated to dryness and chromatographed (0-10% MeOH in DCM) to afford Example 220 (2S,3S,6R,7S,10R,E)-2-((E)-1-(3-fluoro-5-morpholinophenyl)prop-1-en-2-yl)-10-hydroxy-3,7-dimethyl-12-oxooxacyclododec-4-en-6-yl 4-(methyl-d3)piperazine-1-carboxylate (17 mg, 0.029 mmol, 35.0% yield).

TABLE 20

| Characterization of Compound 220 | | |
|---|---|---|
| Ex. | Structure and IUPAC Chemical Name | Characterization |
| 220 | 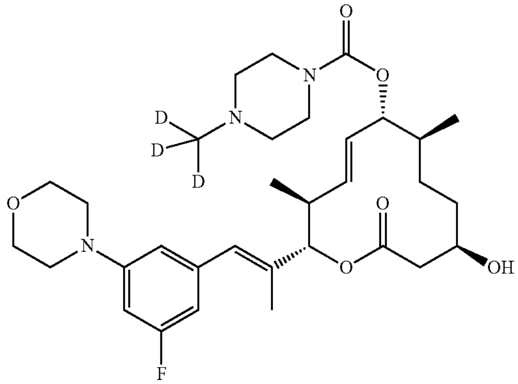 [SMILES: [2H]C([2H])([2H])N1CCN(C(=O)O[C@H]2/C=C/[C@H](C)[C@@H](/C(C)=C/c3cc(F)cc(N4CCOCC4)c3)OC(=O)C[C@H](O)CC[C@@H]2C)CC1] [(2R,3R,4E,6R,7S,10S)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-(trideuteriomethyl)piperazine-1-carboxylate | LCMS (ESI, m/z), 591.4 [M + H] $^1$H NMR (400 MHz, $CDCl_3$) d ppm 0.95-1.05 (m, 6 H) 1.17-1.33 (m, 2 H) 1.88 (d, J = 1.13 Hz, 4 H) 1.91-2.00 (m, 1 H) 2.30-2.43 (m, 4 H) 2.50-2.68 (m, 3 H) 3.11-3.19 (m, 4 H) 3.31-3.42 (m, 1 H) 3.43-3.58 (m, 4 H) 3.67-3.79 (m, 1 H) 3.81-3.90 (m, 4 H) 4.84-4.94 (m, 1 H) 5.21-5.29 (m, 1 H) 5.35-5.46 (m, 1 H) 5.55-5.66 (m, 1 H) 6.43-6.56 (m, 4 H). |

Compounds 221-253 were synthesized according to the general methods of Procedure 35.
Procedure 35.
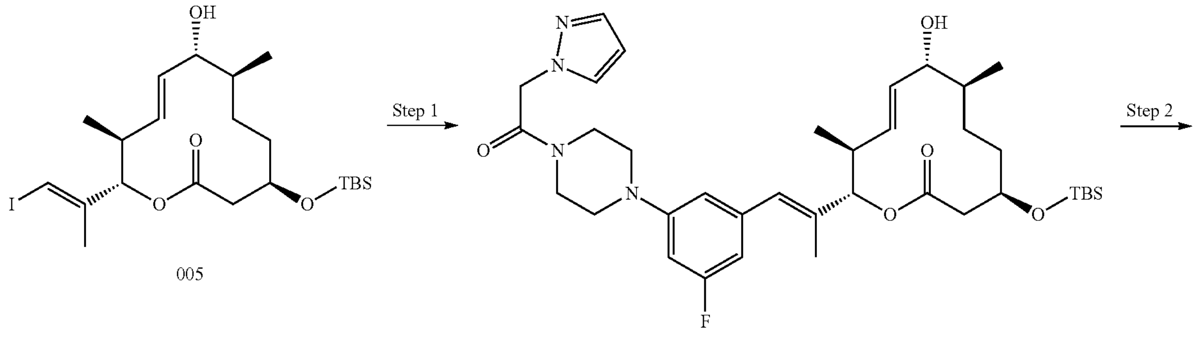
005 060
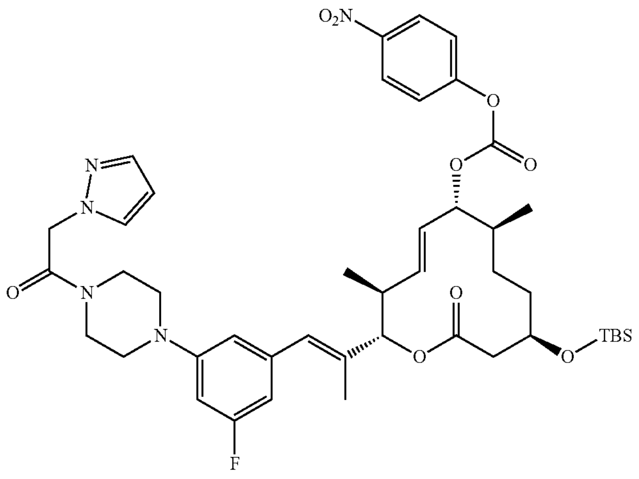
061
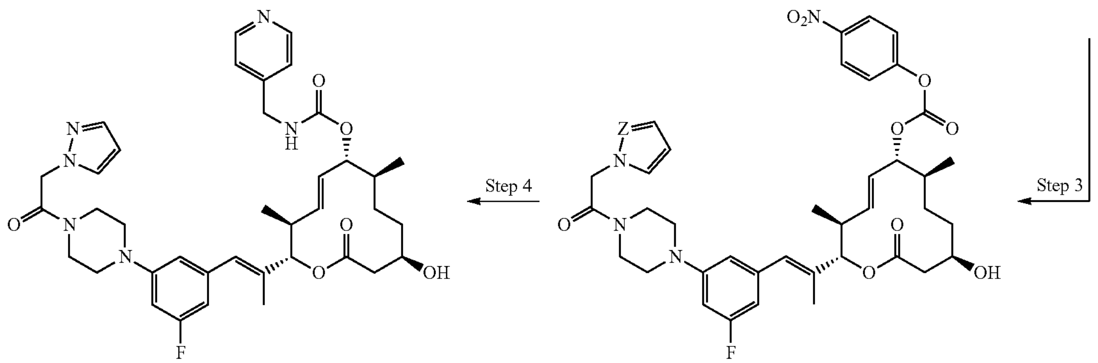
Ex. 221 062

Step 1. Iodide (005) (0.2 g, 0.393 mmol), 1-(4-(3-fluoro-5-(4,4,5,5-tetramethyl-1,3,2-dioxaborolan-2-yl)phenyl)piperazin-1-yl)-2-(1H-pyrazol-1-yl)ethanone (0.179 g, 0.433 mmol), silver oxide (0.456 g, 1.967 mmol), 1,4-dioxane (3.93 ml, 0.393 mmol) were combined and sparged with nitrogen for ~5 min. $Pd(PPh_3)_4$ (0.068 g, 0.059 mmol) was added and the reaction mix sparged with nitrogen for ~5 min. The reaction was then placed in an oil bath at 80° C. and stirred for 3 hours. The reaction mix was filtered and concentrated and chromatographed (0-100% EtOAc in Hexane) to afford (060) (179 mg, 0.268 mmol, 68.0% yield). LCMS (ESI, m/z), 683.55 [M+H].

Step 2. To a solution of alcohol (060) (0.575 g, 0.842 mmol) and DCM (4.21 ml, 0.842 mmol) were added DMAP (0.103 g, 0.842 mmol), Hunig's Base (0.735 ml, 4.21 mmol), 4-nitrophenyl chloroformate (0.305 g, 1.516 mmol). The resulting yellowish suspension was stirred for 12 h until the starting material was gone. The reaction mixture was concentrated and chromatographed to afford (061) (0.58 g, 0.684 mmol, 81% yield). LCMS (ESI, m/z), 848.5 [M+].

Step 3. Carbonate (061) (580 mg, 0.684 mmol), methanol (6839 μl, 0.684 mmol), tosic acid (390 mg, 2.052 mmol) were combined and stirred for 1 hour. Triethylamine (1 mL) was added and the reaction stirred for 15 minutes. The reaction mix was then concentrated to drynesss and dissolved in DCM. The crude reaction mix was stirred with saturated $NaHCO_3$ for 10 minutes and extracted. The organic phases were combined, dried over anhydrous $Na_2SO_4$ and concentrated to dryness to afford (062) (410 mg, 0.559 mmol, 82% yield). LCMS (ESI, m/z), 734.4 [M+H].

Step 4. Carbonate (062) (0.015 g, 0.020 mmol), DCM (0.204 ml, 0.020 mmol), Hunig's Base (7.14 μL, 0.041 mmol) were mixed, and amine (0.007 g, 0.061 mmol) was added and the reactions stirred overnight. The reaction mixture was then concentrated to dryness and chromatographed (reverse-phase HPLC) to afford product Example 221 (2S,3S,6R,7S,10R,E)-2-((E)-1-(3-(4-(2-(1H-pyrazol-1-yl)acetyl)piperazin-1-yl)-5-fluorophenyl)prop-1-en-2-yl)-10-hydroxy-3,7-dimethyl-12-oxooxacyclododec-4-en-6-yl (pyridin-4-ylmethyl)carbamate (9.4 mg, 0.013 mmol, 65.4% yield).

TABLE 21

| Characterization of Compounds 221-253 | | |
|---|---|---|
| Ex. | Structure and IUPAC Chemical Name | Characterization |
| 221 | 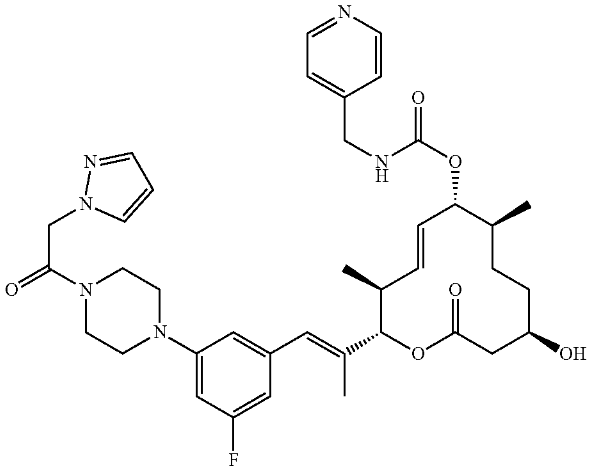 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)NCc2ccncn2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-(pyridin-4-ylmethyl)carbamate | LCMS (ESI, m/z), 703.4 [M + H] $^1$H NMR (400 MHz, METHANOL-d4) δ ppm 0.92-1.00 (m, 3 H) 1.01-1.11 (m, 3 H) 1.24-1.46 (m, 2 H) 1.55-1.70 (m, 2 H) 1.87 (s, 3 H) 1.91-1.99 (m, 1 H) 2.42-2.53 (m, 1 H) 2.57-2.65 (m, 2 H) 3.18-3.29 (m, 4 H) 3.74 (br s, 4 H) 3.77-3.85 (m, 1 H) 4.26-4.37 (m, 2 H) 5.09-5.17 (m, 1 H) 5.20 (s, 2 H) 5.50-5.57 (m, 2 H) 6.33-6.35 (m, 1 H) 6.50-6.54 (m, 1 H) 6.54-6.56 (m, 1 H) 6.60-6.65 (m, 1 H) 6.65-6.67 (m, 1 H) 6.86-6.93 (m, 1 H) 6.89 (d, J = 9.29 Hz, 1 H) 7.29-7.38 (m, 2 H) 7.49-7.55 (m, 1 H) 7.62-7.66 (m, 1 H) 8.09-8.16 (m, 2 H) 8.09-8.15 (m, 1 H) 8.42-8.50 (m, 2 H) |

TABLE 21-continued

Characterization of Compounds 221-253

| Ex. | Structure and IUPAC Chemical Name | Characterization |
|---|---|---|
| 222 | 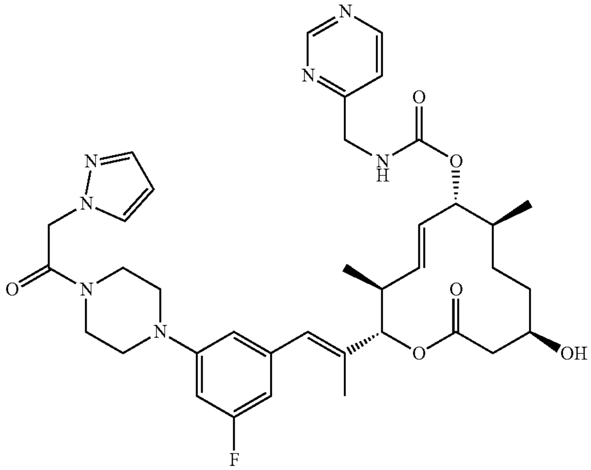 [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-(pyrimidin-4-ylmethyl)carbamate | LCMS (ESI, m/z), 704.5 [M + H] $^1$H NMR (400 MHz, METHANOL-d4) δ ppm 0.98 (d, J = 6.78 Hz, 3 H) 1.06 (br d, J = 6.65 Hz, 3 H) 1.24-1.47 (m, 3 H) 1.55-1.69 (m, 2 H) 1.87 (s, 3 H) 1.91-2.01 (m, 1 H) 2.40-2.52 (m, 1 H) 2.55-2.70 (m, 2 H) 3.16-3.28 (m, 4 H) 3.67-3.76 (m, 4 H) 3.79 (s, 2 H) 4.39 (s, 2 H) 5.09-5.16 (m, 1 H) 5.20 (s, 2 H) 5.49-5.58 (m, 2 H) 6.30-6.38 (m, 1 H) 6.55 (s, 2 H) 6.59-6.70 (m, 2 H) 7.52 (d, J = 1.63 Hz, 1 H) 7.64 (d, J = 2.13 Hz, 1 H) 8.71 (d, J = 5.27 Hz, 1 H) 9.00-9.11 (m, 1 H) |
| 223 | 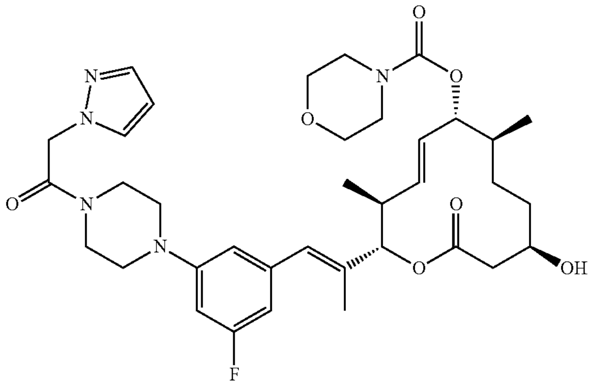 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCOCC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] morpholine-4-carboxylate | LCMS (ESI, m/z), 682.4 [M + H] $^1$H NMR (400 MHz, METHANOL-d4) δ ppm 1.00 (dd, J = 12.05, 6.78 Hz, 6 H) 1.26-1.45 (m, 2 H) 1.57-1.71 (m, 2 H) 1.87 (d, J = 1.25 Hz, 3 H) 1.91-2.02 (m, 1 H) 2.43-2.52 (m, 1 H) 2.57-2.69 (m, 2 H) 3.18-3.28 (m, 4 H) 3.38-3.50 (m, 4 H) 3.60-3.67 (m, 4 H) 3.71-3.76 (m, 4 H) 3.78-3.84 (m, 1 H) 5.11-5.17 (m, 1 H) 5.18-5.22 (m, 2 H) 5.45-5.60 (m, 3 H) 5.49-5.59 (m, 1 H) 6.29-6.36 (m, 1 H) 6.48-6.58 (m, 2 H) 6.59-6.69 (m, 2 H) 7.51-7.53 (m, 1 H) 7.63-7.66 (m, 1 H) |
| 224 | 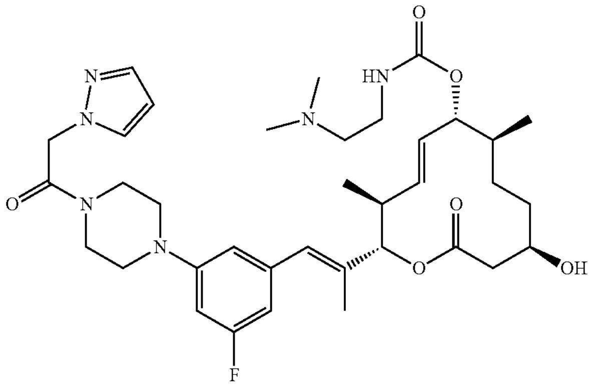 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)NCCN(C)C)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[2-(dimethylamino)ethyl]carbamate | LCMS (ESI, m/z), 683.6 [M + H] $^1$H NMR (400 MHz, METHANOL-d4) δ ppm 0.93-1.10 (m, 6 H) 1.26-1.47 (m, 2 H) 1.55-1.74 (m, 2 H) 1.82-1.93 (m, 4 H) 2.43-2.54 (m, 6 H) 2.57-2.66 (m, 2 H) 2.68-2.77 (m, 1 H) 3.18-3.29 (m, 5 H) 3.68-3.75 (m, 3 H) 3.77-3.84 (m, 1 H) 5.10-5.17 (m, 1 H) 5.19-5.22 (m, 2 H) 5.41-5.58 (m, 3 H) 6.30-6.38 (m, 1 H) 6.47-6.56 (m, 2 H) 6.59-6.70 (m, 2 H) 7.49-7.56 (m, 1 H) 7.60-7.68 (m, 1 H) |

TABLE 21-continued

| Ex. | Structure and IUPAC Chemical Name | Characterization |
|---|---|---|
| | Characterization of Compounds 221-253 | |
| 225 | 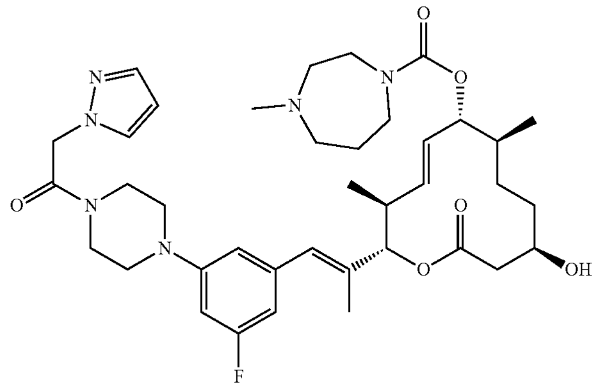 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCCN(C)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-methyl-1,4-diazepane-1-carboxylate | LCMS (ESI, m/z), 709.5 [M + H] $^1$H NMR (400 MHz, METHANOL-d4) δ ppm 0.95-1.01 (m, 3 H) 1.01-1.08 (m, 3 H) 1.26-1.49 (m, 3 H) 1.56-1.73 (m, 2 H) 1.87 (d, J = 1.25 Hz, 3 H) 1.91-2.02 (m, 3 H) 2.42-2.55 (m, 4 H) 2.56-2.70 (m, 2 H) 2.81 (br d, J = 4.27 Hz, 4 H) 3.17-3.29 (m, 5 H) 3.44-3.66 (m, 4 H) 3.67-3.76 (m, 4 H) 3.77-3.86 (m, 1 H) 5.09-5.17 (m, 1 H) 5.20 (s, 2 H) 5.49 (s, 2 H) 6.31-6.37 (m, 1 H) 6.46-6.58 (m, 2 H) 6.59-6.69 (m, 2 H) 7.48-7.55 (m, 1 H) 7.61-7.68 (m, 1 H) |
| 226 | 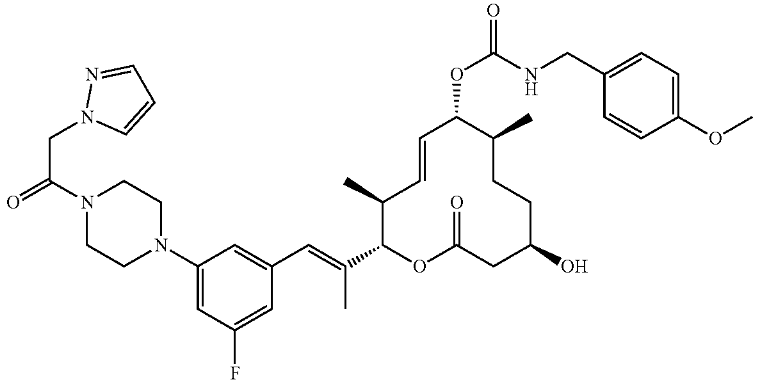 [SMILES: COc1ccc(CNC(=O)O[C@H]2/C=C/[C@H](C)[C@@H](/C(C)=C/c3cc(F)cc(N4CCN(C(=O)Cn5cccn5)CC4)c3)OC(=O)C[C@H](O)CC[C@@H]2C)cc1] [(2R,3R,4E,6R,7S,10S)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[(4-methoxyphenyl)methyl]carbamate | LCMS (ESI, m/z), 732.5 [M + H] $^1$H NMR (400 MHz, $CDCl_3$) δ ppm 0.82-1.09 (m, 6 H) 1.17-1.34 (m, 2 H) 1.40-1.58 (m, 1 H) 1.87 (d, J = 1.13 Hz, 5 H) 2.47-2.75 (m, 3 H) 3.08-3.22 (m, 4 H) 3.67-3.76 (m, 3 H) 3.80 (s, 5 H) 4.30 (br d, J = 5.40 Hz, 2 H) 4.78-4.86 (m, 1 H) 4.87-4.96 (m, 1 H) 5.07 (s, 2 H) 5.23-5.29 (m, 1 H) 5.35-5.45 (m, 1 H) 5.61 (dd, J = 14.93, 9.91 Hz, 1 H) 6.35 (t, J = 2.07 Hz, 1 H) 6.47-6.63 (m, 4 H) 6.82-6.89 (m, 2 H) 7.20 (brd, J = 8.41 Hz, 2 H) 7.52-7.59 (m, 2 H) |
| 227 | 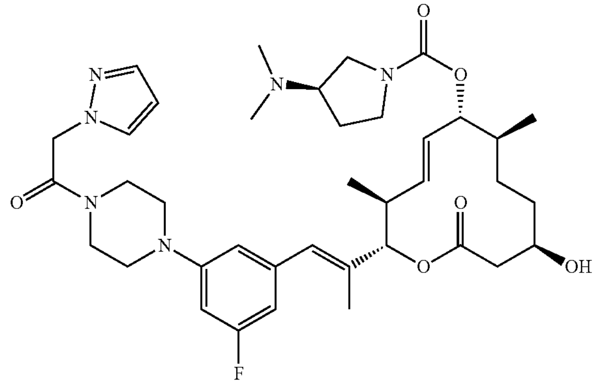 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CC[C@@H](N(C)C)C2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3S)-3-(dimethylamino)pyrrolidine-1-carboxylate | LCMS (ESI, m/z), 710.7 [M + H] $^1$H NMR (400 MHz, METHANOL-d4) δ ppm 0.98 (d, J = 6.78 Hz, 3 H) 1.00-1.06 (m, 3 H) 1.26-1.45 (m, 2 H) 1.64 (br s, 2 H) 1.76-1.84 (m, 1 H), 1.87 (d, J = 1.25 Hz, 3 H) 1.90-2.02 (m, 1 H) 2.13-2.24 (m, 1 H) 2.36 (d, J = 4.64 Hz, 6 H) 2.42-2.51 (m, 1 H) 2.56-2.67 (m, 2 H) 2.88-2.98 (m, 1 H) 3.11-3.19 (m, 1 H) 3.19-3.28 (m, 4 H) 3.52-3.62 (m, 1 H) 3.64-3.70 (m, 1 H) 3.71-3.76 (m, 4 H) 3.77-3.85 (m, 1 H) 5.09-5.18 (m, 1 H) 5.20 (s, 2 H) 5.48 (s, 2 H) 6.34 (s, 1 H) 6.48-6.57 (m, 2 H) 6.59-6.68 (m, 2 H) 7.47-7.55 (m, 1 H) 7.60-7.66 (m, 1 H) |

TABLE 21-continued

| Ex. | Structure and IUPAC Chemical Name | Characterization |
|---|---|---|
| | Characterization of Compounds 221-253 | |
| 228 | 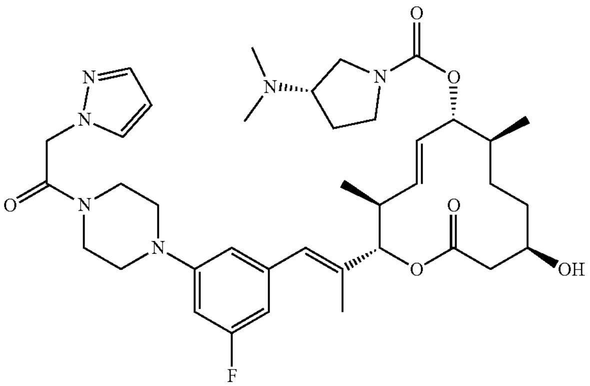 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CC[C@H](N(C)C)C2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3S)-3-(dimethylamino)pyrrolidine-1-carboxylate | LCMS (ESI, m/z), 710.6 [M + H] $^{1}$H NMR (400 MHz, METHANOL-d4) δ ppm 0.98 (d, J = 6.65 Hz, 3 H) 1.00-1.08 (m, 3 H) 1.26-1.47 (m, 2 H) 1.55-1.71 (m, 2 H) 1.74-1.84 (m, 1 H) 1.87 (d, J = 1.13 Hz, 3 H) 1.91-2.03 (m, 1 H) 2.09-2.24 (m, 1 H) 2.35 (d, J = 3.64 Hz, 6 H) 2.42-2.50 (m, 1 H) 2.56-2.69 (m, 2 H) 2.82-3.02 (m, 1 H) 3.11-3.29 (m, 5 H) 3.52-3.70 (m, 2 H) 3.70-3.76 (m, 4 H) 3.78-3.86 (m, 1 H) 5.10-5.17 (m, 1 H) 5.18-5.23 (m, 2 H) 5.44-5.60 (m, 2 H) 6.31-6.37 (m, 1 H) 6.47-6.58 (m, 2 H) 6.59-6.69 (m, 2 H) 7.49-7.55 (m, 1 H) 7.61-7.67 (m, 1 H) |
| 229 | 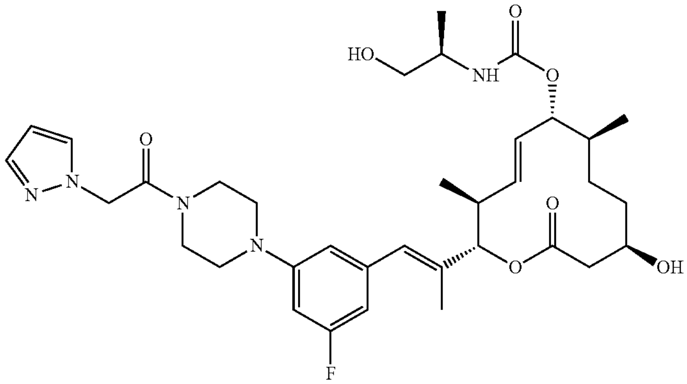 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N[C@H](C)CO)/C=C/[C@@H]1C] [(2R,3R,4E,6R,7S,10S)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[(2S)-1-hydroxypropan-2-yl]carbamate | LCMS (ESI, m/z), 670.4 [M + H] $^{1}$H NMR (400 MHz, METHANOL-d4) δ ppm 1.00 (br dd, J = 16.00, 6.71 Hz, 6 H) 1.12 (d, J = 6.65 Hz, 4 H) 1.34-1.45 (m, 2 H) 1.56-1.71 (m, 3 H) 1.87 (d, J = 1.13 Hz, 4 H) 2.41-2.53 (m, 1 H) 2.56-2.65 (m, 2 H) 3.16-3.26 (m, 3 H) 3.38-3.50 (m, 2 H) 3.60-3.69 (m, 1 H) 3.69-3.77 (m, 3 H) 3.77-3.86 (m, 1 H) 5.10-5.17 (m, 1 H) 5.20 (s, 2 H) 6.35 (t, J = 2.13 Hz, 1 H) 6.48-6.69 (m, 3 H) 7.52 (d, J = 1.76 Hz, 1 H) 7.64 (d, J = 2.26 Hz, 1H) |
| 230 | 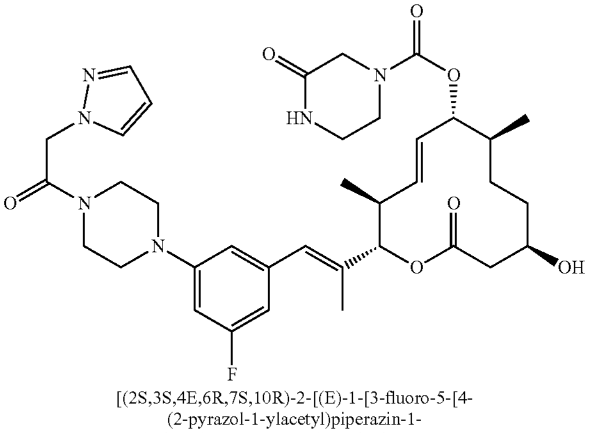 [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 3-oxopiperazine-1-carboxylate | LCMS (ESI, m/z), 695.4 [M + H] $^{1}$H NMR (400 MHz, METHANOL-d4) δ ppm 0.98 (d, J = 6.65 Hz, 3 H) 1.03 (d, J = 6.90 Hz, 3 H) 1.26-1.46 (m, 2 H) 1.58-1.72 (m, 2 H) 1.87 (d, J = 1.13 Hz, 3 H) 1.94-2.05 (m, 1 H) 2.43-2.53 (m, 1 H) 2.58-2.70 (m, 2 H) 3.18-3.29 (m, 4 H) 3.32-3.36 (m, 2 H) 3.58-3.69 (m, 2 H) 3.69-3.77 (m, 4 H) 3.78-3.86 (m, 2 H) 3.99-4.14 (m, 2 H) 5.09-5.18 (m, 1 H) 5.20 (s, 2 H) 5.45-5.63 (m, 2 H) 6.29-6.39 (m, 1 H) 6.45-6.58 (m, 2H) 6.60-6.70 (m, 2 H) 7.49-7.54 (m, 1 H) 7.60-7.68 (m, 1 H) |

TABLE 21-continued

| Characterization of Compounds 221-253 | | |
|---|---|---|
| Ex. | Structure and IUPAC Chemical Name | Characterization |
| 231 | 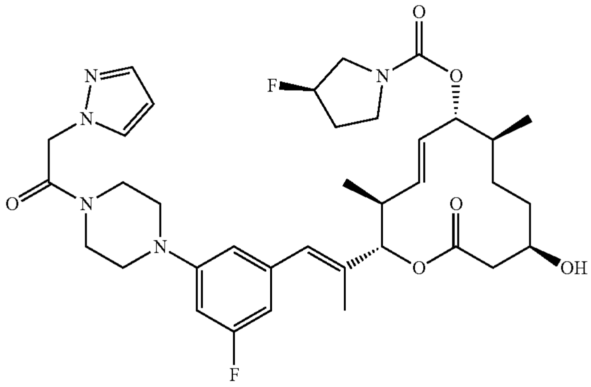 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CC[C@@H](F)C2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3R)-3-fluoropyrrolidine-1-carboxylate | LCMS (ESI, m/z), 684.4 [M + H] $^1H$ NMR (400 MHz, METHANOL-d4) δ ppm 0.95-1.07 (m, 6 H) 1.21-1.31 (m, 2 H) 1.33 (br d, J = 8.41 Hz, 2 H) 1.60-1.72 (m, 2 H) 1.87 (d, J = 0.75 Hz, 3 H) 1.91-2.07 (m, 2 H) 2.14-2.28 (m, 1 H) 2.42-2.52 (m, 1 H) 2.57-2.69 (m, 2 H) 3.18-3.28 (m, 4 H) 3.36-3.51 (m, 2 H) 3.52-3.68 (m, 2 H) 3.70-3.78 (m, 4 H) 3.79-3.86 (m, 1 H) 4.56 (s, 2 H) 5.11-5.17 (m, 2 H) 5.20 (s, 2 H) 5.51-5.63 (m, 2 H) 6.32-6.37 (m, 1 H) 6.49-6.69 (m, 4 H) 7.49-7.55 (m, 1 H) 7.61-7.66 (m, 1 H) |
| 232 | 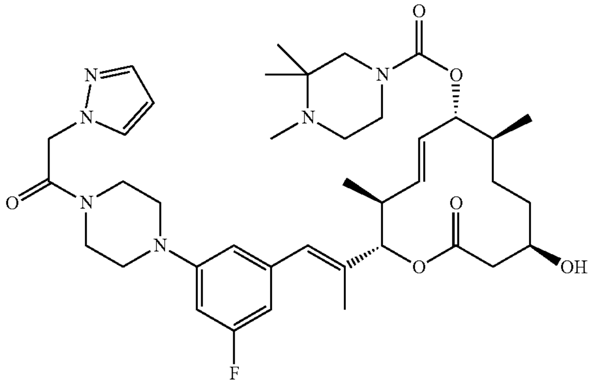 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C)C(C)(C)C2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 3,3,4-trimethylpiperazine-1-carboxylate | LCMS (ESI, m/z), 723.6 [M + H] $^1H$ NMR (400 MHz, METHANOL-d4) δ ppm 0.95-1.04 (m, 6 H) 1.06 (s, 6 H) 1.27-1.46 (m, 3 H) 1.54-1.74 (m, 2 H) 1.82-1.90 (m, 3 H) 1.90-2.02 (m, 1 H) 2.24-2.35 (m, 3 H) 2.41-2.53 (m, 1 H) 2.53-2.69 (m, 4 H) 3.16-3.29 (m, 7 H) 3.49-3.59 (m, 2 H) 3.68-3.76 (m, 4 H) 3.78-3.86 (m, 1 H) 4.52-4.60 (m, 1 H) 5.10-5.18 (m, 1 H) 5.18-5.23 (m, 2 H) 5.49 (s, 5 H) 6.30-6.38 (m, 1 H) 6.47-6.58 (m, 2 H) 6.60-6.70 (m, 2 H) 7.49-7.55 (m, 1 H) 7.62-7.69 (m, 1 H) |
| 233 | 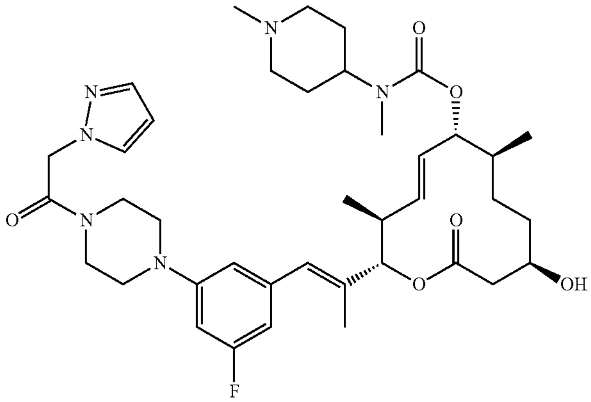 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N(C)C2CCN(C)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-methyl-N-(1-methylpiperidin-4-yl)carbamate | LCMS (ESI, m/z), 723.5 [M + H] $^1H$ NMR (400 MHz, METHANOL-d4) δ ppm 1.00 (dd, J = 14.18, 6.78 Hz, 6 H) 1.25-1.46 (m, 3 H) 1.60-1.69 (m, 2 H) 1.71-1.78 (m, 2 H) 1.87 (d, J = 1.25 Hz, 3 H) 1.89-2.04 (m, 3 H) 2.43-2.68 (m, 8 H) 2.82 (s, 3 H) 3.18-3.28 (m, 7 H) 3.73 (br d, J = 5.27 Hz, 4 H) 3.78-3.86 (m, 1 H) 3.95-4.07 (m, 1 H) 4.53-4.60 (m, 2 H) 5.11-5.17 (m, 1 H) 5.20 (s, 2 H) 5.50-5.58 (m, 2 H) 6.31-6.39 (m, 1 H) 6.49-6.68 (m, 4 H) 7.51-7.56 (m, 1H) 7.63-7.67 (m, 1 H) |

TABLE 21-continued

| Characterization of Compounds 221-253 | | |
|---|---|---|
| Ex. | Structure and IUPAC Chemical Name | Characterization |
| 234 | 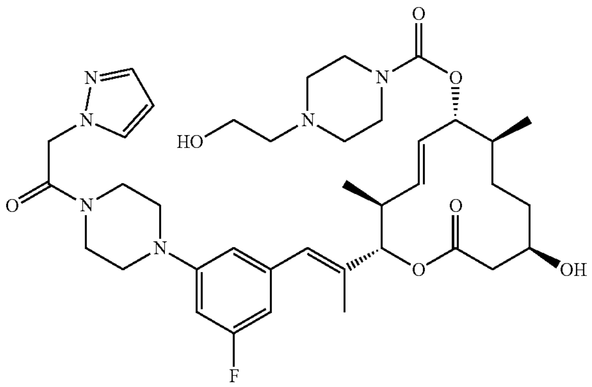 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(CCO)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-(2-hydroxyethyl)piperazine-1-carboxylate | LCMS (ESI, m/z), 725.5 [M + H] $^{1}$H NMR (400 MHz, METHANOL-d4) δ ppm 1.00 (dd, J = 10.35, 6.71 Hz, 6 H) 1.22-1.31 (m, 2 H) 1.32-1.45 (m, 2 H) 1.60-1.69 (m, 2 H) 1.87 (d, J = 1.25 Hz, 3 H) 1.92-2.00 (m, 1 H) 2.46-2.51 (m, 4 H) 2.52-2.57 (m, 2 H) 2.58-2.67 (m, 2 H) 3.19-3.28 (m, 5 H) 3.44-3.53 (m, 4 H) 3.66-3.70 (m, 2 H) 3.72-3.77 (m, 4 H) 3.78-3.86 (m, 1 H) 4.56 (s, 4 H) 5.10-5.17 (m, 1 H) 5.20 (s, 2 H) 5.46-5.61 (m, 2 H) 6.31-6.37 (m, 1 H) 6.49-6.57 (m, 2 H) 6.60-6.68 (m, 2 H) 7.49-7.54 (m, 1 H) 7.62-7.66 (m, 1 H) |
| 235 | 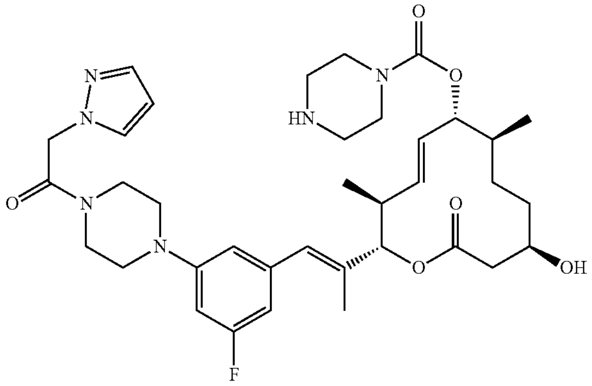 [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] piperazine-1-carboxylate | LCMS (ESI, m/z), 681.4 [M + H] $^{1}$H NMR (400 MHz, $CDCl_3$) δ ppm 0.93-1.04 (m, 6 H) 1.26 (br s, 3 H) 1.42-1.56 (m, 1 H) 1.75-1.84 (m, 1 H) 1.87 (s, 3 H) 1.89-2.01 (m, 1 H) 2.42-2.70 (m, 5 H) 3.11 (br s, 5 H) 3.42-3.59 (m, 3 H) 3.74 (s, 8 H) 4.83-4.99 (m, 1 H) 5.06 (s, 2 H) 5.20-5.31 (m, 1 H) 5.33-5.46 (m, 1 H) 5.54-5.66 (m, 1 H) 6.29-6.37 (m, 1 H) 6.42-6.57 (m, 4 H) 7.55 (d, J = 2.01 Hz, 2 H) |
| 236 | 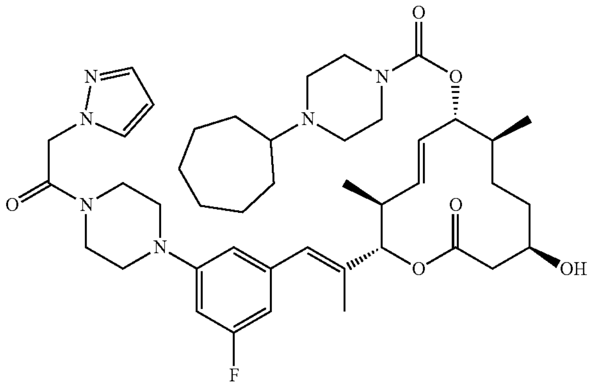 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C3CCCCCC3)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-cycloheptylpiperazine-1-carboxylate | LCMS (ESI, m/z), 778.0 [M + H] $^{1}$H NMR (400 MHz, $CDCl_3$) δ ppm 0.99 (br d, J = 6.53 Hz, 6 H) 1.16-1.33 (m, 3 H) 1.42-1.70 (m, 19 H) 1.74-1.84 (m, 3 H) 1.87 (s, 3 H) 1.88-2.02 (m, 1 H) 2.18-2.33 (m, 2 H) 2.45-2.74 (m, 3 H) 2.81-3.02 (m, 3 H) 3.09-3.20 (m, 3 H) 3.25-3.50 (m, 4 H) 3.62-3.86 (m, 7 H) 4.04-4.32 (m, 2 H) 4.81-4.96 |

TABLE 21-continued

Characterization of Compounds 221-253

| Ex. | Structure and IUPAC Chemical Name | Characterization |
| --- | --- | --- |
| 237 | 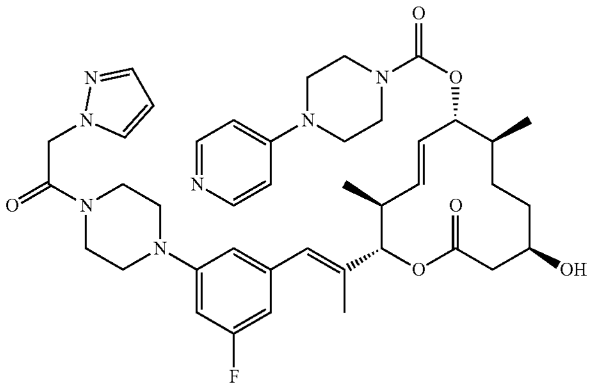 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(c3ccncc3)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-pyridin-4-ylpiperazine-1-carboxylate | LCMS (ESI, m/z), 758.7 [M + H] $^1H$ NMR (400 MHz, METHANOL-d4) δ ppm 0.94-1.06 (m, 6 H) 1.28-1.46 (m, 2 H) 1.56-1.72 (m, 2 H) 1.87 (d, J = 1.13 Hz, 3 H) 1.93-2.05 (m, 1 H) 2.37 (s, 1 H) 2.43-2.52 (m, 1 H) 2.57-2.71 (m, 2 H) 3.18-3.29 (m, 4 H) 3.53-3.61 (m, 4 H) 3.62-3.69 (m, 4 H) 3.71-3.77 (m, 4 H) 3.77-3.86 (m, 1 H) 4.86-4.91 (m, 1 H) 5.12-5.17 (m, 1 H) 5.20 (s, 2 H) 5.46-5.62 (m, 2 H) 6.32-6.36 (m, 1 H) 6.48-6.57 (m, 2 H) 6.59-6.69 (m, 2 H) 7.20-7.25 (m, 1 H) 7.50-7.55 (m, 1 H) 7.63-7.67 (m, 1 H) 7.68-7.74 (m, 1 H) |
| 238 | 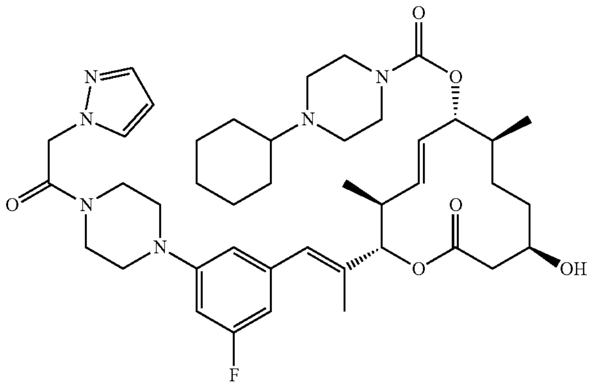 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(C3CCCCC3)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-cyclohexylpiperazine-1-carboxylate | LCMS (ESI, m/z), 763.7 [M + H] $^1H$ NMR (400 MHz, METHANOL-d4) δ ppm 0.94-1.07 (m, 6 H) 1.26-1.46 (m, 2 H) 1.56-1.72 (m, 2 H) 1.87 (d, J = 1.25 Hz, 5 H) 1.92-2.02 (m, 1 H) 2.40-2.52 (m, 1 H) 2.58-2.70 (m, 2 H) 2.84-2.98 (m, 3 H) 3.19-3.29 (m, 4 H) 3.45-3.64 (m, 4 H) 3.70-3.77 (m, 4 H) 3.78-3.86 (m, 1 H) 5.11-5.18 (m, 1 H) 5.20 (s, 2 H) 5.44-5.61 (m, 2 H) 6.34 (s, 1 H) 6.49-6.57 (m, 2 H) 6.60-6.68 (m, 2 H) 7.52 (d, J = 1.51 Hz, 1 H) 7.64 (d, J = 2.01 Hz, 1 H) |
| 239 | 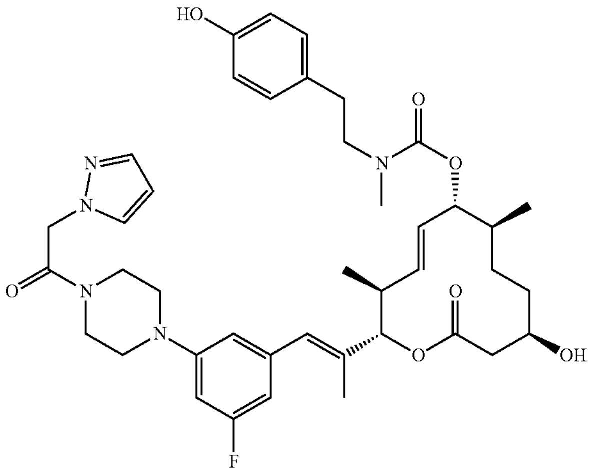 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N(C)CCc2ccc(O)cc2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[2-(4-hydroxyphenyl)ethyl]-N-methylcarbamate | LCMS (ESI, m/z), 746.8 [M + H] |

TABLE 21-continued

| Characterization of Compounds 221-253 | | |
|---|---|---|
| Ex. | Structure and IUPAC Chemical Name | Characterization |
| 240 | 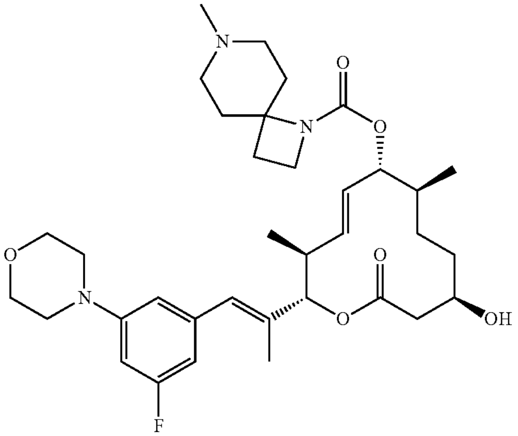 [SMILES: C/C(=C\c1cc(F)cc(N2CCOCC2)c1)[C@H]1OC(=O)C[C@H](O)CC[C@H](C)[C@@H](OC(=O)N2CCC23CCN(C)CC3)/C=C/[C@@H]1C] (2S,3S,6R,7S,10R,E)-2-((E)-1-(3-fluoro-5-morpholinophenyl)prop-1-en-2-yl)-10-hydroxy-3,7-dimethyl-12-oxo-1-oxacyclododec-4-en-6-yl 7-methyl-1,7-diazaspiro[3.5]nonane-1-carboxylate | LCMS (ESI, m/z), 628.7 [M + H] |
| 241 | 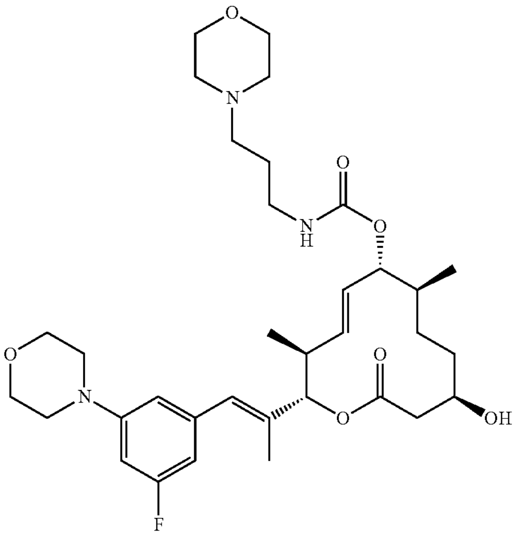 [SMILES: C/C(=C\c1cc(F)cc(N2CCOCC2)c1)[C@H]1OC(=O)C[C@H](O)CC[C@H](C)[C@@H](OC(=O)NCCCN2CCOCC2)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] N-(3-morpholin-4-ylpropyl)carbamate | LCMS (ESI, m/z), 632.4 [M + H] $^1$H NMR (400 MHz, METHANOL-d4) δ ppm 0.95-1.07 (m, 6 H) 1.27-1.49 (m, 4 H) 1.58-1.74 (m, 2 H) 1.78-1.87 (m, 2 H) 1.88-1.91 (m, 3 H) 1.92-2.02 (m, 1 H) 2.42-2.54 (m, 1 H) 2.58-2.67 (m, 2 H) 2.68 (s, 3 H) 3.04-3.14 (m, 2 H) 3.15-3.21 (m, 4 H) 3.76-3.79 (m, 1 H) 3.81 (s, 2H) 3.81-3.94 (m, 7 H) 4.76-4.83 (m, 1 H) 5.09-5.21 (m, 1 H) 5.45-5.62 (m, 2 H) 6.47-6.66 (m, 4 H) |

TABLE 21-continued

| Characterization of Compounds 221-253 | | |
|---|---|---|
| Ex. | Structure and IUPAC Chemical Name | Characterization |
| 242 | 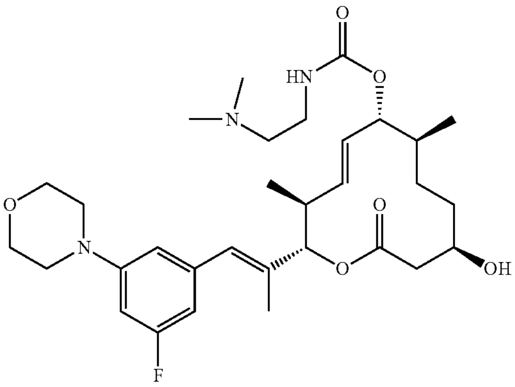 [SMILES: C/C(=C\c1cc(F)cc(N2CCOCC2)c1)[C@H]1OC(=O)C[C@H](O)CC[C@H](C)[C@@H](OC(=O)NCCN(C)C)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] N-[2-(dimethylamino)ethyl]carbamate | LCMS (ESI, m/z), 576.6 [M + H] |
| 243 | 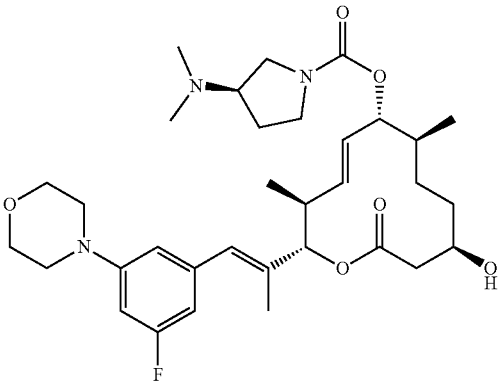 [SMILES: C/C(=C\c1cc(F)cc(N2CCOCC2)c1)[C@H]1OC(=O)C[C@H](O)CC[C@H](C)[C@@H](OC(=O)N2CC[C@@H](N(C)C)C2)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] (3S)-3-(dimethylamino)pyrrolidine-1-carboxylate | LCMS (ESI, m/z), 602.6 [M + H] 1H NMR (400 MHz, METHANOL-d4) δ ppm 0.94-1.06 (m, 6 H) 1.24-1.47 (m, 2 H) 1.55-1.70 (m, 2 H) 1.72-1.82 (m, 1 H) 1.87 (d, J = 1.13 Hz, 3 H) 1.91-2.02 (m, 1 H) 2.09-2.21 (m, 1 H) 2.29 (s, 6 H) 2.39-2.52 (m, 1 H) 2.56-2.68 (m, 2 H) 2.75-2.88 (m, 1 H) 3.10-3.19 (m, 5 H) 3.52-3.71 (m, 2 H) 3.76-3.88 (m, 5 H) 4.72-4.82 (m, 1 H) 5.09-5.18 (m, 1 H) 5.42-5.60 (m, 2 H) 6.46-6.65 (m, 4 H) |
| 244 | 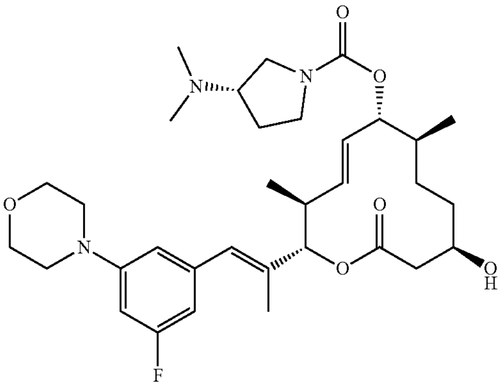 [SMILES: C/C(=C\c1cc(F)cc(N2CCOCC2)c1)[C@H]1OC(=O)C[C@H](O)CC[C@H](C)[C@@H](OC(=O)N2CC[C@H](N(C)C)C2)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] (3S)-3-(dimethylamino)pyrrolidine-1-carboxylate | LCMS (ESI, m/z), 602.6 [M + H 1H NMR (400 MHz, METHANOL-d4) δ ppm 1.00 (dd, J = 18.89, 6.71 Hz, 6 H) 1.36 (br d, J = 19.58 Hz, 2 H) 1.64 (br t, J = 3.01 Hz, 2 H) 1.74-1.85 (m, 1 H) 1.87 (d, J = 1.25 Hz, 3 H) 1.90-2.02 (m, 1 H) 2.10-2.21 (m, 1 H) 2.31 (s, 6 H) 2.40-2.51 (m, 1 H) 2.66 (s, 2 H) 2.76-2.94 (m, 1 H) 3.09-3.19 (m, 5 H) 3.47-3.73 (m, 2 H) 3.75-3.86 (m, 5 H) 5.08-5.18 (m, 1 H) 5.40-5.60 (m, 2 H) 6.43-6.68 (m, 4 H) |

TABLE 21-continued

| Characterization of Compounds 221-253 | | |
|---|---|---|
| Ex. | Structure and IUPAC Chemical Name | Characterization |
| 245 | 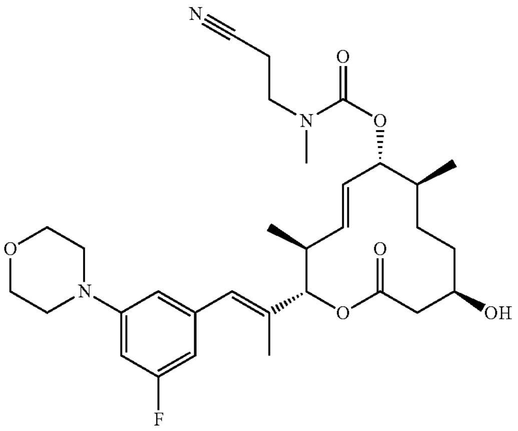 [SMILES: C/C(=C\c1cc(F)cc(N2CCOCC2)c1)[C@H]1OC(=O)C[C@H](O)CC[C@H](C)[C@@H](OC(=O)N(C)CCC#N)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] N-(2-cyanoethyl)-N-methylcarbamate | LCMS (ESI, m/z), 572.5 [M + H] 1H NMR (400 MHz, METHANOL-d4) δ ppm 0.98 (d, J = 6.78 Hz, 6 H) 1.24-1.48 (m, 2 H) 1.56-1.73 (m, 2 H) 1.87 (d, J = 1.13 Hz, 3 H) 1.93-2.05 (m, 1 H) 2.42-2.52 (m, 1 H) 2.57-2.68 (m, 2 H) 2.68-2.76 (m, 2 H) 2.94-3.03 (m, 3 H) 3.10-3.18 (m, 4 H) 3.47-3.65 (m, 2 H) 3.75-3.86 (m, 5 H) 5.10-5.18 (m, 1 H) 5.45-5.60 (m, 2 H) 6.45-6.66 (m, 4 H) |
| 246 | 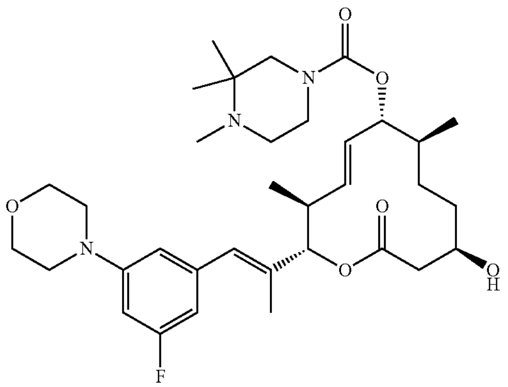 [SMILES: C/C(=C\c1cc(F)cc(N2CCOCC2)c1)[C@H]1OC(=O)C[C@H](O)CC[C@H](C)[C@@H](OC(=O)N2CCN(C)C(C)(C)C2)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 3,3,4-trimethylpiperazine-1-carboxylate | LCMS (ESI, m/z), 616.6 [M + H] 1H NMR (400 MHz, METHANOL-d4) δ ppm 0.89-1.09 (m, 11 H) 1.25-1.48 (m, 2 H) 1.56-1.72 (m, 2 H) 1.87 (d, J = 1.25 Hz, 3 H) 1.91-2.05 (m, 1 H) 2.27 (s, 3 H) 2.42-2.53 (m, 1 H) 2.66 (s, 4 H) 3.10-3.18 (m, 4 H) 3.20-3.28 (m, 2 H) 3.41-3.63 (m, 2 H) 3.81 (dd, J = 10.54, 5.65 Hz, 5 H) 5.09-5.20 (m, 1 H) 5.40-5.62 (m, 2 H) 6.44-6.66 (m, 4 H) |
| 247 | 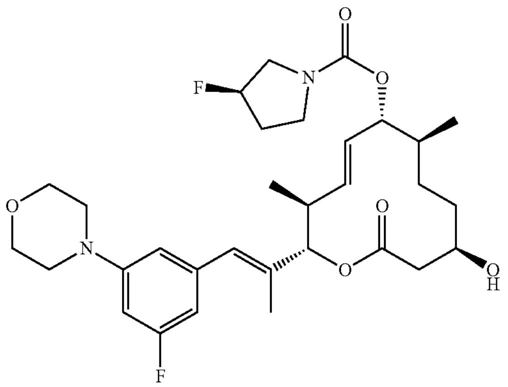 [SMILES: C/C(=C\c1cc(F)cc(N2CCOCC2)c1)[C@H]1OC(=O)C[C@H](O)CC[C@H](C)[C@@H](OC(=O)N2CC[C@@H](F)C2)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] (3R)-3-fluoropyrrolidine-1-carboxylate | LCMS (ESI, m/z), 577.5 [M + H] 1H NMR (400 MHz, METHANOL-d4) δ ppm 0.93-1.06 (m, 6 H) 1.25-1.49 (m, 2 H) 1.56-1.74 (m, 2 H) 1.87 (d, J = 1.00 Hz, 3 H) 1.96 (brs, 3 H) 2.40-2.51 (m, 1 H) 2.43-2.51 (m, 1 H) 2.57-2.65 (m, 2 H) 2.66 (s, 4 H) 3.10-3.19 (m, 4 H) 3.37-3.51 (m, 1 H) 3.53-3.73 (m, 2 H) 3.76-3.87 (m, 5 H) 5.09-5.34 (m, 1 H) 5.09-5.16 (m, 1 H) 5.15-5.21 (m, 1 H) 5.28-5.34 (m, 1 H) 5.41-5.62 (m, 2 H) 6.43-6.65 (m, 4 H) |

TABLE 21-continued

| Characterization of Compounds 221-253 | | |
|---|---|---|
| Ex. | Structure and IUPAC Chemical Name | Characterization |
| 248 | 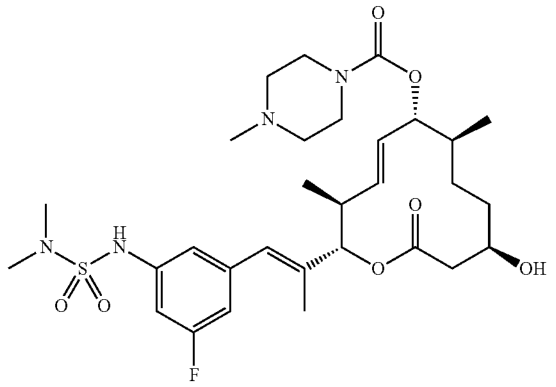 [SMILES: C/C(=C\c1cc(F)cc(NS(=O)(=O)N(C)C)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-(dimethylsulfamoylamino)-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 625.5 [M + H] 1H NMR (400 MHz, METHANOL-d4) δ ppm 1.00 (dd, J = 14.31, 6.78 Hz, 6 H) 1.25-1.47 (m, 2 H) 1.56-1.72 (m, 2 H) 1.88 (d, J = 1.13 Hz, 3 H) 1.93-2.04 (m, 1 H) 2.39 (s, 3 H) 2.44-2.56 (m, 4 H) 2.57-2.64 (m, 2 H) 2.80 (s, 7 H) 3.42-3.59 (m, 4 H) 3.76-3.88 (m, 1 H) 5.09-5.19 (m, 1 H) 5.49 (s, 3 H) 6.53 (s, 1 H) 6.68-6.76 (m, 1 H) 6.82-6.90 (m, 1 H) 6.90-6.98 (m, 1 H) |
| 249 | 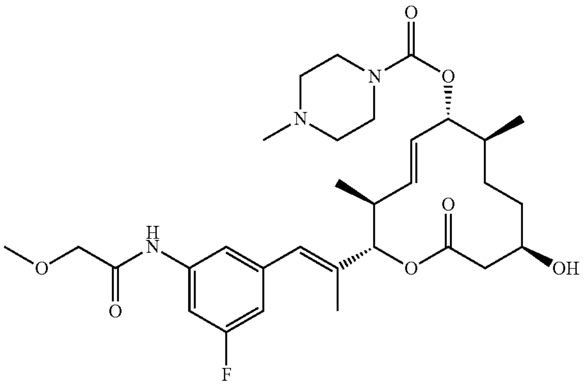 [SMILES: COCC(=O)Nc1cc(F)cc(/C=C(\C)[C@H]2OC(=O)C[C@H](O)CC[C@H](C)[C@@H](OC(=O)N3CCN(C)CC3)/C=C/[C@@H]2C)c1] [(2S,3S,4E,6R,7R,10S)-2-[(E)-1-[3-fluoro-5-[(2-methoxyacetyl)amino]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 590.6 [M + H] 1H NMR (400 MHz, METHANOL-d4) δ ppm 1.00 (dd, J = 10.67, 6.78 Hz, 6 H) 1.25-1.45 (m, 2 H) 1.57-1.70 (m, 2 H) 1.89 (d, J = 1.25 Hz, 3 H) 1.92-2.00 (m, 1 H) 2.30 (s, 3 H) 2.35-2.43 (m, 4 H) 2.44-2.51 (m, 1 H) 2.58-2.68 (m, 2 H) 3.48 (s, 6 H) 3.79 (s, 1 H) 4.03 (s, 2 H) 5.14 (d, J = 10.54 Hz, 1 H) 5.49 (s, 2 H) 6.55 (s, 1 H) 6.76-6.81 (m, 1 H) 7.33-7.37 (m, 1 H) 7.41-7.47 (m, 1 H) |
| 250 | 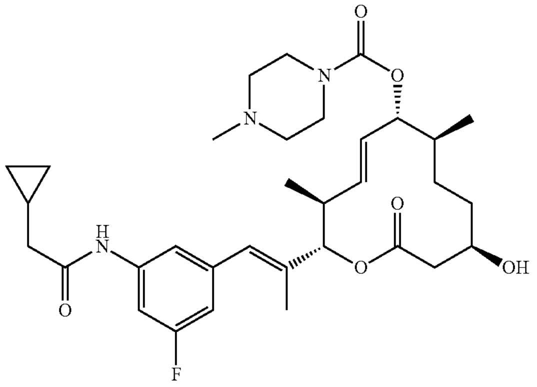 [SMILES: C/C(=C\c1cc(F)cc(NC(=O)CC2CC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-[(2-cyclopropylacetyl)amino]-5-fluorophenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 600.6 [M + H] 1H NMR (400 MHz, METHANOL-d4) δ ppm 0.21-0.27 (m, 2 H) 0.54-0.61 (m, 2 H) 1.00 (dd, J = 10.79, 6.78 Hz, 6 H) 1.12 (s, 1 H) 1.34 (br s, 2 H) 1.57-1.73 (m, 2 H) 1.89 (d, J = 1.25 Hz, 3 H) 1.92-2.01 (m, 1 H) 2.24-2.29 (m, 2 H) 2.30 (s, 3 H) 2.34-2.43 (m, 4 H) 2.43-2.53 (m, 1 H) 2.57-2.69 (m, 2 H) 3.39-3.58 (m, 4 H) 3.79 (s, 1 H) 5.14 (d, J = 10.67 Hz, 1 H) 5.44-5.61 (m, 3 H) 6.54 (s, 1 H) 6.71-6.80 (m, 1 H) 7.26 (s, 1 H) 7.36-7.45 (m, 1 H) |

TABLE 21-continued

| Characterization of Compounds 221-253 | | |
|---|---|---|
| Ex. | Structure and IUPAC Chemical Name | Characterization |
| 251 | 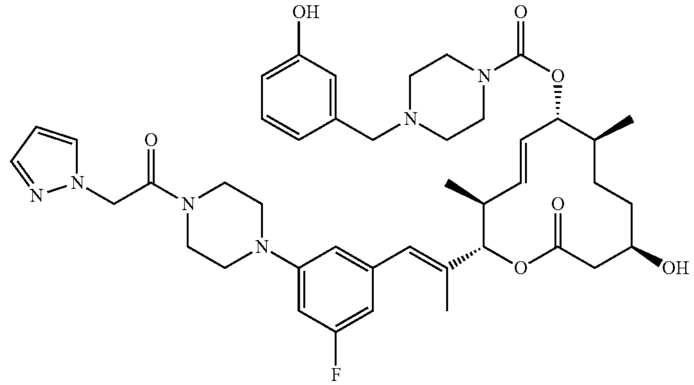 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(Cc3cccc(O)c3)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-[(3-hydroxyphenyl)methyl]piperazine-1-carboxylate | LCMS (ESI, m/z), 787.7 [M + H] |
| 252 | 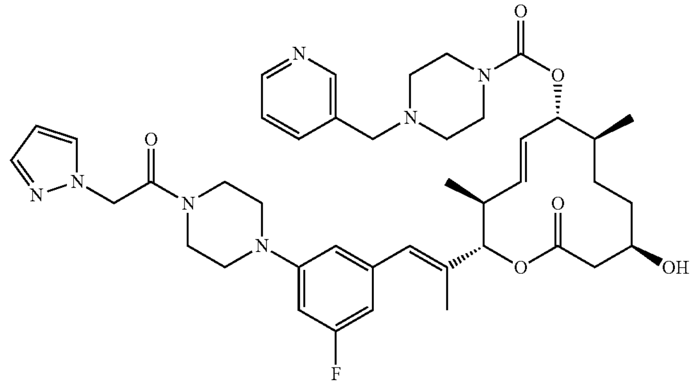 [SMILES: C/C(=C\c1cc(F)cc(N2CCN(C(=O)Cn3cccn3)CC2)c1)[C@H]1OC(=O)C[C@H](O)CC[C@H](C)[C@@H](OC(=O)N2CCN(Cc3cccnc3)CC2)/C=C/[C@@H]1C] [(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-(pyridin-3-ylmethyl)piperazine-1-carboxylate | LCMS (ESI, m/z), 772.7 [M + H] |
| 253 | 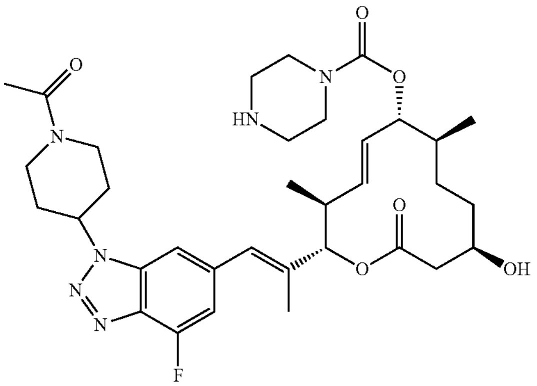 [SMILES: CC(=O)N1CCC(n2nnc3c(F)cc(/C=C(\C)[C@H]4OC(=O)C[C@H](O)CC[C@H](C)[C@@H](OC(=O)N5CCNCC5)/C=C/[C@@H]4C)cc32)CC1] [(2S,3S,4E,6R,7S,10R)-2-[(E)-1-[3-(1-acetylpiperidin-4-yl)-7-fluorobenzotriazol-5-yl]prop-1-en-2-yl]-10-hydroxy-3,7-dimethyl-12-oxo-1-oxacyclododec-4-en-6-yl] piperazine-1-carboxylate | LCMS (ESI, m/z), 655.8 [M + H] $^{1}H$ NMR (400 MHz, $CDCl_3$) d ppm 1.03 (br dd, J = 6.78, 4.14 Hz, 12 H) 1.22-1.36 (m, 2 H) 1.45-1.67 (m, 3 H) 1.74-1.87 (m, 1 H) 1.88-1.94 (m, 3 H) 1.94-2.00 (m, 1 H) 2.20 (s, 3 H) 2.22-2.32 (m, 3 H), 2.35-2.54 (m, 2 H) 2.54-2.72 (m, 3 H) 2.72-2.90 (m, 4 H) 2.91-3.12 (m, 2 H) 3.31-3.48 (m, 5 H) 3.68-,3.81 (m, 1 H) 4.04-4.15 (m, 1 H) 4.68-4.80 (m, 1 H) 4.80-4.93 (m, 2 H) 5.26-5.34 (m, 1 H) 5.39-5.49 (m, v1 H) 5.56-5.68 (m, 1 H) 6.65-6.75 (m, 1 H) 6.92-7.04 (m, 1 H) 7.11-7.18 (m, 1 H) |

Compounds 254-261 were synthesized according to the general methods of Procedure 36.
Procedure 36.
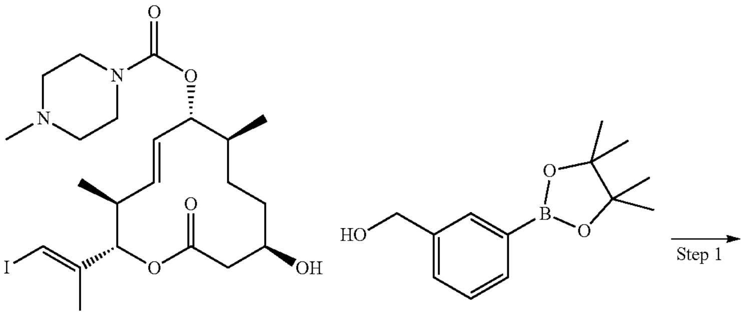
008 063
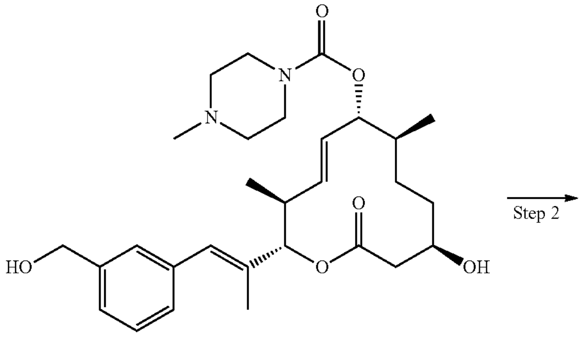
064
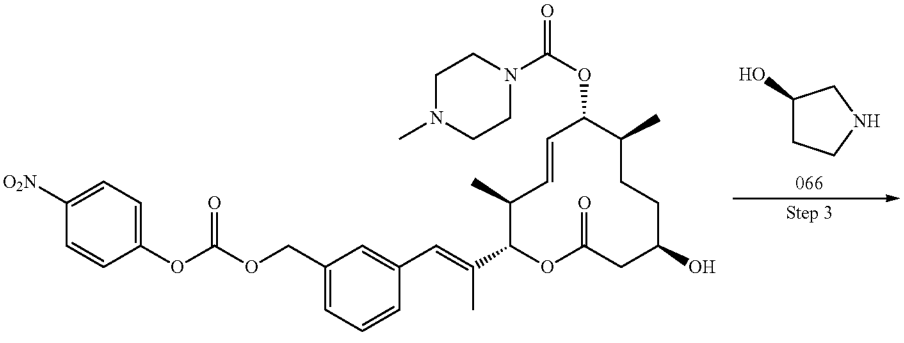
065
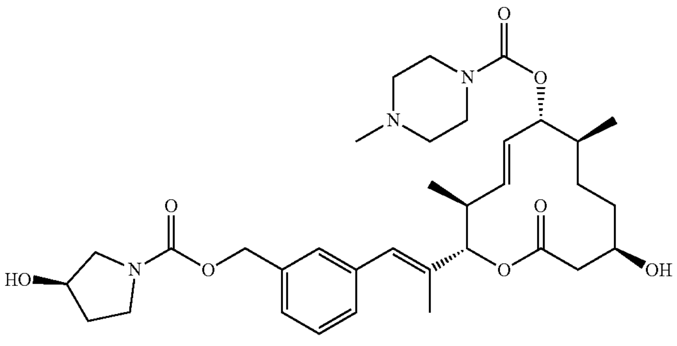
Ex. 254

Step 1: To a stirred solution of iodide (008) (120 mg, 0.225 mmol) and boronate (063) (63 mg, 0.269 mmol) in 3.4 ml of p-dioxane were added silver oxide (156 mg, 0.674 mmol) and tetrakis(triphenylphosphine)palladium(0) (25.9 mg, 0.022 mmol). The mixture was degassed and heated to 80° C. for 60 minutes. Upon completion by UPLC, the reaction mixture was cooled to room temperature, filtered, and concentrated. Purification by column chromatography eluting with a 0-20% MeOH/DCM gradient afforded (064) (59 mg, 51% yield) as a colorless oil. LCMS (ESI, m/z), 515.5 $[M+H]^+$. $^1H$ NMR (400 MHz, $CDCl_3$) δ ppm 1.00 (m, 6H) 1.14-1.36 (m, 2H) 1.50 (m, 1H) 1.64-1.84 (m, 1H) 1.84-1.94 (m, 4H) 2.29 (s, 3H) 2.35 (br s, 4H) 2.45-2.66 (m, 3H) 3.48 (br s, 4H) 3.59-3.76 (m, 1H) 4.69 (s, 2H) 4.88 (t, J=10.04 Hz, 1H) 5.28 (d, J=10.54 Hz, 1H) 5.40 (dd, J=14.93, 9.66 Hz, 1H) 5.60 (dd, J=14.93, 9.91 Hz, 1H) 6.59 (s, 1H) 7.18-7.35 (m, 4H).

Step 2: To a stirred solution of (064) (59 mg, 0.115 mmol) in 2 ml of 1,2-dichloroethane at 0° C. was added 4-nitrophenyl carbonochloridate (27.7 mg, 0.138 mmol), triethylamine (0.083 ml, 0.573 mmol), then N, N-dimethylpyridine-4-amine (2.8 mg, 0.023 mmol). The mixture stirred at 0° C. for 21 h. Completion was determined by UPLC.

Step 3: To the mixture from the previous step containing (065) (approximately 7.8 mg, 0.011 mmol) in 200 μL of 1,2-dichloroethane was added (R)-pyrrolidin-3-ol (066) (4 mg, 0.046 mmol). The resulting mixture was stirred at room temperature. Upon completion by UPLC, the reaction mixture was concentrated. Purification by HPLC afforded the title compound Example 254 (3.4 mg, 49% yield).

TABLE 22

Characterization of Compounds 254-261

| Ex. | Structure and IUPAC Chemical Name | Characterization |
|---|---|---|
| 254 | 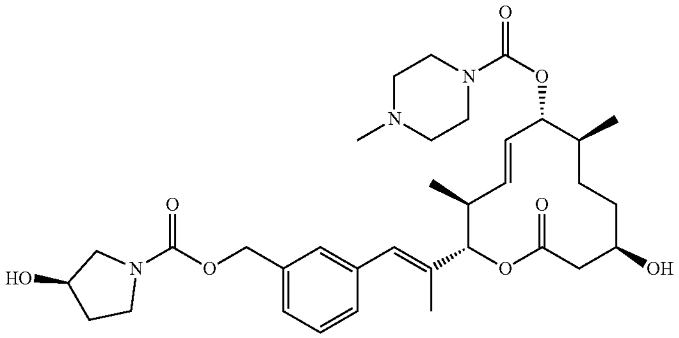 [SMILES: C/C(=C\c1cccc(COC(=O)N2CC[C@@H](O)C2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-2-[(E)-1-[3-[[(3R)-3-hydroxypyrrolidine-1-carbonyl]oxymethyl]phenyl]prop-1-en-2-yl]-3,7-dimethyl-12-oxo-1-oxacyclododec-4-en-6-yl] 4-methylpiperazine-1-carboxylate | LCMS (ESI, m/z), 628.5 $[M + H]^+$. $^1H$ NMR (400 MHz, DMSO-d6) d ppm 0.89-0.90 (m, J = 6.78 Hz, 6 H) 1.15-1.35 (m, 3 H) 1.40-1.52 (m, 2 H) 1.72-1.90 (m, 6 H) 2.11-2.32 (m, 6 H) 2.54-2.59 (m, 4 H) 3.27-3.36 (m, 1 H) 3.40-3.49 (m, 7 H) 3.62-3.79 (m, 1 H) 4.30-4.35 (m, 1 H) 4.61-4.72 (m, 2 H) 4.94-5.09 (m, 3 H) 5.37-5.50 (m, 2 H) 6.5 (s, 1 H) 7.23-7.30 (m, 3 H) 7.36 (m, 1 H). |
| 255 | 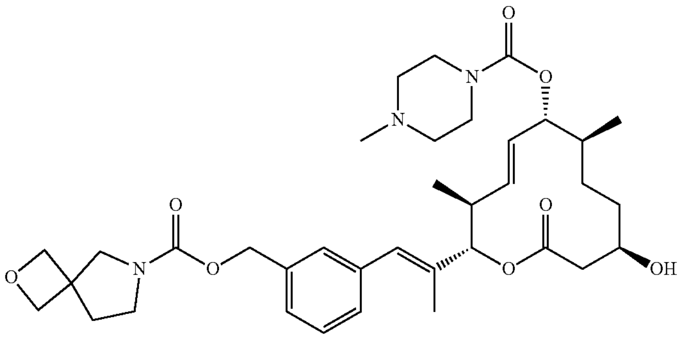 [3-[(E)-2-[(2S,3S,4E,6R,7S,10R)-10-hydroxy-3,7-dimethyl-6-(4-methylpiperazine-1-carbonyl)oxy-12-oxo-1-oxacyclododec-4-en-2-yl]prop-1-enyl]phenyl]methyl 2-oxa-7-azaspiro[3.4]octane-7-carboxylate | LCMS (ESI, m/z), 254.6 [M + H]+. 1H NMR (400 MHz, DMSO-d6) d ppm 0.89 (d, J = 6.65 Hz, 6 H) 1.14-1.36 (m, 3 H) 1.40-1.57 (m, 2 H) 1.76-1.87 (m, 4 H) 2.07-2.19 (m, 2 H) 2.19-2.46 (m, 5H) 2.52-2.59 (m, 4 H) 3.31-3.57 (m, 8 H) 3.71 (m, 1 H) 4.43 (m, 2 H) 4.48-4.55 (m, 2 H) 4.61-4.73 (m, 2 H) 4.98-5.09 (m, 3 H) 5.37-5.50 (m, 2 H) 6.54 (br s, 1 H) 7.22-7.29 (m, 3 H) 7.31-7.43 (m, 1 H) |

TABLE 22-continued

Characterization of Compounds 254-261

| Ex. | Structure and IUPAC Chemical Name | Characterization |
| --- | --- | --- |
| 256 | 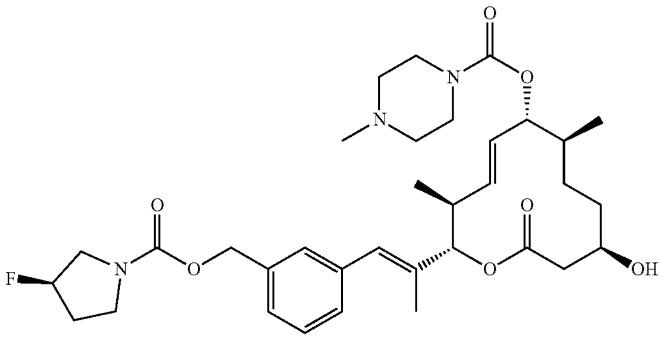 [SMILES: C/C(=C\c1cccc(COC(=O)N2CC[C@@H](F)C2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-2-[(E)-1-[2-[(2R)-2-(hydroxymethyl)pyrrolidin-1-yl]pyridin-4-yl]prop-1-en-2-yl]-3,7-dimethyl-12-oxo-1-oxacyclododec-4-en-6-yl] 4-methylpiperazine-1-carboxylate | LCMS (ESI, m/z), 630.6 [M + H]+. 1H NMR (400 MHz, DMSO-d6) d ppm 0.89 (d, J = 6.65 Hz, 6 H) 1.14-1.36 (m, 2 H) 1.47 (br d, J = 8.78 Hz, 2 H) 1.81 (br s, 4 H) 1.98-2.19 (m, 2 H) 2.19-2.37 (m, 5 H) 2.52-2.59 (m, 4 H) 3.29-3.59 (m, 9 H) 3.65-3.92 (m, 1 H) 4.60-4.75 (m, 2 H) 5.0 (m, 1H) 5.08 (s, 2 H) 5.23 (s, 1 H) 5.37-5.49 (m, 2H) 6.55 (s, 1 H) 7.23-7.30 (m, 3 H) 7.32-7.47 (m, 1 H) |
| 257 | 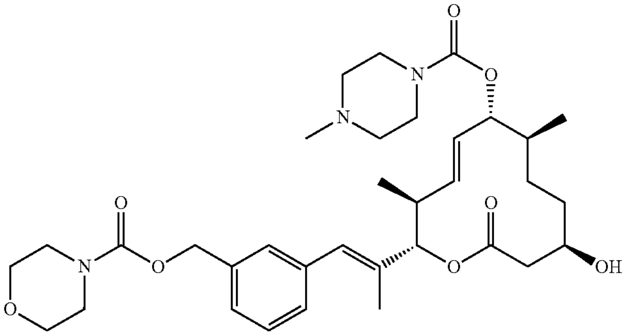 [SMILES: C/C(=C\c1cccc(COC(=O)N2CCOCC2)c1)[C@H]1OC(=O)C[C@H](O)CC[C@H](C)[C@@H](OC(=O)N2CCN(C)CC2)/C=C/[C@@H]1C] [3-[(E)-2-[(2S,3S,4E,6R,7S,10R)-10-hydroxy-3,7-dimethyl-6-(4-methylpiperazine-1-carbonyl)oxy-12-oxo-1-oxacyclododec-4-en-2-yl]prop-1-enyl]phenyl]methyl morpholine-4-carboxylate | LCMS (ESI, m/z), 628.6 [M + H]+. 1H NMR (400 MHz, DMSO-d6) d ppm 0.89 (d, J = 6.78 Hz, 6H) 1.11-1.36 (m, 3 H) 1.37-1.63 (m, 2 H) 1.73-1.89 (m, 4 H) 2.12-2.31 (m, 5 H) 2.52-2.62 (m, 4 H) 3.28-3.47 (m, 8 H) 3.53-3.56 (m, 4 H), 3.65-3.81 (m, 1 H) 4.58-4.76 (m, 2 H) 4.97-5.06 (m, 1 H) 5.09 (s, 2 H) 5.33-5.53 (m, 2 H) 6.47-6.58 (m, 1 H) 7.20-7.31 (m, 3 H) 7.33-7.46 (m, 1 H). |
| 258 | 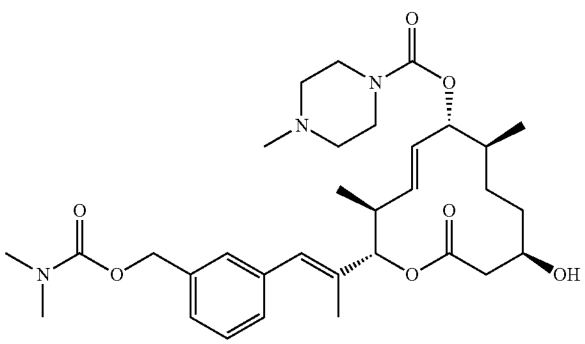 [SMILES: C/C(=C\c1cccc(COC(=O)N(C)C)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-(dimethylcarbamoyloxymethyl)phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 586.5 [M + H]+. 1H NMR (400 MHz, DMSO-d6) d ppm 0.89 (d, J = 6.78 Hz, 6 H) 1.11-1.37 (m, 3 H) 1.40-1.57 (m, 2 H) 1.82 (s, 4 H) 2.23 (m, 5 H) 2.54-2.58 (m, 4 H) 2.85 (m, 6 H) 3.38-3.49 (m, 4 H) 3.64-3.77 (m, 1 H) 4.59-4.75 (m, 2 H) 5.05 (s, 3 H) 5.34-5.53 (m, 2 H) 6.49-6.59 (m, 1 H) 7.20-7.30 (m, 3 H) 7.30-7.44 (m, 1 H). |

TABLE 22-continued

| Characterization of Compounds 254-261 | | |
|---|---|---|
| Ex. | Structure and IUPAC Chemical Name | Characterization |
| 259 | 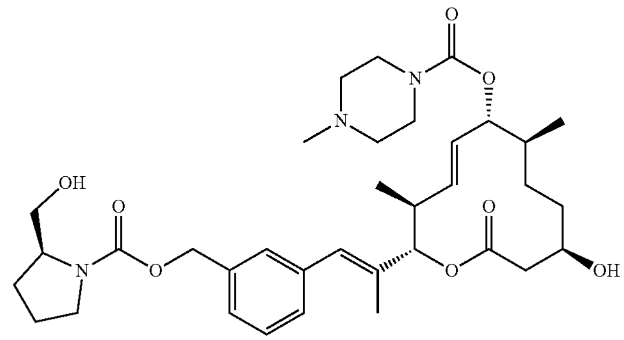 [SMILES: C/C(=C\c1cccc(COC(=O)N2CCC[C@H]2CO)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-2-[(E)-1-[3-[[(2R)-2-(hydroxymethyl)pyrrolidine-1-carbonyl]oxymethyl]phenyl]prop-1-en-2-yl]-3,7-dimethyl-12-oxo-1-oxacyclododec-4-en-6-yl] 4-methylpiperazine-1-carboxylate | LCMS (ESI, m/z), 642.6 [M + H]+. 1H NMR (400 MHz, DMSO-d6) d ppm 0.89 (d, J = 6.78 Hz, 6 H) 1.14-1.36 (m, 3 H) 1.37-1.52 (m, 2 H) 1.73-1.87 (m, 9 H) 2.20-2.46 (m, 5 H) 2.52-2.61 (m, 4 H) 3.25-3.53 (m, 4 H) 3.52 (m, 2H) 3.63-3.82 (m, 3 H) 4.61-4.73 (m, 2 H) 4.73-4.83 (m, 1 H) 5.05 (s, 3 H) 5.30-5.58 (m, 2 H) 6.42-6.59 (m, 1 H) 7.25 (s, 3 H) 7.31-7.44 (m, 1 H) |
| 260 | 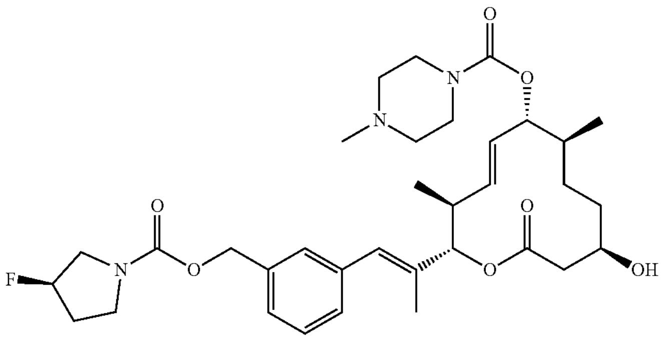 [SMILES: C/C(=C\c1cccc(COC(=O)N2CC[C@@H](F)C2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-2-[(E)-1-[3-[[(3R)-3-fluoropyrrolidine-1-carbonyl]oxymethyl]phenyl]prop-1-en-2-yl]-10-hydroxy-3,7-dimethyl-12-oxo-1-oxacyclododec-4-en-6-yl] 4-methylpiperazine-1-carboxylate | LCMS (ESI, m/z), 630.6 [M + H]$^+$. 1H NMR (400 MHz, DMSO-d6) d ppm 0.89 (d, J = 6.65 Hz, 6 H) 1.14-1.36 (m, 2 H) 1.47 (br d, J = 8.78 Hz, 2 H) 1.81 (br s, 4 H) 1.98-2.19 (m, 2 H) 2.19-2.37 (m, 5 H) 2.52-2.59 (m, 4 H) 3.29-3.59 (m, 9 H) 3.65-3.92 (m, 1 H) 4.60-4.75 (m, 2 H) 5.0 (m, 1H) 5.08 (s, 2 H) 5.23 (s, 1 H) 5.37-5.49 (m, 2H) 6.55 (s, 1 H) 7.23-7.30 (m, 3 H) 7.32-7.47 (m, 1 H). |
| 261 | 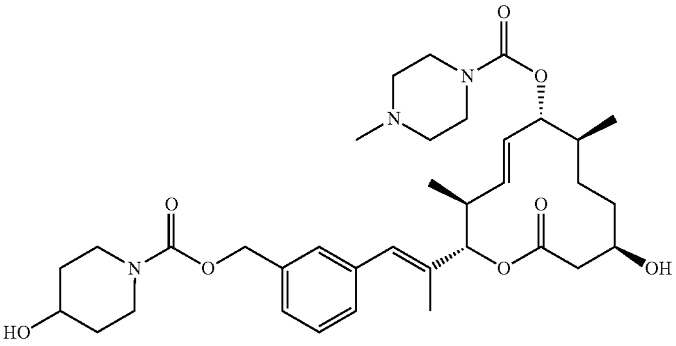 [SMILES: C/C(=C\c1cccc(COC(=O)N2CCC(O)CC2)c1)[C@H]1OC(=O)C[C@H](O)CC[C@H](C)[C@@H](OC(=O)N2CCN(C)CC2)/C=C/[C@@H]1C] [(2S,3S,4E,6R,7S,10R)-10-hydroxy-2-[(E)-1-[3-[(4-hydroxypiperidine-1-carbonyl)oxymethyl]phenyl]prop-1-en-2-yl]-3,7-dimethyl-12-oxo-1-oxacyclododec-4-en-6-yl] 4-methylpiperazine-1-carboxylate | LCMS (ESI, m/z), 642.6 [M + H]+. 1H NMR (400 MHz, DMSO-d6) d ppm 0.89 (d, J = 6.65 Hz, 6 H) 1.13-1.38 (m, 2 H) 1.40-1.57 (m, 1 H) 1.62-1.75 (m, 2 H) 1.78-1.88 (m, 4 H) 2.23-2.46 (m, 5 H) 2.52-2.60 (m, 4 H) 2.91-3.17 (m, 4 H) 3.24-3.45 (m, 4 H) 3.56-3.83 (m, 3 H) 4.56-4.73 (m, 3 H) 4.78 (d, J = 4.02 Hz, 2 H) 4.92-5.15 (m, 3 H) 5.43 (m, 3 H) 6.53 (s, 1 H) 7.18-7.27 (m, 3 H) 7.30-7.42 (m, 1 H). |

Compounds 262 and 263 were synthesized according to the general methods of Procedures 37 and 38.

Procedure 37.

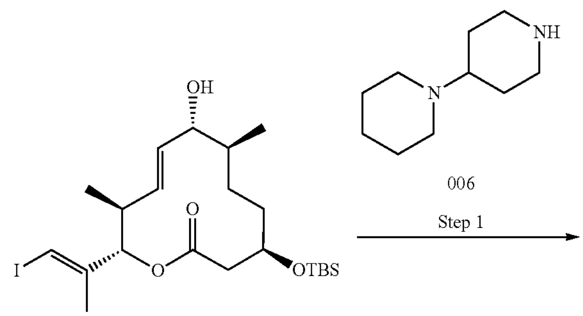

005

006

-continued

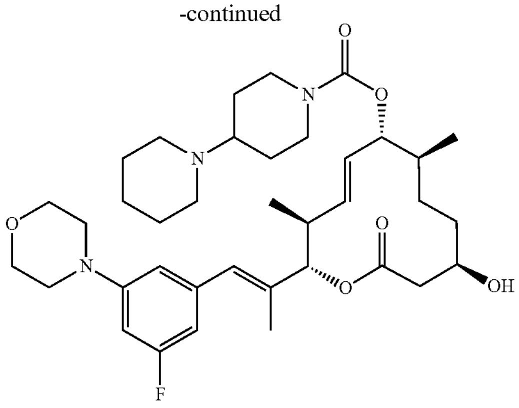

Ex. 262

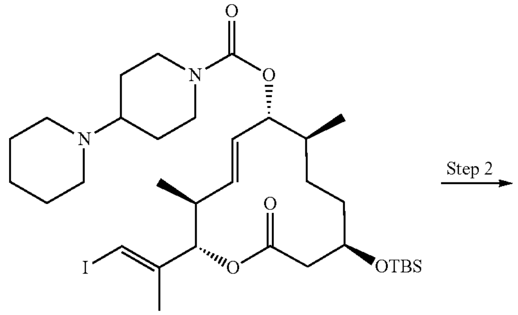

067

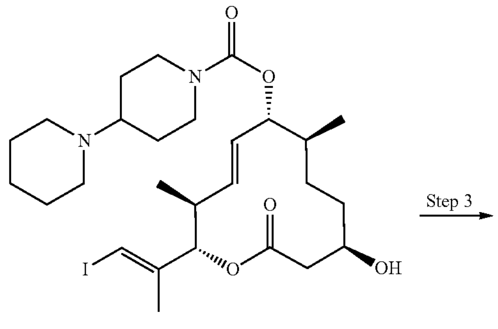

068

Step 1: A solution of DMAP (140 mg, 1.148 mmol), N1,N1,N8,N8-tetramethylnaphthalene-1,8-diamine (246 mg, 1.148 mmol) and triethylamine (0.667 ml, 4.878 mmol) in 9 ml diethyl ether was stirred for 60 mins at room temperature. To this mixture was added iodide (005) (500 mg, 0.957 mmol) as a solution in 3 mL diethyl ether (dropwise over 2 min) and stirred at room temperature for 7 h. At this point, 1,4'-bipiperidine (066) (725 mg, 4.306 mmol) was added and the mixture stirred for 19 h. The mixture was diluted with 10:1 heptane/MTBE and the organics washed multiple times with 1:1 saturated sodium bicarbonate solution/1M NaOH. The organics were then washed with brine and concentrated. The crude product was purified by flash chromatography through silica gel with MeOH/EtOAc gradient to isolate (067) (600 mg, 87%). 1H NMR (400 MHz, $CDCl_3$) δ ppm 0.88 (d, J=3.76 Hz, 6H) 1.68-1.74 (m, 12H) 1.78 (d, J=6.78 Hz, 3H) 2.03 (m, 1H) 2.18-2.42 (m, 12H) 2.61 (s, 6H) 3.13-3.35 (m, 8H) 3.47-3.62 (m, 2H) 4.64-4.71 (m, 1H) 5.01 (m, 1H) 5.60 (t, J=9.72 Hz, 1H) 5.90 (d, J=10.67 Hz, 1H) 6.15-6.33 (m, 2H) 8.08 (s, 1H).

Step 2: A solution of bipiperidine (067) (600 mg, 0.837 mmol) in 6 ml methanol was added 4-methylbenzenesulfonic acid hydrate (478 mg, 2.51 mmol) and stirred for 2 h. At this time, excess triethylamine was added and concentrated. Diluted in ethyl acetate, washed with saturated sodium bicarbonate solution, then brine. The organics were dried with sodium sulfate, filtered, and concentrated. The crude mixture was purified by flash chromatography through silica gel to deliver (068) (456 mg, 90%). LCMS (ESI, m/z), 603.4 $[M+H]^+$. 1H NMR (400 MHz, $CDCl_3$) δ ppm 0.90 (d, J=6.65 Hz, 3H) 0.98 (d, J=6.90 Hz, 3H) 1.12-1.30 (m, 2H) 1.34-1.50 (m, 4H) 1.57 (m, 4H) 1.74-1.85 (m, 6H) 1.90 (m, 1H) 1.99 (s, 1H) 2.35-2.54 (m, 6H) 2.57-2.76 (m, 3H) 3.48 (s, 1H) 3.71 (br dd, J=6.53, 3.26 Hz, 1H) 4.16 (br d, J=11.04 Hz, 2H) 4.83 (t, J=10.04 Hz, 1H) 5.25-5.40 (m, 2H) 5.47-5.55 (m, 1H) 6.47 (d, J=1.00 Hz, 1H) 7.26 (s, 1H).

Step 3: Example 262 was synthesized following the procedure described in Procedure 5, by substituting dipiperidine (068) and 4-(3-fluoro-5-(4,4,5,5-tetramethyl-1,3,2-dioxaborolan-2-yl)phenyl)morpholine to deliver the title compound Example 262. LCMS (ESI, m/z), 656.6 $[M+H]^+$. 1H NMR (400 MHz, $CDCl_3$) δ ppm 0.99 (m, 6H) 1.18-1.31 (m, 3H) 1.36-1.56 (m, 4H) 1.59 (br s, 4H) 1.82 (m, 4H) 1.86 (s, 3H) 1.91 (m, 1H) 2.41 (m, 1H) 2.47-2.65 (m, 6H) 2.72 (m, 2H) 3.12-3.17 (m, 4H) 3.37 (br s, 1H) 3.72 (br s, 1H) 3.82-3.87 (m, 4H) 4.09-4.26 (m, 2H) 4.86 (t, J=10.04 Hz, 1H) 5.23-5.26 (m, 1H) 5.39 (dd, J=15.06, 9.66 Hz, 1H) 5.58 (dd, J=14.93, 9.91 Hz, 1H) 6.45-6.53 (m, 4H).

Procedure 38.
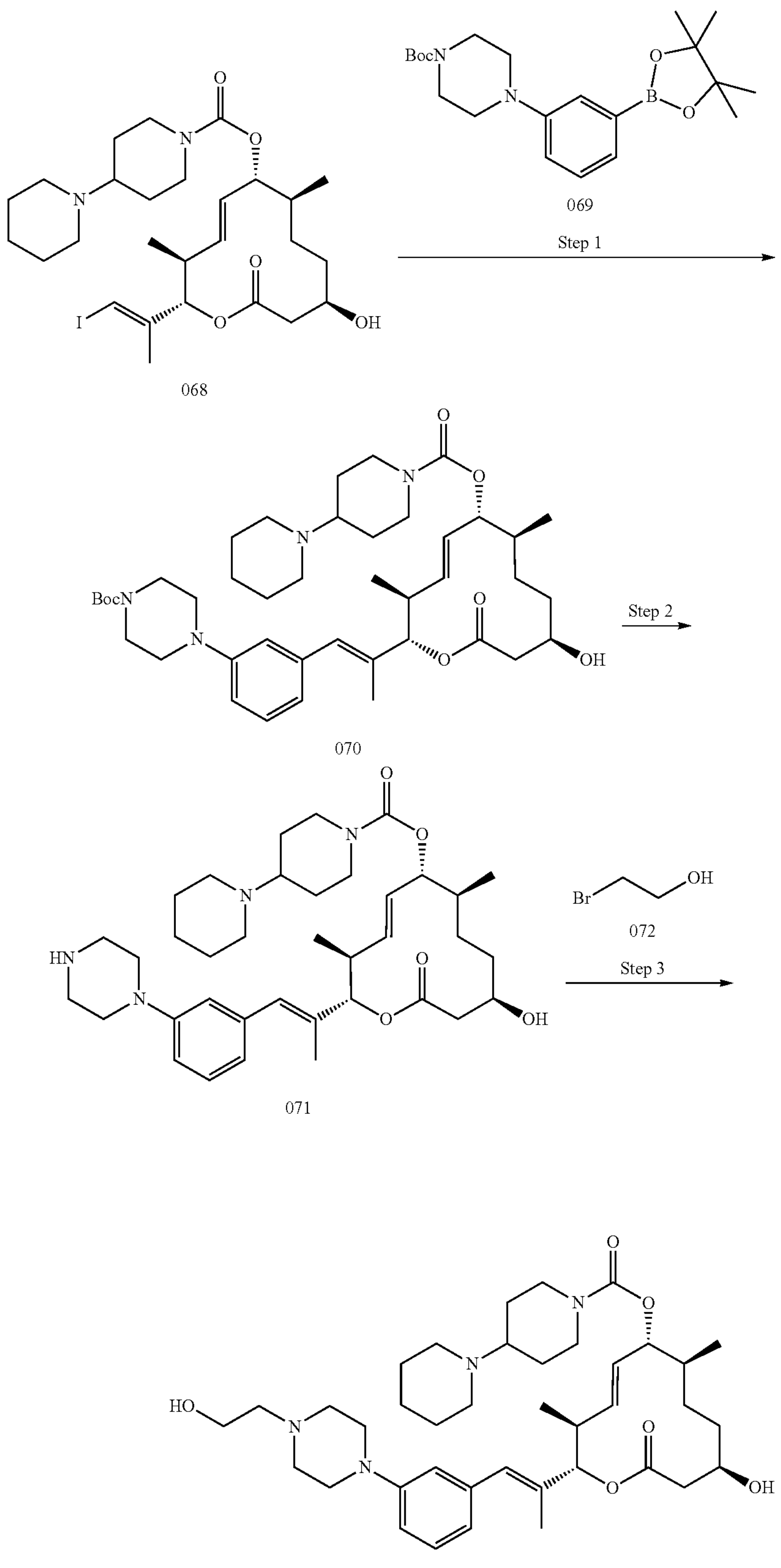
068, 069, 070, 071, 072
Ex. 263

Step 1: The compound was synthesized following the procedure described in Procedure 5 by substituting dipiperidine (068) and boronate (069) (38.7 mg, 0.10 mmol) to dipiperidine (070). LCMS (ESI, m/z), 738.5 $[M+H]^+$. 1H NMR (400 MHz, $CDCl_3$) δ ppm 0.99 (t, J=6.27 Hz, 6H) 1.15-1.36 (m, 2H) 1.39-1.56 (m, 13H) 1.64 (br s, 4H) 1.74-1.95 (m, 7H) 2.17 (s, 1H) 2.46-2.66 (m, 8H) 2.73 (br t, J=12.11 Hz, 2H) 3.04-3.20 (m, 4H) 3.53-3.61 (m, 4H) 3.72 (br s, 1H) 4.12-4.32 (m, 2H) 4.87 (t, J=10.04 Hz, 1H) 5.27 (d, J=10.54 Hz, 1H) 5.39 (dd, J=14.93, 9.66 Hz, 1H) 5.59 (dd, J=15.00, 9.98 Hz, 1H) 6.55 (s, 1H) 6.78-6.83 (m, 3H) 7.21-7.27 (m, 2H).

Step 2. To a stirred solution of dipiperidine (070) (19 mg, 0.026 mmol) (Example 8, Step b) in 7.7 ml DCM at 0° C. was added TFA (40 ul, 0.516 mmol). The mixture was warmed to room temperature and stirred for 2 days. At that point, the reaction was diluted in DCM, washed with saturated sodium bicarbonate solution, dried with sodium sulfate, filtered and concentrated. The crude was purified through flash chromatography through C-18 column with acetonitrile/water gradient to deliver (071) (11 mg, 670). LCMS (ESI, m/z), 328.9 [(M+Na+H)/2]+.

Step 3. To a stirred solution of dipiperidine (071) (11 mg, 0.017 mmol) in 0.2 ml DCM was added 2-bromoethanol (072) (2.45 ul, 0.035 mmol) and triethylamine (9.6 ul, 0.069 mmol). The mixture was stirred until completion of the reaction based on LC/MS. At that point, the reaction was diluted in DCM, washed with saturated sodium bicarbonate solution, dried with sodium sulfate, filtered and concentrated. The crude material was purified by flash chromatography through silica gel to deliver the title compound Example 263 (8.4 mg, 71%).

TABLE 23

Characterization of Compounds 262-263

| Ex. | Structure and IUPAC Chemical Name | Characterization |
|---|---|---|
| 262 | 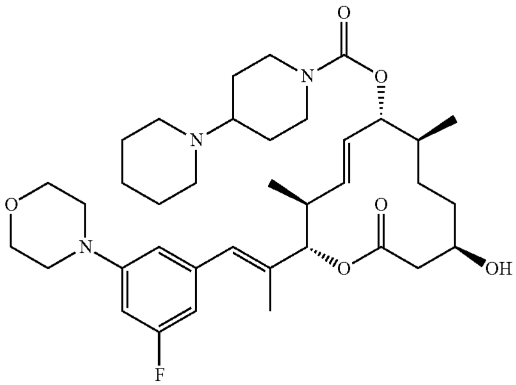 [SMILES: C/C(=C\c1cc(F)cc(N2CCOCC2)c1)[C@H]1OC(=O)C[C@H](O)CC[C@H](C)[C@@H](OC(=O)N2CCC(N3CCCCC3)CC2)/C=C/[C@@H]1C] [(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl] 4-piperidin-1-ylpiperidine-1-carboxylate | LCMS (ESI, m/z), 656.6 [M + H]+. 1H NMR (400 MHz, $CDCl_3$) d ppm 0.99 (m, 6 H) 1.18-1.31 (m, 3 H) 1.36-1.56 (m, 4 H) 1.59 (br s, 4 H) 1.82 (m, 4H) 1.86 (s, 3H) 1.91 (m, 1 H) 2.41 (m, 1 H) 2.47-2.65 (m, 6 H) 2.72 (m, 2H) 3.12-3.17 (m, 4 H) 3.37 (br s, 1 H) 3.72 (br s, 1 H) 3.82-3.87 (m, 4 H) 4.09-4.26 (m, 2 H) 4.86 (t, J = 10.04 Hz, 1 H) 5.23-5.26 (m, 1 H) 5.39 (dd, J = 15.06, 9.66 Hz, 1 H) 5.58 (dd, J = 14.93, 9.91 Hz, 1 H) 6.45-6.53 (m, 4 H) |
| 263 | 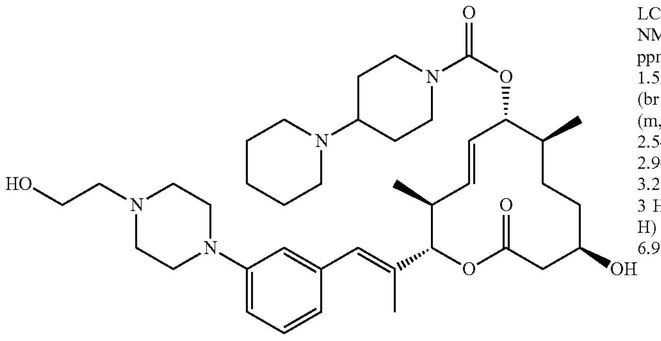 [(2S,3S,4E,6R,7S,10R)-10-hydroxy-2-[(E)-1-[3-[4-(2-hydroxyethyl)piperazin-1-yl]phenyl]prop-1-en-2-yl]-3,7-dimethyl-12-oxo-1-oxacyclododec-4-en-6-yl] 4-piperidin-1-ylpiperidine-1-carboxylate | LCMS (ESI, m/z), 681.6 [M + H]+. 1H NMR (400 MHz, METHANOL-d4) d ppm 1.00 (m, 6 H) 1.23-1.51 (m, 3 H) 1.52-1.61 (m, 2 H) 1.65 (br s, 4 H) 1.70 (br s, 1H) 1.80-2.02 (m, 9 H) 2.06-2.16 (m, 3 H) 2.47 (dd, J = 13.99, 5.33 Hz, 1 H) 2.54-2.72 (m, 2 H) 2.76-2.90 (m, 4 H) 2.90-3.00 (m, 4 H) 3.06-3.23 (m, 4 H) 3.23-3.28 (m, 4 H) 3.79 (br t, J = 5.52 Hz, 3 H) 4.29 (m, 2 H) 5.15 (d, J = 10.54 Hz, 1 H) 5.44-5.60 (m, 2 H) 6.57 (s, 1 H) 6.80-6.93 (m, 3 H) 7.24 (t, J = 7.91 Hz, 1 H) |

Biological Methods and Materials

Scintillation Proximity Assay (SPA) with [$^3$H]-Labelled Pladienolide Probe

Batch immobilization of anti-SF3B1 antibody (MBL) to anti-mouse PVT SPA scintillation beads (PerkinElmer) was prepared as follows: for every 2.5 mg of nuclear extracts, 5 g anti-SF3B1 antibody and 1.5 mg of beads were mixed in 150 μl PBS. The antibody-bead mixture was incubated for 30 min at RT and centrifuged at 18,000 g for 5 min. 150 μl PBS was used to resuspend every 1.5 mg antibody-bead mixture. The beads were suspended and added to the prepared nuclear extracts. The slurry was incubated for 2 h at 4° C. with gentle mixing. The beads were then collected by centrifuging at 18,000 g for 5 min, and washed twice with PBS+0.1% Triton X-100. After a final centrifugation step, every 1.5 mg of beads was suspended with 150 μl of PBS. The SF3b complexes were tested for [$^3$H]-labelled pladienolide probe binding ([$^3$H]—PB), synthesized as previously described (Kotake et al., 2007). 100 μL binding reactions were prepared with 50 μl bead slurry and by adding varying concentrations of PB or PB-OH, and after 30 min pre-incubation, 2.5 nM [$^3$H]—PB was added. The mixture was incubated for 30 min, and luminescence signals were read using a MicroBeta2 Plate Counter (PerkinElmer). Prism 6 (Graphpad) was used for non-linear regression curve fitting of the data.

a.
b. HeLa nuclear extract preparation (for in vitro splicing modulation assay below)
c. HeLa S3 cell pellets were resuspended in hypotonic buffer (10 mM HEPES pH 7.9, 1.5 mM $MgCl_2$, 10 mM KCl, 0.2 mM PMSF, and 0.5 mM DTT) and the suspension was brought up to a total of 5 packed cell volume (PCV). After centrifugation, the supernatant was discarded, and the cells were brought up to 3 PCV with hypotonic buffer and incubated on ice for 10 minutes. Cells were lysed using a dounce homogenizer and then centrifuged. The supernatant was discarded, and the pellet was resuspended with 12 packed nuclear volume (PNV) of low salt buffer (20 mM HEPES pH 7.9, 1.5 mM $MgCl_2$, 20 mM KCl, 0.2 mM EDTA, 25% glycerol, 0.2 mM PMSF, 0.5 mM DTT), followed by 1%2 PNV of high salt buffer (same as low salt buffer except 1.4 M KCl was used). The nuclei were gently mixed for 30 minutes before centrifuging. The supernatant (nuclear extract) was then dialyzed into storage buffer (20 mM HEPES pH 7.9, 100 mM KCl, 0.2 mM EDTA, 20% glycerol, 0.2 mM PMSF, 0.5 mM DTT). Protein concentration was determined using NanoDrop 8000 UV-Vis spectrophotometer (ThermoFisher Scientific).
d. In vitro splicing assay (IVS)

All Ad2-derived (Pellizzoni et al., 1998) sequences were cloned into pcDNA3.1(+) vector (Promega) using 5' EcoRI and 3' XbaI restriction sites. The plasmids were linearized using XbaI and used as DNA templates in the in vitro transcription reactions. The FtzΔi intron-less plasmid (Luo and Reed, 1999) was linearized using EcoRI. All RNAs were in vitro transcribed and then purified using MEGAScript T7 (Invitrogen) and MegaClear (Invitrogen) kits, respectively. For splicing reactions using Ad2 variant pre-mRNAs, 1 μL reactions were prepared using 8 μg nuclear extracts prepared from HeLa S3, 2 ng pre-mRNA, 0.2 ng FTZΔi, and varying concentrations of exemplary payloads or DMSO. After a 15 minute pre-incubation at 30° C., 1 μL splicing activation buffer (0.5 mM ATP, 20 mM creatine phosphate, 1.6 mM $MgCl_2$) was added, and the reactions were incubated for 90 minutes at 30° C. The reactions were then quenched with 13 μL DMSO, and 25 nL was used for RT-qPCR. RT-qPCR reactions were prepared using TaqMan RNA-to-$C_T$ 1-step kit (Life Technologies), RNA from splicing reactions, Ad2 (forward: ACTCTCTTCCG-CATCGCTGT; reverse: CCGACGGGTTTCCGATCCAA; probe: CTGTTGGGCTCGCGGTTG) and Ftz (forward: TGGCATCAGATTGCAAAGAC; reverse: ACGCCGGGT-GATGTATCTAT; probe: CGAAACGCACCCGTCA-GACG) mRNA primer-probe sets. Prism 6 (Graphpad) was used for non-linear regression curve fitting of the formed spliced product and normalized to the control (DMSO) sample.

Cell Lines

Panc 10.05 (CRL-2547), Panc 05.04 (CRL-2557), NCI-H1568 (CRL-5876) and NCI-H1650 (CRL-5883) were purchased from ATCC. Cell lines were maintained in RPMI-1640 (ATCC 30-2001) supplemented with 10% fetal bovine serum (FBS). The Panc lines were supplemented in addition with insulin and FBS up to 15% total. Panc 10.05 are WT for SF3b whereas Panc 05.04 are SF3b K700E mutant and have differential sensitivity to SF3b modulators.

NCI-H1568 cells express high MCL1 and undergo apoptosis upon SF3b modulator treatment, whereas NCI-H1650 are not dependent on MCL1 and therefore insensitive to SF3b modulator treatment, showing only cytostasis but no lethality (Aird et al., (2015). Abstract $C_8$: Targeting MCL1-dependent cancers with SF3B splicing modulators. Molecular Cancer Therapeutics. 14. C8-C8. 10.1158/1535-7163.TARG-15-C8.).

Compound Preparation and Presentation to Cells

Compounds for assay were prepared as stocks in 90% dimethyl sulfoxide (DMSO), assessed for purity by LC/MS, and serially diluted in DMSO using a low-volume liquid handler (VIAFLO ASSIST and VIAFLO II electronic 16-channel pipette, 0.5-12.5 L) in an 11-point half-log serial dilution to create a master dose response (MDR) source used for all tests.

Transfer of compounds from the MDR source plate to cell assay-ready plates were accomplished directly by low-energy acoustic transfer (ATS100, EDC Biosystems). After transfer of compounds to the assay plate, the dose-response range experienced by cells was typically 10 μM-100 pM (5 logs), and final DMSO concentration in the assay was 0.1%, uniformly. Each assay plate was self-anchored containing vehicle/DMSO negative controls, medium-only/positive controls, and cidal control dose-responses of bortezomib and staurosporine. Assay-ready plates were heat-sealed and stored at −20° C. until used, no longer than one month.

On the day of assay, cells were harvested, diluted from 37,500 to 25,000 cells per mL, and then 50 μL (750-500 cells) were dispensed onto assay-ready plates using a bulk liquids reagent dispenser (Using a Multidrop™ Combi Reagent Dispenser, Thermo Scientific). A DMSO-matched time zero (TO) plate was read and then all other plates were incubated at 37° C. with 5% $CO_2$ and 95% relative humidity until the end of assay. Cell proliferation and viability assays were performed 72 hours post-treatment depending on cell growth where at least one doubling would have occurred.

Measurement of Anti-Proliferative Activity of Treated Cells

Assessment of viability and proliferation was by measurement of cell ATP content using CellTiter-Glo® Luminescent Cell Viability Assay reagent (Promega) according to the manufacturer's instructions (CellTiter-Glo® Luminescent Cell Viability Assay Technical Bulletin Instructions for Use of Product(s) G7570, G7571, G7572, G7573 Literature #T1B288, Revised 3/15), using a microtiter plate reader (Envision, PE).

Cell proliferation was evaluated using the time zero (TO) signal as the positive control and the within-plate vehicle wells (DMSO) as the negative control. Data was converted to percent inhibition and falls into the range from −100% to 100% of growth where −100% equals a cidal response and 100% equals uninhibited or maximal growth. Cell growth at or near 0% is considered a static response.

TABLE 24

| Biological Assay Results | | | | | | | | |
|---|---|---|---|---|---|---|---|---|
| Ex. | SPA-ATS GMean IC50 (nM) SF3B1 (WT) | qPCR-IVS-ATS GMean IC50 (nM) Ad2.1 | qPCR-IVS-ATS GMean IC50 (nM) Ad2.2 | Ratio Ad2.1/2.2 | CTGlo-ATS GMean GI50 (nM) 72 h PANC0 504.1 | CTGlo-ATS Mean Min Response % 72 h PANC0 504.1 | CTGlo-ATS GMean GI50 (nM) 72 h NCIH1 568.1 | CTGlo-ATS Mean Min Response % 72 h NCIH1 568.1 |
| 1 | 19.803 | 28.938 | 18.709 | 1.547 | 54.801 | −79.550 | 61.245 | −71.582 |
| 2 | 14.700 | 29.282 | 24.750 | 1.183 | 30.291 | −76.626 | 40.606 | −70.665 |
| 3 | 1.744 | 18.620 | 10.306 | 1.807 | 2.955 | −87.809 | 2.423 | −78.460 |
| 4 | 3.796 | >25000.000 | 58.659 | 426.192 | 26.904 | −27.423 | 15.481 | −46.416 |
| 5 | 6.607 | 1499.846 | 94.734 | 15.832 | 47.221 | −17.631 | 59.671 | −38.293 |
| 6 | 8.853 | >25000.000 | 75.297 | 332.020 | 15.693 | −88.664 | 29.143 | −17.149 |
| 7 | 2.885 | 1247.783 | 25.138 | 49.637 | 8.957 | −89.436 | 15.136 | −56.359 |
| 8 | | 14172.621 | 42.184 | 335.973 | 19.268 | −94.207 | | |
| 9 | 14.917 | 106.832 | 26.999 | 3.957 | 63.852 | −87.085 | 116.290 | −83.308 |
| 10 | 18.088 | 811.844 | 39.511 | 20.547 | 73.839 | −87.077 | 123.385 | −69.020 |
| 11 | 9.490 | >25000.000 | 93.381 | 267.720 | 54.219 | −91.789 | 84.398 | −43.979 |
| 12 | 4.879 | 14.745 | 13.542 | 1.089 | 7.551 | −73.954 | 3.638 | −92.161 |
| 13 | 7.427 | 19.311 | 15.877 | 1.216 | 32.728 | −94.040 | 20.826 | −95.312 |
| 14 | 2.717 | 584.420 | 54.679 | 10.688 | 19.581 | −91.489 | 14.050 | −65.049 |
| 15 | 6.330 | 21.602 | 12.286 | 1.758 | 6.231 | −80.816 | 7.581 | −74.931 |
| 16 | 57.019 | 100.255 | 39.239 | 2.555 | 41.517 | −85.810 | 59.115 | −88.977 |
| 17 | 10.673 | 46.759 | 34.009 | 1.375 | 57.794 | −72.749 | 53.407 | −87.647 |
| 18 | 16.748 | 77.450 | 34.312 | 2.257 | 19.945 | −83.683 | 26.089 | −60.339 |
| 19 | 60.256 | 353.840 | 82.303 | 4.299 | 40.549 | −82.122 | 67.494 | −65.760 |
| 20 | 7.757 | 61.280 | 40.259 | 1.522 | 14.578 | −78.467 | 17.600 | −68.668 |
| 21 | 10.335 | 1612.616 | 52.275 | 30.849 | 23.638 | −90.919 | 31.212 | −50.841 |
| 22 | 5.764 | 876.293 | 38.831 | 22.567 | 11.553 | −84.195 | 12.792 | −69.453 |
| 23 | 4.231 | 369.160 | 28.305 | 13.042 | 10.429 | −90.781 | 10.847 | −64.974 |
| 24 | 5.186 | 192.475 | 30.664 | 6.277 | 8.286 | −89.895 | 10.866 | −67.459 |
| 25 | 4.943 | 430.092 | 46.405 | 9.268 | 20.469 | −88.378 | 20.618 | −49.158 |
| 26 | 11.379 | 107.167 | 43.532 | 2.462 | 18.968 | −88.278 | 26.479 | −68.566 |
| 27 | 10.473 | 39.853 | 42.297 | 0.942 | 11.911 | −84.822 | 12.297 | −71.773 |
| 28 | 10.051 | 8.549 | 61.513 | 0.139 | 42.924 | −41.132 | 89.619 | −39.539 |
| 29 | 5.601 | >25000.000 | 90.701 | 275.631 | 34.668 | −90.429 | 53.788 | −19.404 |
| 30 | | 19.063 | 10.990 | 1.734 | 7.020 | −75.997 | 5.890 | −78.664 |
| 31 | 43.243 | 50.141 | 14.624 | 3.429 | 53.037 | −90.716 | 89.383 | −98.108 |
| 32 | 3.243 | 19.498 | 16.198 | 1.204 | 6.528 | −69.289 | 10.016 | −74.701 |
| 33 | 5.583 | 28.419 | 27.607 | 1.029 | 10.030 | −77.334 | 11.999 | −73.122 |
| 34 | 3.180 | 56.541 | 26.903 | 2.102 | 14.046 | −85.656 | 9.461 | −55.438 |
| 35 | 4.783 | 913.307 | 27.076 | 33.732 | 53.186 | −87.702 | 106.908 | −46.227 |
| 36 | 3.488 | 236.343 | 32.930 | 7.177 | 19.014 | −84.494 | 25.362 | −54.389 |
| 37 | 2.267 | 85.797 | 20.173 | 4.253 | 4.612 | −86.134 | 4.748 | −82.247 |
| 38 | 3.095 | 1022.501 | 25.191 | 40.589 | 14.409 | −88.672 | 19.555 | −54.093 |
| 39 | 25.961 | 63.120 | 31.983 | 1.974 | 50.069 | −89.747 | 45.607 | −97.412 |
| 40 | 3.984 | 55.865 | 28.124 | 1.986 | 7.751 | −82.881 | 13.254 | −72.259 |
| 41 | 8.256 | 221.329 | 39.233 | 5.641 | 15.842 | −82.009 | 21.437 | −77.375 |
| 42 | 2.924 | 330.409 | 12.646 | 26.129 | 4.757 | −86.319 | 6.130 | −63.030 |
| 43 | 11.951 | >25000.000 | 139.415 | 179.321 | 57.498 | −88.777 | 89.062 | −36.254 |
| 44 | 8.263 | 12765.261 | 86.608 | 147.392 | 41.465 | −92.314 | 67.162 | −14.871 |
| 45 | 15.877 | 36.326 | 18.285 | 1.987 | 35.719 | −92.006 | 18.874 | −98.435 |
| 46 | 12.199 | >25000.000 | 114.487 | 218.366 | 40.026 | 0.031 | 78.415 | −10.684 |
| 47 | | 16947.874 | 79.628 | 212.839 | 78.160 | −87.783 | 66.450 | −44.494 |
| 48 | 11.279 | >25000.000 | 187.531 | 133.311 | 95.203 | −89.415 | 121.439 | −38.837 |
| 49 | 3.039 | 16254.945 | 28.331 | 573.757 | 9.015 | −93.022 | 11.720 | −35.275 |
| 50 | 1.463 | 17856.646 | 60.163 | 296.807 | 28.290 | −82.642 | 43.578 | −65.255 |
| 51 | 19.740 | >25000.000 | 88.061 | 283.894 | 80.862 | −78.388 | 111.651 | −31.962 |
| 52 | 8.296 | 39.595 | 45.397 | 0.872 | 13.573 | −76.609 | 23.254 | −63.079 |
| 53 | 14.104 | 1905.683 | 30.477 | 62.529 | 81.130 | −92.947 | 81.762 | −59.250 |
| 54 | 4.286 | 12.450 | 15.804 | 0.788 | 8.658 | −94.487 | 7.806 | −96.584 |
| 55 | 2.370 | 19926.430 | 45.284 | 440.028 | 17.209 | −85.478 | 21.239 | −57.557 |
| 56 | 1.937 | 16.055 | 15.295 | 1.050 | 1.849 | −90.320 | 4.423 | −67.625 |
| 57 | 9.161 | >25000.000 | 228.152 | 109.576 | 49.719 | −71.380 | 41.349 | −47.783 |
| 58 | 6.544 | 30.122 | 22.020 | 1.368 | 6.969 | −91.132 | 6.998 | −70.067 |
| 59 | 2.750 | 13563.090 | 46.122 | 294.071 | 17.527 | −95.512 | 14.534 | −44.526 |
| 60 | 2.987 | >25000.000 | 55.461 | 450.767 | 26.744 | −87.159 | 29.909 | −42.456 |
| 61 | 13.472 | >25000.000 | 114.387 | 218.556 | 41.974 | −93.599 | 46.822 | −38.996 |
| 62 | 7.865 | 586.891 | 52.933 | 11.088 | 40.541 | −94.536 | 54.936 | −57.446 |

TABLE 24-continued

Biological Assay Results

| Ex. | SPA-ATS GMean IC50 (nM) SF3B1 (WT) | qPCR-IVS-ATS GMean IC50 (nM) Ad2.1 | qPCR-IVS-ATS GMean IC50 (nM) Ad2.2 | Ratio Ad2.1/2.2 | CTGlo-ATS GMean GI50 (nM) 72 h PANC0 504.1 | CTGlo-ATS Mean Min Response % 72 h PANC0 504.1 | CTGlo-ATS GMean GI50 (nM) 72 h NCIH1 568.1 | CTGlo-ATS Mean Min Response % 72 h NCIH1 568.1 |
|---|---|---|---|---|---|---|---|---|
| 63 | 12.307 | 18789.671 | 52.047 | 361.016 | 41.172 | −96.440 | 39.304 | −50.769 |
| 64 | 3.081 | 116.017 | 24.425 | 4.750 | 7.959 | −92.050 | 6.499 | −66.274 |
| 65 | 2.835 | 26.222 | 17.310 | 1.515 | 5.742 | −88.951 | 5.878 | −68.297 |
| 66 | 2.233 | 206.385 | 33.895 | 6.089 | 8.224 | −89.623 | 11.718 | −64.699 |
| 67 | 1.955 | 22.653 | 20.232 | 1.120 | 7.272 | −87.661 | 8.603 | −75.182 |
| 68 | 3.393 | 1866.932 | 35.703 | 52.291 | 11.676 | −93.925 | 12.401 | −67.270 |
| 69 | 3.830 | 36.743 | 20.881 | 1.760 | 7.480 | −86.274 | 4.035 | −76.018 |
| 70 | 1.550 | 17.647 | 16.459 | 1.072 | 5.944 | −83.969 | 3.371 | −77.042 |
| 71 | 3.713 | 29.685 | 18.942 | 1.567 | 11.503 | −68.599 | 6.391 | −92.527 |
| 72 | 4.659 | 35.841 | 13.972 | 2.565 | 5.683 | −75.581 | 4.189 | −80.730 |
| 73 | 2.423 | 13.107 | 13.586 | 0.965 | 6.908 | −79.201 | 5.850 | −76.720 |
| 74 | 4.880 | 34.483 | 20.848 | 1.654 | 13.134 | −64.747 | 4.694 | −99.528 |
| 75 | 2.154 | 18.981 | 15.420 | 1.231 | 3.693 | −81.995 | 3.579 | −85.064 |
| 76 | 4.197 | 21.475 | 17.666 | 1.216 | 5.166 | −90.504 | 3.021 | −77.948 |
| 77 | 1.784 | 16.111 | 13.305 | 1.211 | 3.903 | −86.524 | 1.786 | −82.189 |
| 78 | 1.760 | 24.338 | 13.783 | 1.766 | 7.332 | −93.916 | 2.498 | −74.454 |
| 79 | 2.139 | 17.991 | 12.323 | 1.460 | | | 4.013 | −72.802 |
| 80 | 1.590 | 6.641 | 8.572 | 0.775 | | | 2.681 | −69.196 |
| 81 | 2.591 | 9.069 | 4.952 | 1.831 | | | 2.176 | −83.963 |
| 82 | 3.795 | 68.613 | 28.180 | 2.435 | 8.738 | −88.044 | 12.243 | −60.656 |
| 83 | 4.567 | 159.090 | 49.023 | 3.245 | 15.634 | −94.723 | 17.288 | −68.447 |
| 84 | 2.749 | 29.576 | 22.131 | 1.336 | 5.608 | −89.010 | 4.299 | −80.428 |
| 85 | 4.735 | 21.984 | 27.018 | 0.814 | 8.418 | −90.914 | 14.112 | −80.438 |
| 86 | 12.173 | 929.495 | 89.619 | 10.372 | 34.772 | −93.814 | 32.453 | −39.164 |
| 87 | 4.984 | 62.738 | 26.981 | 2.325 | 4.193 | −79.550 | 3.679 | −85.463 |
| 88 | 1.021 | >25000.000 | 154.434 | 161.881 | 86.265 | −5.029 | 156.578 | −20.194 |
| 89 | 3.246 | 24720.040 | 95.397 | 259.128 | 109.364 | −16.694 | 218.842 | −22.815 |
| 90 | | >25000.000 | 168.183 | 148.647 | 141.083 | −12.315 | 106.927 | −8.495 |
| 91 | 6.036 | 14.666 | 18.860 | 0.778 | 4.639 | −90.776 | 6.857 | −64.491 |
| 92 | 80.020 | >25000.000 | 664.298 | 37.634 | 433.353 | −37.359 | 401.466 | −3.918 |
| 93 | 24.701 | 219.281 | 41.634 | 5.267 | 108.516 | −97.726 | 73.797 | −57.108 |
| 94 | 7.481 | 5565.342 | 37.521 | 148.326 | 30.367 | −94.671 | 35.506 | −40.948 |
| 95 | 2.317 | 10.347 | 10.014 | 1.033 | 2.586 | −93.120 | 2.513 | −73.174 |
| 96 | 2.405 | >25000.000 | 108.152 | 231.155 | 167.999 | −14.554 | 304.650 | −29.687 |
| 97 | 240.267 | >25000.000 | 2894.085 | 8.638 | 9144.823 | 46.987 | 4369.614 | 11.801 |
| 98 | 3.447 | 159.084 | 35.908 | 4.430 | 10.333 | −87.759 | 11.545 | −75.954 |
| 99 | 4.138 | >25000.000 | 156.062 | 160.193 | 77.983 | −69.788 | 93.243 | −73.818 |
| 100 | 1.131 | 32.113 | 10.860 | 2.957 | 2.888 | −91.579 | 3.696 | −68.437 |
| 101 | 1.097 | 1809.361 | 4.130 | 438.113 | 9.778 | −94.474 | 7.680 | −64.073 |
| 102 | 29.757 | >25000.000 | 506.758 | 49.333 | 3023.428 | 24.371 | 4903.112 | 31.099 |
| 103 | 258.210 | >25000.000 | 4256.594 | 5.873 | >10000.000 | 80.958 | >10000.000 | 78.168 |
| 104 | 2.104 | 31.908 | 13.892 | 2.297 | 4.579 | −86.795 | 5.100 | −69.040 |
| 105 | 2.867 | 68.782 | 21.791 | 3.156 | 5.852 | −90.949 | 6.952 | −68.464 |
| 106 | 145.787 | 21316.281 | 555.636 | 38.364 | 1946.074 | 25.144 | 9024.448 | 49.516 |
| 107 | 8.762 | 189.979 | 25.441 | 7.467 | 8.464 | −83.679 | 7.274 | −87.564 |
| 108 | 2.031 | 16.802 | 14.335 | 1.172 | 3.313 | −82.618 | 2.470 | −79.118 |
| 109 | 2.847 | 26.481 | 13.998 | 1.892 | 3.546 | −84.673 | 2.001 | −84.780 |
| 110 | 42.069 | 141.880 | 63.236 | 2.244 | 41.768 | −74.667 | 40.946 | −93.755 |
| 111 | 27.997 | 69.785 | 27.292 | 2.557 | 13.896 | −71.803 | 12.823 | −81.303 |
| 112 | 12.794 | 36.638 | 24.108 | 1.520 | 8.289 | −80.066 | 6.234 | −86.973 |
| 113 | 8.195 | 29.264 | 18.814 | 1.555 | 48.965 | −80.966 | 41.765 | −73.107 |
| 114 | 18.232 | 103.149 | 39.101 | 2.638 | 12.323 | −82.856 | 9.346 | −87.102 |
| 115 | 144.378 | 335.063 | 233.242 | 1.437 | 85.228 | −97.417 | 88.916 | −93.625 |
| 116 | 4.448 | 24.986 | 19.171 | 1.303 | 2.203 | −76.511 | 1.547 | −90.483 |
| 117 | 9.759 | >25000.000 | 69.572 | 359.342 | 50.241 | −95.049 | 79.845 | −55.709 |
| 118 | 3.756 | 21.956 | 19.869 | 1.105 | 4.547 | −79.169 | 3.004 | −82.113 |
| 119 | 11.656 | 31.021 | 21.652 | 1.433 | 8.431 | −75.344 | 8.838 | −81.451 |
| 120 | 3.971 | 25.336 | 26.526 | 0.955 | 9.424 | −78.098 | 11.196 | −75.164 |
| 121 | 2.994 | 25.480 | 21.964 | 1.160 | 3.729 | −88.956 | 2.656 | −80.331 |
| 122 | 5.505 | 18.838 | 14.314 | 1.316 | 2.097 | −70.057 | 1.995 | −85.128 |
| 123 | 1.697 | 16.462 | 13.079 | 1.259 | 2.753 | −71.328 | 2.263 | −86.056 |
| 124 | 3.444 | 12.855 | 9.437 | 1.362 | 5.982 | −86.148 | 3.264 | −78.963 |
| 125 | 5.058 | 17.638 | 14.945 | 1.180 | 6.759 | −83.226 | 4.508 | −83.586 |
| 126 | | | | | | | | |
| 127 | 19.133 | >25000.000 | 452.324 | 55.270 | 1071.042 | 11.995 | 835.105 | −18.734 |
| 128 | 8.763 | 3350.427 | 18.070 | 185.417 | 44.222 | −96.227 | 25.733 | −62.651 |
| 129 | 4.376 | 31.998 | 15.613 | 2.049 | 11.278 | −94.183 | 4.734 | −70.909 |
| 130 | 37.142 | 43.909 | 30.032 | 1.462 | 18.296 | −93.452 | 11.962 | −72.458 |
| 131 | 4.040 | 356.631 | 45.767 | 7.792 | 27.067 | −94.995 | 19.218 | −65.430 |

TABLE 24-continued

Biological Assay Results

| Ex. | SPA-ATS GMean IC50 (nM) SF3B1 (WT) | qPCR-IVS-ATS GMean IC50 (nM) Ad2.1 | qPCR-IVS-ATS GMean IC50 (nM) Ad2.2 | Ratio Ad2.1/2.2 | CTGlo-ATS GMean GI50 (nM) 72 h PANC0 504.1 | CTGlo-ATS Mean Min Response % 72 h PANC0 504.1 | CTGlo-ATS GMean GI50 (nM) 72 h NCIH1 568.1 | CTGlo-ATS Mean Min Response % 72 h NCIH1 568.1 |
|---|---|---|---|---|---|---|---|---|
| 132 | 4.913 | 34.109 | 12.752 | 2.675 | 13.574 | −94.673 | 11.510 | −68.423 |
| 133 | 6.986 | 1671.083 | 92.470 | 18.072 | 25.554 | −94.957 | 17.704 | −69.167 |
| 134 | 2.055 | 26.469 | 13.270 | 1.995 | 4.113 | −92.570 | 3.920 | −79.743 |
| 135 | 3.672 | 14.929 | 14.858 | 1.005 | 2.463 | −90.575 | 2.411 | −84.225 |
| 136 | 8.107 | 8.637 | 14.479 | 0.597 | | | 7.168 | −90.722 |
| 137 | 1.209 | 27.636 | 12.146 | 2.275 | 1.615 | −86.584 | 1.174 | −81.149 |
| 138 | 8.696 | >25000.000 | 57.468 | 435.028 | 120.328 | −85.916 | 70.303 | −80.330 |
| 139 | 4.318 | >25000.000 | 93.194 | 268.259 | 240.142 | −21.195 | 142.072 | −61.022 |
| 140 | 1.728 | 11.563 | 11.755 | 0.984 | 1.631 | −80.398 | 1.251 | −82.434 |
| 141 | 12.956 | >25000.000 | 61.283 | 407.944 | 72.446 | −94.865 | 48.767 | −63.745 |
| 142 | 1.348 | 12.904 | 6.986 | 1.847 | | | 2.189 | −69.213 |
| 143 | 3.200 | 19.245 | 17.177 | 1.120 | 3.675 | −87.719 | 1.751 | −84.803 |
| 144 | 12.945 | 22.998 | 17.838 | 1.289 | | | 4.117 | −95.432 |
| 145 | 69.448 | 688.137 | 38.070 | 18.076 | | | 24.952 | −66.236 |
| 146 | 22.736 | 11.142 | 12.673 | 0.879 | | | 2.795 | −88.975 |
| 147 | 7.302 | 9.573 | 7.431 | 1.288 | | | 1.560 | −91.884 |
| 148 | 2.243 | 12.371 | 3.566 | 3.469 | | | 1.420 | −85.010 |
| 149 | 1.863 | 9.132 | 8.715 | 1.048 | | | 1.663 | −73.106 |
| 150 | 1.316 | 8.579 | 10.968 | 0.782 | | | 2.187 | −68.000 |
| 151 | 3.409 | 17.913 | 11.423 | 1.568 | | | 2.239 | −83.213 |
| 152 | 3.835 | 16.214 | 8.392 | 1.932 | | | 1.511 | −80.509 |
| 153 | 4.830 | 14.527 | 14.848 | 0.978 | | | 2.338 | −81.206 |
| 154 | 3.752 | 20.021 | 8.724 | 2.295 | | | 1.852 | −85.459 |
| 155 | 2.214 | 8.445 | 5.877 | 1.437 | | | 1.905 | −83.475 |
| 156 | 3.949 | 8.369 | 7.912 | 1.058 | | | 1.267 | −87.369 |
| 157 | 2.266 | 8.466 | 7.491 | 1.130 | | | 1.288 | −90.424 |
| 158 | 13.917 | 18.895 | 18.193 | 1.039 | | | 6.574 | −87.167 |
| 159 | 1.839 | 88.302 | 10.196 | 8.660 | | | 3.446 | −65.047 |
| 160 | 1.648 | 4.681 | 4.688 | 0.999 | 1.147 | −82.399 | 0.896 | −86.403 |
| 161 | 2.507 | 8.501 | 6.311 | 1.347 | | | 0.772 | −85.783 |
| 162 | 1.077 | 9.290 | 7.400 | 1.255 | | | 1.471 | −75.943 |
| 163 | | | | | | | | |
| 164 | 3.594 | 20.692 | 27.869 | 0.742 | | | 1.539 | −87.159 |
| 165 | 18.724 | 29.539 | 15.222 | 1.941 | | | 10.028 | −78.159 |
| 166 | 23.795 | 1509.545 | 48.288 | 31.261 | | | 17.605 | −66.370 |
| 167 | 3.189 | >25000.000 | 46.455 | 538.154 | 34.052 | −85.316 | 52.392 | −70.414 |
| 168 | 3.049 | 27.565 | 16.451 | 1.676 | 10.386 | −86.930 | 5.963 | −75.760 |
| 169 | 1.429 | 96.624 | 19.836 | 4.871 | 8.899 | −90.232 | 8.264 | −66.086 |
| 170 | 4.926 | 10988.155 | 30.980 | 354.686 | 23.187 | −96.570 | 25.872 | −56.895 |
| 171 | 1.509 | 18827.426 | 42.614 | 441.815 | 23.552 | −92.998 | 19.645 | −50.083 |
| 172 | 5.584 | 22.596 | 15.368 | 1.470 | 17.920 | −88.455 | 8.722 | −74.177 |
| 173 | 20.954 | 88.062 | 28.433 | 3.097 | | | 15.154 | −79.437 |
| 174 | 3.144 | 13.142 | 10.739 | 1.224 | 6.035 | −80.529 | 3.858 | −92.525 |
| 175 | 5.827 | 9.503 | 8.125 | 1.170 | | | 9.488 | −99.134 |
| 176 | 38.494 | 49.735 | 31.244 | 1.592 | | | 19.031 | −88.183 |
| 177 | 2.380 | 18.243 | 10.348 | 1.763 | | | 3.618 | −80.643 |
| 178 | 2.159 | 20.409 | 4.309 | 4.736 | | | 6.847 | −77.714 |
| 179 | 6.147 | 31.411 | 14.211 | 2.210 | | | 8.698 | −82.684 |
| 180 | 42.275 | 29.896 | 24.606 | 1.215 | | | 14.432 | −86.471 |
| 181 | 8.204 | 19.659 | 19.152 | 1.026 | | | 9.736 | −85.226 |
| 182 | 86.414 | 207.933 | 40.096 | 5.186 | | | 23.384 | −69.521 |
| 183 | 66.316 | 713.164 | 20.288 | 35.151 | | | 53.565 | −66.270 |
| 184 | 14.417 | 18.135 | 11.589 | 1.565 | | | 59.779 | −85.535 |
| 185 | 186.395 | 542.957 | 46.594 | 11.653 | | | 114.397 | −99.538 |
| 186 | 12.625 | 41.845 | 17.450 | 2.398 | | | 14.473 | −70.969 |
| 187 | 43.164 | 157.172 | 59.645 | 2.635 | | | 65.000 | −54.197 |
| 188 | 2.610 | 7.414 | 5.626 | 1.318 | | | 2.767 | −79.922 |
| 189 | 6.800 | 16.928 | 10.256 | 1.651 | | | 9.532 | −76.052 |
| 190 | 6.547 | 33.521 | 15.729 | 2.131 | | | 19.847 | −69.142 |
| 191 | 3.472 | 11.620 | 7.474 | 1.555 | | | 6.329 | −83.895 |
| 192 | 3.846 | 14.134 | 10.277 | 1.375 | | | 7.490 | −75.900 |
| 193 | 126.764 | 47.796 | 19.577 | 2.441 | | | 17.220 | −89.438 |
| 194 | 10.679 | 30.128 | 25.852 | 1.165 | | | 6.729 | −75.631 |
| 195 | 69.302 | 91.936 | 58.257 | 1.578 | | | 6.595 | −95.559 |
| 196 | 13.226 | 29.980 | 19.611 | 1.529 | | | 1.829 | −90.418 |
| 197 | 2.665 | 98.532 | 22.818 | 4.318 | 3.526 | −91.100 | 4.693 | −69.290 |
| 198 | 7.815 | 2386.120 | 43.208 | 55.224 | 21.688 | −96.773 | 15.506 | −56.095 |
| 199 | 8.992 | 1822.689 | 47.173 | 38.638 | 33.778 | −95.445 | 22.936 | −52.026 |
| 200 | 8.028 | 8049.493 | 27.048 | 297.600 | 17.434 | −94.085 | 24.228 | −51.281 |

TABLE 24-continued

Biological Assay Results

| Ex. | SPA-ATS GMean IC50 (nM) SF3B1 (WT) | qPCR-IVS-ATS GMean IC50 (nM) Ad2.1 | qPCR-IVS-ATS GMean IC50 (nM) Ad2.2 | Ratio Ad2.1/2.2 | CTGlo-ATS GMean GI50 (nM) 72 h PANC0 504.1 | CTGlo-ATS Mean Min Response % 72 h PANC0 504.1 | CTGlo-ATS GMean GI50 (nM) 72 h NCIH1 568.1 | CTGlo-ATS Mean Min Response % 72 h NCIH1 568.1 |
|---|---|---|---|---|---|---|---|---|
| 201 | 5.641 | 619.579 | 17.460 | 35.485 | 40.947 | −91.697 | 27.494 | −48.055 |
| 202 | 14.089 | 4467.112 | 25.183 | 177.387 | 24.666 | −93.824 | 29.369 | −59.083 |
| 203 | 10.093 | 14444.856 | 69.732 | 207.149 | 44.957 | −94.627 | 47.257 | −36.664 |
| 204 | 23.530 | >25000.000 | 113.702 | 219.873 | 81.984 | −94.081 | 81.900 | −24.924 |
| 205 | 16.221 | >25000.000 | 107.697 | 232.132 | 70.845 | −91.576 | 85.857 | −28.455 |
| 206 | 1.813 | >25000.000 | 112.801 | 221.630 | 62.322 | −83.659 | 72.151 | −57.585 |
| 207 | 3.456 | 22.522 | 15.523 | 1.451 | 15.083 | −92.266 | 16.872 | −63.380 |
| 208 | 1.770 | 1378.136 | 25.142 | 54.813 | 9.265 | −94.342 | 11.644 | −47.371 |
| 209 | 4.781 | 3132.451 | 30.034 | 104.297 | 16.373 | −93.368 | 12.134 | −51.998 |
| 210 | 4.353 | 10999.791 | 32.727 | 336.112 | 27.842 | −96.896 | 17.045 | −51.154 |
| 211 | 11.856 | 651.389 | 83.449 | 7.806 | 47.630 | −91.820 | 60.600 | −52.358 |
| 212 | 8.790 | >25000.000 | 93.796 | 266.536 | 60.172 | −59.089 | 128.747 | −49.302 |
| 213 | 3.227 | 9.836 | 7.955 | 1.236 | 3.196 | −85.603 | 6.031 | −64.116 |
| 214 | 2.297 | 3924.472 | 19.217 | 204.217 | 3.290 | −91.986 | 6.370 | −48.793 |
| 215 | 6.829 | 20476.683 | 50.708 | 403.817 | 20.031 | −81.853 | 25.032 | −42.412 |
| 216 | 3.325 | 11066.674 | 35.740 | 309.648 | 29.022 | −85.005 | 47.209 | −32.014 |
| 217 | 3.180 | 18.360 | 16.585 | 1.107 | 14.978 | −91.288 | 13.777 | −71.339 |
| 218 | 2.795 | 30.466 | 5.616 | 5.425 | | | 6.197 | −75.420 |
| 219 | 7.958 | >25000.000 | 71.481 | 349.744 | 24.575 | −91.460 | 42.396 | −42.617 |
| 220 | 3.174 | 19.337 | 14.390 | 1.344 | 4.362 | −90.506 | 2.012 | −76.936 |
| 221 | 9.334 | 9.597 | 4.864 | 1.973 | | | 11.415 | −66.213 |
| 222 | 23.560 | 115.933 | 53.192 | 2.179 | | | 69.418 | −58.410 |
| 223 | 15.882 | 93.895 | 6.961 | 13.488 | | | 33.076 | −62.835 |
| 224 | 3.139 | 41.136 | 5.884 | 6.991 | | | 16.428 | −61.875 |
| 225 | 18.247 | 7.559 | 22.404 | 0.337 | | | 10.999 | −73.768 |
| 226 | 1.171 | 8.742 | 101.817 | 0.086 | | | 34.694 | −64.963 |
| 227 | 3.250 | 5.848 | 10.285 | 0.569 | | | 2.367 | −81.522 |
| 228 | 3.965 | 6.310 | 5.330 | 1.184 | | | 3.287 | −77.633 |
| 229 | 17.110 | 329.387 | 12.200 | 27.000 | | | 13.389 | −65.653 |
| 230 | 12.876 | 11.748 | 10.902 | 1.078 | | | 15.854 | −69.108 |
| 231 | 26.032 | 512.816 | 5.284 | 97.051 | | | 22.694 | −59.209 |
| 232 | 5.015 | 15.326 | 9.504 | 1.613 | | | 4.674 | −78.974 |
| 233 | 2.458 | 5.872 | 6.047 | 0.971 | | | 1.984 | −87.288 |
| 234 | 3.163 | 13.069 | 16.472 | 0.793 | | | 5.202 | −81.384 |
| 235 | 5.564 | 16.010 | 15.144 | 1.057 | 1.937 | −84.459 | 2.347 | −84.925 |
| 236 | 84.028 | 49.935 | 56.184 | 0.889 | | | 9.924 | −90.096 |
| 237 | 8.375 | 18.550 | 9.327 | 1.989 | | | 12.024 | −78.619 |
| 238 | 18.054 | 32.210 | 68.149 | 0.473 | | | 5.789 | −88.447 |
| 239 | 149.765 | 103.261 | 47.999 | 2.151 | | | 63.497 | −77.758 |
| 240 | | | | | | | | |
| 241 | 20.455 | >25000.000 | 130.264 | 191.917 | 120.417 | −88.873 | 225.056 | −59.521 |
| 242 | 15.329 | 7146.158 | 62.113 | 115.051 | 68.920 | −92.786 | 180.037 | −65.744 |
| 243 | 3.592 | 98.426 | 38.548 | 2.553 | 10.379 | −92.290 | 10.582 | −71.678 |
| 244 | 3.376 | 3581.722 | 38.506 | 93.018 | 27.607 | −95.630 | 20.195 | −65.165 |
| 245 | 17.436 | 8875.216 | 64.831 | 136.897 | 112.774 | −95.548 | 62.255 | −46.475 |
| 246 | 5.802 | 279.340 | 36.136 | 7.730 | 16.490 | −95.467 | 12.136 | −68.331 |
| 247 | 14.431 | 50.833 | 34.641 | 1.467 | 40.535 | −77.509 | 31.375 | −67.545 |
| 248 | 6.624 | >25000.000 | 76.389 | 327.274 | 75.840 | −92.622 | 97.040 | −46.753 |
| 249 | 5.164 | 6351.906 | 33.622 | 188.921 | 13.815 | −93.297 | 14.524 | −49.016 |
| 250 | 3.626 | 2185.864 | 44.144 | 49.517 | 23.101 | −94.381 | 15.593 | −58.677 |
| 251 | 52.399 | 49.653 | 28.136 | 1.765 | | | 13.373 | −87.236 |
| 252 | 21.819 | 22.624 | 27.410 | 0.825 | | | 10.275 | −76.109 |
| 253 | 1.924 | 10.022 | 8.586 | 1.167 | 12.915 | −80.763 | 2.424 | −84.782 |
| 254 | 5.123 | 22048.355 | 52.240 | 422.058 | 29.045 | −77.065 | 23.704 | −41.424 |
| 255 | 7.321 | >25000.000 | 89.728 | 278.618 | 65.836 | −61.401 | 67.624 | −24.942 |
| 256 | 15.609 | >25000.000 | 112.177 | 222.862 | 43.369 | −88.839 | 60.856 | −5.090 |
| 257 | 5.745 | >25000.000 | 116.875 | 213.903 | 71.477 | −75.412 | 265.710 | −4.151 |
| 258 | 11.739 | >25000.000 | 73.832 | 338.606 | 28.684 | −65.918 | 29.773 | −12.669 |
| 259 | | >25000.000 | 83.063 | 300.977 | 31.491 | −86.489 | 133.009 | −43.329 |
| 260 | 0.196 | >25000.000 | 99.444 | 251.398 | 39.499 | −47.734 | 42.267 | −44.621 |
| 261 | | 23290.387 | 76.557 | 304.222 | 32.328 | −89.906 | 57.557 | −36.811 |
| 262 | 5.655 | 4102.465 | 51.625 | 79.467 | 29.341 | −91.709 | 41.697 | −65.862 |
| 263 | 37.684 | 93.581 | 25.451 | 3.677 | 64.532 | −88.783 | 102.396 | −67.601 |
| 264 | 35.694 | 33.402 | 72.404 | 0.461 | | | 143.328 | −21.716 |
| 265 | 5.3 | >25000.000 | 71.6 | 349.0 | 36.7 | 25.1 | 47.5 | −9.0 |

Administration of at Least One Compound Chosen from Compounds of Formula I (Including Formulas IIa-e, IIIa, IVa, and Va) and/or Pharmaceutically Acceptable Salts Thereof CT26 colon cancer cells ($0.25\times10^6$; ATCC Cat. #CRL-2638) are implanted subcutaneously into the right flank of eight-week old female Balb/c mice (Envigo) in 100 μL of PVS lacking Matrigel. CT26 tumors are allowed to grow to an average of ~100 $mm^3$ before animals are enrolled into the efficacy study. Each treatment group contains 12 mice. Mice are treated with at least one compound chosen from compounds of Formula I (including Formulas IIa-e, IIIa, IVa, and Va) and/or pharmaceutically acceptable salts thereof, an anti-CTLA4 antibody, or a combination thereof, at various doses and via various routes of administration. The at least one compound chosen from compounds of Formula I (including Formulas IIa-e, IIIa, IVa, and Va) and/or pharmaceutically acceptable salts thereof is formulated in a composition containing 5% ethanol and 95% methylcellulose solution (0.5% methylcellulose). The anti-CTLA4 antibody is formulated in PBS at pH 7. Tumors are measured 3 times per week for up to 19 days. Tumor volumes are calculated using the ellipsoid formula: Tumor Volume=(length×width$^2$)/2.

Other Embodiments

Embodiment 1. A compound chosen from compounds of Formula I:

I

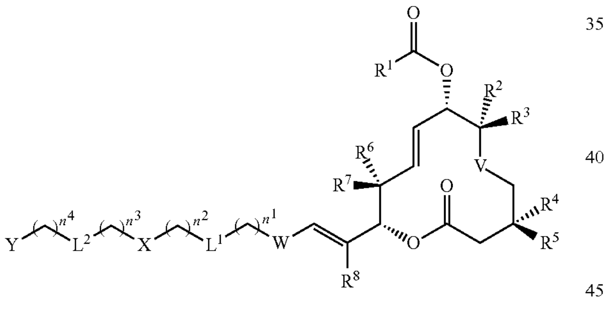

and pharmaceutically acceptable salts thereof, wherein:

$R^1$ is chosen from:

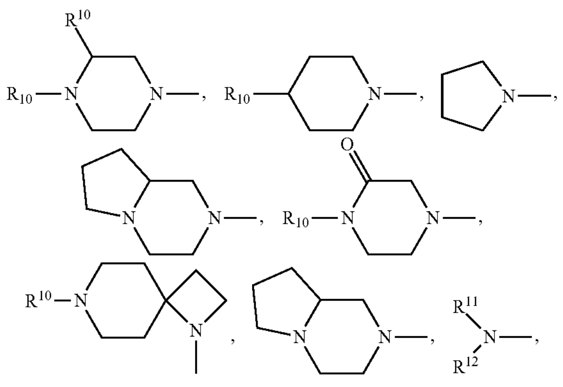

-continued

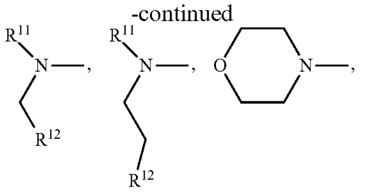

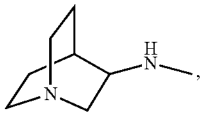

and

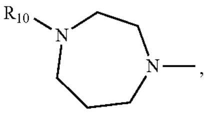

each of which may be optionally substituted with 1 to 3 groups independently chosen from halogens, hydroxyl groups, $C_1$-$C_6$ alkyl groups, $C_1$-$C_6$ alkoxy groups, $C_3$-$C_8$ cycloalkyl groups, hydroxy $C_1$-$C_6$ alkyl groups, dimethylamino groups, and methoxy $C_1$-$C_6$ alkyl groups;

$R^2$, $R^3$, $R^4$, $R^1$, $R^6$, and $R^7$ are each independently chosen from hydrogen, hydroxyl groups, —O—$R^{10}$ groups, and $C_1$-$C_6$ alkyl groups;

$R^8$, $R^9$, and $R^{13}$ are each independently chosen from hydrogen and $C_1$-$C_6$ alkyl groups;

$R^{10}$ is chosen from hydrogen, $C_1$-$C_6$ alkyl groups, $C_1$-$C_6$ aminoalkyl groups, $C_1$-$C_6$ alkylamino groups, $C_1$-$C_6$ alkylcarboxylic acid groups, $C_3$-$C_8$ cycloalkyl groups, benzyl groups, $C_3$-$C_8$ heterocyclyl groups, —$CH_2$—$C_3$-$C_8$ heterocyclyl groups, —C(O)—$C_3$-$C_8$ heterocyclyl groups, acyl groups, hydroxy $C_1$-$C_6$ alkyl groups, methoxy $C_1$-$C_6$ alkyl groups, —$CD_3$, and —C(O)—$NR^{11}R^{12}$ groups;

$R^{11}$ and $R^{12}$ are independently chosen from hydrogen, $C_1$-$C_6$ alkyl groups, $C_1$-$C_6$ aminoalkyl groups, $C_1$-$C_6$ alkylamino groups, $C_3$-$C_8$ cycloalkyl groups, and $C_3$-$C_8$ heterocyclyl groups;

V is chosen from —$CH_2$— and —N($R^9$)—;

W is chosen from 3 to 8 membered carbocycles and 3 to 8 membered heterocycles, each of which may be optionally substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be optionally substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—; and each n is independently chosen from 0 to 4.

Embodiment 2. The compound of embodiment 1, wherein $R^1$ is chosen from

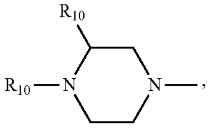

and

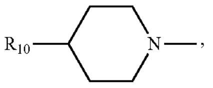

each of which may be substituted with 1 to 3 groups chosen from halogens and $C_1$-$C_6$ alkyl groups.

Embodiment 3. The compound of embodiment 1 or embodiment 2, wherein $R^1$ is chosen from

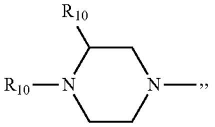

which may be substituted with 1 to 3 groups chosen from $C_1$-$C_6$ alkyl groups.

Embodiment 4. The compound of any one of embodiments 1-3, wherein $R^1$ is chosen from unsubstituted

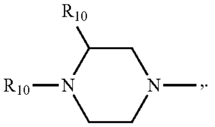

Embodiment 5. The compound of any one of embodiments 1-4, wherein $R^2$ is methyl and $R^3$ is hydrogen.

Embodiment 6. The compound of any one of embodiments 1-5, wherein $R^4$ is hydrogen, and and $R^5$ is hydroxyl.

Embodiment 7. The compound of any one of embodiments 1-6, wherein $R^6$ is hydrogen and and $R^7$ is methyl.

Embodiment 8. The compound of any one of embodiments 1-7, wherein $R^8$ is methyl.

Embodiment 9. The compound of any one of embodiments 1-8, wherein V is —$CH_2$—.

Embodiment 10. The compound of any one of embodiments 1-9, wherein W is chosen from a benzene ring, pyridine ring, benzimidazole ring, benzotriazole ring, indazole ring, 1,2,3,6-tetrahydropyridine ring, and imidazopyridine ring, each of which may be optionally substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups.

Embodiment 11. The compound of any one of embodiments 1-10, wherein W is a benzene ring, which may be optionally substituted with 1 to 3 groups chosen from halogens and $C_1$-$C_6$ alkyl groups.

Embodiment 12. The compound of any one of embodiments 1-11, wherein X and Y are each independently chosen from a bond,

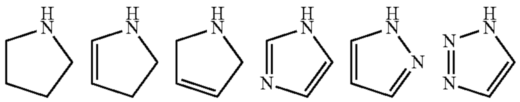

-continued

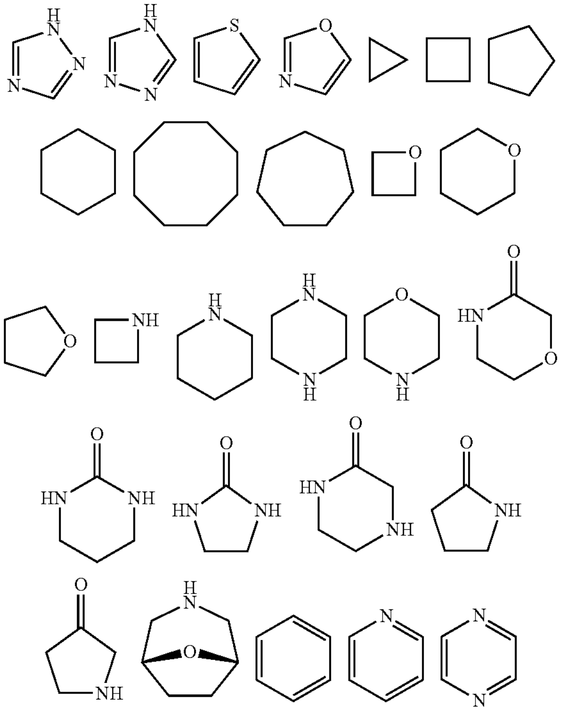

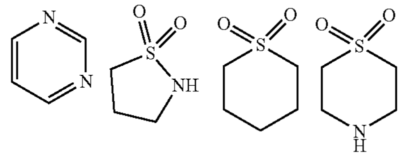

and

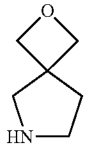

each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 13. The compound of any embodiments 1-11, wherein Y is hydrogen, and X is chosen from:

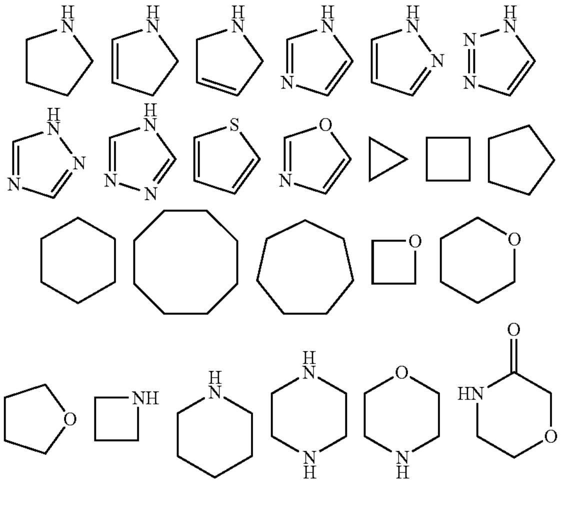

-continued

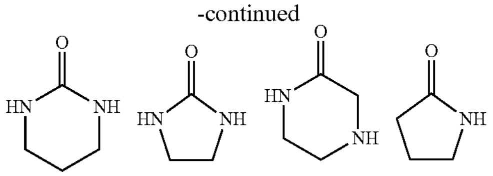

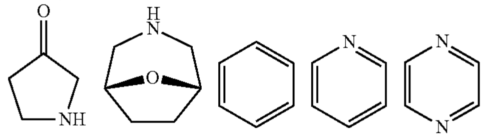

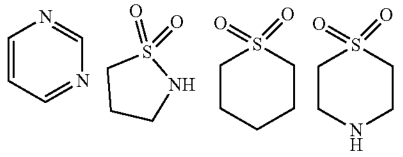

and

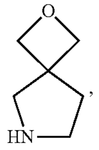

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 14. A compound chosen from compounds of Formula IIa:

IIa

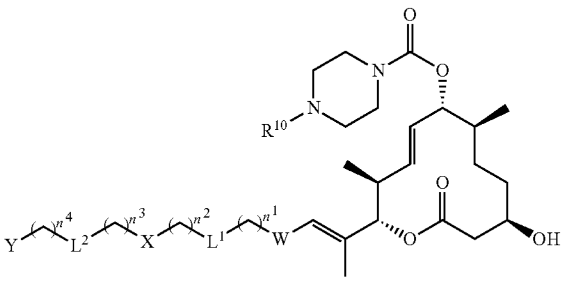

and pharmaceutically acceptable salts thereof, wherein:

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl-groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

Embodiment 15. The compound of embodiment 14, wherein W is chosen from a benzene ring, pyridine ring, benzimidazole ring, benzotriazole ring, indazole ring, 1,2,3,6-tetrahydropyridine ring, and imidazopyridine ring, each of which may be optionally substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups Embodiment 16. The compound of embodiment 14 or embodiment 15, wherein W is a benzene ring, which may be optionally substituted with 1 to 3 groups chosen from halogens and $C_1$-$C_6$ alkyl groups.

Embodiment 17. The compound of any one of embodiments 14-16, wherein X and Y are each independently chosen from a bond,

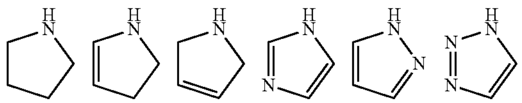

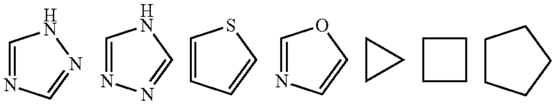

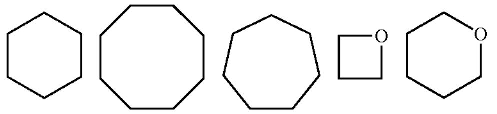

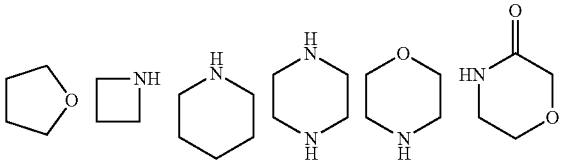

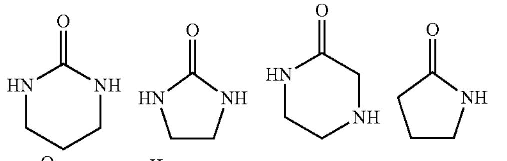

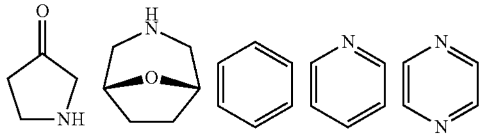

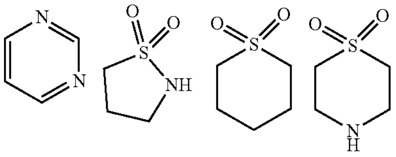

and

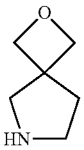

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 18. The compound of any embodiments 14-17, wherein Y is hydrogen, and X is chosen from:

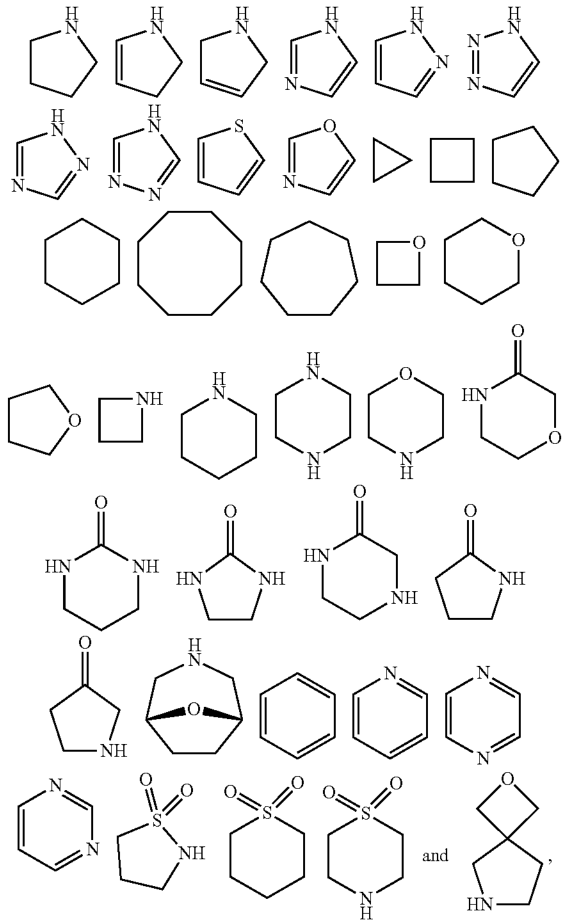

and each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 19. The compound of any one of embodiments 14-17, wherein Y is hydrogen and X is a bond.

Embodiment 20. A compound chosen from compounds of Formula IIb:

IIb

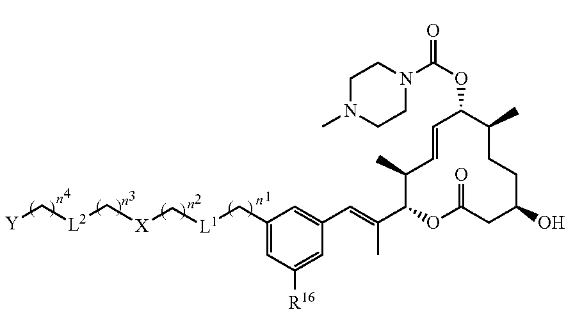

and pharmaceutically acceptable salts thereof, wherein:

$R^{16}$ is chosen from hydrogen and fluoro;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —$N(R^{13})$—C(O)—, —C(O)—$N(R^{13})$—, —$N(R^{13})$—$S(O_2)$—, —$S(O_2)$—$N(R^{13})$—, —$S(O_2)$—, and —$N(R^{13})$—, wherein $R^{13}$ is chosen from hydrogen and $C_1$-$C_6$ alkyl groups; and each n is independently chosen from 0 to 4.

Embodiment 21. The compound of embodiment 20, wherein X and Y are each independently chosen from a bond,

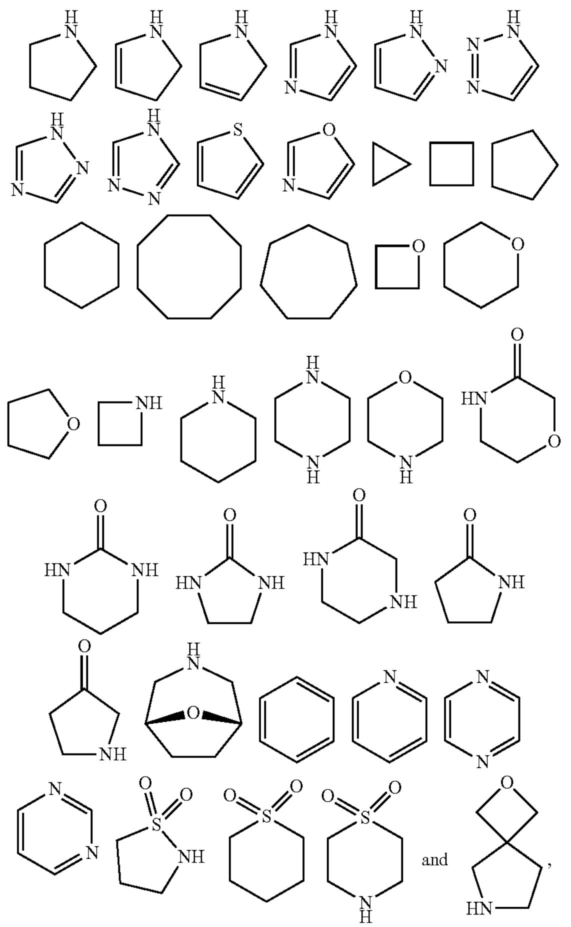

and each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 22. The compound of embodiment 20 or embodiment 21, wherein Y is hydrogen, and X is chosen from:

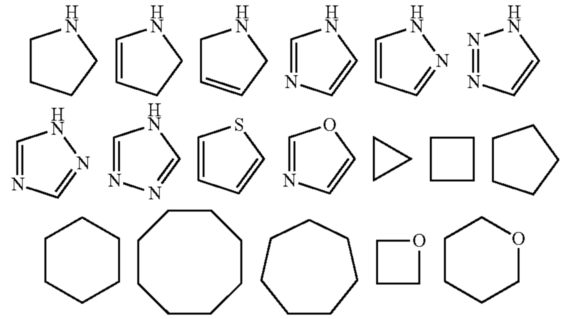

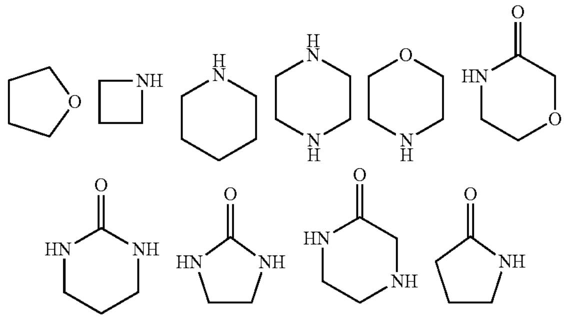

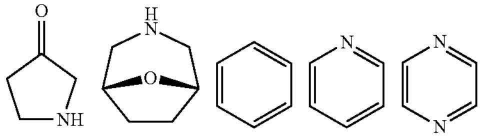

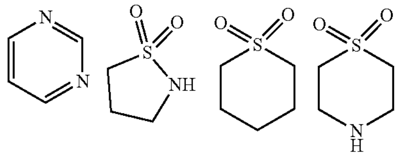

and

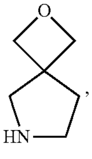

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 23. The compound of any one of embodiments 20-22, wherein Y is hydrogen and X is a bond.

Embodiment 24. The compound of any one of embodiments 20-23, wherein $R^{16}$ is fluoro.

Embodiment 25. A compound chosen from compounds of Formula IIc:

IIc

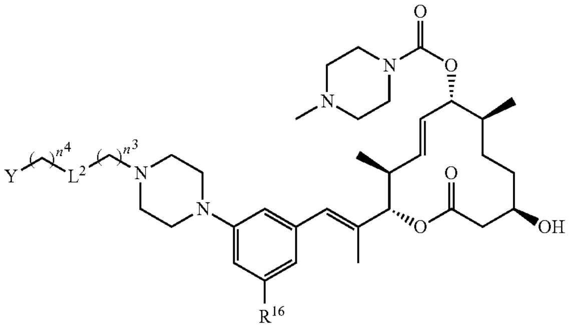

and pharmaceutically acceptable salts thereof, wherein:

$R^{16}$ is chosen from hydrogen and fluoro;

Y is chosen from hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy$C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^2$ is chosen from a bond, —O—, —C(O)—, —C(O)O—, —$N(R^{13})$—C(O)—, —C(O)—$N(R^{13})$—, —$N(R^{13})$—$S(O_2)$—, —$S(O_2)$—$N(R^{13})$—, —$S(O_2)$—, and —$N(R^{13})$—, wherein $R^{13}$ is chosen from hydrogen and $C_1$-$C_6$ alkyl groups;

$n^3$ is 0; and $n^4$ is chosen from 0 to 4.

Embodiment 26. The compound of embodiment 25, wherein Y is chosen from hydrogen,

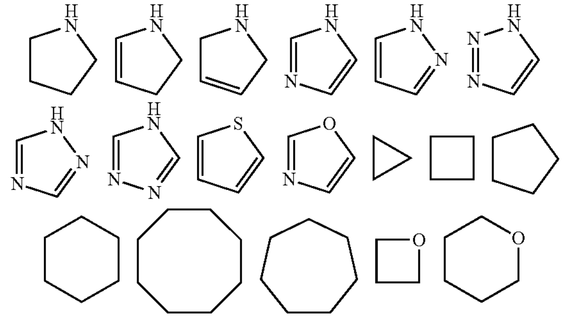

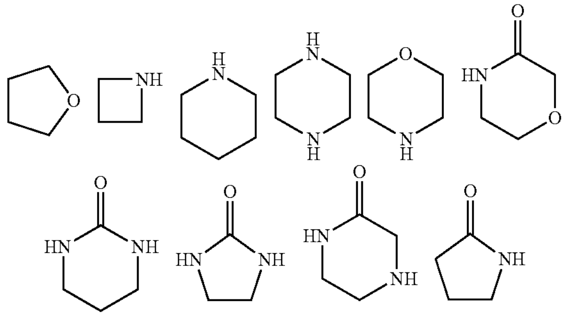

-continued

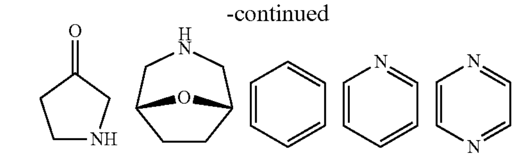

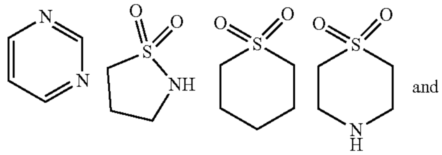

and

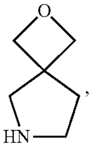

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 27. The compound of embodiment 25 or embodiment 26, wherein $L^2$ is a bond.

Embodiment 28. The compound of any one of embodiments 25-27, wherein $R^{16}$ is fluoro.

Embodiment 29. A compound chosen from compounds of Formula IId:

IId

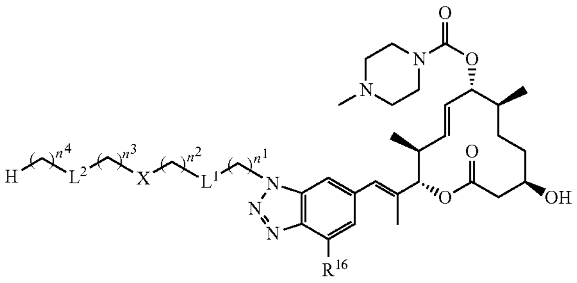

and pharmaceutically acceptable salts thereof, wherein:

$R^{16}$ is chosen from hydrogen and fluoro;

X is chosen from hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

Embodiment 30. The compound of embodiment 29, wherein X is chosen from a bond,

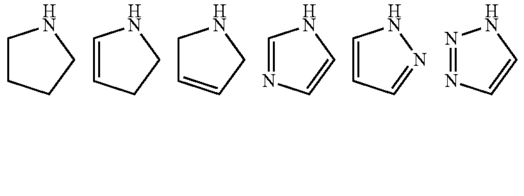

-continued

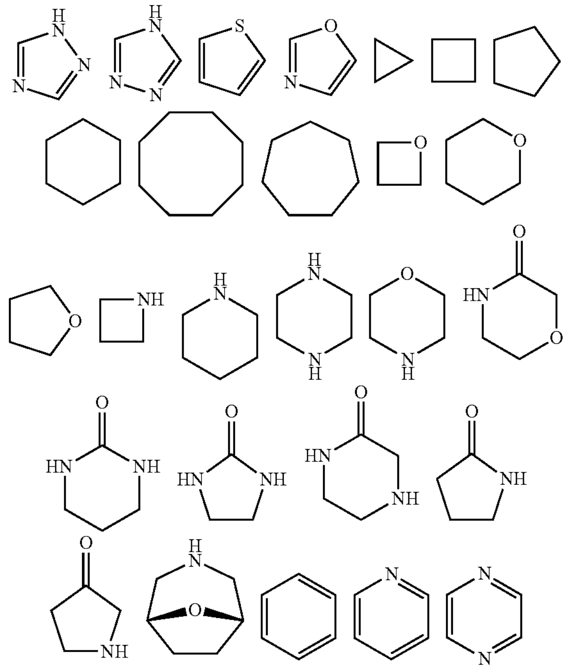

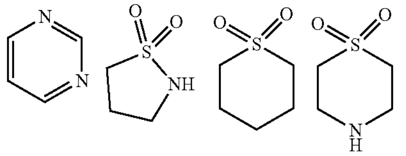

and

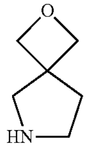

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 31. The compound of embodiment 29 or embodiment 30, wherein X, $L^1$, and $L^2$ are each a bond.

Embodiment 32. The compound of any one of embodiments 25-27, wherein $R^{16}$ is fluoro.

Embodiment 33. A compound chosen from compounds of Formula IIe:

IIe

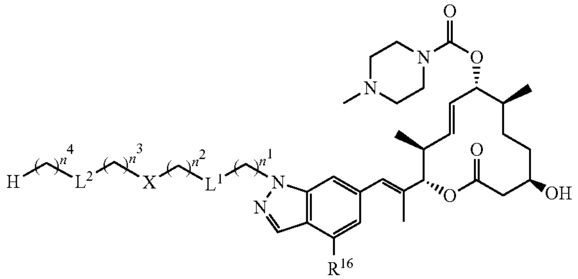

and pharmaceutically acceptable salts thereof, wherein:

$R^{16}$ is chosen from hydrogen and fluoro;

X is independently chosen from hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^5$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

Embodiment 34. The compound of embodiment 33, wherein X is chosen from a bond,

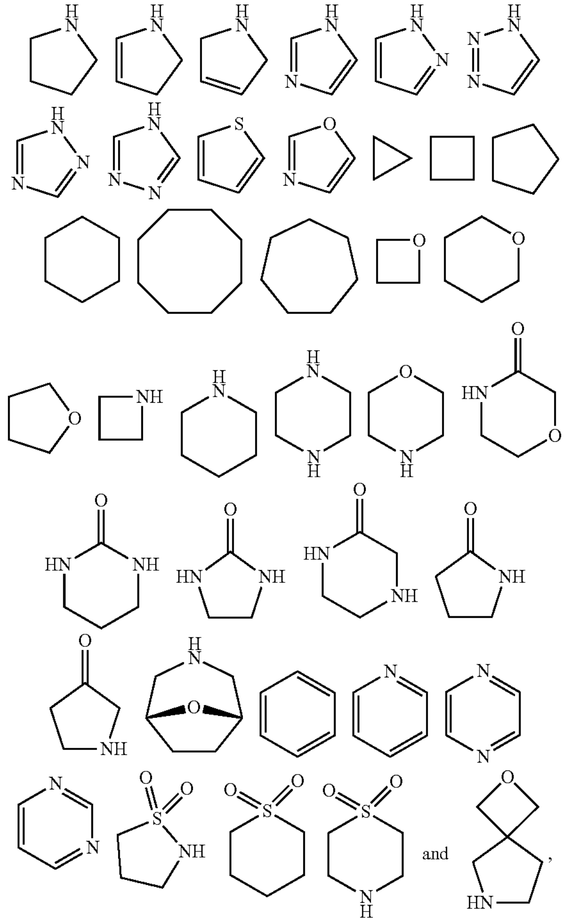

and , each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 35. The compound of embodiment 33 or embodiment 34, wherein X, $L^1$, and $L^2$ are each a bond.

Embodiment 36. The compound of any one of embodiments 33-35, wherein $R^{16}$ is fluoro.

Embodiment 37. A compound chosen from compounds of Formula IIIa:

IIIa

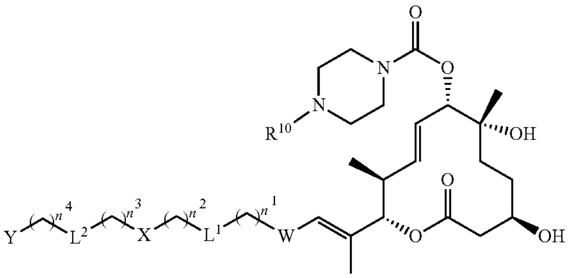

and pharmaceutically acceptable salts thereof, wherein:

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl-groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

Embodiment 38. A compound chosen from compounds of Formula IVa:

IVa

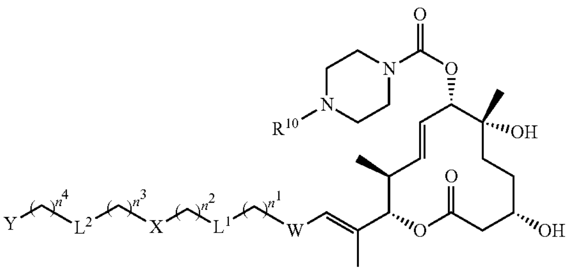

or a pharmaceutically acceptable salt thereof, wherein:

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$—$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl-groups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

Embodiment 39. The compound of embodiment 38, wherein W is chosen from a benzene ring, pyridine ring, benzimidazole ring, benzotriazole ring, indazole ring, 1,2,3,6-tetrahydropyridine ring, and imidazopyridine ring, each of which may be optionally substituted with 1 to 3 groups independently chosen from halogens, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups Embodiment 40. The compound of embodiment 38 or embodiment 39, wherein W is a benzene ring, which may be optionally substituted with 1 to 3 groups chosen from halogens and $C_1$-$C_6$ alkyl groups.

Embodiment 41. The compound of any one of embodiments 38-40, wherein X and Y are each independently chosen from a bond,

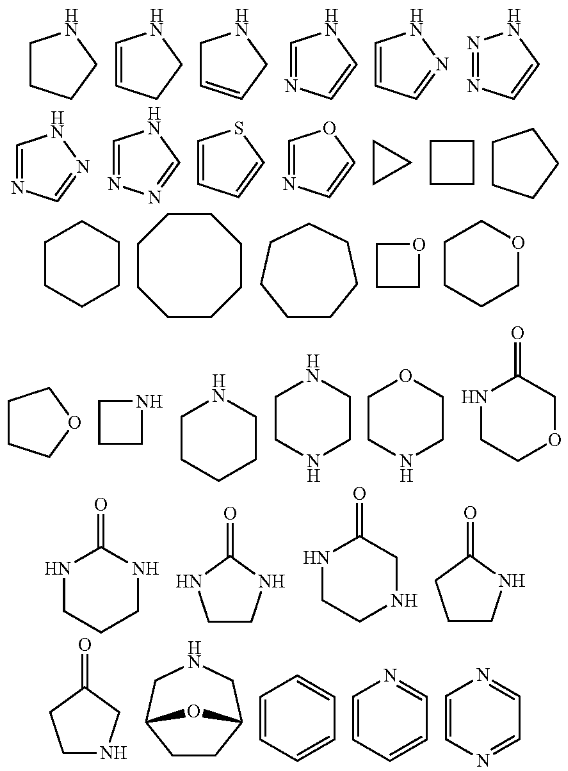

-continued

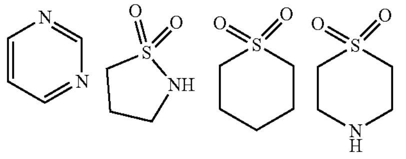

and

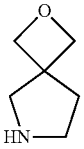

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 42. The compound of any embodiments 38-41, wherein Y is hydrogen, and X is chosen from:

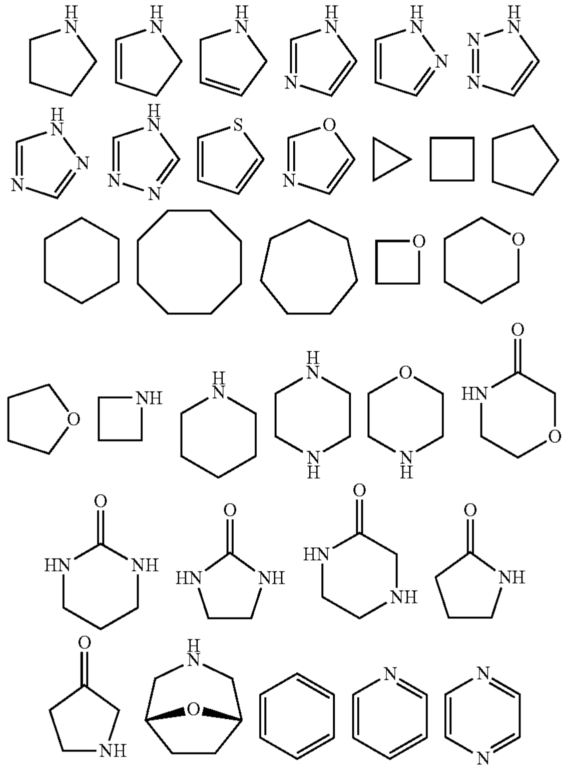

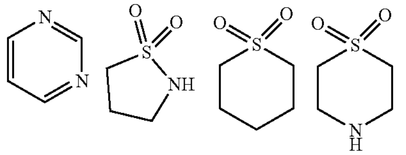

and

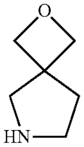

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 43. The compound of any one of embodiments 38-42, wherein Y is hydrogen and X is a bond.

Embodiment 44. A compound chosen from compounds of Formula Va:

Va

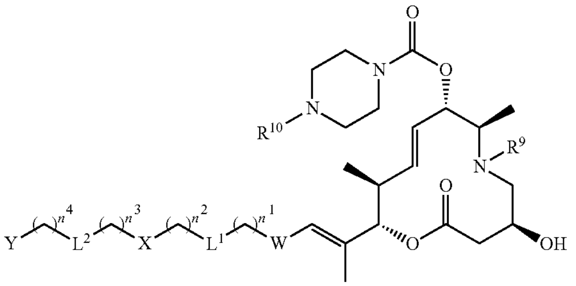

or a pharmaceutically acceptable salt thereof, wherein:

$R^9$ is chosen from hydrogen and $C_1$-$C_6$ alkyl groups;

$R^{10}$ is chosen from hydrogen and methyl;

W is chosen from 3 to 8 membered carbocycles and 3 to 8 membered heterocycles, each of which may be substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups;

X and Y are each independently chosen from a bond, hydrogen, 3 to 8 membered carbocycles, and 3 to 8 membered heterocycles, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkylgroups, and —$NR^{14}R^{15}$ groups, wherein $R^{14}$ and $R^{15}$ are each independently chosen from hydrogen and $C_1$-$C_6$ alkyl groups;

$L^1$ and $L^2$ are each independently chosen from a bond, —O—, —C(O)—, —C(O)O—, —N($R^{13}$)—C(O)—, —C(O)—N($R^{13}$)—, —N($R^{13}$)—S($O_2$)—, —S($O_2$)—N($R^{13}$)—, —S($O_2$)—, and —N($R^{13}$)—, wherein $R^{13}$ is chosen from hydrogen and $C_1$-$C_6$ alkyl groups; and each n is independently chosen from 0 to 4.

Embodiment 45. The compound of embodiment 44, wherein W is chosen from a benzene ring, pyridine ring, benzimidazole ring, benzotriazole ring, indazole ring, 1,2,3,6-tetrahydropyridine ring, and imidazopyridine ring, each of which may be optionally substituted with 1 to 3 groups independently chosen from halogens, —$NR^8R^9$ groups, $C_1$-$C_6$ alkyl groups, $C_1$-$C_6$ alkoxy groups, methoxy $C_1$-$C_6$ alkyl groups, hydroxy $C_1$-$C_6$ alkyl groups, and $C_3$-$C_5$ cycloalkyl groups Embodiment 46. The compound of embodiment 44 or embodiment 45, wherein W is a benzene ring, which may be substituted with 1 to 3 groups chosen from halogens and $C_1$-$C_6$ alkyl groups.

Embodiment 47. The compound of any one of embodiments 44-46, wherein X and Y are each independently chosen from a bond,

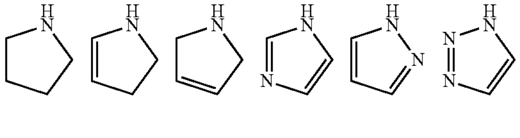

-continued

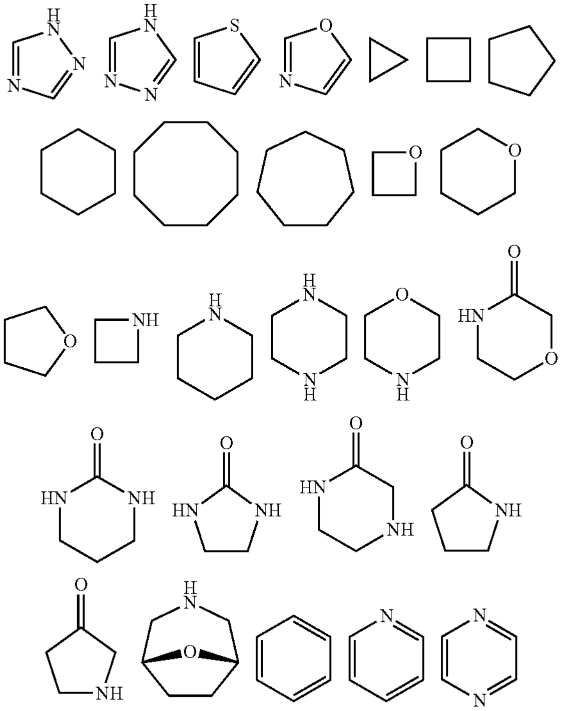

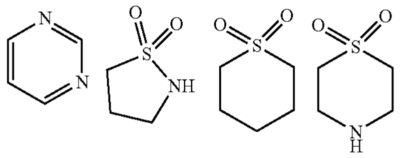

and

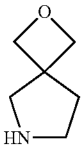

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 48. The compound of any embodiments 44-47, wherein Y is hydrogen, and X is chosen from:

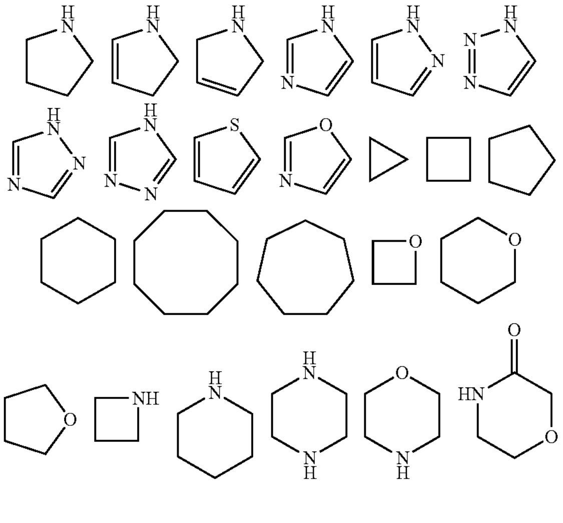

-continued

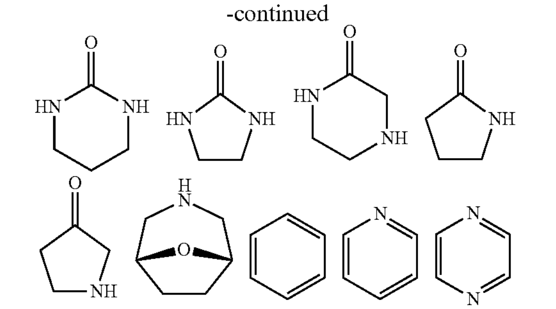

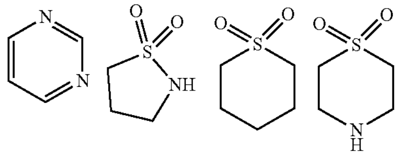

and

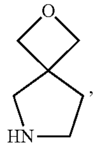

, each of which may be substituted with 1 to 3 groups independently chosen from halogens, hydroxyl groups, $C_1$-$C_6$ alkyl groups, hydroxy $C_1$-$C_6$ alkyl groups, $C_1$-$C_6$ alkoxy groups, methoxy $C_1$-$C_6$ alkyl groups, —$SO_2$—$C_1$-$C_6$ alkyl groups, and —$NR^{14}R^{15}$ groups, wherein $R^{14}$ and $R^{15}$ are each independently chosen from hydrogen and $C_1$-$C_6$ alkyl groups.

Embodiment 49. The compound of any one of embodiments 44-48, wherein Y is hydrogen and X is a bond.

Embodiment 50. A compound chosen from:

[(2S,3S,4E,6R,7S,10R)-10-hydroxy-3,7-dimethyl-12-oxo-2-[(E)-1-(3-piperazin-1-ylphenyl)prop-1-en-2-yl]-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-(4-methylpiperazin-1-yl)phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-(1H-indazol-6-yl)prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-(1H-indazol-4-yl)prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(2-morpholin-4-ylpyridin-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-(2-fluoro-5-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(4-fluoro-3-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[(3R)-3-(methylamino)pyrrolidin-1-yl]phenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[(3 S)-3-(methylamino)pyrrolidin-1-yl]phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(2-fluoro-5-morpholin-4-ylphenyl)prop-1-en-2-yl]-10-hydroxy-3,7-dimethyl-12-oxo-1-oxacyclododec-4-en-6-yl]4-piperidin-1-ylpiperidine-1-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl]4-piperidin-1-ylpiperidine-1-carboxylate;

[(2S,3S,4E,6R,7S,10R)-2-[(E)-1-[3-fluoro-5-[(3R)-3-fluoropyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-(hydroxymethyl)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(2R,6S)-2,6-dimethylmorpholin-4-yl]-5-fluorophenyl]prop-1-en-2-yl]-10-hydroxy-3,7-dimethyl-12-oxo-1-oxacyclododec-4-en-6-yl]4-piperidin-1-ylpiperidine-1-carboxylate;

[(2S,3S,4E,6R,7S,10R)-2-[(E)-1-[3-[(3 S)-3-(dimethylamino)pyrrolidin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(3-methyl-5-morpholin-4-ylphenyl)prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-morpholin-4-yl-5-(trifluoromethyl)phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(3-chloro-5-morpholin-4-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(2-hydroxyethyl)piperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-methyl-N-(1-methylpiperidin-4-yl)carbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3R)-3,4-dimethylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-propan-2-ylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-tert-butylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-cyclobutylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-cyclopentylpiperazine-1-carboxylate;

[(2S,3S,4E,6R,7S,10R)-2-[(E)-1-(3,5-difluorophenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(dimethylamino)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(4-hydroxypiperidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-(1-methylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(1R,5S)-8-oxa-3-azabicyclo[3.2.1]octan-3-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-oxa-7-azaspiro[3.4]octan-7-yl)phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[(3R)-3-hydroxypyrrolidin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-(3-oxopyrrolidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(oxan-4-yl)piperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-methyl-N-(1-methylpiperidin-3-yl)carbamate;

[(2S,3S,4E,6R,7S,10R)-2-[(E)-1-[3-fluoro-5-(3-fluoroazetidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-(methylamino)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]3-(dimethylamino)piperidine-1-carboxylate;

[(2S,3S,4E,6R,7S,10R)-2-[(E)-1-[3-fluoro-5-[(2R)-2-methylpyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-oxopyrrolidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-methylpyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2R)-2-(hydroxymethyl)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3R)-3-(methylamino)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(5-chloropyridin-3-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-methyl-N-(pyridin-4-ylmethyl)carbamate;

[(2S,3S,4E,6R,7S,10R)-2-[(E)-1-(3,5-dichlorophenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1,1-dioxo-1,2-thiazolidin-2-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(1,3-dimethylindazol-6-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1,1-dioxo-1,4-thiazinan-4-yl)-5-fluorophenyl]prop-1-en-2-yl]-10-hydroxy-3,7-dimethyl-12-oxo-1-oxacyclododec-4-en-6-yl]N,N-dimethylcarbamate;

[(2S,3S,4E,6R,7S,10R)-2-[(E)-1-[3-(1,1-dioxo-1,4-thiazinan-4-yl)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] morpholine-4-carboxylate;

[(2S,3S,4E,6R,7S,10R)-2-[(E)-1-[3-fluoro-5-[4-(2-hydroxyethyl)piperazin-1-yl]phenyl]prop-1-en-2-yl]-10-hydroxy-3,7-dimethyl-12-oxo-1-oxacyclododec-4-en-6-yl] N-methyl-N-(1-methylpiperidin-4-yl)carbamate;

[(2S,3S,4E,6R,7S,10R)-10-hydroxy-3,7-dimethyl-2-[(E)-1-(1-methylindazol-6-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-fluoro-5-(3-oxomorpholin-4-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-(cyclopentylsulfamoyl)-2-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(4-methylsulfonylpiperazin-1-yl)phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-(4-fluoro-1H-indazol-6-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-imidazol-1-ylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6S,7R,10S)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-methylpiperazine-1-carboxylate;

[(2S,3S,4E,6S,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-piperidin-1-ylpiperidine-1-carboxylate;

[(2S,3S,4E,6S,7R,10S)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-piperidin-1-ylpiperidine-1-carboxylate;

[(2S,3S,4E,6R,7S,10R)-2-[(E)-1-[3-fluoro-5-(2-oxoimidazolidin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[3-(2-hydroxyethyl)-2-oxoimidazolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[3-(2-fluoroethynyl)-2-oxoimidazolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[3-(2-morpholin-4-ylethyl)-2-oxoimidazolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[3-(cyclopropylmethyl)-2-oxoimidazolidin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-methylmorpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-methylmorpholin-4-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(2S,3 S)-3-hydroxy-2-methylpentyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(2R,3 S)-3-hydroxy-2-methylpentanoyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-morpholin-4-ylethylsulfonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(4-ethenylsulfonylpiperazin-1-yl)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3R)-3-methylmorpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2S)-2-(hydroxymethyl)morpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-(hydroxymethyl)morpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2R)-2-(methylcarbamoyl)morpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(2-oxo-1,3-diazinan-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[3-(cyclopropylmethyl)-2-oxo-1,3-diazinan-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(2R)-2-hydroxypropanoyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]3,4,6,7,8,8a-hexahydro-1H-pyrrolo[1,2-a]pyrazine-2-carboxylate;

[(2S,3S,4E,6R,7S,10R)-2-[(E)-1-[3-fluoro-5-[(3 S)-3-methylmorpholin-4-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(2-cyclopropyl-2-oxoethyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-oxo-2-pyrazin-2-ylethyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6S,7R,10R)-2-[(E)-1-(3-fluoro-5-morpholin-4-ylphenyl)prop-1-en-2-yl]-7,10-dihydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[1-(cyclopropylmethyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-imidazo[1,2-a]pyridin-6-ylprop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(7-methyl-1H-indazol-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[4-(cyclopropylsulfamoyl)-3-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[2-fluoro-5-(4-hydroxypiperidin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(2,2,2-trifluoroethyl)piperazine-1-carboxylate;

[(2S,3S,4E,6R,7S,10R)-10-hydroxy-3,7-dimethyl-12-oxo-2-[(E)-1-(3-piperazin-1-ylsulfonylphenyl)prop-1-en-2-yl]-1-oxacyclododec-4-en-6-yl]4-methylpiperazine-1-carboxylate;

[(2S,3S,4E,6R,7S,10R)-2-[(E)-1-[3-(4-formylpiperazin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-(4-hydroxypiperidin-1-yl)sulfonylphenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(6-methyl-1H-indazol-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-(1,3-dimethylindazol-4-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-(1-azabicyclo[2.2.2]octan-3-yl)-N-methylcarbamate;

[(2S,3S,4E,6R,7S,10R)-2-[(E)-1-[2-(cyclopropylmethyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-(2-hydroxyethyl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(4-fluoro-1-methylindazol-6-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-[1-(pyridin-4-ylmethyl)pyrazol-4-yl]prop-1-en-2-yl]-1-oxacyclododec-4-en-6-yl]4-methylpiperazine-1-carboxylate;

[(2S,3S,4E,6R,7S,10R)-10-hydroxy-3,7-dimethyl-2-[(E)-1-(1-methylpyrazol-4-yl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyethyl)-3-oxopiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-methoxyethyl)-3-oxopiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[1-(1-methylpiperidin-4-yl)pyrazol-4-yl]prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2,2,2-trifluoroethyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-methoxyacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(cyclopropanecarbonyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(4-methoxyphenyl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylpyrazol-4-yl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(4-pyridin-3-ylsulfonylpiperazin-1-yl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylimidazol-4-yl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(cyclohexanecarbonyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylindol-6-yl)sulfonylpiperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-(oxan-4-yl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-2-(oxan-4-yl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxane-4-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-morpholin-4-ylacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1-methylimidazole-4-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[4-(2-cyclopropylacetyl)piperazin-1-yl]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(1,3-oxazole-5-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyethylsulfonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxetan-3-ylsulfonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-(oxetan-3-ylsulfonyl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-(1-hydroxyisoquinolin-7-yl)prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-[2-(methylamino)-2-oxoethyl]indazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[4-fluoro-1-(2-oxo-2-pyrrolidin-1-ylethyl)indazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[4-fluoro-1-(2-morpholin-4-yl-2-oxoethyl)indazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[1-(cyanomethyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[1-[2-(dimethylamino)-2-oxoethyl]-4-fluoroindazol-6-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[1-(cyclopropylmethyl)-3-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(3-methoxypropanoyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-hydroxyacetyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(3-hydroxypropyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(cyclopropylmethyl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[2-(cyclopropylmethyl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[1-(cyclopropylmethyl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(oxan-4-yl) benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-2-(oxan-4-yl) benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(2-methoxyethyl)benzimidazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxolane-3-carbonyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[7-fluoro-3-[1-[(2-methylpropan-2-yl)oxycarbonyl]piperidin-4-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(4-chlorophenyl) methyl]-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1-acetylpiperidin-4-yl)-7-fluorobenzimidazol-5-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[7-fluoro-3-((1R,4S)-4-hydroxycyclohexyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(oxan-4-ylmethyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(2S)-1-hydroxypropan-2-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(2R)-1-hydroxypropan-2-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(3 S)-oxolane-3-carbonyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-[(3R)-oxolane-3-carbonyl]piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(oxetane-3-carbonyl)piperazin-1-yl]phenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[4-(3-methyloxetane-3-carbonyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(3-hydroxypropanoyl)piperazin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(4-methyloxan-4-yl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(1-methylsulfonylpiperidin-4-yl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1,1-dioxothian-4-yl)-7-fluorobenzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(2-methoxyethyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(1-acetylpiperidin-4-yl)-7-fluorobenzotriazol-5-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[7-fluoro-3-[(3R)-oxan-3-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(3 S)-oxan-3-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(3R,4S)-3-hydroxyoxan-4-yl]benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-cyclohexyl-7-fluorobenzotriazol-5-yl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-(4-methoxyphenyl)benzotriazol-5-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[7-fluoro-3-[(4-methoxyphenyl)methyl]benzotriazol-5-yl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-(3-chloro-5-fluorophenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl(oxan-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl (oxetan-3-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[methyl(oxan-4-yl)amino]phenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[methyl(oxetan-3-yl)amino]phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-[(1,1-dioxothian-4-yl)-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[(1-methylsulfonylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-(1-methylsulfonylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[ethyl-(1-methylsulfonylpiperidin-4-yl)amino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(1-methylsulfonylpiperidin-4-yl)-propan-2-ylamino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-acetylpiperidin-4-yl)-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[methyl-(1-propanoylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[[1-(2-methoxyacetyl)piperidin-4-yl]-methylamino]phenyl] prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-benzoylpiperidin-4-yl)-methylamino]-5-fluorophenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[3-fluoro-5-[methyl-[1-(2,2,2-trifluoroacetyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-(1-propylsulfonylpiperidin-4-yl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-cyclopentylsulfonylpiperidin-4-yl)-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(1-methylimidazol-4-yl)sulfonylpiperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[[1-(benzenesulfonyl) piperidin-4-yl]-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(1-acetylpiperidin-4-yl)methyl-methylamino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[(1-methylsulfonylpiperidin-4-yl)methyl]amino]phenyl] prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(1,3-oxazole-5-carbonyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(pyrazine-2-carbonyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(1-methylimidazole-4-carbonyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(propan-2-ylcarbamoyl)piperidin-4-yl]amino]phenyl] prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(propylcarbamoyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[methyl-[1-(phenylcarbamoyl)piperidin-4-yl]amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-(1-methylsulfonylpiperidin-4-yl)oxyphenyl]prop-1-en-2-yl]-10-hydroxy-3,7-dimethyl-12-oxo-1-oxacyclododec-4-en-6-yl] 4-methylpiperazine-1-carboxylate;

[(2S,3S,4E,6R,7S,10R)-2-[(E)-1-[1-(4,4-difluorocyclohexyl)-4-fluoroindazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[4-fluoro-1-(1-methylsulfonylpiperidin-4-yl)indazol-6-yl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-pyrrolidin-1-ylsulfonylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(azetidin-1-ylsulfonyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-[(3R)-3-hydroxypyrrolidin-1-yl]sulfonylphenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-[(2R)-2-methylpyrrolidin-1-yl]sulfonylphenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-2-[(E)-1-[3-[(1-hydroxy-2-methylpropan-2-yl)sulfamoyl]phenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-[3-(4,4-difluoropiperidin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-(4-methyl-3-pyrrolidin-1-ylsulfonylphenyl)prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-(3,3-difluoropyrrolidin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-(5-pyrrolidin-1-ylsulfonylpyridin-3-yl)prop-1-en-2-yl]-1-oxacyclododec-4-en-6-yl]4-methylpiperazine-1-carboxylate;

[(2S,3S,4E,6R,7S,10R)-2-[(E)-1-[3-(3,3-difluoroazetidin-1-yl)sulfonylphenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[4-methyl-3-(2-oxopyrrolidin-1-yl)phenyl]prop-1-en-2-yl]-12-oxo-1-oxacyclododec-4-en-6-yl]4-methylpiperazine-1-carboxylate;

[(2S,3S,4E,6R,7S,10R)-2-[(E)-1-[3-(tert-butylsulfamoyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-[3-(propan-2-ylsulfamoyl)phenyl]prop-1-en-2-yl]-1-oxacyclododec-4-en-6-yl]4-methylpiperazine-1-carboxylate;

[(2S,3S,4E,6R,7S,10R)-2-[(E)-1-[3-(ethylsulfamoyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-(4-methylpiperazin-1-yl)sulfonylphenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[3-(methylsulfamoyl)phenyl]prop-1-en-2-yl]-12-oxo-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-(3-piperidin-1-ylsulfonylphenyl)prop-1-en-2-yl]-1-oxacyclododec-4-en-6-yl]4-methylpiperazine-1-carboxylate;

[(2S,3S,4E,6R,7S,10R)-10-hydroxy-3,7-dimethyl-12-oxo-2-[(E)-1-(3-pyrrolidin-1-ylsulfonylphenyl)prop-1-en-2-yl]-1-oxacyclododec-4-en-6-yl]4-methylpiperazine-1-carboxylate;

[(2S,3S,4E,6R,7S,10R)-2-[(E)-1-(3-cyclopropylsulfonylphenyl)prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-(cyclopropylsulfonylamino)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-(methanesulfonamido)pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(3 S)-3-[(2-methoxyacetyl)amino]pyrrolidin-1-yl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-3,7-dimethyl-2-[(E)-1-[1-[(2-methylpropan-2-yl)oxycarbonyl]-3,6-dihydro-2H-pyridin-5-yl]prop-1-en-2-yl]-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-(trideuteriomethyl) piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-(pyridin-4-ylmethyl)carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-(pyrimidin-4-ylmethyl)carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] morpholine-4-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[2-(dimethylamino)ethyl]carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-methyl-1,4-diazepane-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[(4-methoxyphenyl)methyl]carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3R)-3-(dimethylamino)pyrrolidine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3S)-3-(dimethylamino)pyrrolidine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[(2R)-1-hydroxypropan-2-yl]carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 3-oxopiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] (3R)-3-fluoropyrrolidine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 3,3,4-trimethylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-methyl-N-(1-methylpiperidin-4-yl)carbamate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-(2-hydroxyethyl)piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-cycloheptylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-pyridin-4-ylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-cyclohexylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] N-[2-(4-hydroxyphenyl)ethyl]-N-methylcarbamate;

(2S,3S,6R,7S,10R,E)-2-((E)-1-(3-fluoro-5-morpholinophenyl)prop-1-en-2-yl)-10-hydroxy-3,7-dimethyl-12-oxo-1-oxacyclododec-4-en-6-yl 7-methyl-1,7-diazaspiro[3.5]nonane-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-(3-morpholin-4-ylpropyl)carbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-[2-(dimethylamino)ethyl]carbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3R)-3-(dimethylamino)pyrrolidine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3S)-3-(dimethylamino)pyrrolidine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]N-(2-cyanoethyl)-N-methylcarbamate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]3,3,4-trimethylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl](3R)-3-fluoropyrrolidine-1-carboxylate;

[(2S,3S,4E,6R,7S,10R)-2-[(E)-1-[3-(dimethylsulfamoylamino)-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[(2-methoxyacetyl)amino]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-[(2-cyclopropylacetyl)amino]-5-fluorophenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-[(3-hydroxyphenyl)methyl]piperazine-1-carboxylate;

[(2S,3S,4E,6R,7S,10R)-2-[(E)-1-[3-fluoro-5-[4-(2-pyrazol-1-ylacetyl)piperazin-1-yl]phenyl]prop-1-en-2-yl]-10-hydroxy-3,7-dimethyl-12-oxo-1-oxacyclododec-4-en-6-yl] 4-(pyridin-3-ylmethyl)piperazine-1-carboxylate;

[(2S,3S,4E,6R,7S,10R)-2-[(E)-1-[3-(1-acetylpiperidin-4-yl)-7-fluorobenzotriazol-5-yl]prop-1-en-2-yl]-10-hydroxy-3,7-dimethyl-12-oxo-1-oxacyclododec-4-en-6-yl] piperazine-1-carboxylate;

[(2S,3S,4E,6R,7S,10R)-10-hydroxy-2-[(E)-1-[3-[[(3R)-3-hydroxypyrrolidine-1-carbonyl]oxymethyl]phenyl]prop-1-en-2-yl]-3,7-dimethyl-12-oxo-1-oxacyclododec-4-en-6-yl]4-methylpiperazine-1-carboxylate;

[3-[(E)-2-[(2S,3 S,4E,6R,7S,10R)-10-hydroxy-3,7-dimethyl-6-(4-methylpiperazine-1-carbonyl)oxy-12-oxo-1-oxacyclododec-4-en-2-yl]prop-1-enyl]phenyl]methyl 2-oxa-7-azaspiro[3.4]octane-7-carboxylate;

[(2S,3S,4E,6R,7S,10R)-10-hydroxy-2-[(E)-1-[3-[[(3R)-3-fluoro-pyrrolidine-1-carbonyl]oxymethyl]phenyl]prop-1-en-2-yl]-3,7-dimethyl-12-oxo-1-oxacyclododec-4-en-6-yl]4-methylpiperazine-1-carboxylate;

[3-[(E)-2-[(2S,3 S,4E,6R,7S,10R)-10-hydroxy-3,7-dimethyl-6-(4-methylpiperazine-1-carbonyl)oxy-12-oxo-1-oxacyclododec-4-en-2-yl]prop-1-enyl]phenyl]methyl morpholine-4-carboxylate;

[(2S,3S,4E,6R,7S,10R)-2-[(E)-1-[3-(dimethylcarbamoyloxymethyl)phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-[[(2S)-2-(hydroxymethyl)pyrrolidine-1-carbonyl]oxymethyl]phenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-[3-[[(3R)-3-fluoropyrrolidine-1-carbonyl]oxymethyl]phenyl]prop-1-en-2-yl]-10-hydroxy-3,7-dimethyl-12-oxo-1-oxacyclododec-4-en-6-yl]4-methylpiperazine-1-carboxylate;

[(2S,3S,4E,6R,7S,10R)-10-hydroxy-2-[(E)-1-[3-[(4-hydroxypiperidine-1-carbonyl)oxymethyl]phenyl]prop-1-en-2-yl]-3,7-dimethyl-12-oxo-1-oxacyclododec-4-en-6-yl]4-methylpiperazine-1-carboxylate;

[(2S,3S,4E,6R,7S,10R)-2-[(E)-1-(3-fluoro-5-morpholin-4-ylphenyl)prop-1-en-2-yl]-10-hydroxy-3,7-dimethyl-12-oxo-1-oxacyclododec-4-en-6-yl]4-piperidin-1-ylpiperidine-1-carboxylate;

[(2S,3S,4E,6R,7S,10R)-10-hydroxy-2-[(E)-1-[3-[4-(2-hydroxyethyl)piperazin-1-yl]phenyl]prop-1-en-2-yl]-3,7-dimethyl-12-oxo-1-oxacyclododec-4-en-6-yl]4-piperidin-1-ylpiperidine-1-carboxylate;

2-[4-[3-fluoro-5-[(E)-2-[(2S,3 S,4E,6R,7S,10R)-10-hydroxy-3,7-dimethyl-12-oxo-6-(piperazine-1-carbonyloxy)-1-oxacyclododec-4-en-2-yl]prop-1-enyl]phenyl] piperazin-1-yl]acetic acid;

(2S,3S,6R,7S,10R,E)-2-((E)-1-(3-(dimethylamino)phenyl) prop-1-en-2-yl)-10-hydroxy-3,7-dimethyl-12-oxooxacyclododec-4-en-6-yl 4-methylpiperazine-1-carboxylate;

(2S,3S,6R,7S,10R,E)-2-((E)-1-(3-(dimethylamino)phenyl) prop-1-en-2-yl)-10-hydroxy-3,7-dimethyl-12-oxooxacyclododec-4-en-6-yl piperazine-1-carboxylate;

(2S,3S,6R,7S,10R,E)-2-((E)-1-(5-chloropyridin-3-yl)prop-1-en-2-yl)-10-hydroxy-3,7-dimethyl-12-oxooxacyclododec-4-en-6-yl piperazine-1-carboxylate;

(2S,3S,6R,7S,10R,E)-10-hydroxy-3,7-dimethyl-12-oxo-2-((E)-1-(3-(pyrrolidin-1-ylsulfonyl)phenyl)prop-1-en-2-yl)oxacyclododec-4-en-6-yl piperazine-1-carboxylate; and pharmaceutically acceptable salts thereof.

Embodiment 51. The compound of any one of embodiments 1-50, wherein said compound comprises greater than about 80% by weight of one stereoisomer of the compound.

Embodiment 52. The compound of embodiment any one of embodiments 1-50, wherein said compound comprises greater than about 90% by weight of one stereoisomer of the compound.

Embodiment 53. The compound of any one of embodiments 1-50, wherein said compound comprises greater than about 95% by weight of one stereoisomer of the compound.

Embodiment 54. The compound of any one of embodiments 1-50, wherein said compound comprises greater than about 97% by weight of one stereoisomer of the compound.

Embodiment 55. A pharmaceutical composition comprising at least one compound chosen from compounds and/or pharmaceutically acceptable salts thereof of any one of embodiments 1-54.

Embodiment 56. The pharmaceutical composition of embodiment 55, wherein said composition is formulated for intravenous, oral, subcutaneous, or intramuscular administration.

Embodiment 57. The pharmaceutical composition of embodiment 56, wherein said composition is formulated for oral administration.

Embodiment 58. A method of treating cancer in a subject in need thereof, comprising administering to said subject a therapeutically effective amount of at least one compound chosen from compounds and/or pharmaceutically acceptable salts thereof of any one of embodiments 1-54, or the pharmaceutical composition of any one of embodiments 55-57, wherein the cancer is chosen from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

Embodiment 59. The method of embodiment 58, wherein said cancer is chosen from myelodysplastic syndrome, chronic lymphocytic leukemia, acute lymphoblastic leukemia, chronic myelomonocytic leukemia, and acute myeloid leukemia.

Embodiment 60. The method of embodiment 58, wherein said cancer is myelodysplastic syndrome.

Embodiment 61. The method of embodiment 58, wherein said cancer is chronic myelomonocytic leukemia.

Embodiment 62. The method of embodiment 58, wherein said cancer is acute myeloid leukemia.

Embodiment 63. The method of embodiment 58, wherein said cancer is chronic lymphocytic leukemia.

Embodiment 64. The method of embodiment 58, wherein said cancer is acute lymphoblastic leukemia.

Embodiment 65. The method of embodiment 58, wherein said cancer is endometrial cancer.

Embodiment 66. The method of embodiment 58, wherein said cancer is ovarian cancer.

Embodiment 67. The method of embodiment 58, wherein said cancer is breast cancer.

Embodiment 68. The method of embodiment 58, wherein said cancer is uveal melanoma.

Embodiment 69. The method of embodiment 58, wherein said cancer is gastric cancer.

Embodiment 70. The method of embodiment 58, wherein said cancer is cholangiocarcinoma.

Embodiment 71. The method of embodiment 58, wherein said cancer is lung cancer Embodiment 72. The method of embodiment 58, wherein said cancer is colon cancer.

Embodiment 73. The method of embodiment 58, wherein said cancer is pancreatic cancer.

Embodiment 74. The method of any one of embodiments 58-73, wherein said cancer is positive for one or more mutations in a spliceosome gene or protein.

Embodiment 75. The method of embodiment 74, wherein said spliceosome gene or protein is chosen from splicing factor 3B subunit 1 (SF3B1), U2 small nuclear RNA auxiliary factor 1 (U2AF1), serine/arginine-rich splicing factor 2 (SRSF2), zinc finger (CCCH type) RNA-binding motif and serine/arginine rich 2 (ZRSR2), pre-mRNA-processing-splicing factor 8 (PRPF8), U2 small nuclear RNA auxiliary factor 2 (U2AF2), splicing factor 1 (SF1), splicing factor 3a subunit 1 (SF3A1), PRP40 pre-mRNA processing factor 40 homolog B (PRPF40B), RNA binding motif protein 10 (RBM10), poly(rC) binding protein 1 (PCBP1), crooked neck pre-mRNA splicing factor 1 (CRNKL1), DEAH (Asp-Glu-Ala-His) box helicase 9 (DHX9), peptidyl-prolyl cis-trans isomerase-like 2 (PPIL2), RNA binding motif protein 22 (RBM22), small nuclear ribonucleoprotein Sm D3 (SNRPD3), probable ATP-dependent RNA helicase DDX5 (DDX5), pre-mRNA-splicing factor ATP-dependent RNA helicase DHX15 (DHX15), and polyadenylate-binding protein 1 (PABPC1).

Embodiment 76. The method of embodiment 75, wherein the spliceosome gene or protein is splicing factor 3B subunit 1.

Embodiment 77. A method of treating cancer in a subject in need thereof, comprising administering to said subject a therapeutically effective amount of at least one compound chosen from compounds and/or pharmaceutically acceptable salts thereof of any one of embodiments 1-54, or the pharmaceutical composition of any one of embodiments 55-57, and at least one additional therapy.

Embodiment 78. The method of embodiment 77, wherein the at least one additional therapy comprises at least one, at least two, at least three, at least four, or at least five additional therapies.

Embodiment 79. The method of embodiment 77, wherein the therapeutically effective amount of at least one compound chosen from compounds and/or pharmaceutically acceptable salts thereof of any one of embodiments 1-54, or the pharmaceutical composition of any one of embodiments 55-57, and/or the at least one additional therapy is reduced by 10%, 15%, 20%, 25%, 30%, 35%, 40%, 45%, 50%, 75%, or 90%, relative to a standard dosage of a compound of Formula I, or pharmaceutically acceptable salt thereof, and/or the at least one additional therapy.

Embodiment 80. The method of any one of embodiments 77 to 79, wherein the at least one compound chosen from compounds and/or pharmaceutically acceptable salts thereof of any one of embodiments 1-54, or the pharmaceutical composition of any one of embodiments 55-57, and/or the at least one additional therapy is administered at least 10%, 15%, 20%, 25%, 30%, 35%, 40%, 45%, 50%, 75%, or 90% less frequently, relative to a standard dosing regimen of the at least one compound chosen from compounds and/or pharmaceutically acceptable salts thereof of any one of embodiments 1-54, or the pharmaceutical composition of any one of embodiments 55-57, and/or the at least one additional therapy.

Embodiment 81. The method of any one of embodiments 77 to 80, wherein the administered amount and/or dosage of the at least one compound chosen from compounds and/or pharmaceutically acceptable salts thereof of any one of embodiments 1-54, or the pharmaceutical composition of any one of embodiments 55-57, and/or the at least one additional therapy results in lower systemic toxicity and/or improved tolerance.

Embodiment 82. The method of embodiment 77, wherein administration of the at least one compound chosen from compounds and/or pharmaceutically acceptable salts thereof of any one of embodiments 1-54, or the pharmaceutical composition of any one of embodiments 55-57, is initiated before administration of the at least one additional therapy.

Embodiment 83. The method of embodiment 77, wherein administration of the at least one compound chosen from compounds and/or pharmaceutically acceptable salts thereof of any one of embodiments 1-54, or the pharmaceutical composition of any one of embodiments 55-57, is initiated after administration of the at least one additional therapy.

Embodiment 84. The method of embodiment 77, wherein administration of the at least one compound chosen from compounds and/or pharmaceutically acceptable salts thereof of any one of embodiments 1-54, or the pharmaceutical composition of any one of embodiments 55-57, is initiated concurrently with administration of the at least one additional therapy.

Embodiment 85. The method of any one of embodiments 77 to 84, wherein administration of the at least one compound chosen from compounds and/or pharmaceutically acceptable salts thereof of any one of embodiments 1-54, or the pharmaceutical composition of any one of embodiments 55-57, is repeated at least once after initial administration.

Embodiment 86. The method of embodiment 85, wherein the amount of the at least one compound chosen from compounds and/or pharmaceutically acceptable salts thereof of any one of embodiments 1-54, or the pharmaceutical composition of any one of embodiments 55-57, used for repeated administration is reduced relative to the amount used for initial administration.

Embodiment 87. The method of embodiment 85, wherein the amount of the at least one compound chosen from compounds and/or pharmaceutically acceptable salts thereof of any one of embodiments 1-54, or the pharmaceutical composition of any one of embodiments 55-57, used for repeated administration is reduced relative to a standard dosage of the at least one compound chosen from compounds and/or pharmaceutically acceptable salts thereof of any one of embodiments 1-54, or the pharmaceutical composition of any one of embodiments 55-57.

Embodiment 88. The method of embodiment 85, wherein the amount of the at least one compound chosen from compounds and/or pharmaceutically acceptable salts thereof of any one of embodiments 1-54, or the pharmaceutical composition of any one of embodiments 55-57, used for repeated administration is reduced by 10%, 15%, 20%, 25%, 30%, 35%, 40%, 45%, 50%, 75%, or 90%, relative to a standard dosage of the at least one compound chosen from compounds and/or pharmaceutically acceptable salts thereof of any one of embodiments 1-54, or the pharmaceutical composition of any one of embodiments 55-57.

Embodiment 89. The method of any one of embodiments 77 to 88, wherein administration of the at least one additional therapy is repeated at least once after initial administration.

Embodiment 90. The method of embodiment 89, wherein the amount of the at least one additional therapy used for repeated administration is reduced relative to the amount used for initial administration.

Embodiment 91. The method of embodiment 89, wherein the amount of the at least one additional therapy used for repeated administration is reduced relative to a standard dosage of the at least one additional therapy.

Embodiment 92. The method of embodiment 89, wherein the amount of the at least one additional therapy used for repeated administration is reduced by 10%, 15%, 20%, 25%, 30%, 35%, 40%, 45%, 50%, 75%, or 90%, relative to a standard dosage of the at least one additional therapy.

Embodiment 93. The method of any one of embodiments 77 to 92, wherein repeated administration of the at least one compound chosen from compounds and/or pharmaceutically acceptable salts thereof of any one of embodiments 1-54, or the pharmaceutical composition of any one of embodiments 55-57, is concurrent with repeated administration of the at least one additional therapy.

Embodiment 94. The method of any one of embodiments 77 to 92, wherein repeated administration of the at least one compound chosen from compounds and/or pharmaceutically acceptable salts thereof of any one of embodiments 1-54, or the pharmaceutical composition of any one of embodiments 55-57, is sequential or staggered with repeated administration of the at least one additional therapy.

Embodiment 95. The method of any one of embodiments 77 to 94, wherein the at least one additional therapy comprises administering a checkpoint inhibitor.

Embodiment 96. The method of embodiment 95, wherein the subject is intolerant, non-responsive, or poorly responsive to the checkpoint inhibitor when administered alone.

Embodiment 97. The method of embodiment 95, wherein the checkpoint inhibitor targets CTLA4, PD1, PDL1, OX40, CD40, GITR, LAG3, TIM3, and/or KIR.

Embodiment 98. The method of embodiment 95, wherein the checkpoint inhibitor targets CTLA4, OX40, CD40, and/or GITR.

Embodiment 99. The method of embodiment 97 or embodiment 98, wherein the checkpoint inhibitor comprises a cytotoxic T-lymphocyte-associated antigen 4 pathway (CTLA4) inhibitor.

Embodiment 100. The method of embodiment 99, wherein the CTLA4 inhibitor is an anti-CTLA4 antibody.

Embodiment 101. The method of embodiment 100, wherein the anti-CTLA4 antibody is ipilimumab.

Embodiment 102. The method of embodiment 97 or embodiment 98, wherein the checkpoint inhibitor comprises a programmed death-1 pathway (PD1) inhibitor.

Embodiment 103. The method of embodiment 102, wherein the PD1 inhibitor is an anti-PD1 antibody.

Embodiment 104. The method of embodiment 103, wherein the anti-PD1 antibody is nivolumab.

Embodiment 105. The method of embodiment 102, wherein the PD1 inhibitor is an anti-PDL1 antibody.

Embodiment 106. The method of embodiment 105, wherein the anti-PDL1 antibody is atezolizumab.

Embodiment 107. The method of embodiment 97 or embodiment 98, wherein the checkpoint inhibitor comprises a CTLA4 inhibitor and a PD1 inhibitor.

Embodiment 108. The method of embodiment 107, wherein the CTLA4 inhibitor is an anti-CTLA4 antibody.

Embodiment 109. The method of embodiment 108, wherein the anti-CTLA4 antibody is ipilimumab.

Embodiment 110. The method of embodiment 107 or embodiment 108, wherein the PD1 inhibitor is an anti-PD1 antibody.

Embodiment 111. The method of embodiment 110, wherein the anti-PD1 antibody is nivolumab.

Embodiment 112. The method of embodiment 107 or embodiment 108, wherein the PD1 inhibitor is an anti-PDL1 antibody.

Embodiment 113. The method of embodiment 112, wherein the anti-PDL1 antibody is atezolizumab.

Embodiment 114. The method of any one of embodiments 77 to 94, wherein the at least one additional therapy comprises administering a cytokine or cytokine analog.

Embodiment 115. The method of embodiment 114, wherein the subject is intolerant, non-responsive, or poorly responsive to the cytokine or cytokine analog when administered alone.

Embodiment 116. The method of embodiment 114, wherein the cytokine or cytokine analog comprises a T-cell enhancer.

Embodiment 117. The method of embodiment 114, wherein the cytokine or cytokine analog comprises IL-2, IL-10, IL-12, IL-15, IFNγ, and/or TNFα.

Embodiment 118. The method of any one of embodiments 77 to 94, wherein the at least one additional therapy comprises engineered tumor-targeting T-cells.

Embodiment 119. The method of any one of embodiments 77 to 118, wherein the subject has a non-synonymous mutational burden of about 150 mutations or less.

Embodiment 120. The method of any one of embodiments 77 to 119, wherein the subject has a non-synonymous mutational burden of about 100 mutations or less.

Embodiment 121. The method of any one of embodiments 77 to 120, wherein the subject has a non-synonymous mutational burden of about 50 mutations or less.

Embodiment 122. The method of any one of embodiments 77 to 121, wherein the cancer is a hematological malignancy or a solid tumor. The method of embodiment 122, wherein the hematological malignancy is chosen from a B-cell malignancy, a leukemia, a lymphoma, and a myeloma.

Embodiment 123. The method of embodiment 122 or embodiment 123, wherein the hematological malignancy is chosen from acute myeloid leukemia and multiple myeloma.

Embodiment 124. The method of embodiment 122, wherein the solid tumor is chosen from breast cancer, gastric cancer, prostate cancer, ovarian cancer, lung cancer, uterine cancer, salivary duct carcinoma, melanoma, colon cancer, and esophageal cancer.

Embodiment 125. The method of any one of embodiments 77 to 121, wherein the cancer is chosen from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

Embodiment 126. A method of inducing at least one neoantigen, comprising contacting a neoplastic cell with a therapeutically effective amount of at least one compound chosen from compounds and/or pharmaceutically acceptable salts thereof of any one of embodiments 1-54, or the pharmaceutical composition of any one of embodiments 55-57, thereby inducing production of at least one neoantigen.

Embodiment 127. The method of embodiment 126, wherein the neoplastic cell is present in an in vitro cell culture.

Embodiment 128. The method of embodiment 126 or embodiment 127, wherein the neoplastic cell is obtained from a subject.

Embodiment 129. The method of embodiment 126, wherein the neoplastic cell is present in a subject.

Embodiment 130. The method of any one of embodiments 126 to 129, wherein the neoplastic cell is derived from a hematological malignancy or a solid tumor.

Embodiment 131. The method of embodiment 130, wherein the hematological malignancy is selected from a B-cell malignancy, a leukemia, a lymphoma, and a myeloma.

Embodiment 132. The method of embodiment 130 or embodiment 131, wherein the hematological malignancy is selected from acute myeloid leukemia and multiple myeloma.

Embodiment 133. The method of embodiment 130, wherein the solid tumor is selected from breast cancer, gastric cancer, prostate cancer, ovarian cancer, lung cancer, uterine cancer, salivary duct carcinoma, melanoma, colon cancer, and esophageal cancer.

Embodiment 134. A method of inducing at least one neoantigen and/or a T-cell response in a subject having or suspected of having a neoplastic disorder, comprising administering to the subject a therapeutically effective amount of at least one compound chosen from compounds and/or pharmaceutically acceptable salts thereof of any one of embodiments 1-54, or the pharmaceutical composition of any one of embodiments 55-57.

Embodiment 135. A method of treating a subject having or suspected of having a neoplastic disorder, comprising administering to the subject a therapeutically effective amount of at least one compound chosen from compounds and/or pharmaceutically acceptable salts thereof of any one of embodiments 1-54, or the pharmaceutical composition of any one of embodiments 55-57, wherein administration of the at least one compound or the pharmaceutical composition induces at least one neoantigen and/or a T-cell response.

Embodiment 136. The method of embodiment 135, wherein the amount of the at least one compound or the pharmaceutical composition administered is reduced due to induction of at least one neoantigen and/or a T-cell response, relative to a standard dosage of the at least one compound or the pharmaceutical composition.

Embodiment 137. The method of embodiment 136, wherein the administered amount of the at least one compound or the pharmaceutical composition is reduced by 10%, 15%, 20%, 25%, 30%, 35%, 40%, 45%, 50%, 75%, or 90%, relative to a standard dosage of the at least one compound or the pharmaceutical composition.

Embodiment 138. The method of any one of embodiments 135 to 137, wherein the at least one compound or the pharmaceutical composition is administered at least 10%, 15%, 20%, 25%, 30%, 35%, 40%, 45%, 50%, 75%, or 90% less frequently, relative to a standard dosing regimen of the at least one compound or the pharmaceutical composition.

Embodiment 139. The method of any one of embodiments 135 to 137, wherein the administered amount and/or dosage of the at least one compound or the pharmaceutical composition results in lower systemic toxicity and/or improved tolerance.

Embodiment 140. The method of any one of embodiments 134 to 119, further comprising administering at least one additional therapy.

We claim:

1. A method for treating a subject having a neoplastic disorder or a subject suspected of having a neoplastic disorder, wherein the method comprises administering to the subject in need thereof a therapeutically effective amount of at least one compound of the following formula:

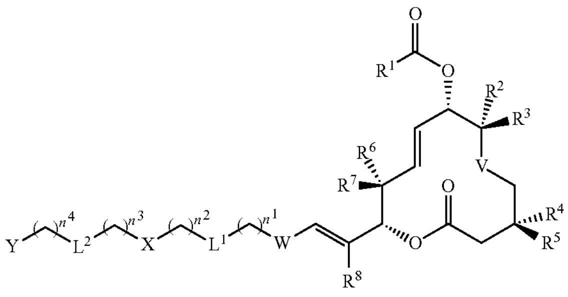

or a pharmaceutically acceptable salt thereof, wherein:

$R^1$ is:

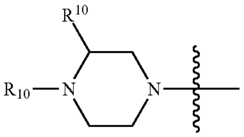
,
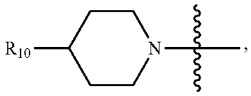
,
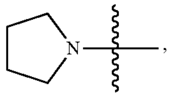
,
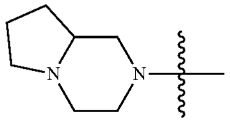
,
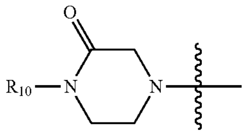
,
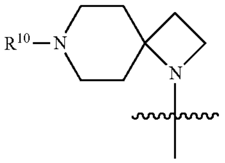
, -continued

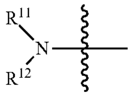 , 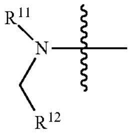 , 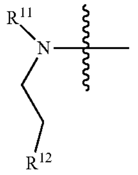 ,

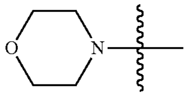 , 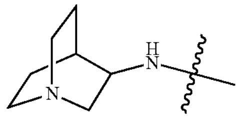 , or

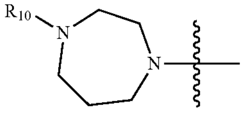 , wherein $R^1$ is optionally substituted with 1, 2, or 3 substituents independently selected from the group consisting of halogen, OH, a $C_1$-$C_6$alkyl group, a $C_1$-$C_6$alkoxy group, a $C_3$-$C_8$ cycloalkyl group, a hydroxy-$C_1$-$C_6$alkyl group, $N(CH_3)_2$, and a methoxy-$C_1$-$C_6$ alkyl group;

$R^2$ is hydrogen, a $C_1$-$C_6$alkyl group, or an $OR^{10}$ group;

$R^3$ is hydrogen, a $C_1$-$C_6$alkyl group, or an $OR^{10}$ group;

$R^4$ is hydrogen, a $C_1$-$C_6$alkyl group, or an $OR^{10}$ group;

$R^5$ is hydrogen, a $C_1$-$C_6$ alkyl group, or an $OR^{10}$ group;

$R^6$ is hydrogen, a $C_1$-$C_6$ alkyl group, or an $OR^{10}$ group;

$R^7$ is hydrogen, a $C_1$-$C_6$ alkyl group, or an $OR^{10}$ group;

V is —$CH_2$— or —$NR^9$—;

W is a 3- to 8-membered carbocyclyl group or a 3- to 10-membered heterocyclyl group, wherein the 3- to 8-membered carbocyclyl group or the 3- to 10-membered heterocyclyl group is optionally substituted with 1, 2, or 3 substituents independently selected from the group consisting of halogen, $NR^8R^9$, a $C_1$-$C_6$ alkyl group, a $C_1$-$C_6$ alkoxy group, a methoxy-$C_1$-$C_6$ alkyl group, a hydroxy-$C_1$-$C_6$ alkyl group, and a $C_3$-$C_5$ cycloalkyl group;

each $R^8$ is independently hydrogen or a $C_1$-$C_6$ alkyl group;

each $R^9$ is independently hydrogen or a $C_1$-$C_6$ alkyl group;

each $R^{10}$ is independently hydrogen, a $C_1$-$C_6$ alkyl group, a $C_1$-$C_6$ aminoalkyl group, a $C_1$-$C_6$ alkylamino group, a $C_1$-$C_6$ alkylcarboxylic acid group, a $C_3$-$C_8$ cycloalkyl group, a benzyl group, a $C_3$-$C_8$ heterocyclyl group, a $CH_2$—$C_3$-$C_8$ heterocyclyl group, a C(O)—$C_3$-$C_8$ heterocyclyl group, an acyl group, a hydroxy-$C_1$-$C_6$ alkyl group, a methoxy-$C_1$-$C_6$ alkyl group, $CD_3$, or C(O)—$NR^{11}R^{12}$;

each $R^{11}$ is independently hydrogen, a $C_1$-$C_6$ alkyl group, a $C_1$-$C_6$ aminoalkyl group, a $C_1$-$C_6$ alkylamino group, a $C_3$-$C_8$ cycloalkyl group, or a $C_3$-$C_8$ heterocyclyl group;

each $R^{12}$ is independently hydrogen, a $C_1$-$C_6$ alkyl group, a $C_1$-$C_6$ aminoalkyl group, a $C_1$-$C_6$ alkylamino group, a $C_3$-$C_8$ cycloalkyl group, or a $C_3$-$C_8$ heterocyclyl group;

$L^1$ is a bond, —O—, —C(O)—, —C(O)—O—, —$NR^{13}$—C(O)—, —C(O)—$NR^{13}$—, —$NR^{13}$—$S(O)_2$—, —$S(O)_2$—$NR^{13}$—, —$S(O)_2$—, or —$NR^{13}$—;

X is a bond, a 3- to 8-membered carbocyclyl group, or a 3- to 8-membered heterocyclyl group, wherein the 3- to 8-membered carbocyclyl group or the 3- to 8-membered heterocyclyl group is optionally substituted with 1, 2, or 3 substituents independently selected from the group consisting of halogen, OH, a $C_1$-$C_6$ alkyl group, a hydroxy-$C_1$-$C_6$ alkyl group, a $C_1$-$C_6$ alkoxy group, a methoxy-$C_1$-$C_6$ alkyl group, an $S(O)_2$—$C_1$-$C_6$ alkyl group, and $NR^{14}R^{15}$;

$L^2$ is a bond, —O—, —C(O)—, —C(O)—O—, —$NR^{13}$—C(O)—, —C(O)—$NR^{13}$—, —$NR^{13}$—$S(O)_2$—, —$S(O)_2$—$NR^{13}$—, —$S(O)_2$—, or —$NR^{13}$—;

Y is hydrogen, a 3- to 8-membered carbocyclyl group, or a 3- to 8-membered heterocyclyl group, wherein the 3- to 8-membered carbocyclyl group or the 3- to 8-membered heterocyclyl group is optionally substituted with 1, 2, or 3 substituents independently selected from the group consisting of halogen, OH, a $C_1$-$C_6$ alkyl group, a hydroxy-$C_1$-$C_6$ alkyl group, a $C_1$-$C_6$ alkoxy group, a methoxy-$C_1$-$C_6$ alkyl group, a $S(O)_2$—$C_1$-$C_6$ alkyl group, and $NR^{14}R^{15}$;

each $R^{13}$ is independently hydrogen or a $C_1$-$C_6$ alkyl group;

each $R^{14}$ is independently hydrogen or a $C_1$-$C_6$ alkyl group;

each $R^{15}$ is independently hydrogen or a $C_1$-$C_6$ alkyl group;

$n^1$ is 0, 1, 2, 3, or 4;

$n^2$ is 0, 1, 2, 3, or 4;

$n^3$ is 0, 1, 2, 3, or 4; and $n^4$ is 0, 1, 2, 3, or 4;

wherein administration of the therapeutically effective amount of the at least one compound or pharmaceutically acceptable salt thereof to the subject in need thereof:

(i) induces at least one neoantigen; or (ii) induces a T-cell response; or (iii) induces at least one neoantigen and a T-cell response.

2. The method of claim 1, wherein the neoplastic disorder is a solid tumor selected from the group consisting of breast cancer, gastric cancer, prostate cancer, ovarian cancer, lung cancer, uterine cancer, salivary duct carcinoma, melanoma, colon cancer, and esophageal cancer.

3. The method of claim 1, wherein the neoplastic disorder is a hematological malignancy selected from the group consisting of a B-cell malignancy, a leukemia, a lymphoma, and a myeloma.

4. The method of claim 1, wherein the amount of the at least one compound administered is reduced relative to a standard dosage of the at least one compound, due to the induction of at least one neoantigen and/or the induction of the T-cell response.

5. The method of claim 4, wherein the administered amount of the at least one compound is reduced by at least 10% relative to a standard dosage of the at least one compound.

6. The method of claim 5, wherein the at least one compound is administered at least 10% less frequently, relative to a standard dosing regimen of the at least one compound.

7. The method of claim 1, wherein $R^1$ is

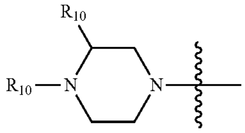 or 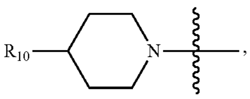 , and wherein $R^1$ is optionally substituted with 1, 2, or 3 substituents independently selected from the group consisting of halogen and a $C_1$-$C_6$ alkyl group.

8. The method of claim 1, wherein $R^1$ is

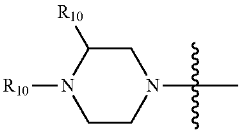

and wherein $R^1$ is optionally substituted with 1, 2, or 3 substituents independently selected from $C_1$-$C_6$ alkyl groups.

9. The method of claim 1, wherein $R^1$ is unsubstituted

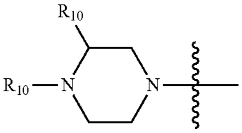

10. The method of claim 1, wherein $R^2$ is hydrogen and $R^3$ is methyl.

11. The method of claim 1, wherein $R^4$ is hydrogen and $R^5$ is OH.

12. The method of claim 1, wherein $R^6$ is hydrogen and $R^7$ is methyl.

13. The method of claim 1, wherein $R^8$ is methyl.

14. The method of claim 1, wherein V is $—CH_2—$.

15. The method of claim 1, wherein W is a benzene ring, a pyridine ring, a benzimidazole ring, a benzotriazole ring, an indazole ring, a 1,2,3,6-tetrahydropyridine ring, or an imidazopyridine ring, wherein the benzene ring, the pyridine ring, the benzimidazole ring, the benzotriazole ring, the indazole ring, the 1,2,3,6-tetrahydropyridine ring, or the imidazopyridine ring is optionally substituted with 1, 2, or 3 substituents independently selected from the group consisting of halogen, $NR^8R^9$, a $C_1$-$C_6$ alkyl group, a $C_1$-$C_6$ alkoxy group, a methoxy-$C_1$-$C_6$ alkyl group, a hydroxy-$C_1$-$C_6$ alkyl group, and a $C_3$-$C_5$ cycloalkyl group.

16. The method of claim 1, wherein W is a benzene ring optionally substituted with 1, 2, or 3 substituents independently selected from the group consisting of halogen and a $C_1$-$C_6$ alkyl group.

17. The method of claim 1, wherein X is a bond or a 3- to 8-membered carbocyclyl or heterocyclyl group and Y is a 3- to 8-membered carbocyclyl or heterocyclyl group, wherein the 3- to 8-membered carbocyclyl or heterocyclyl group of X and Y are independently selected from the group consisting of

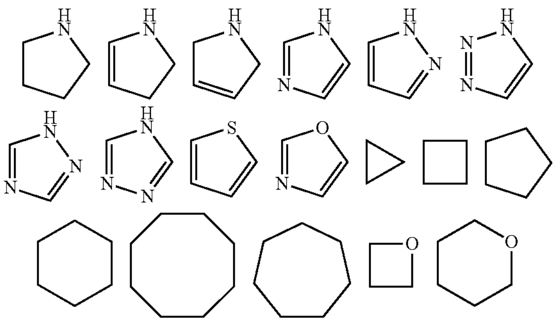

-continued

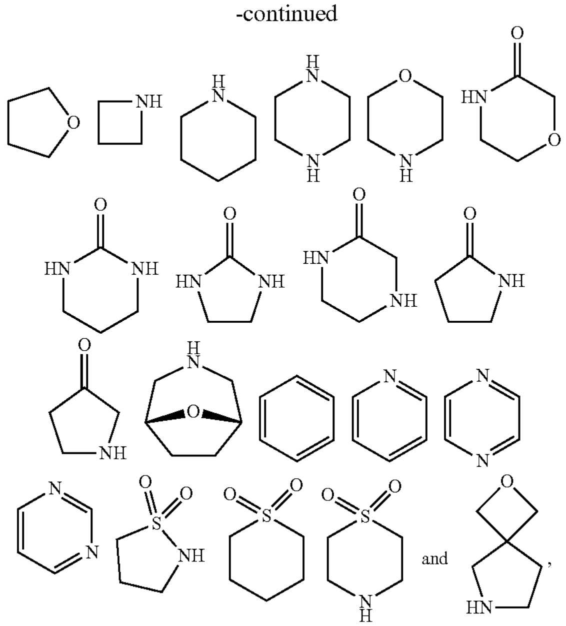

and

, wherein the 3- to 8-membered carbocyclyl or heterocyclyl group is optionally substituted with 1, 2, or 3 substituents independently selected from the group consisting of halogen, OH, a $C_1$-$C_6$ alkyl group, a hydroxy-$C_1$-$C_6$ alkyl group, a $C_1$-$C_6$ alkoxy group, a methoxy-$C_1$-$C_6$ alkyl group, an $S(O)_2—C_1$-$C_6$ alkyl group, and $NR^{14}R^{15}$.

18. The method of claim 1, wherein Y is hydrogen and X is a 3- to 8-membered carbocyclyl or heterocyclyl group selected from the group consisting of

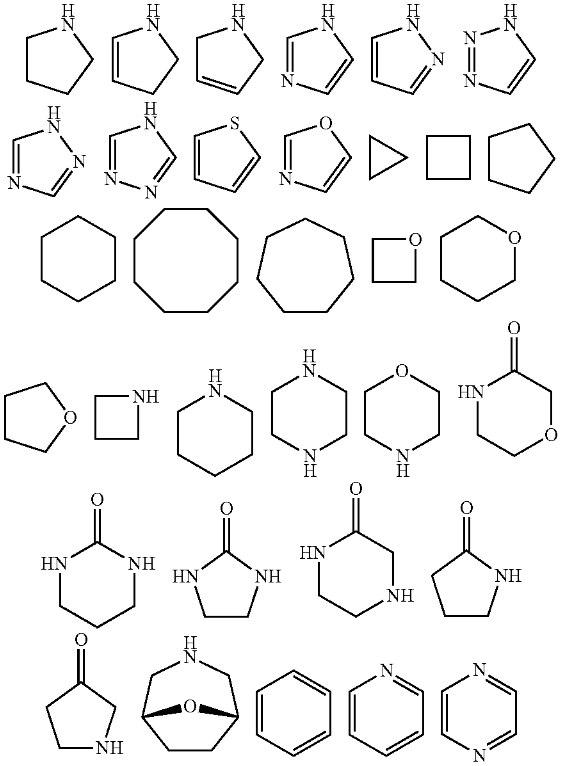

-continued

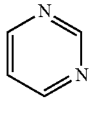 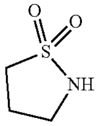 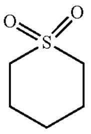 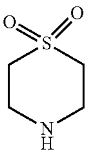 and 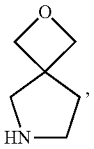, wherein the 3- to 8-membered carbocyclyl or heterocyclyl group is optionally substituted with 1, 2, or 3 substituents independently selected from the group consisting of halogen, OH, a $C_1$-$C_6$ alkyl group, a hydroxy-$C_1$-$C_6$ alkyl group, a $C_1$-$C_6$ alkoxy group, a methoxy-$C_1$-$C_6$ alkyl group, an $S(O)_2$—$C_1$-$C_6$ alkyl group, and $NR^{14}R^{15}$.

19. The method of claim 1, wherein Y is hydrogen and X is a bond.

20. The method of claim 1, further comprising administering at least one additional therapy.

21. A method for treating a subject having a neoplastic disorder or a subject suspected of having a neoplastic disorder, wherein the method comprises administering to the subject in need thereof a therapeutically effective amount of at least one compound of selected from the group consisting of:

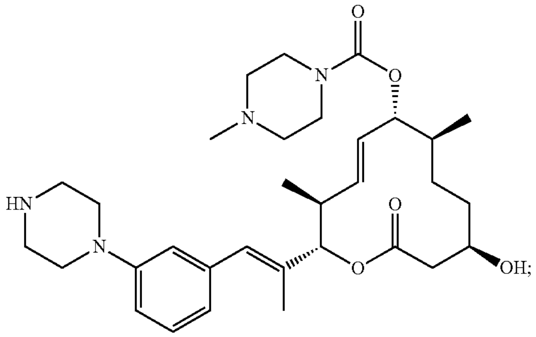;

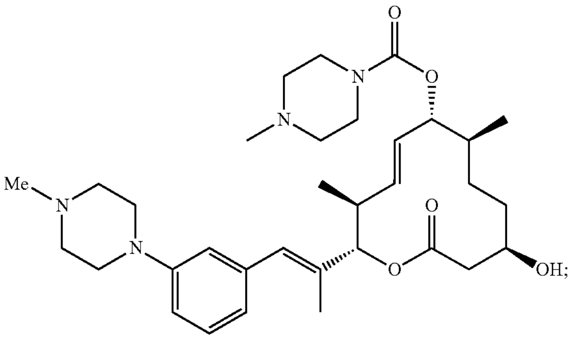;

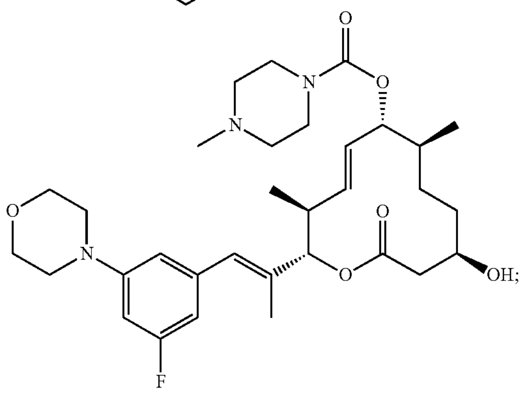;

-continued

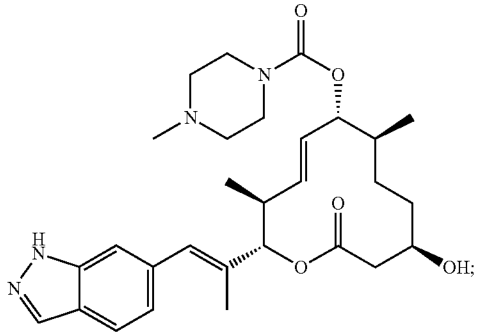;

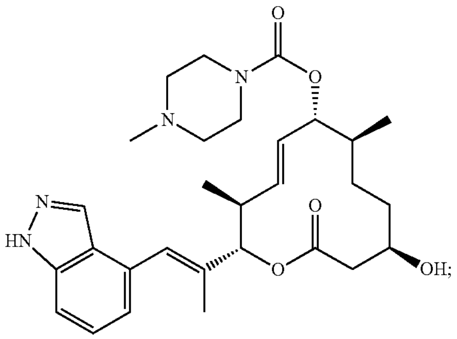;

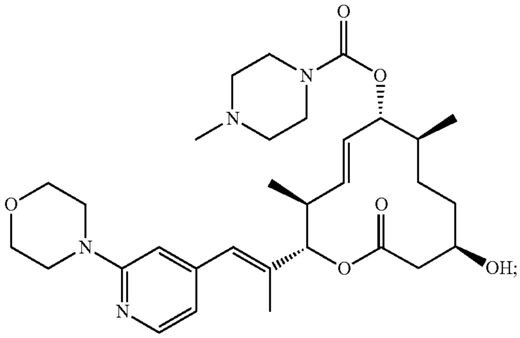;

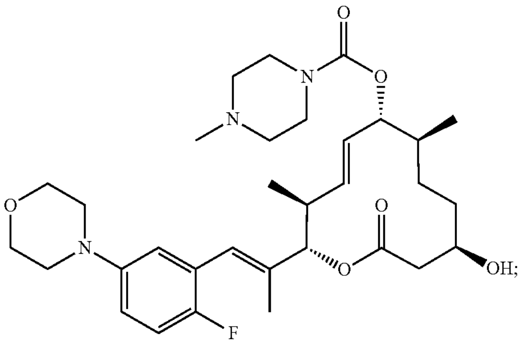;

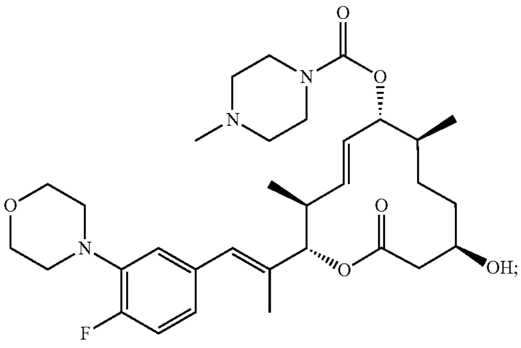;

-continued
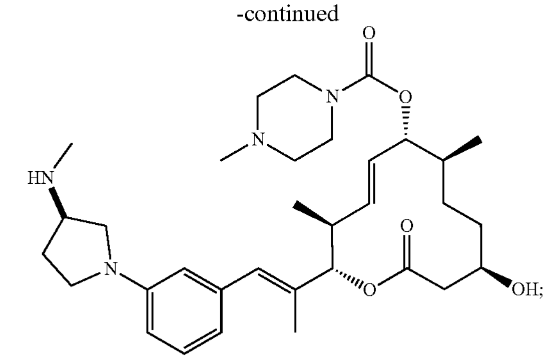
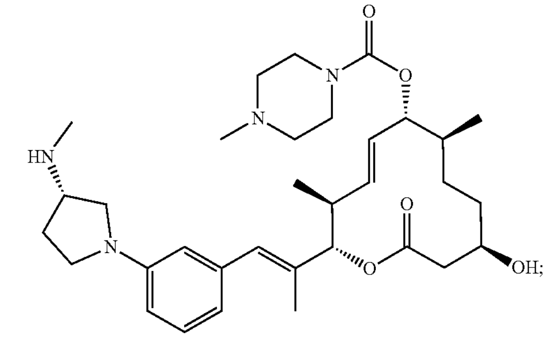
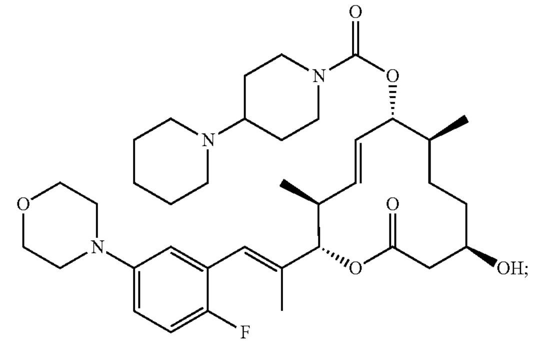
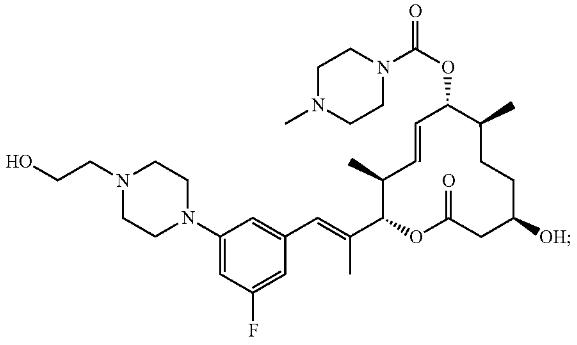
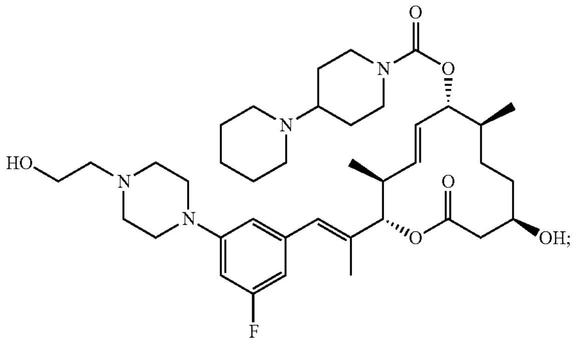
-continued
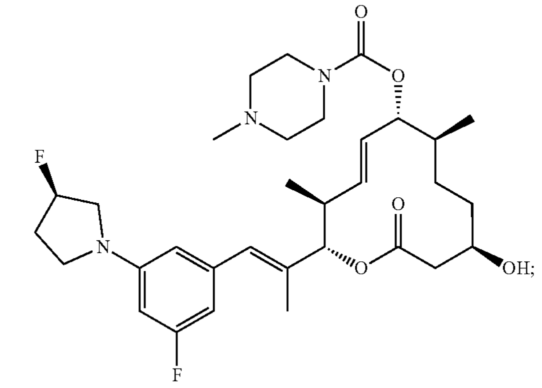
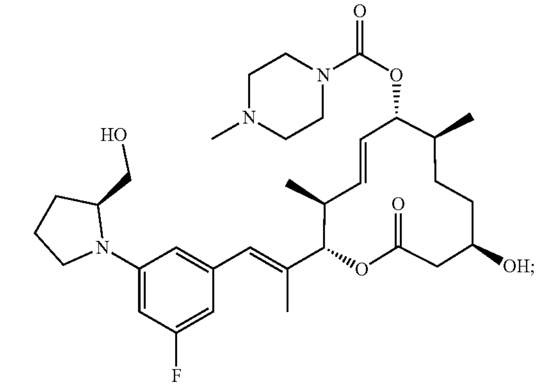
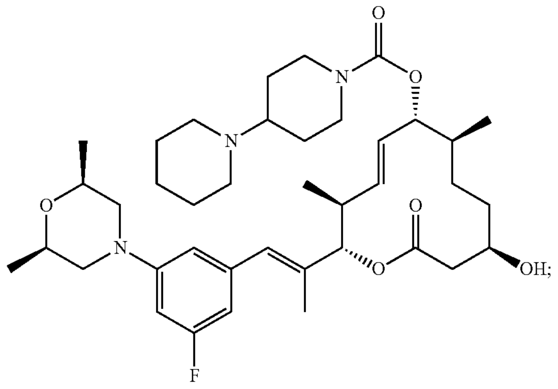
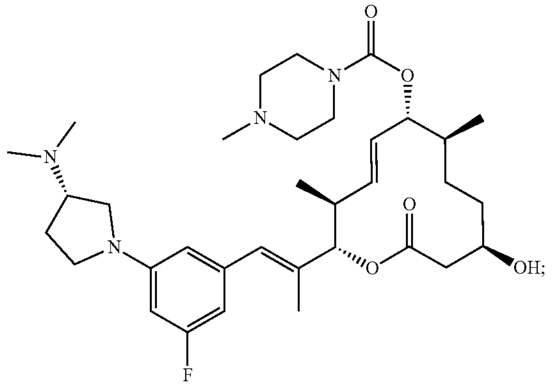

-continued
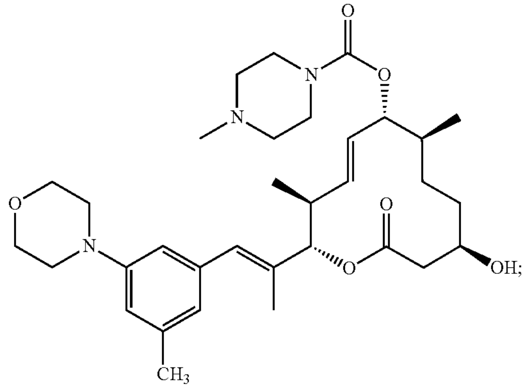
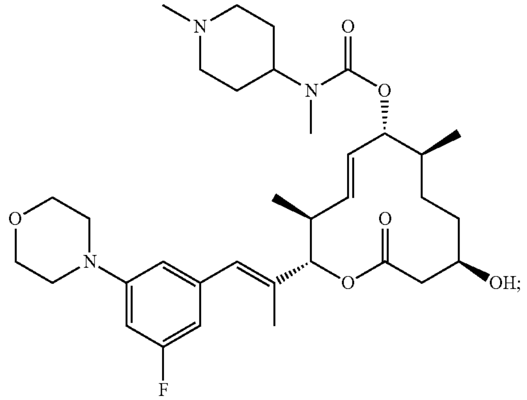
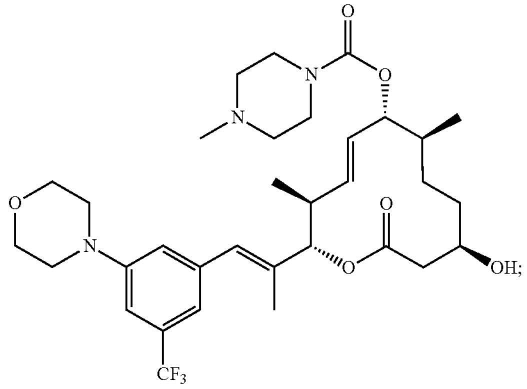
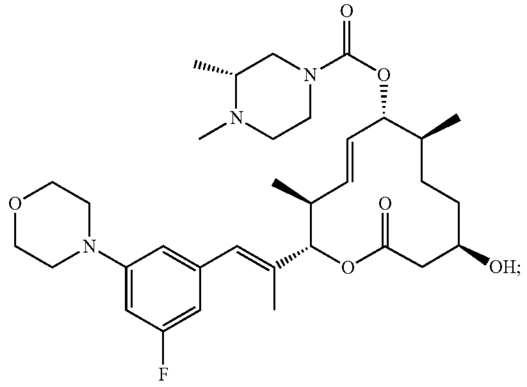
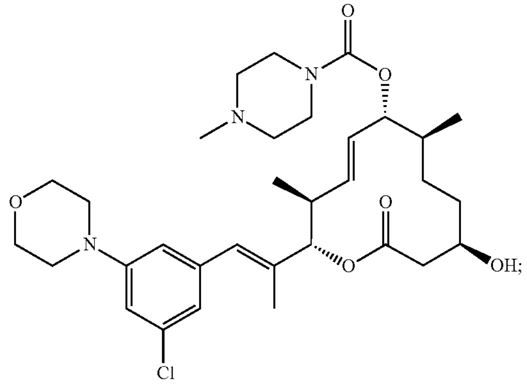
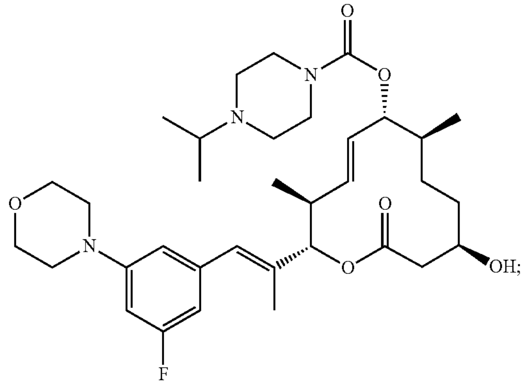
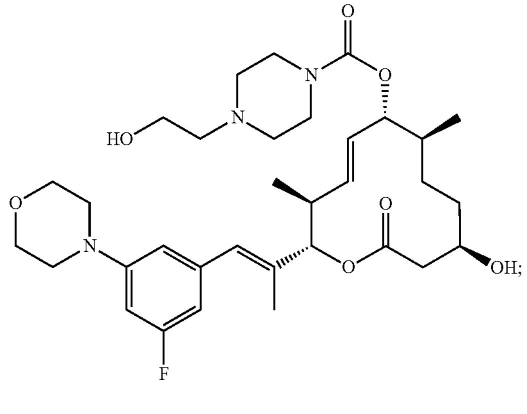
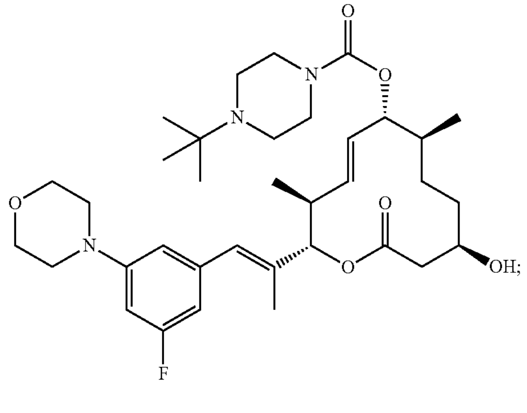

-continued
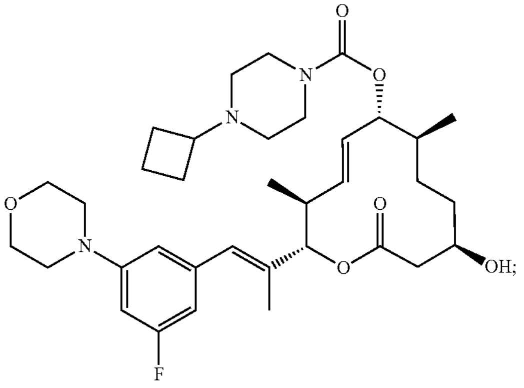
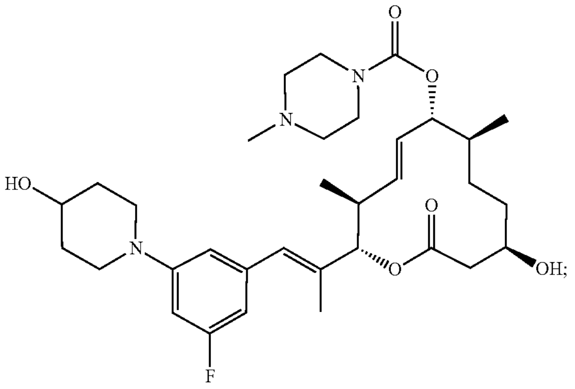
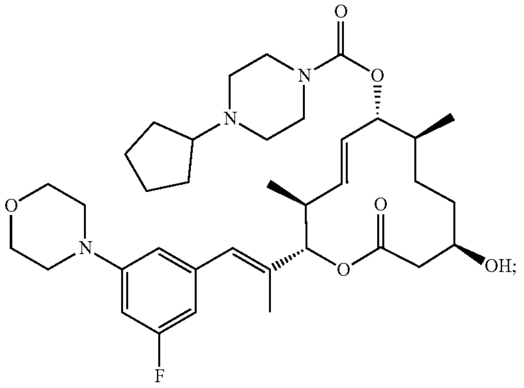
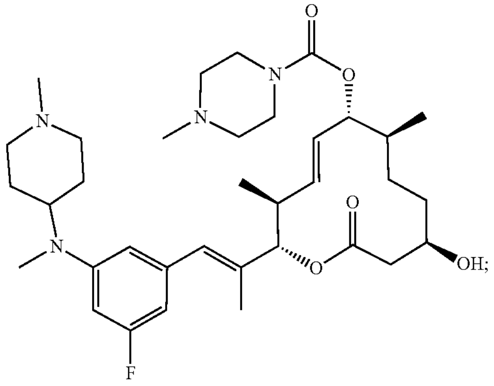
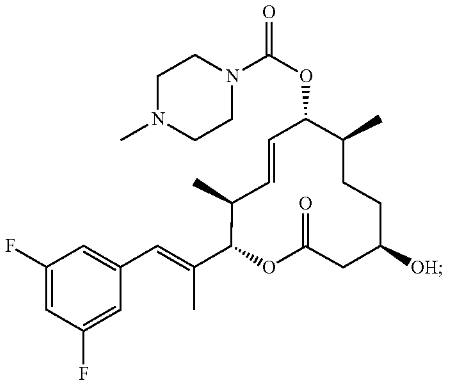
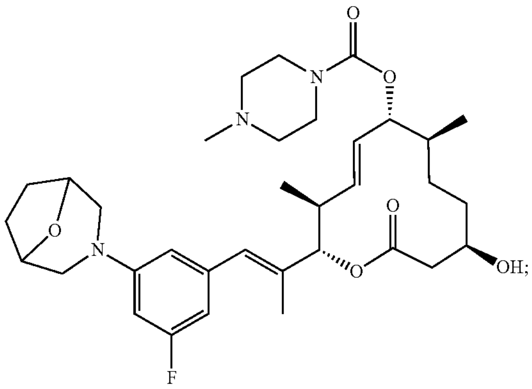
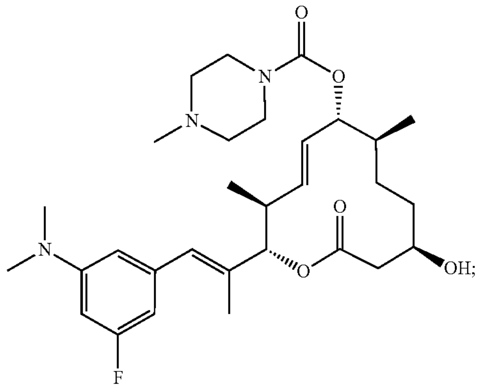
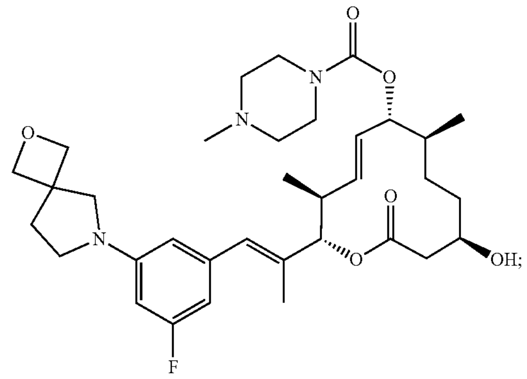

-continued
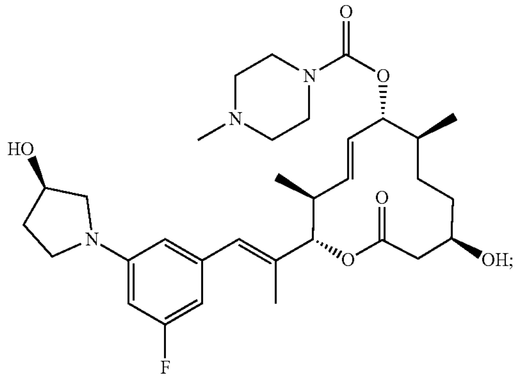
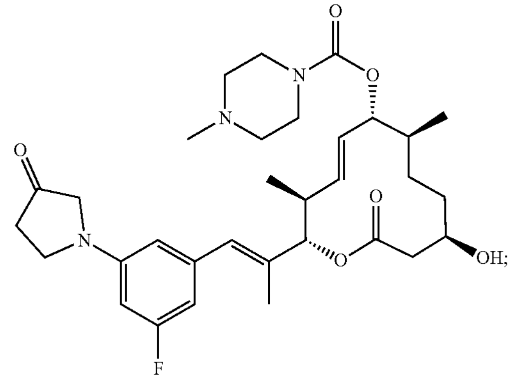
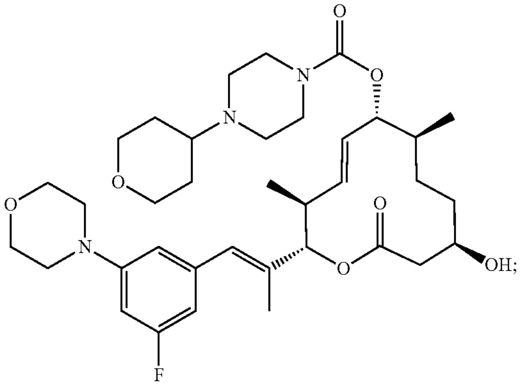
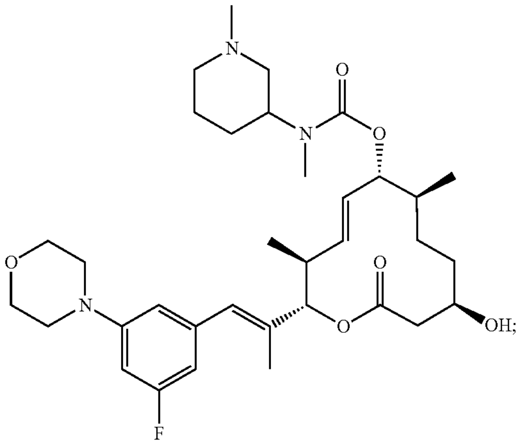
-continued
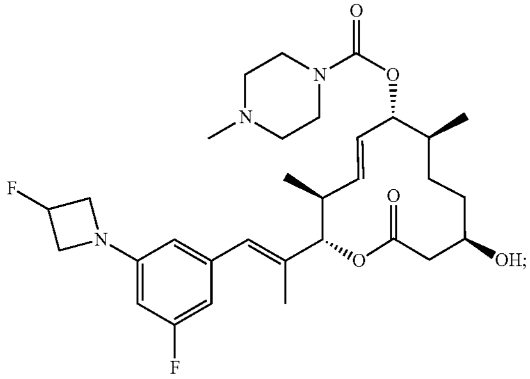
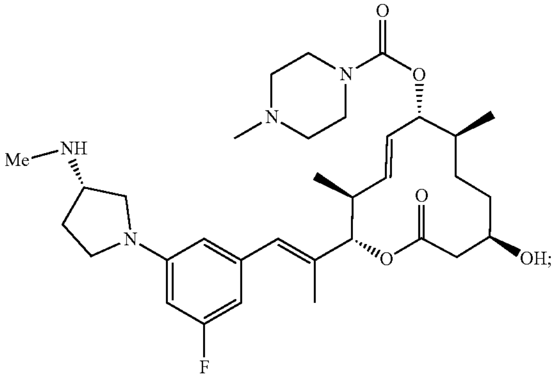
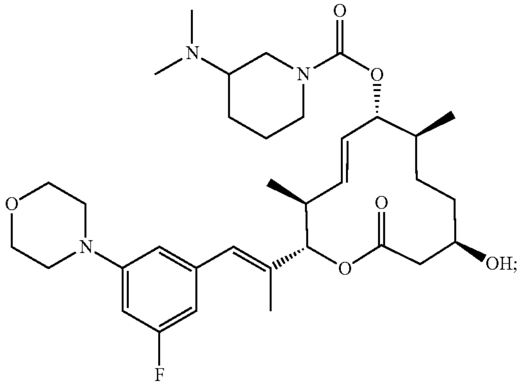
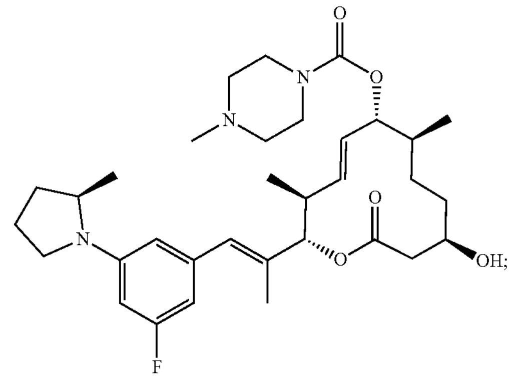

-continued
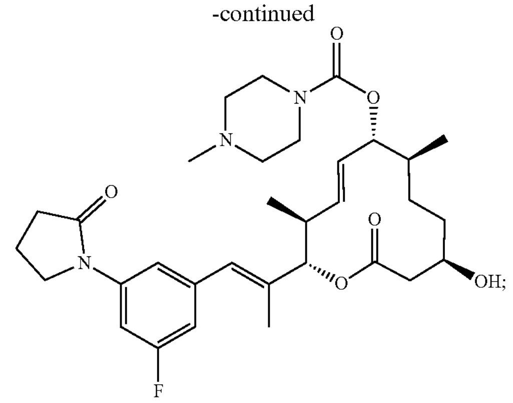
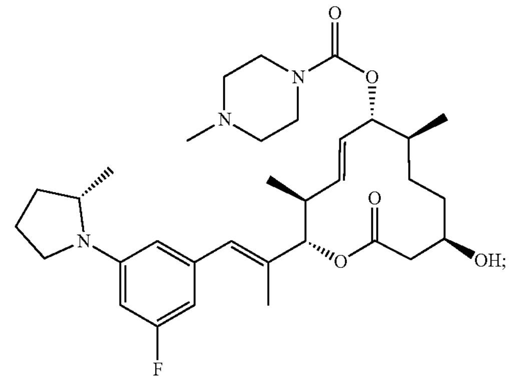
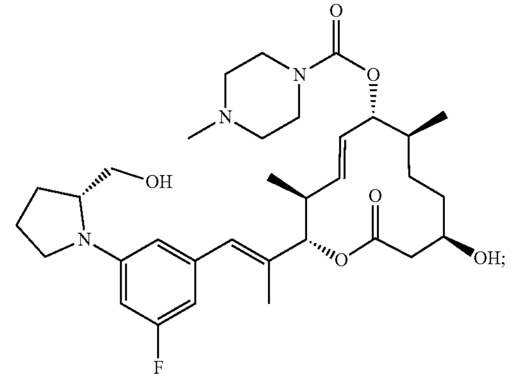
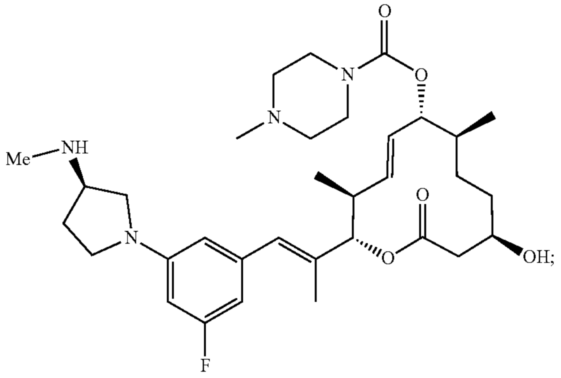
-continued
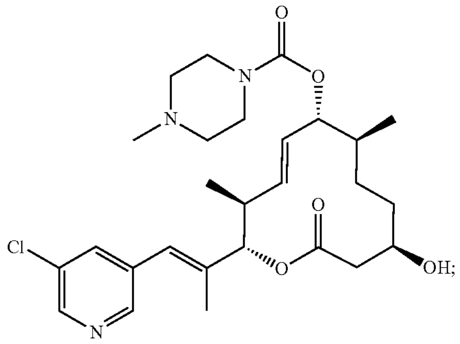
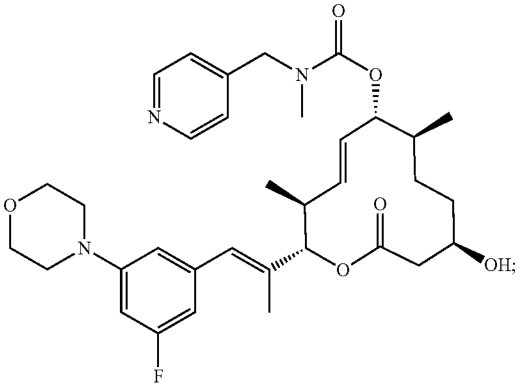
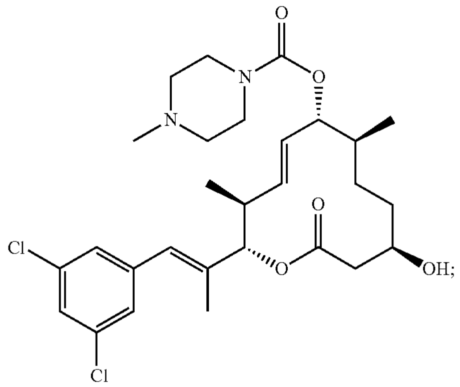
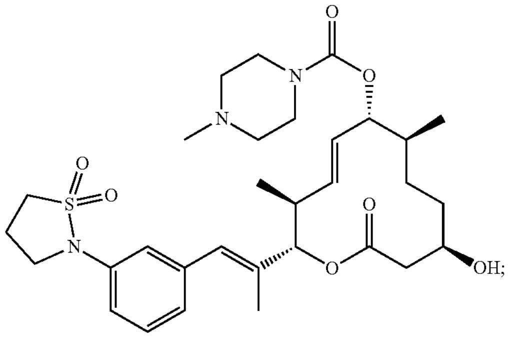

-continued
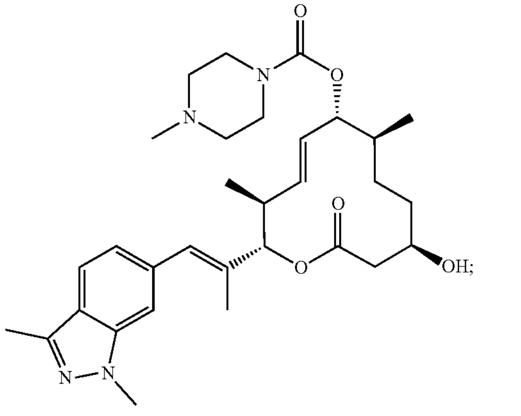
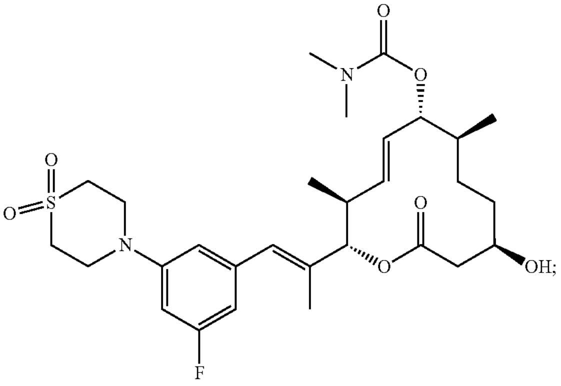
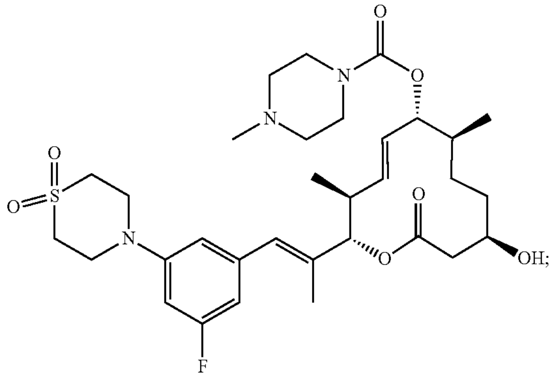
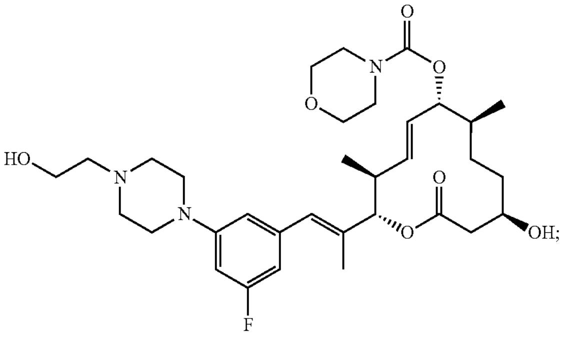
-continued
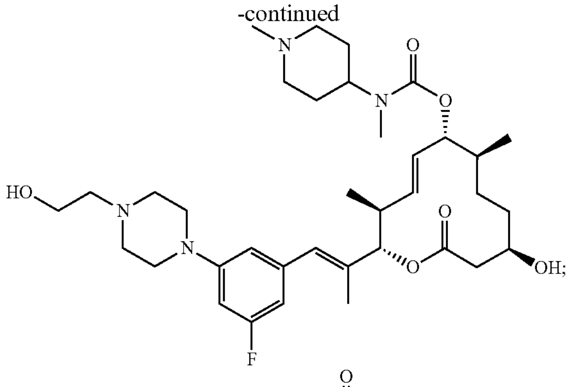
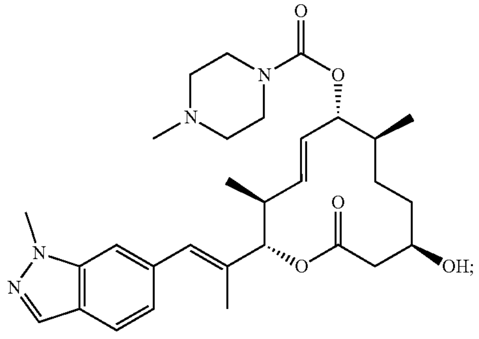
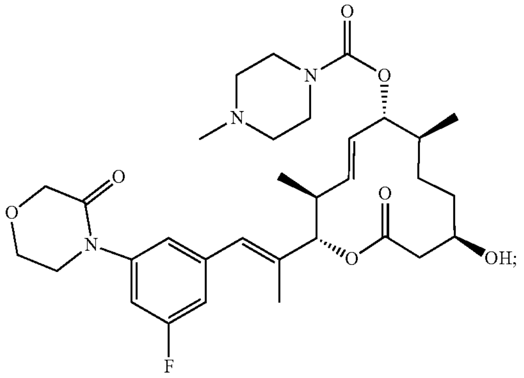
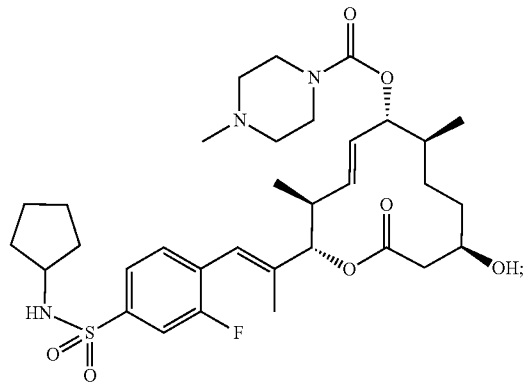

-continued
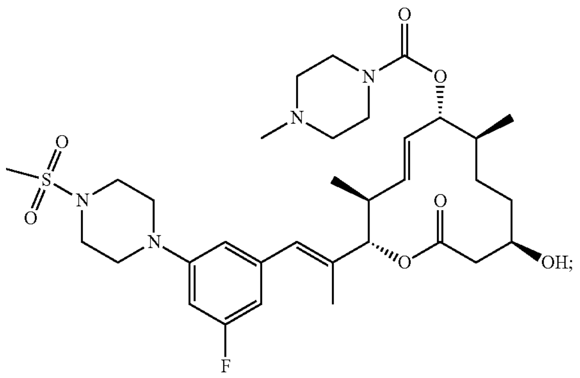
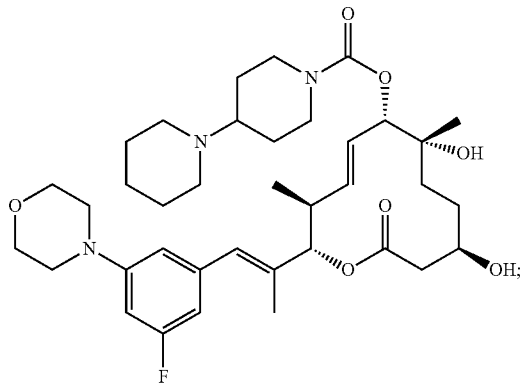
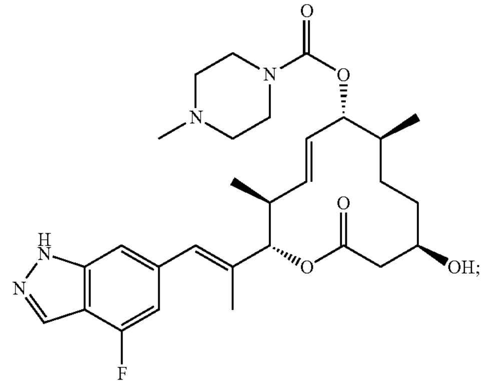
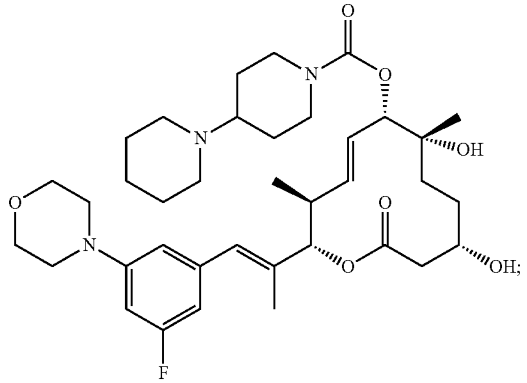
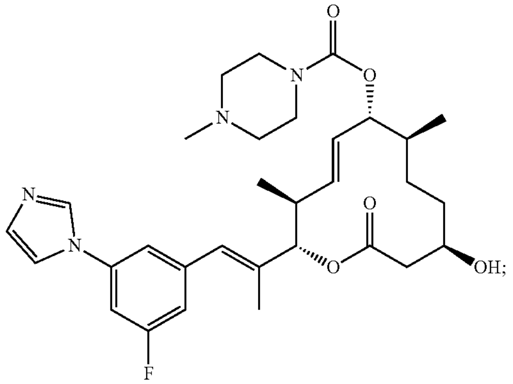
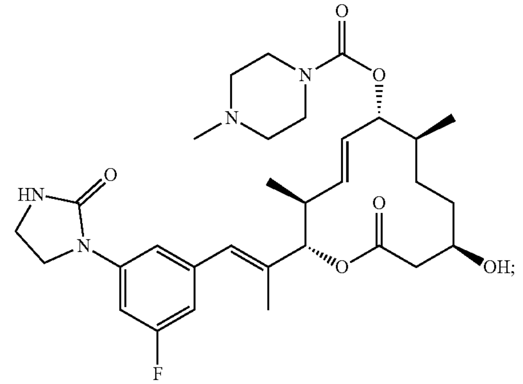
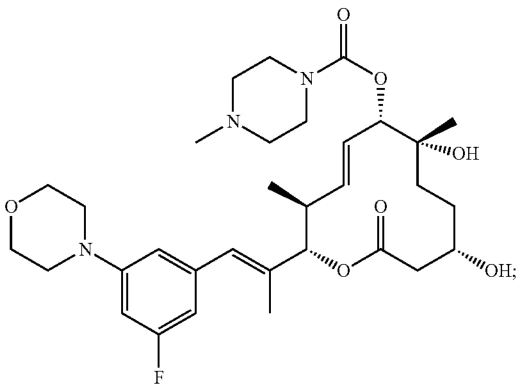
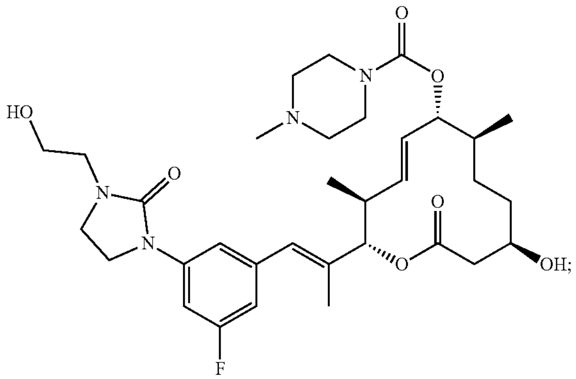

-continued
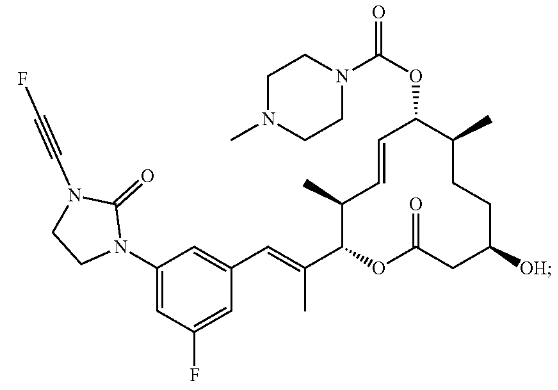
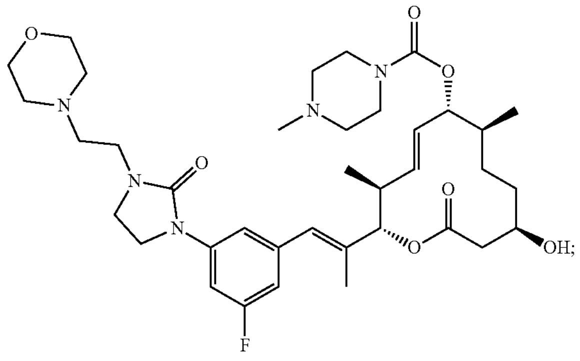
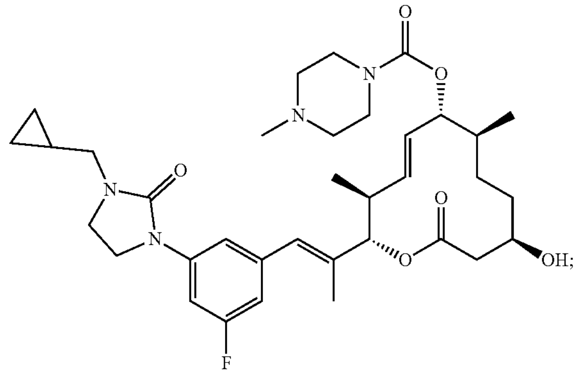
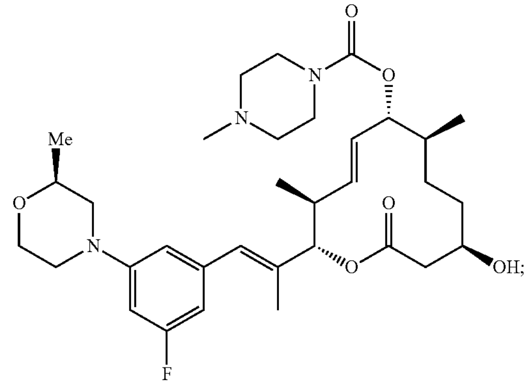
-continued
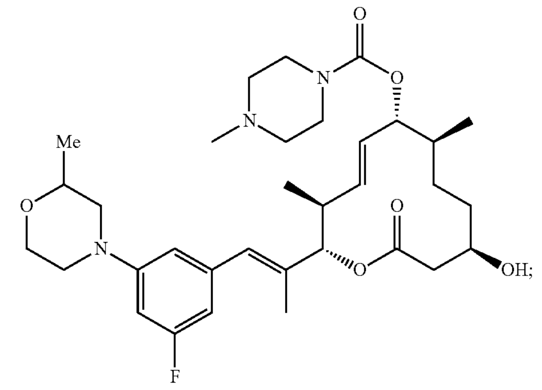
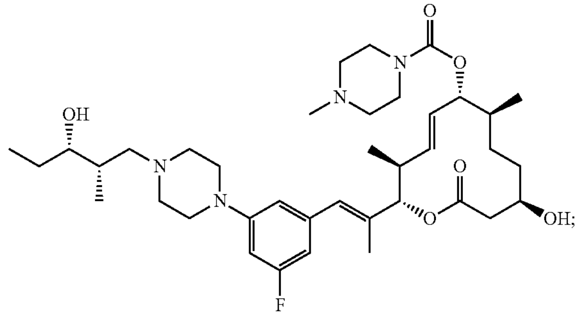
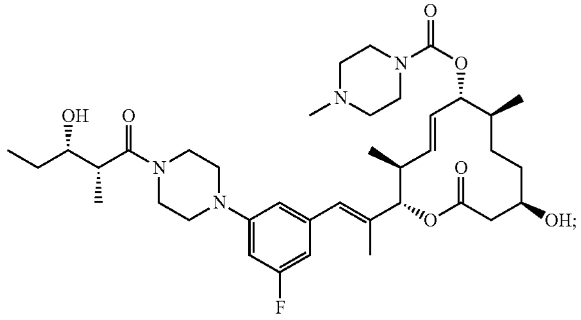
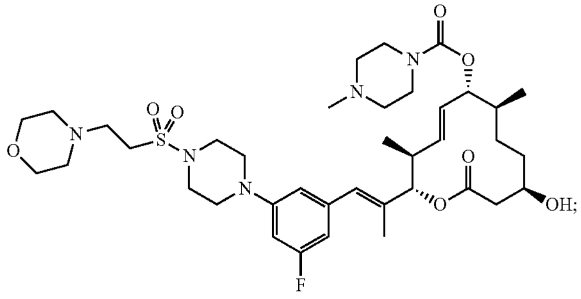
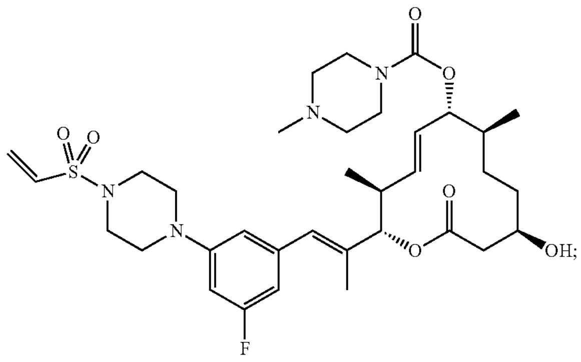

-continued
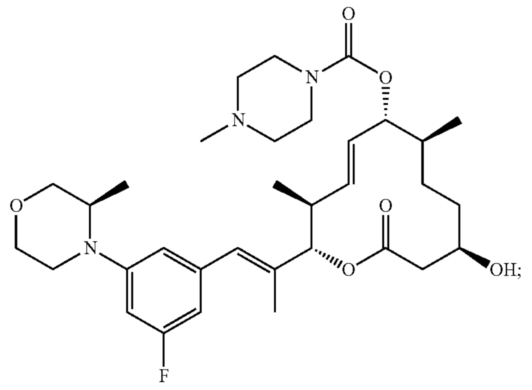
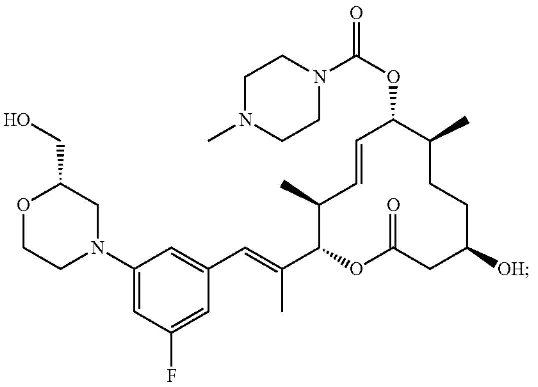
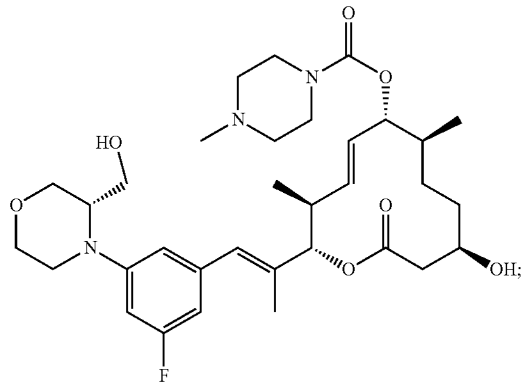
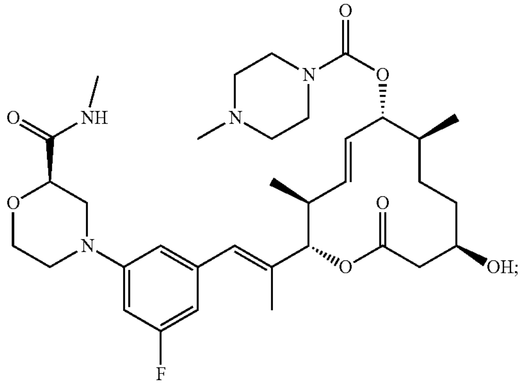
-continued
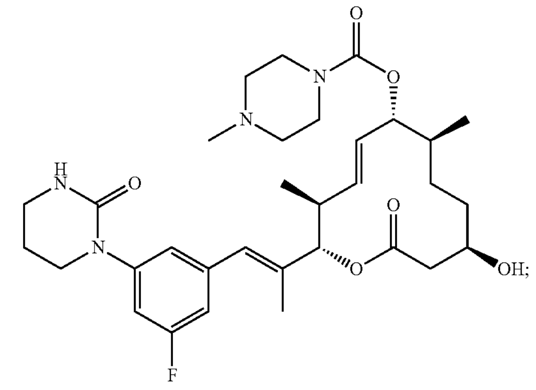
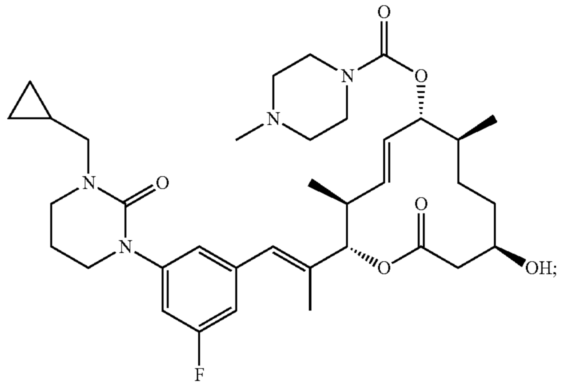
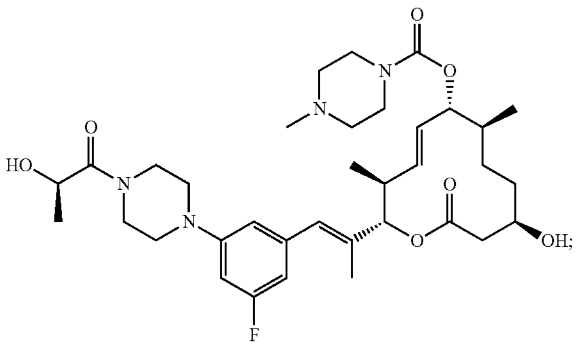
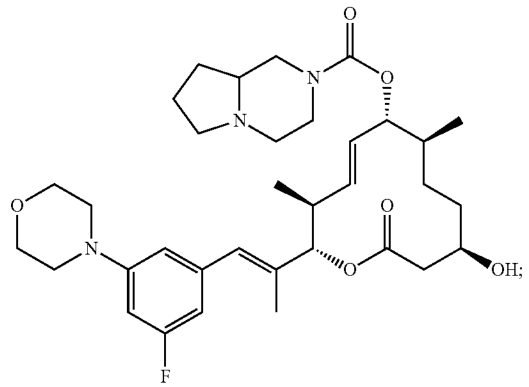

-continued
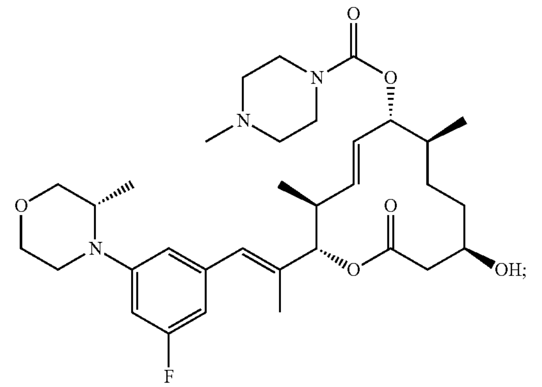
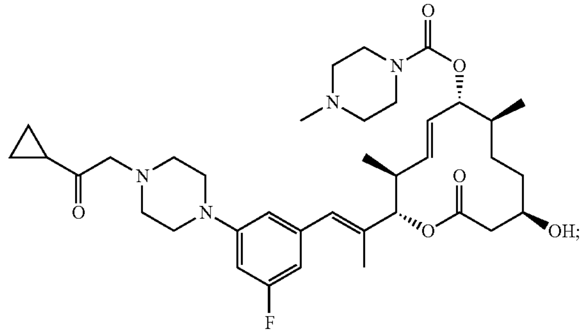
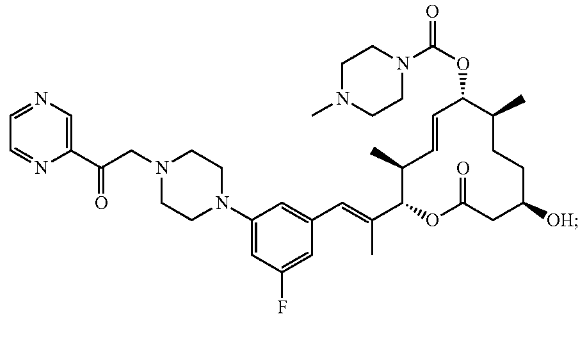
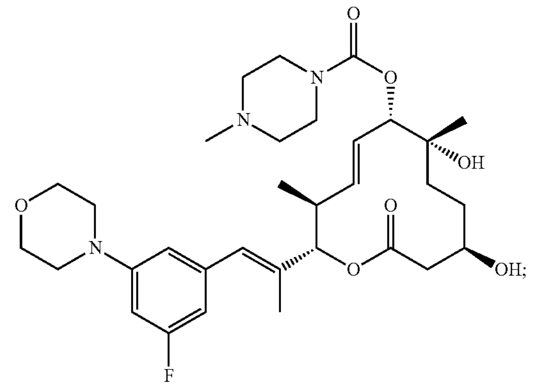
-continued
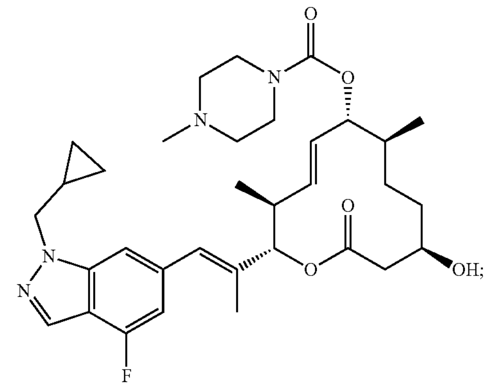
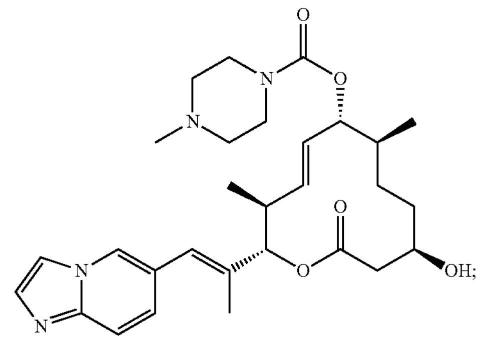
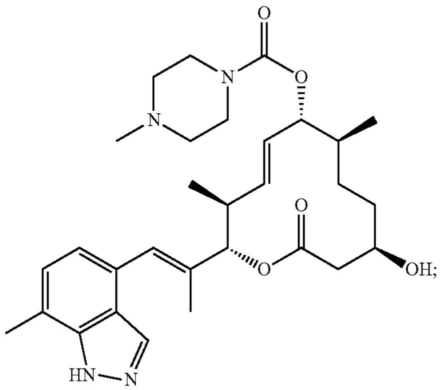
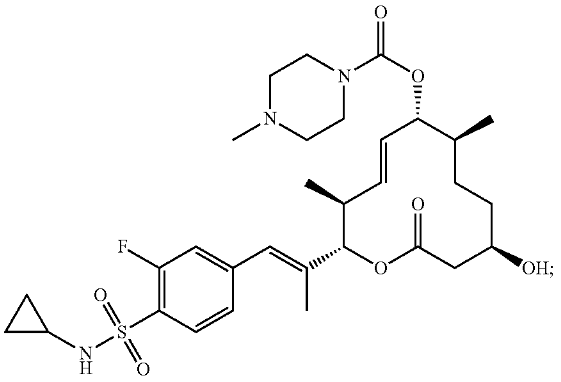

-continued
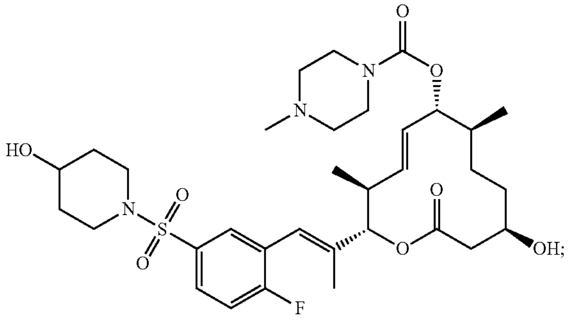
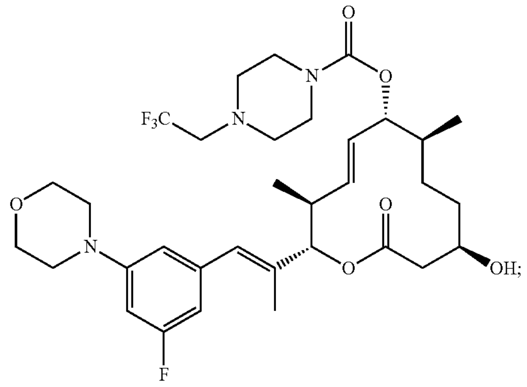
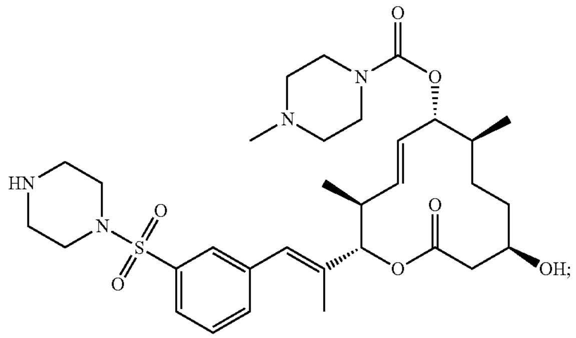
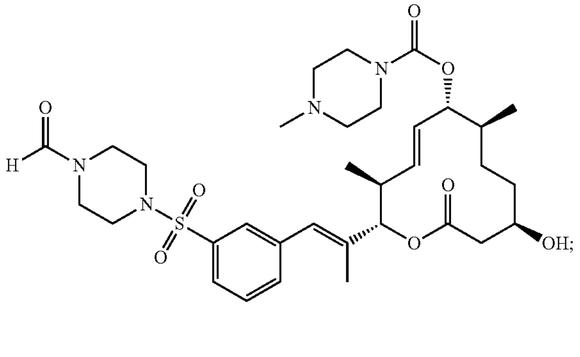
-continued
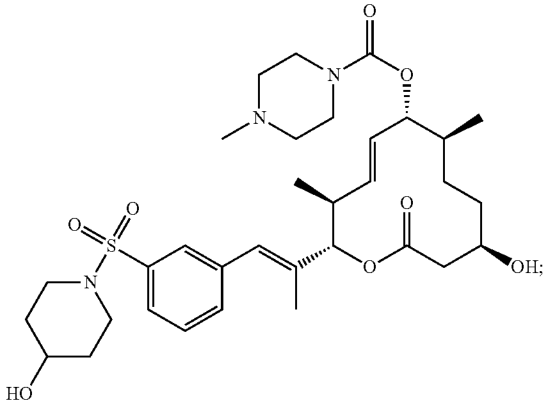
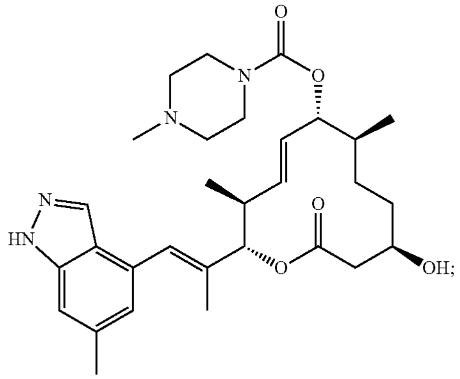
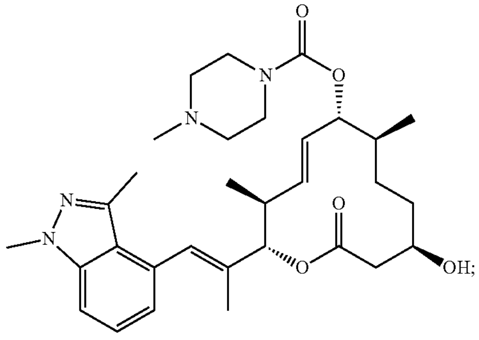
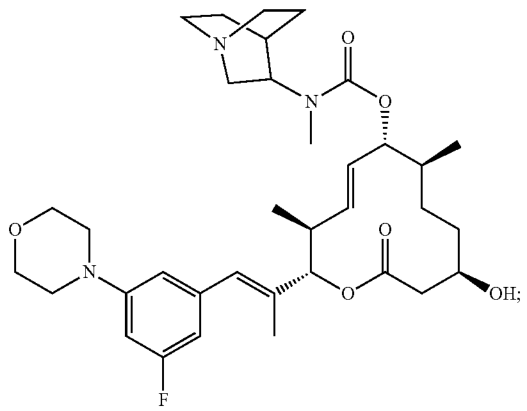

-continued
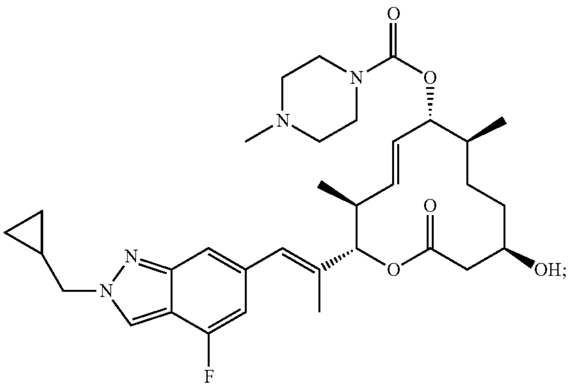
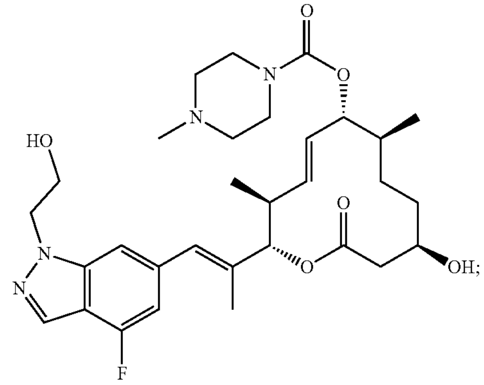
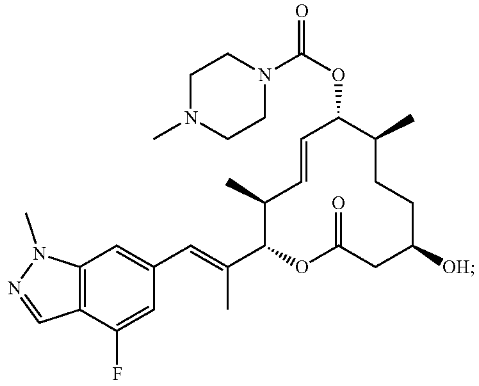
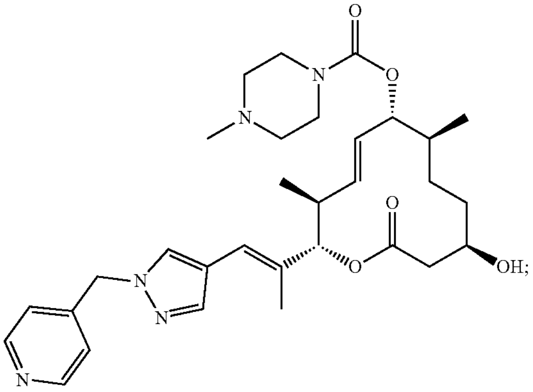
-continued
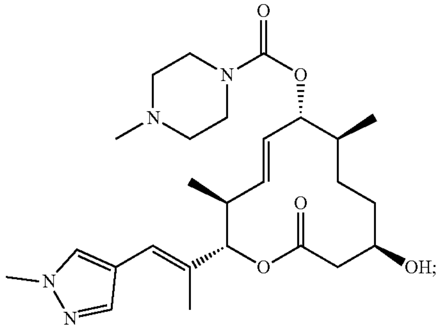
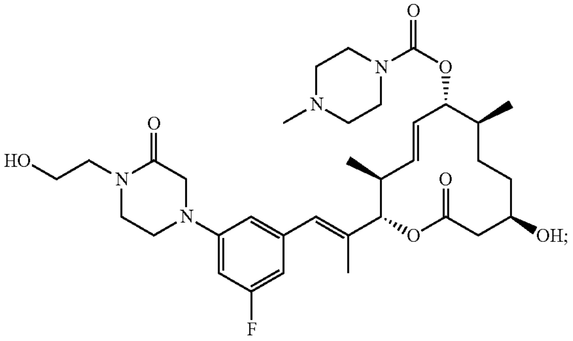
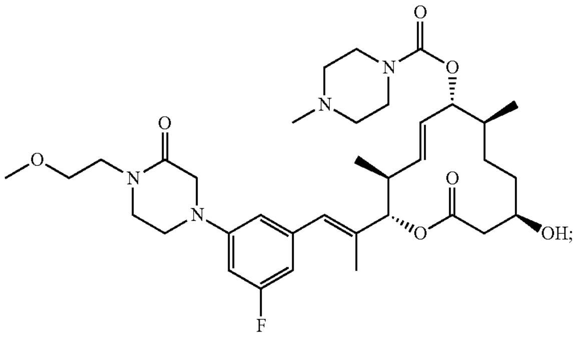
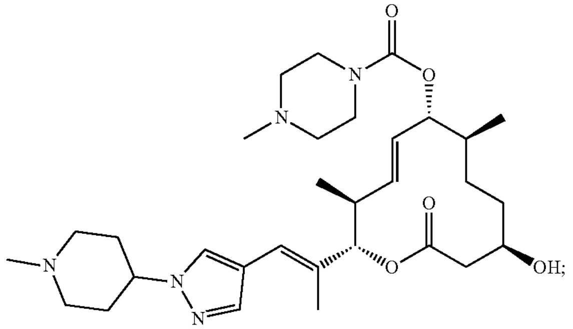
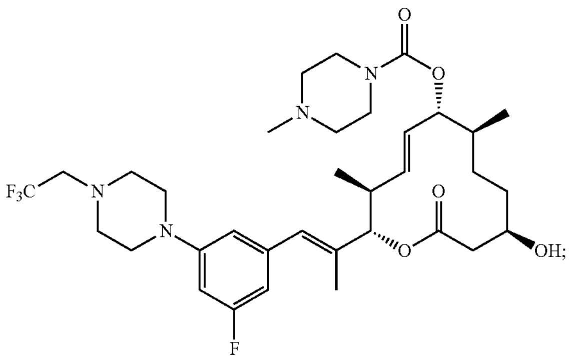

-continued
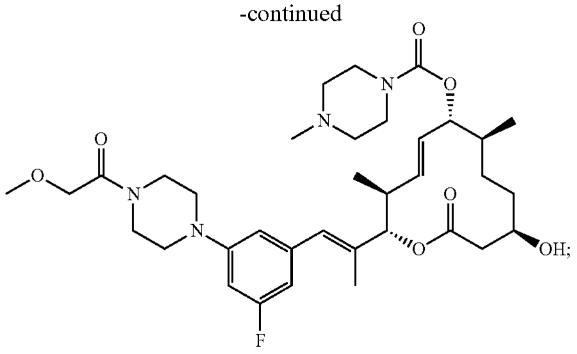
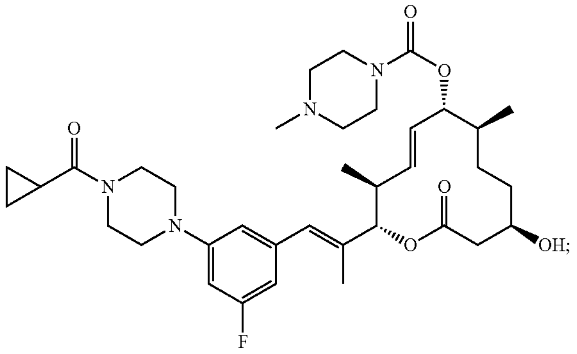
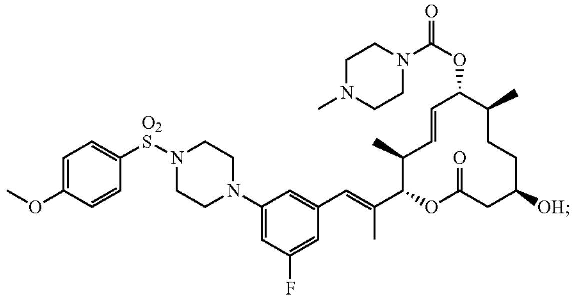
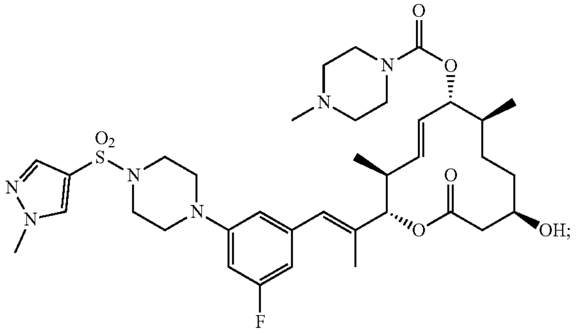
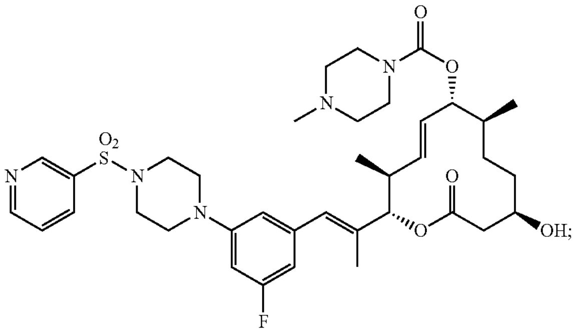
-continued
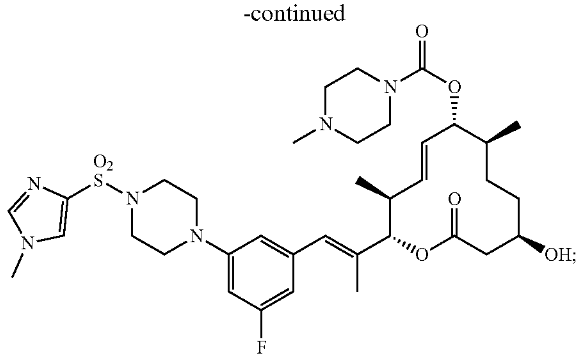
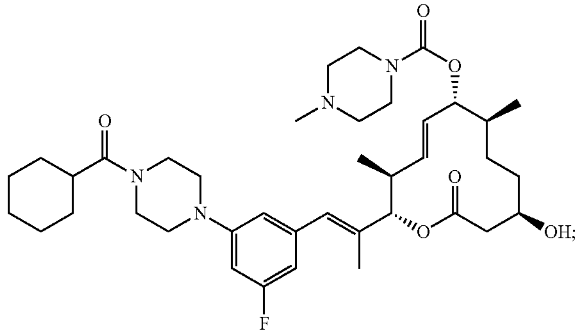
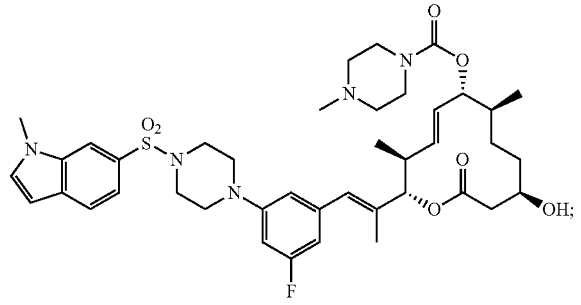
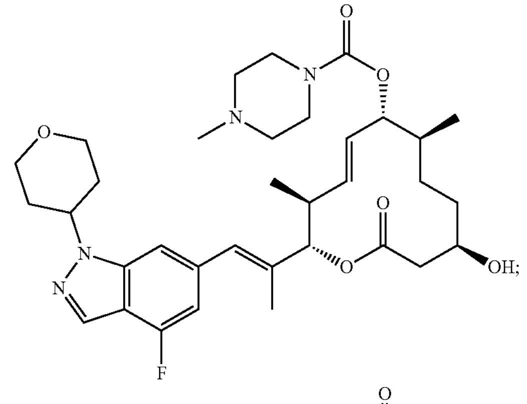
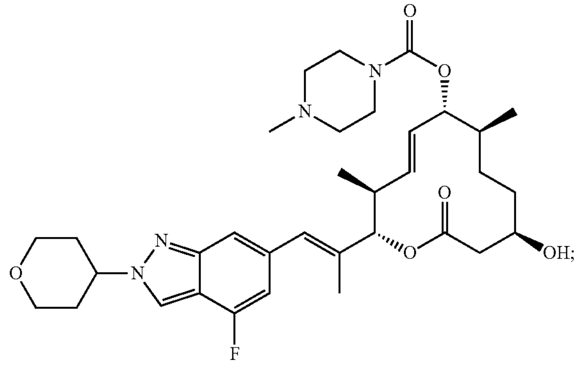

-continued
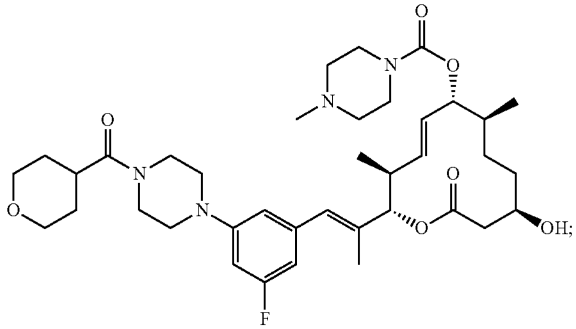
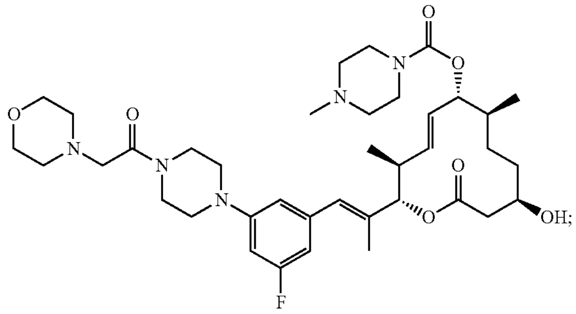
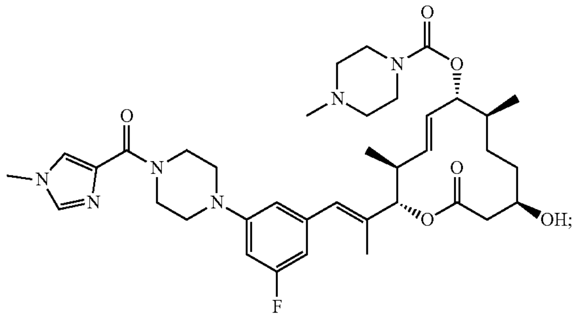
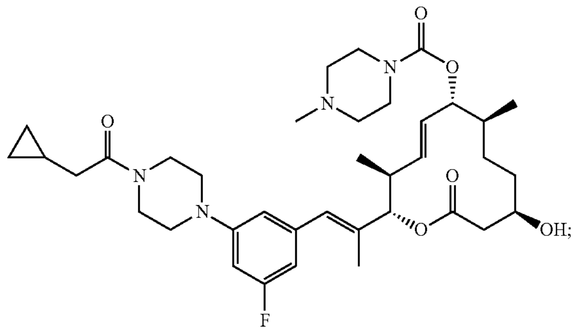
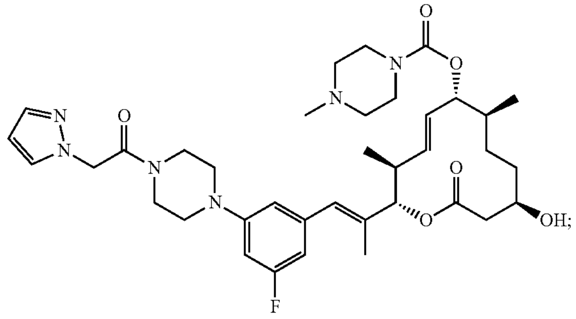
-continued
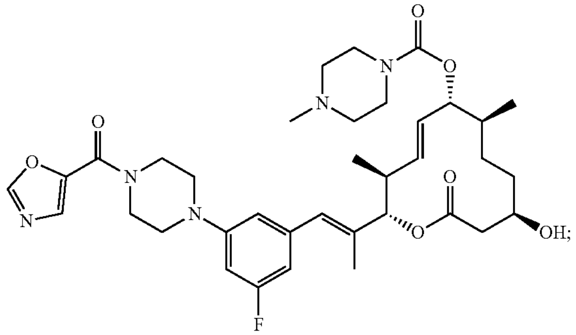
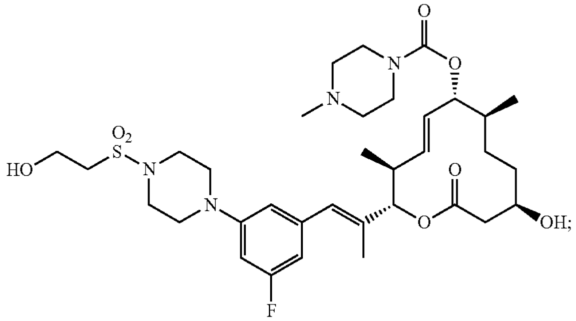
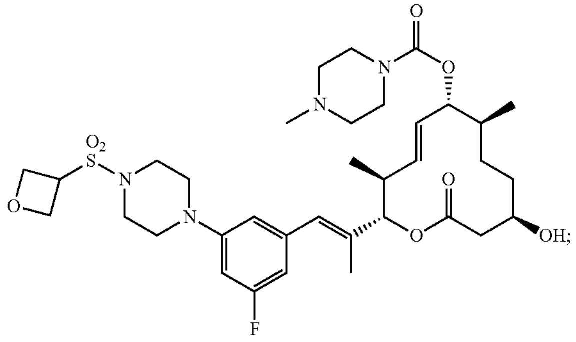
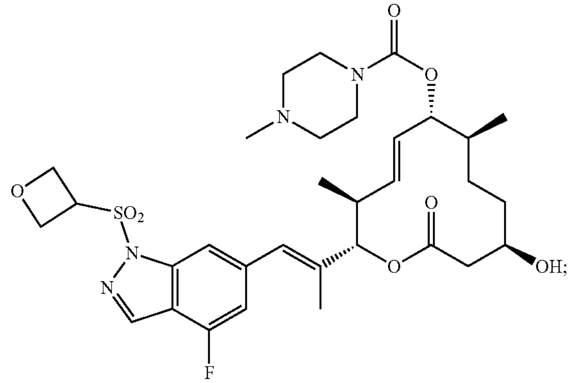
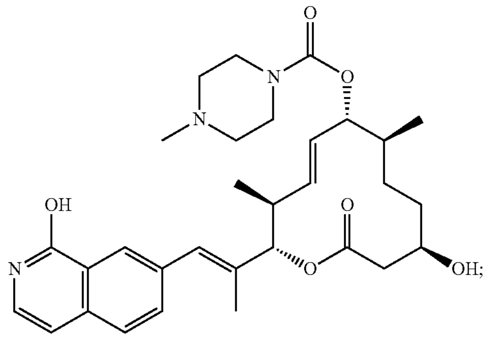

-continued
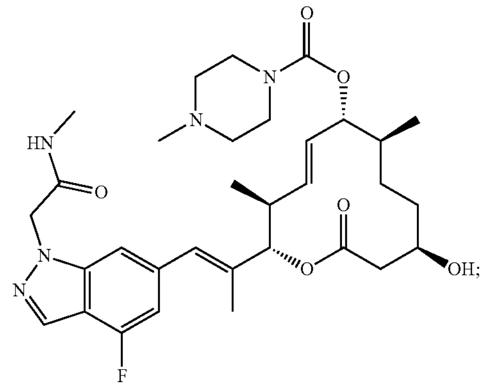
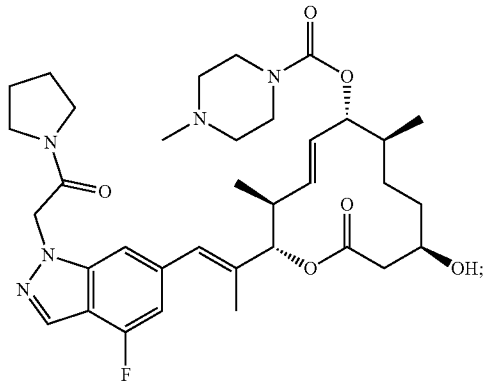
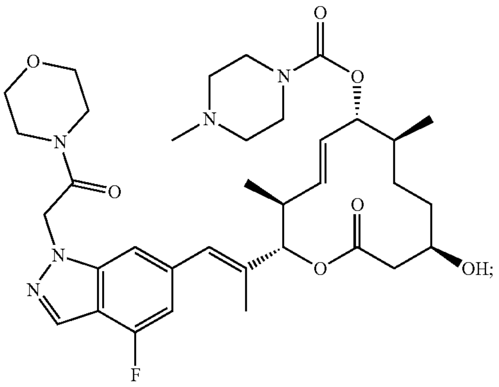
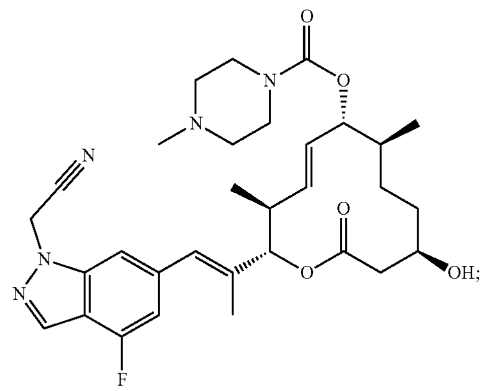
-continued
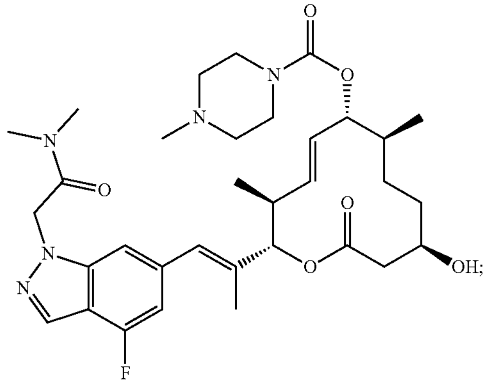
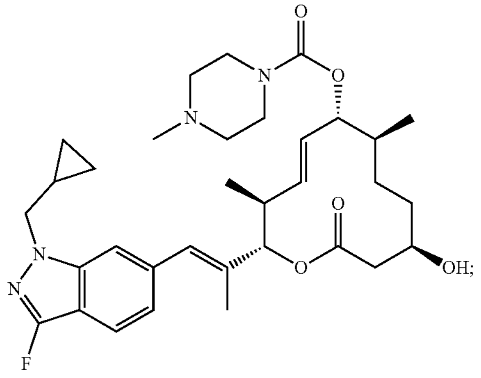
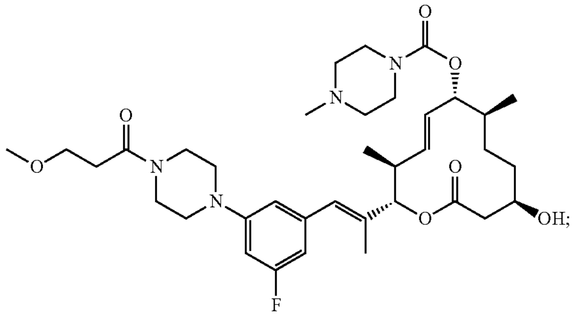
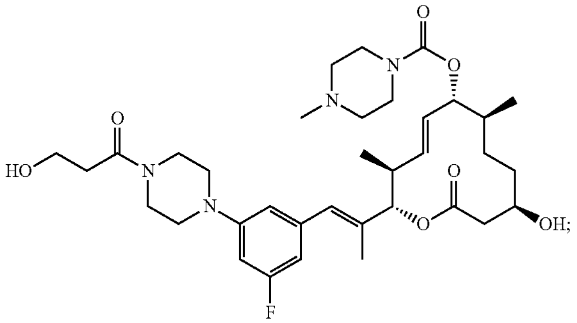
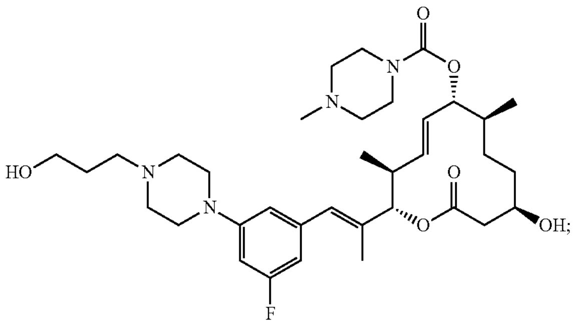

-continued
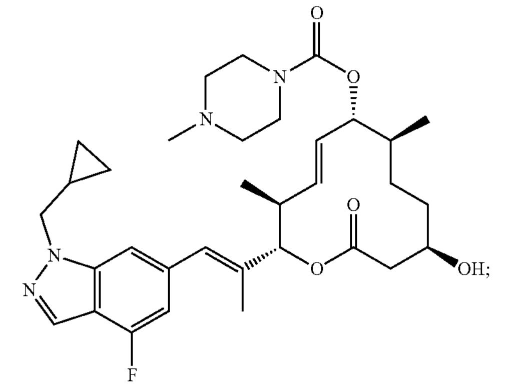
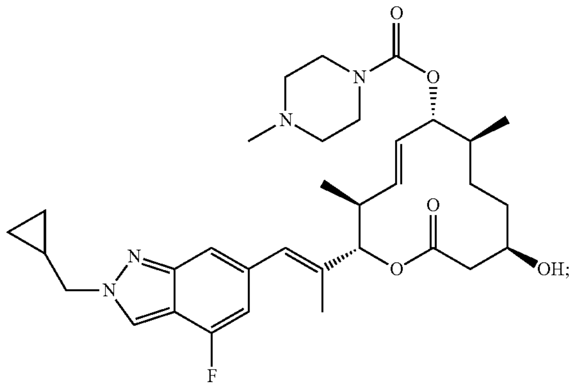
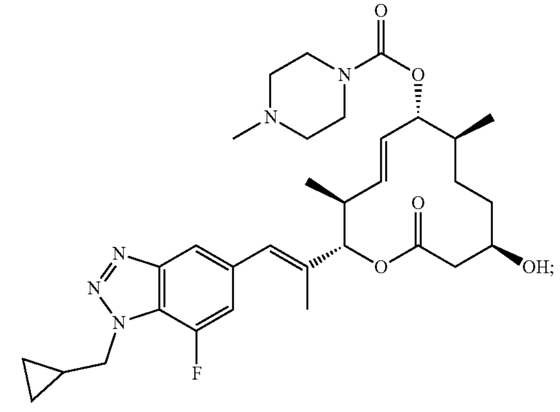
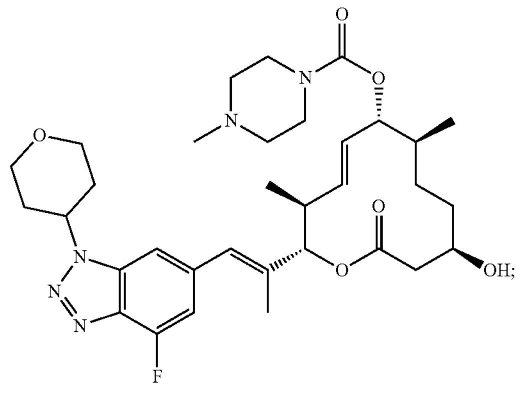
-continued
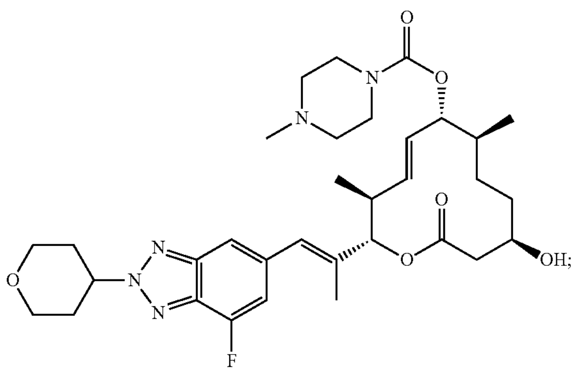
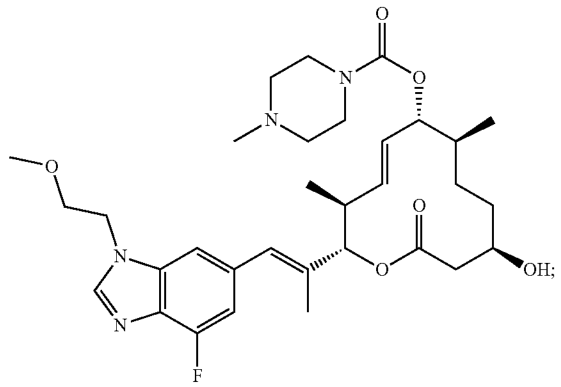
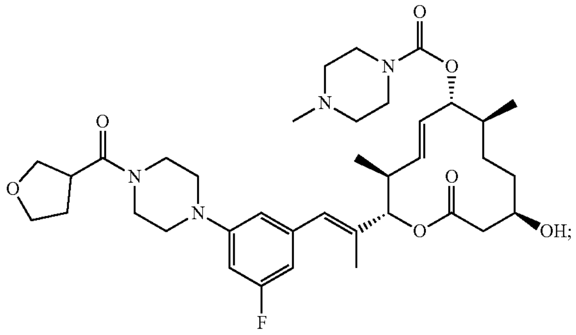
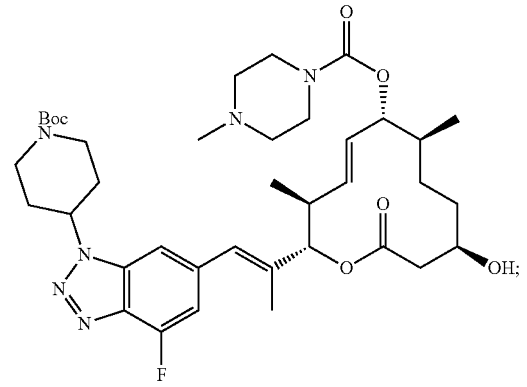

-continued
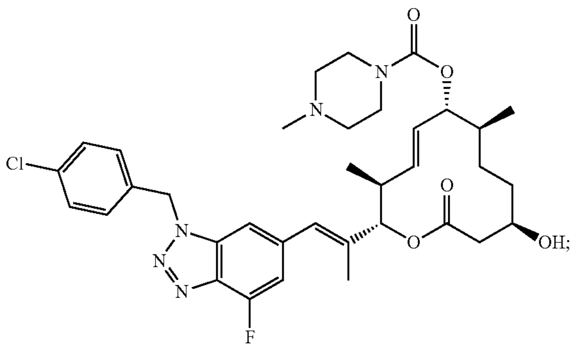
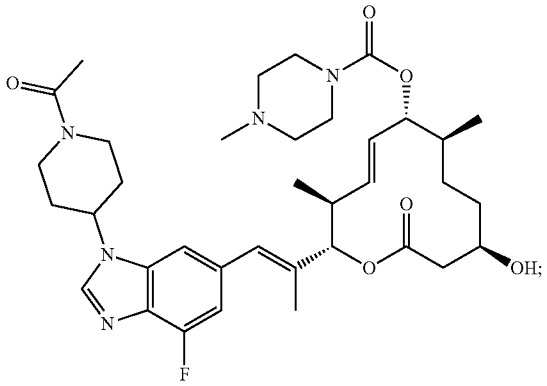
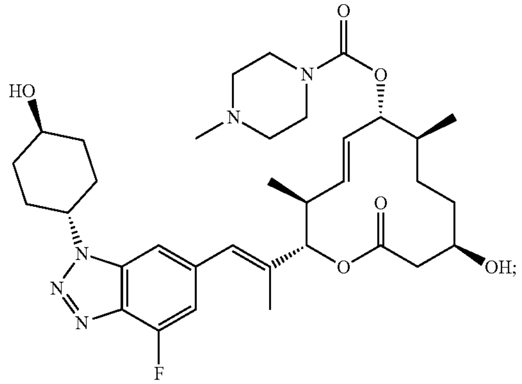
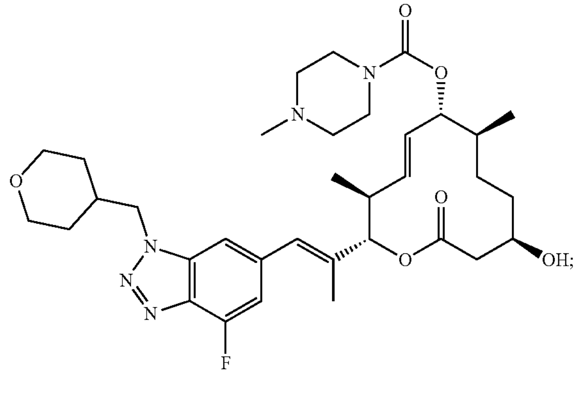
-continued
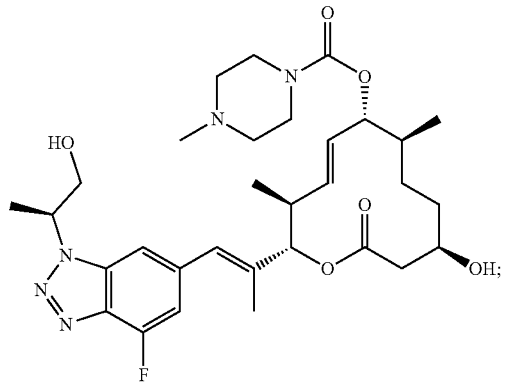
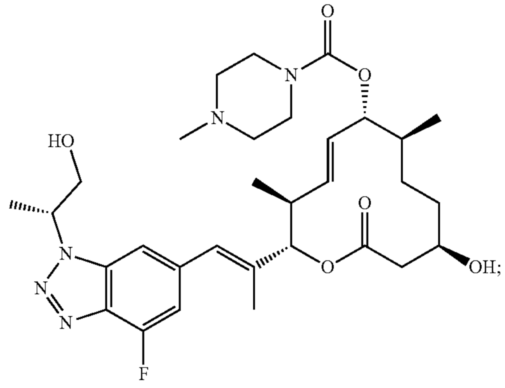
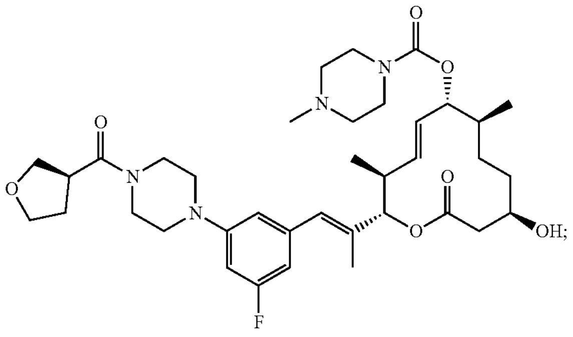
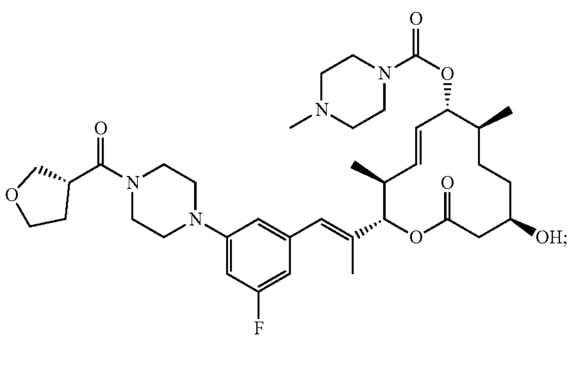

-continued
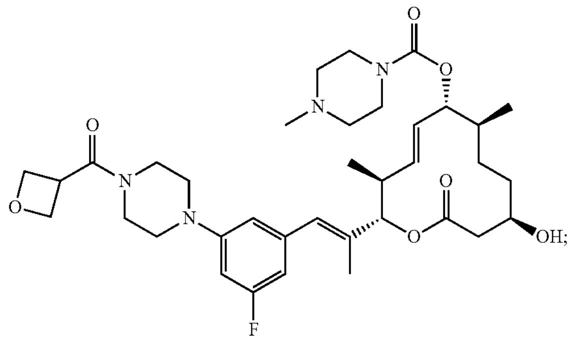
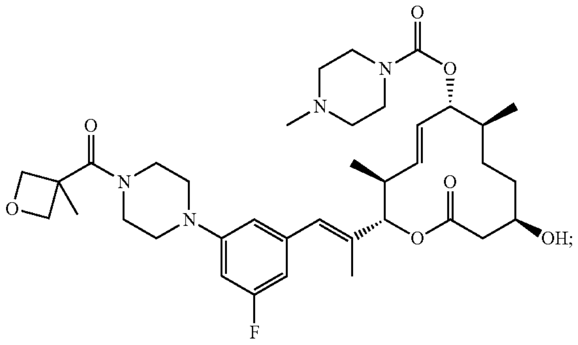
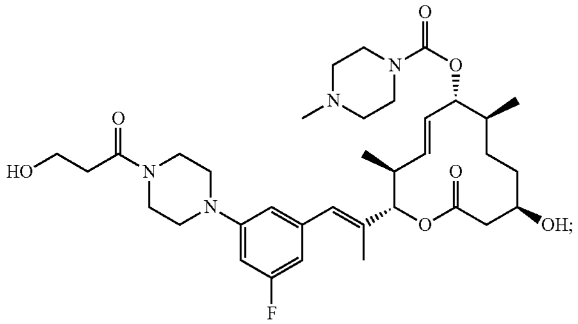
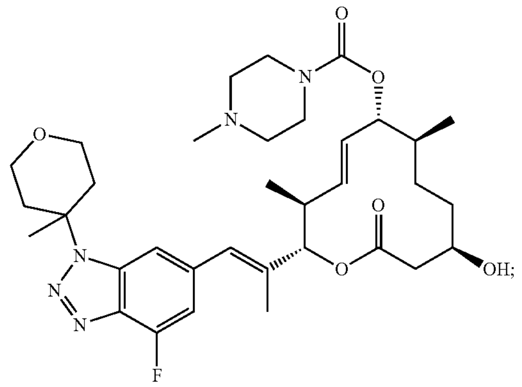
-continued
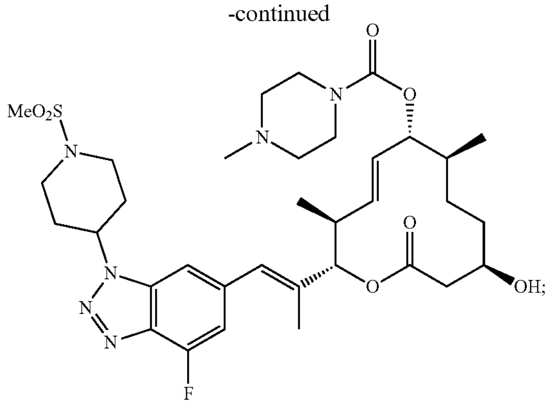
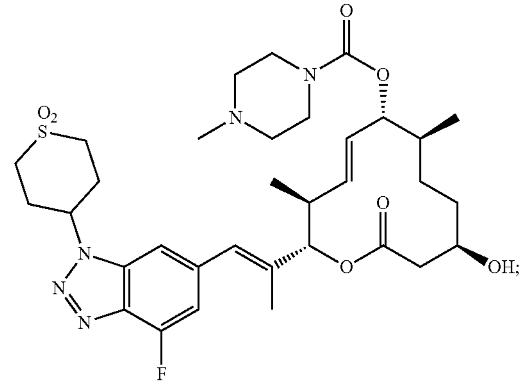
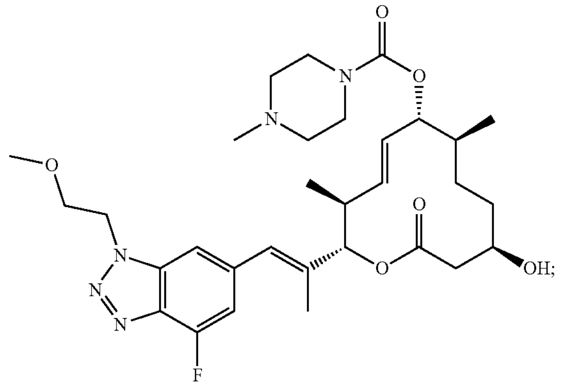
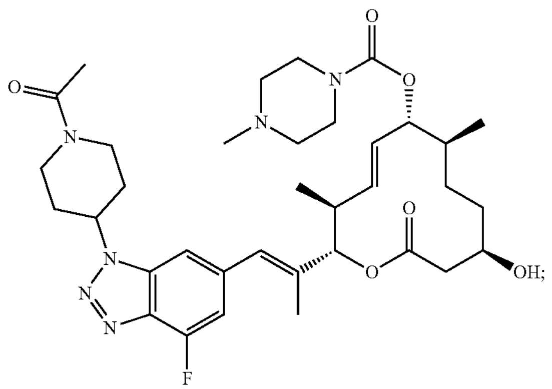

-continued
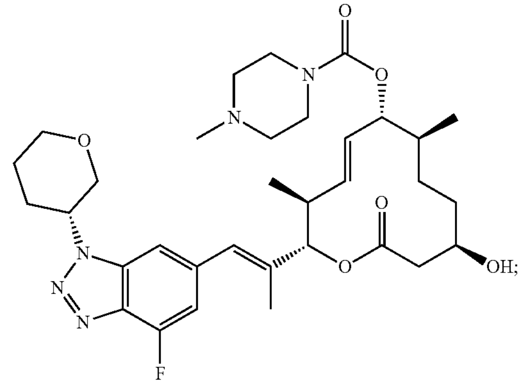
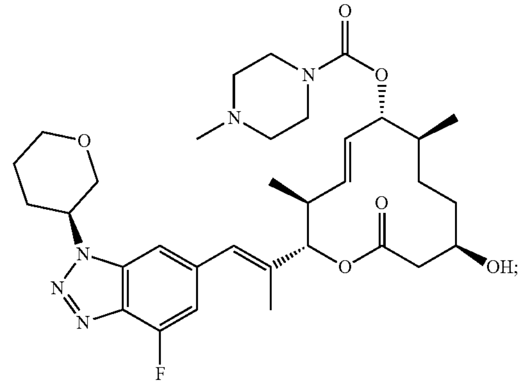
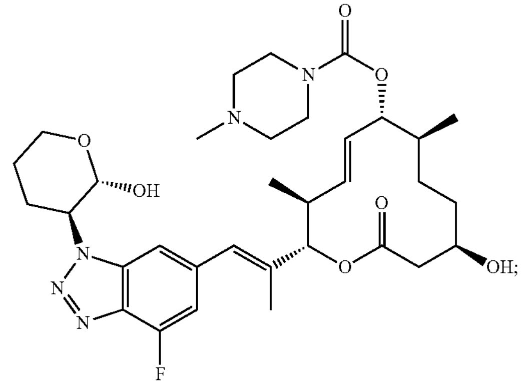
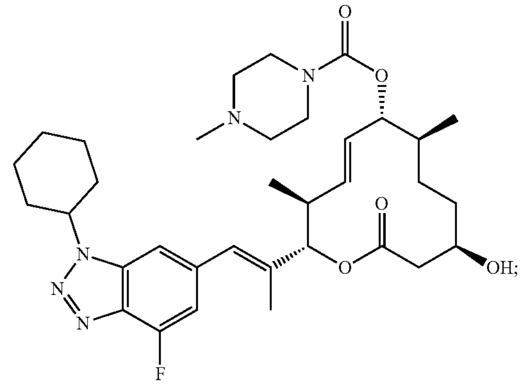
-continued
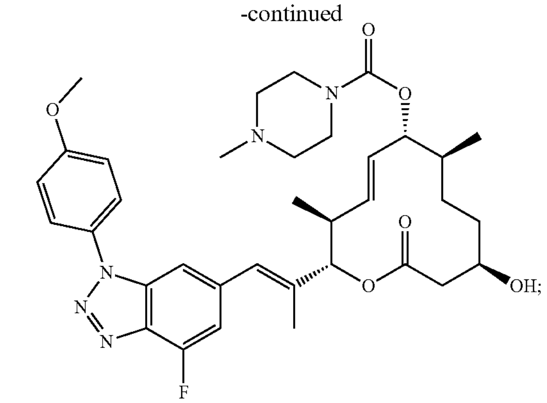
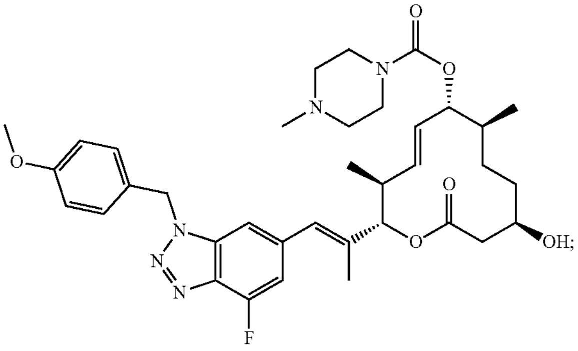
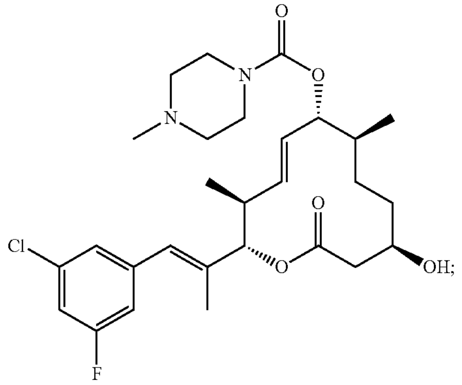
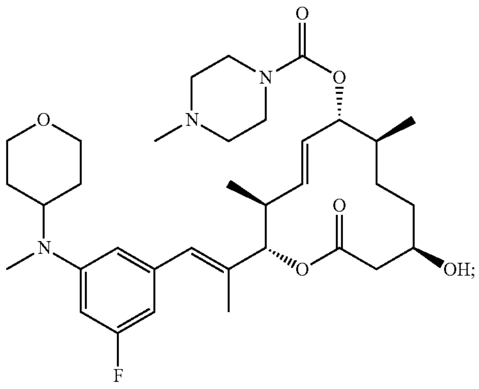

-continued
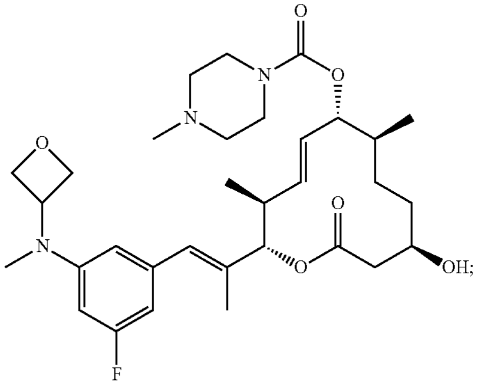
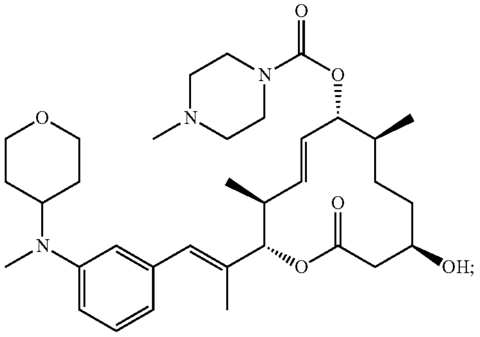
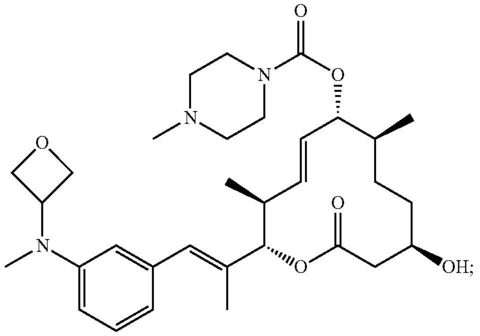
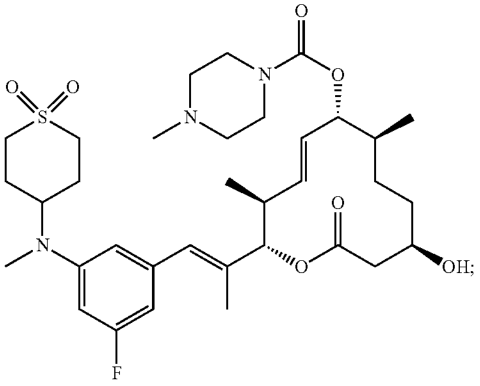
-continued
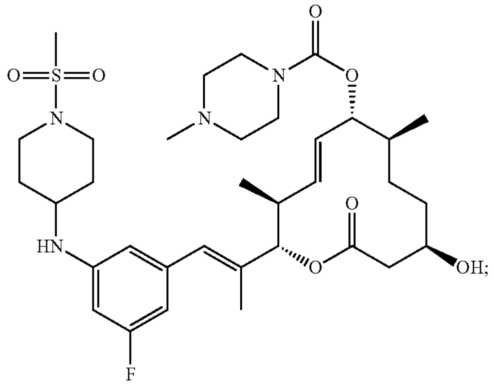
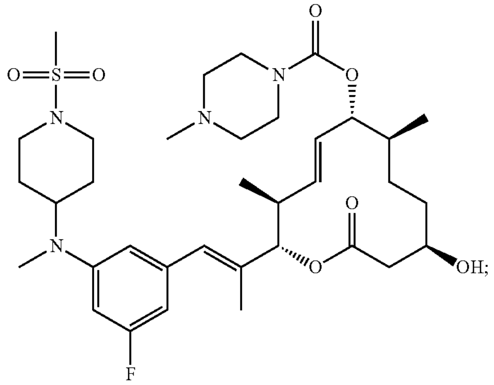
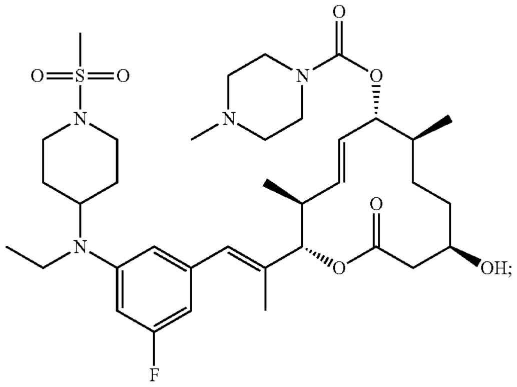
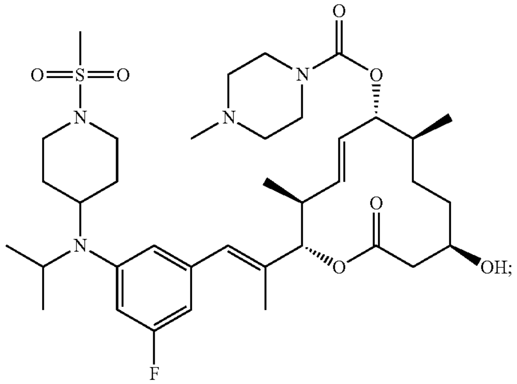

-continued
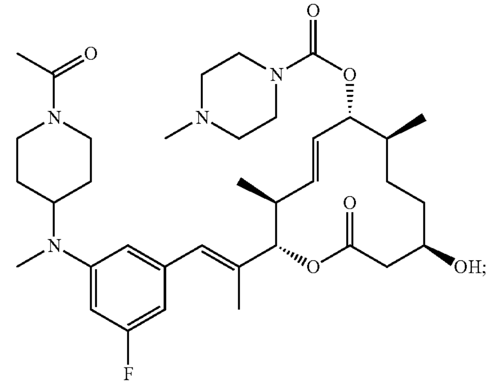
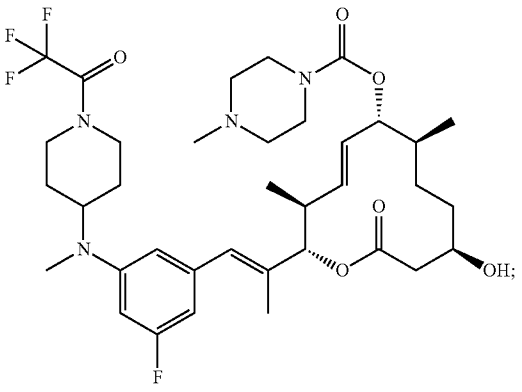
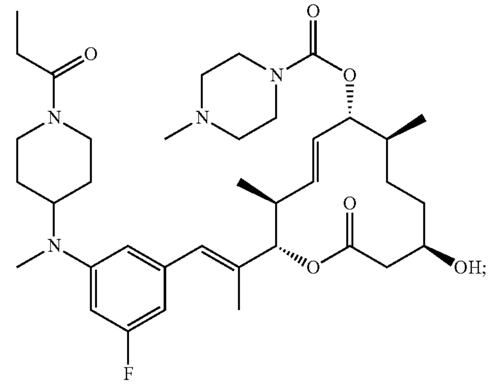
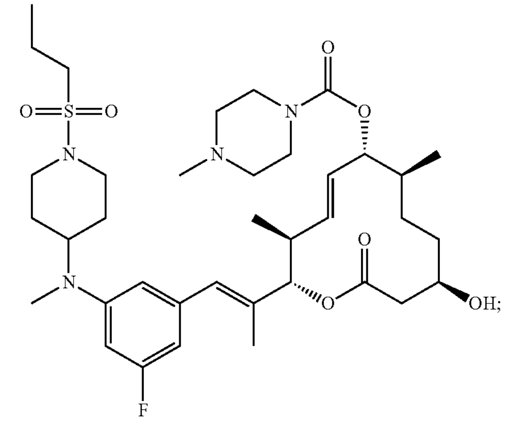
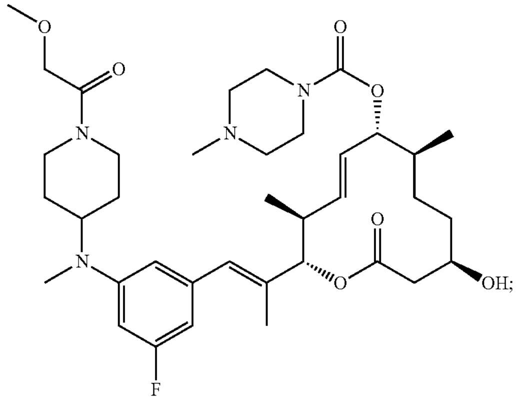
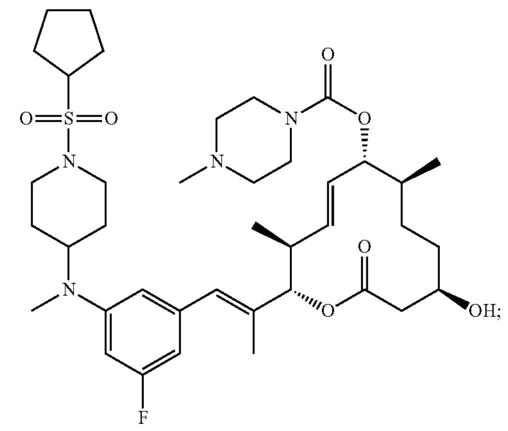
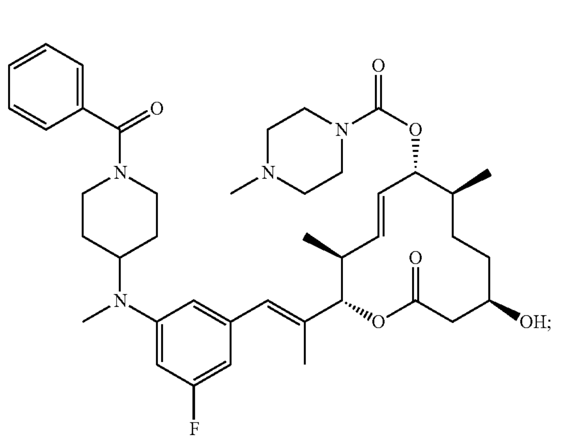
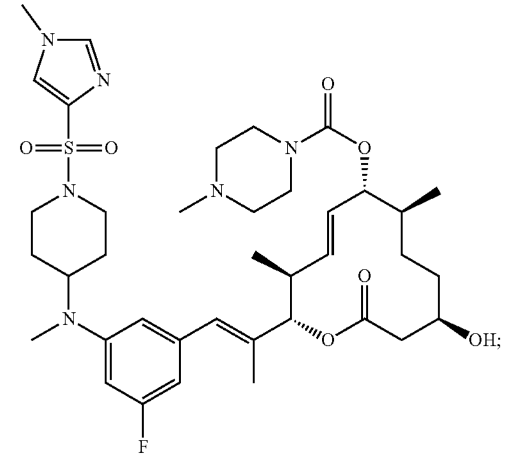

-continued
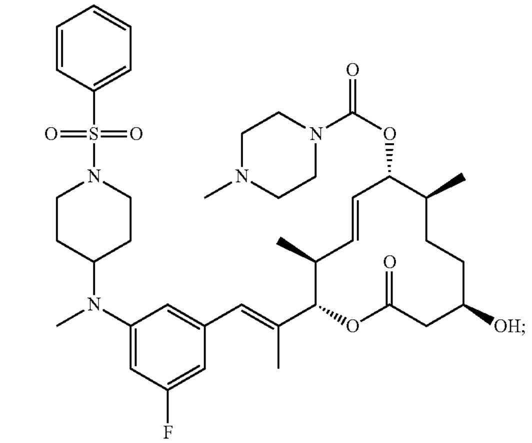
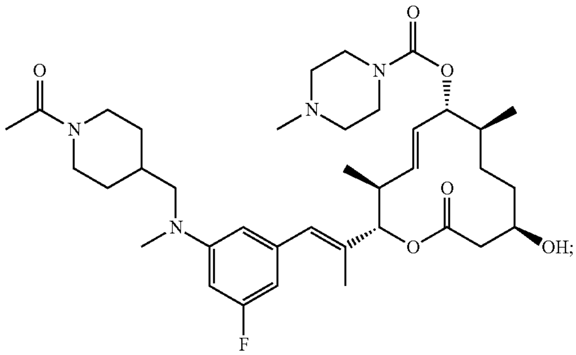
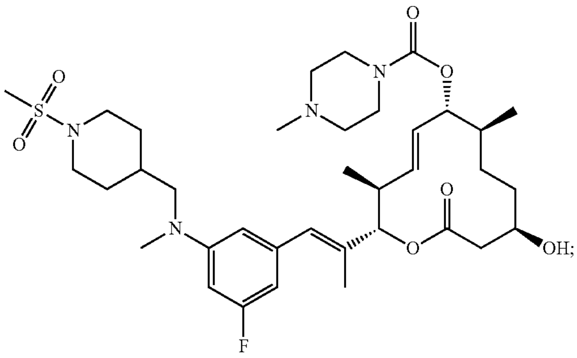
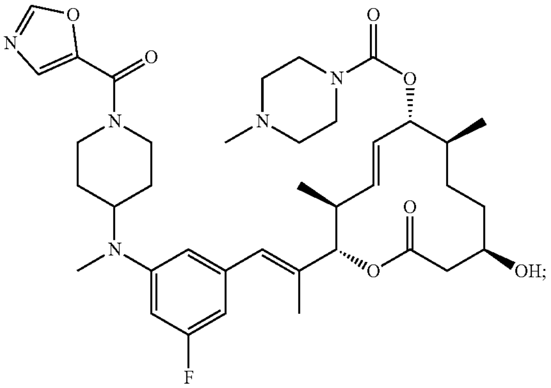
-continued
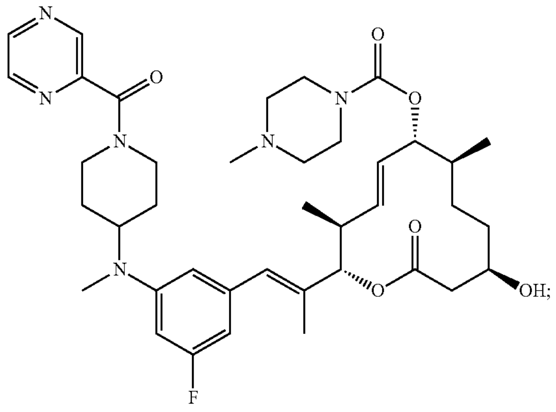
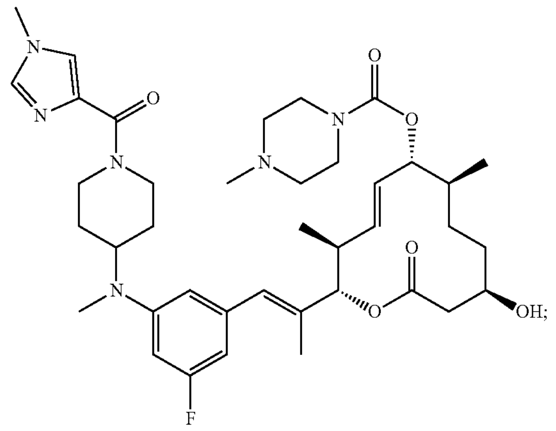
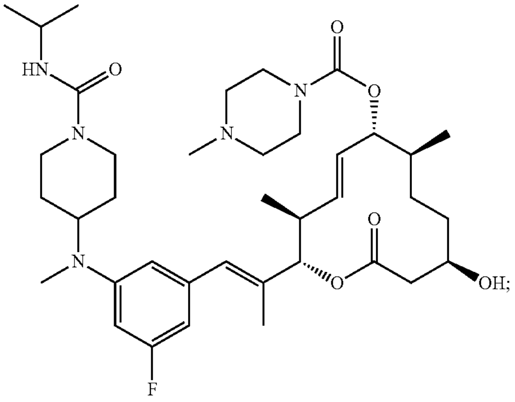
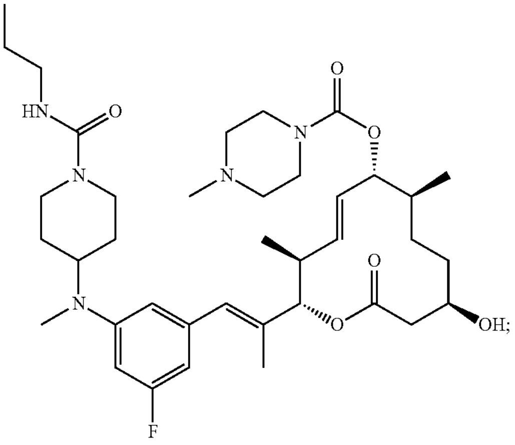

-continued
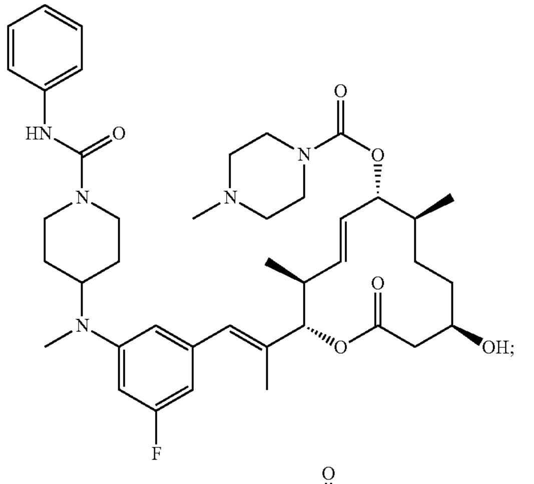
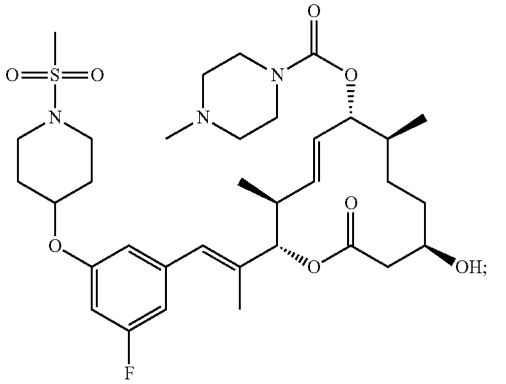
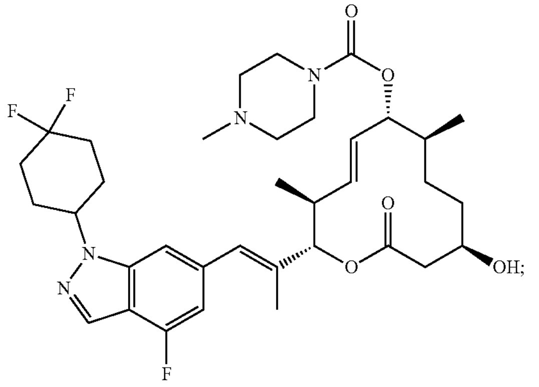
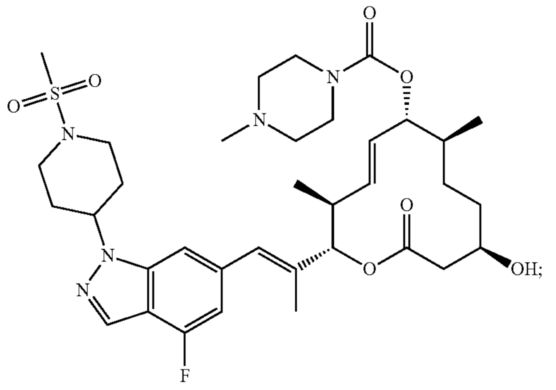
-continued
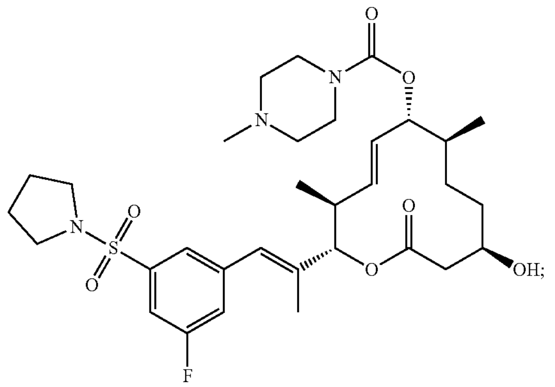
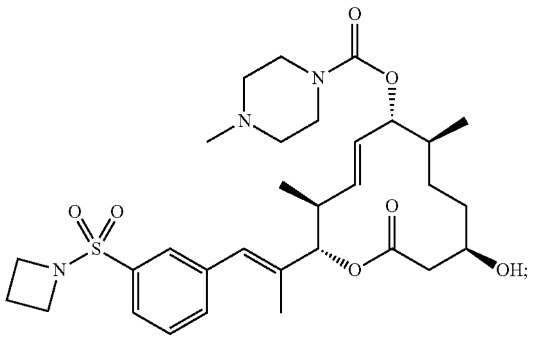
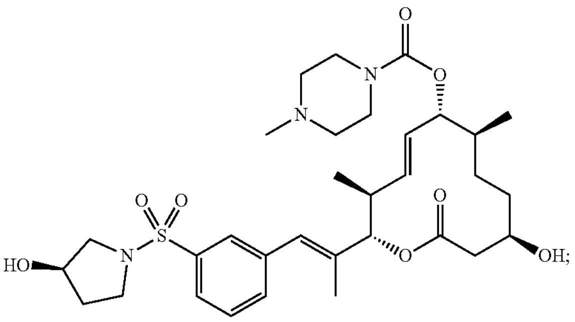
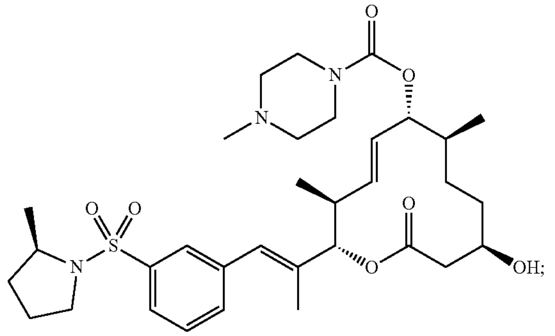
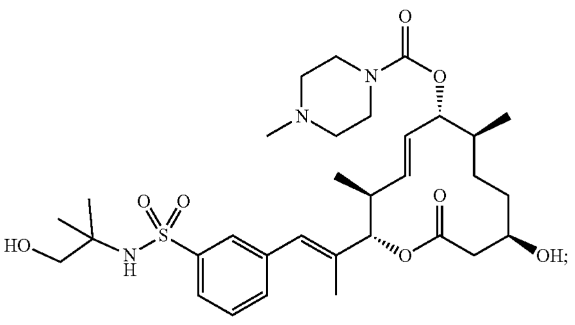

-continued
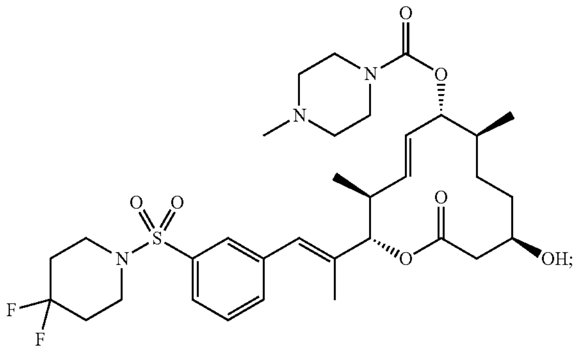
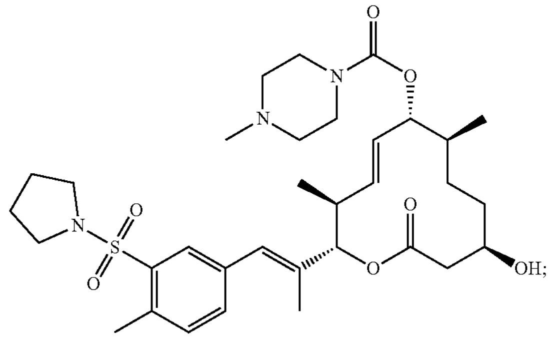
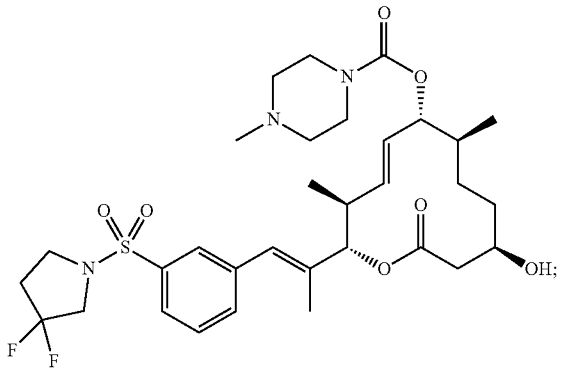
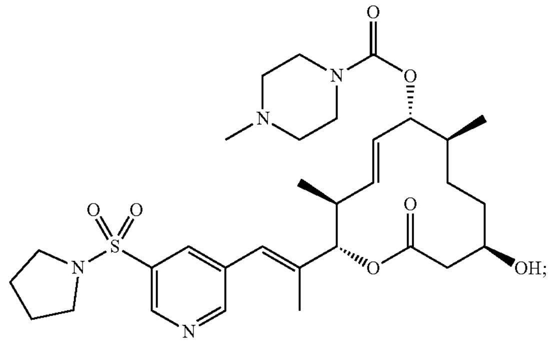
-continued
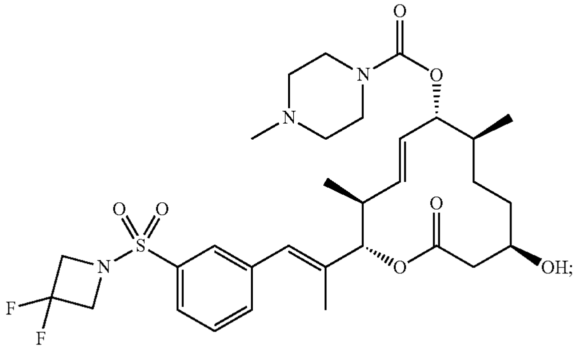
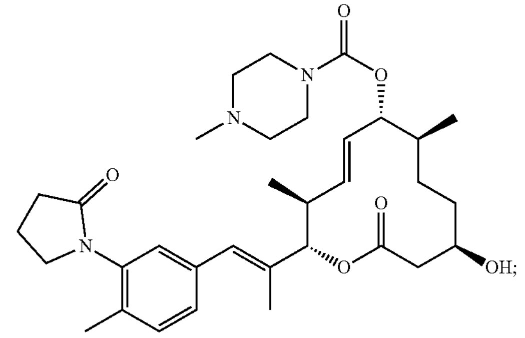
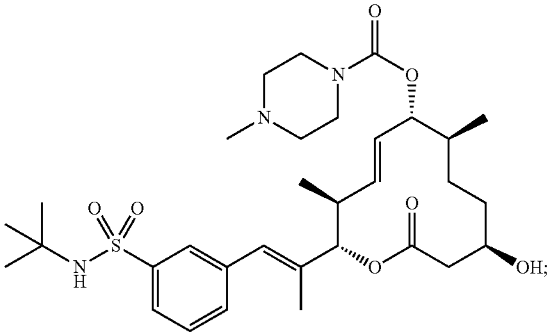
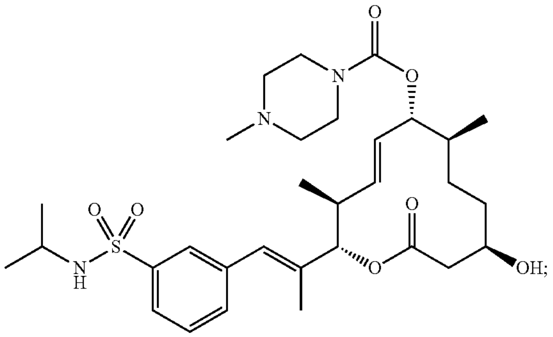
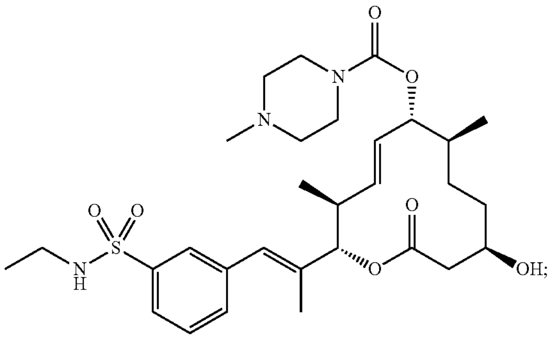

-continued
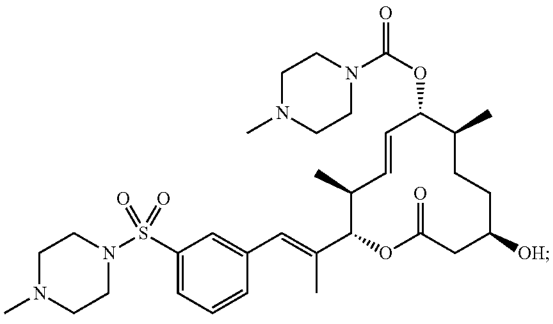
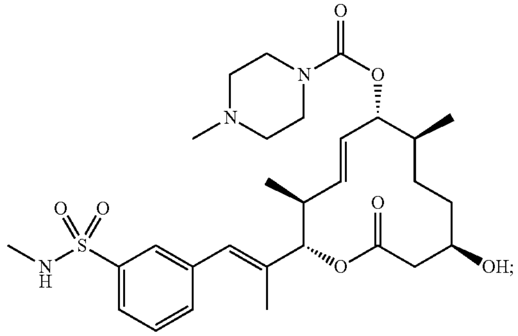
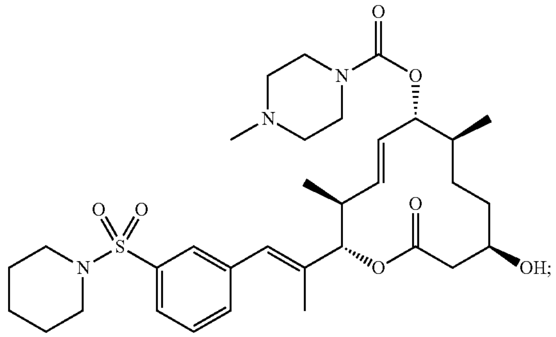
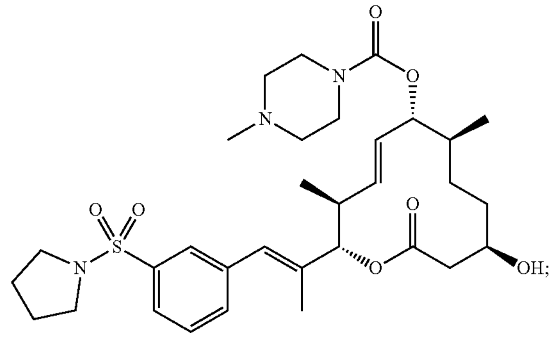
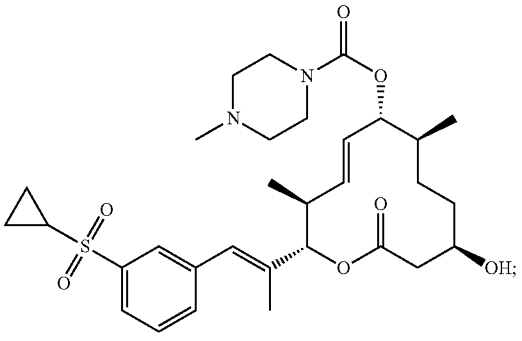
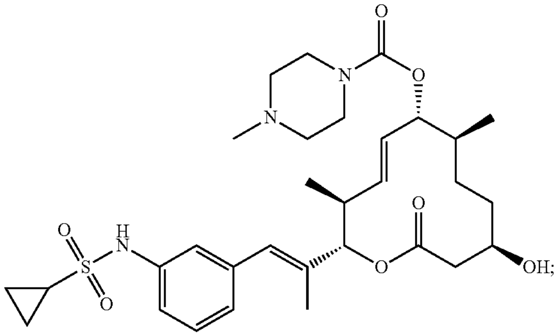
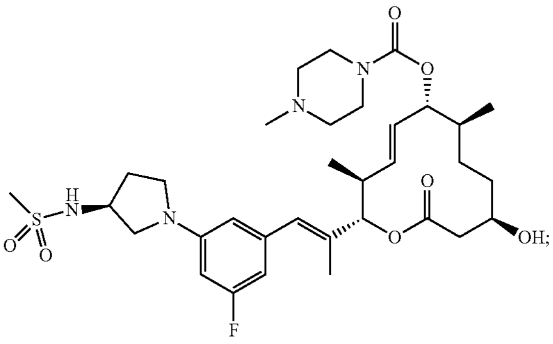
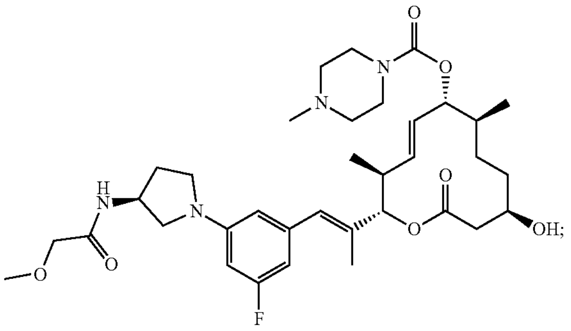
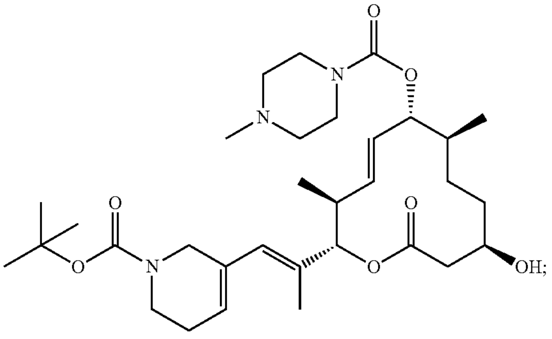
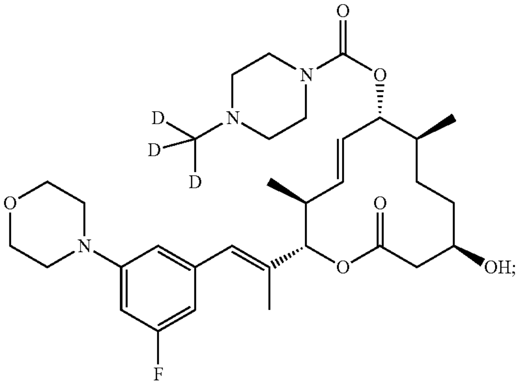

-continued
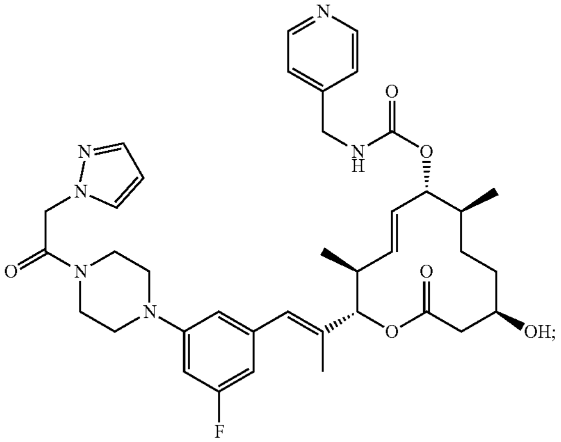
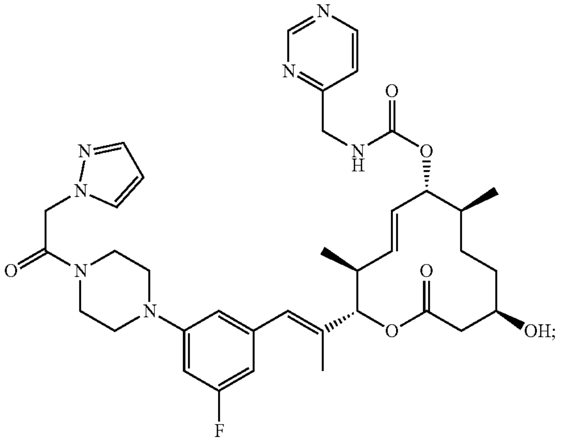
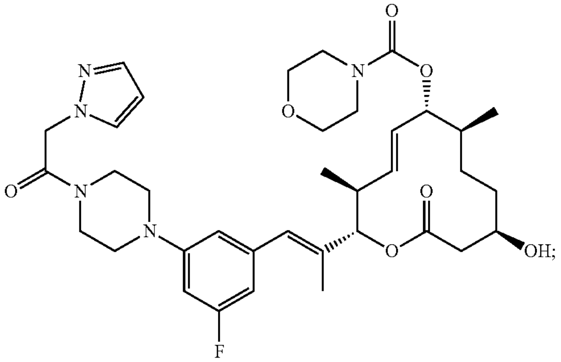
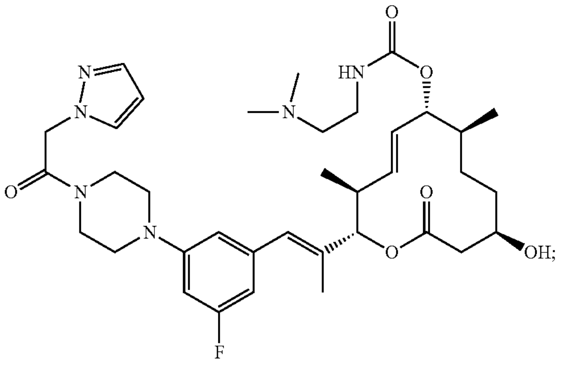
-continued
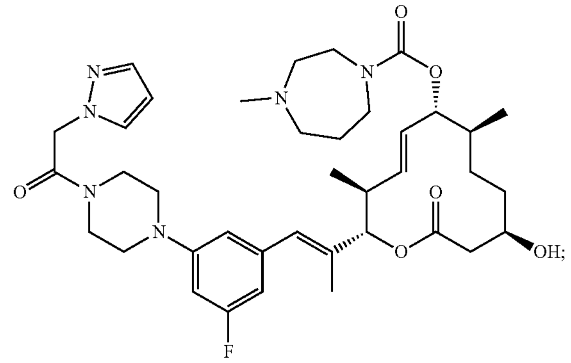
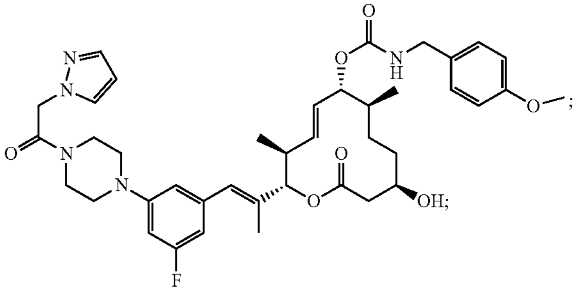
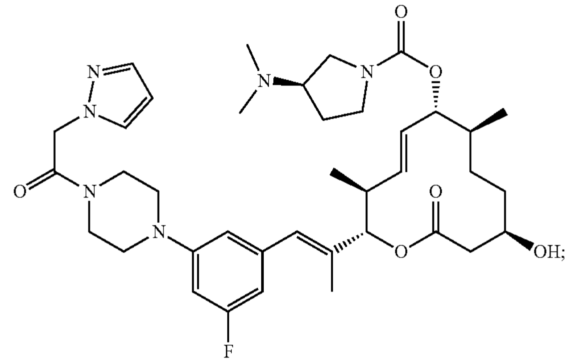
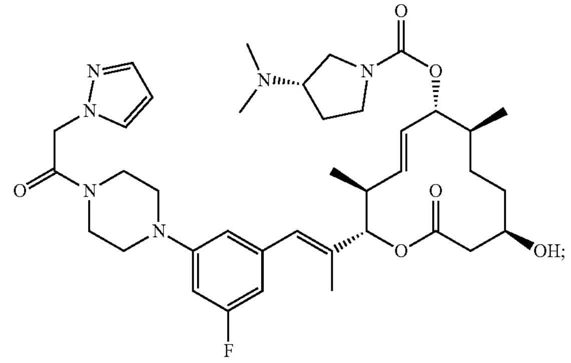
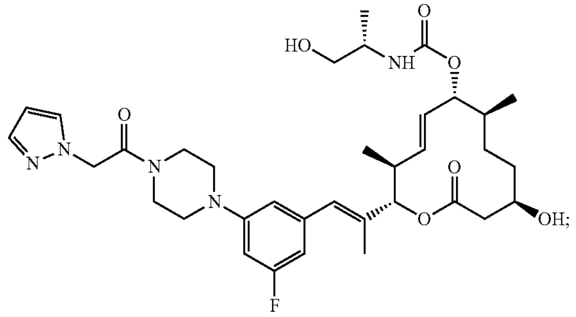

-continued
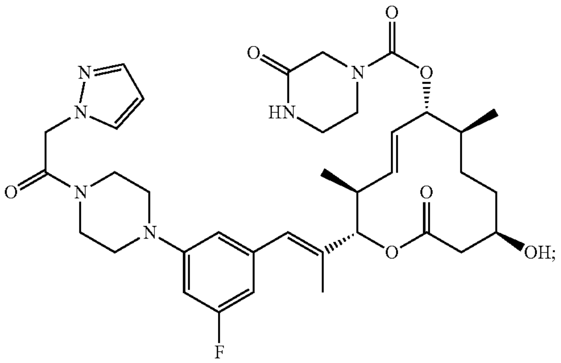
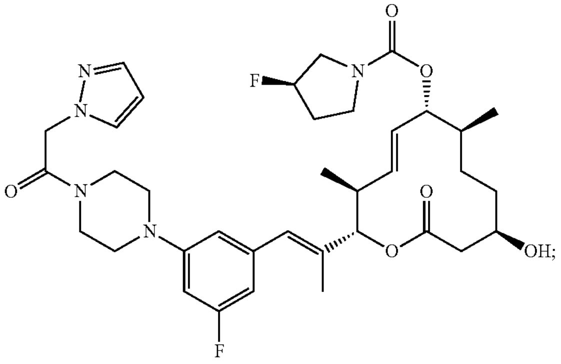
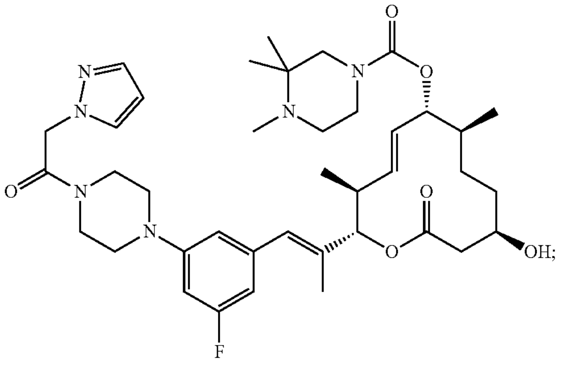
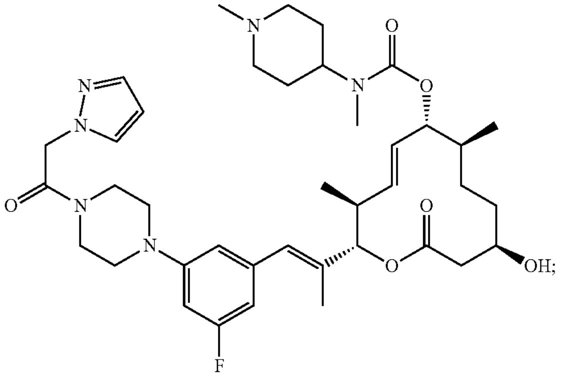
-continued
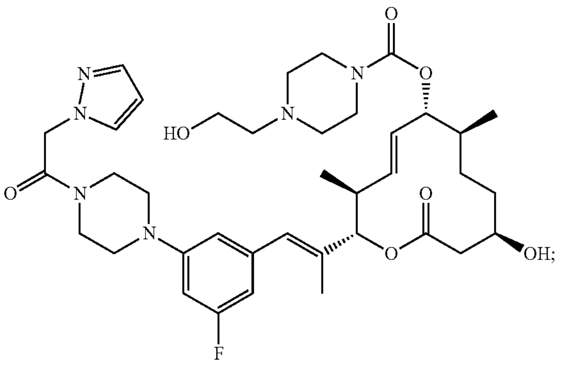
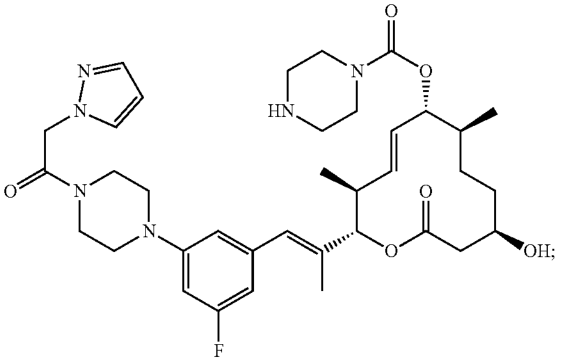
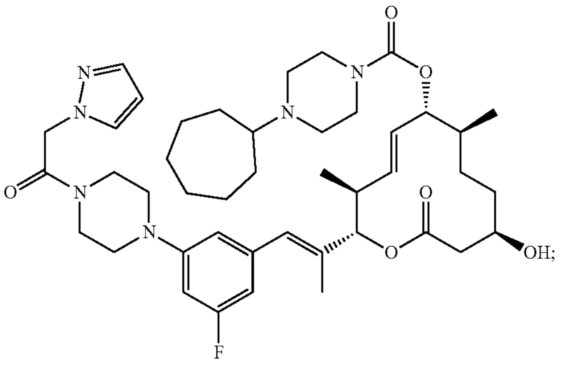
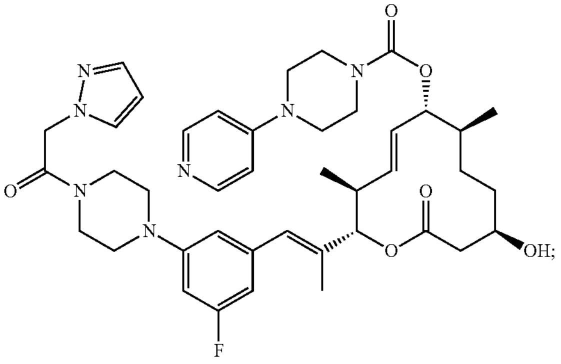

-continued
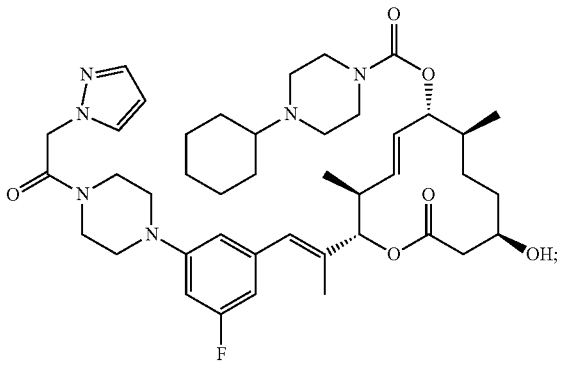
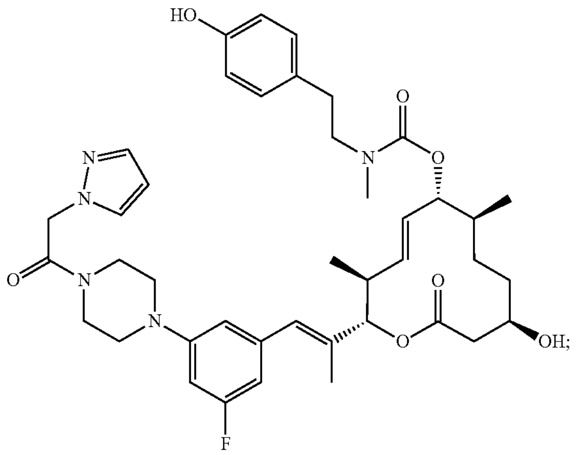
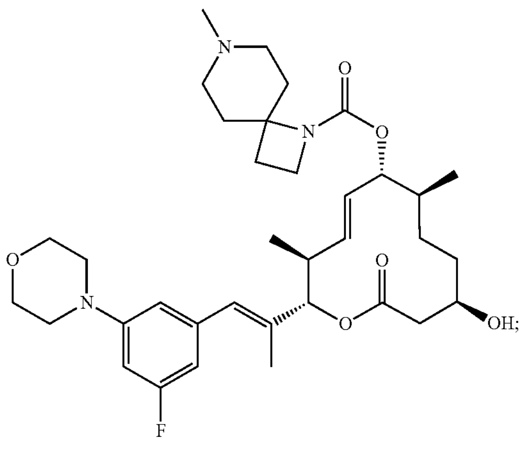
-continued
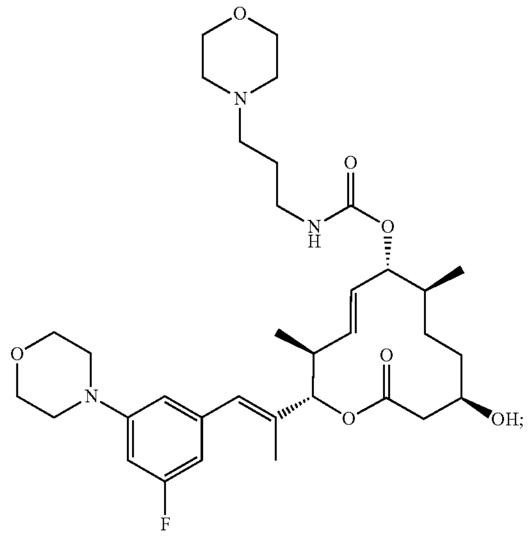
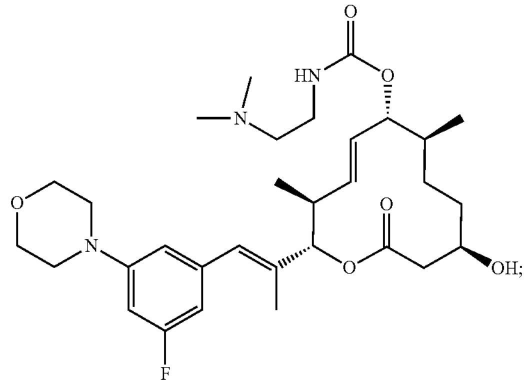
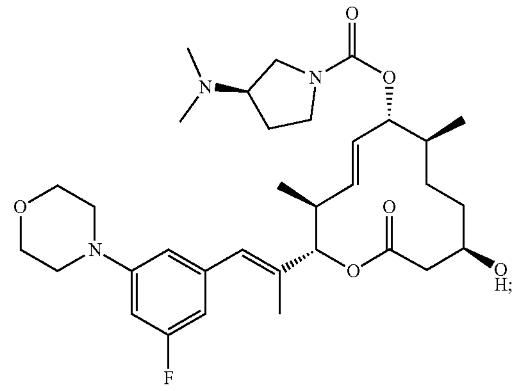
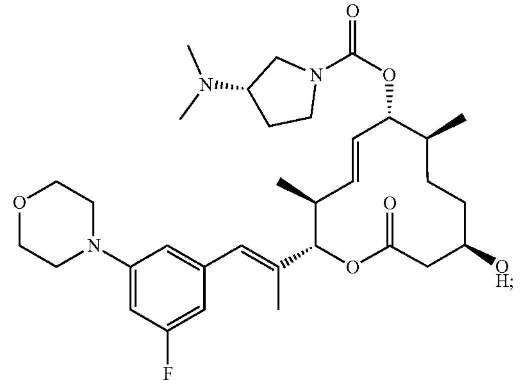

-continued
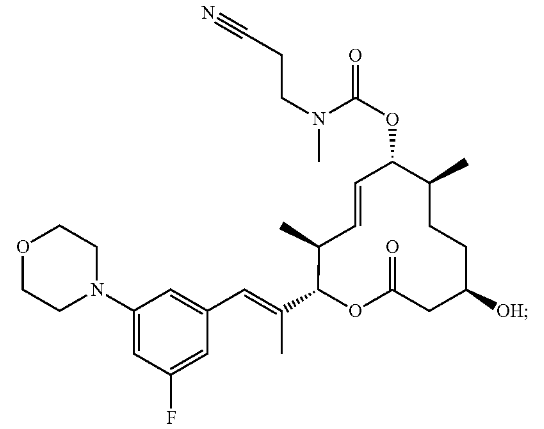
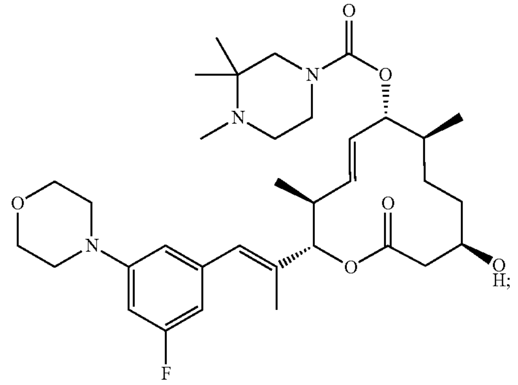
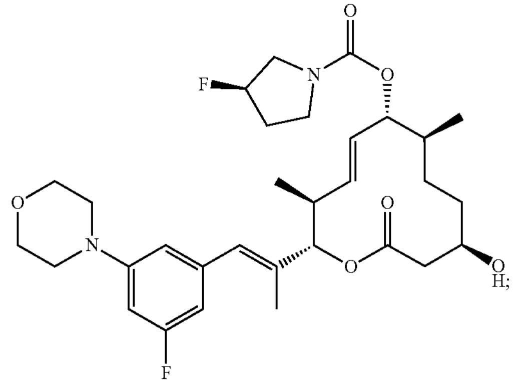
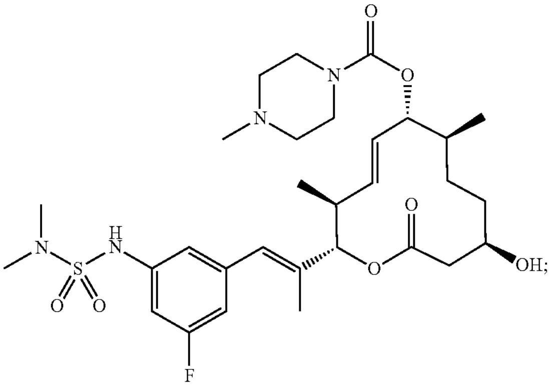
-continued
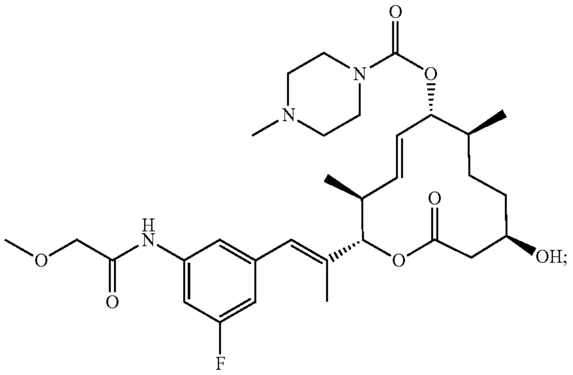
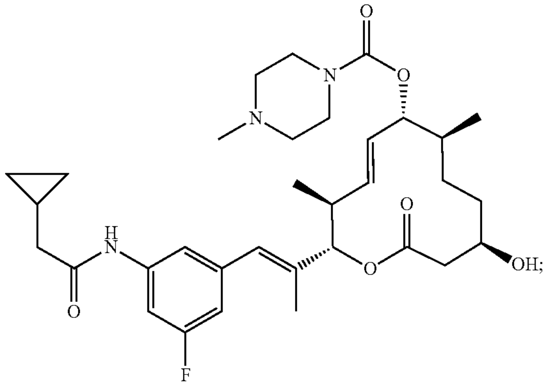
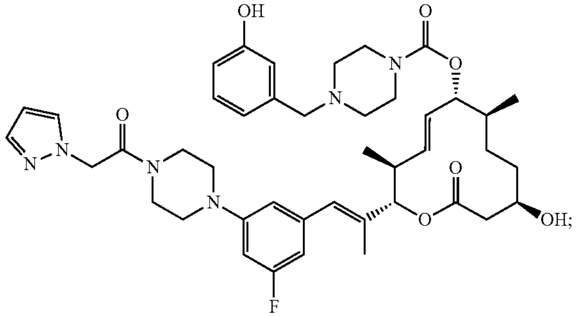
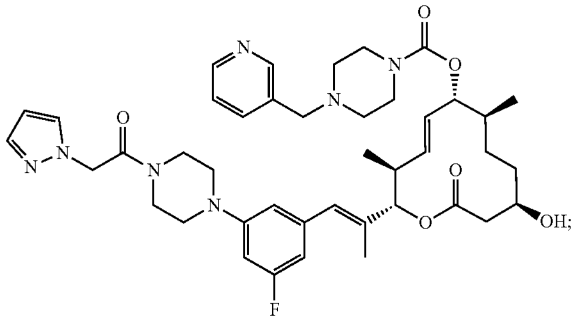

-continued
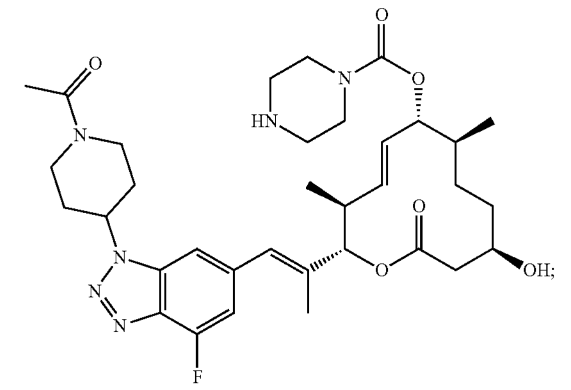
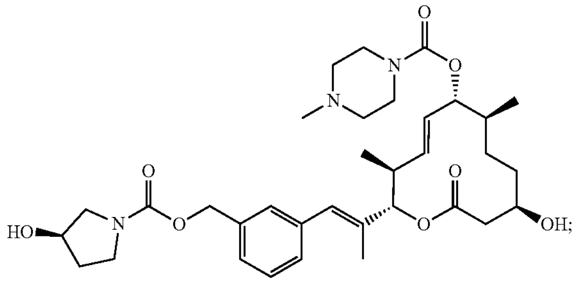
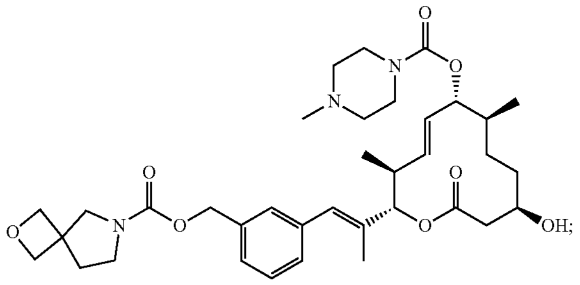
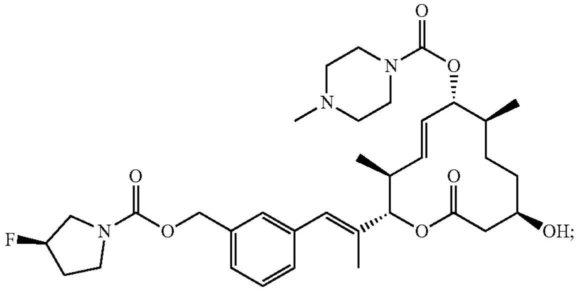
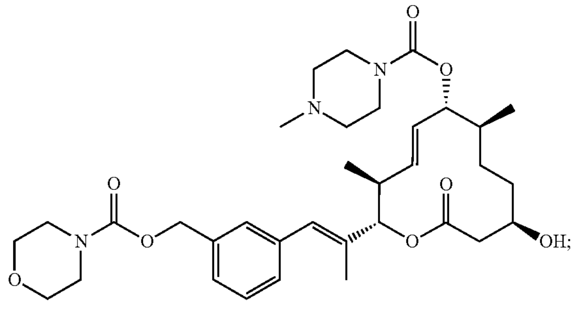
-continued
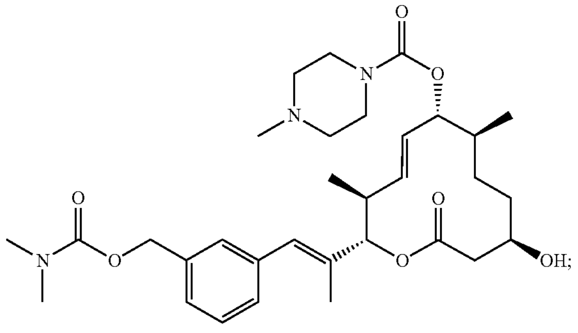
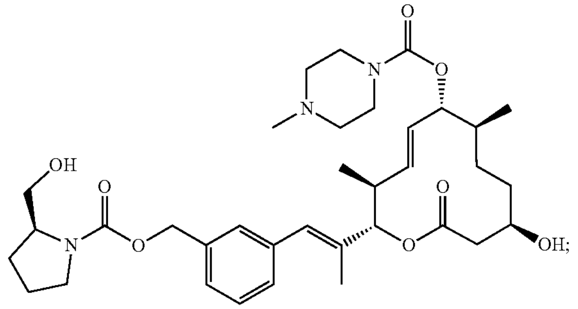
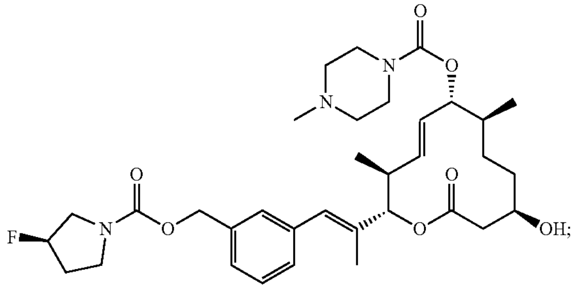
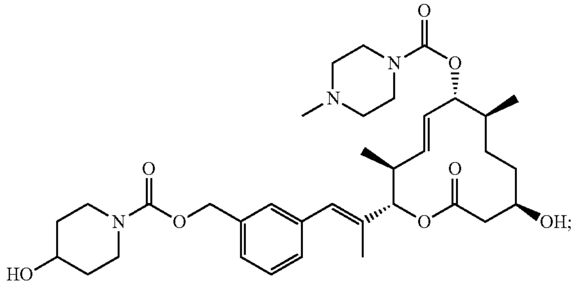
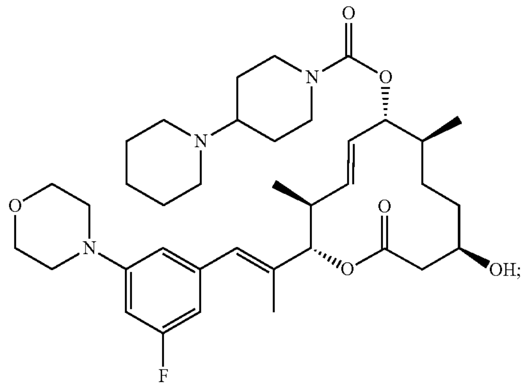

-continued

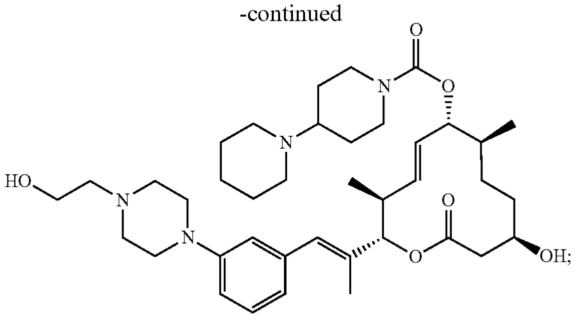

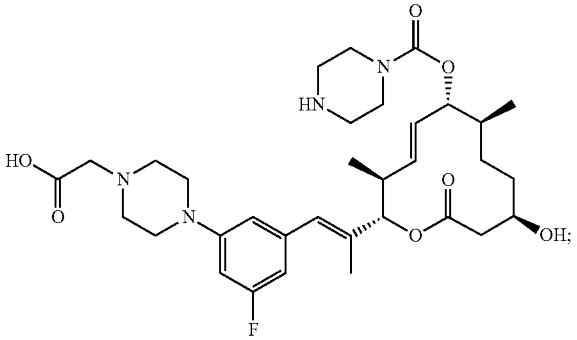

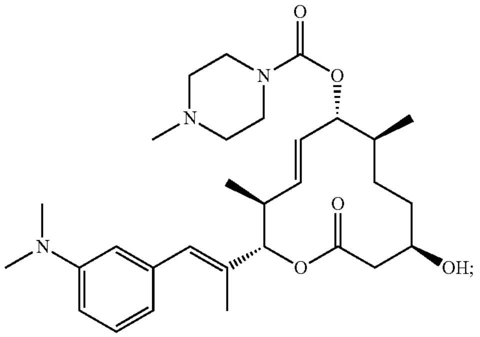

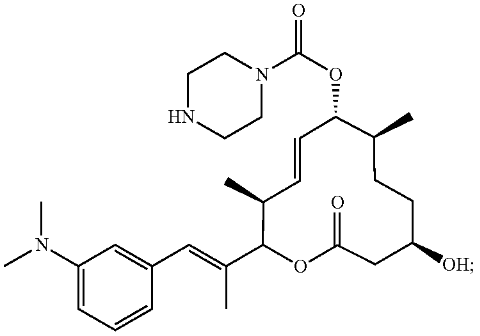

-continued

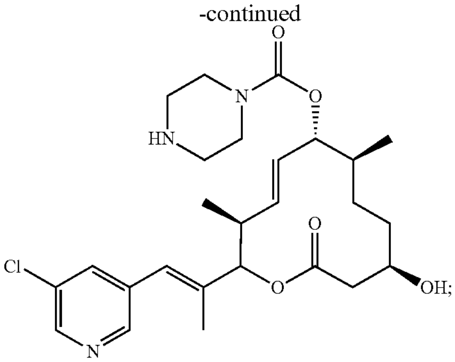

and

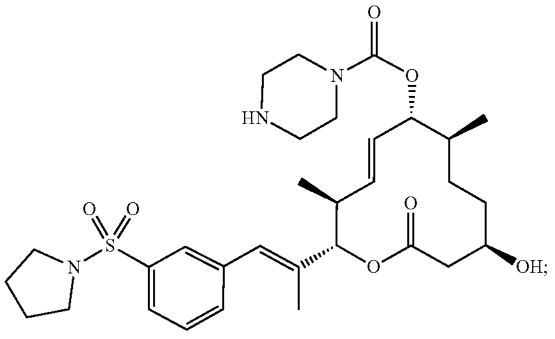

or a pharmaceutically acceptable salt thereof, wherein administration of the therapeutically effective amount of the at least one compound or pharmaceutically acceptable salt thereof to the subject in need thereof:

(i) induces at least one neoantigen; or (ii) induces a T-cell response; or (iii) induces at least one neoantigen and a T-cell response.

22. The method of claim 21, wherein the neoplastic disorder is a solid tumor selected from the group consisting of breast cancer, gastric cancer, prostate cancer, ovarian cancer, lung cancer, uterine cancer, salivary duct carcinoma, melanoma, colon cancer, and esophageal cancer.

23. The method of claim 21, wherein the neoplastic disorder is a hematological malignancy selected from the group consisting of a B-cell malignancy, a leukemia, a lymphoma, and a myeloma.

* * * * *